(12) United States Patent
Cha et al.

(10) Patent No.: US 11,031,560 B2
(45) Date of Patent: Jun. 8, 2021

(54) COMPOUND AND ORGANIC ELECTRONIC ELEMENT COMPRISING SAME

(71) Applicant: LG CHEM, LTD., Seoul (KR)

(72) Inventors: Yongbum Cha, Daejeon (KR); Sung Kil Hong, Daejeon (KR); Hyok Joon Kwon, Daejeon (KR); Minjun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 328 days.

(21) Appl. No.: 15/578,973

(22) PCT Filed: Jun. 7, 2016

(86) PCT No.: PCT/KR2016/006014
§ 371 (c)(1),
(2) Date: Dec. 1, 2017

(87) PCT Pub. No.: WO2016/195461
PCT Pub. Date: Dec. 8, 2016

(65) Prior Publication Data
US 2018/0138422 A1    May 17, 2018

(30) Foreign Application Priority Data
Jun. 5, 2015   (KR) .......................... 10-2015-0080126

(51) Int. Cl.
*H01L 51/00*   (2006.01)
*C07D 487/04*   (2006.01)
(Continued)

(52) U.S. Cl.
CPC ........ *H01L 51/0072* (2013.01); *C07D 487/04* (2013.01); *C07F 9/65616* (2013.01); *C09K 11/06* (2013.01); *H01L 51/006* (2013.01); *H01L 51/0052* (2013.01); *H01L 51/0056* (2013.01); *H01L 51/0058* (2013.01);
(Continued)

(58) Field of Classification Search
CPC ... C07D 487/04; C07F 9/65616; C09K 11/06; C09K 2211/1029; C09K 2211/185; H01L 51/0052; H01L 51/0056; H01L 51/0058; H01L 51/006; H01L 51/0061; H01L 51/0067; H01L 51/0071; H01L 51/0072; H01L 51/0073; H01L 51/0074; H01L 51/0085; H01L 51/50; H01L 51/5012; H01L 51/5016; H01L 51/5056; H01L 51/5072; H01L 51/5088; H01L 51/5092; H01L 51/5096

See application file for complete search history.

(56) References Cited

U.S. PATENT DOCUMENTS

2004/0124766 A1*  7/2004  Nakagawa .......... H01L 51/0064
                                                    313/504
2004/0251816 A1   12/2004  Leo et al.
(Continued)

FOREIGN PATENT DOCUMENTS

EP         2719741 A2    4/2014
KR      1020070062920 A    6/2007
(Continued)

*Primary Examiner* — Dawn L Garrett
(74) *Attorney, Agent, or Firm* — Dentons US LLP

(57) ABSTRACT

The present application relates to a compound and an organic electronic device comprising the same.

16 Claims, 1 Drawing Sheet

(51) Int. Cl.
*C09K 11/06* (2006.01)
*H01L 51/50* (2006.01)
*C07F 9/6561* (2006.01)

(52) U.S. Cl.
CPC ...... *H01L 51/0061* (2013.01); *H01L 51/0067* (2013.01); *H01L 51/0071* (2013.01); *H01L 51/0073* (2013.01); *H01L 51/0074* (2013.01); *H01L 51/0085* (2013.01); *H01L 51/50* (2013.01); *C09K 2211/1029* (2013.01); *C09K 2211/185* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2007/0131929 A1 6/2007 Bae et al.
2013/0328030 A1* 12/2013 Matsuura ............ C07C 13/567
257/40

FOREIGN PATENT DOCUMENTS

| KR | 1020100062973 A | 6/2010 |
| KR | 1020110008784 A | 1/2011 |
| KR | 1020140064686 A | 5/2014 |
| KR | 1020150010016 A | 1/2015 |
| WO | 03012890 A2 | 2/2003 |
| WO | 2011010842 A2 | 1/2011 |
| WO | 2015009076 A1 | 1/2015 |

* cited by examiner

【FIG. 1】
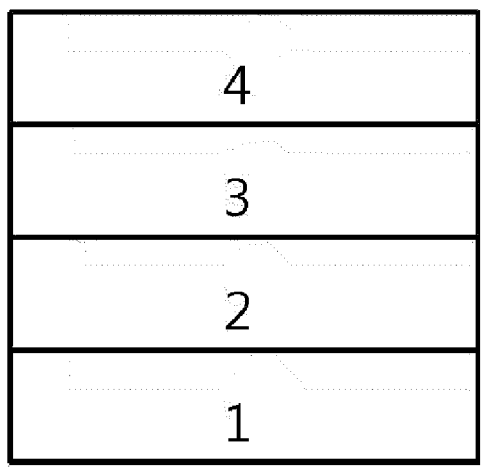
【FIG. 2】
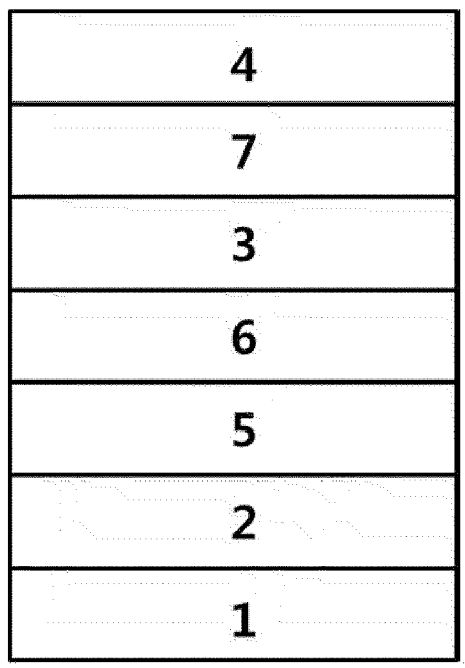

COMPOUND AND ORGANIC ELECTRONIC ELEMENT COMPRISING SAME

This application is a National Stage Application of International Application No. PCT/KR2016/006014, filed Jun. 7, 2016, and claims the benefit of Korean Patent Application No. 10-2015-0080126, filed Jun. 5, 2015, contents of which are incorporated herein by reference in their entirety for all purposes as if fully set forth below.

TECHNICAL FIELD

The present specification claims priority to and the benefits of Korean Patent Application No. 10-2015-0080126, filed with the Korean Intellectual Property Office on Jun. 5, 2015, the entire contents of which are incorporated herein by reference.

The present application relates to a compound and an organic electronic device Comprising the same.

BACKGROUND ART

A typical example of an organic electronic device includes an organic light emitting device. An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Materials used in an organic light emitting device are mostly pure organic materials or complex compounds in which organic materials and metals form complexes. The materials used in an organic light emitting device may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting layer material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferable that materials used in an organic light emitting device additionally have properties as follows.

First, materials used in an organic light emitting device preferably have excellent thermal stability. This is due to joule heating produced by charge transfer in the organic light emitting device. NPB normally used as a hole transfer layer material of an organic light emitting device currently has a glass transition temperature of 100° C. or lower, and has a problem in that it is difficult to be used in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a HOMO or LUMO energy level. PEDOT:PSS currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifespan.

In addition thereto, materials used in an organic light emitting device need to have excellent chemical stability, degree of charge transfer, and interface properties with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials need to improve an interface with electrodes including metals or metal oxides.

Development of organic materials satisfying such requirements has been required in the art.

DISCLOSURE

Technical Problem

The present application is directed to providing a compound and an organic electronic device comprising the same.

Technical Solution

One embodiment of the present application provides a compound represented by the following Chemical Formula 1.

[Chemical Formula 1]

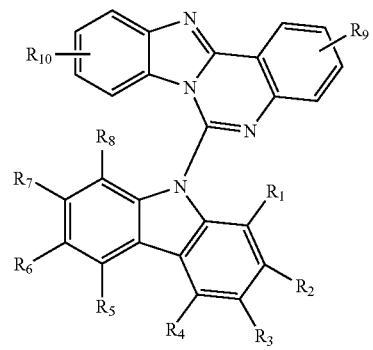

In Chemical Formula 1, at least one of $R_1$ to $R_8$ is $-(L)_m-(Ar)_n$, and the rest are the same as or different from each other and each independently hydrogen; deuterium; a halogen group; a nitro group; a cyano group; an ester group; a carbonyl group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, or bond to adjacent groups to form a ring, L is a direct bond; a substituted or unsubstituted arylene group; or a substituted or unsubstituted divalent heterocyclic group, m is an integer of 1 to 3, when m is an integer of 2 or greater, a plurality of Ls are the same as or different from each other, Ar is hydrogen; deuterium; a halogen group; a nitro group; a cyano group; an ester group; a carbonyl group; a substituted or unsubstituted alkyl group; a substituted or unsubstituted cycloalkyl group; a substituted or unsubstituted alkoxy group; a substituted or unsubstituted alkenyl group; a substituted monocyclic aryl group; a substituted or unsubstituted multicyclic aryl group; a substituted or unsubstituted heterocyclic group; a substituted or unsubstituted amine group; a substituted or unsubstituted silyl group; or a substituted or unsubstituted phosphoryl group, n is 1 or 2, and when n is 2, a plurality of Ars are the same as or different from each other, and $R_9$ and $R_{10}$ are the same as or different from each other, and each independently hydrogen; deuterium; a halogen group; a nitro group; a cyano group; an ester group; a carbonyl group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group.

Another embodiment of the present application provides an organic electronic device comprising a first electrode; a second electrode provided opposite to the first electrode; and one or more organic material layers provided between the first electrode and the second electrode, wherein one or more layers of the organic material layers comprise the above-described compound.

Advantageous Effects

A compound according to one embodiment of the present application is used in an organic electronic device including an organic light emitting device, and is capable of lowering a driving voltage of the organic electronic device, enhancing light efficiency, and enhancing a device lifespan property by thermal stability of the compound.

DESCRIPTION OF DRAWINGS

FIG. 1 illustrates an example of an organic light emitting device in which a substrate (1), an anode (2), a light emitting layer (3) and a cathode (4) are consecutively laminated.

FIG. 2 illustrates an example of an organic light emitting device in which a substrate (1), an anode (2), a hole injection layer (5), a hole transfer layer (6), a light emitting layer (3), an electron transfer layer (7) and a cathode (4) are consecutively laminated.

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

One embodiment of the present specification provides a compound represented by Chemical Formula 1.

According to one embodiment of the present application, the compound of Chemical Formula 1 performs a role of limiting conjugation by having a core structure in which an imidazoquinazoline group and a carbazole group are directly linked. A conjugation length of a compound and an energy band gap thereof are closely related. Specifically, as a conjugation length of a compound increases, an energy band gap thereof decreases. As described above, the core of the compound of Chemical Formula 1 includes limited conjugation, and therefore, the energy bad gap is large. Normally, an energy band gap is readily controlled by introducing substituents to a core structure having a large energy band gap, however, when a core structure has a small energy band gap, controlling the energy band gap to be large by introducing substituents is difficult. In this light, the compound of Chemical Formula 1 has a structure with a large band gap, and therefore, the band gap is readily controlled, and for example, compounds having various energy band gaps may be synthesized by introducing various substituents to $R_1$ to $R_8$ positions of Chemical Formula 1. Accordingly, HOMO and LUMO energy levels of the compound may be controlled as well by introducing various substituents to $R_1$ to $R_8$ of Chemical Formula 1.

For example, by introducing substituents normally used as a hole injection layer material, a hole transfer layer material, a light emitting layer material and an electron transfer layer material used for manufacturing an organic light emitting device to the core structure, materials satisfying needs required from each organic material layer may be synthesized. For example, when Chemical Formula 1 includes an arylamine structure in the core structure, it may have a proper energy level as a hole injection and/or hole transfer material in an organic light emitting device. Accordingly, in the present application, a device having low driving voltage and high light efficiency may be obtained by selecting a compound having a proper energy level among the compounds of Chemical Formula 1 depending on substituents, and using the compound in an organic light emitting device.

In addition, by symmetrically or asymmetrically introducing various substituents to the core structure, the energy band gap may be finely controlled, and meanwhile, properties at interfaces between organic materials are enhanced, and material applications may become diverse.

In addition, the compound of Chemical Formula 1 exhibits stable redox characteristics. Stability for oxidation-reduction may be identified using a cyclovoltammetry (CV) method. As a specific example, when an oxidation voltage is repeatedly applied many times, the compound of Chemical Formula 1 is oxidized at the same voltage and shows the same current amount, and this indicates that the compound has excellent stability for oxidation.

Meanwhile, the compound of Chemical Formula 1 has excellent thermal stability with a high glass transition temperature (Tg). For example, the compound of Chemical Formula 1 has a glass transition temperature of 131° C., which is significantly higher than NPB (Tg: 96° C.) that has been generally used in the art. Such an increase in the thermal stability becomes an important factor in providing driving stability to a device.

In addition, the compound of Chemical Formula 1 has very excellent solubility for solvents used in a manufacturing process of a device, for example, polar solvents such as xylene, dichloroethane or NMP, and is readily formed into a thin film through methods using a solution. Accordingly, a solution coating method may be used as well as a vacuum deposition method in the manufacturing process. Herein, the solution coating method means spin coating, dip coating, ink jet printing, screen printing, a spray method, roll coating and the like, but is not limited thereto. Normally, a light emission wavelength in a thin film formed using a solution coating method or in a solid state is often shifted to a longer wavelength compared to a light emission wavelength in a solution state due to the interaction between molecules, and compounds having a structure such as the compound of Chemical Formula 1 have an advantage in that such a wavelength shift hardly occurs.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a cyano group; a nitro group; a hydroxyl group; a germanium group; an alkyl group; a cycloalkyl group; an alkenyl group; an amine group; a silyl group; a phosphoryl group; an aryl group; and a heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the number of carbon atoms of the ester group is not particularly limited, but is preferably from 1 to 50. Specifically, compounds having the following structural formulae may be included, but the ester group is not limited thereto.

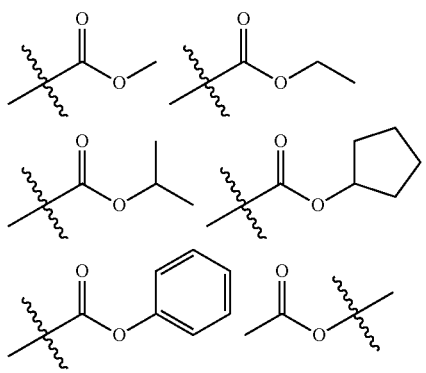

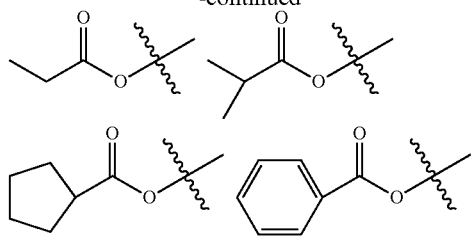

In the present specification, the number of carbon atoms of the carbonyl group is not particularly limited, but is preferably from 1 to 50. Specifically, compounds having structures as below may be included, but the carbonyl group is not limited thereto.

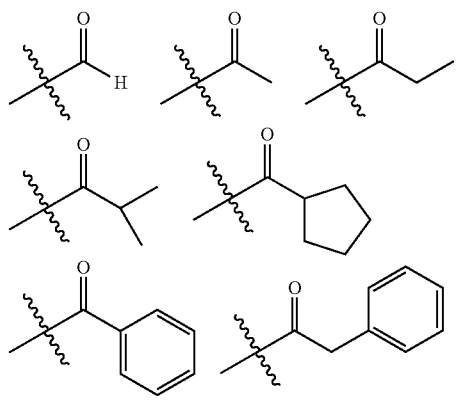

In the present specification, the alkyl group may be linear or branched, and although not particularly limited thereto, the number of carbon atoms is preferably from 1 to 50. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 60 carbon atoms, and specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may be linear, branched or cyclic. The number of carbon atoms of the alkoxy group is not particularly limited, but is preferably from 1 to 20. Specific examples thereof may include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group and the like, but are not limited thereto.

In the present specification, the alkenyl group may be linear or branched, and although not particularly limited thereto, the number of carbon atoms is preferably from 2 to 40. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

When the aryl group is a monocyclic aryl group in the present specification, the number of carbon atoms is not particularly limited, but is preferably from 6 to 25. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably from 10 to 24. Specific examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

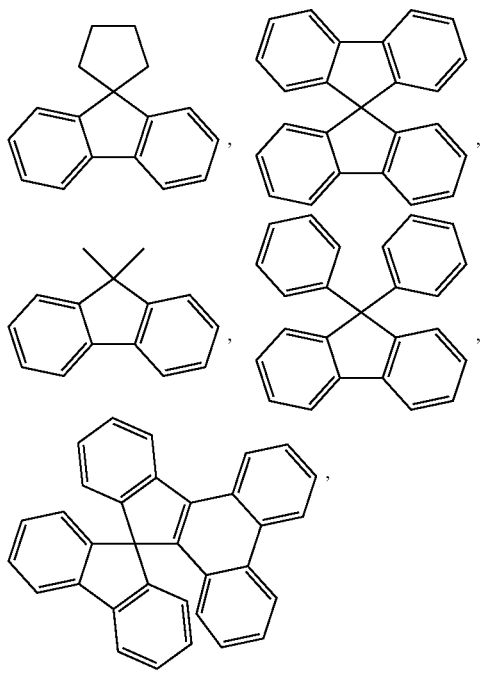

When the fluorenyl group is substituted, and the like may be included, however, the structure is not limited thereto.

In the present specification, the heterocyclic group includes one or more atoms that are not carbon, that is, heteroatoms, and the heteroatom may include one or more atoms selected from the group consisting of O, N, Se, S and the like. The number of carbon atoms of the heterocyclic group is not particularly limited, but is preferably from 2 to 60. Examples of the heterocyclic group may include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a phenanthrolinyl group, a thiazolyl group, an isoxazolyl group, an oxadiazolyl group, a thiadiazolyl group, a benzothiazolyl group, a phenothiazinyl group, a phenoxazinyl group, a dibenzofuran group, fused structures thereof and the like, but are not limited thereto. In addition thereto, examples of the heterocyclic group may include a sulfonyl group-including heteroring structure, for example,

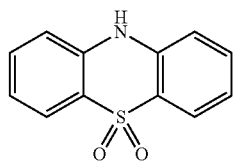 [SMILES: O=S1(=O)c2ccccc2Nc2ccccc21]

and the like.

In the present specification, the fused ring may be a structure in which an aromatic hydrocarbon ring is fused to the corresponding substituent. For example, examples of the fused ring of benzimidazole may include

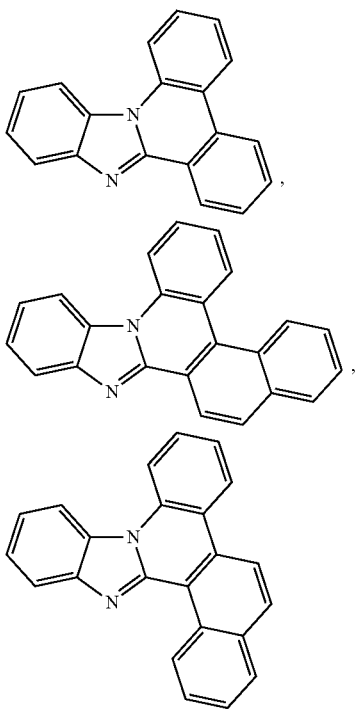

and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the meaning of adjacent groups bonding to each other to form a ring is, as described above, adjacent groups bonding to each other to form a 5-membered to 8-membered hydrocarbon ring or a 5-membered to 8-membered heteroring. The ring may be monocyclic or multicyclic, may be aliphatic, aromatic or a fused form thereof, but is not limited thereto.

In the present specification, the hydrocarbon ring or the heteroring may be selected from among examples of the cycloalkyl group, the aryl group or the heterocyclic group described above except for being monovalent, and may be monocyclic or multicyclic, may be aliphatic, aromatic or a fused form thereof, but is not limited thereto.

In the present specification, the amine group means monovalent amine in which at least one hydrogen atom of the amino group (—NH$_2$) is substituted with other substituents. For example, the amine group is represented by —NR$_{100}$R$_{101}$, and R$_{100}$ and R$_{101}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group (however, at least one of R$_{100}$ and R$_{101}$ is not hydrogen). For example, specific examples of the amine group having an alkyl group and an aryl group as a substituent may include a diphenylamine group, a biphenylbiphenylamine group, a phenylbiphenylamine group, a phenylterphenylamine group, a phenylfluorenylamine group, a phenyl(dimethylfluorenyl)amine group, a biphenyl(dimethylfluorenyl)amine group and the like, but are not limited thereto.

In the present specification, the phosphoryl group is a substituent including P(=O) and having the P atom directly linked as a radical, and is represented by —P(=O)R$_{102}$R$_{103}$. R$_{102}$ and R$_{103}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. For example, specific examples of the phosphoryl group having an aryl group as a substituent may include a diphenylphosphoryl group, a phenylbiphenylphosphoryl group, a biphenylbiphenylphosphoryl group, a phenylterphenylphosphoryl group, a biphenylterphenylphosphoryl group and the like, but are not limited thereto.

In the present specification, the silyl group is a substituent including Si and having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. For example, specific examples of the silyl group having an alkyl group as a substituent may include a trimethylsilyl group, but are not limited thereto. In addition, specific examples of the silyl group having an aryl group as a substituent may include a triphenylsilyl group, but are not limited thereto.

In the present specification, the germanium group may be represented by the chemical formula of —GeR$_a$R$_b$R$_c$, and R$_a$, R$_b$ and R$_c$ may each be hydrogen; a substituted or unsubstituted alkyl group; or a substituted or unsubstituted aryl group. Specific examples of the germanium group may include a trimethylgermanium group, a triethylgermanium group, a t-butyldimethylgermanium group and the like, but are not limited thereto.

In the present specification, descriptions on the aryl group provided above may be applied to the aryl group in the aryloxy group and the arylthio group.

In the present specification, descriptions on the alkyl group provided above may be applied to the alkyl group in the aralkyl group.

In the present specification, descriptions on the heterocyclic group provided above may be applied to the heteroaryl group except for being aromatic.

In the present specification, descriptions on the alkyl group provided above may be applied to the alkoxy group in the alkoxycarbonyl group, and descriptions on the carbonyl group provided above may be applied to the carbonyl group in the alkoxycarbonyl group.

According to one embodiment of the present application, adjacent one pair among R$_1$ to R$_4$ bond to each other to form a ring.

According to one embodiment of the present application, adjacent one pair among R$_1$ to R$_4$ bond to each other to form an aromatic hydrocarbon ring.

According to one embodiment of the present application, adjacent one pair among R$_1$ to R$_4$ bond to each other to form an aromatic 6-membered ring.

According to one embodiment of the present application, adjacent one pair among R$_5$ to R$_8$ bond to each other to form a ring.

According to one embodiment of the present application, adjacent one pair among $R_5$ to $R_8$ bond to each other to form an aromatic hydrocarbon ring.

According to one embodiment of the present application, adjacent one pair among $R_5$ to $R_8$ bond to each other to form an aromatic 6-membered ring.

According to one embodiment of the present application, Chemical Formula 1 is represented by the following Chemical Formula 2 or 3.

[Chemical Formula 2]

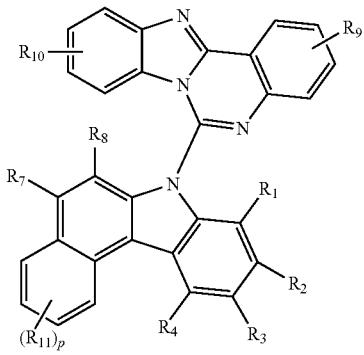

[Chemical Formula 3]

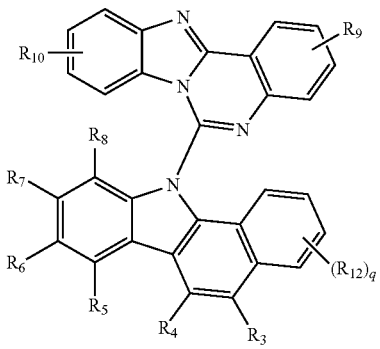

In Chemical Formulae 2 and 3, $R_1$ to $R_{10}$ have the same definitions as in Chemical Formula 1, $R_{11}$ and $R_{12}$ are the same as or different from each other, and each independently hydrogen; deuterium; a halogen group; a nitro group; a cyano group; an ester group; a carbonyl group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, and p and q are each an integer of 0 to 4.

According to one embodiment of the present application, $R_3$ is $-(L)_m-(Ar)_n$.

According to one embodiment of the present application, $R_2$ is $-(L)_m-(Ar)_n$.

According to one embodiment of the present application, $R_3$ and $R_6$ are $-(L)_m-(Ar)_n$, and $R_3$ and $R_6$ are the same as or different from each other.

According to one embodiment of the present application, $R_2$ and $R_7$ are $-(L)_m-(Ar)_n$, and $R_2$ and $R_7$ are the same as or different from each other.

According to one embodiment of the present application, Chemical Formula 1 is represented by any one of the following Chemical Formulae 4 to 7.

[Chemical Formula 4]

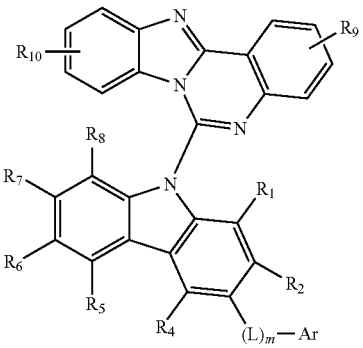

[Chemical Formula 5]

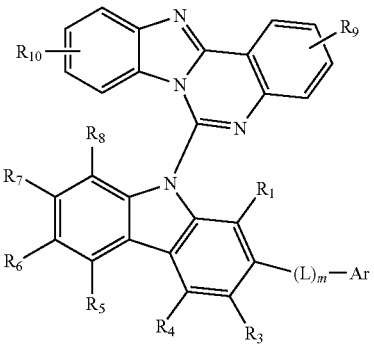

[Chemical Formula 6]

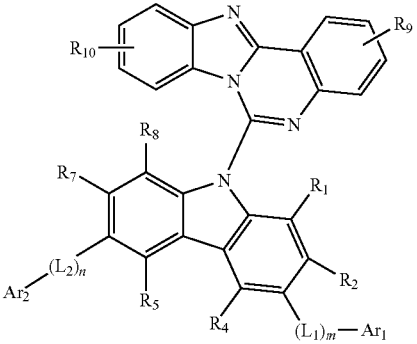

[Chemical Formula 7]

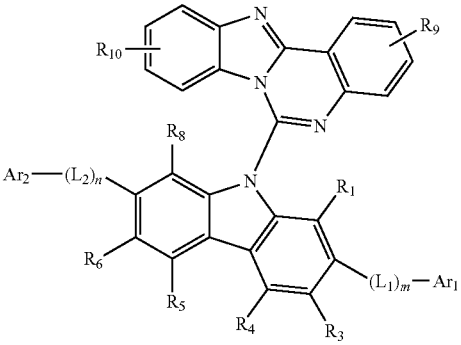

In Chemical Formulae 4 to 7, L, $L_1$ and $L_2$ have the same definitions as L of Chemical Formula 1, Ar, $Ar_1$ and $Ar_2$ have the same definitions as Ar of Chemical Formula 1, m and n have the same definitions as m of Chemical Formula 1, and $R_1$ to $R_{10}$ have the same definitions as in Chemical Formula 1.

According to one embodiment of the present application, L is a direct bond or a substituted or unsubstituted arylene group.

According to one embodiment of the present application, L is selected from the group consisting of a direct bond; a substituted or unsubstituted phenylene group; a substituted or unsubstituted biphenylene group; a substituted or unsubstituted naphthylene group; a substituted or unsubstituted anthracenylene group; a substituted or unsubstituted fluorenylene group; a substituted or unsubstituted phenanthrenylene group; a substituted or unsubstituted pyrenylene group; and a substituted or unsubstituted chrysenylene group.

According to one embodiment of the present application, L is selected from the group consisting of a direct bond; a phenylene group; a biphenylene group; a naphthylene group; an anthracenylene group; a fluorenylene group; a phenanthrenylene group; a pyrenylene group; and a chrysenylene group.

According to one embodiment of the present application, L is a direct bond; or a substituted or unsubstituted phenylene group.

According to one embodiment of the present application, L is a direct bond; or a phenylene group.

According to one embodiment of the present application, m is 1.

According to one embodiment of the present application, m is 2, and two Ls are the same as or different from each other.

According to one embodiment of the present application, m is 3, and three Ls are the same as or different from each other.

According to one embodiment of the present application, $L_1$ and $L_2$ have the same definitions as L described above.

According to one embodiment of the present application, Ar is a substituted monocyclic aryl group; a substituted or unsubstituted multicyclic aryl group; a substituted or unsubstituted heterocyclic group; a substituted or unsubstituted amine group; a substituted or unsubstituted silyl group; or a substituted or unsubstituted phosphoryl group.

According to one embodiment of the present application, Ar is a substituted monocyclic aryl group; a substituted or unsubstituted multicyclic aryl group; a substituted or unsubstituted heterocyclic group; a substituted or unsubstituted amine group; a substituted or unsubstituted silyl group; or a substituted or unsubstituted phosphoryl group, and the substituted or unsubstituted means being substituted with at least one selected from the group consisting of deuterium; a halogen group; a cyano group; a $C_1$ to $C_{60}$ alkyl group; a $C_6$ to $C_{60}$ cycloalkyl group; a $C_6$ to $C_{60}$ aryl group; and a $C_2$ to $C_{60}$ heterocyclic group, or unsubstituted.

According to one embodiment of the present application, Ar is a substituted monocyclic aryl group; a substituted or unsubstituted multicyclic aryl group; a substituted or unsubstituted heterocyclic group; a substituted or unsubstituted amine group; a substituted or unsubstituted silyl group; or a substituted or unsubstituted phosphoryl group, and the substituted or unsubstituted means being substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group, or unsubstituted.

According to one embodiment of the present application, the substituted monocyclic aryl group is a phenyl group substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group.

According to one embodiment of the present application, the substituted monocyclic aryl group is a phenyl group substituted with at least one selected from the group consisting of deuterium; a halogen group; a methyl group; a t-butyl group; a cyano group; a phenyl group; a biphenyl group; a naphthyl group; an anthracenyl group; a phenanthrenyl group; a pyridyl group; a pyrimidyl group; and a triazinyl group.

According to one embodiment of the present application, the multicyclic aryl group is a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group.

According to one embodiment of the present application, the multicyclic aryl group is a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group, and the substituted or unsubstituted means being substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group, or unsubstituted.

According to one embodiment of the present application, the multicyclic aryl group is a substituted or unsubstituted naphthyl group; a substituted or unsubstituted anthracenyl group; a substituted or unsubstituted phenanthrenyl group; a substituted or unsubstituted chrysenyl group; a substituted or unsubstituted pyrenyl group; a substituted or unsubstituted triphenylenyl group; or a substituted or unsubstituted fluorenyl group, and the substituted or unsubstituted means being substituted with at least one selected from the group consisting of deuterium; a halogen group; a methyl group; a t-butyl group; a cyano group; a phenyl group; a biphenyl group; a naphthyl group; an anthracenyl group; a phenanthrenyl group; a pyridyl group; a pyrimidyl group; and a triazinyl group, or unsubstituted.

According to one embodiment of the present application, the heterocyclic group is a substituted or unsubstituted pyridyl group; a substituted or unsubstituted pyrimidyl group; a substituted or unsubstituted triazinyl group; a substituted or unsubstituted thiophenyl group; a substituted or unsubstituted furanyl group; a substituted or unsubstituted benzofuranyl group; a substituted or unsubstituted benzothiophenyl group; a substituted or unsubstituted dibenzofuranyl group; a substituted or unsubstituted dibenzothiophenyl group; a substituted or unsubstituted carbazolyl group; a substituted or unsubstituted benzocarbazolyl group; a substituted or unsubstituted dibenzocarbazolyl group; a substituted or unsubstituted imidazolyl group; a substituted or unsubstituted benzimidazolyl group; a substituted or unsubstituted dibenzimidazolyl group; a substituted or unsubstituted thiazolyl group; a substituted or unsubstituted benzothiazolyl group; a substituted or unsubstituted oxazolyl group; a substituted or unsubstituted benzoxazolyl group; a substituted or unsubstituted phenanthrolinyl group; a substituted or unsubstituted phenothiazinyl group; a substituted or unsubstituted phenoxazinyl group; a substituted or unsubstituted quinolinyl group; a substituted or unsubstituted monovalent

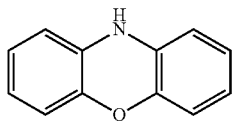

group; a substituted or unsubstituted monovalent

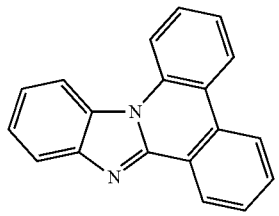 [SMILES: c1ccc2c(c1)nc1c3ccccc3c3ccccc3n21]

group; a substituted or unsubstituted monovalent

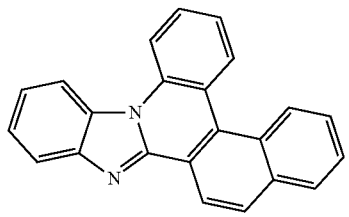 [SMILES: c1ccc2c(c1)ccc1c2c2ccccc2n2c3ccccc3nc12]

group; or a substituted or unsubstituted monovalent

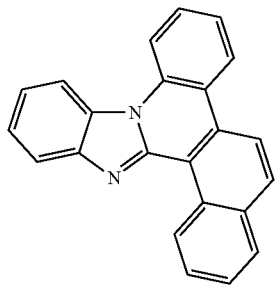 [SMILES: c1ccc2c(c1)ccc1c3ccccc3n3c4ccccc4nc3c21]

group, and the substituted or unsubstituted means being substituted with at least one selected from the group consisting of deuterium; a halogen group; a $C_1$ to $C_{20}$ alkyl group; a cyano group; a $C_6$ to $C_{20}$ aryl group; and a $C_2$ to $C_{20}$ heterocyclic group, or unsubstituted.

According to one embodiment of the present application, the heterocyclic group is a substituted or unsubstituted pyridyl group; a substituted or unsubstituted pyrimidyl group; a substituted or unsubstituted triazinyl group; a substituted or unsubstituted thiophenyl group; a substituted or unsubstituted furanyl group; a substituted or unsubstituted benzofuranyl group; a substituted or unsubstituted benzothiophenyl group; a substituted or unsubstituted dibenzofuranyl group; a substituted or unsubstituted dibenzothiophenyl group; a substituted or unsubstituted carbazolyl group; a substituted or unsubstituted benzocarbazolyl group; a substituted or unsubstituted dibenzocarbazolyl group; a substituted or unsubstituted imidazolyl group; a substituted or unsubstituted benzimidazolyl group; a substituted or unsubstituted dibenzimidazolyl group; a substituted or unsubstituted thiazolyl group; a substituted or unsubstituted benzothiazolyl group; a substituted or unsubstituted oxazolyl group; a substituted or unsubstituted benzoxazolyl group; a substituted or unsubstituted phenanthrolinyl group; a substituted or unsubstituted phenothiazinyl group; a substituted or unsubstituted phenoxazinyl group; a substituted or unsubstituted quinolinyl group; a substituted or unsubstituted monovalent

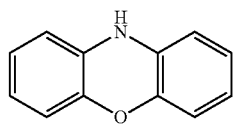 [SMILES: c1ccc2c(c1)Nc1ccccc1O2]

group; a substituted or unsubstituted monovalent

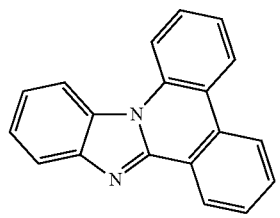 [SMILES: c1ccc2c(c1)nc1c3ccccc3c3ccccc3n21]

group; a substituted or unsubstituted monovalent

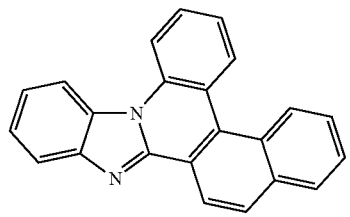 [SMILES: c1ccc2c(c1)ccc1c2c2ccccc2n2c3ccccc3nc12]

group; or a substituted or unsubstituted monovalent

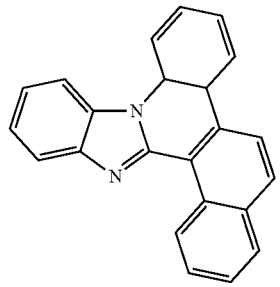 [SMILES: C1=CC2c3ccc4ccccc4c3-c3nc4ccccc4n3C2C=C1]

group, and the substituted or unsubstituted means being substituted with at least one selected from the group consisting of deuterium; a halogen group; a methyl group; a t-butyl group; a cyano group; a phenyl group; a biphenyl group; a naphthyl group; an anthracenyl group; a phenanthrenyl group; a pyridyl group; a pyrimidyl group; and a triazinyl group, or unsubstituted.

According to one embodiment of the present application, $Ar_1$ and $Ar_2$ have the same definitions as Ar described above.

According to one embodiment of the present application, the amine group is represented by $-NR_{100}R_{101}$, and $R_{100}$ and $R_{101}$ are the same as or different from each other, and may be each independently a substituted or unsubstituted $C_1$ to $C_{60}$ alkyl group; a substituted or unsubstituted $C_6$ to $C_{60}$ cycloalkyl group; a substituted or unsubstituted $C_6$ to $C_{60}$ aryl group; or a substituted or unsubstituted $C_2$ to $C_{60}$ heterocyclic group.

According to one embodiment of the present application, $R_{100}$ and $R_{101}$ are a substituted or unsubstituted $C_6$ to $C_{60}$ aryl group, and $R_{100}$ and $R_{101}$ may be the same as or different from each other.

According to one embodiment of the present application, $R_{100}$ and $R_{101}$ are a $C_6$ to $C_{60}$ aryl group unsubstituted or substituted with a $C_1$ to $C_{60}$ alkyl group, and $R_{100}$ and $R_{101}$ may be the same as or different from each other.

According to one embodiment of the present application, $R_{100}$ and $R_{101}$ are the same as or different from each other, and may be each independently a phenyl group, a biphenyl group, a naphthyl group, a terphenyl group, a fluorene group or a dimethylfluorene group.

According to one embodiment of the present application, the phosphoryl group is represented by $-P(=O)R_{102}R_{103}$, and $R_{102}$ and $R_{103}$ are the same as or different from each other, and may be each independently a substituted or unsubstituted $C_1$ to $C_{60}$ alkyl group; a substituted or unsubstituted $C_6$ to $C_{60}$ cycloalkyl group; a substituted or unsubstituted $C_6$ to $C_{60}$ aryl group; or a substituted or unsubstituted $C_2$ to $C_{60}$ heterocyclic group.

According to one embodiment of the present application, $R_{102}$ and $R_{103}$ is a substituted or unsubstituted $C_6$ to $C_{60}$ aryl group, and $R_{102}$ and $R_{103}$ may be the same as or different from each other.

According to one embodiment of the present application, $R_{102}$ and $R_{103}$ are the same as or different from each other, and may be each independently a phenyl group, a biphenyl group, a naphthyl group, a terphenyl group, a fluorene group or a dimethylfluorene group.

According to one embodiment of the present application, the silyl group is represented by $-SiR_{104}R_{105}R_{106}$, and $R_{104}$ to $R_{106}$ are the same as or different from each other, and may be each independently a substituted or unsubstituted $C_1$ to $C_{60}$ alkyl group; a substituted or unsubstituted $C_6$ to $C_{60}$ cycloalkyl group; a substituted or unsubstituted $C_6$ to $C_{60}$ aryl group; or a substituted or unsubstituted $C_2$ to $C_{60}$ heterocyclic group.

According to one embodiment of the present application, $R_{104}$ to $R_{106}$ are the same as or different from each other, and each independently a substituted or unsubstituted $C_1$ to $C_{60}$ alkyl group; or a substituted or unsubstituted $C_6$ to $C_{60}$ aryl group.

According to one embodiment of the present application, $R_{104}$ to $R_{106}$ are the same as or different from each other, and may be each independently a methyl group, an ethyl group, a phenyl group, a biphenyl group, a naphthyl group, a terphenyl group, a fluorene group or a dimethylfluorene group.

According to one embodiment of the present application, $-(L)_m-(Ar)_n$ may be any one selected from among structural formulae of the following Groups 1 to 4.

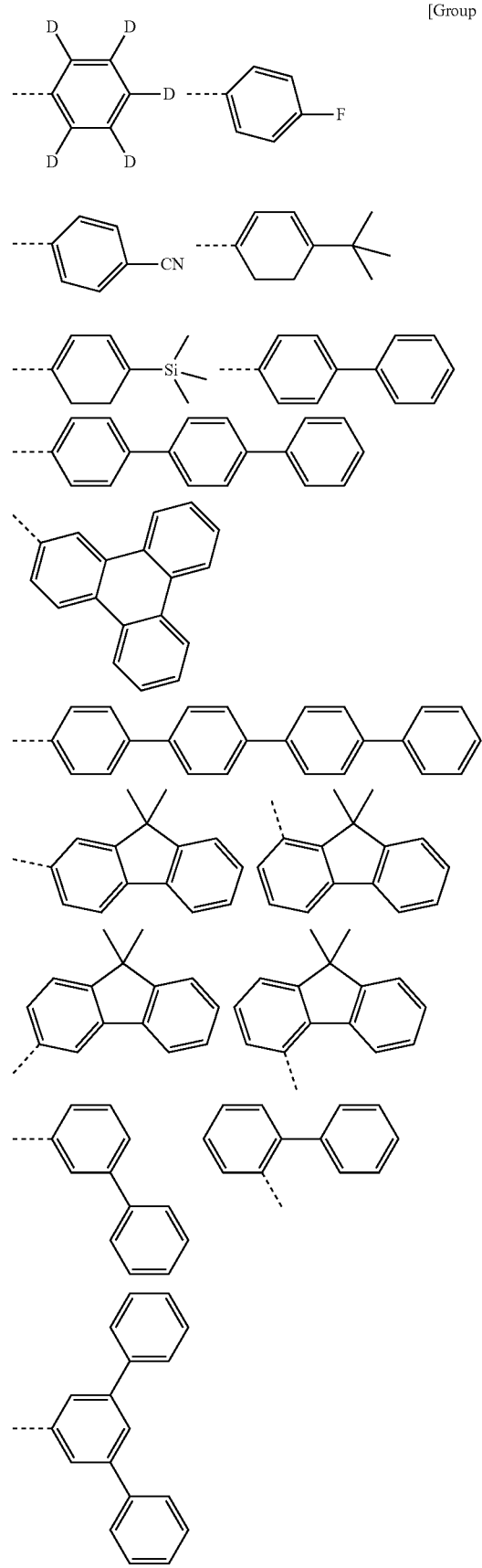

[Group 1]

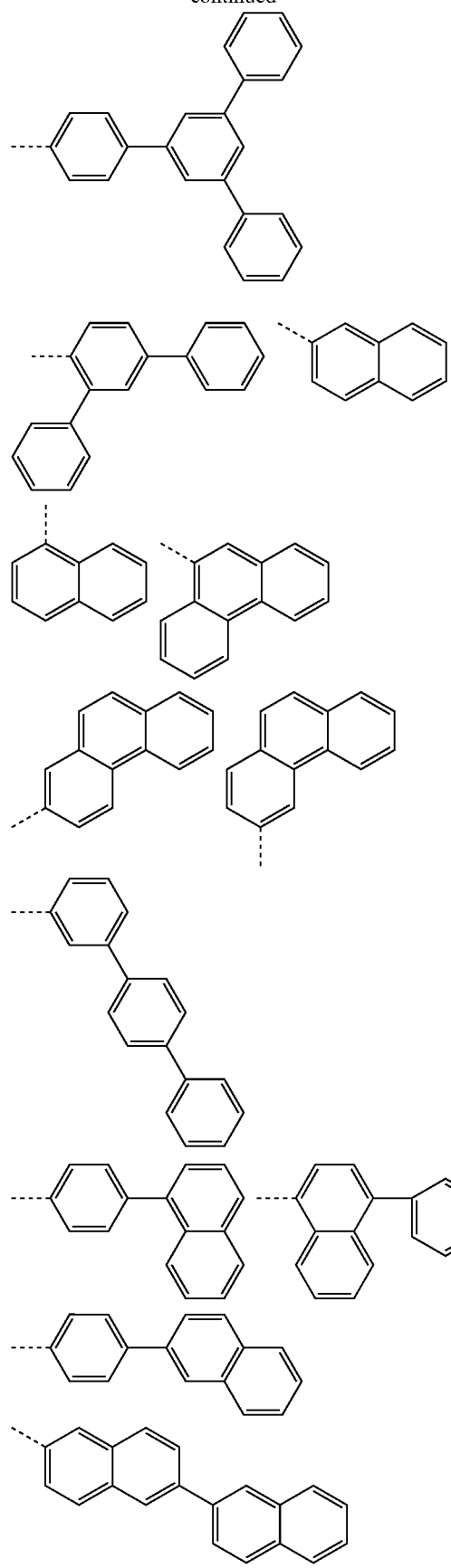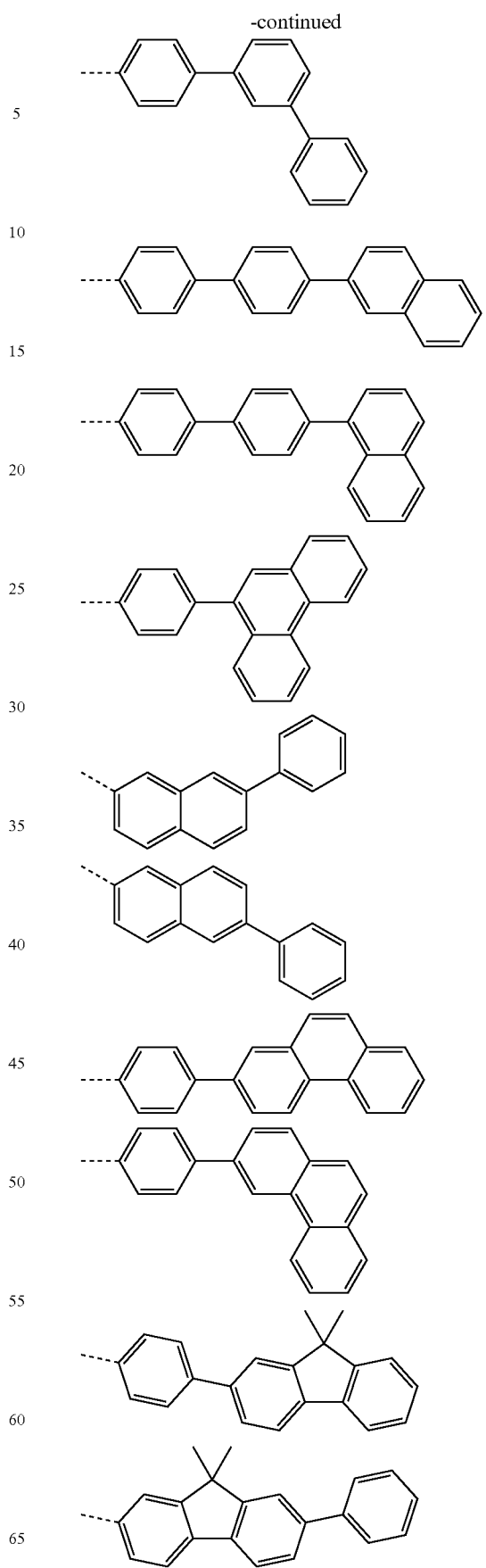

-continued
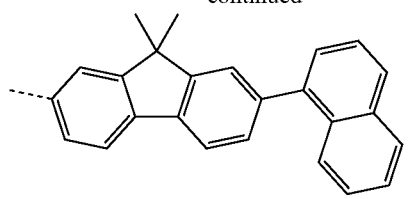
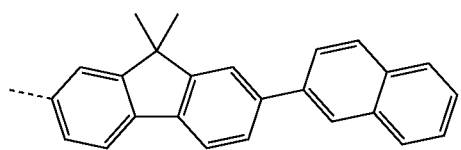
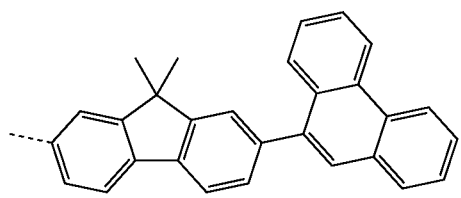
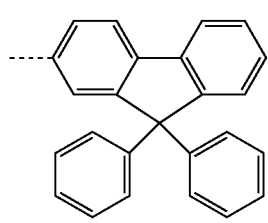
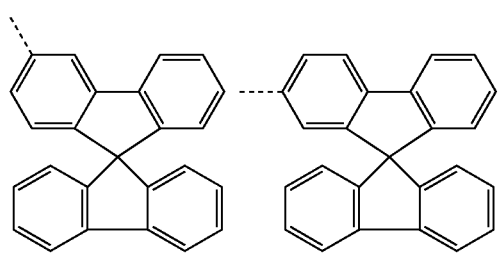
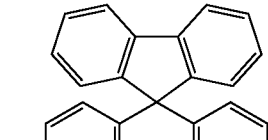
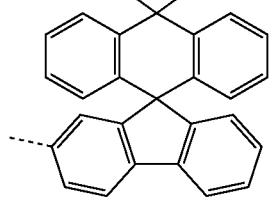
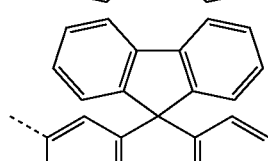
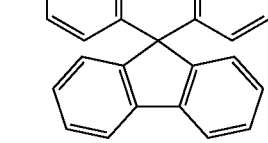
-continued
[Group 2]
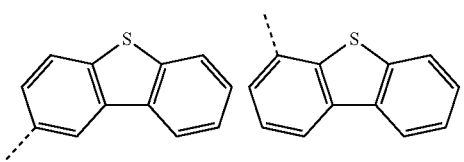
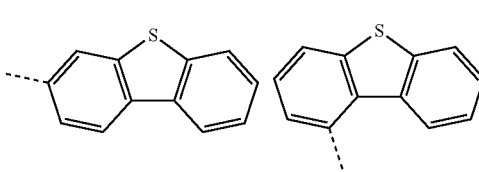
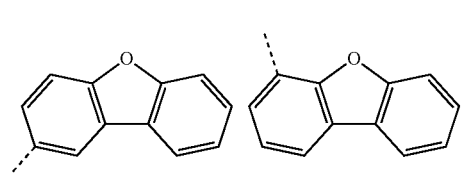
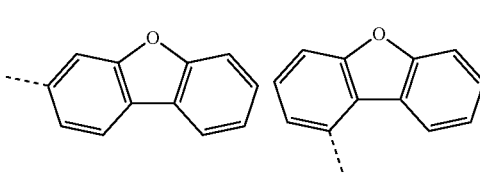
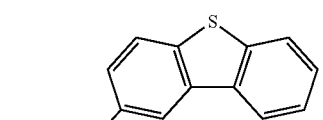
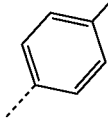
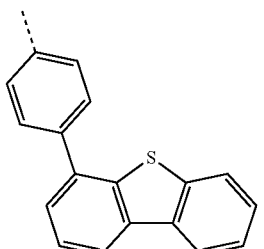
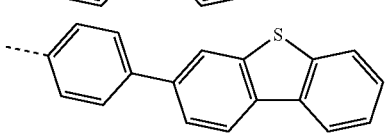
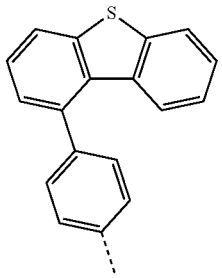

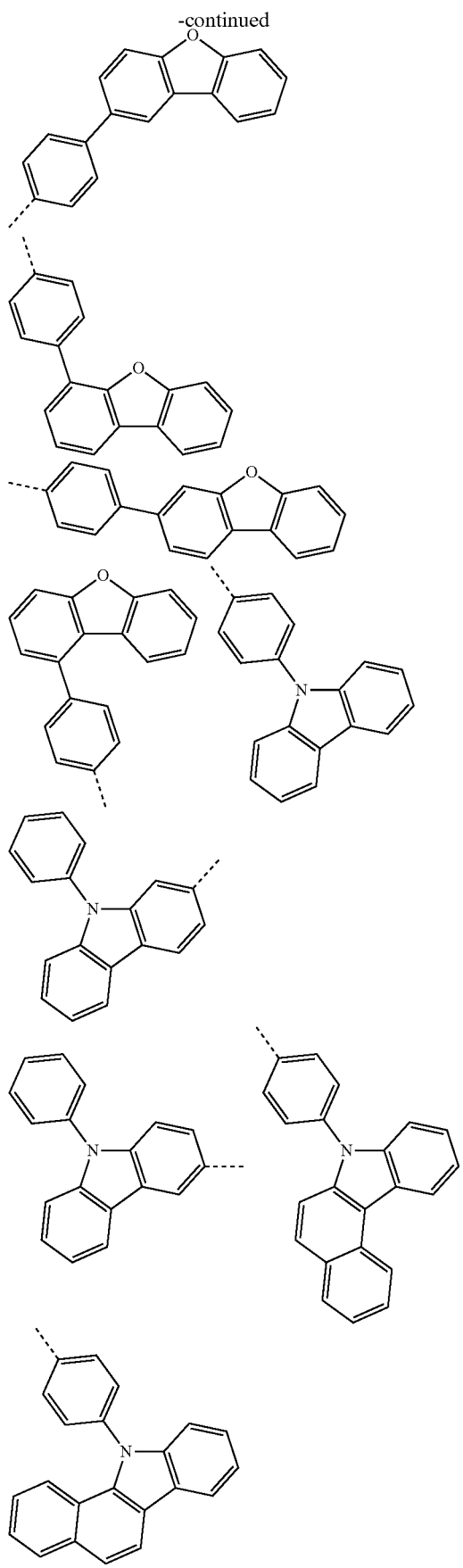
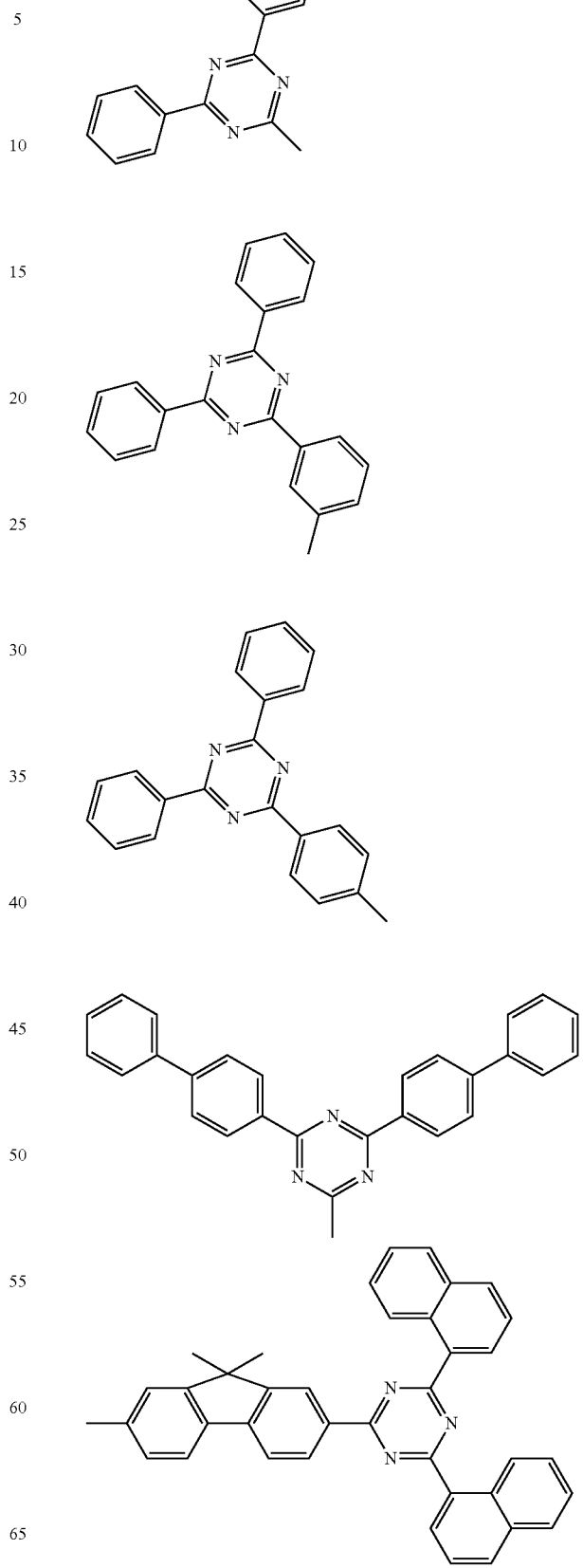

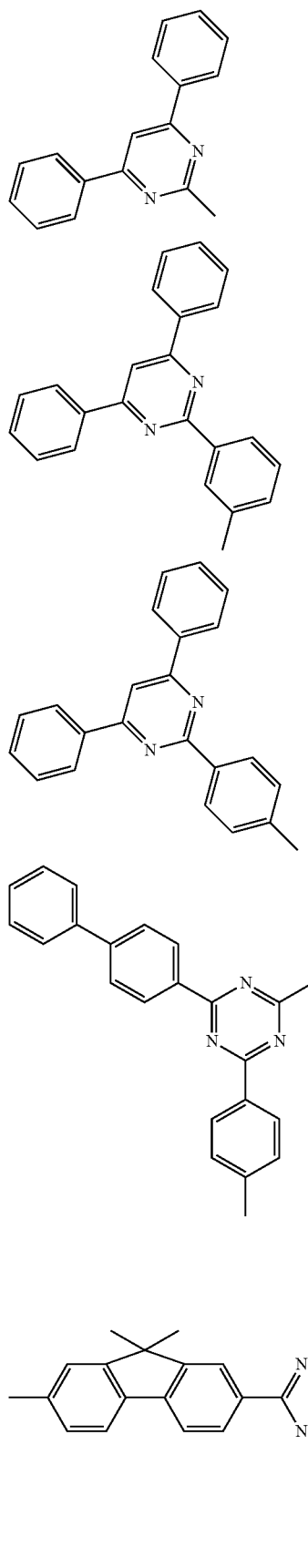
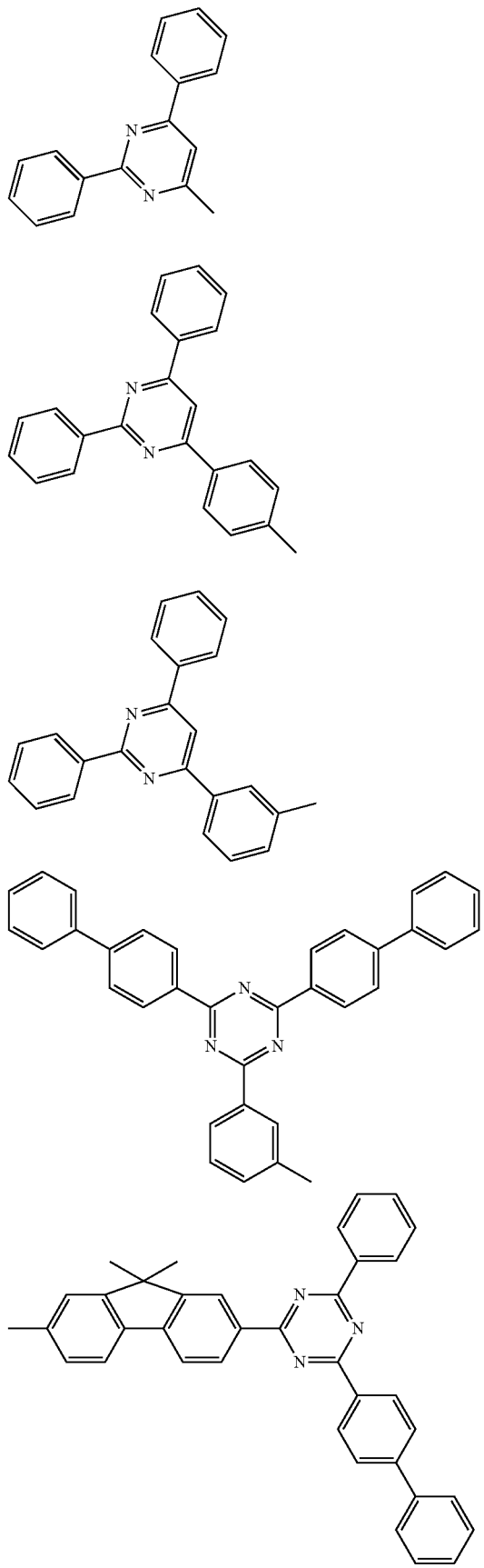

-continued
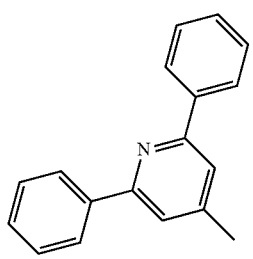
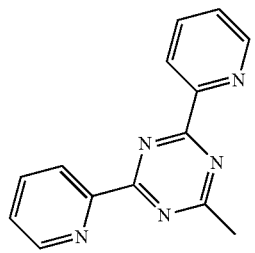

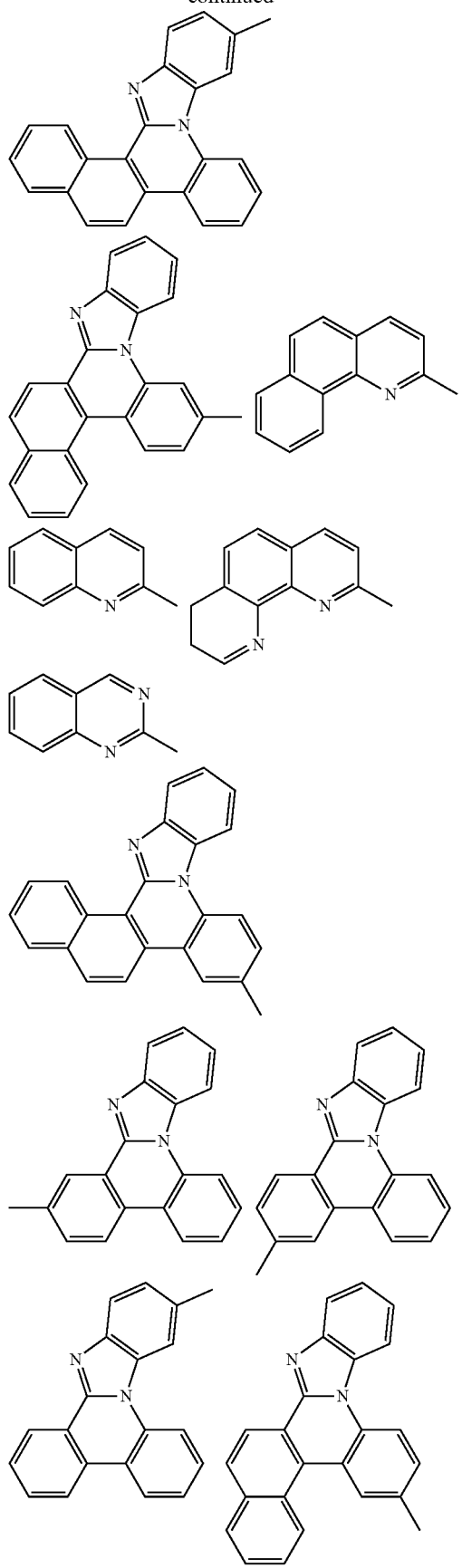
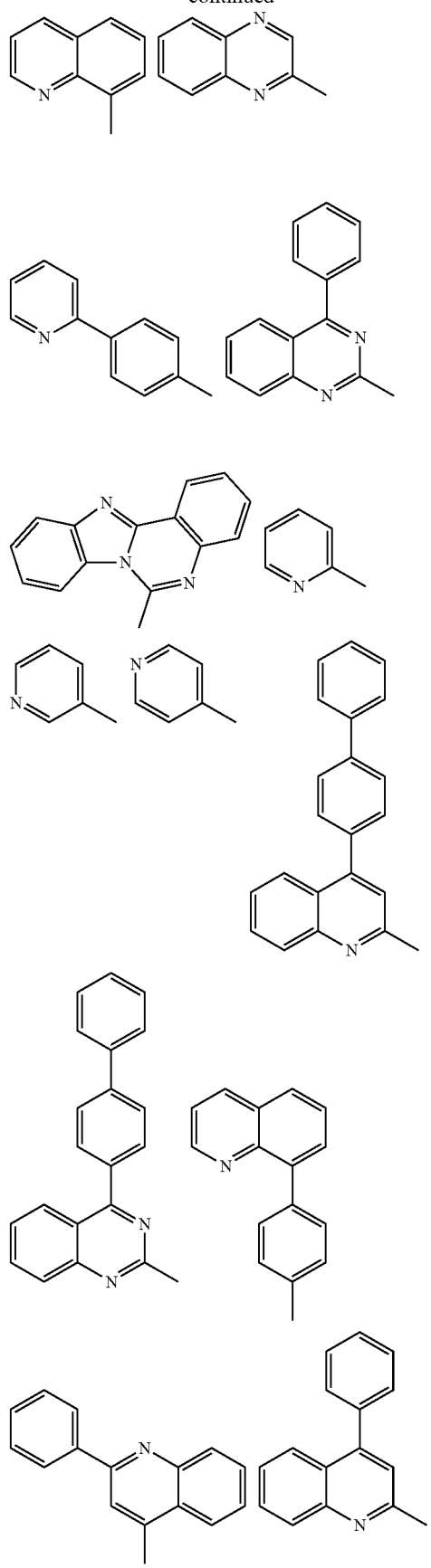

31
-continued
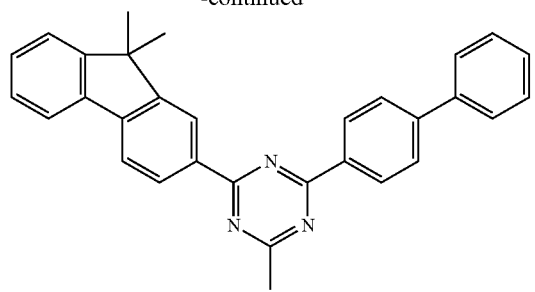
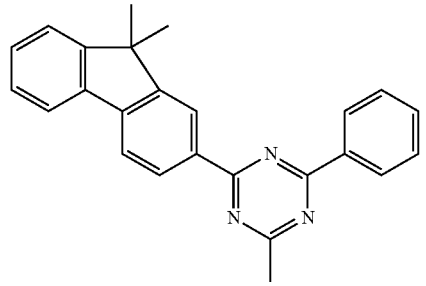
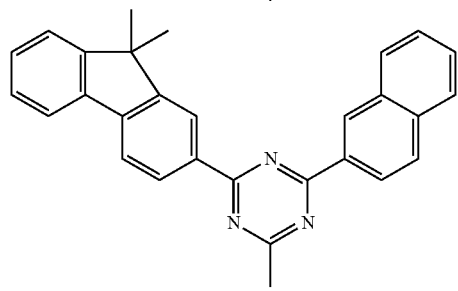
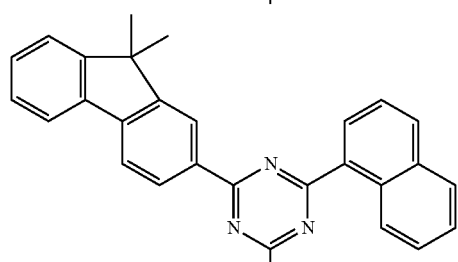
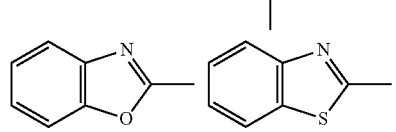
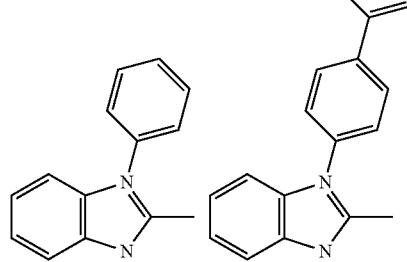
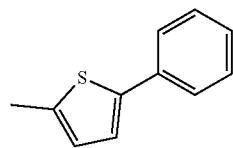
32
-continued
[Group 3]
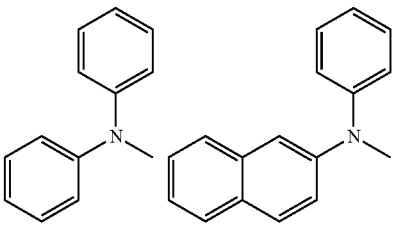
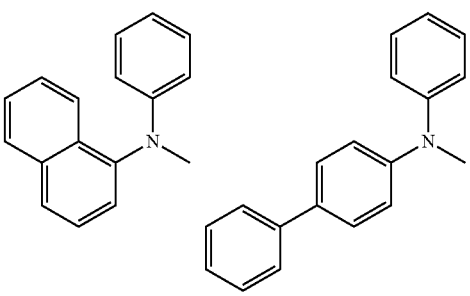
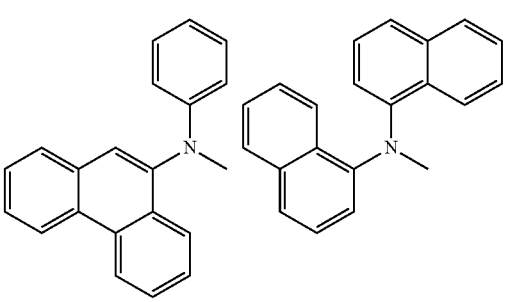
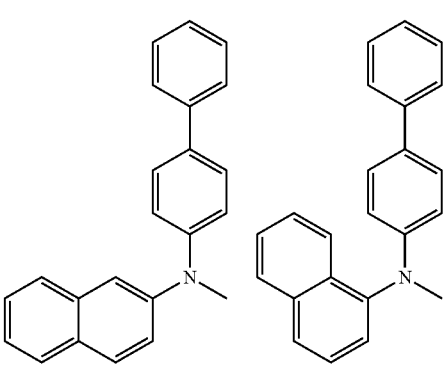
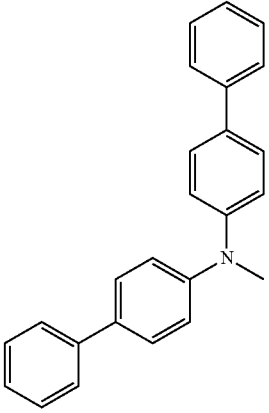

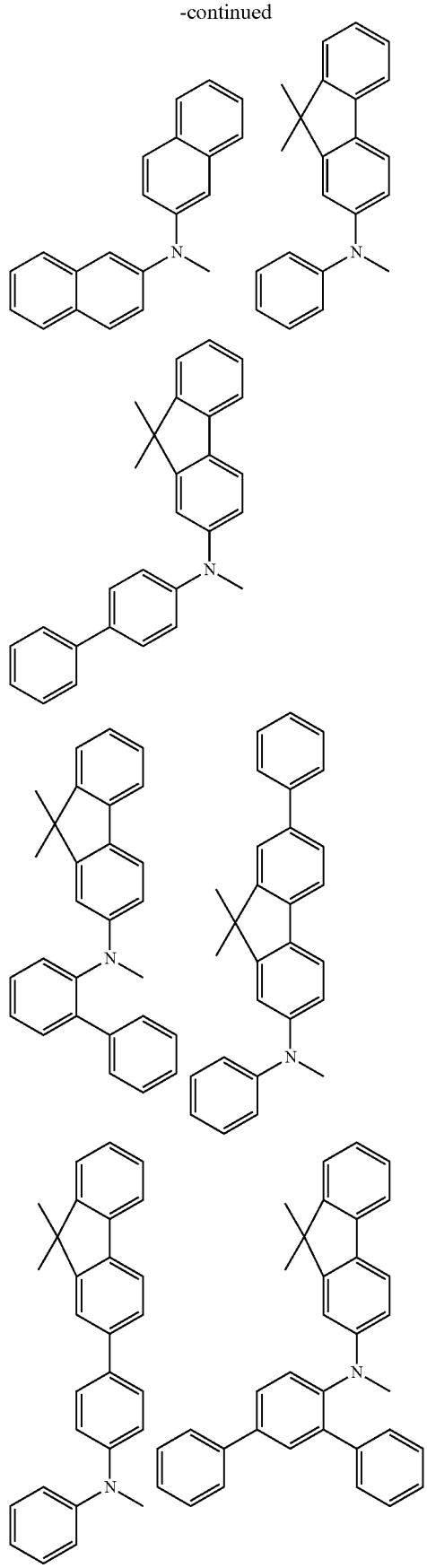
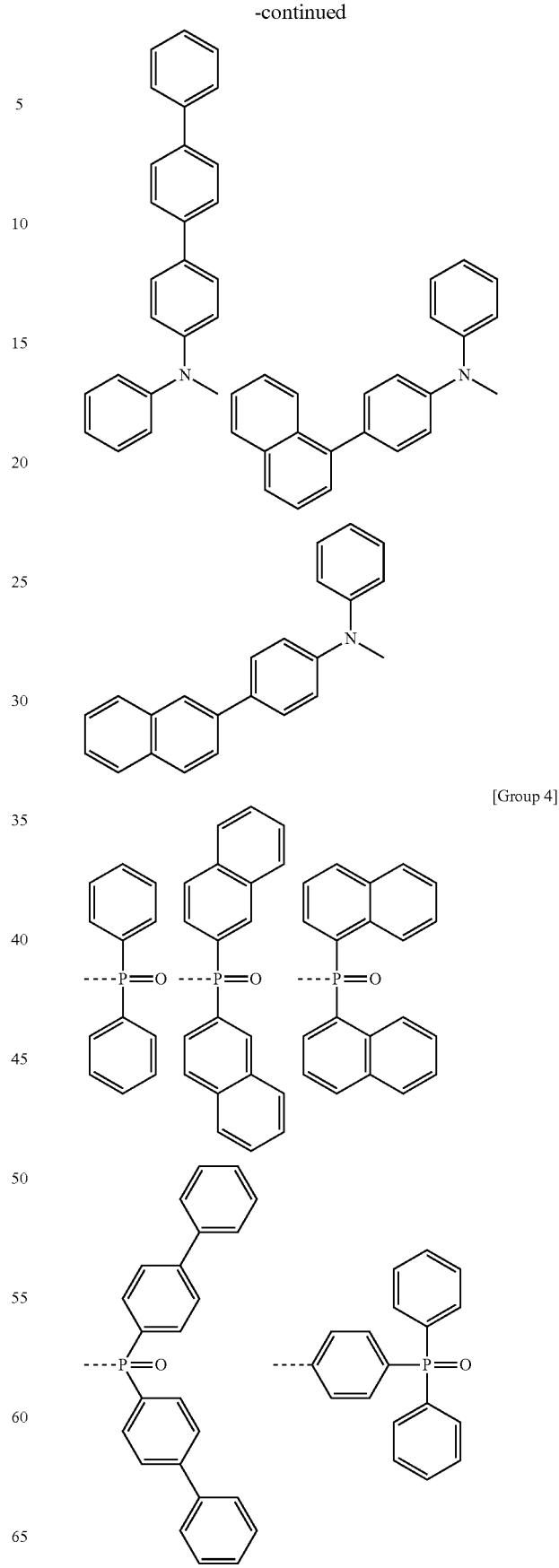
[Group 4]

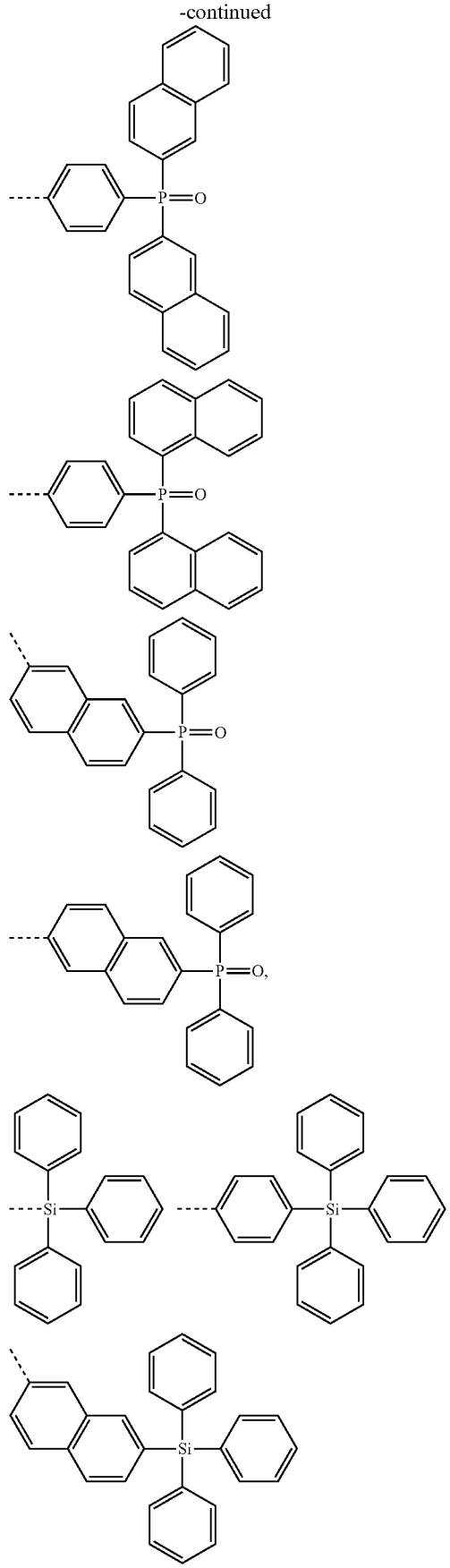

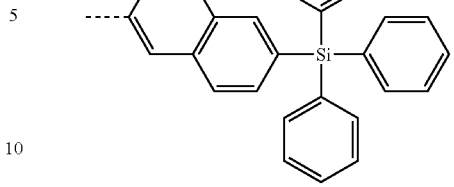

In Groups 1, 2 and 4, "-----" means a bonding site.

In Group 2, "—" means a bonding site except for a methyl group substituting a fluorene group.

In Group 3, "—" means a bonding site except for a methyl group substituting a fluorene group. In other words, "—" linked to N means a bonding site.

According to one embodiment of the present application, n is 1.

According to one embodiment of the present application, n is 2, and two Ars are the same as or different from each other.

According to one embodiment of the present application, the compound represented by Chemical Formula 1 may be any one selected from among the following structural formulae.

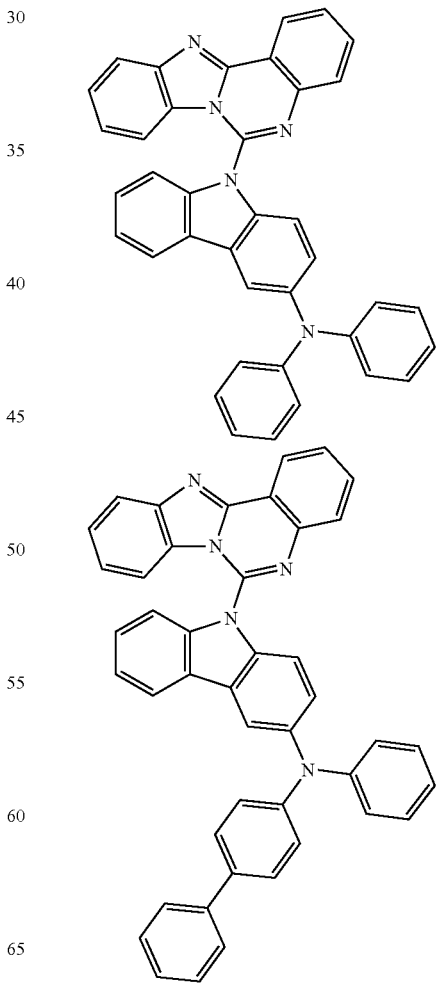

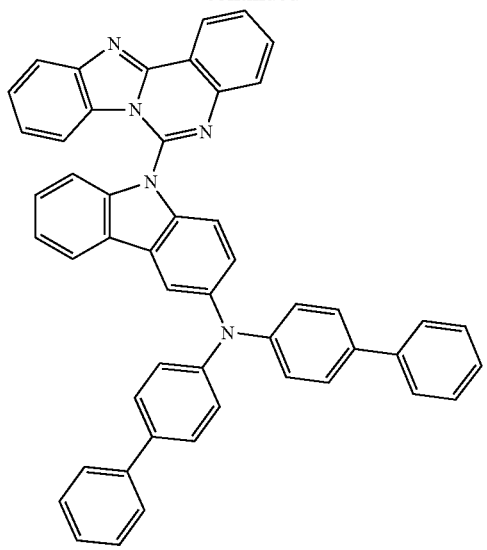
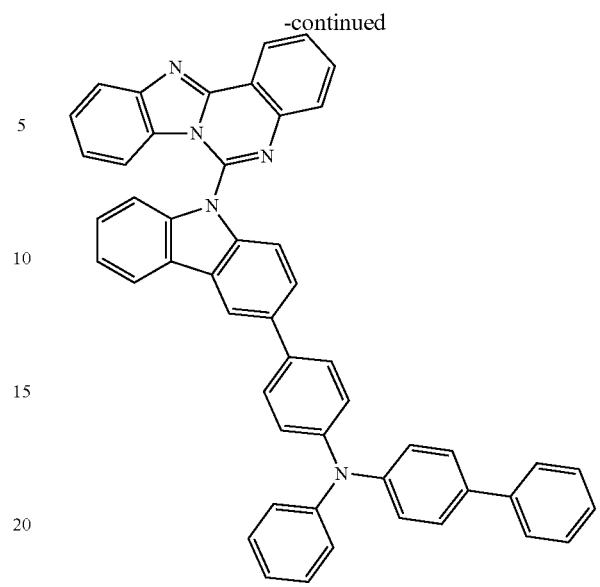
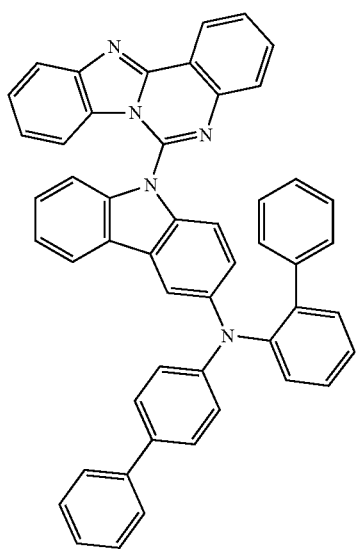
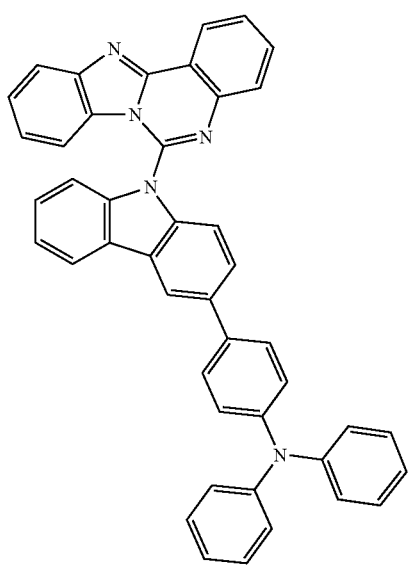
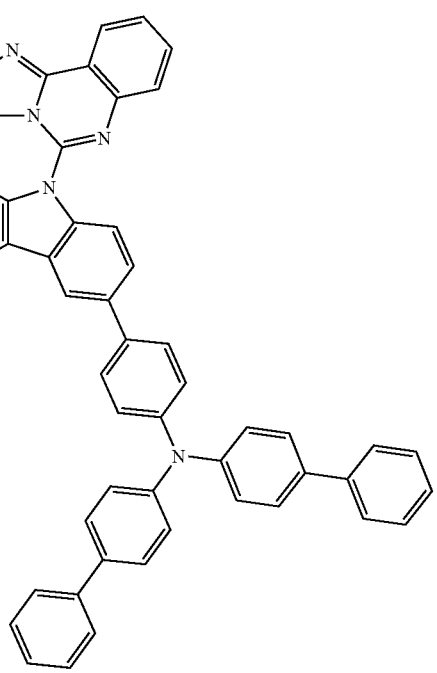

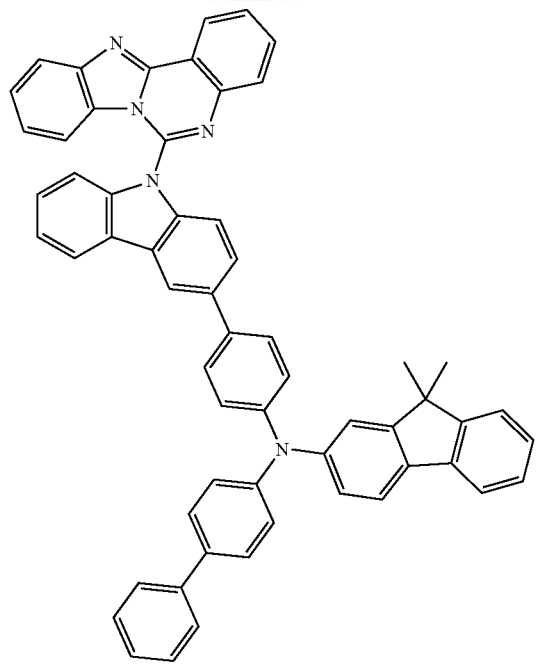
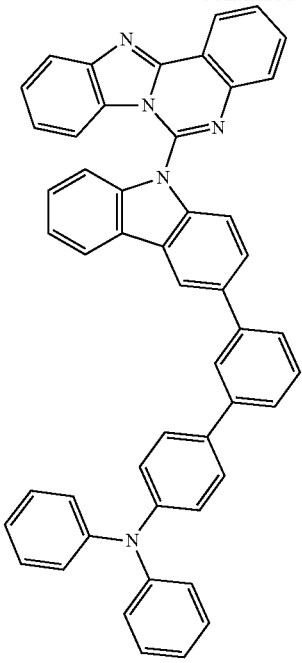
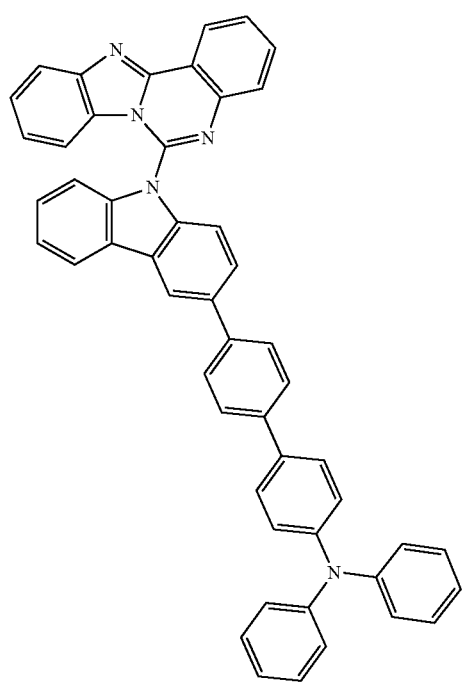
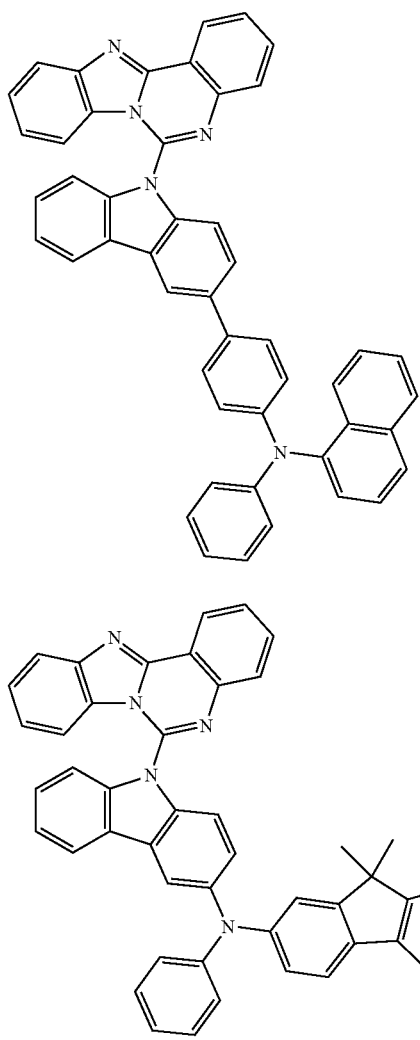

41
-continued
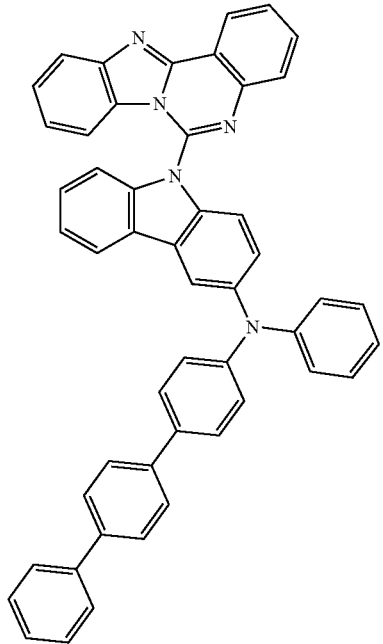
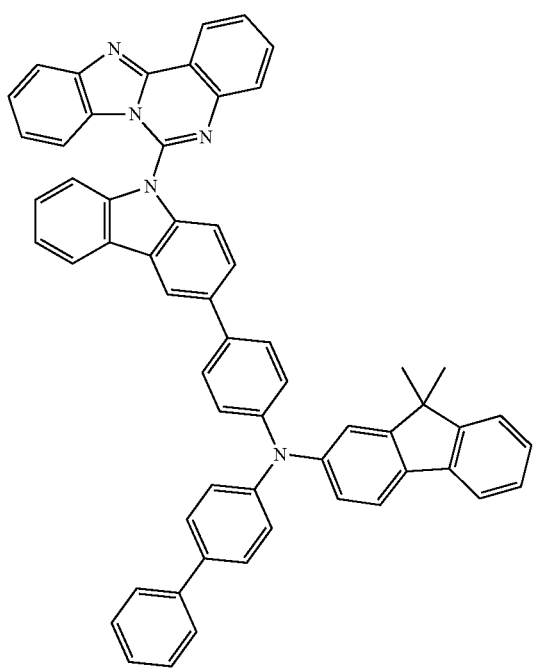
42
-continued
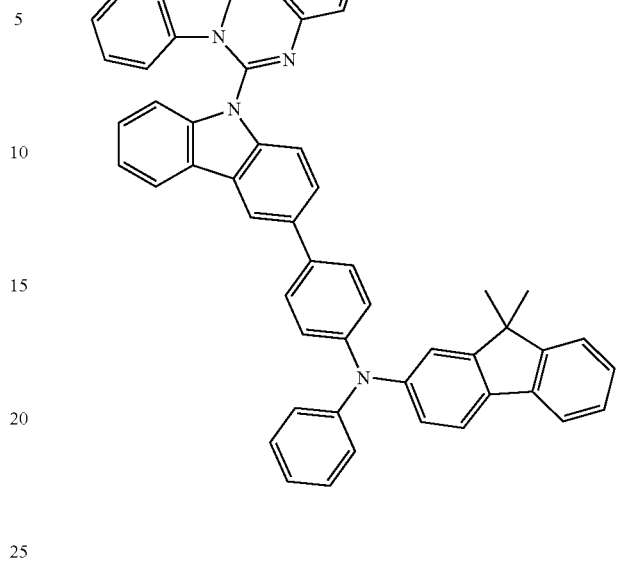
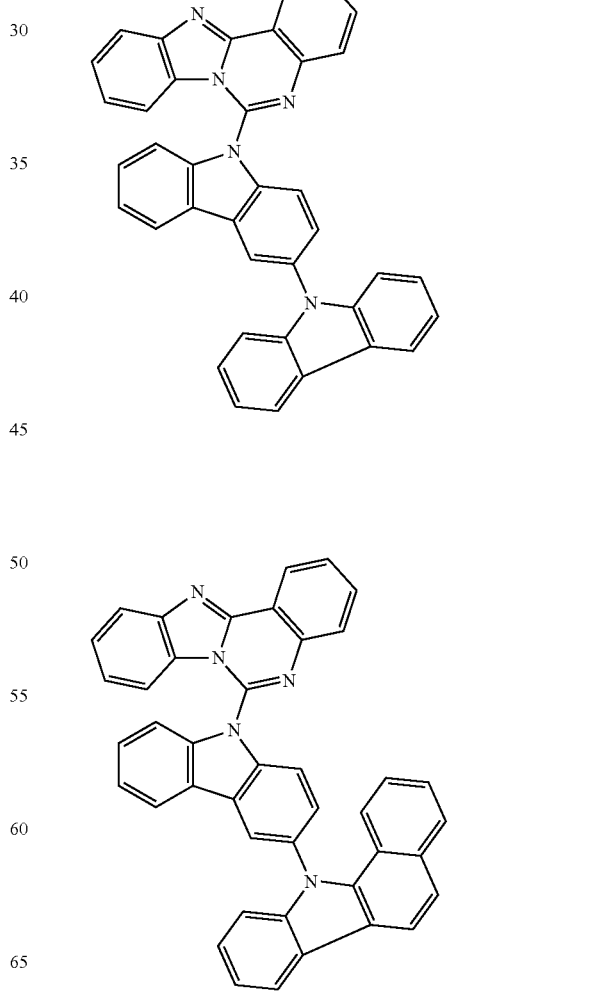

-continued
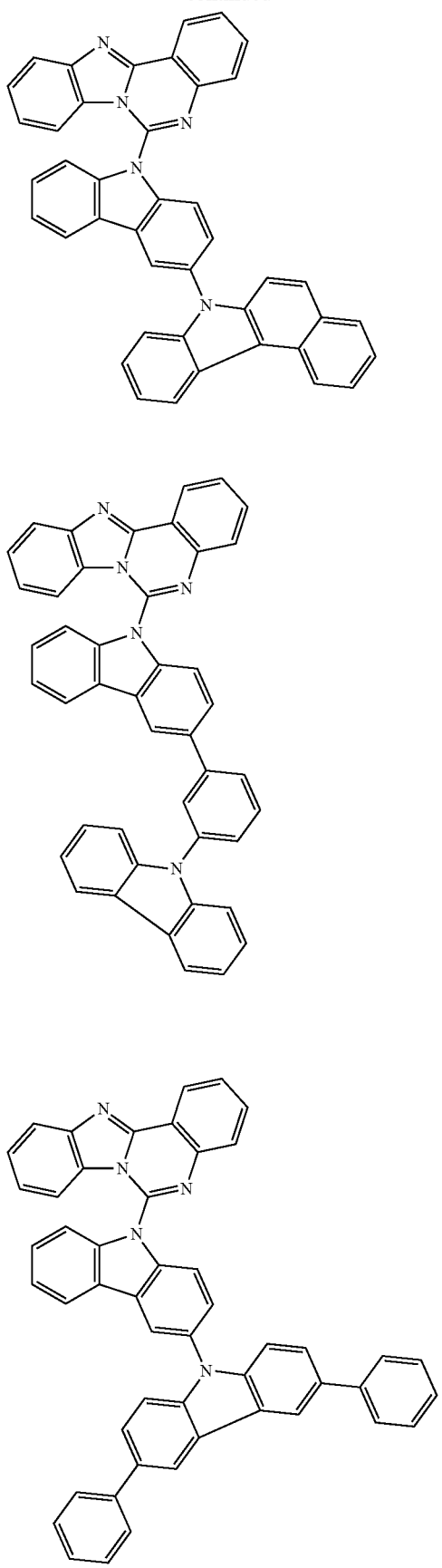
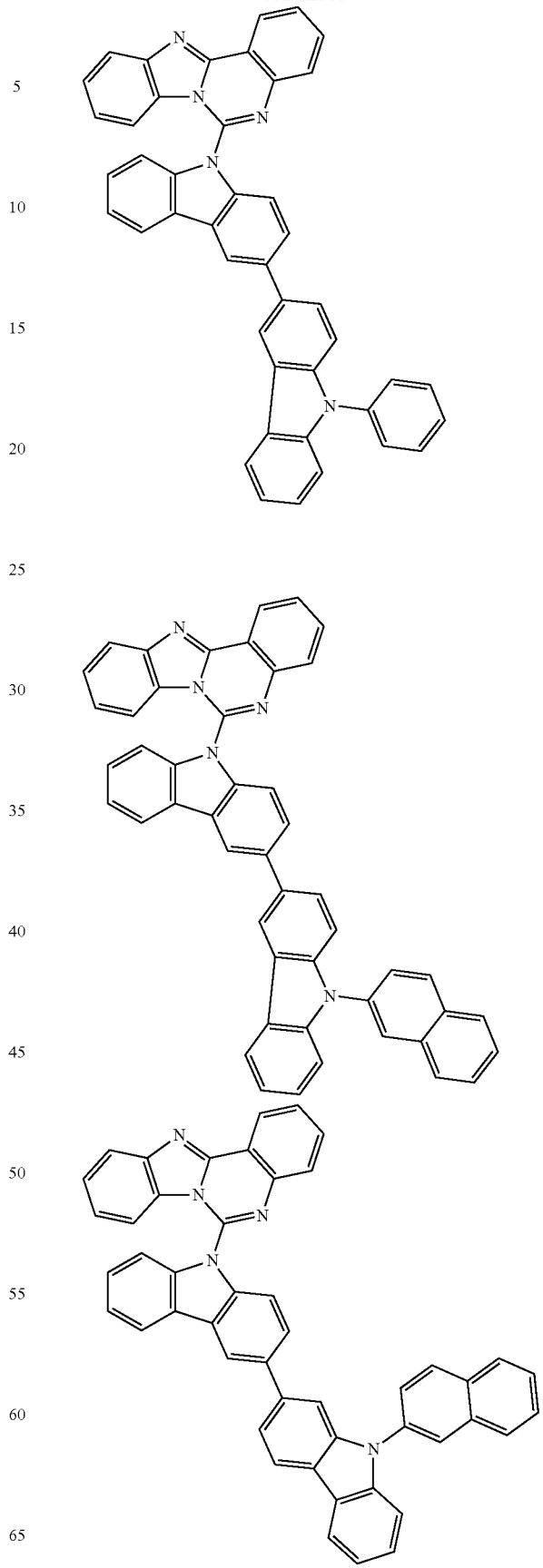

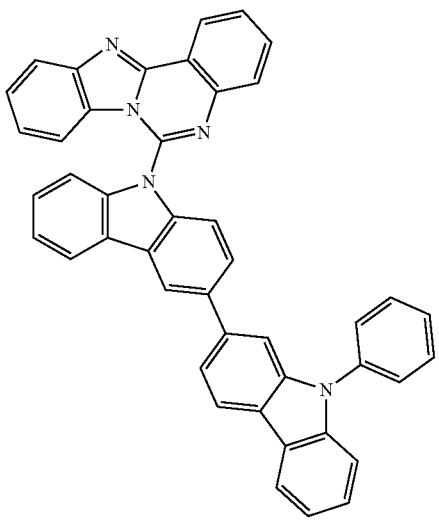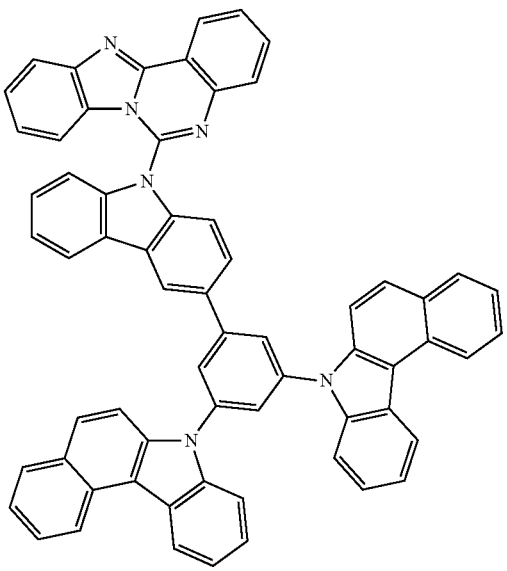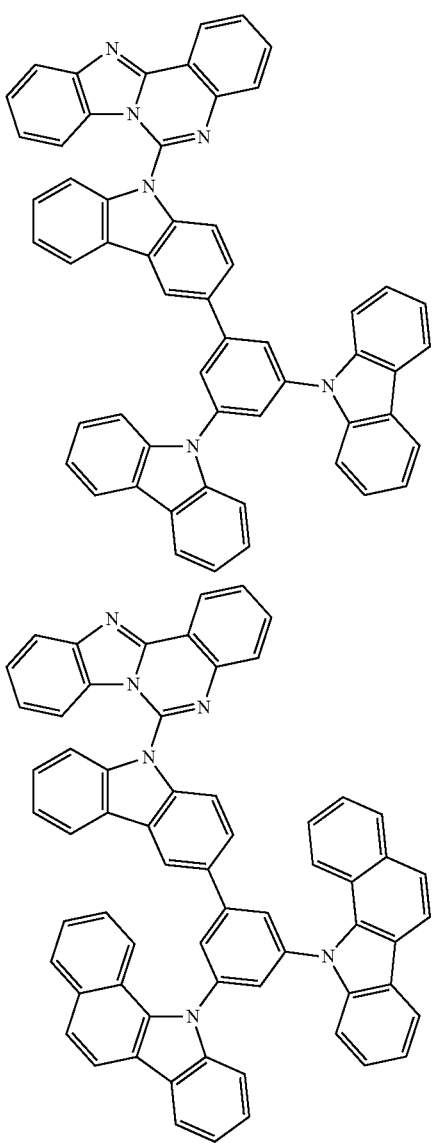

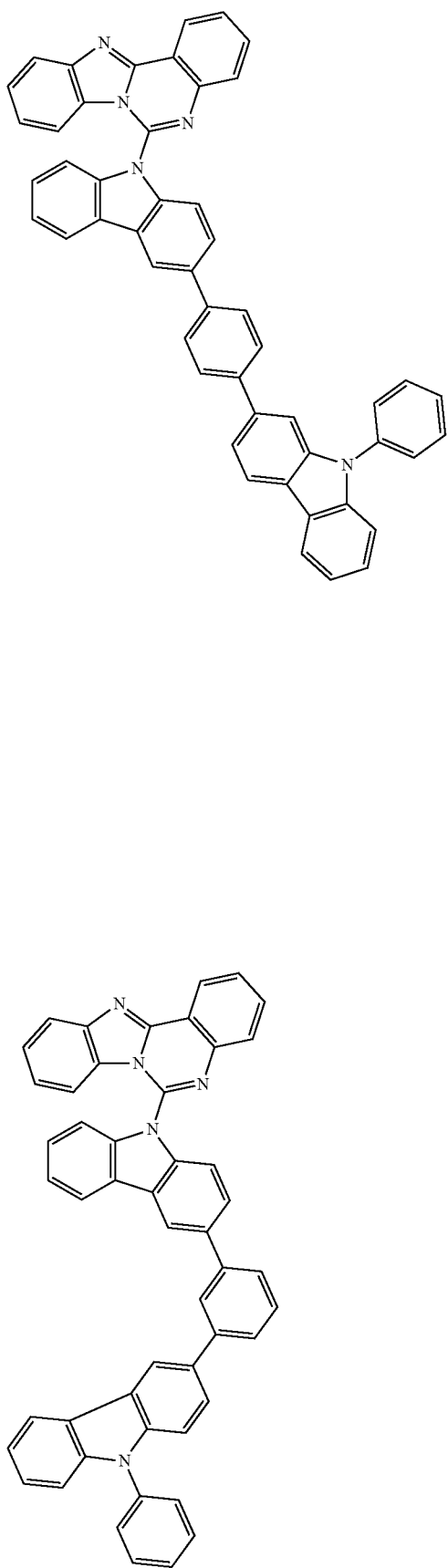
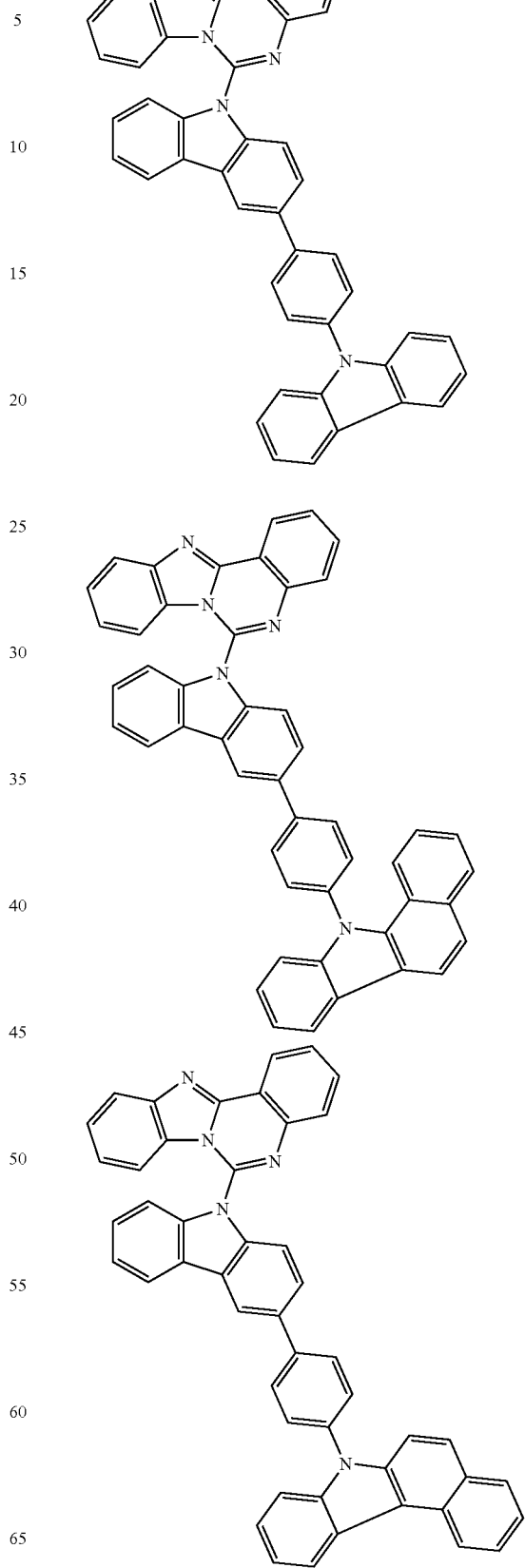

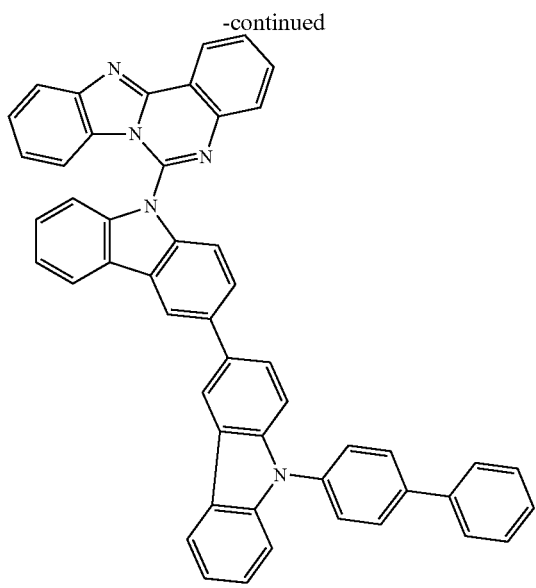
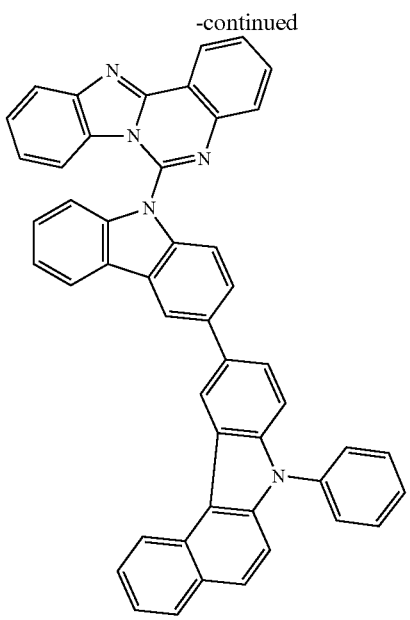
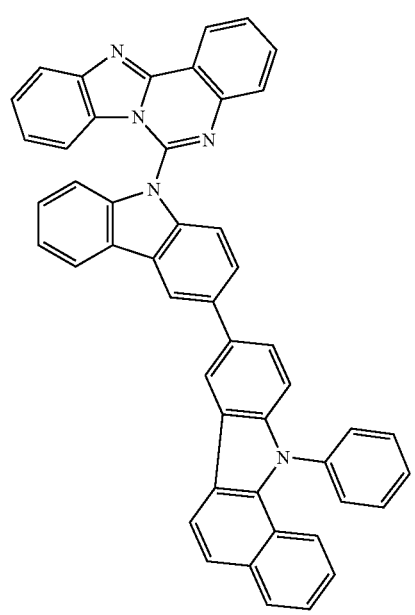
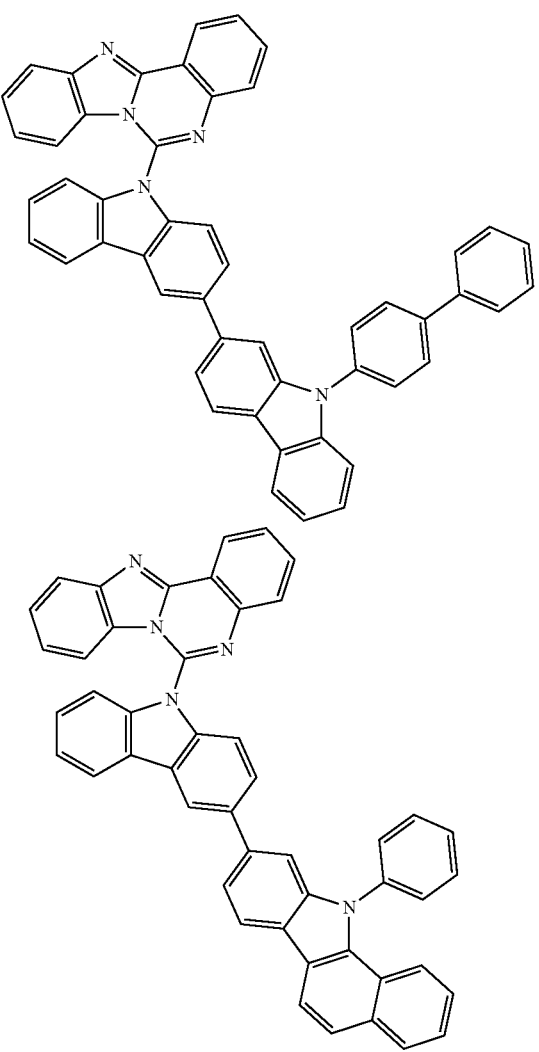

51
-continued
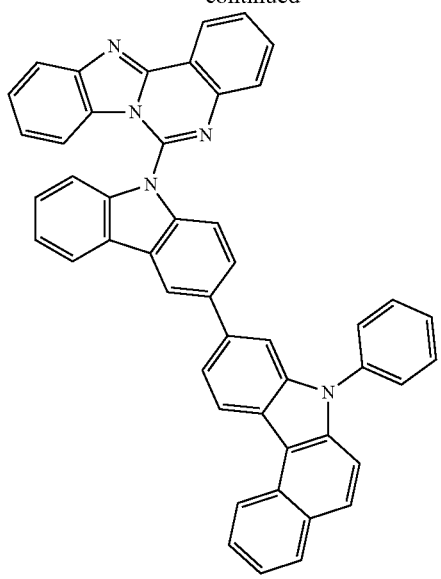
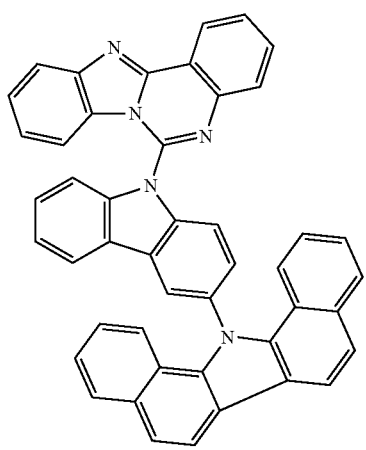
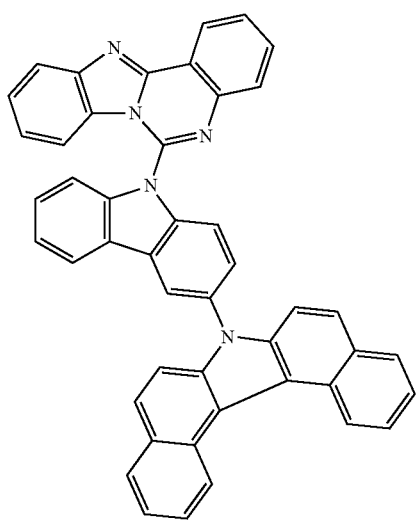
52
-continued
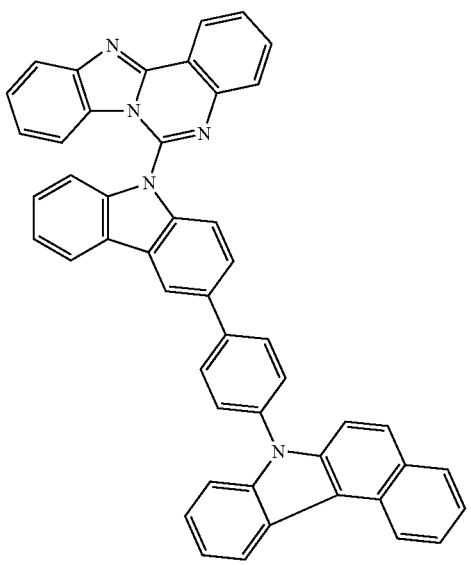
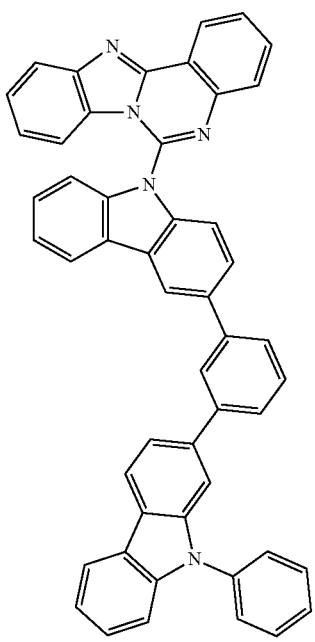

53
-continued
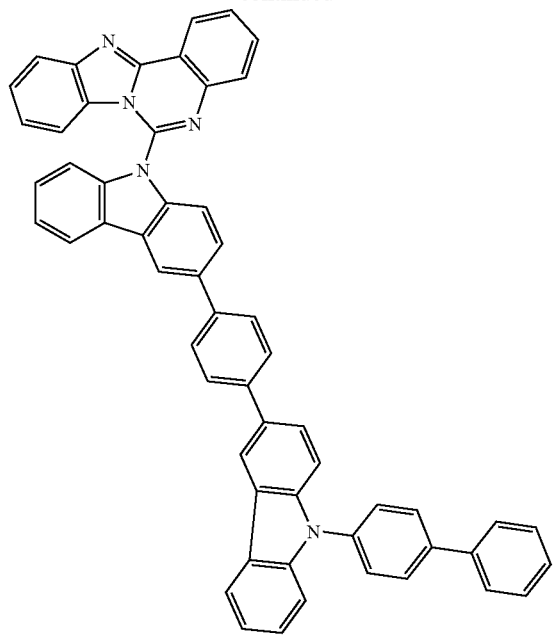
54
-continued
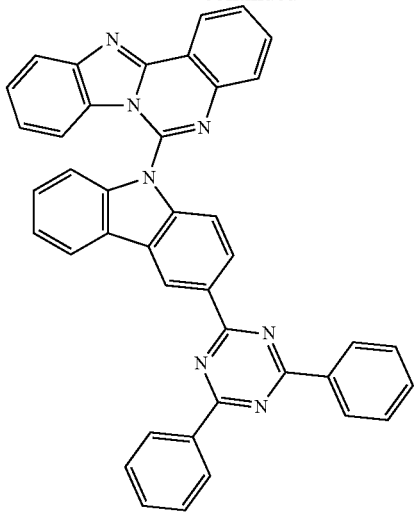
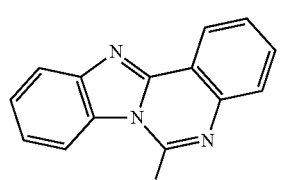
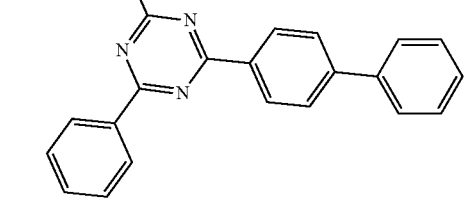
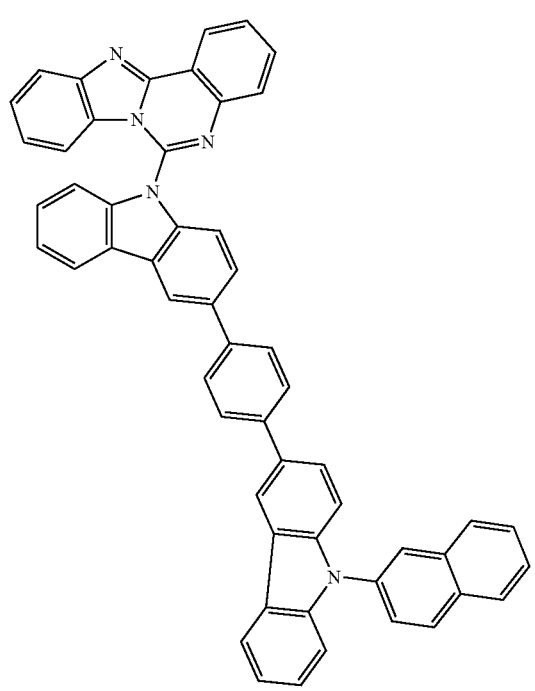
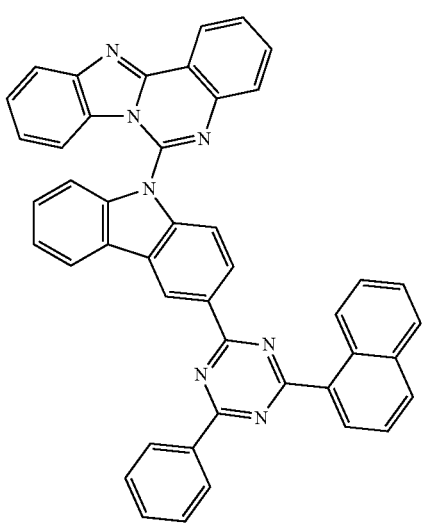

-continued
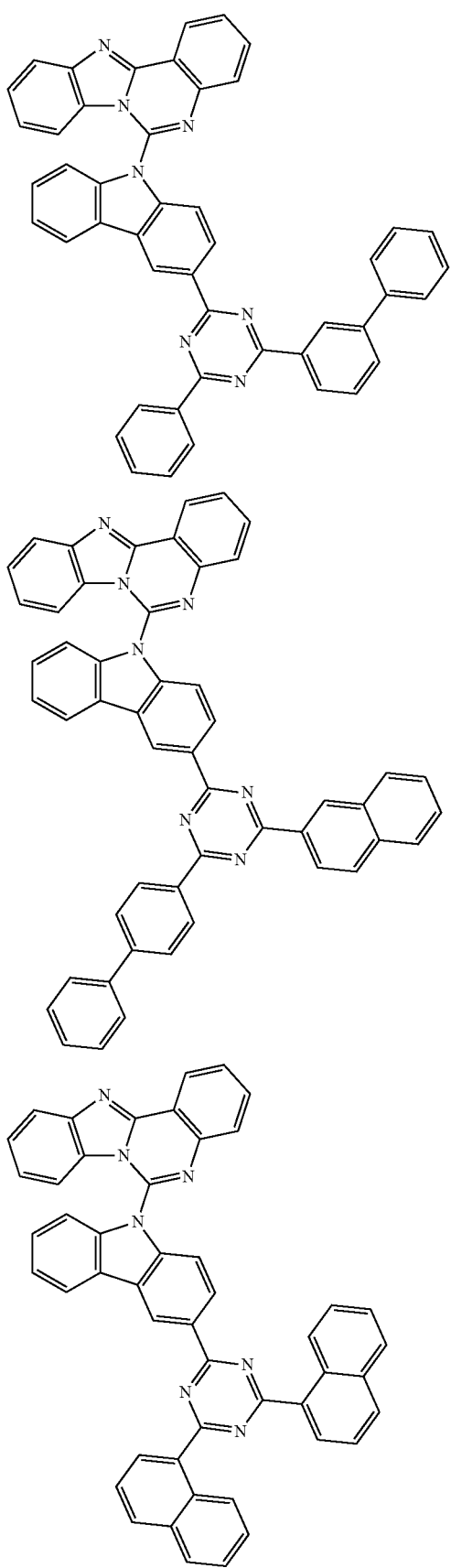
-continued
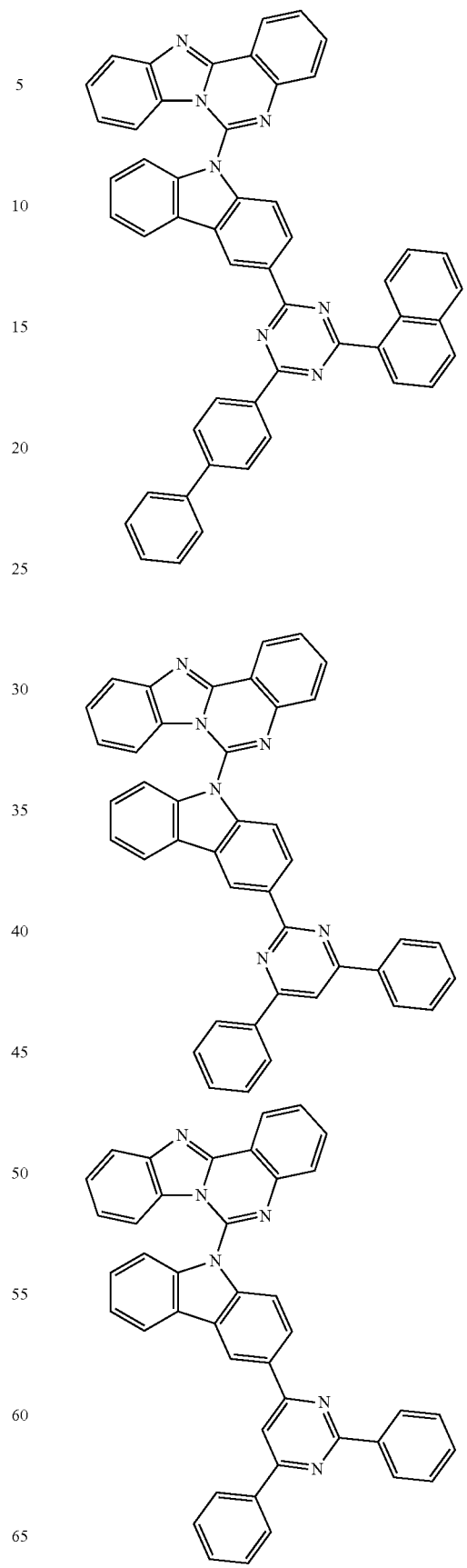

57
-continued
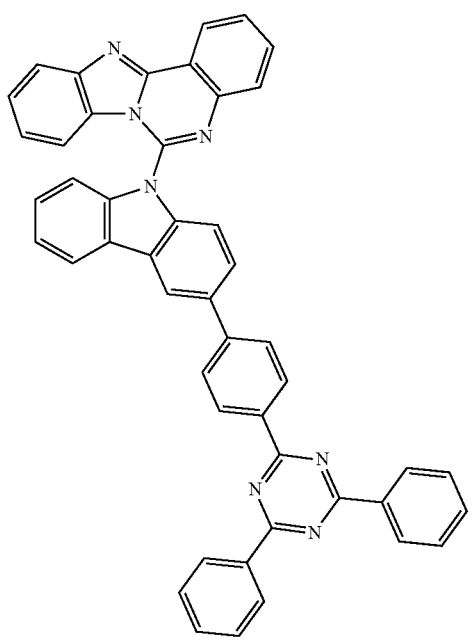
58
-continued
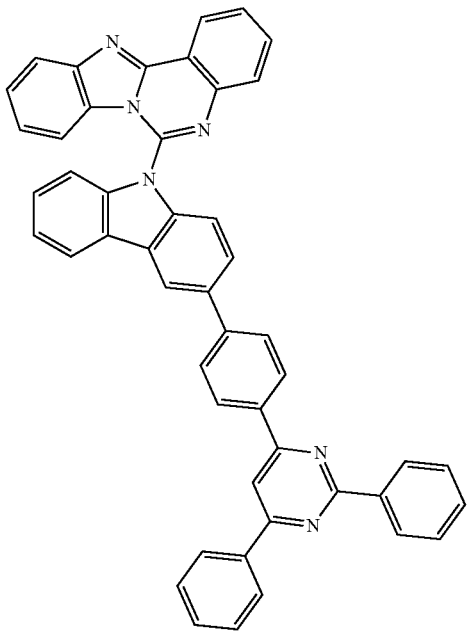

-continued
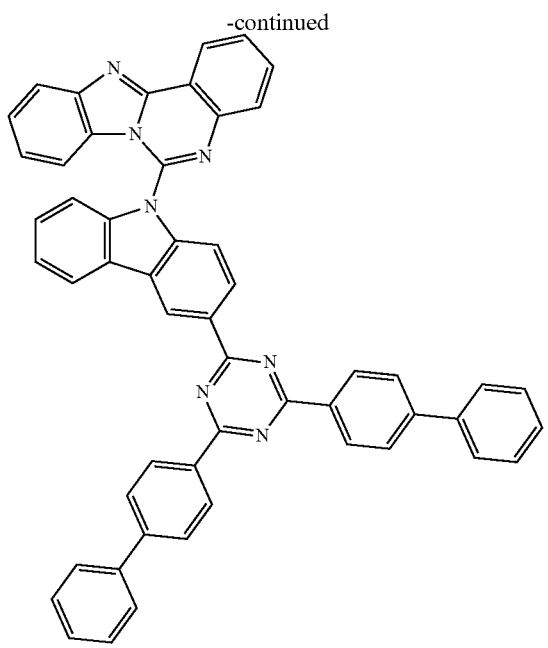
-continued
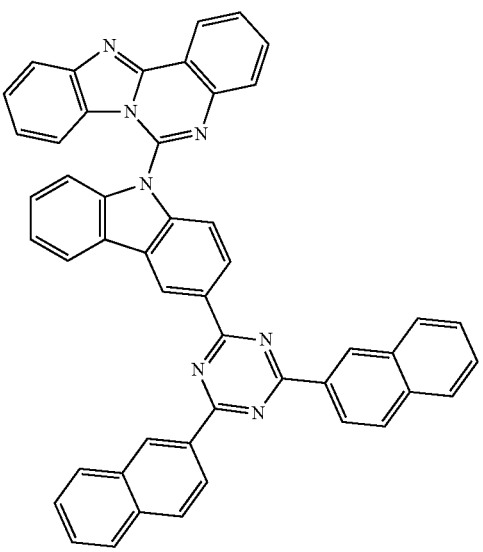
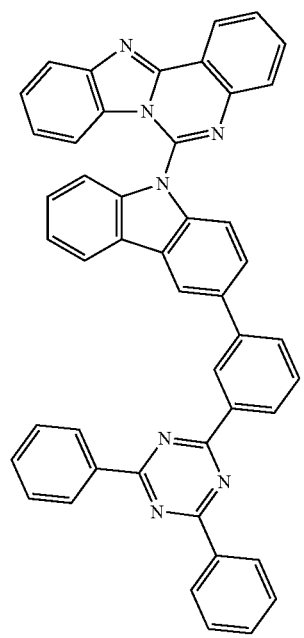
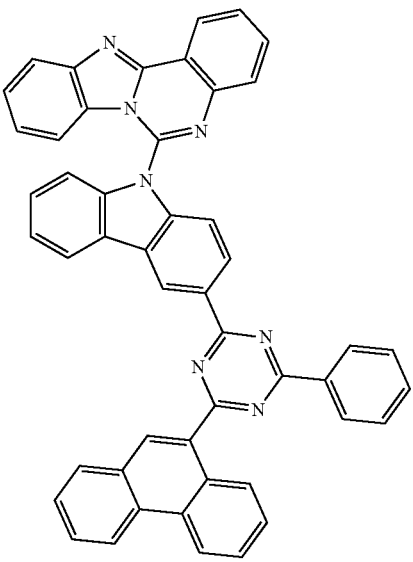

61
-continued
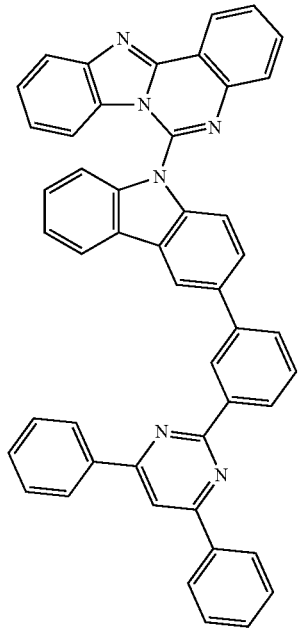
62
-continued
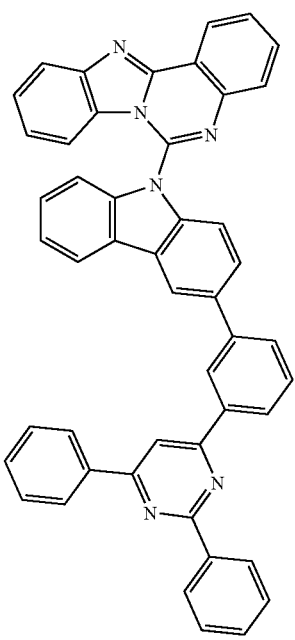
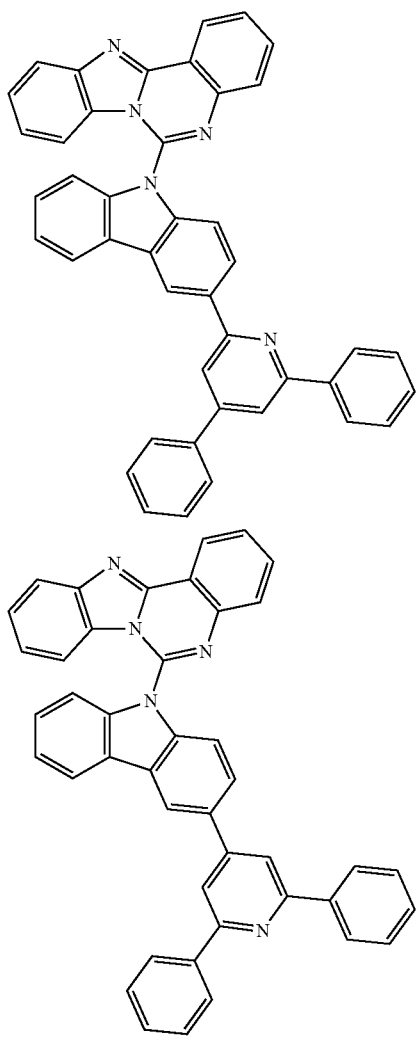
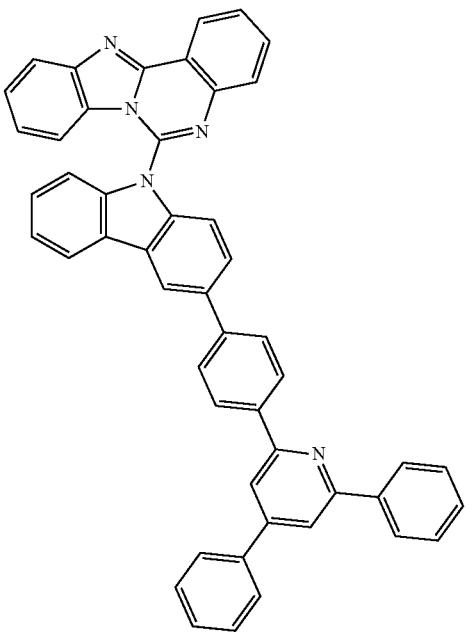

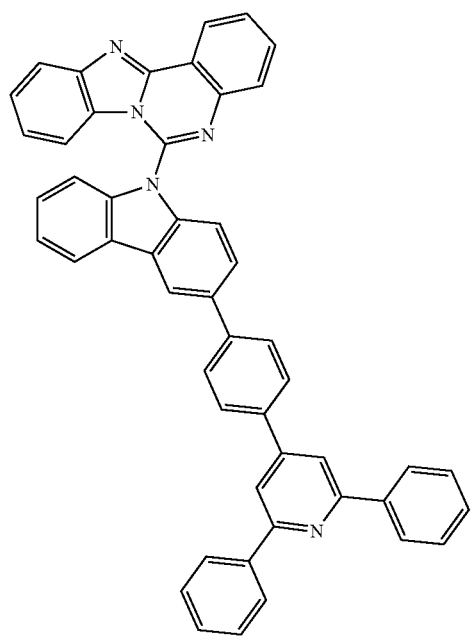
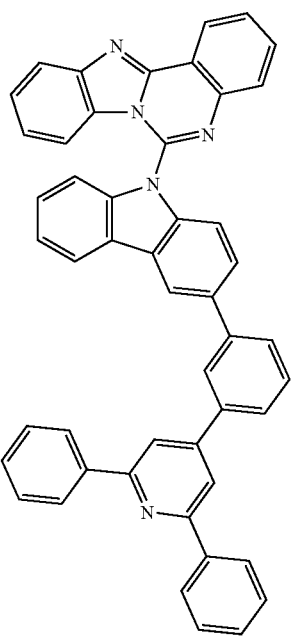
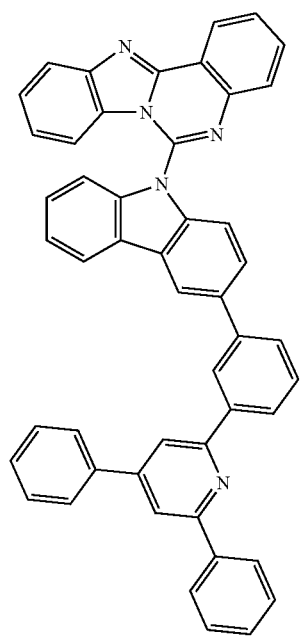
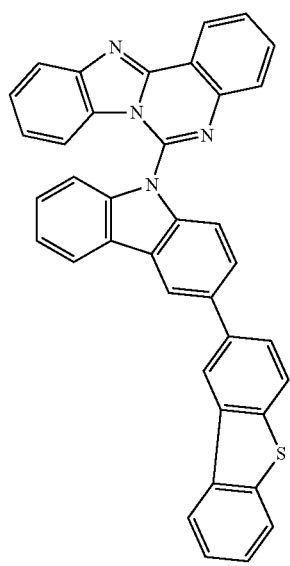

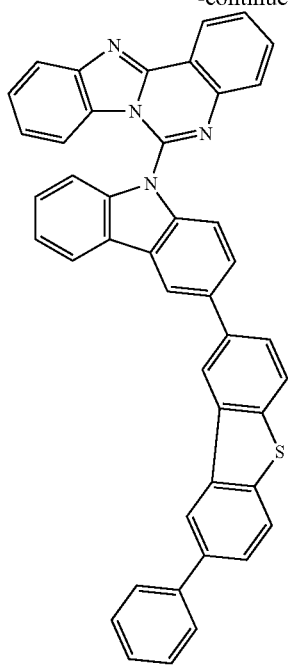
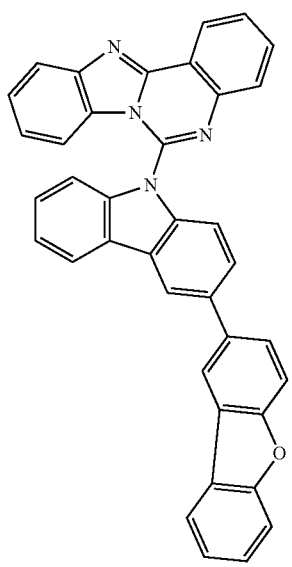
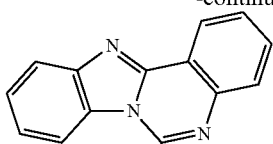
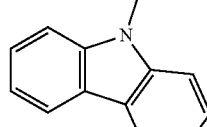
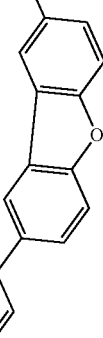
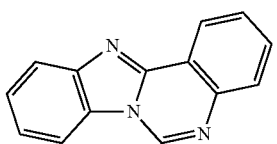
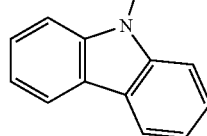
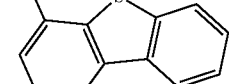
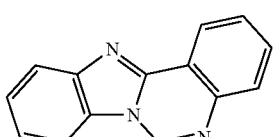
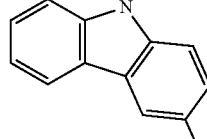

67
-continued
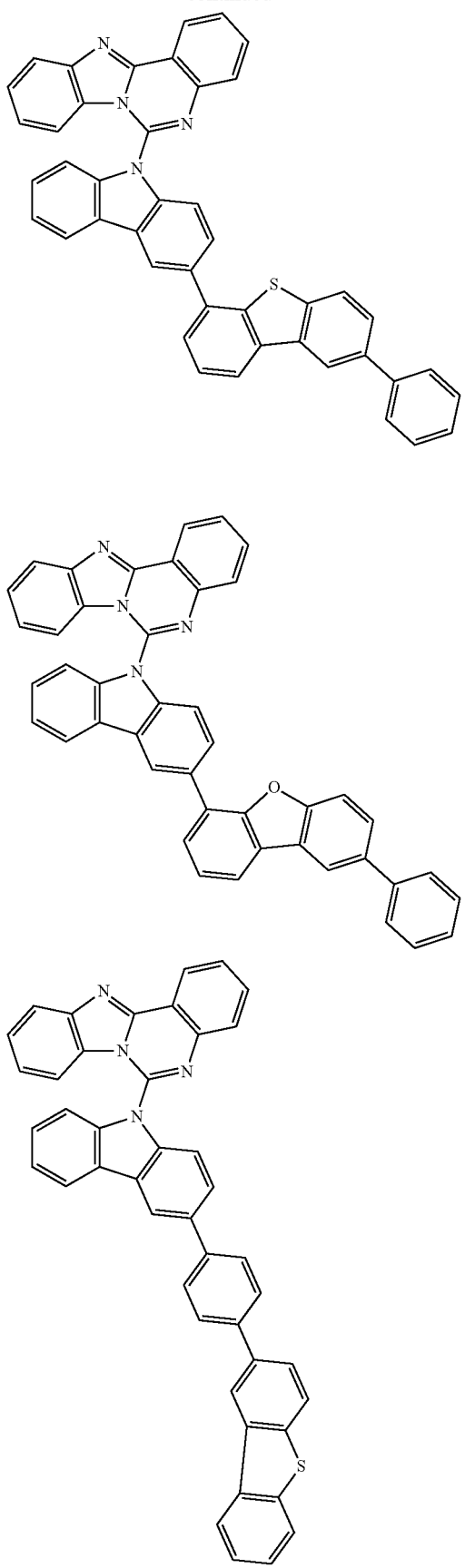
68
-continued
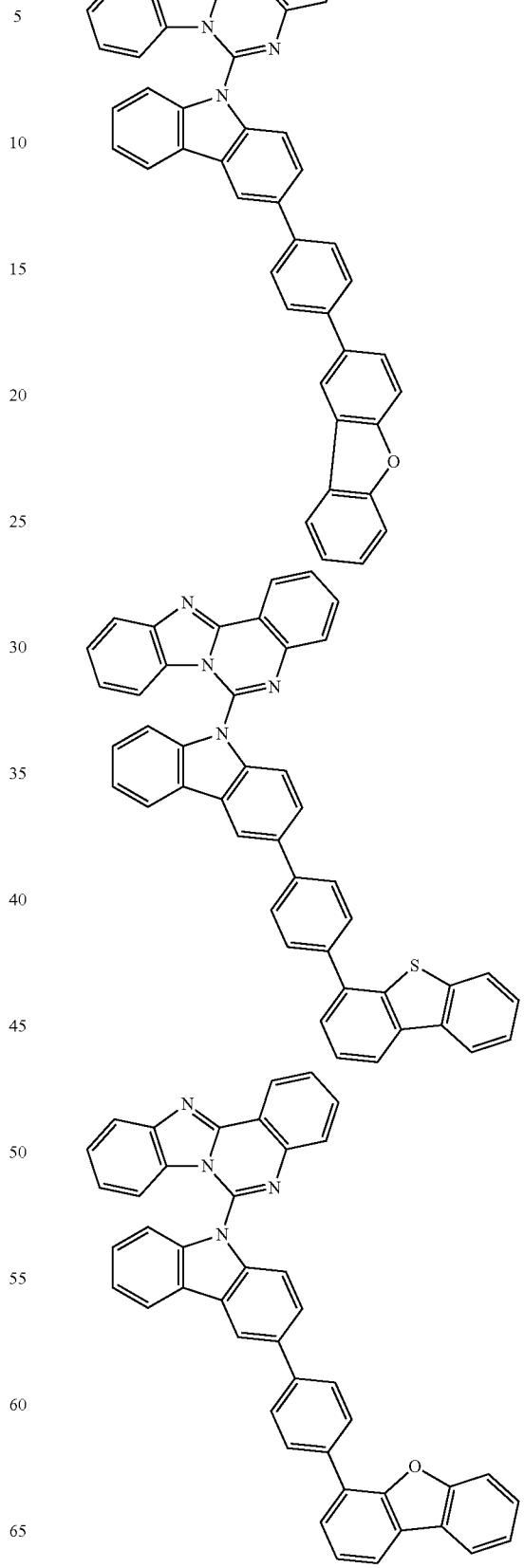

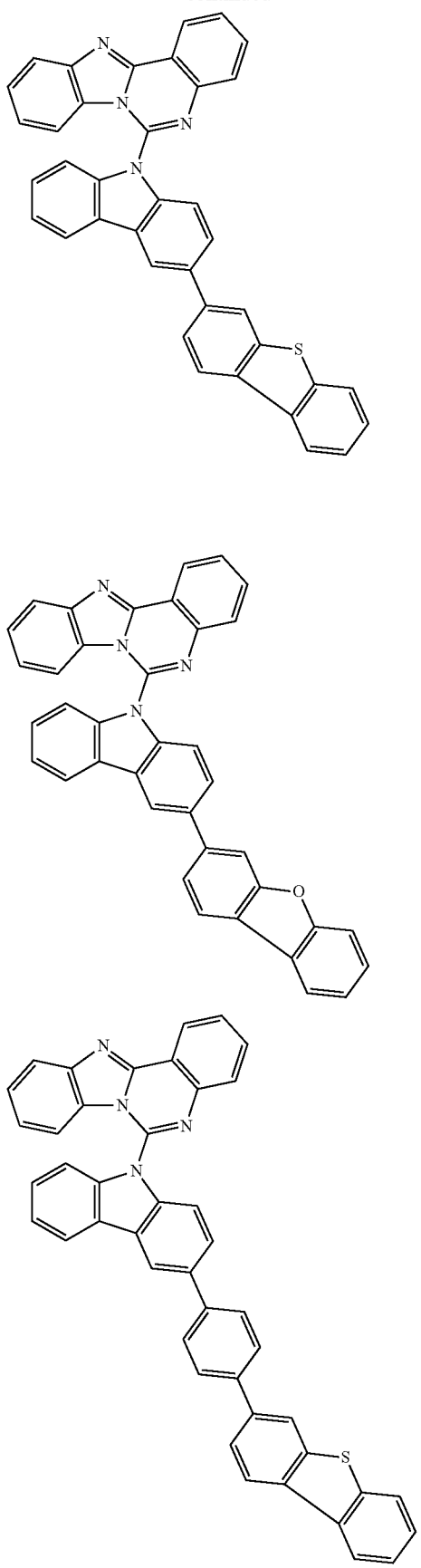
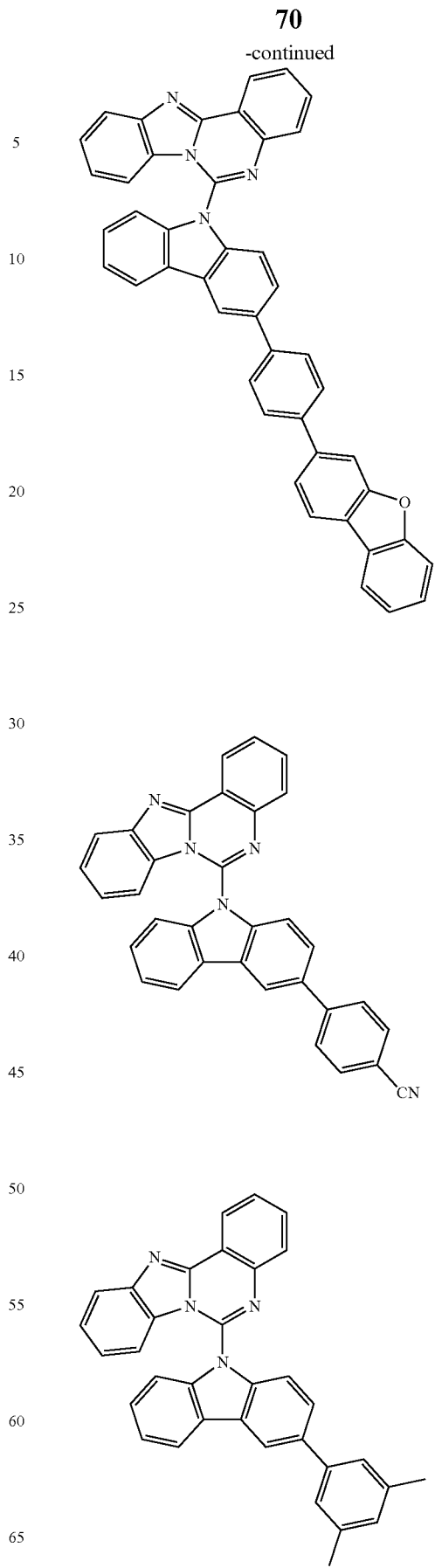

-continued
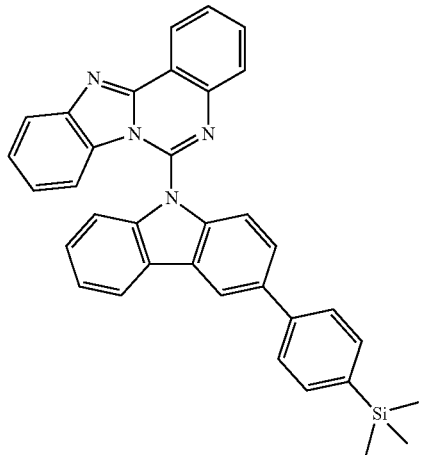
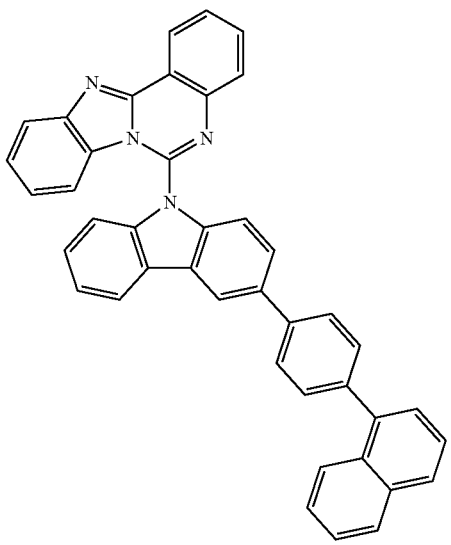
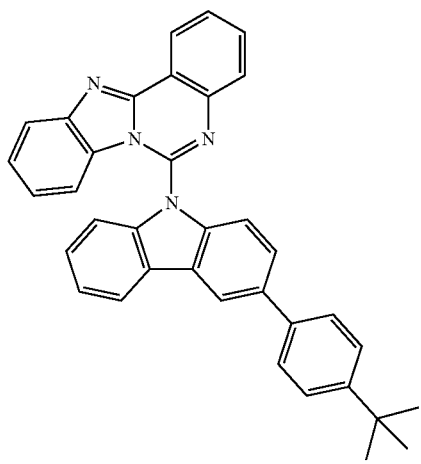
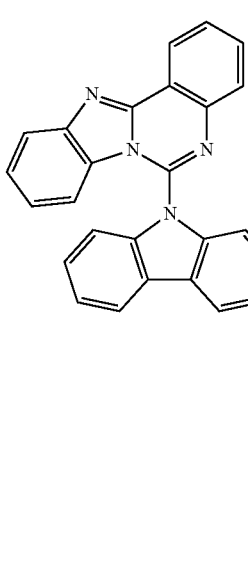
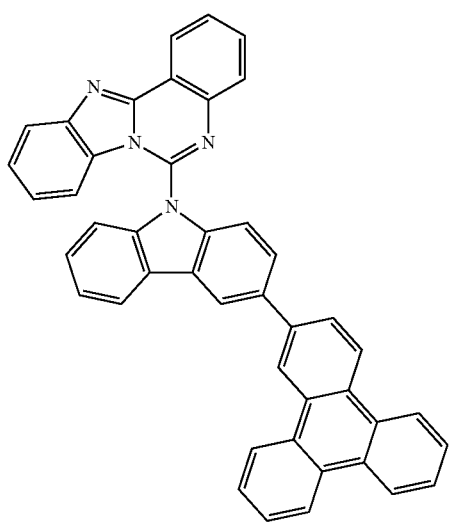
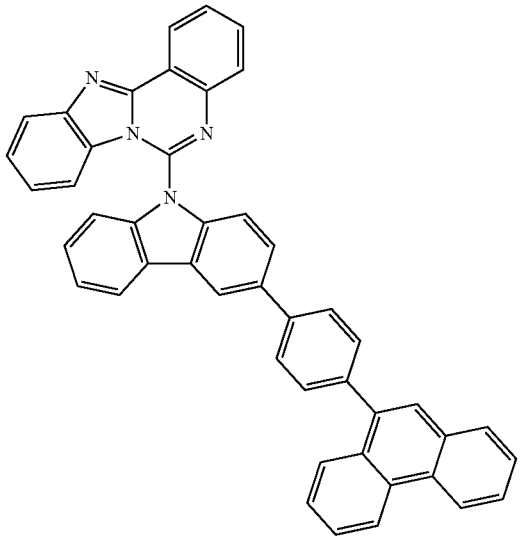

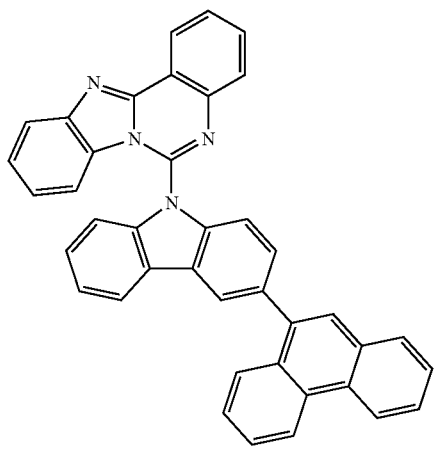
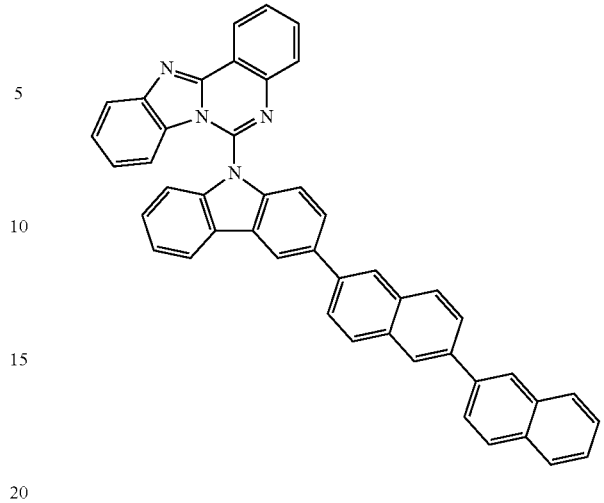
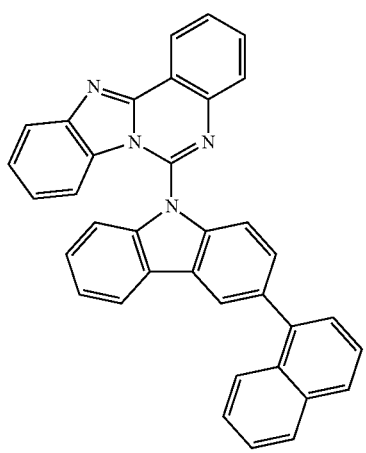
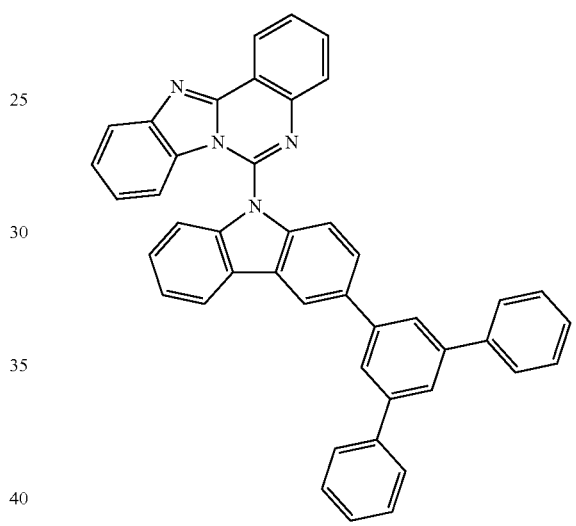
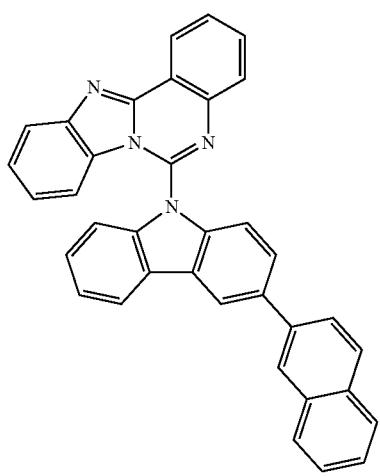
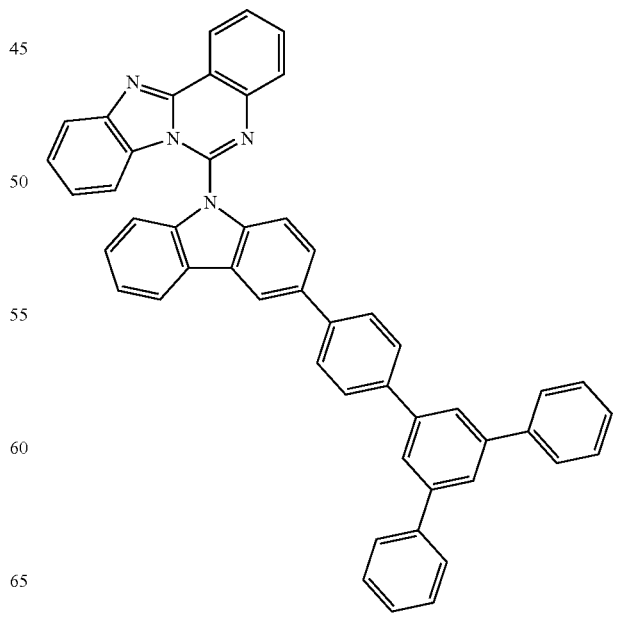

-continued
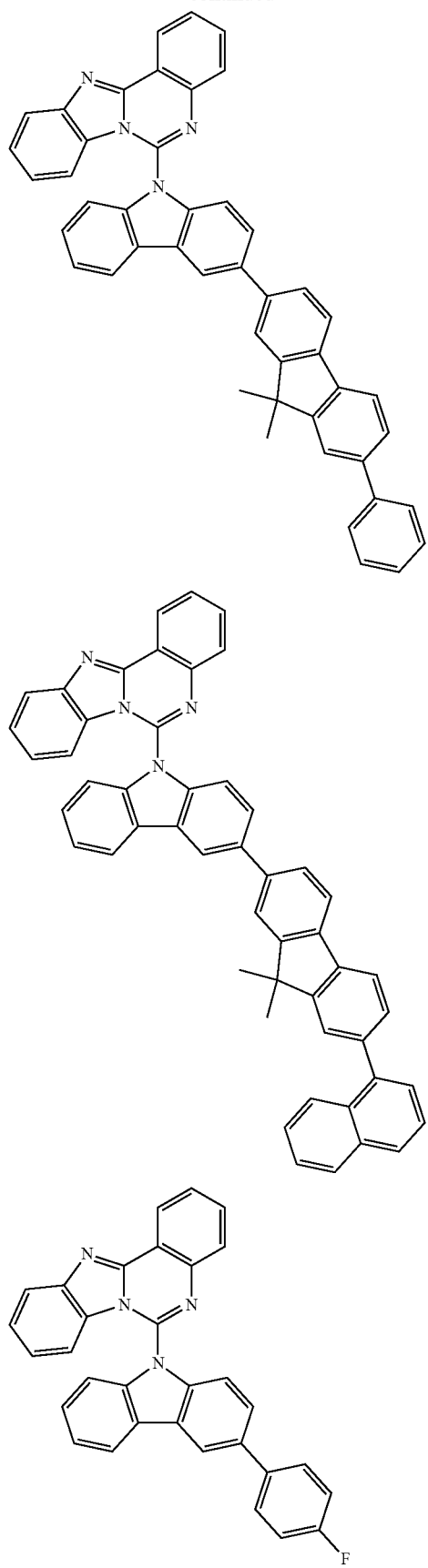
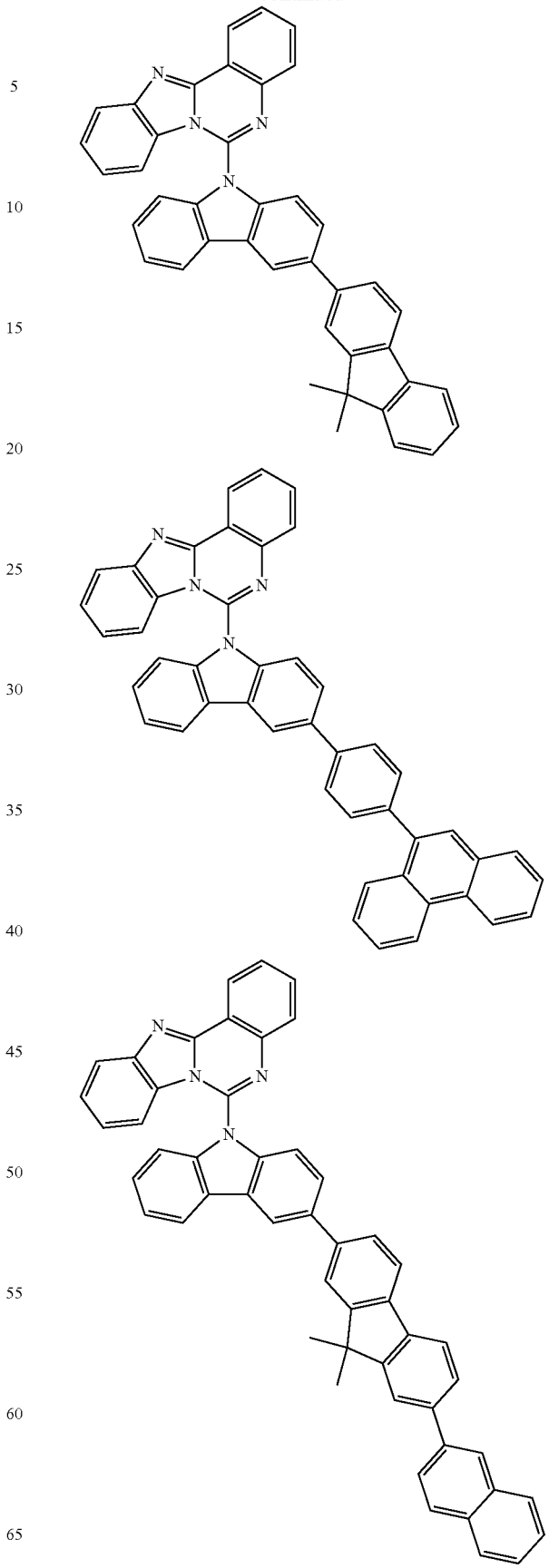

77
-continued
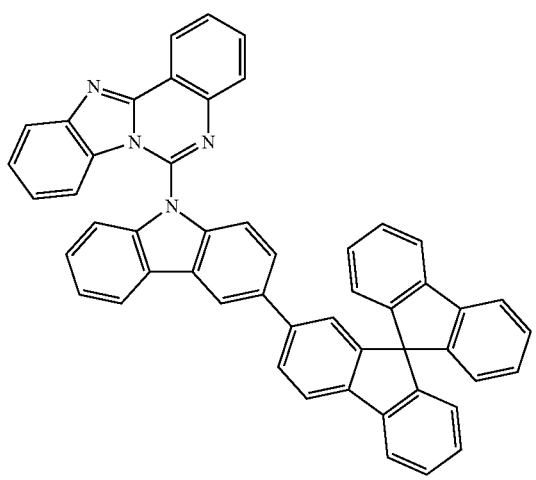
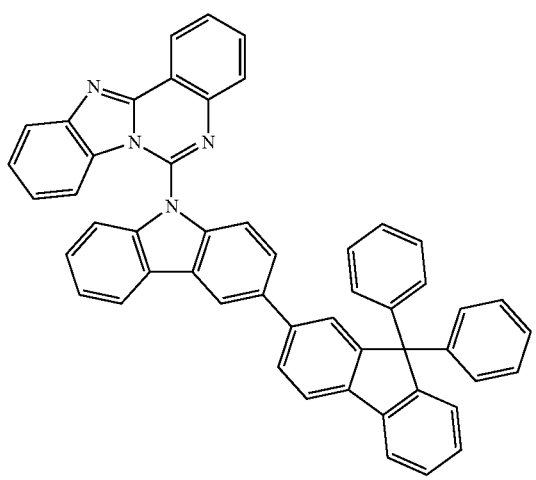
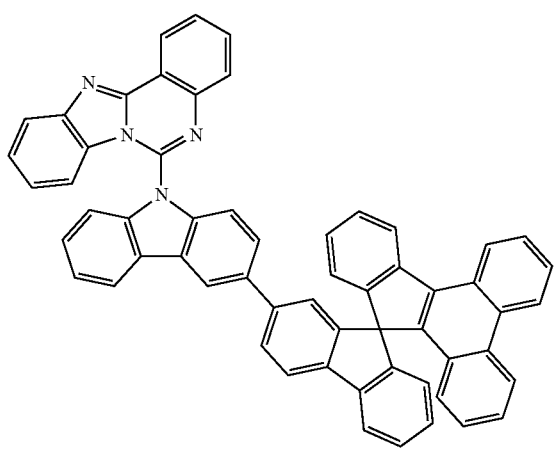
78
-continued
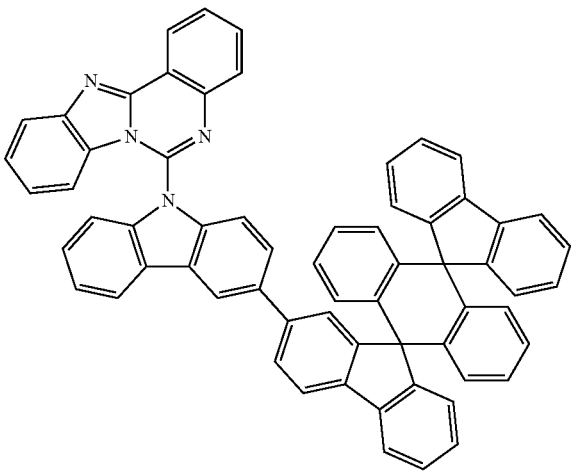
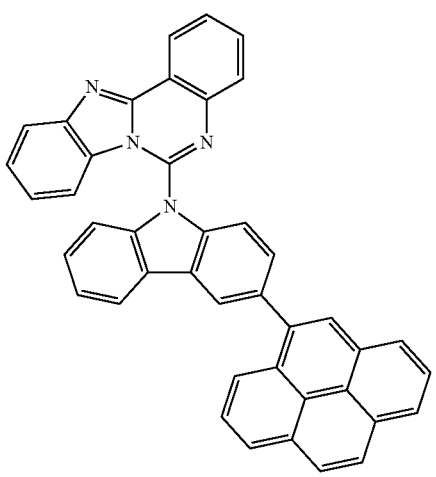
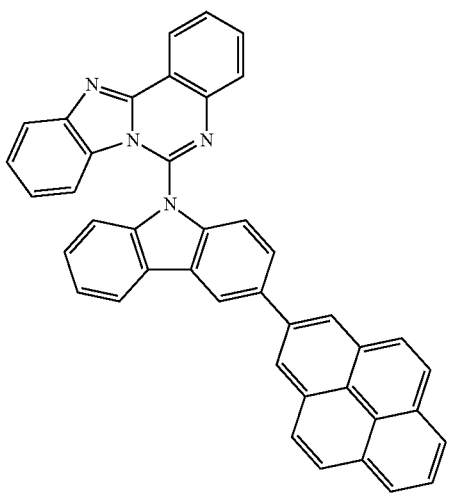

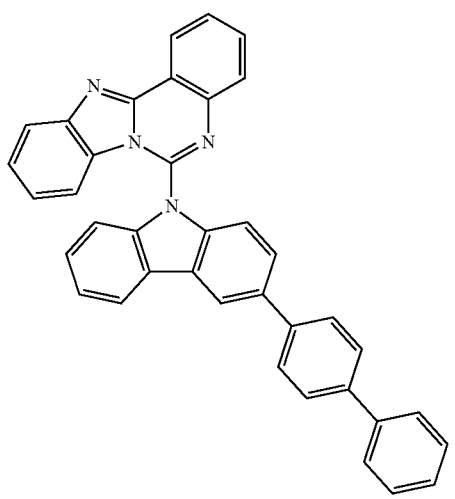
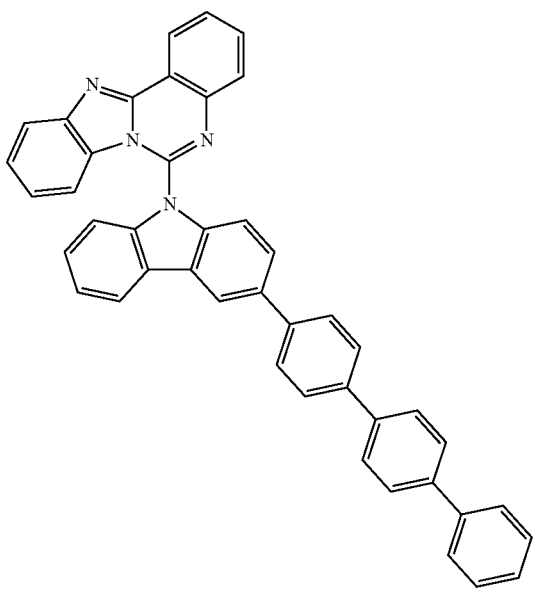
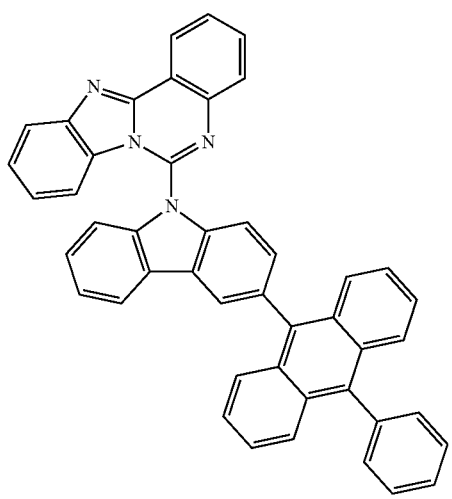
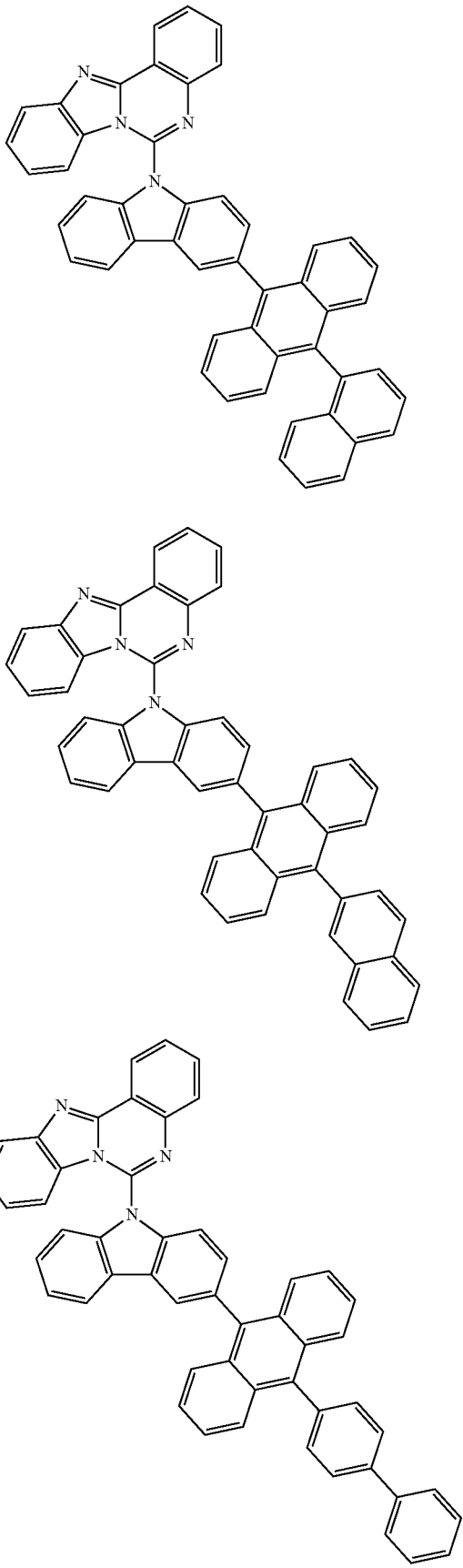

81
-continued
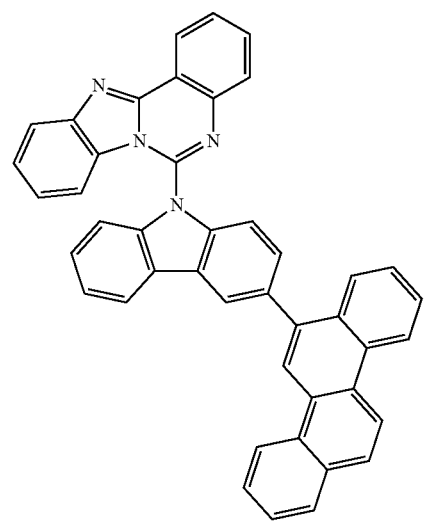
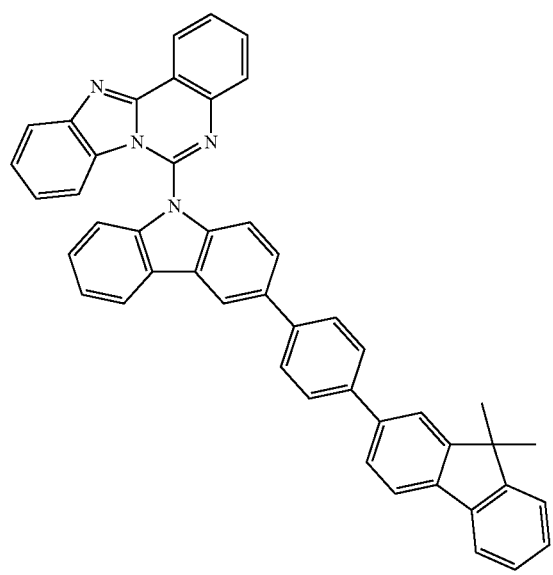
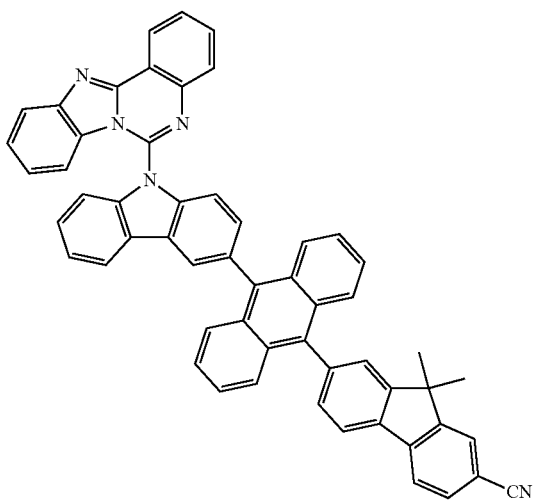
82
-continued
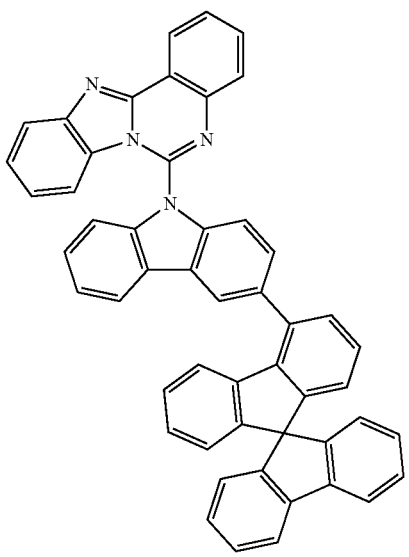
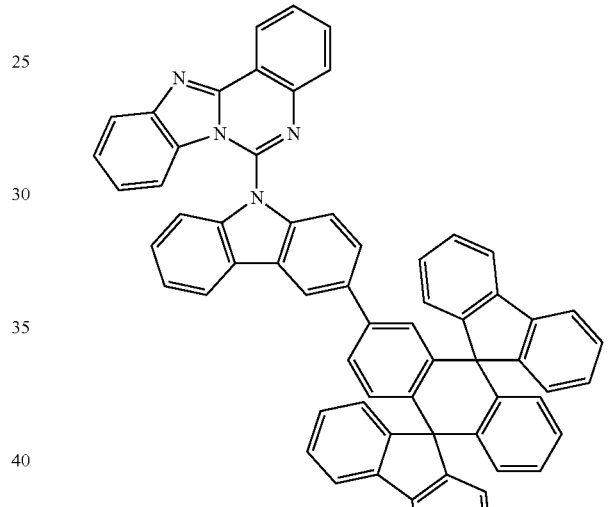
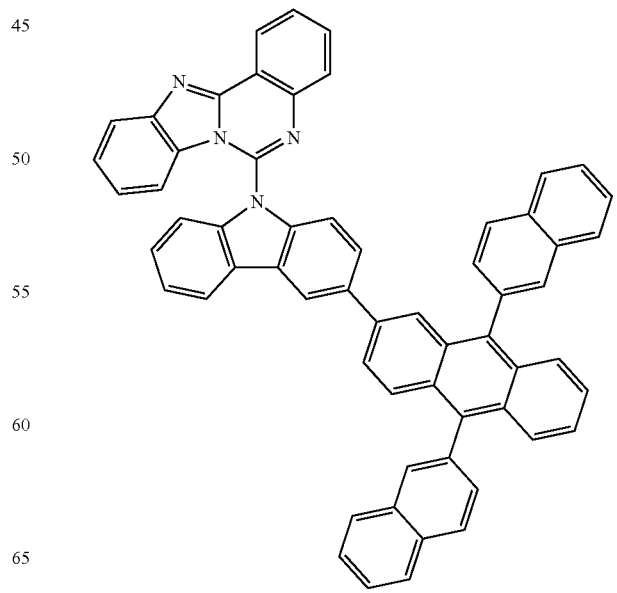

83
-continued
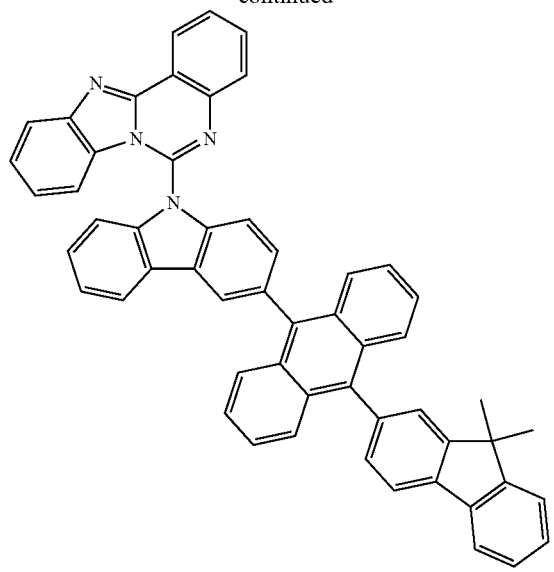
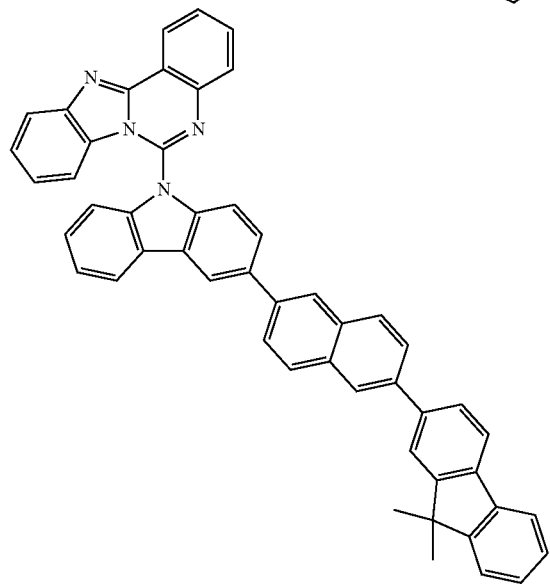
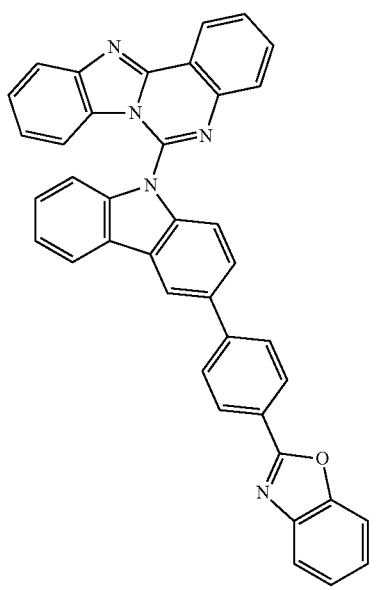
84
-continued
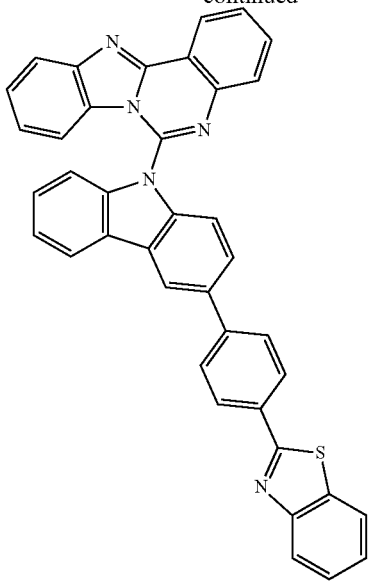
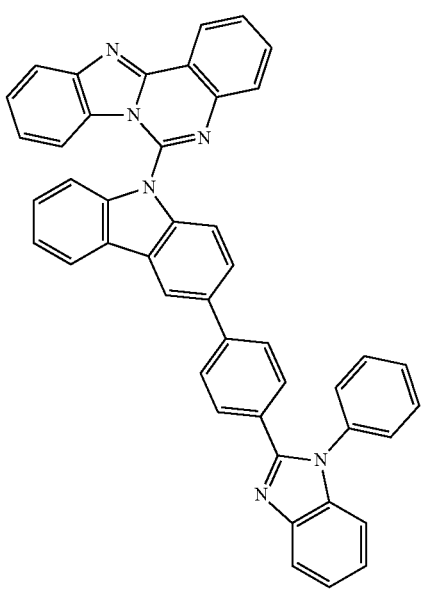
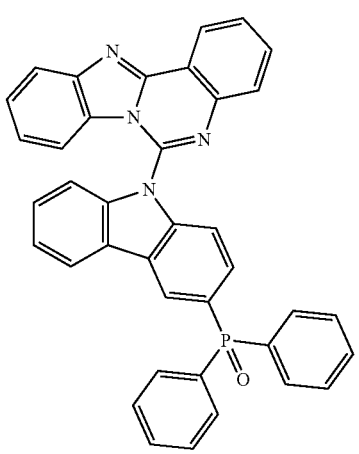

85
-continued
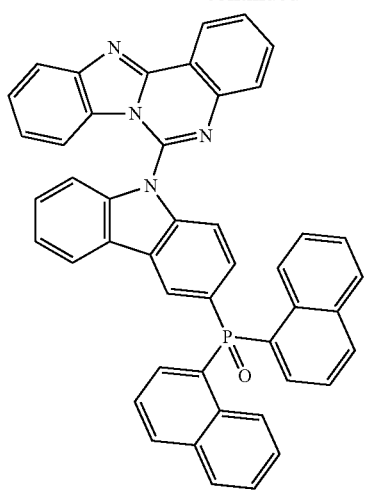
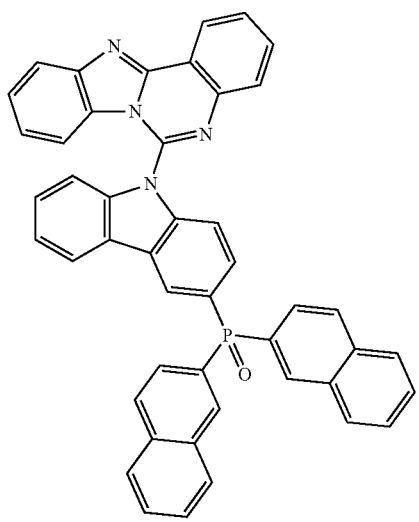
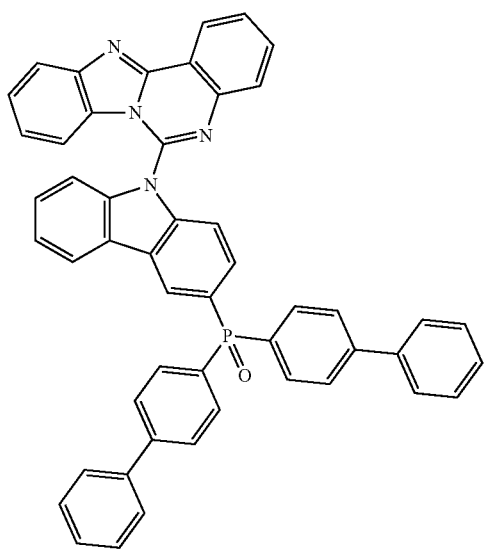
86
-continued
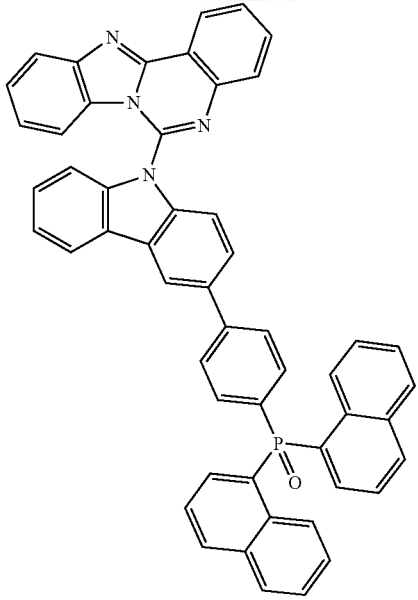
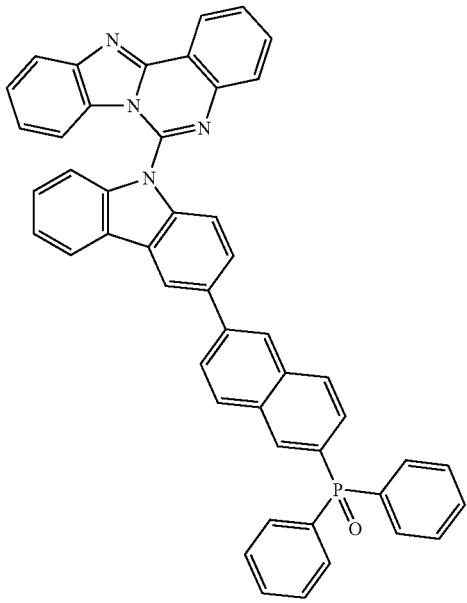
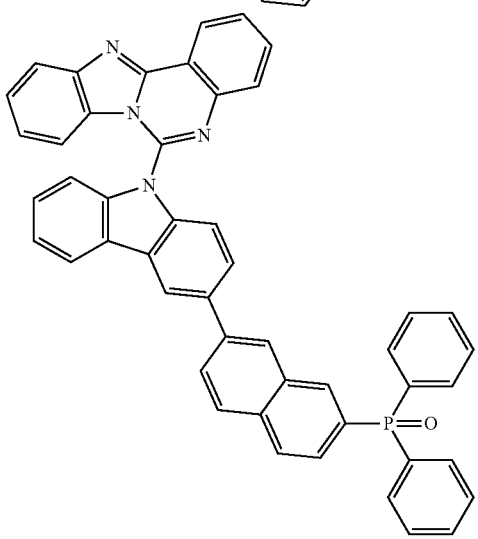

87
-continued
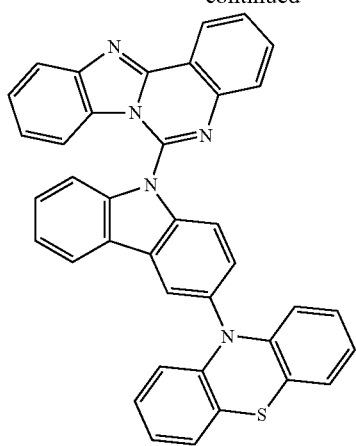
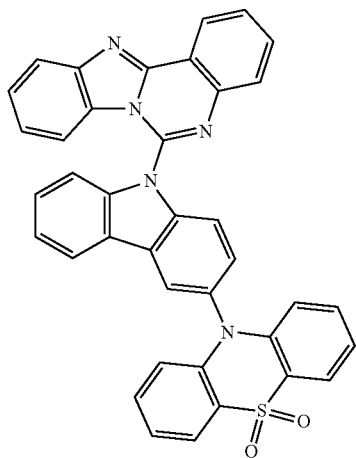
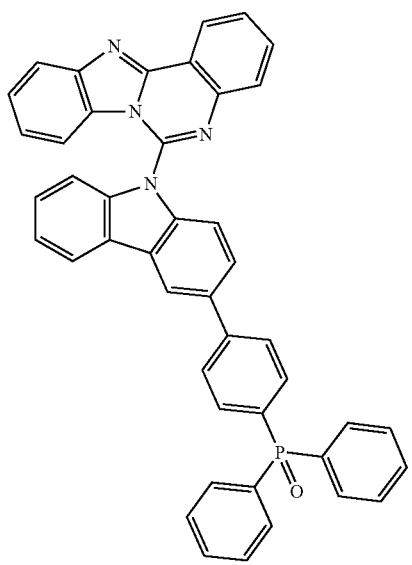
88
-continued
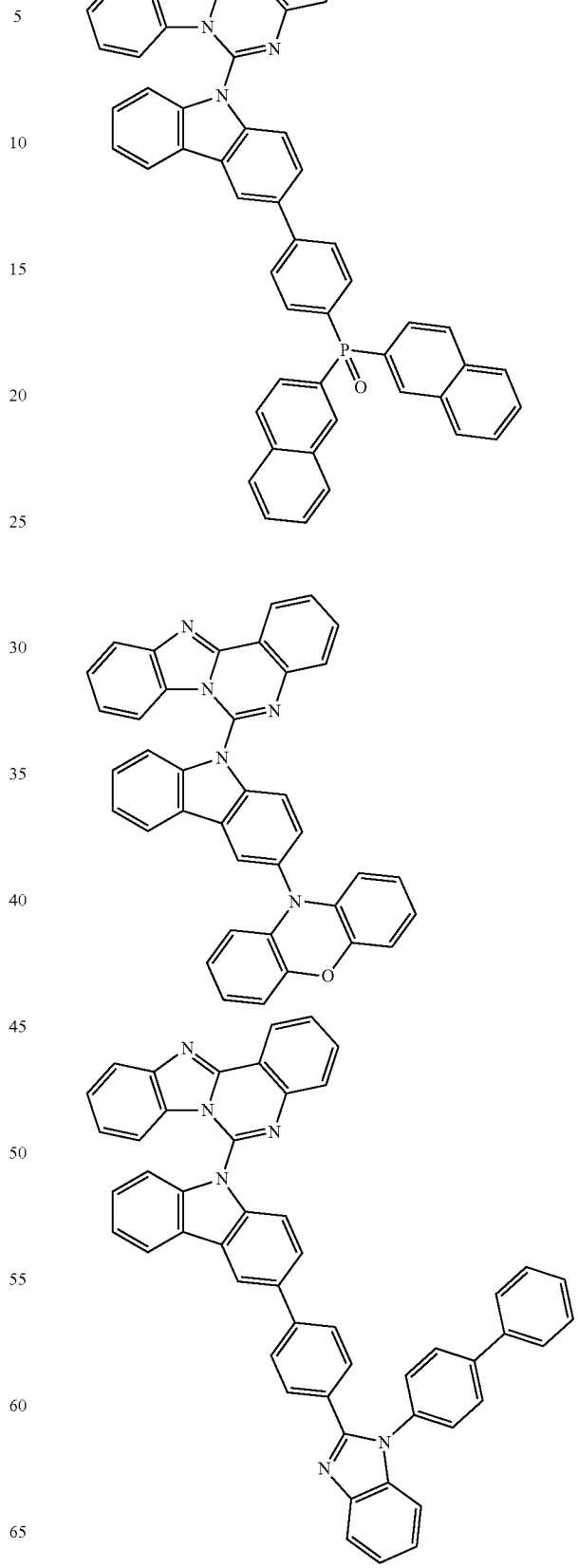

89
-continued
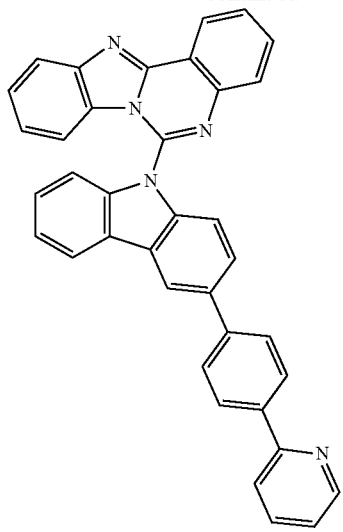
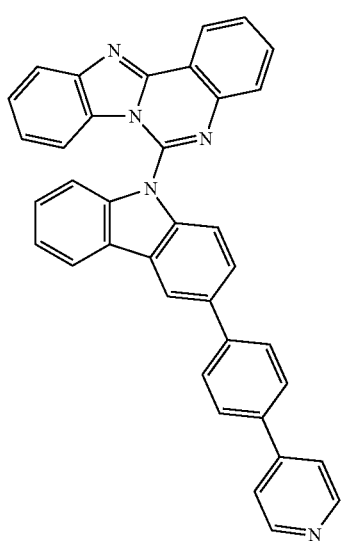
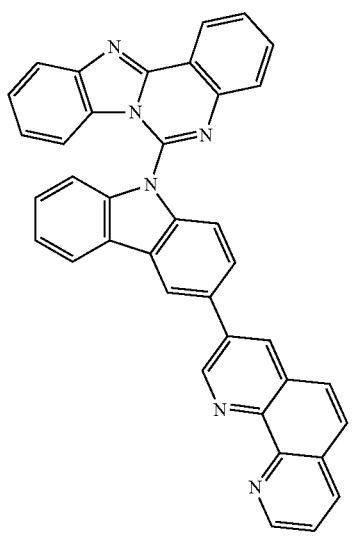
90
-continued
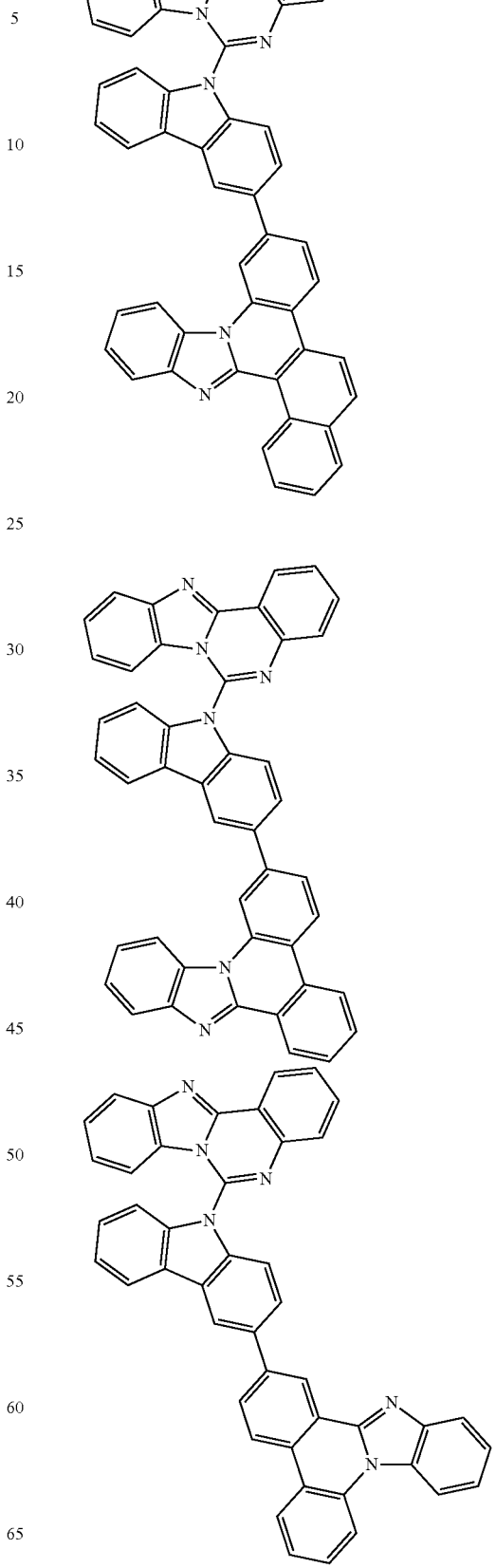

91
-continued
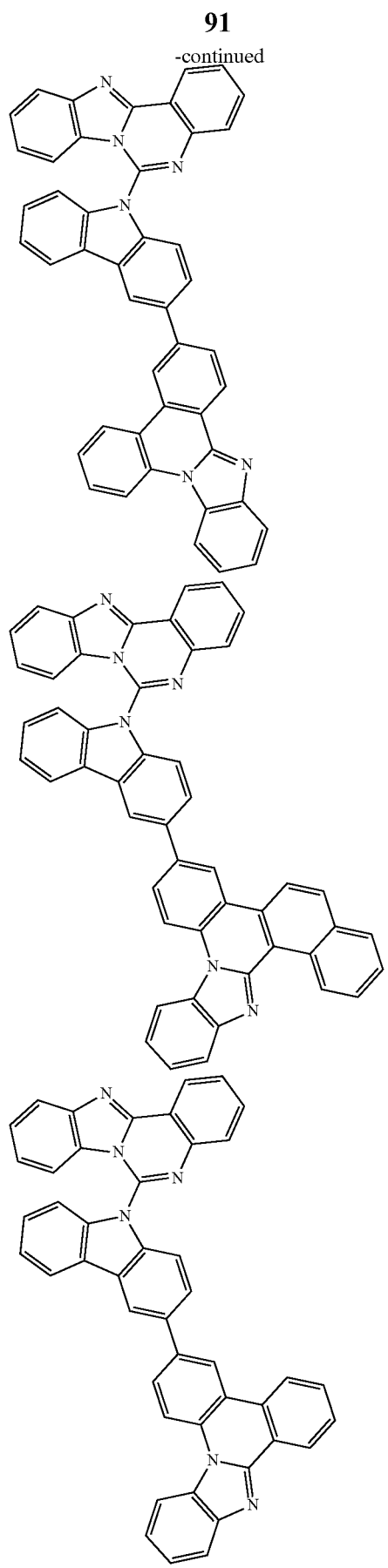
92
-continued
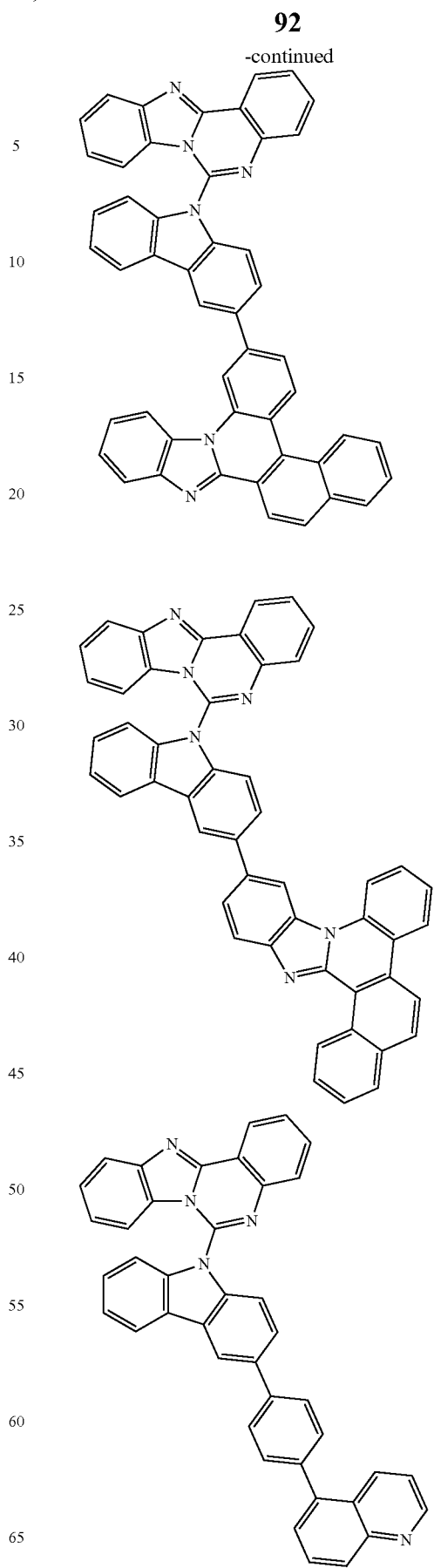

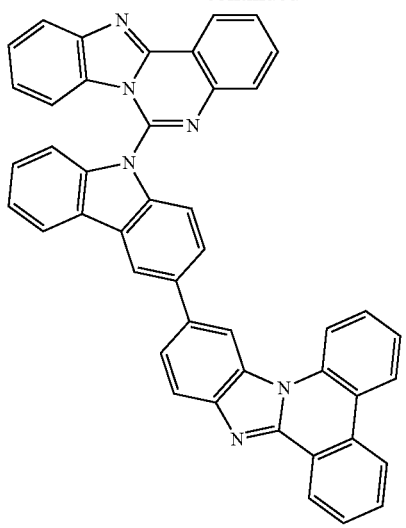
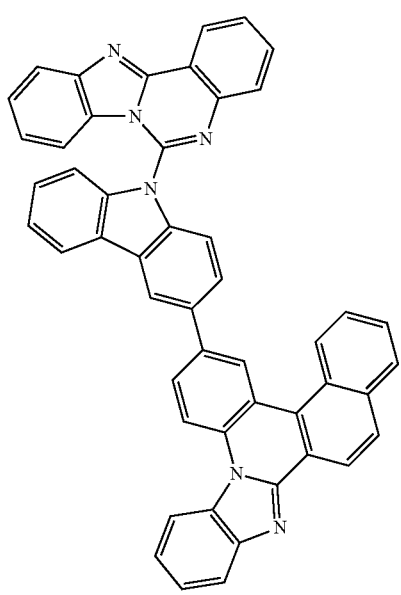 [SMILES: c1ccc2c(c1)ccc1c2c2cc(-c3ccc4c(c3)c3ccccc3n4-c3nc4ccccc4c4nc5ccccc5n34)ccc2n2c3ccccc3nc12]
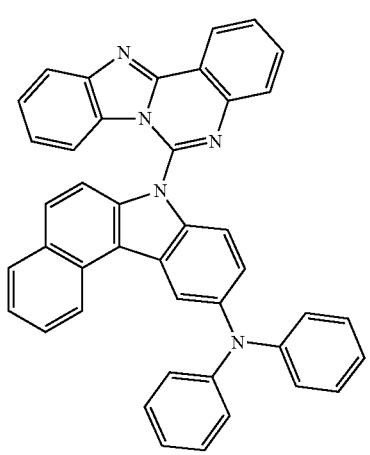
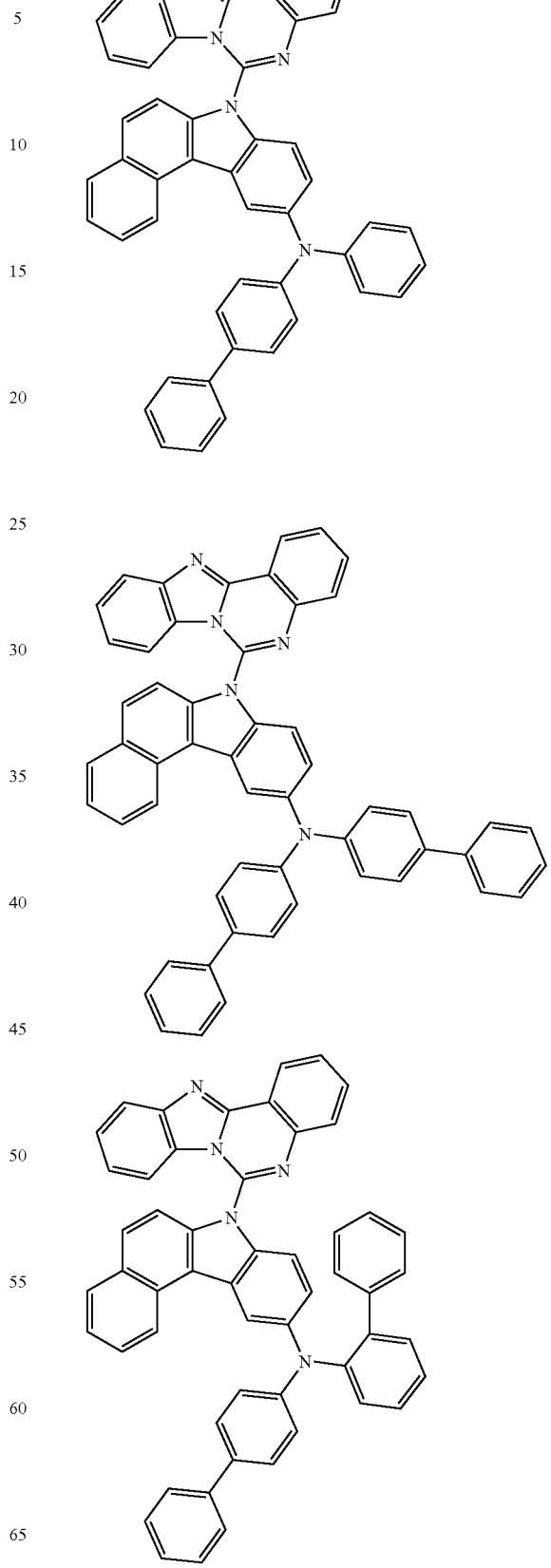

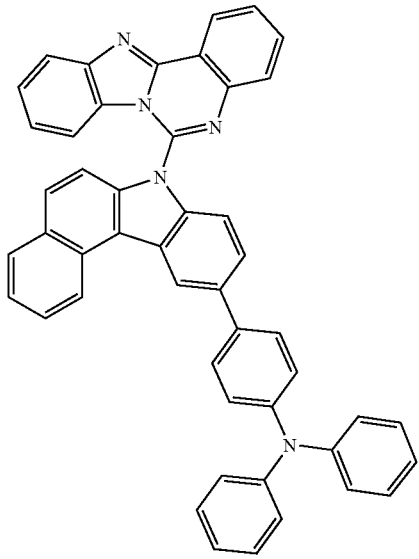
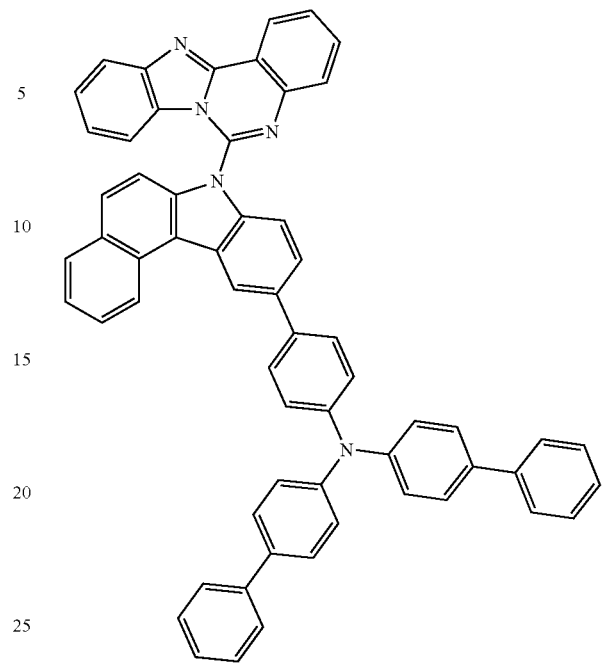
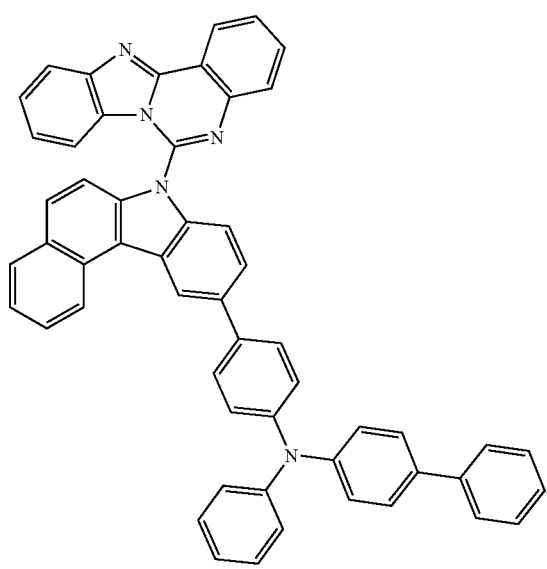
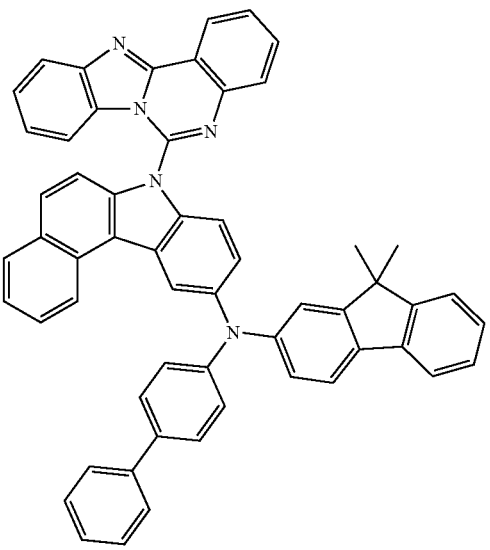

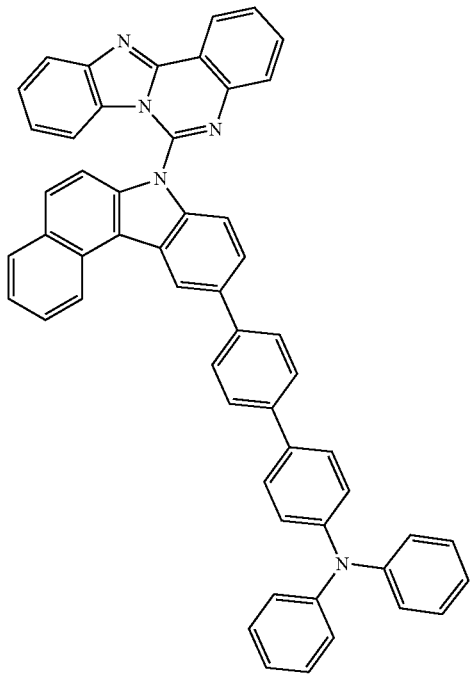
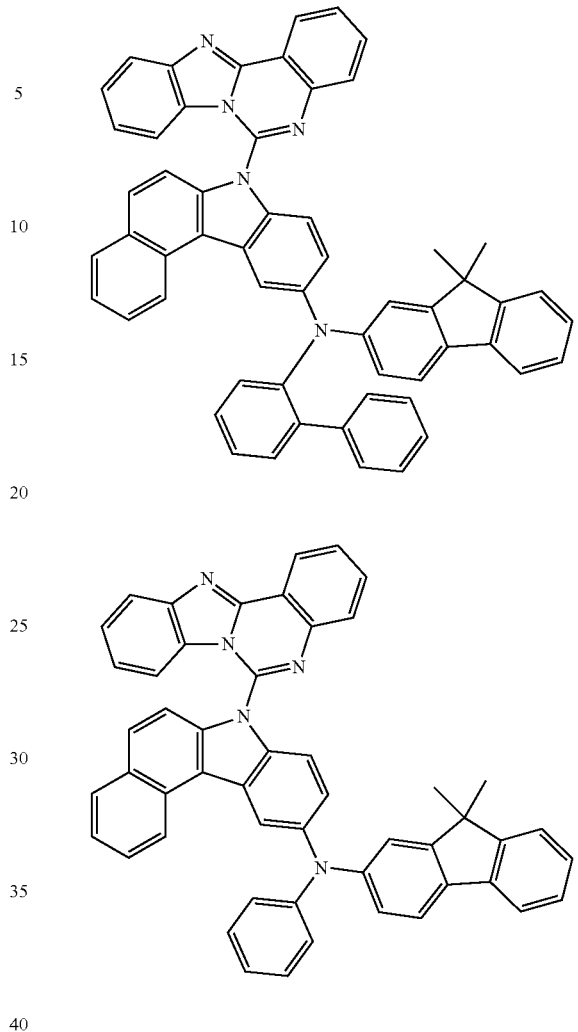

99
-continued
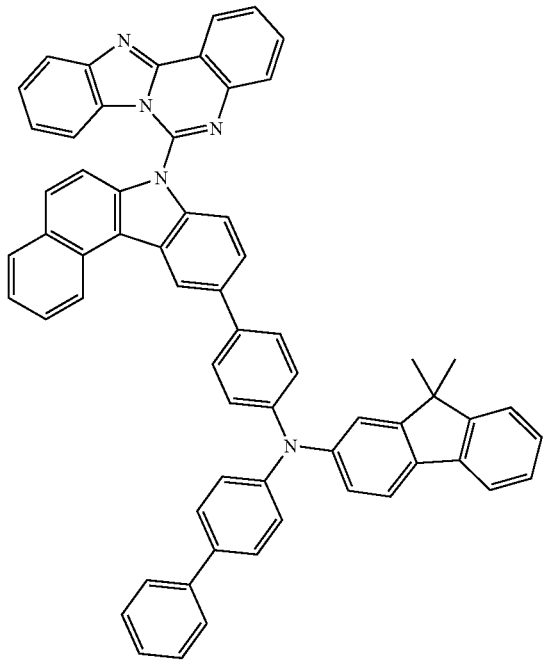
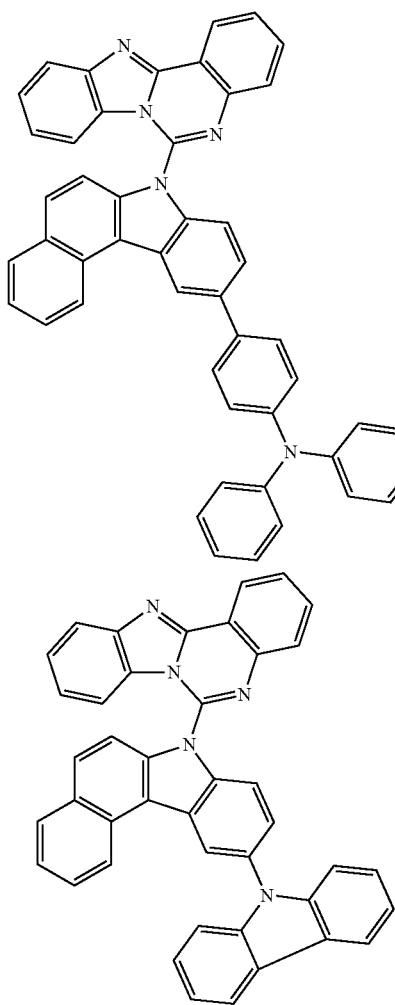
100
-continued
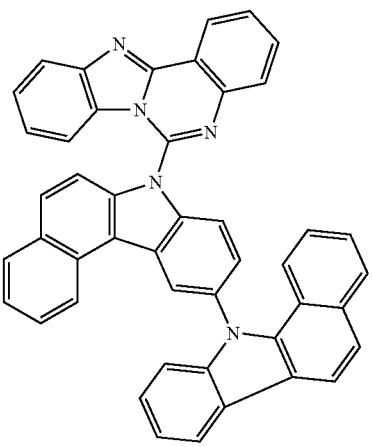
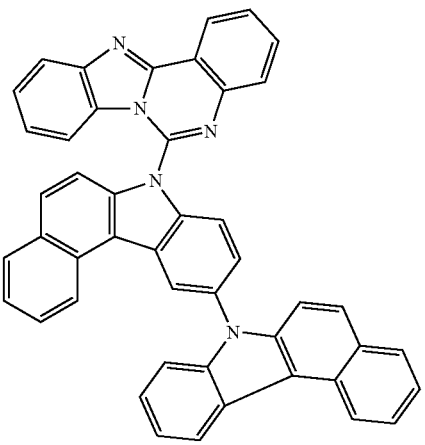
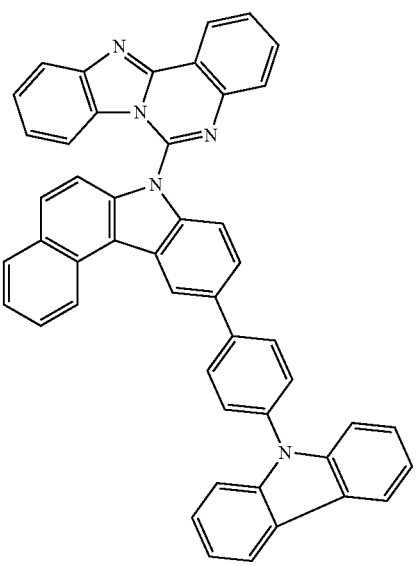

101
-continued
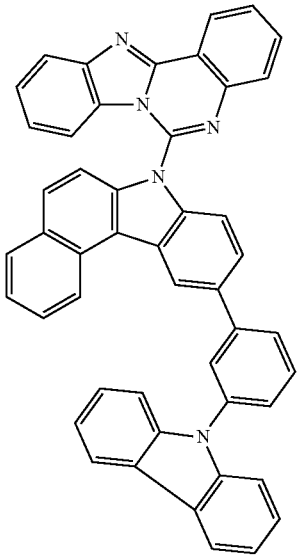
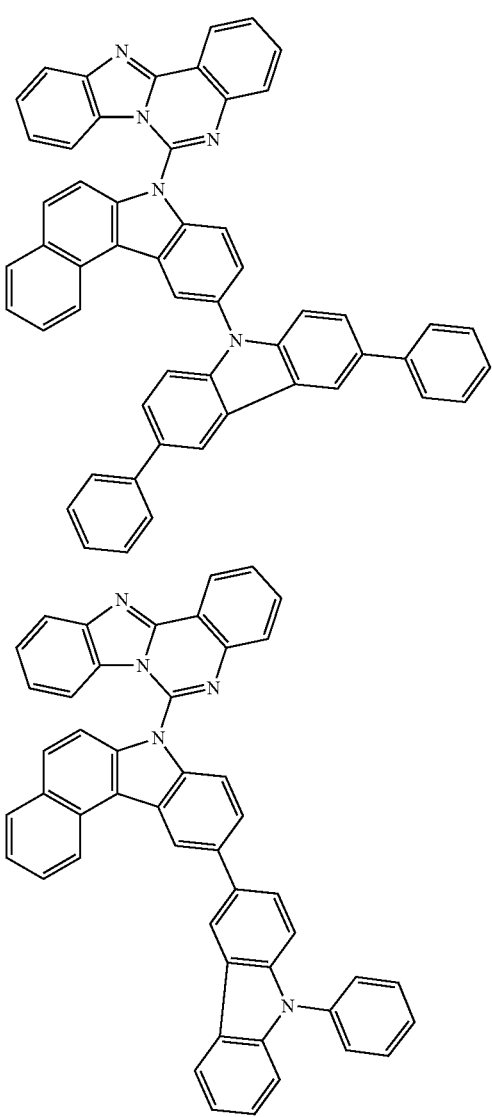
102
-continued
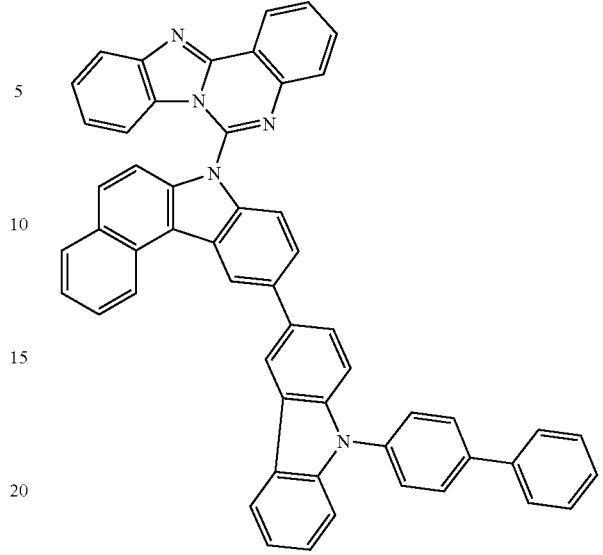
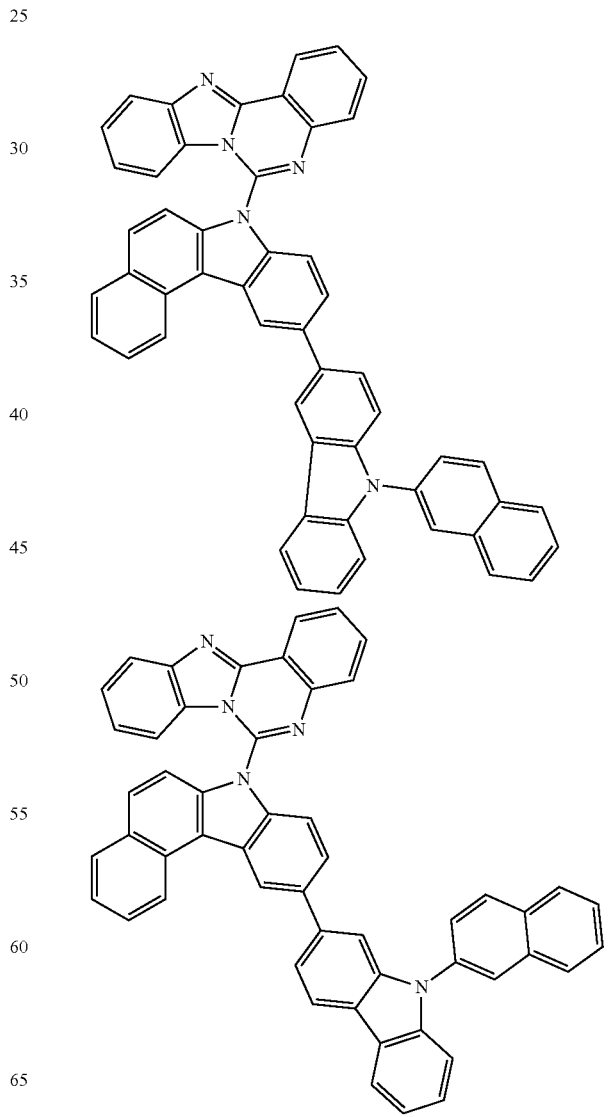

103
-continued
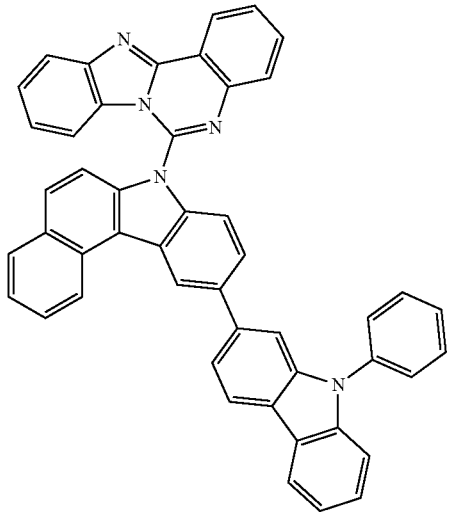
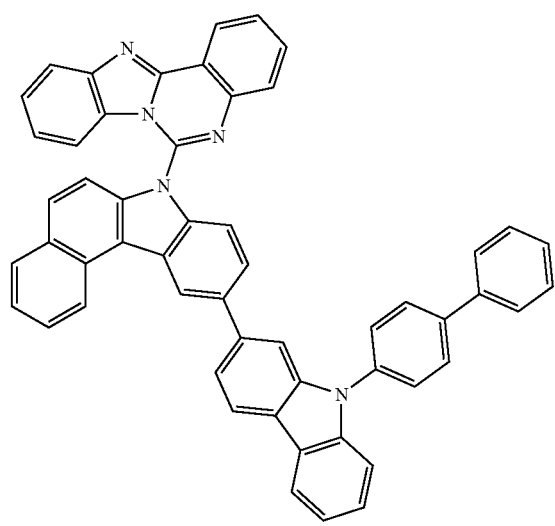
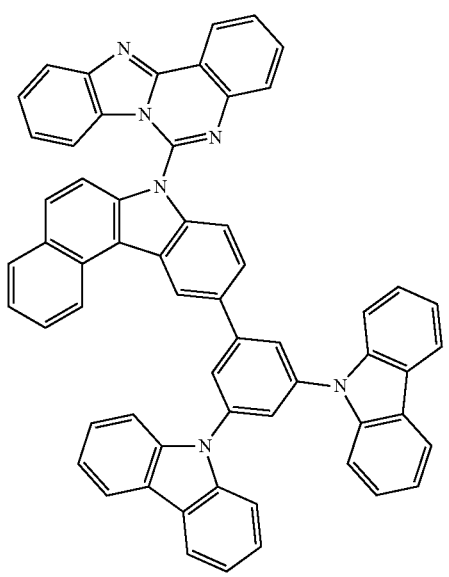
104
-continued
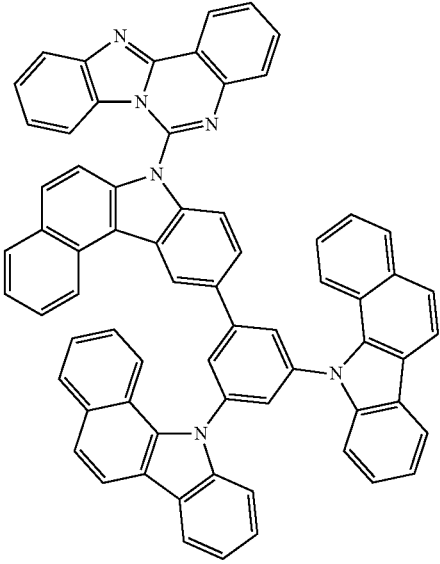
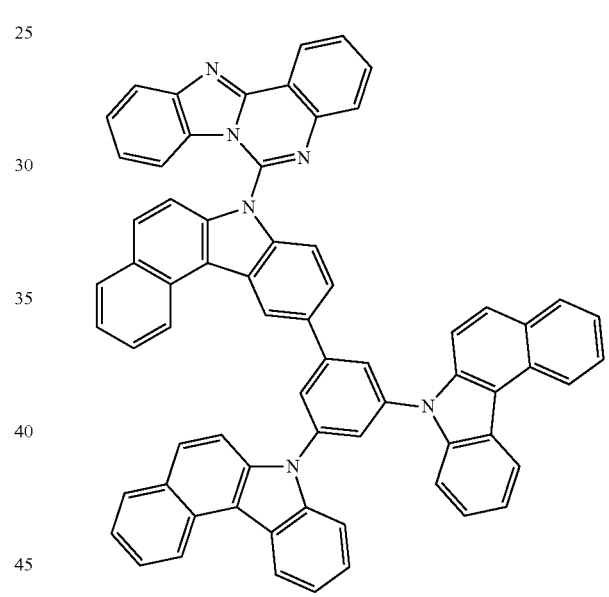
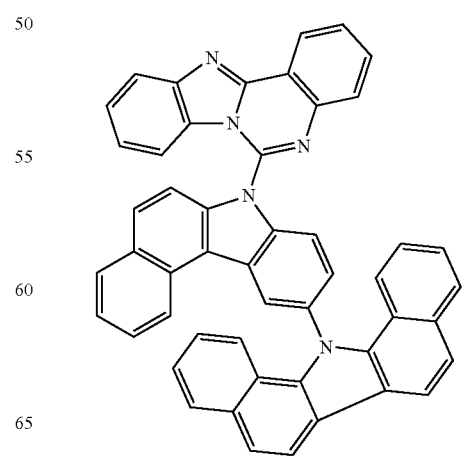

105
-continued
106
-continued
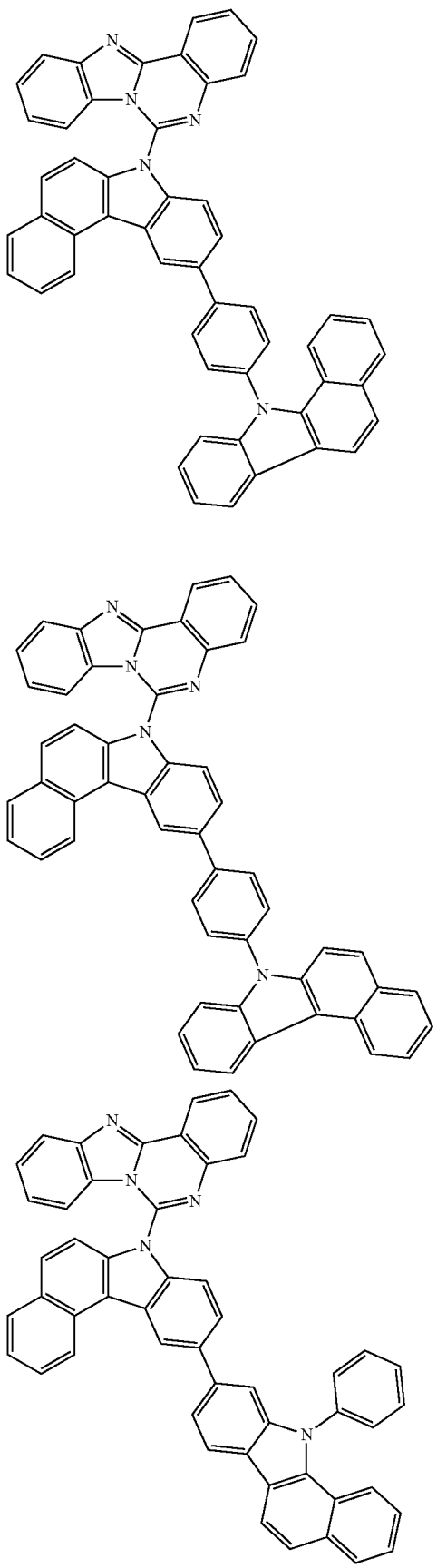
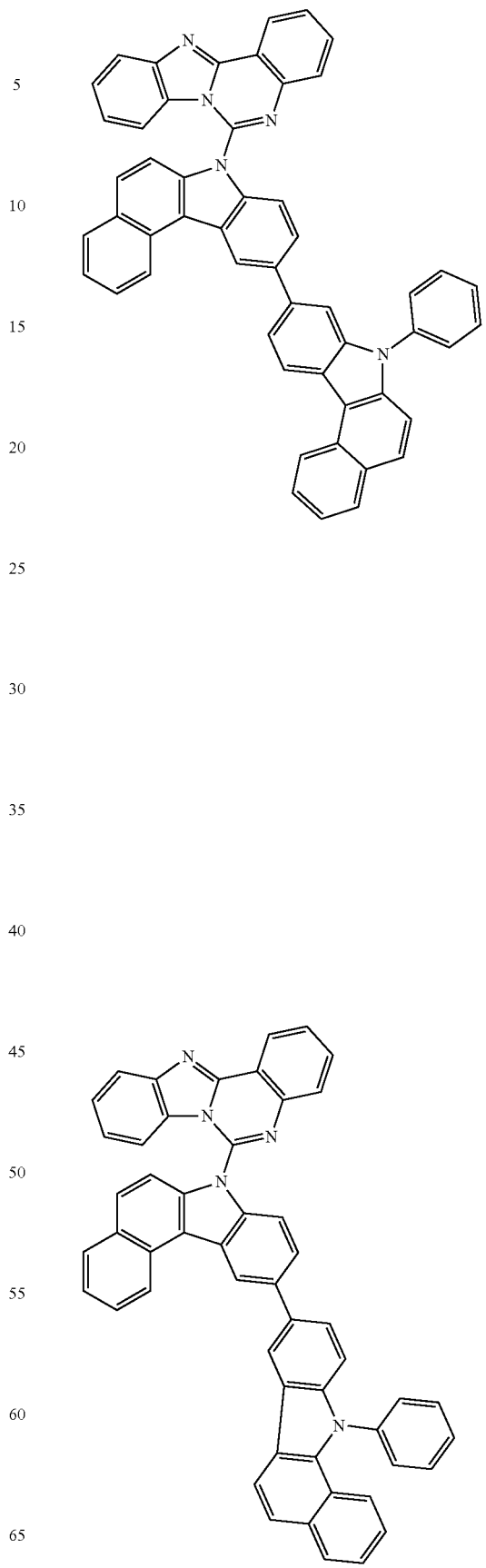

107
-continued
108
-continued
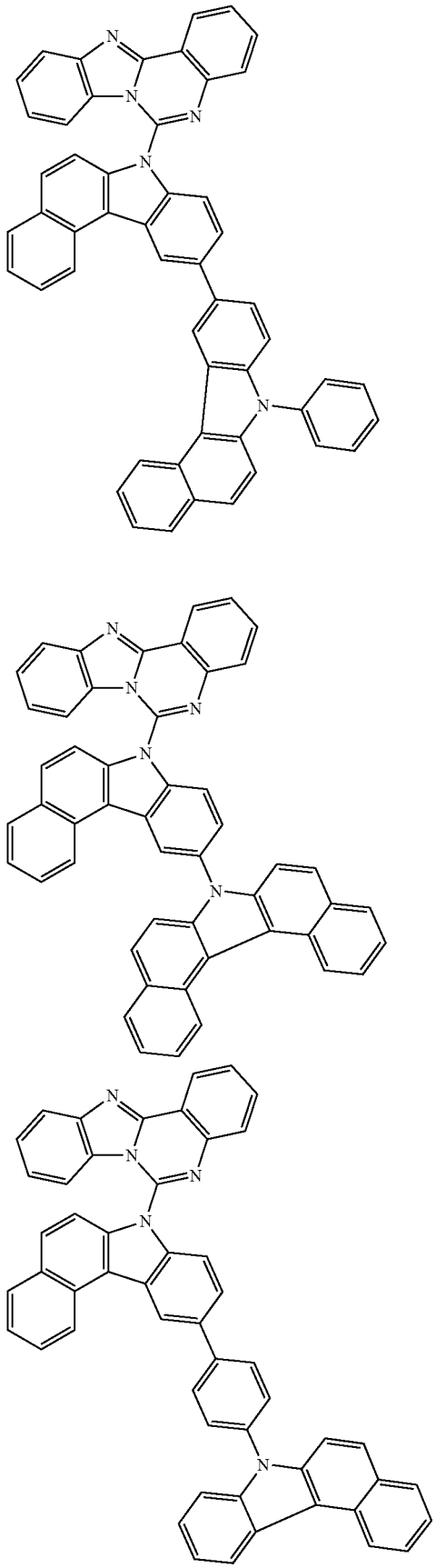
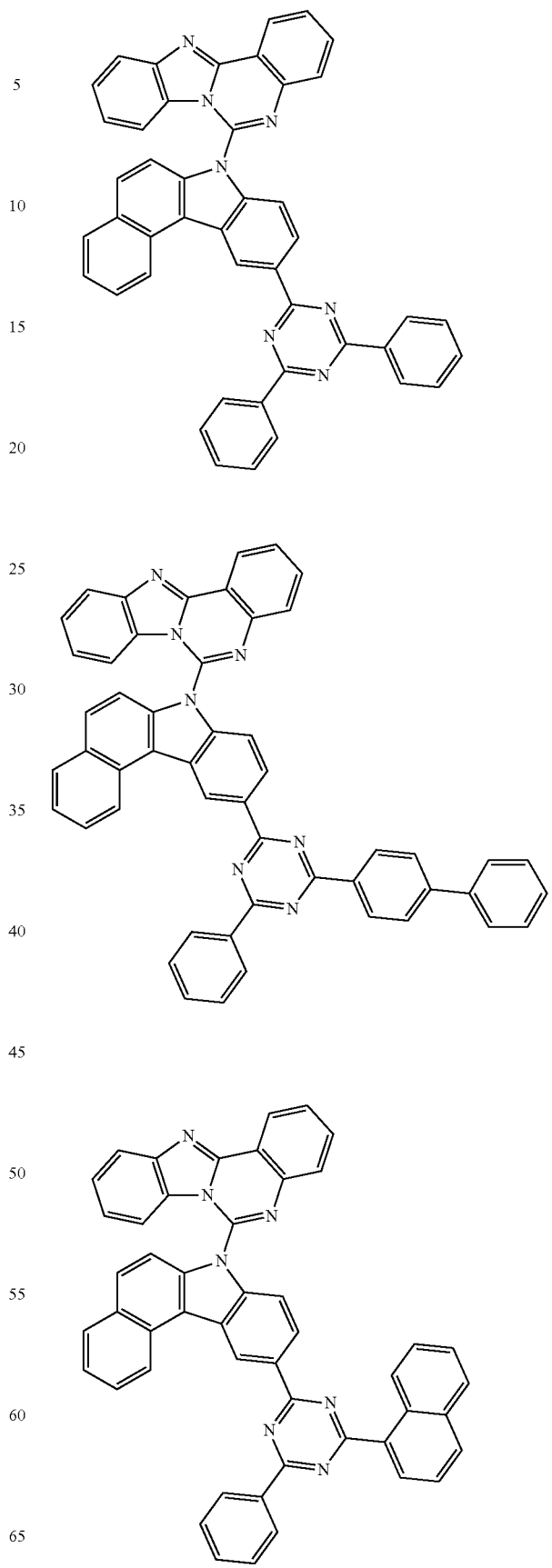

109
-continued
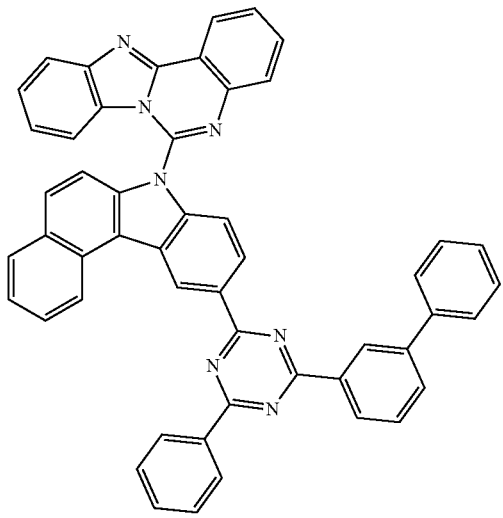
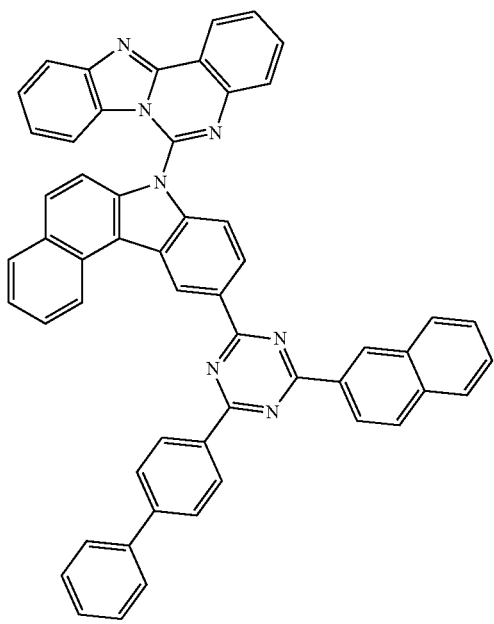
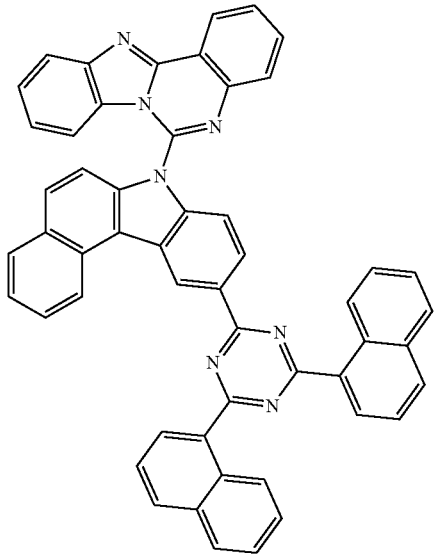
110
-continued
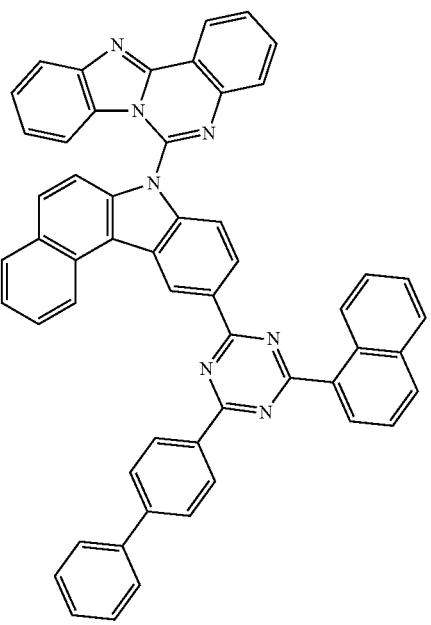
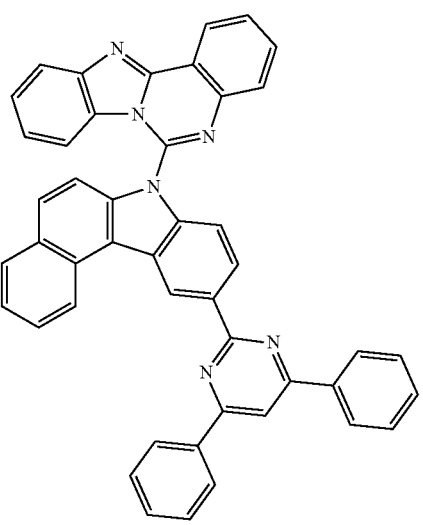
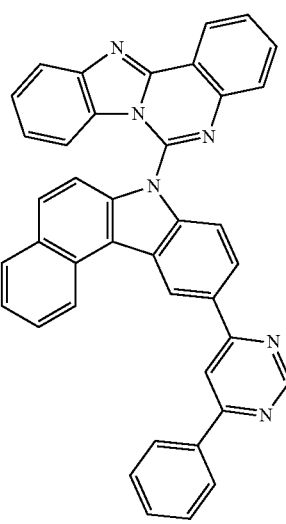

111
-continued
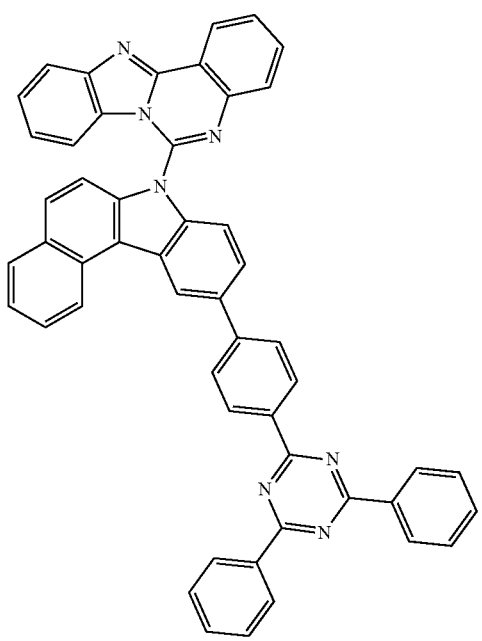
112
-continued
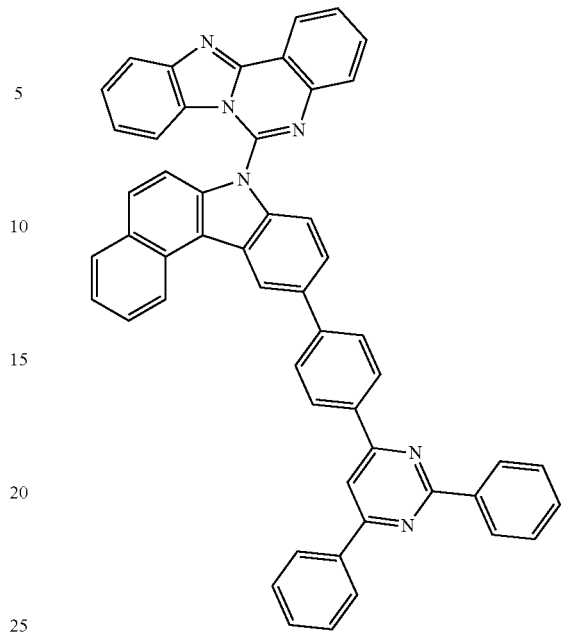
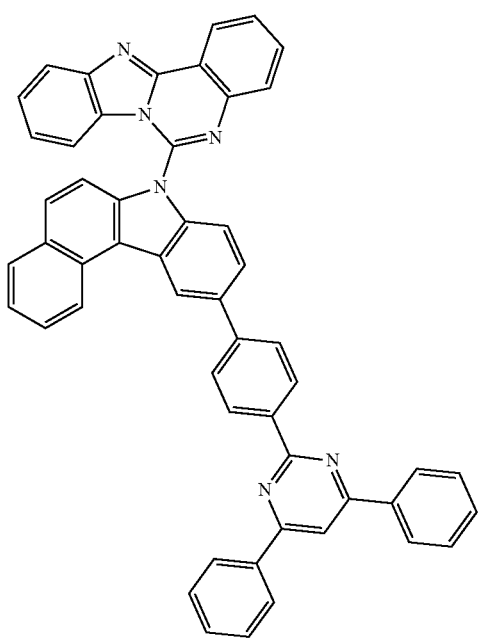
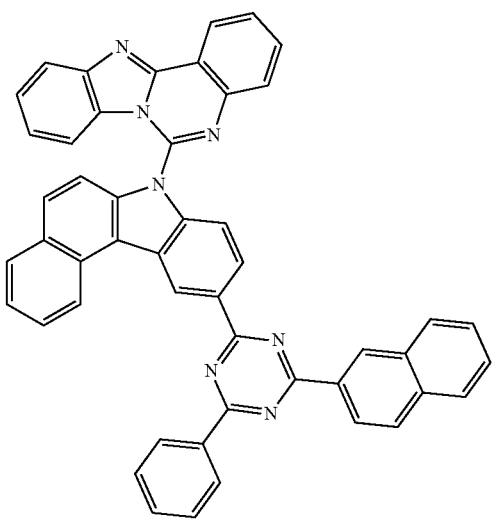

113
-continued
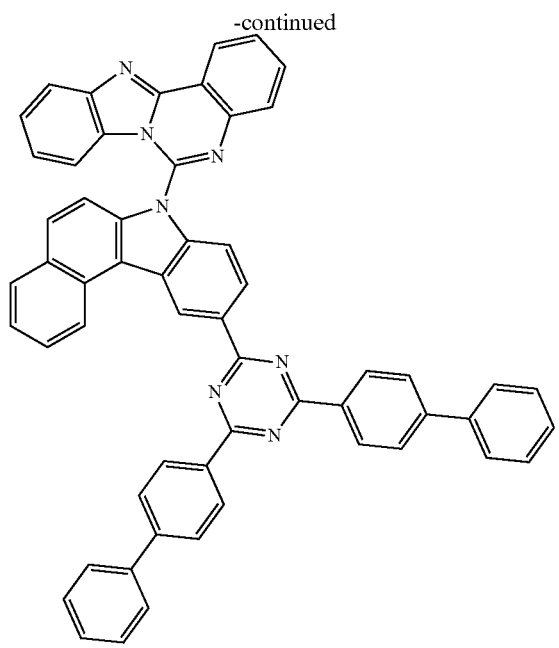
114
-continued
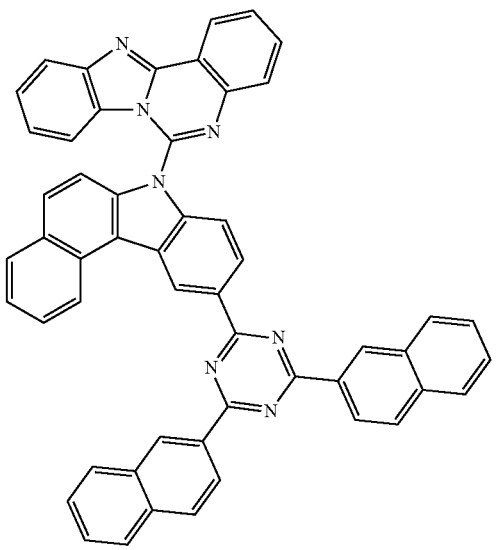
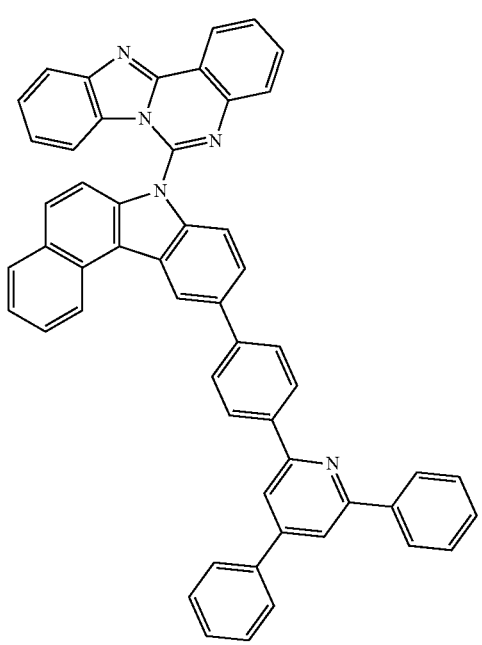
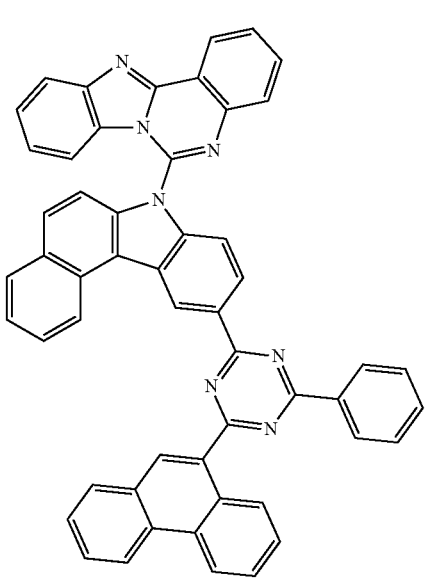

115
-continued
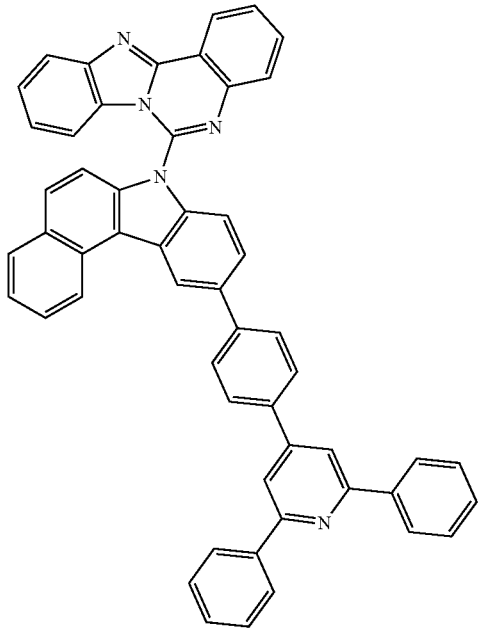
116
-continued
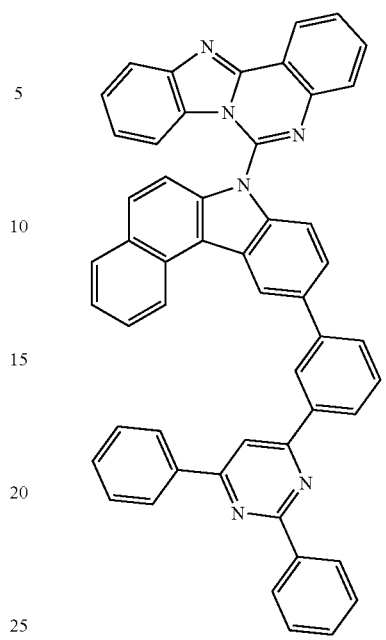
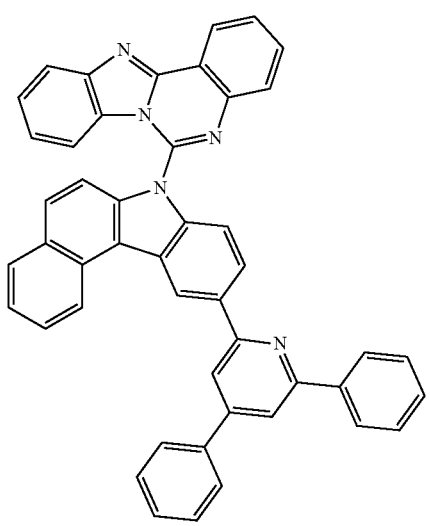
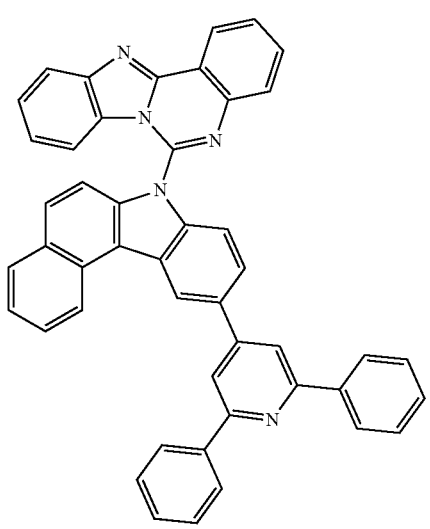

117
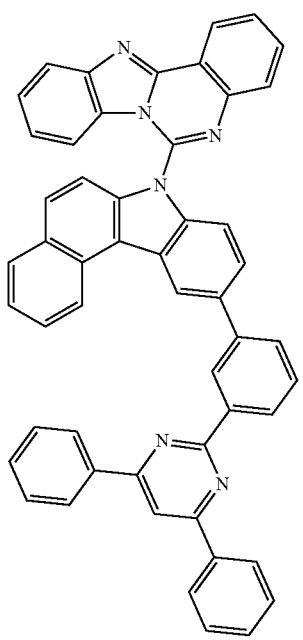
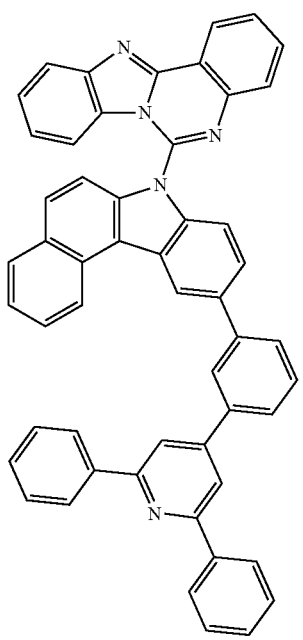
118
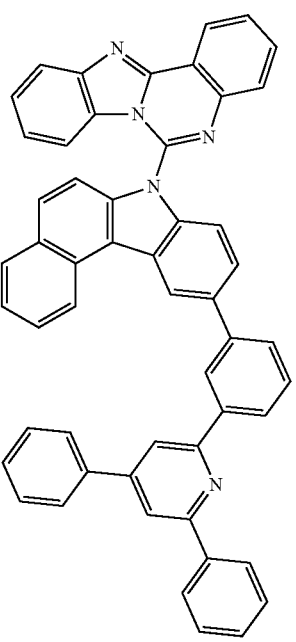
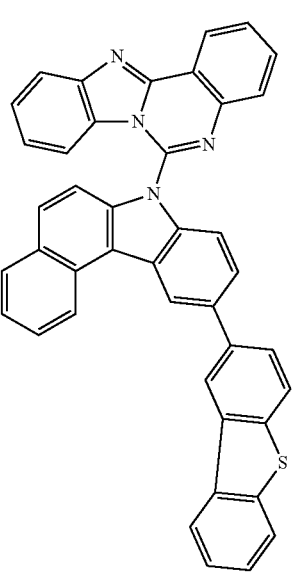

119
-continued
120
-continued
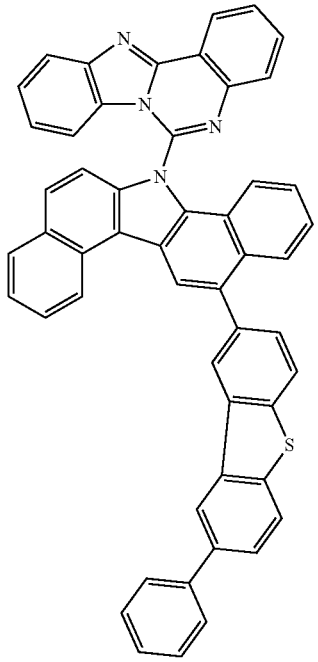
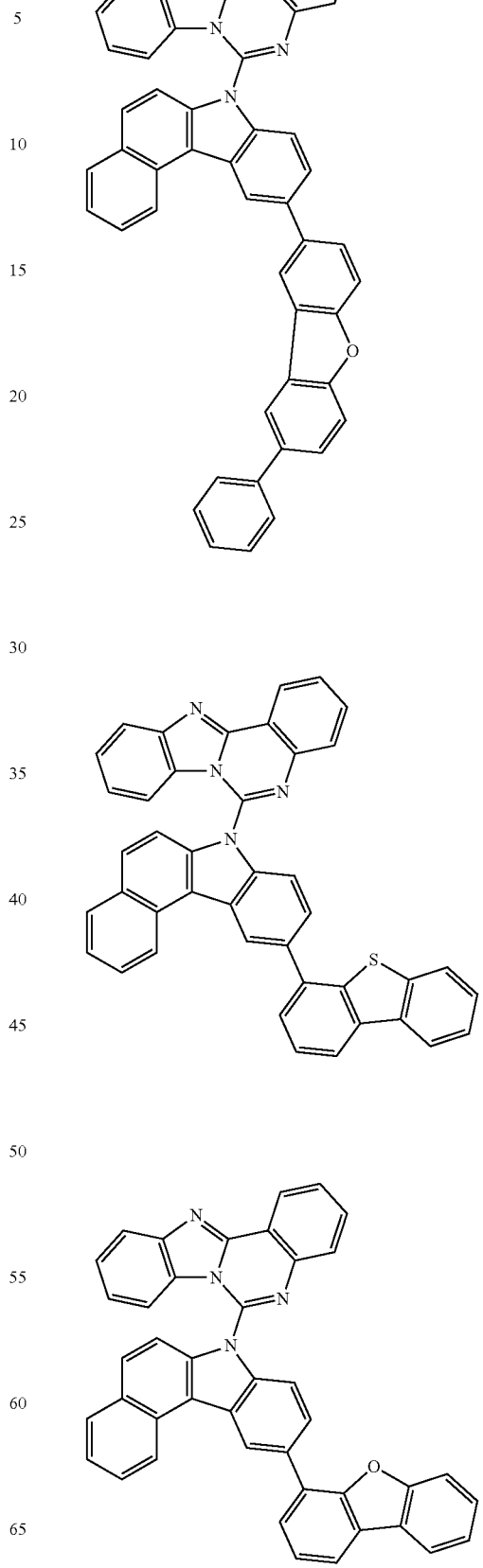

121
-continued
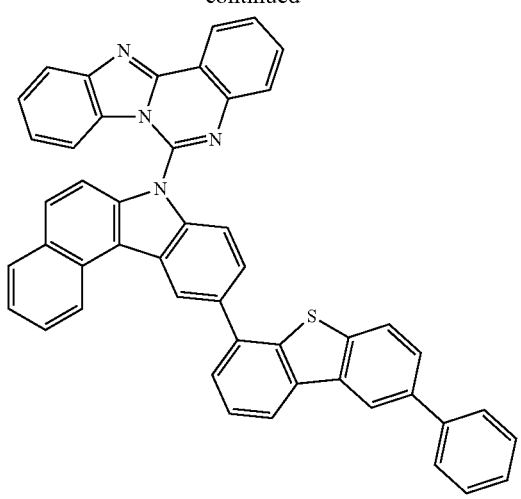
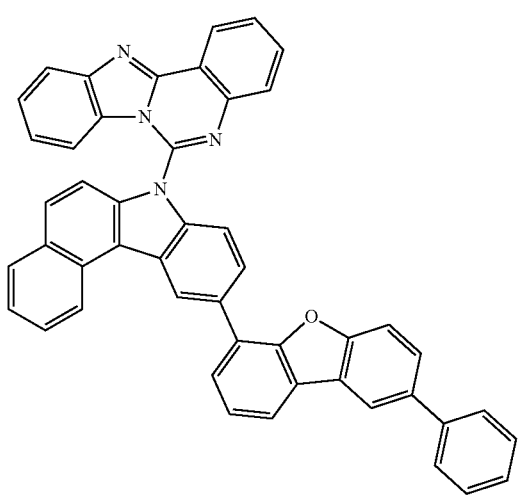
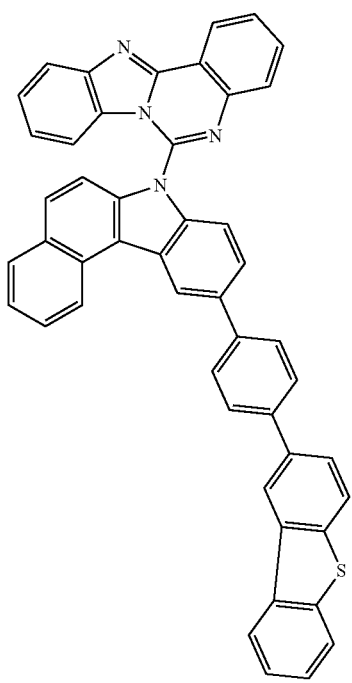
122
-continued
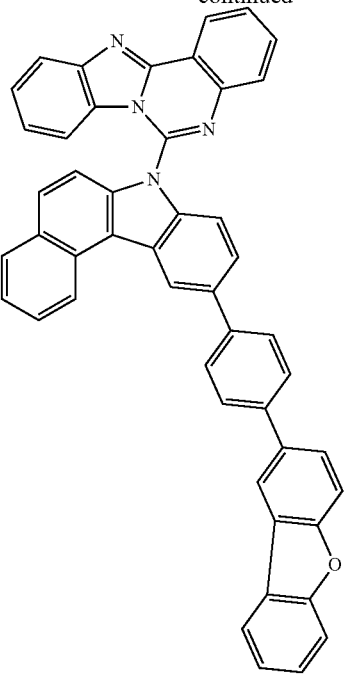
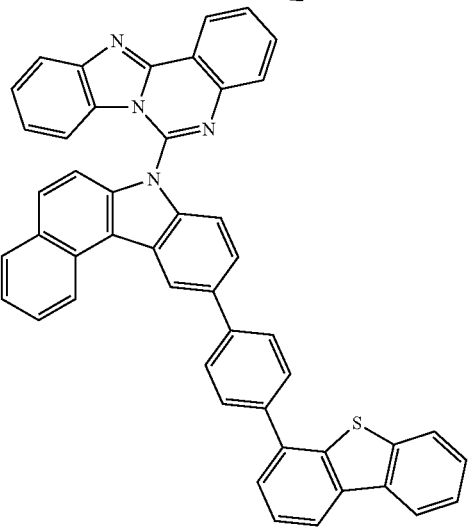
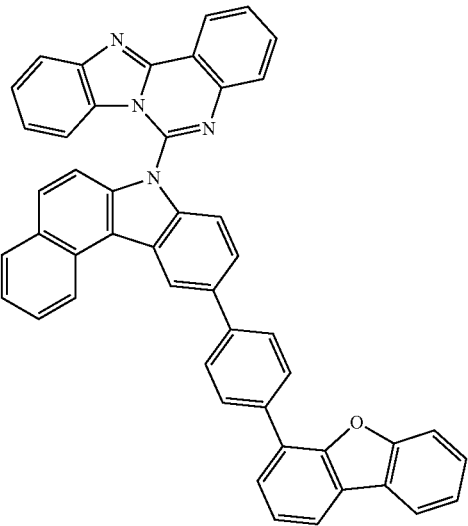

123
-continued
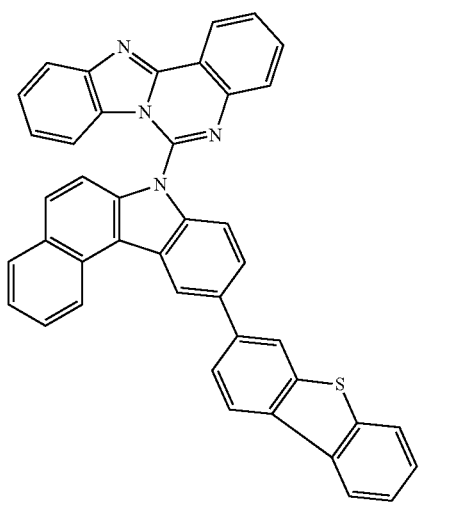
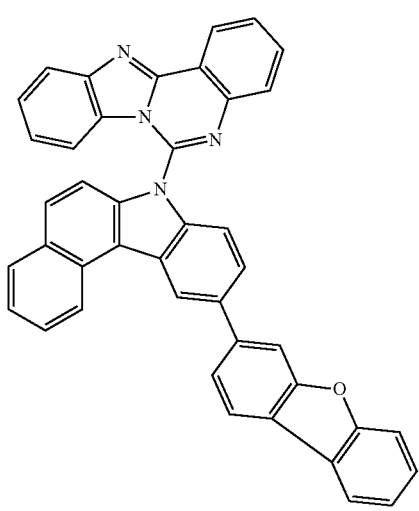
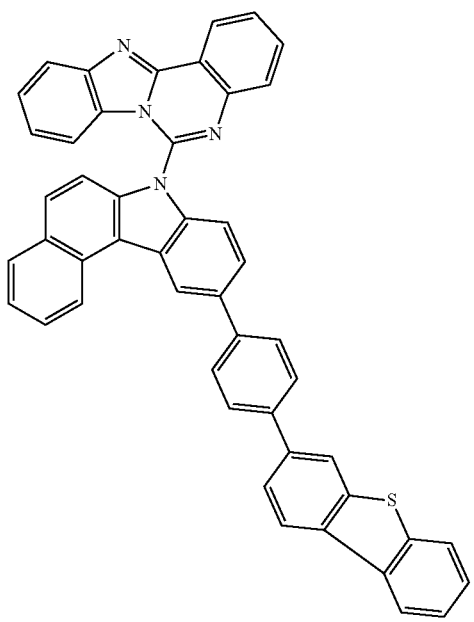
124
-continued
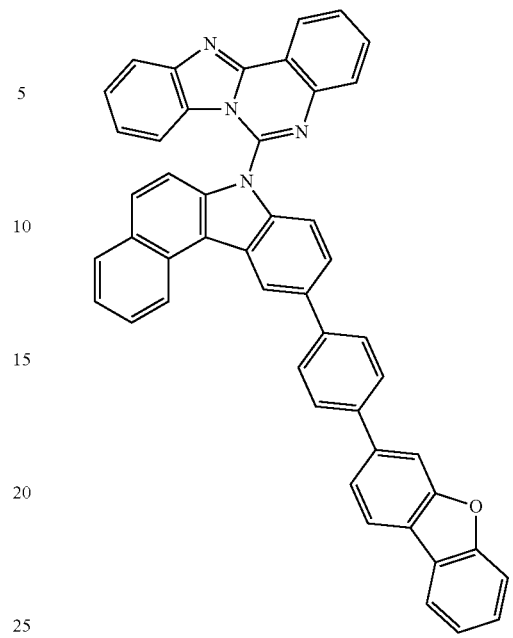
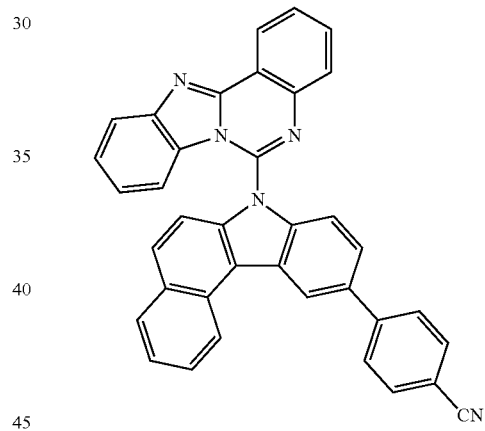
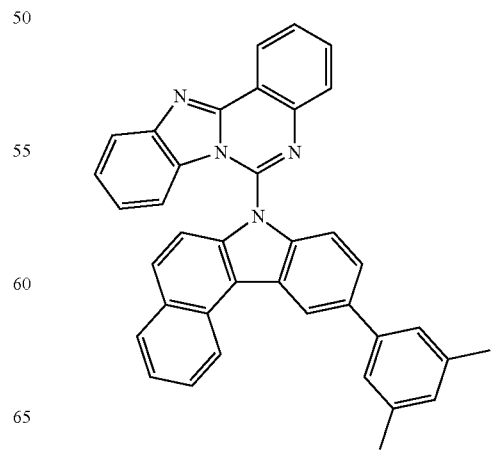

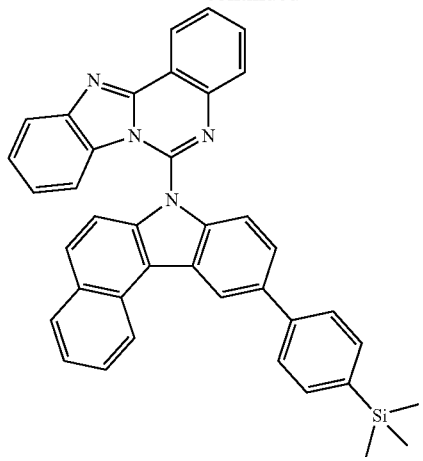
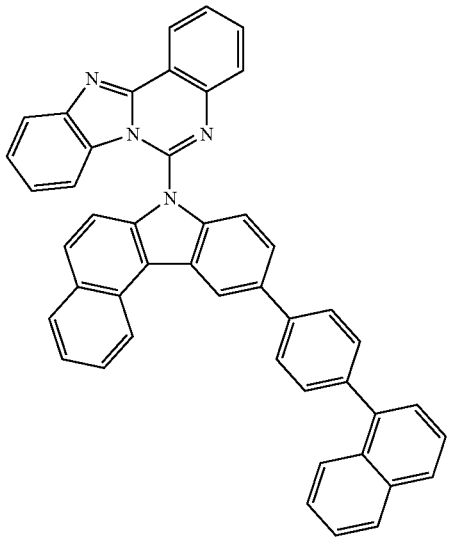
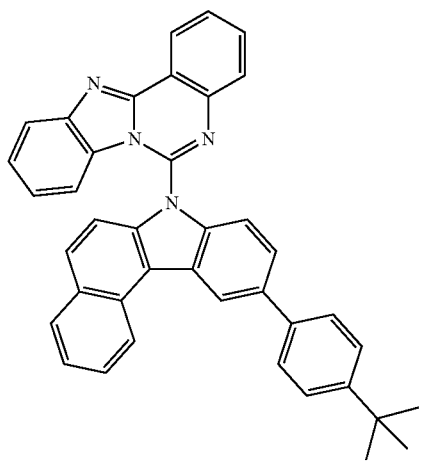
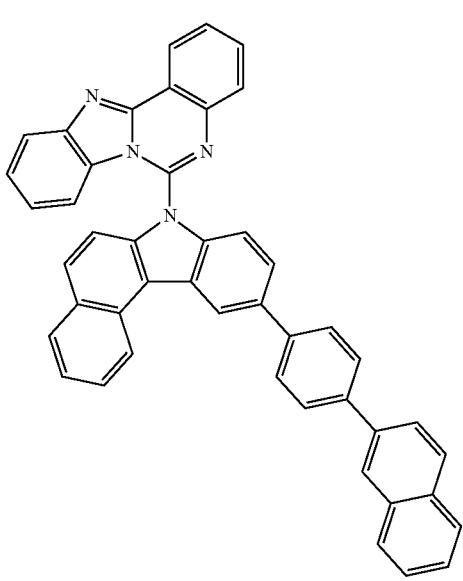
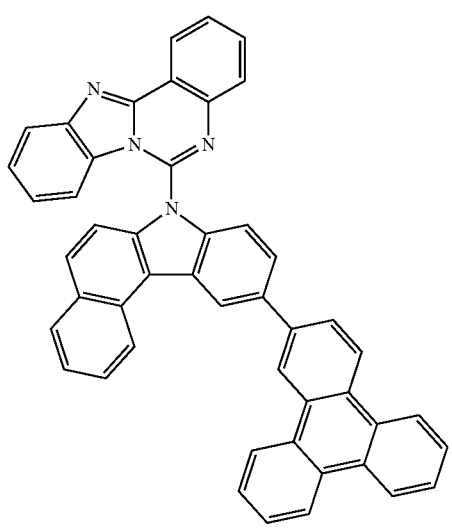
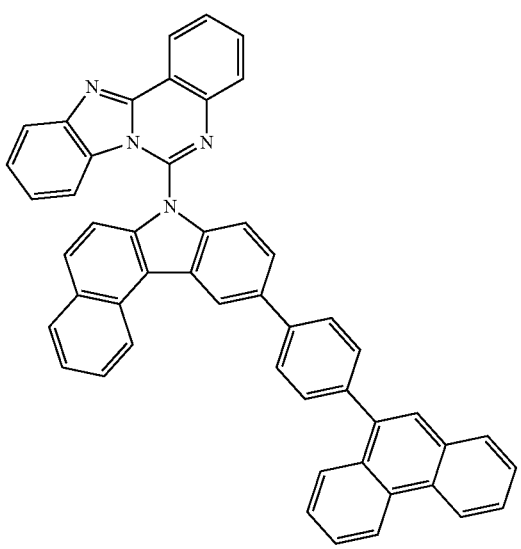

127
-continued
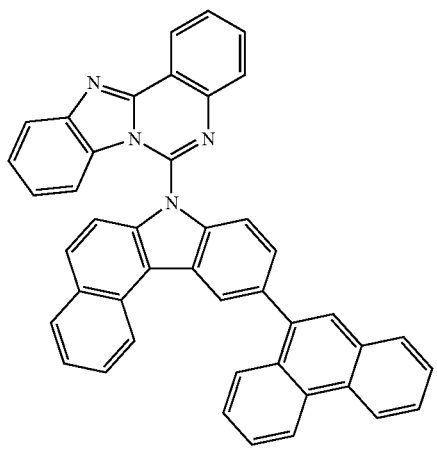
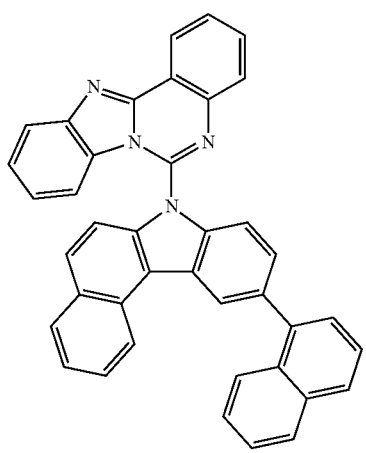
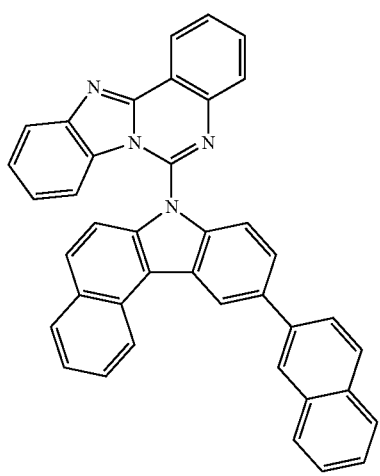
128
-continued
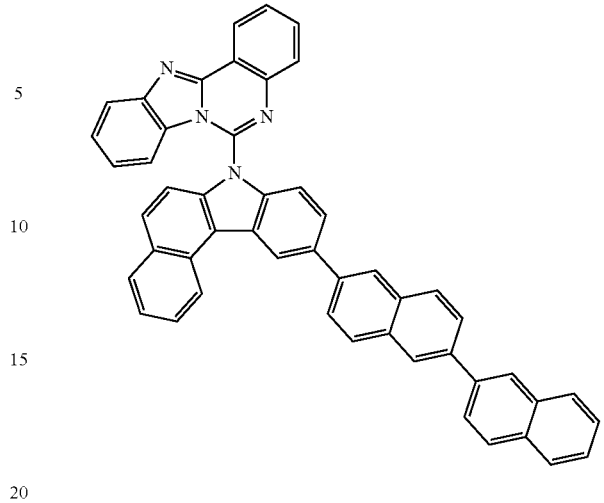
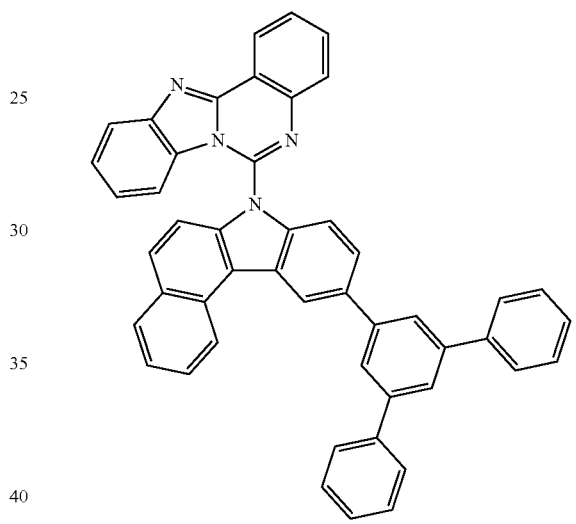
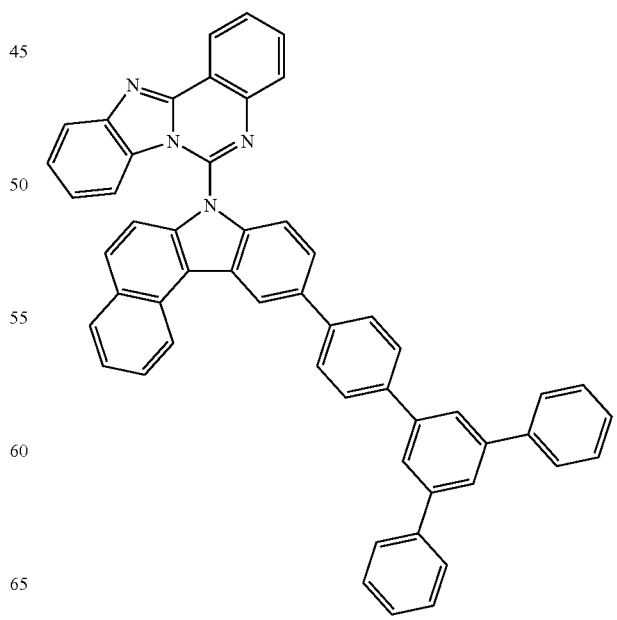

129
-continued
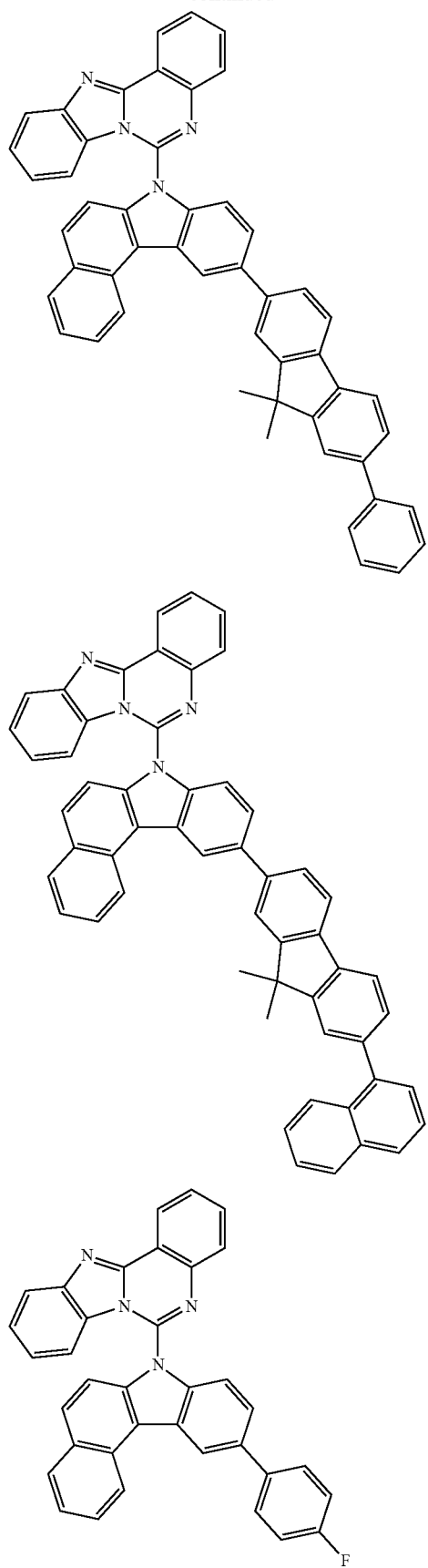
130
-continued
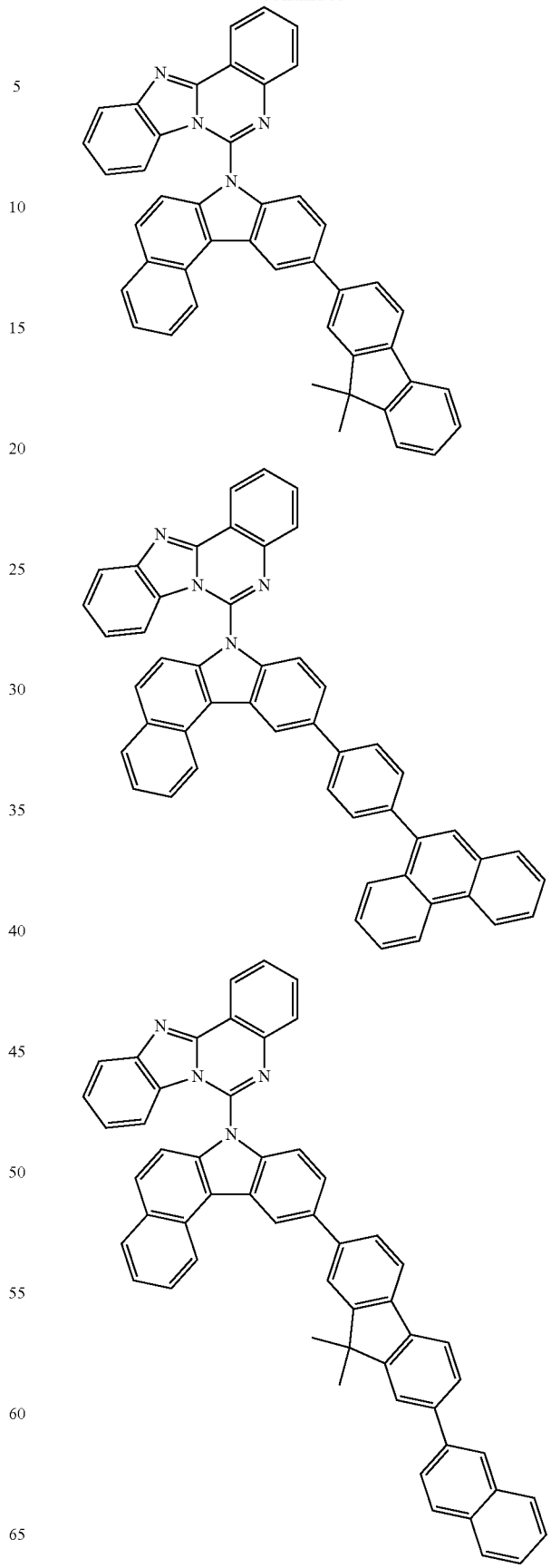

131
-continued
132
-continued
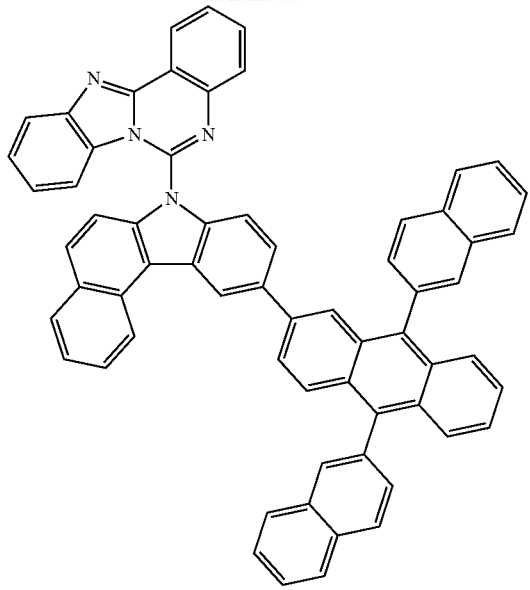
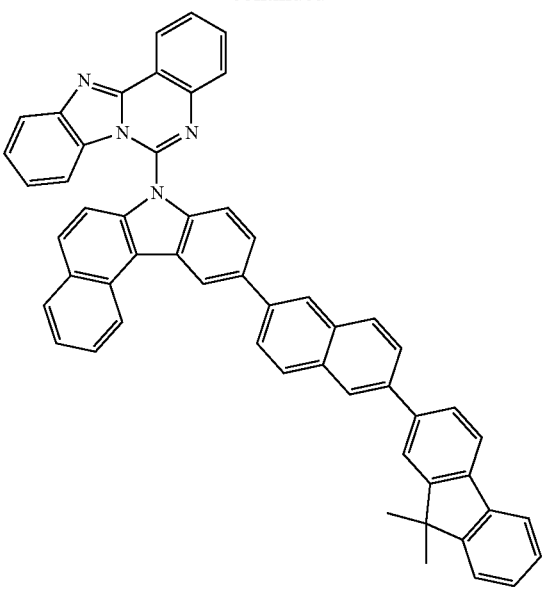
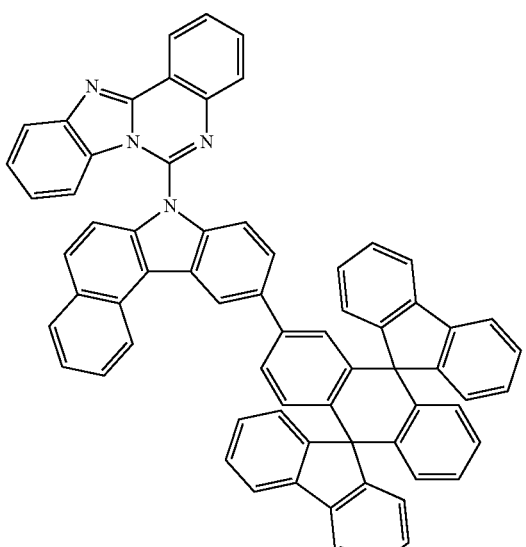
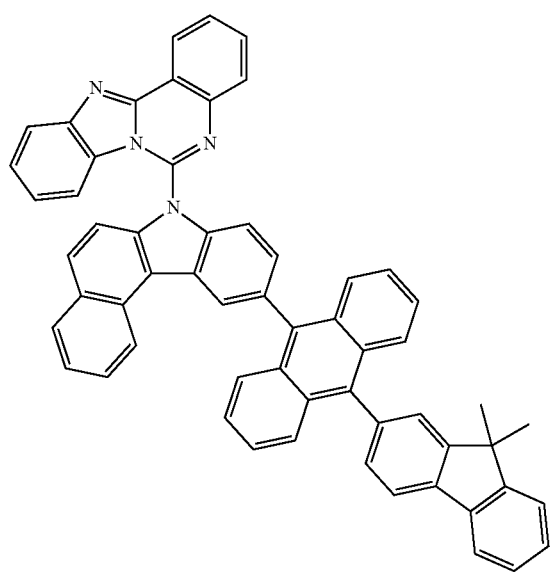
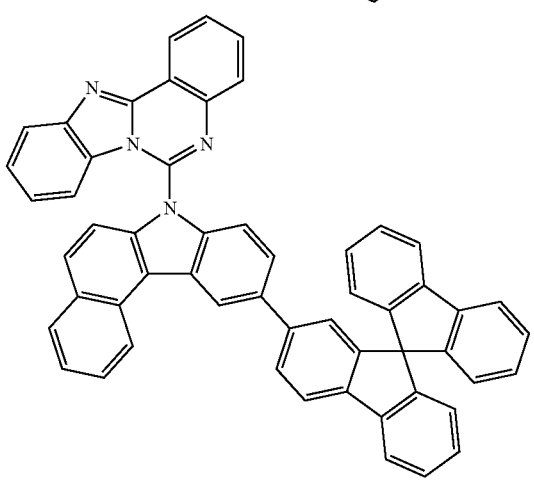

133
-continued
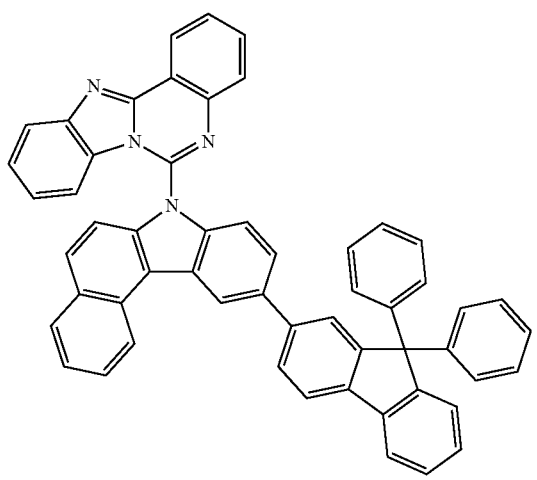
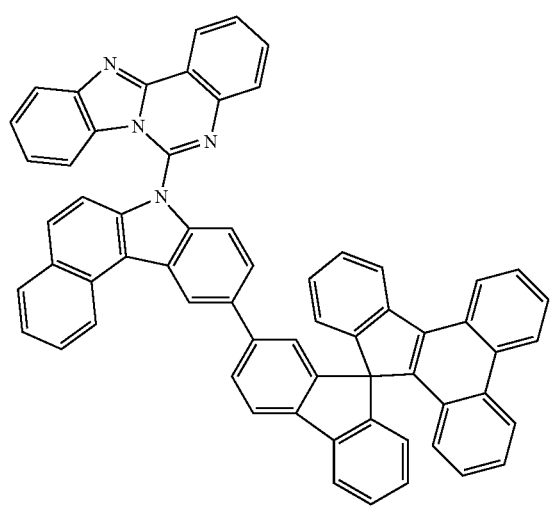
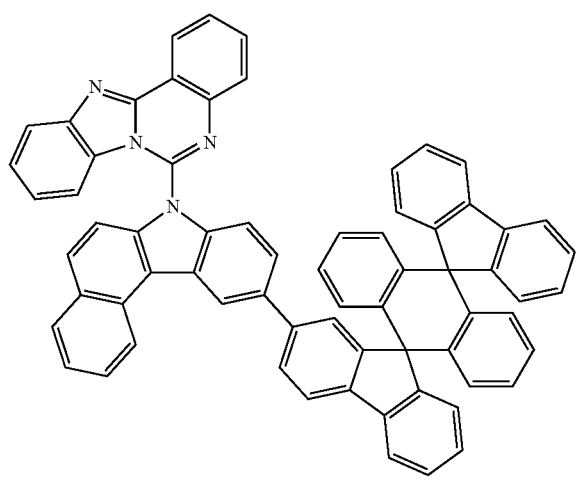
134
-continued
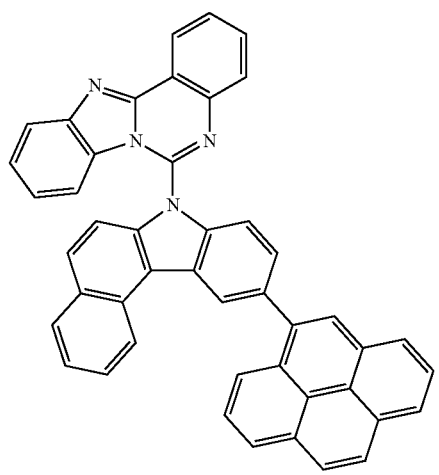
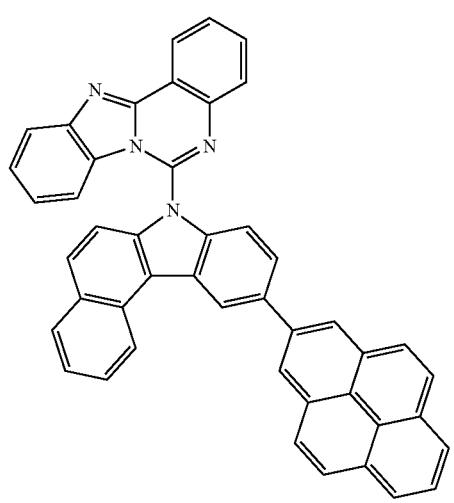
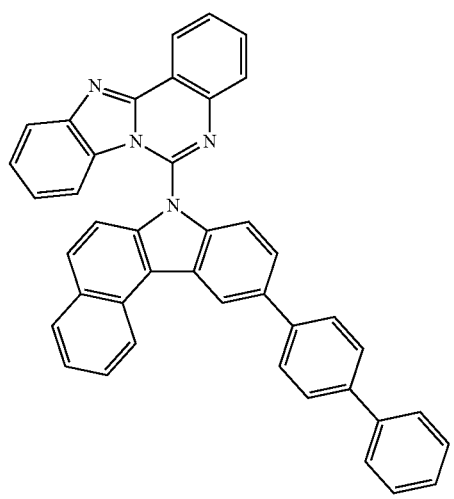

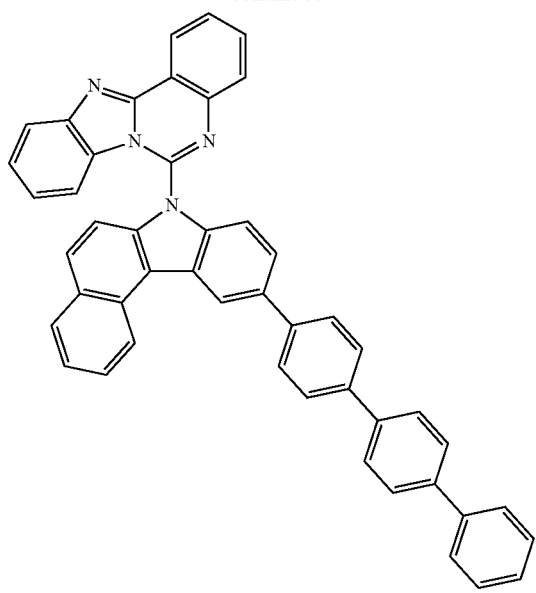
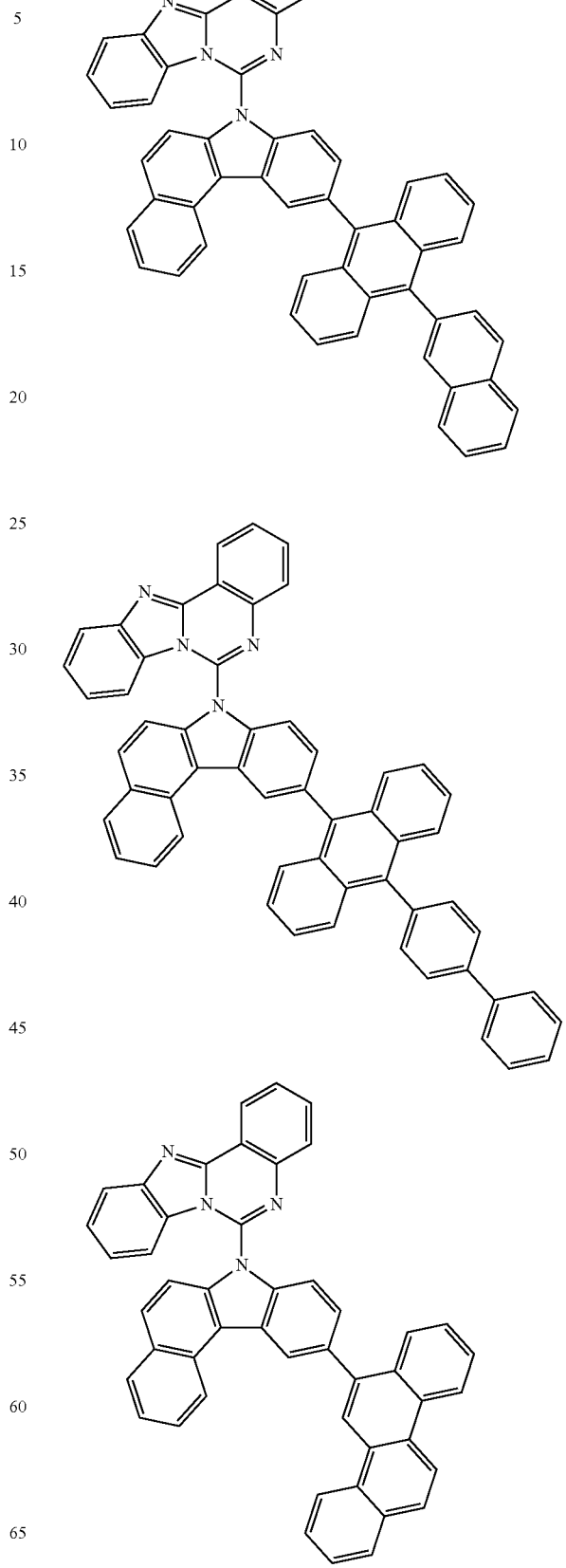

137
-continued
138
-continued
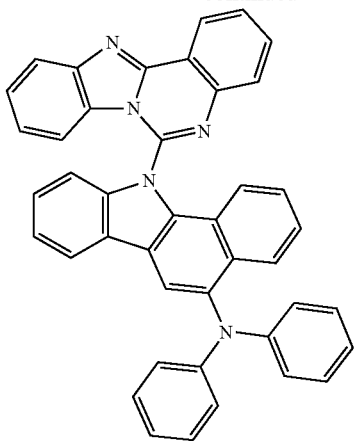
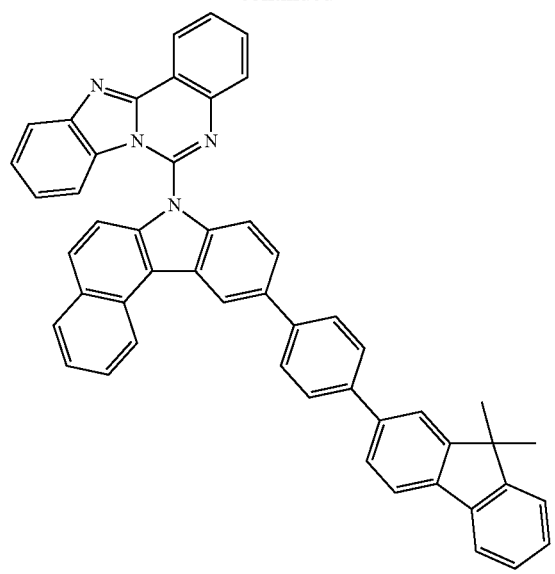
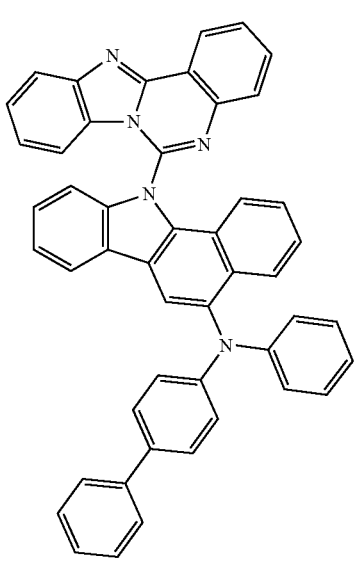
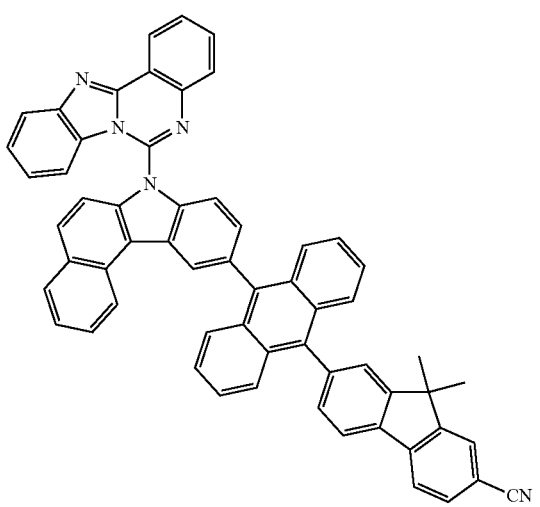
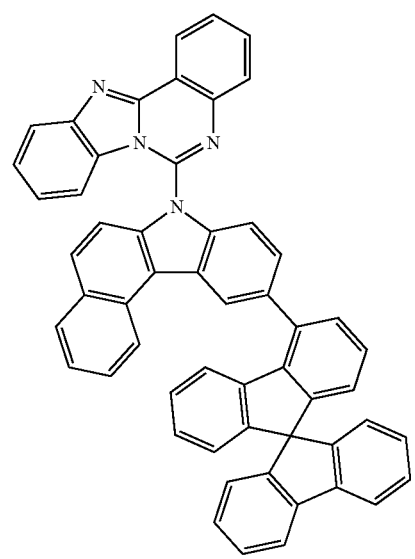 [SMILES: c1ccc2c(c1)-c1ccccc1C21c2ccccc2-c2c(-c3ccc4c(c3)c3c5ccccc5ccc3n4-c3nc4ccccc4c4nc5ccccc5n34)cccc21]

139
-continued
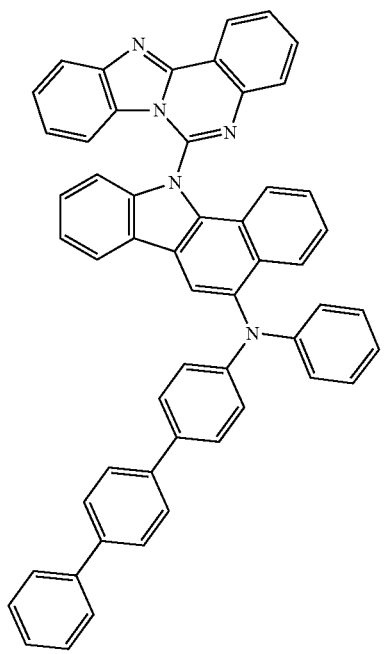
140
-continued
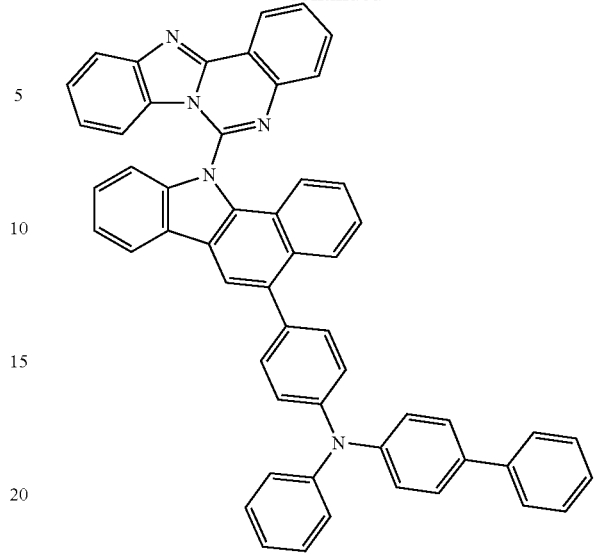
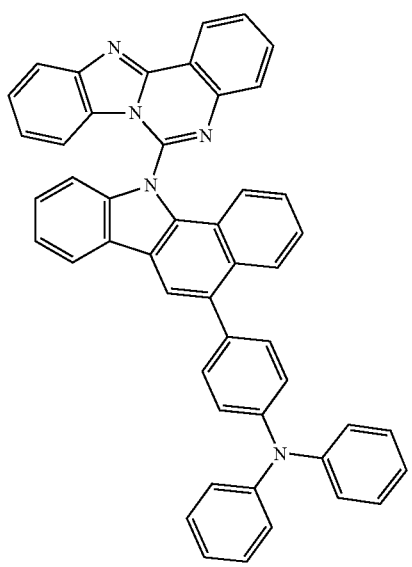
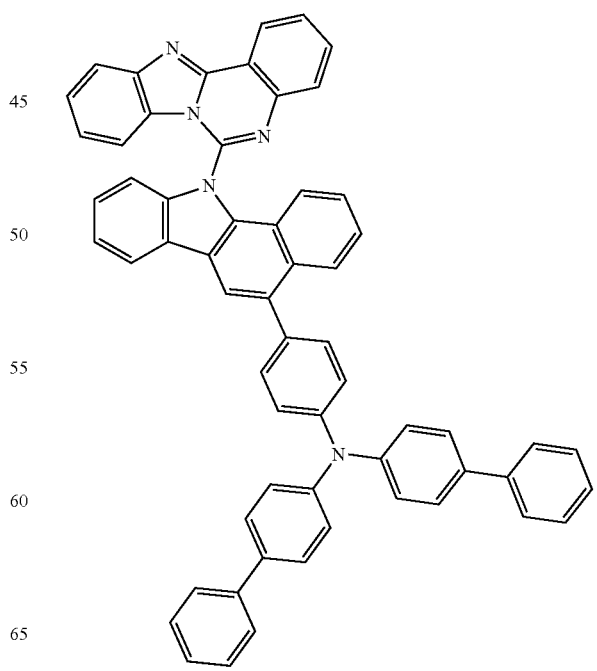

141
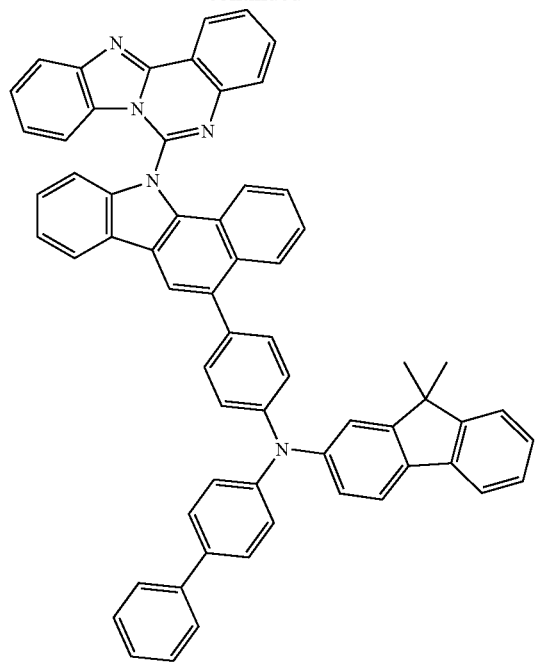
142
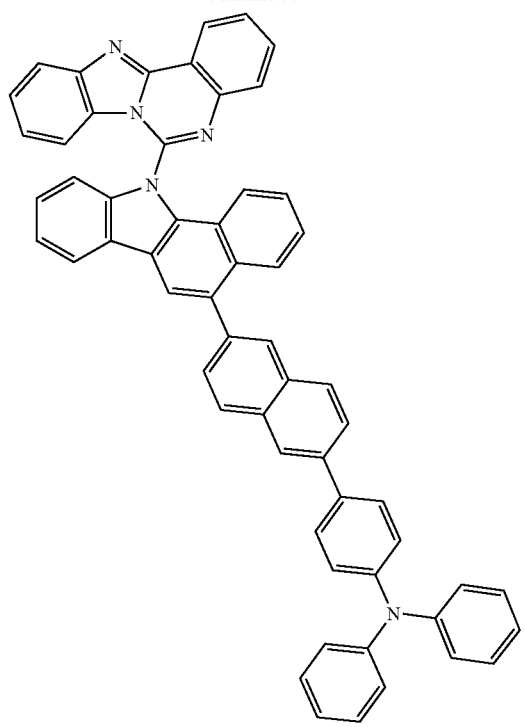
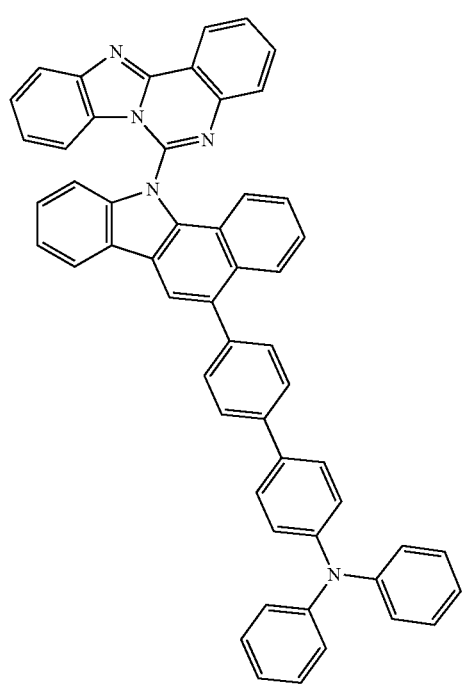
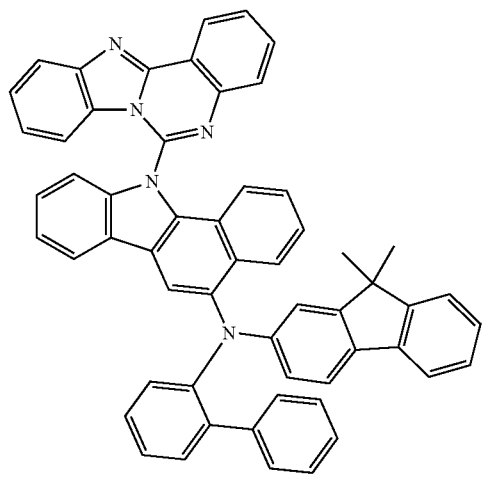

143
-continued
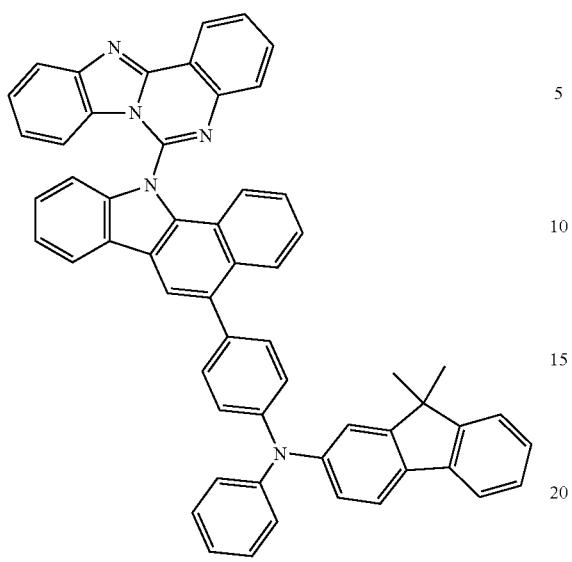
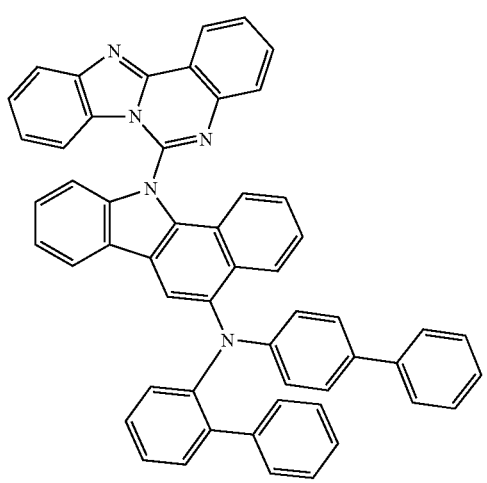
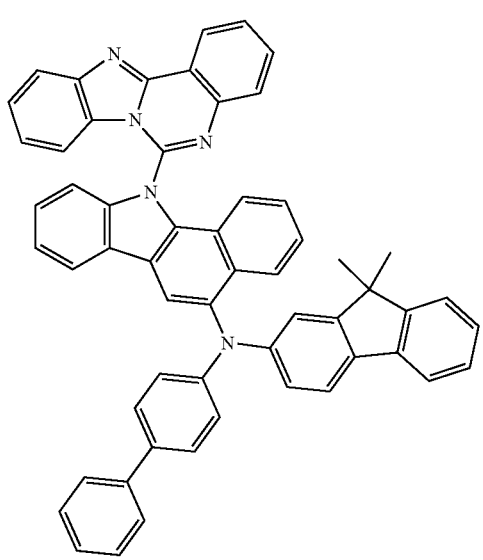
144
-continued
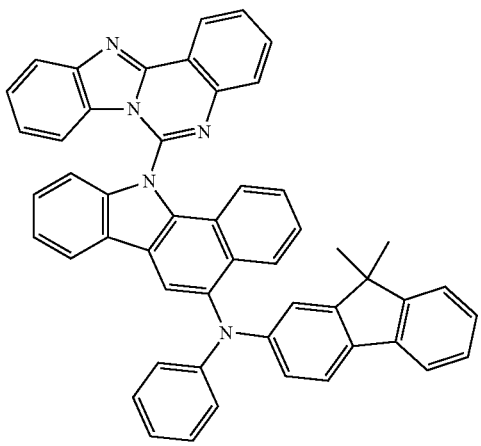
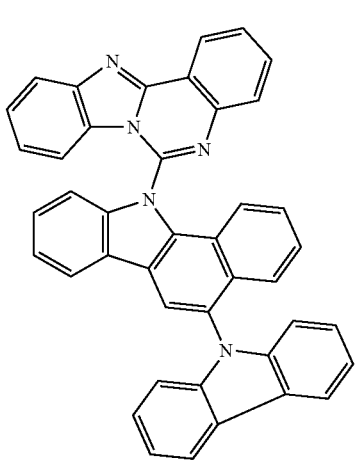
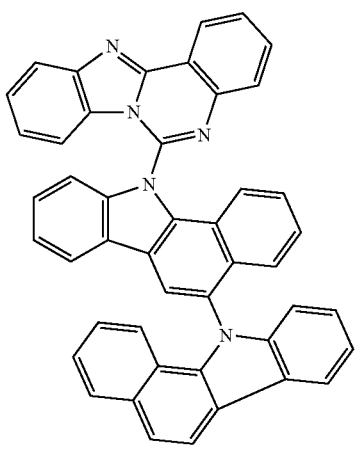

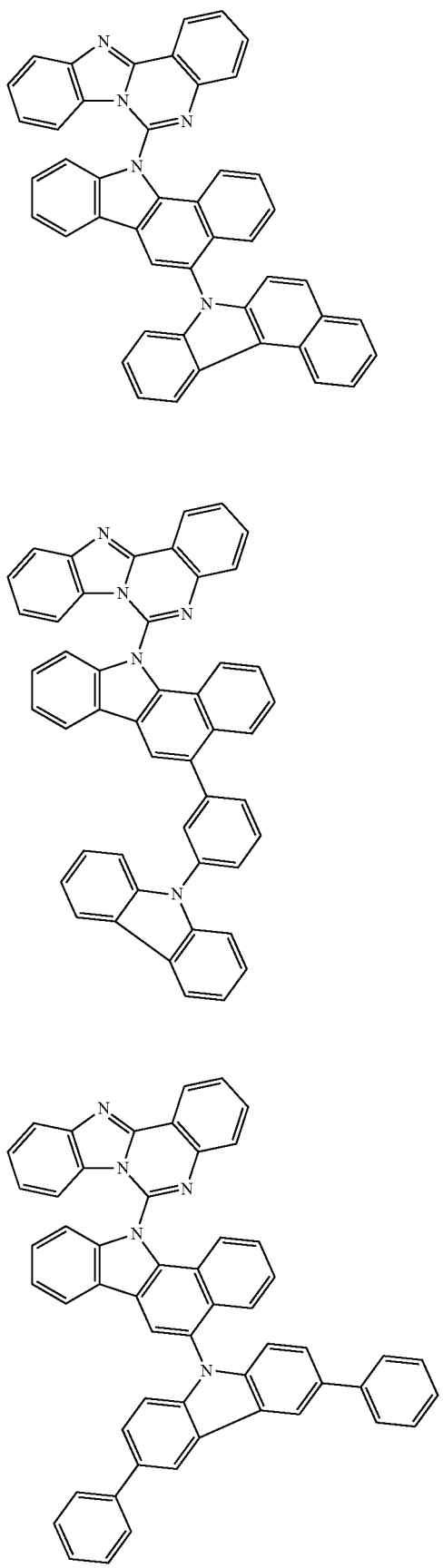
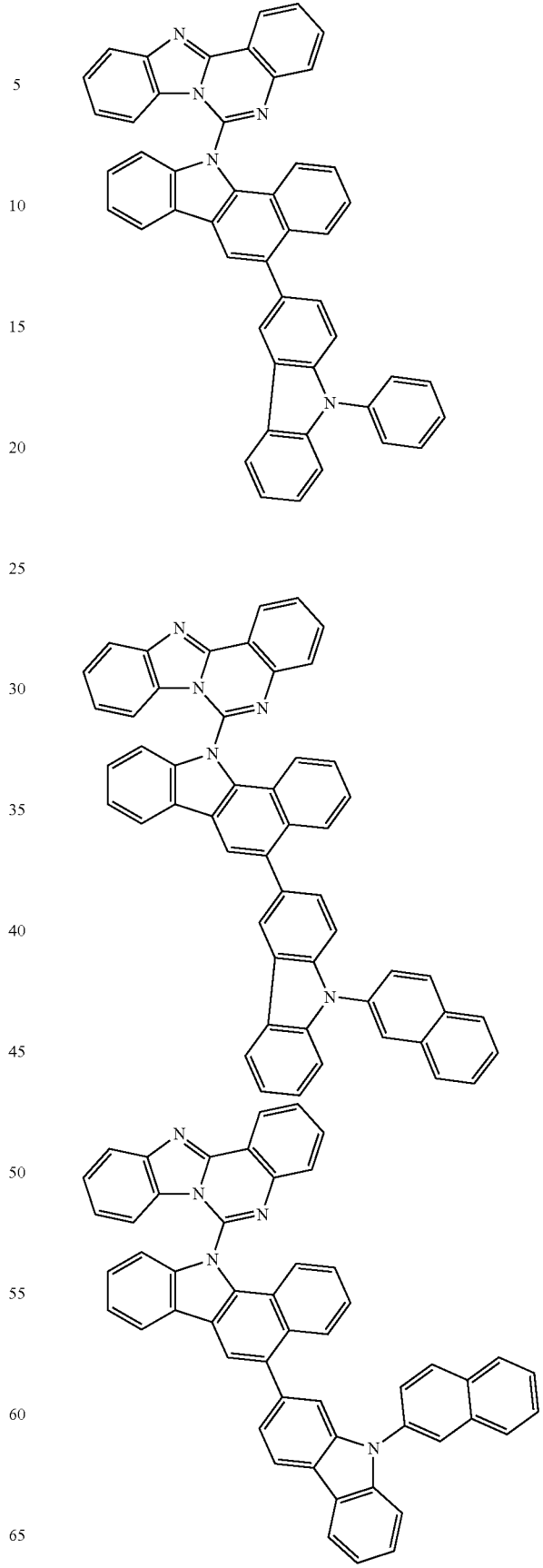

147
-continued
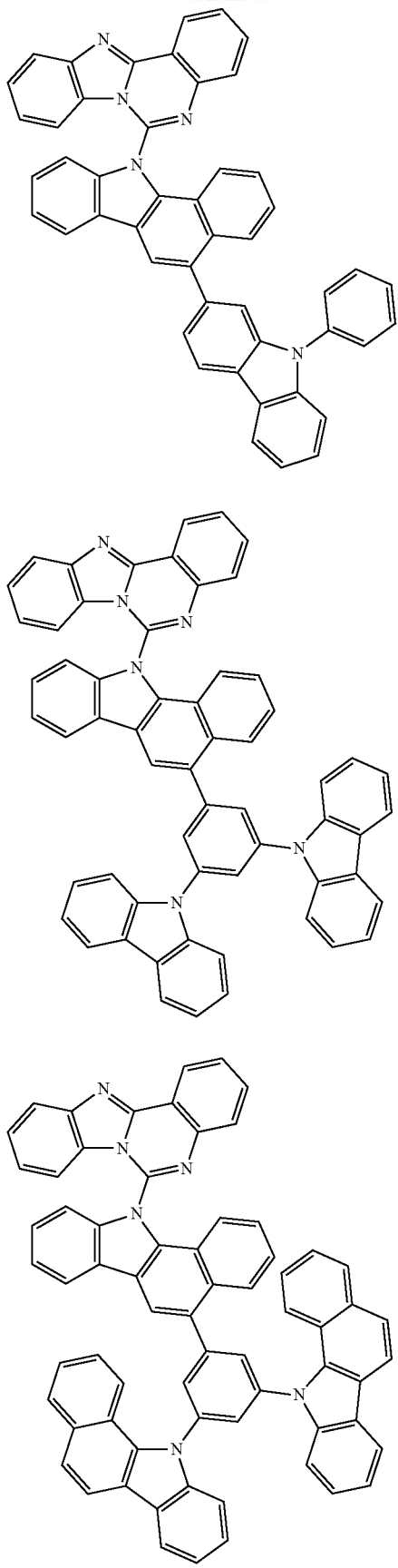
148
-continued
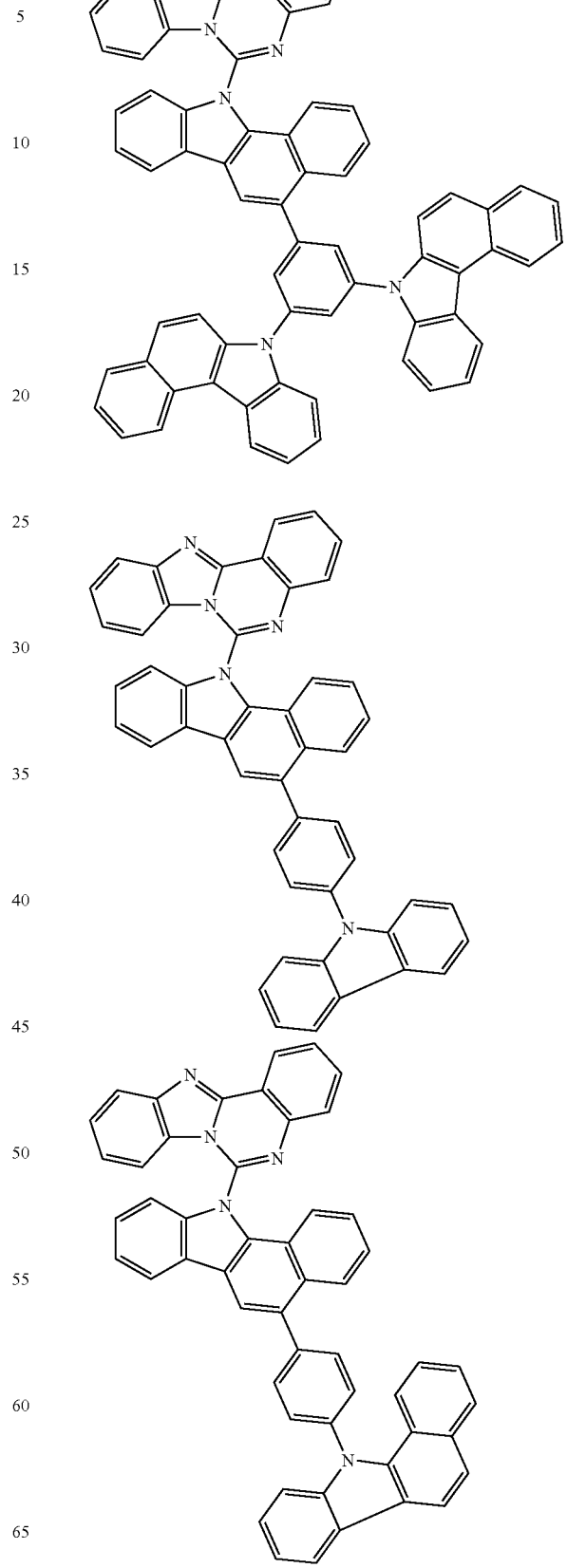

149
-continued
150
-continued
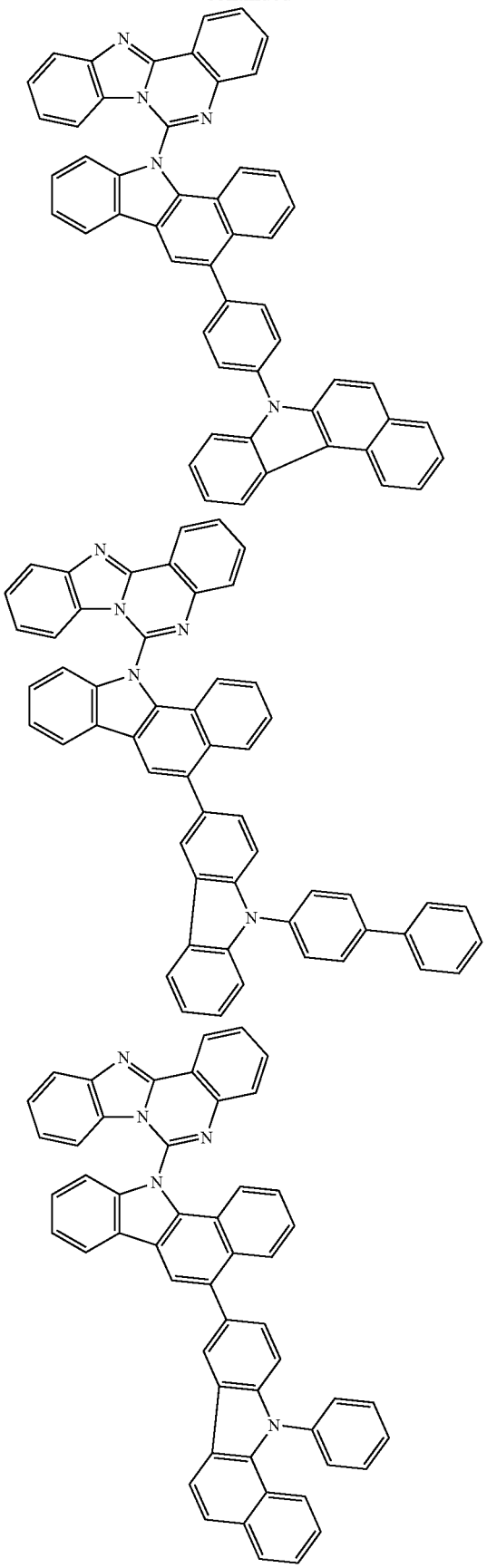
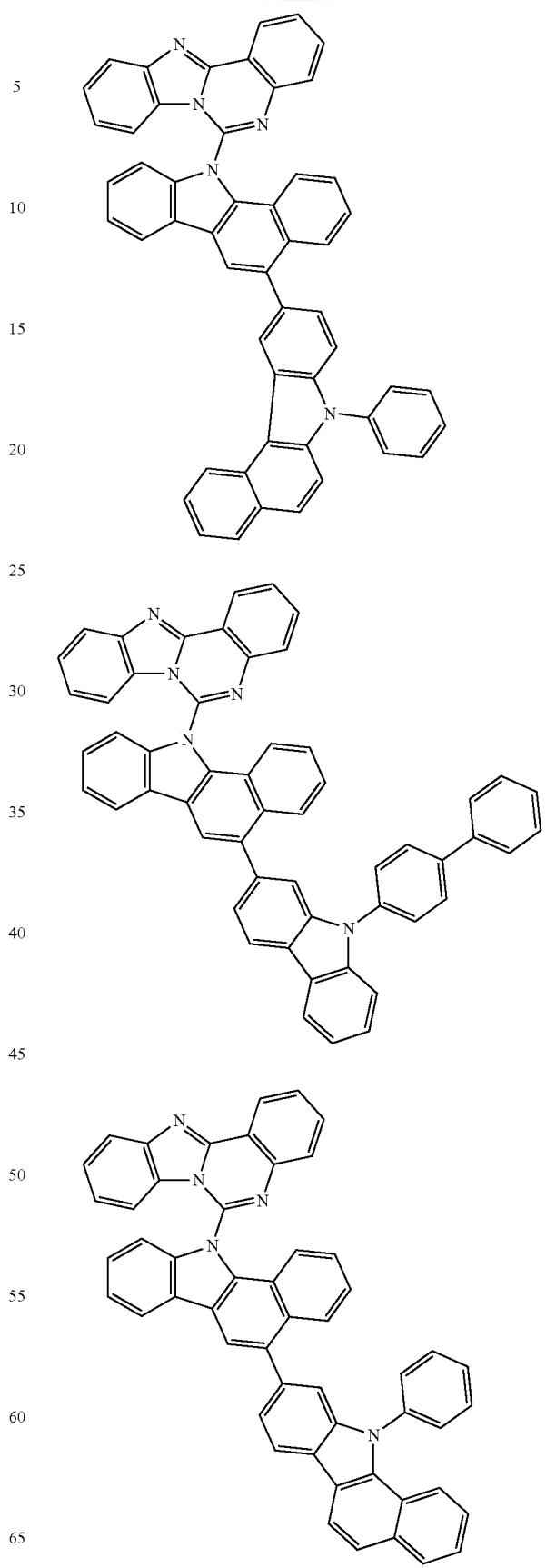

151
-continued
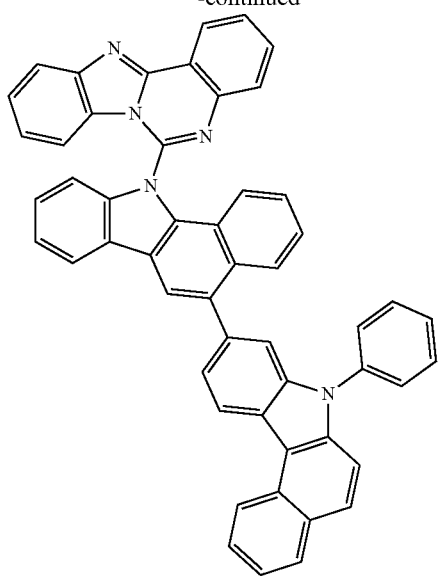
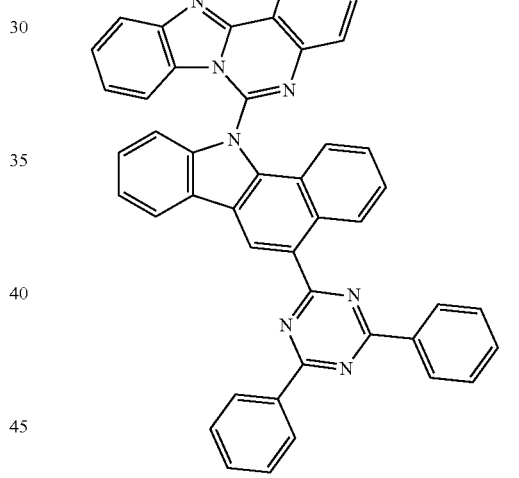
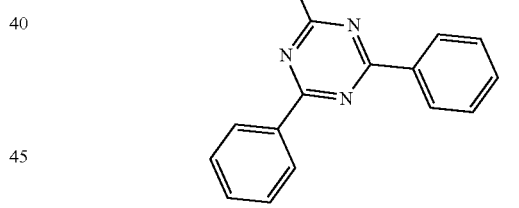
152
-continued
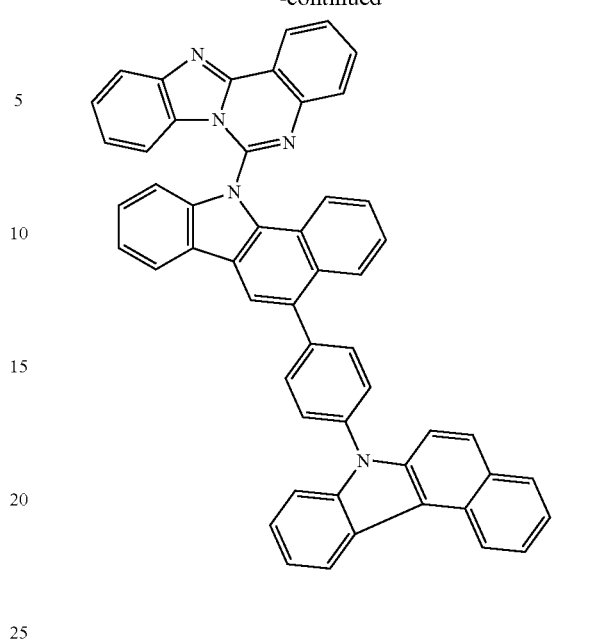
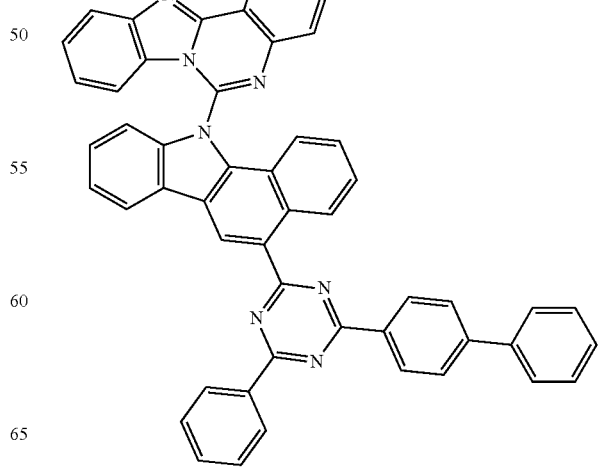
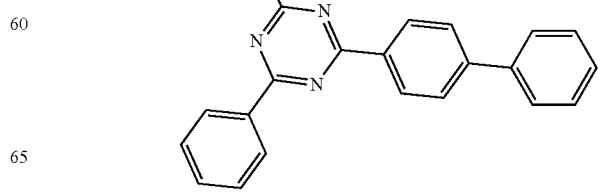

153
-continued
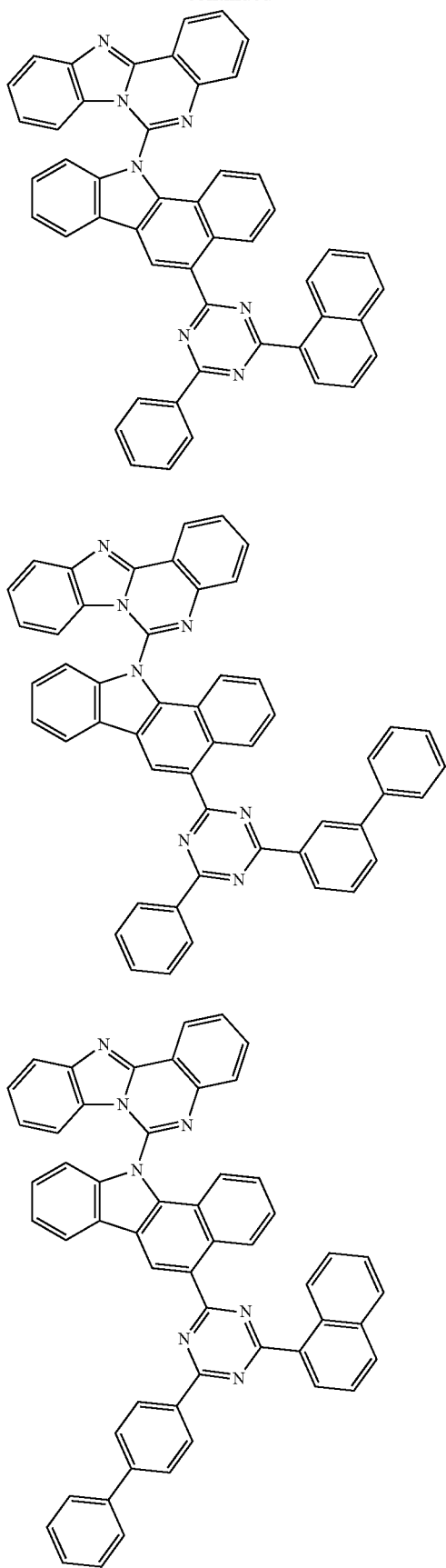
154
-continued
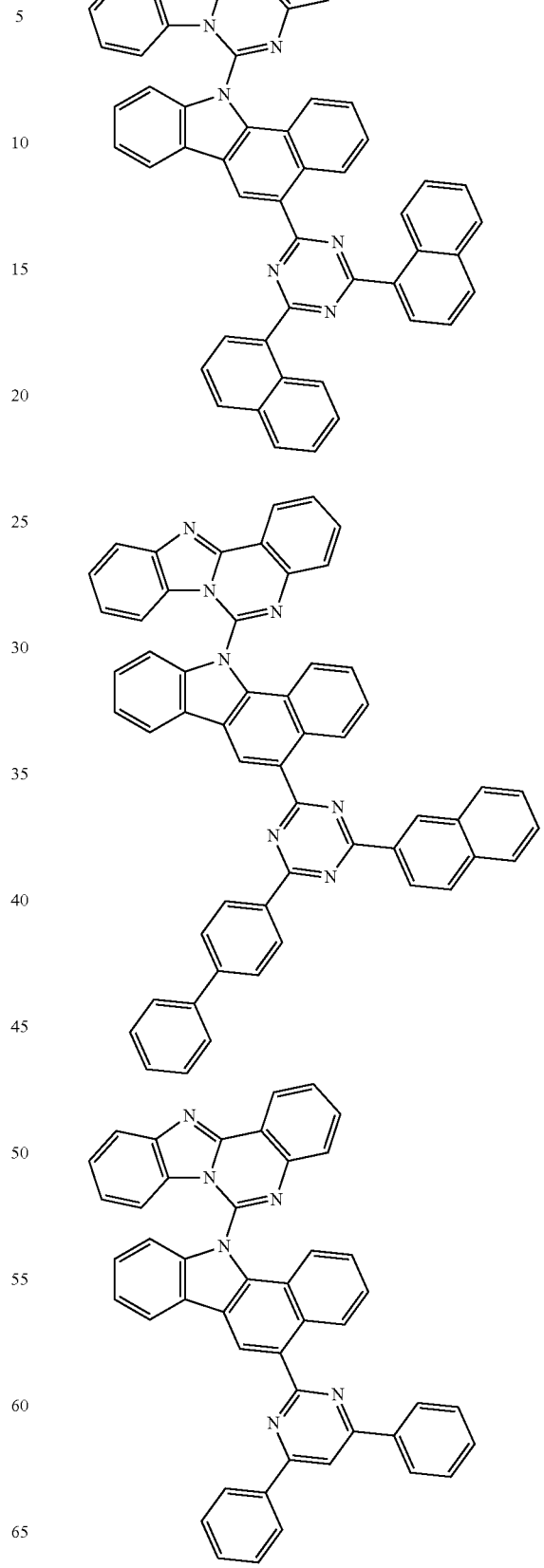

155
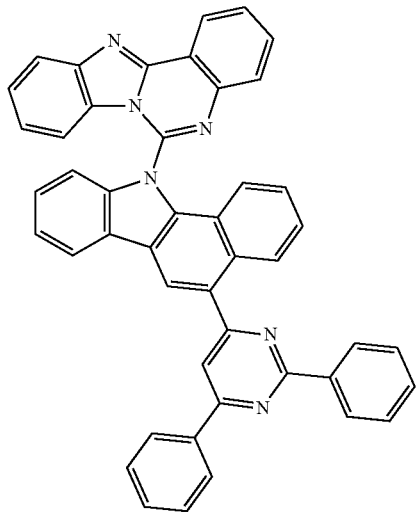
156
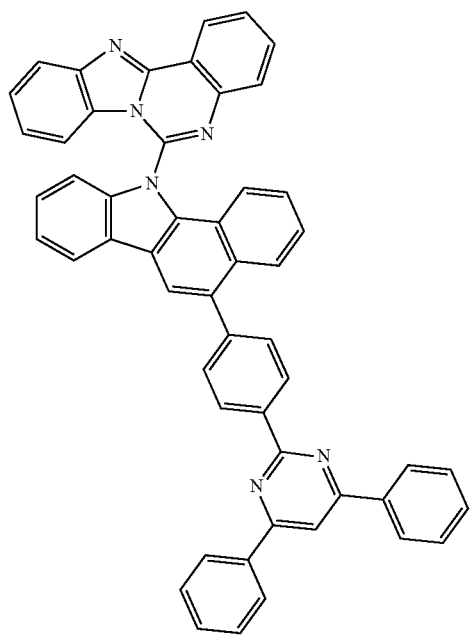
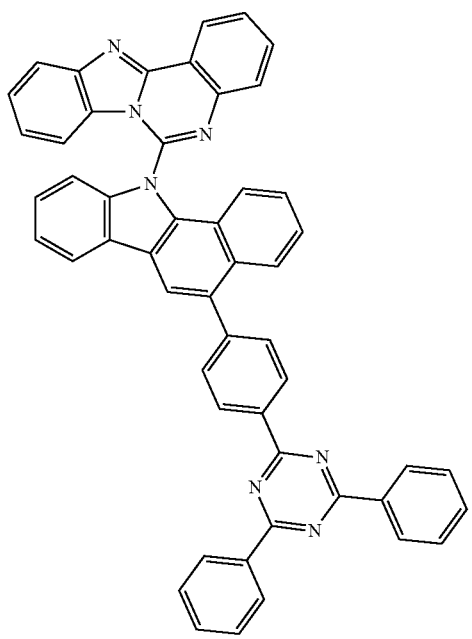
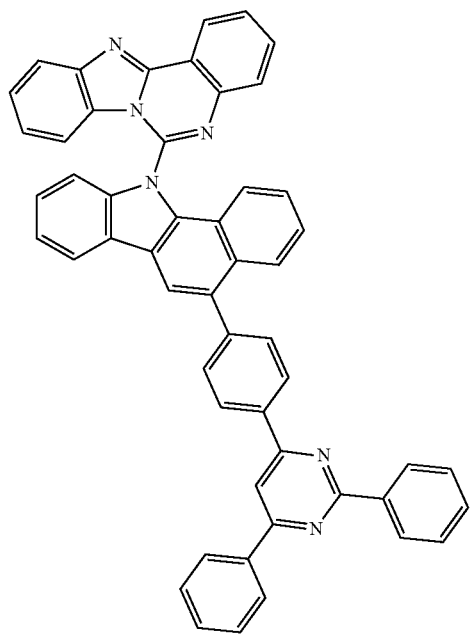

157
-continued
158
-continued
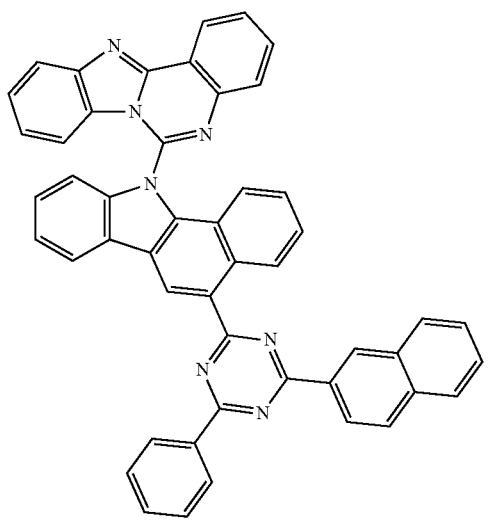
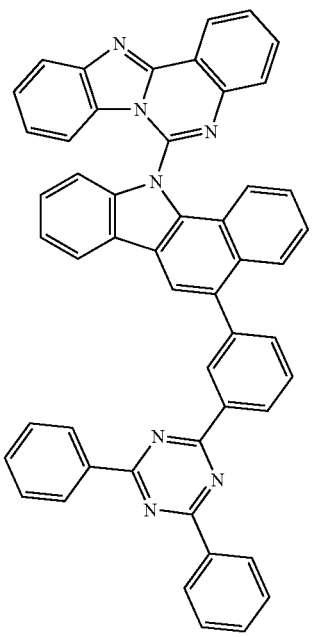
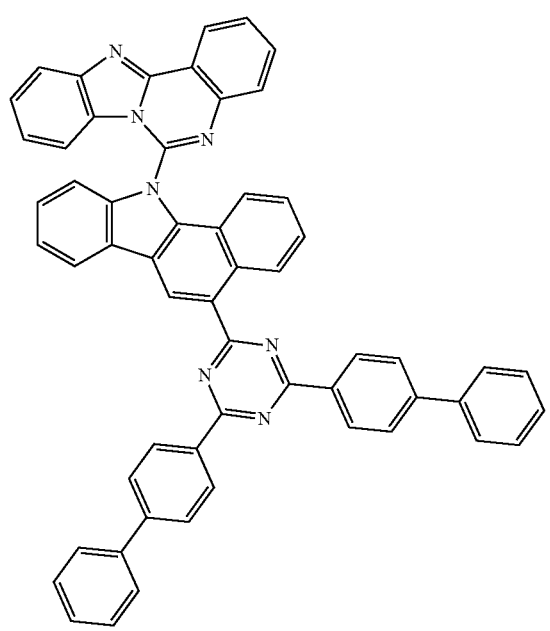
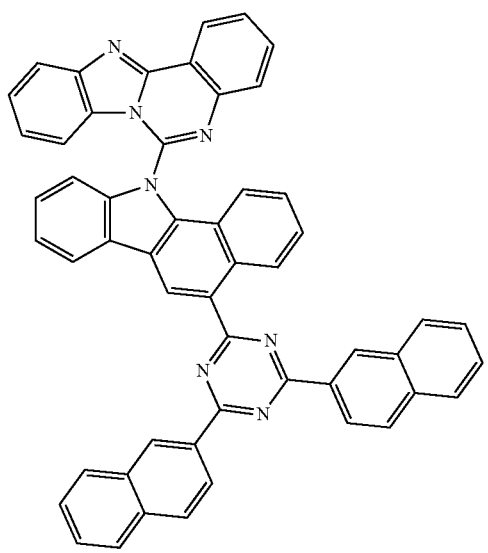

159
-continued
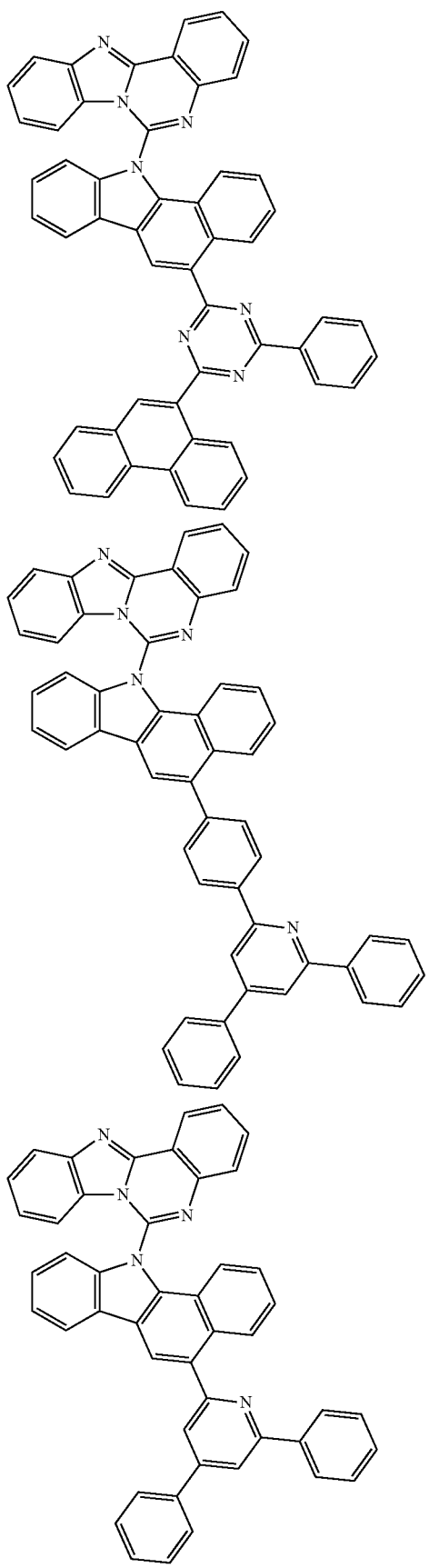
160
-continued
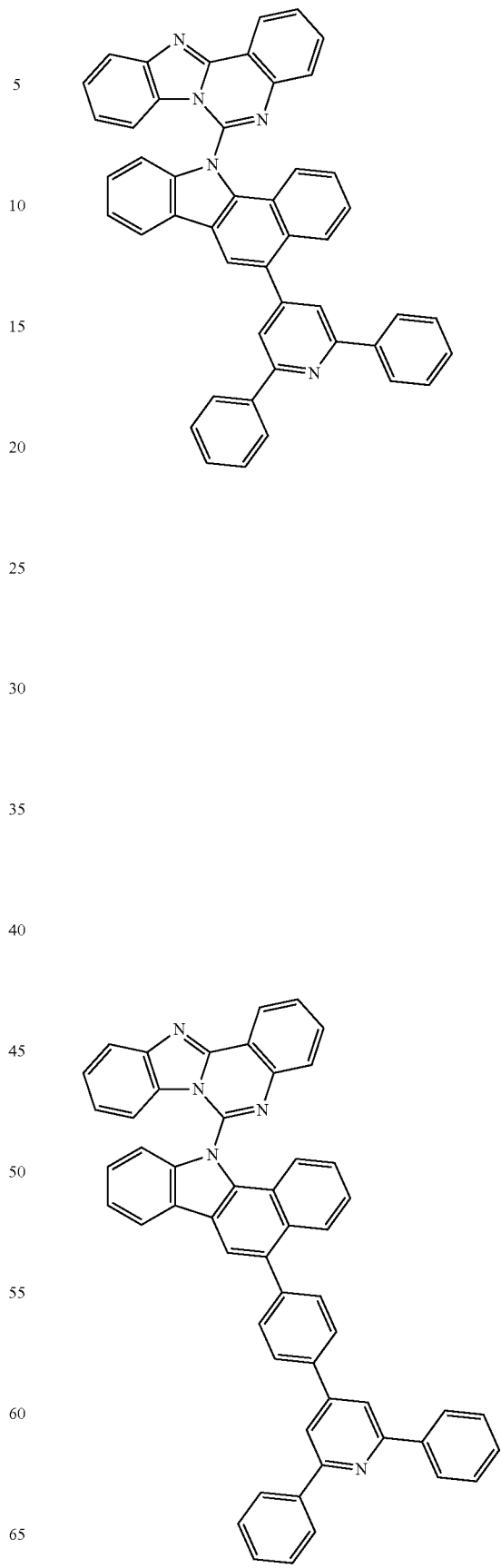

161
-continued
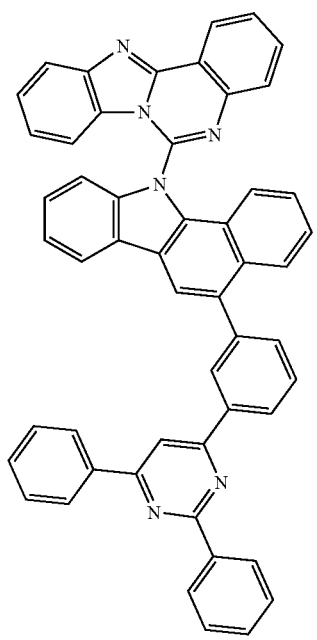
162
-continued
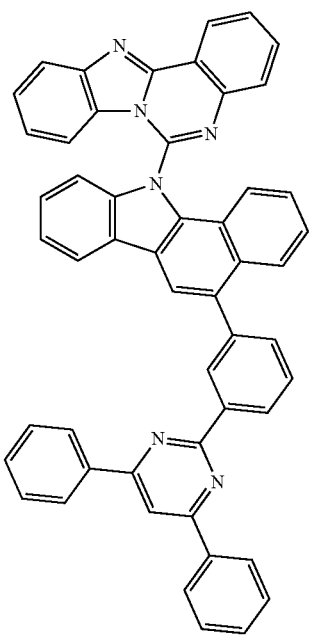
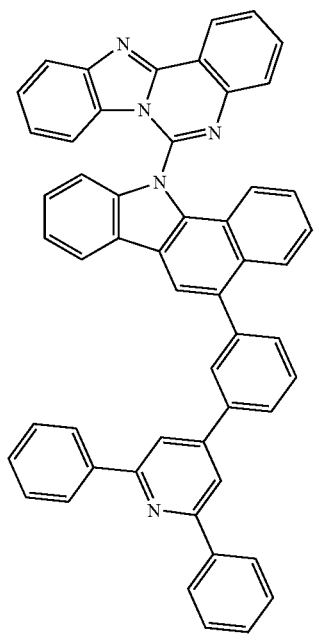
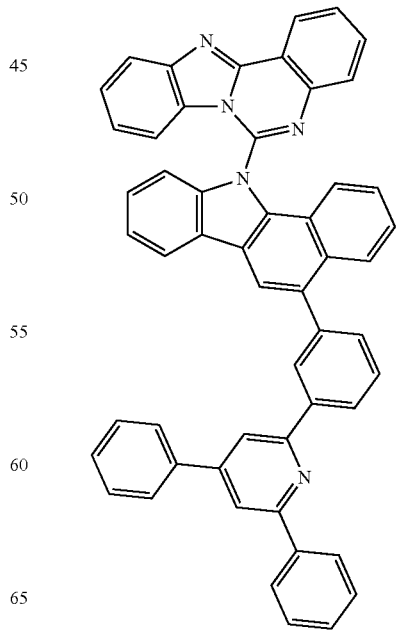

163
-continued
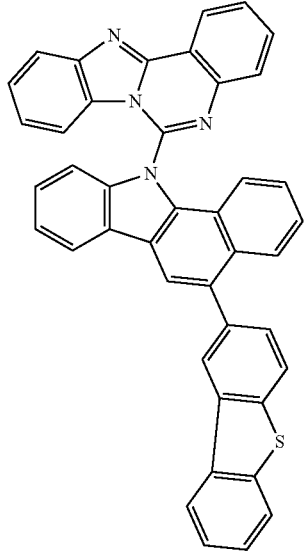
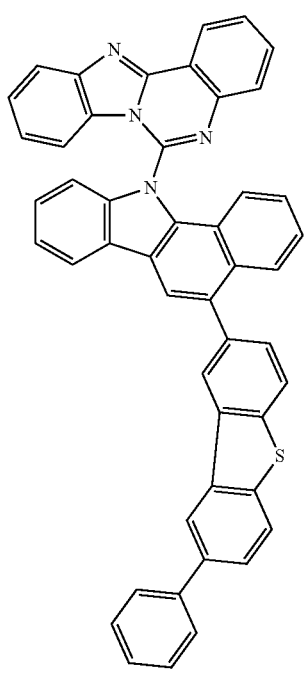
164
-continued
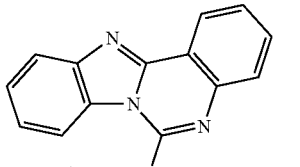
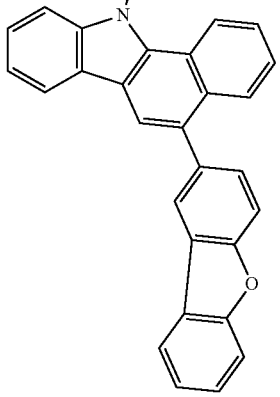
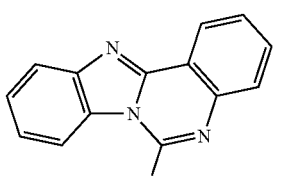
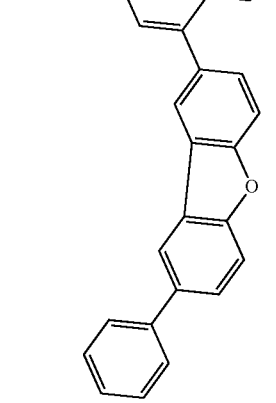
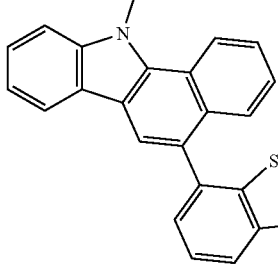

165
-continued
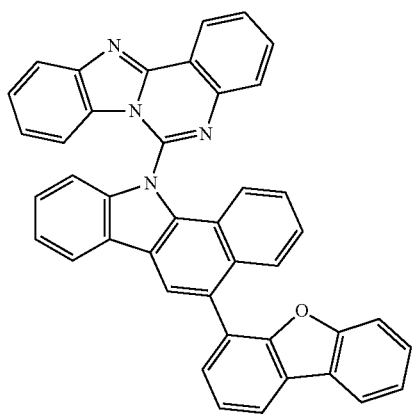
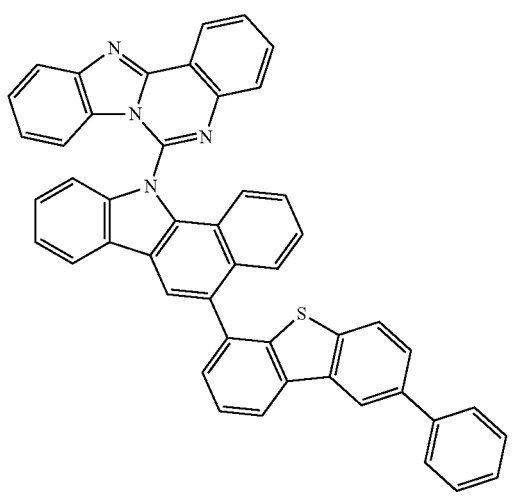
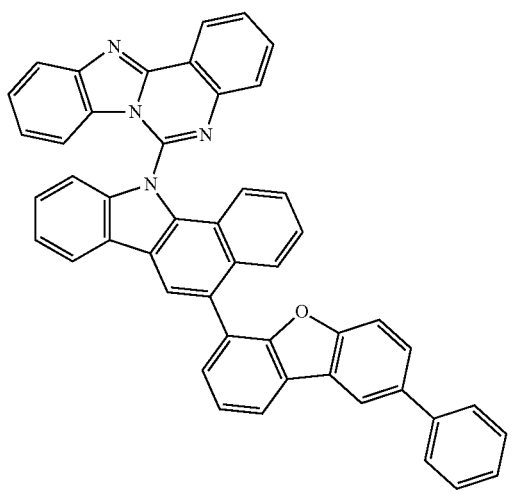
166
-continued
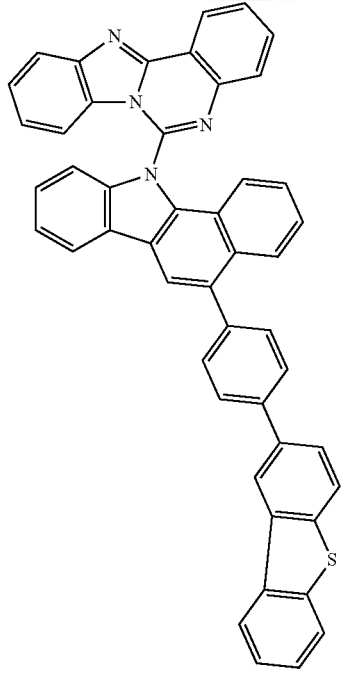
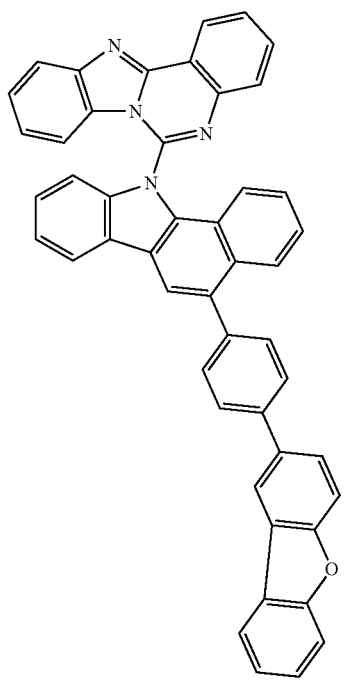

167
-continued
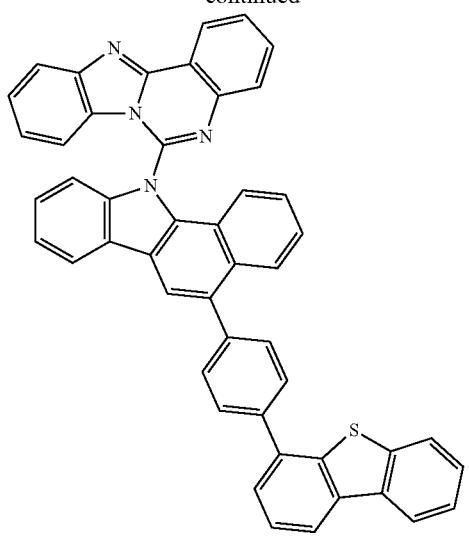
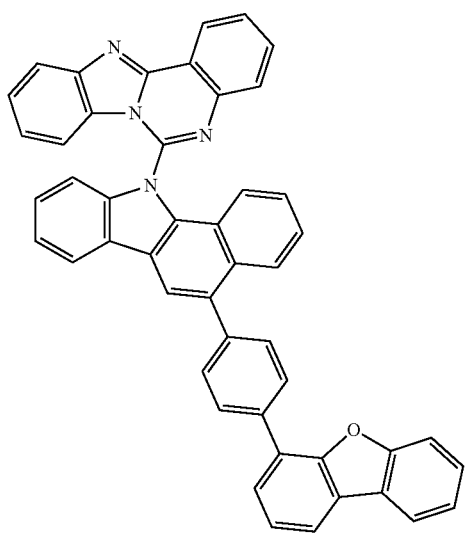
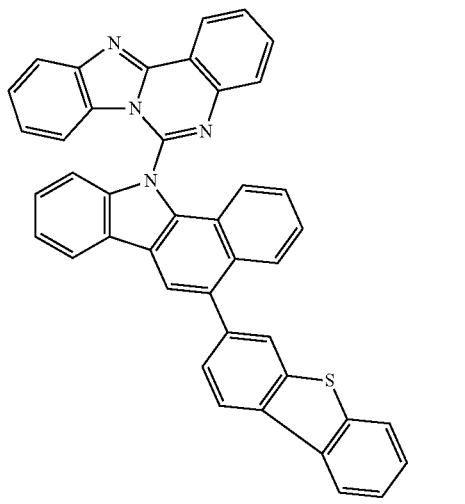
168
-continued
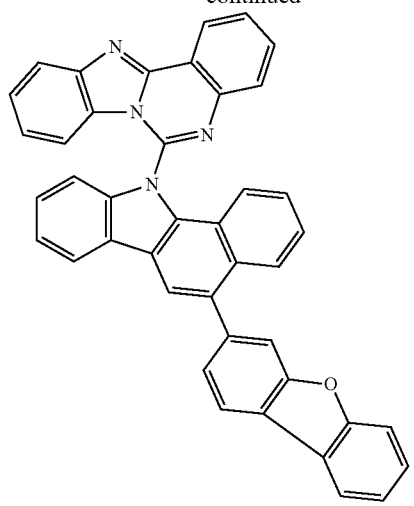
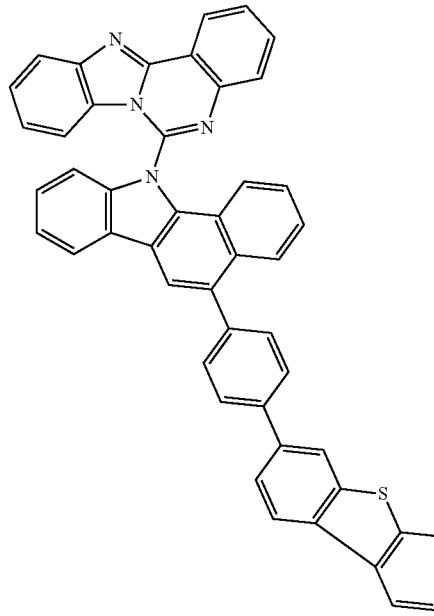

169
-continued
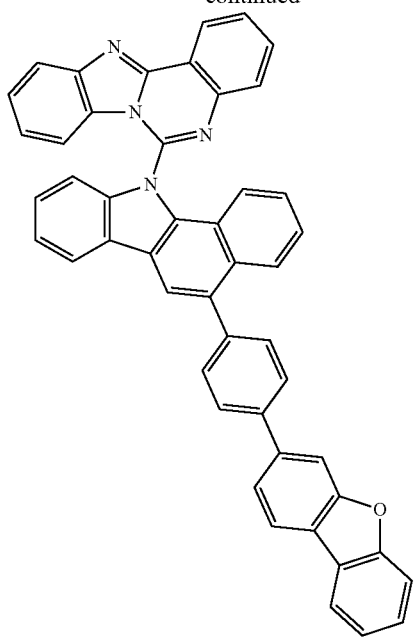
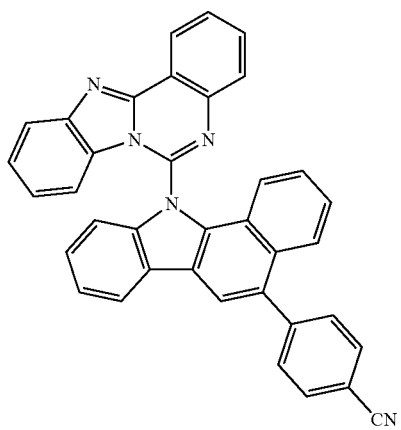
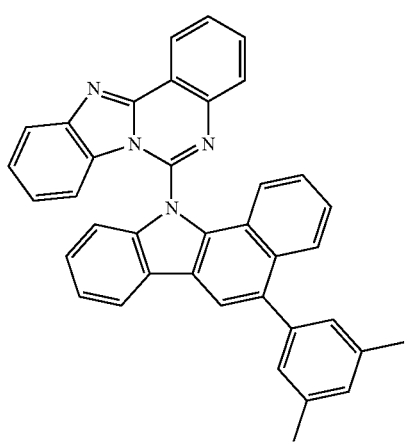
170
-continued
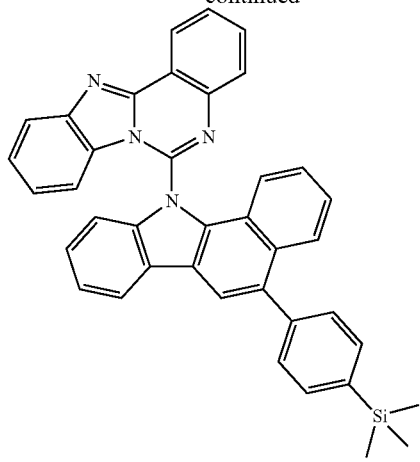
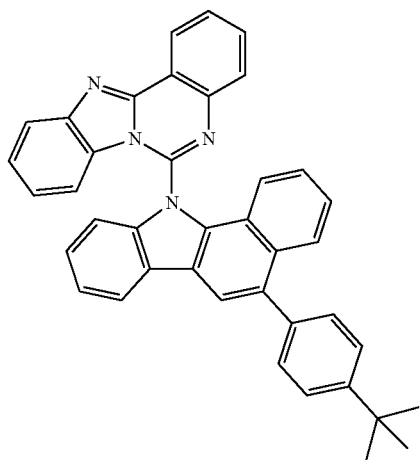
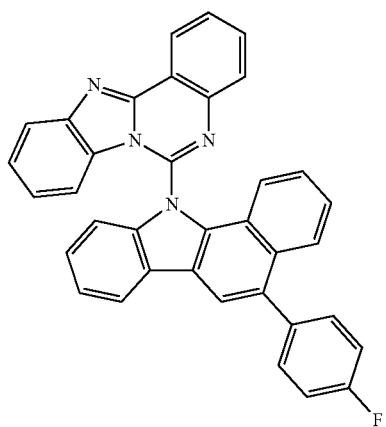

171
-continued
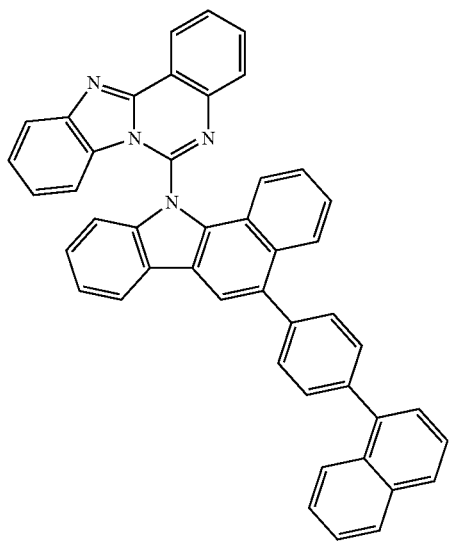
172
-continued
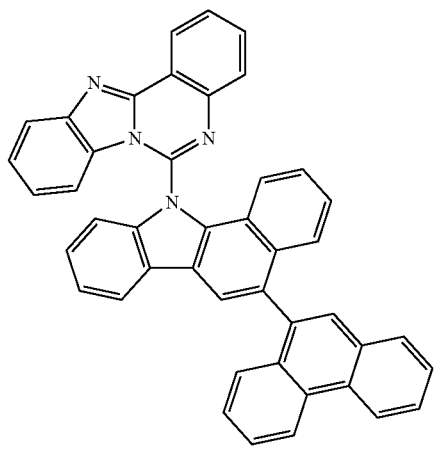
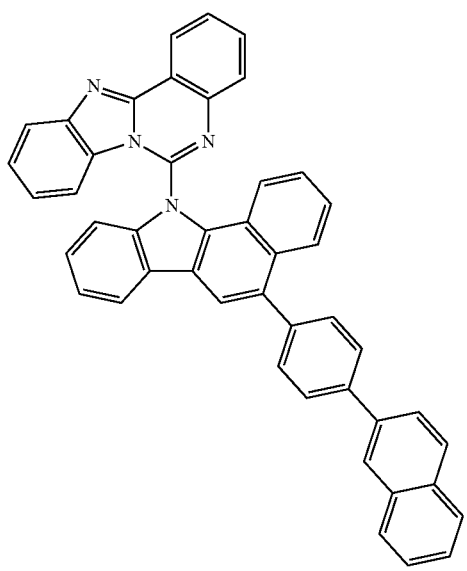
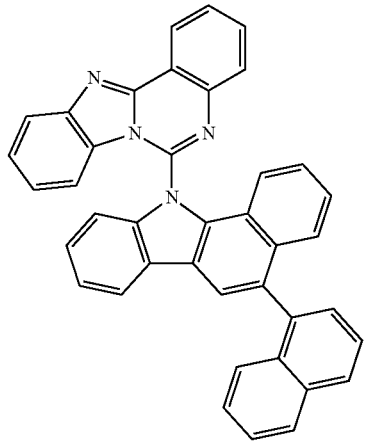
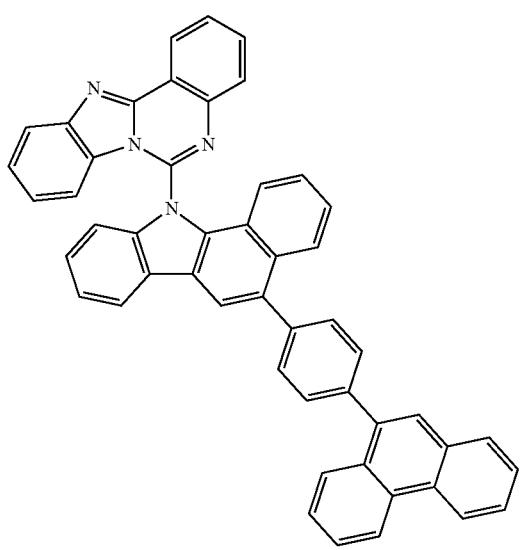
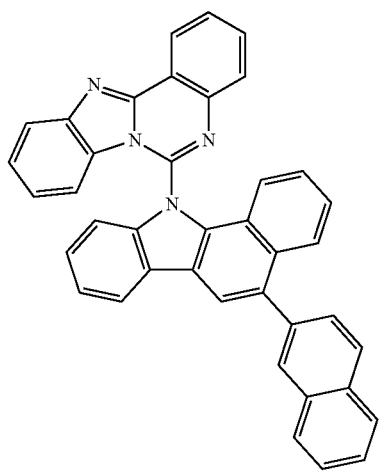

173
-continued
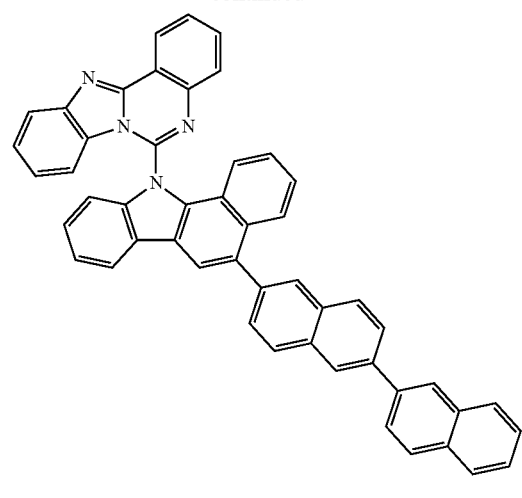
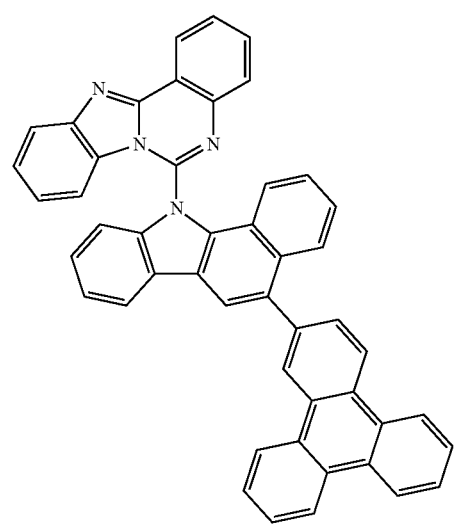
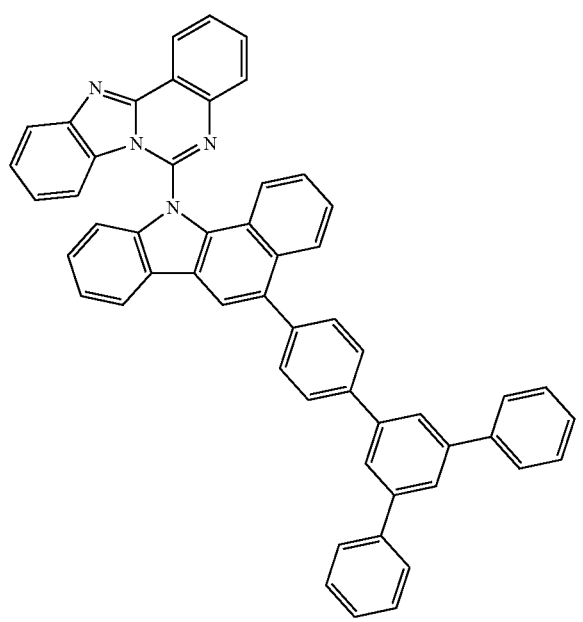
174
-continued
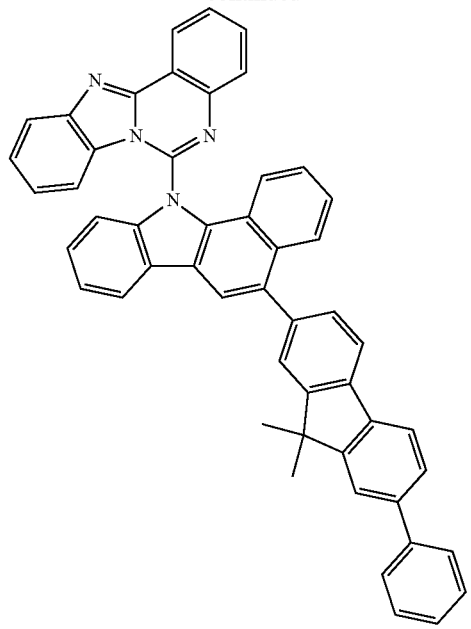
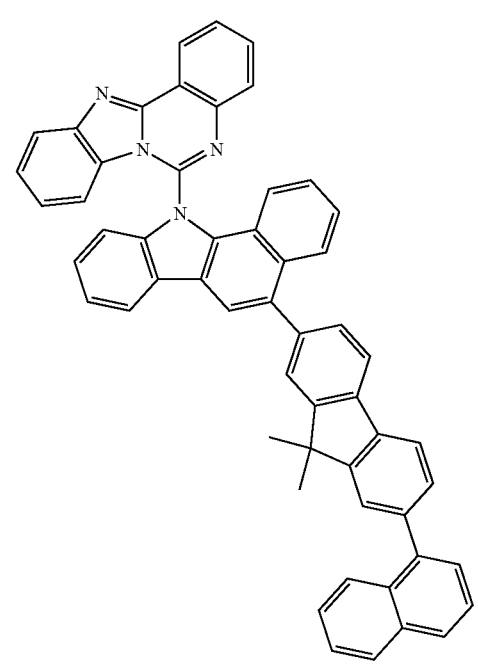

-continued
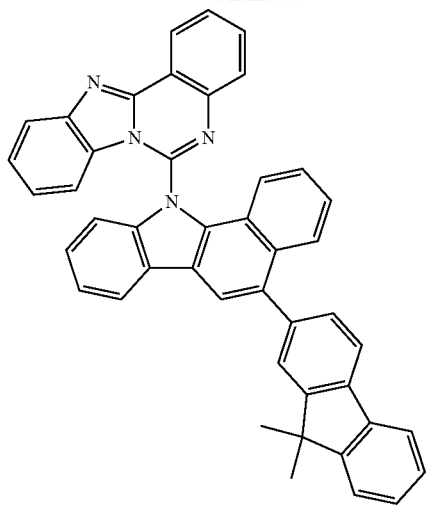
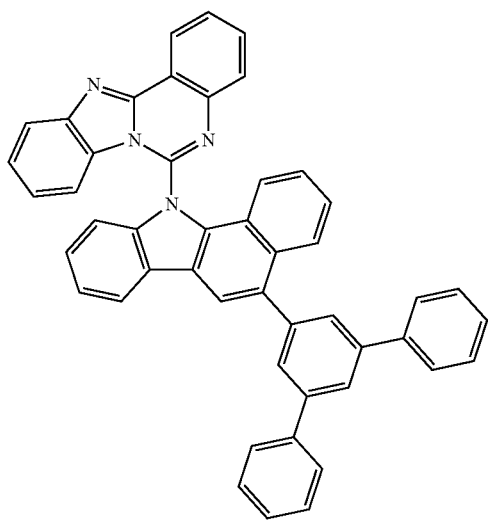
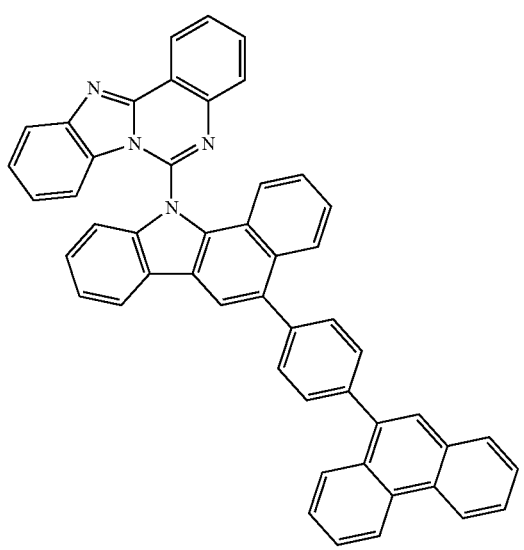
-continued
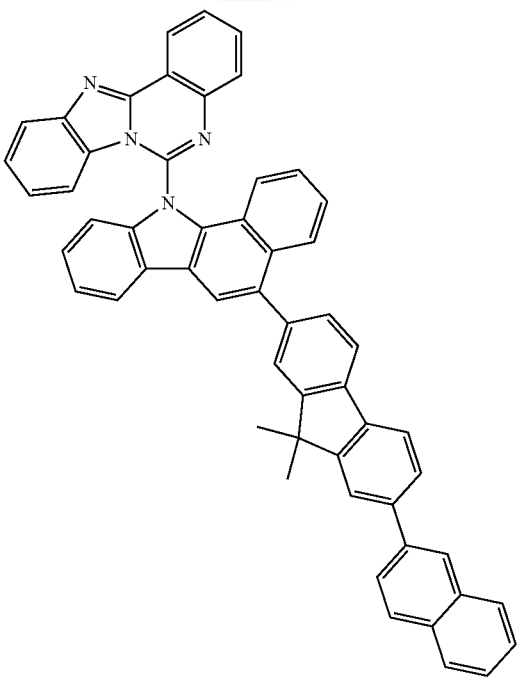
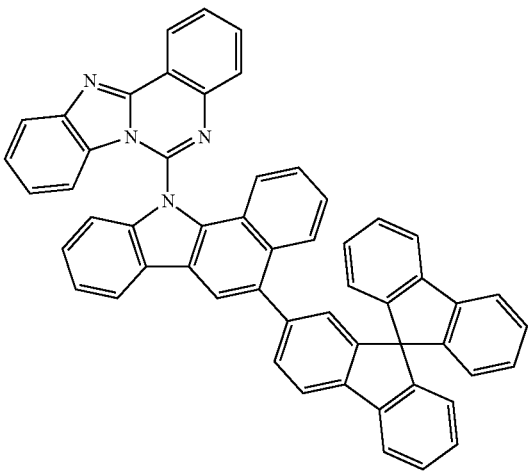
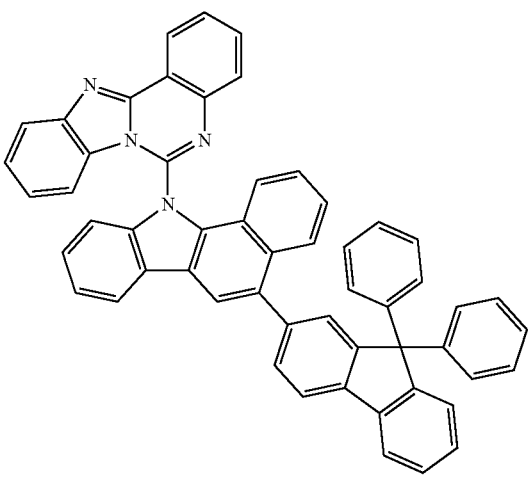

177
-continued
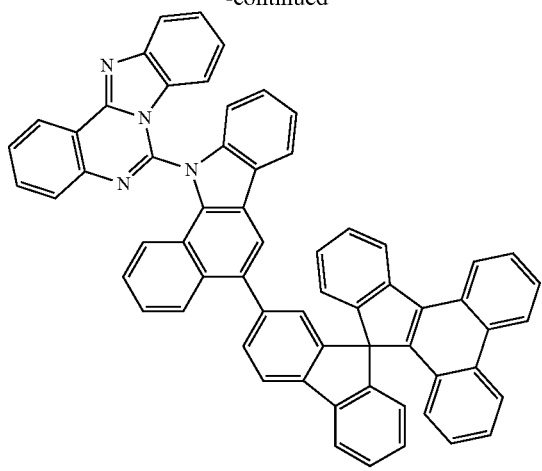
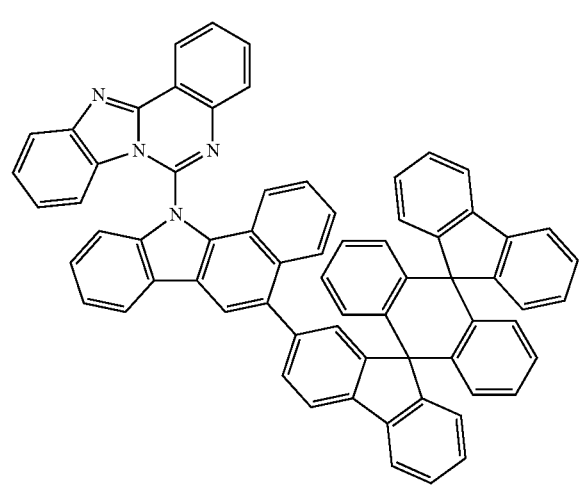
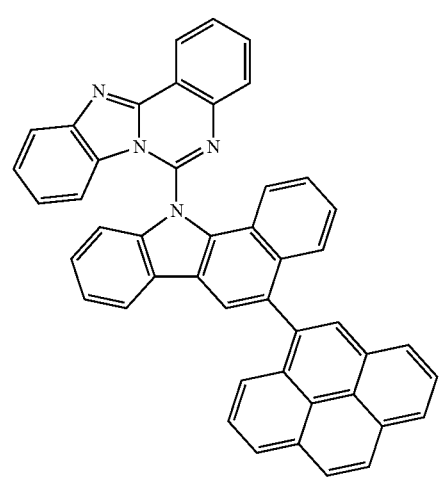
178
-continued
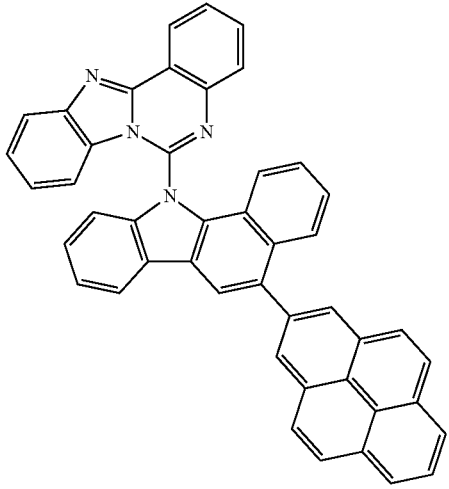
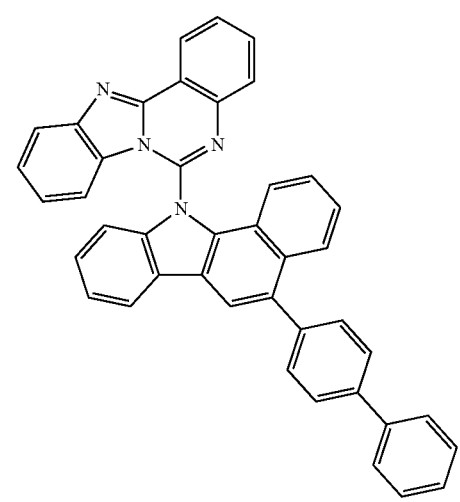

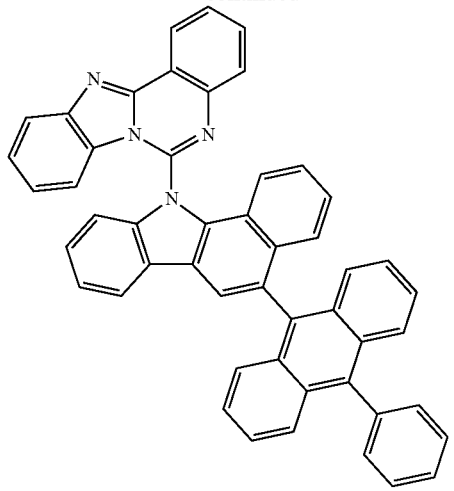
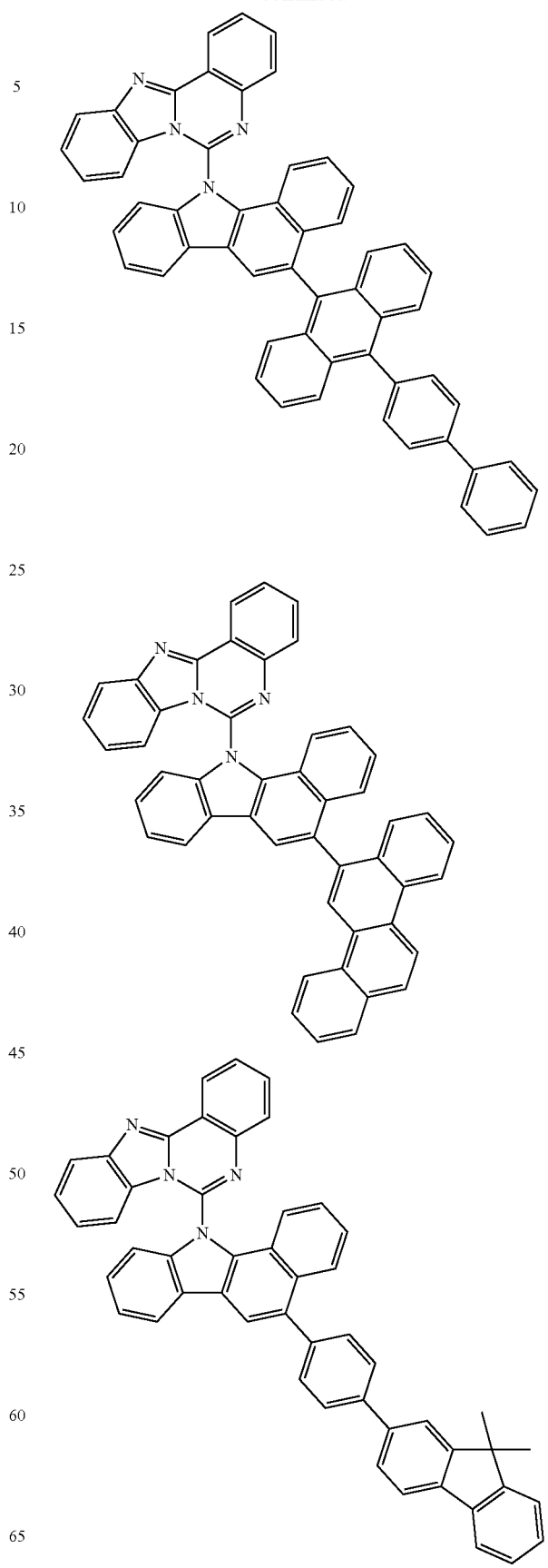

-continued
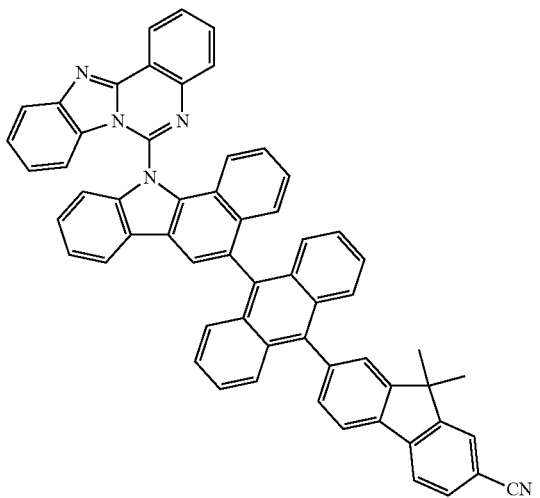
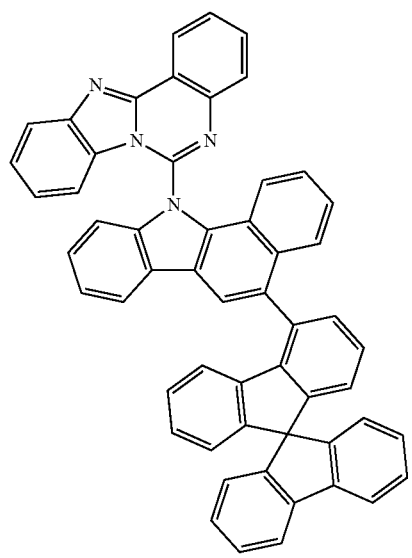
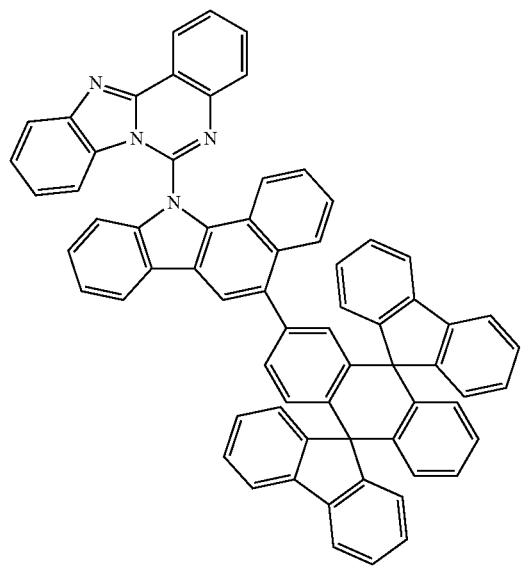
-continued
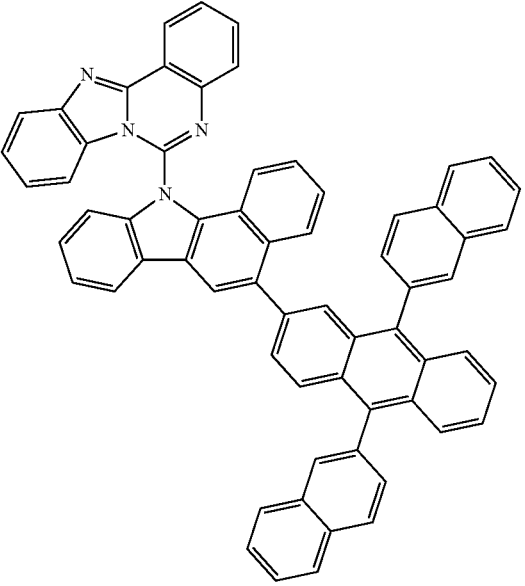
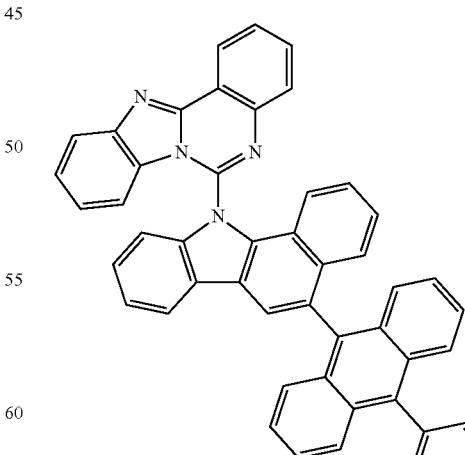
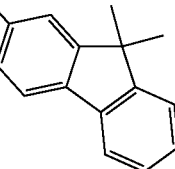

183
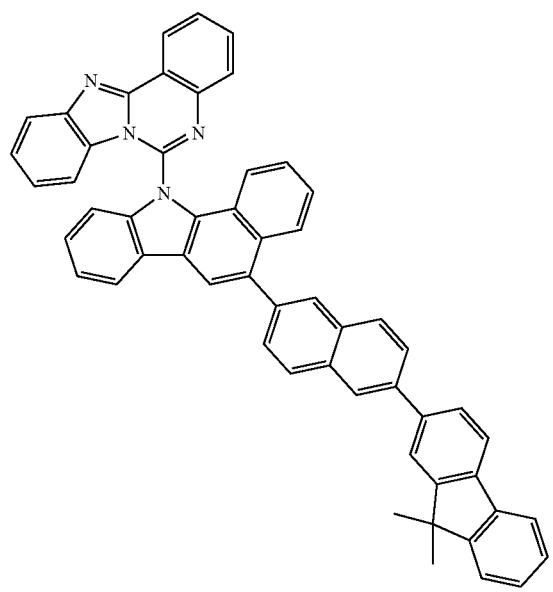
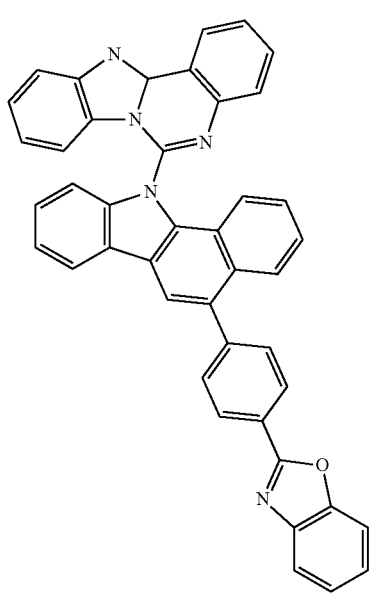
184
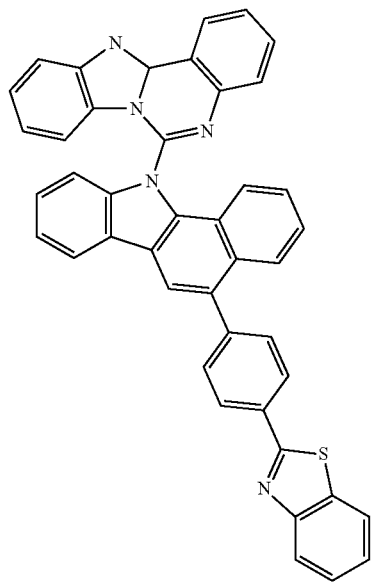

185
-continued
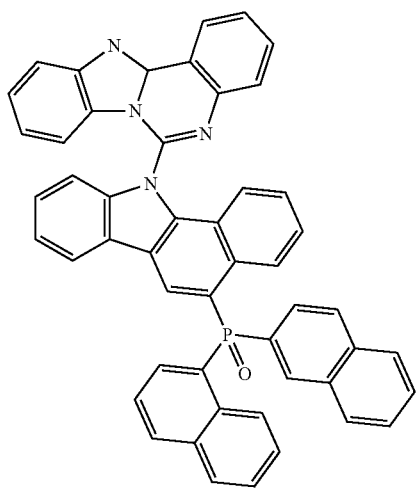
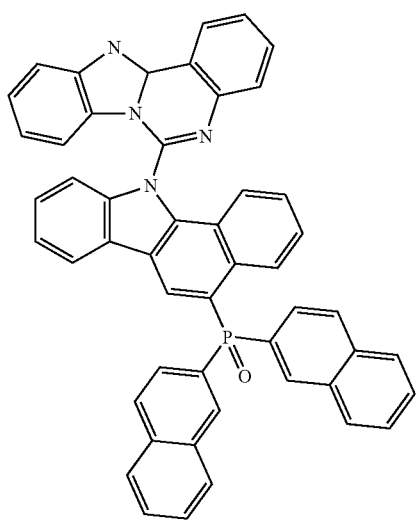
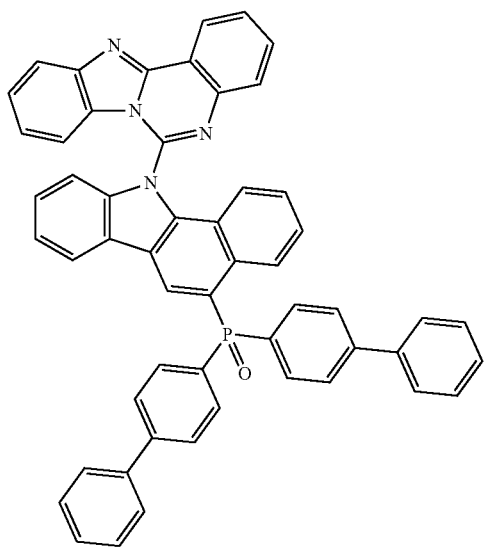
186
-continued
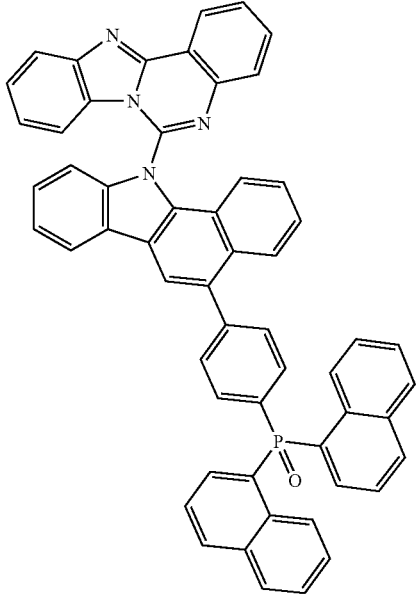
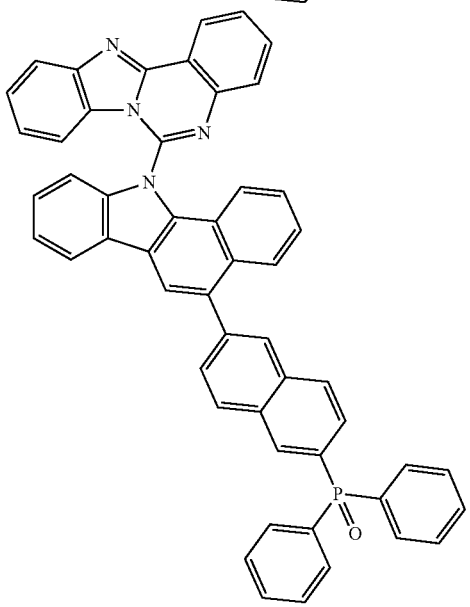
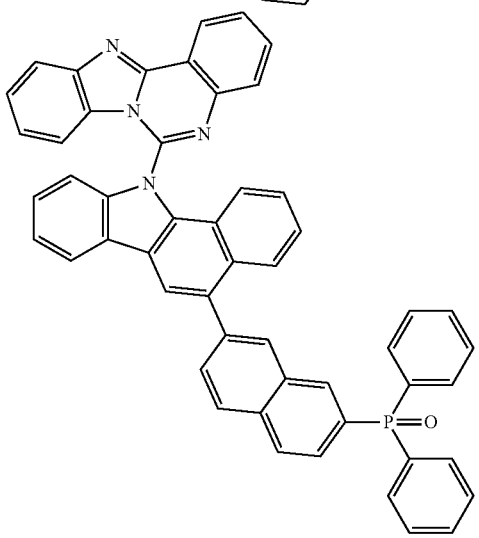

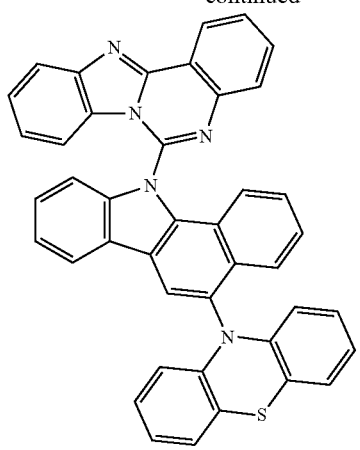
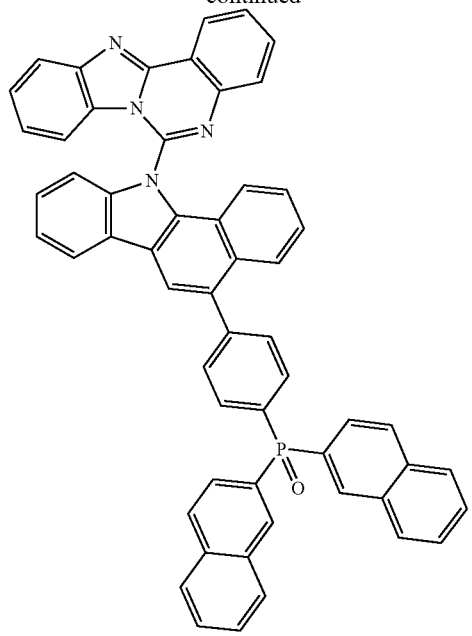
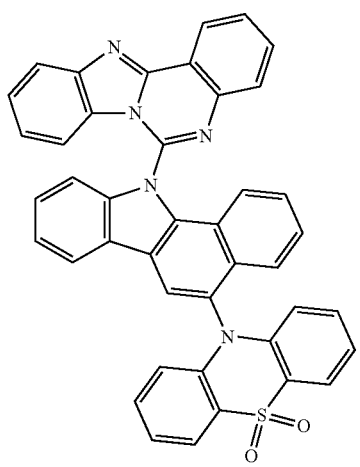
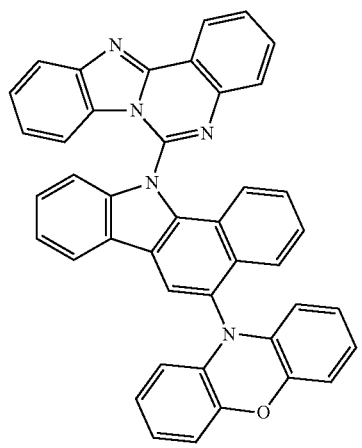
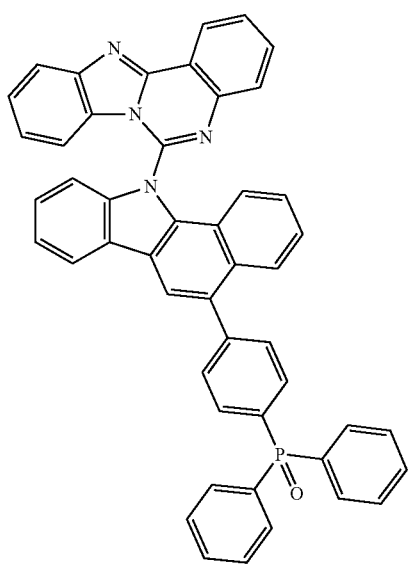
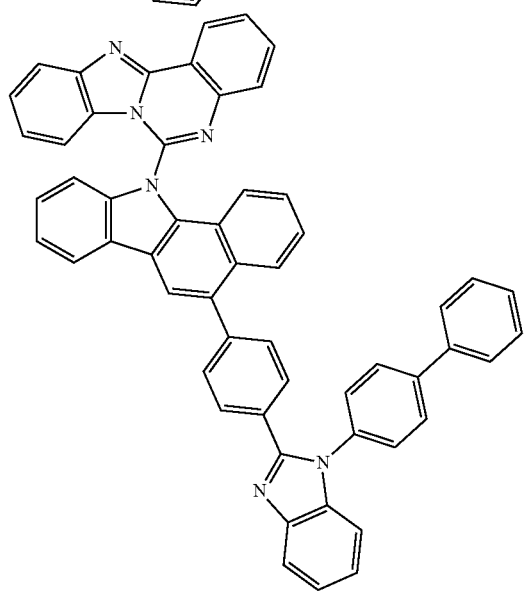

189
-continued
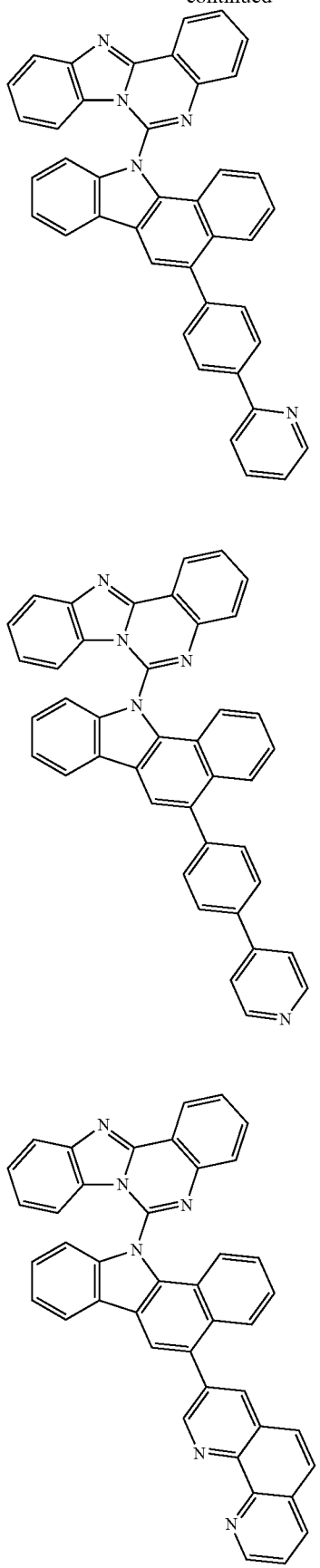
190
-continued
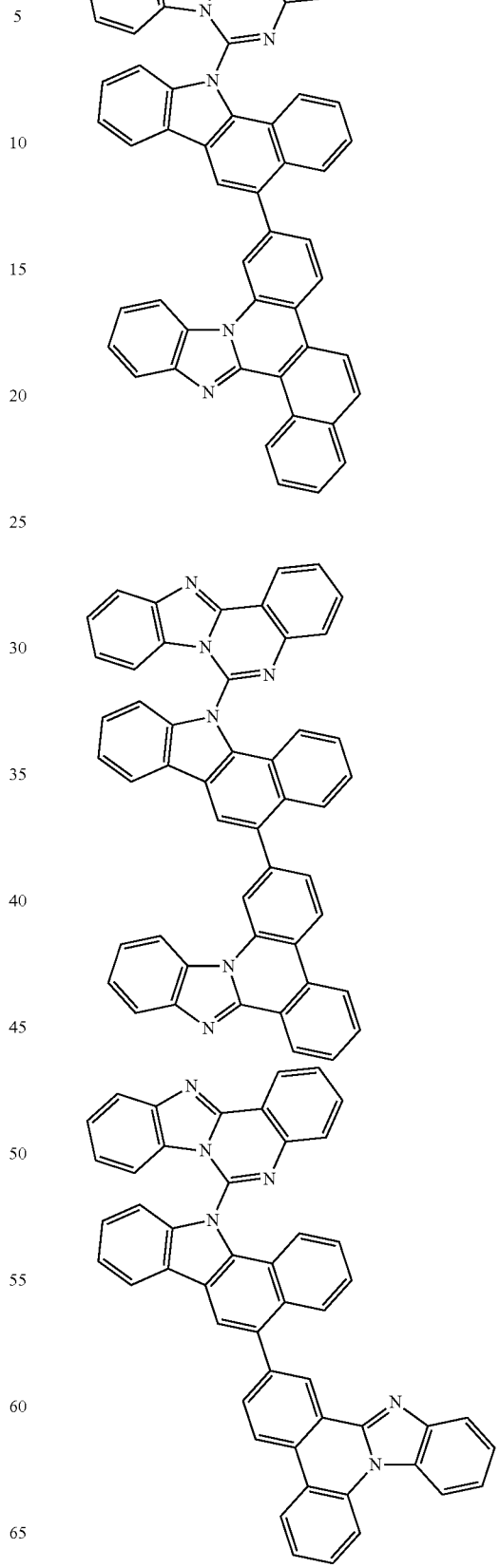

191
-continued
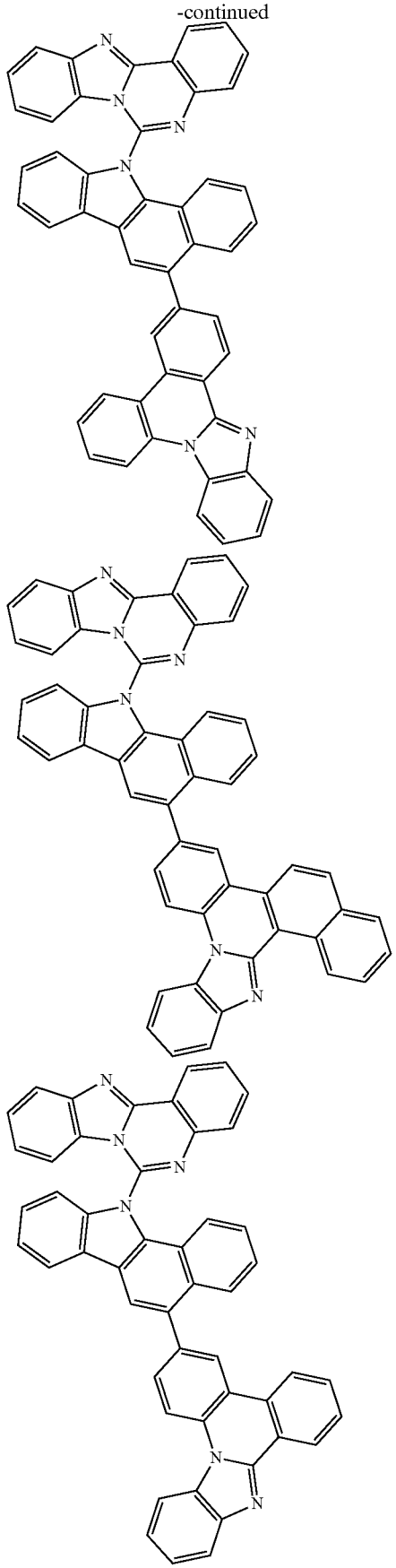
192
-continued
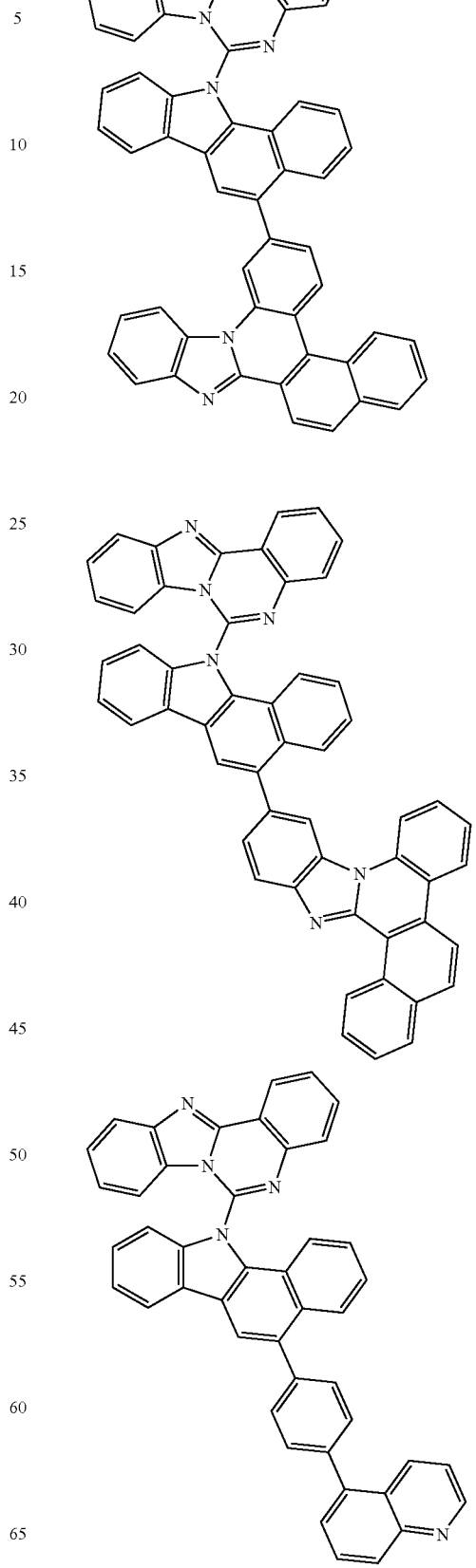

193
-continued
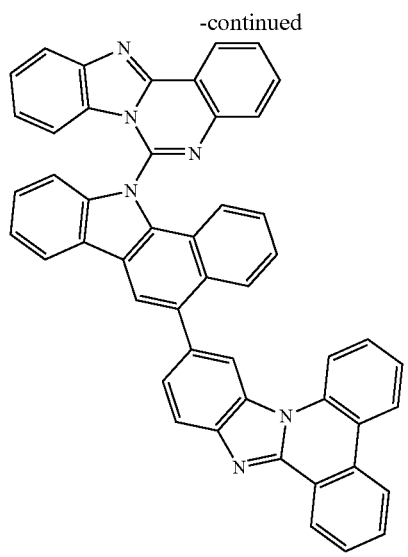
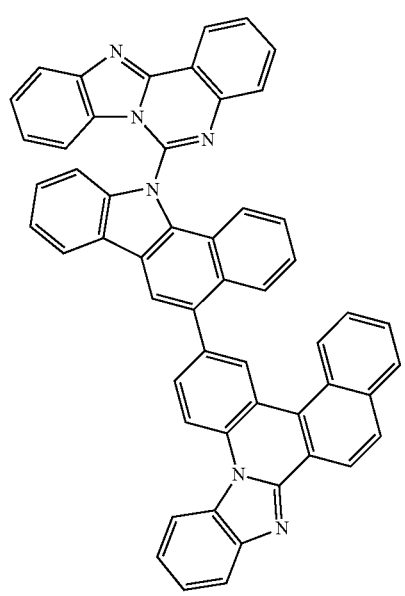
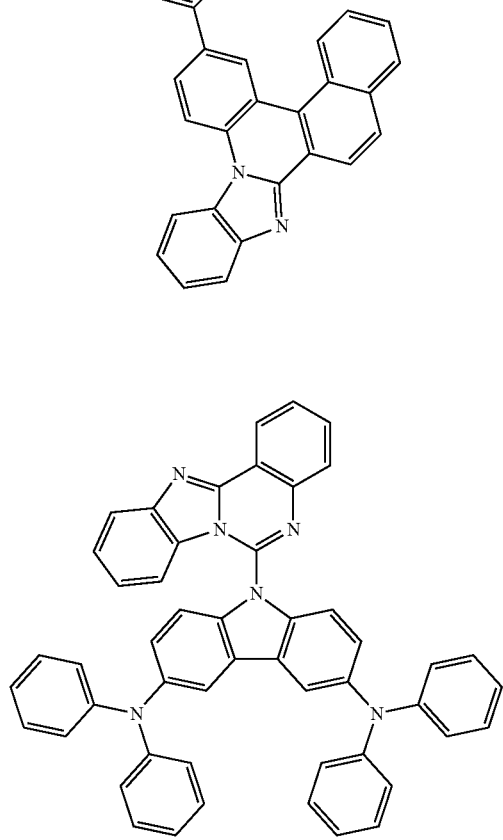
194
-continued
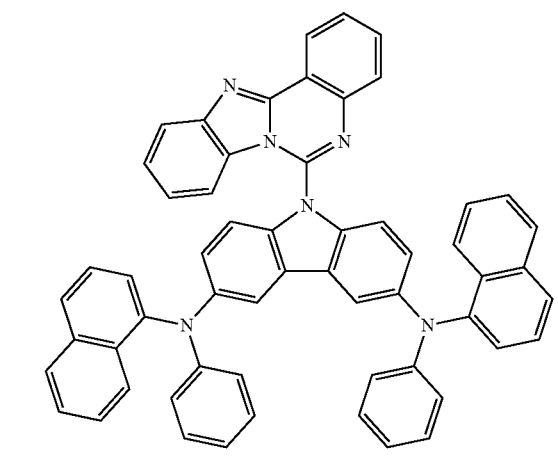
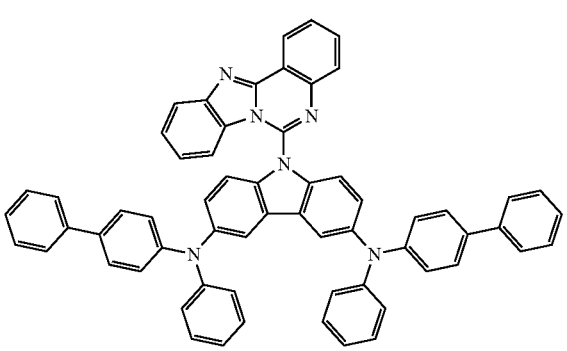
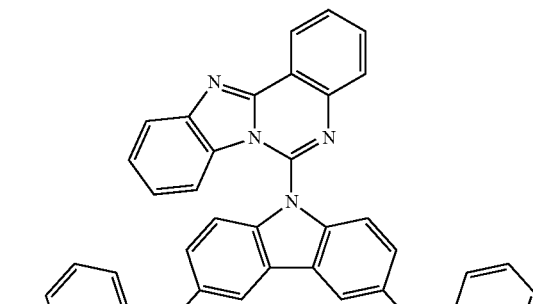
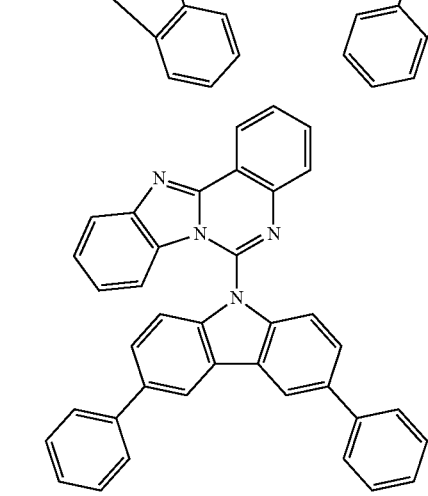

195
-continued
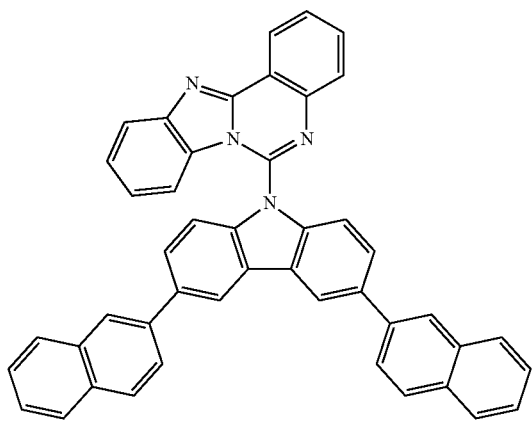
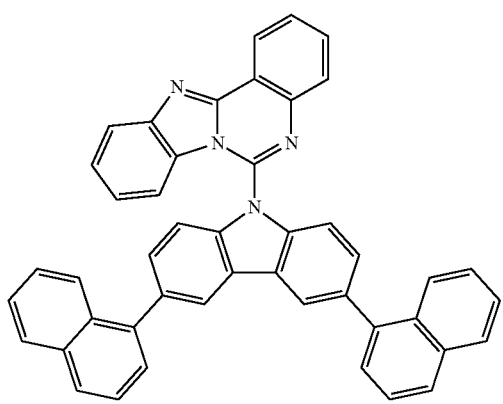
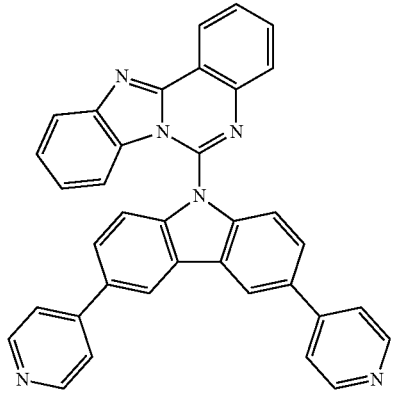
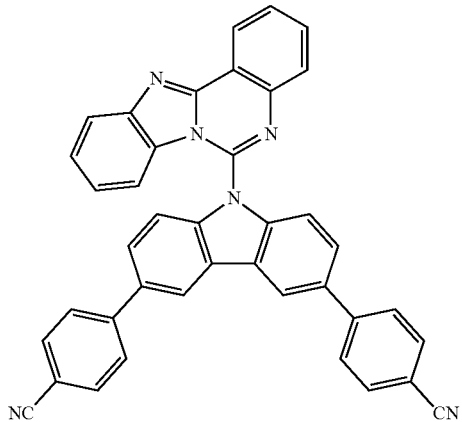
196
-continued
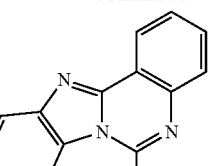
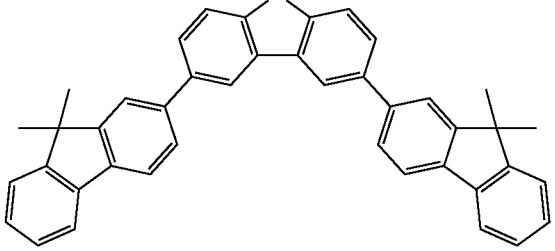
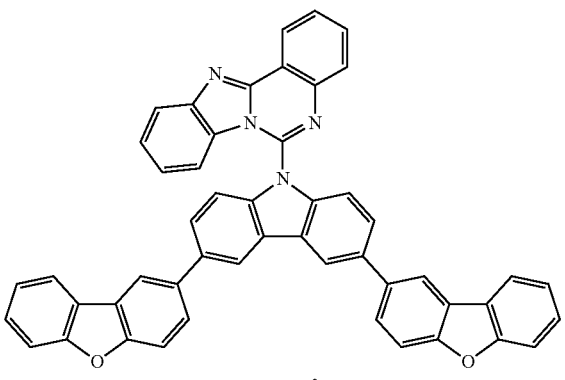
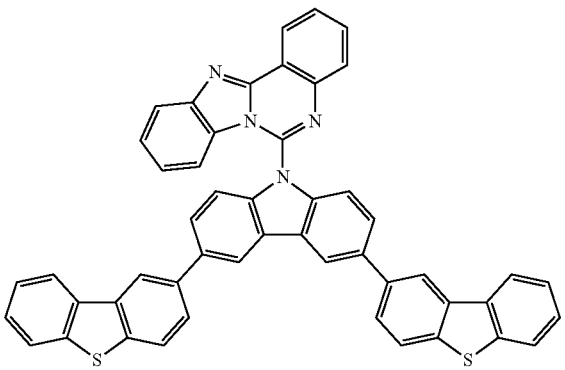
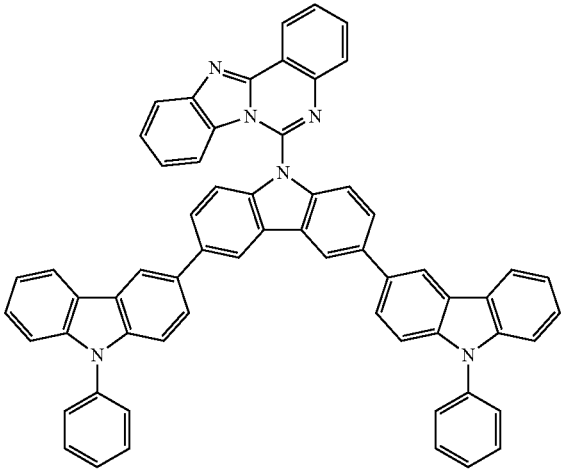

197
-continued
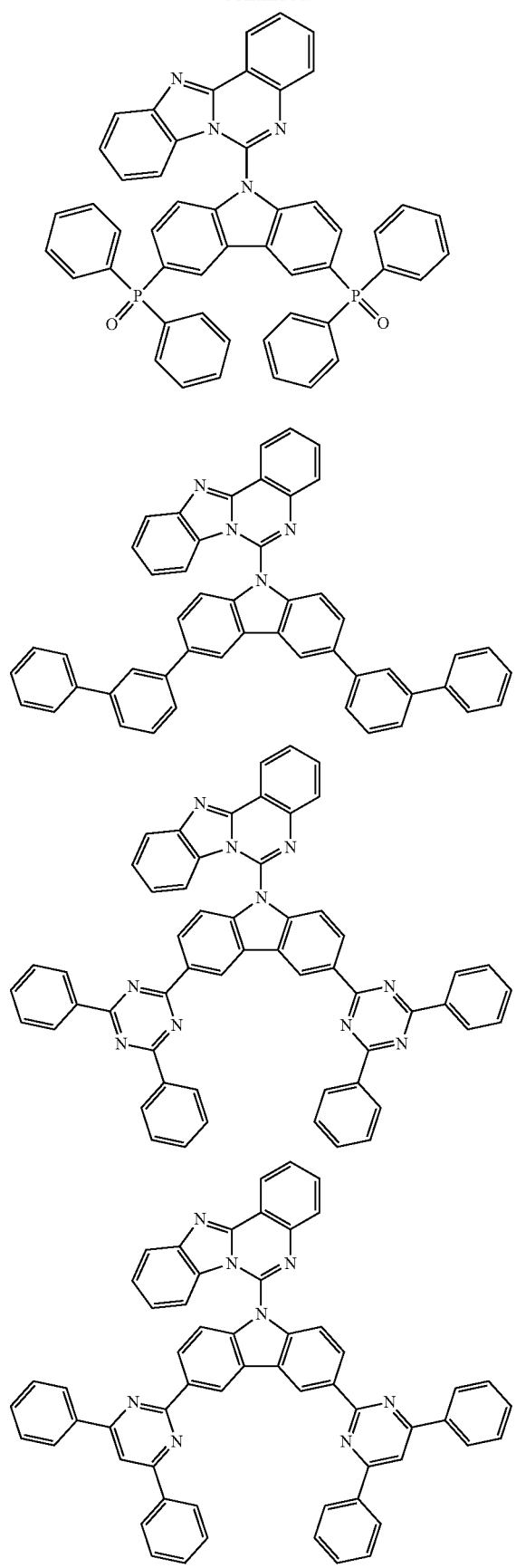
198
-continued
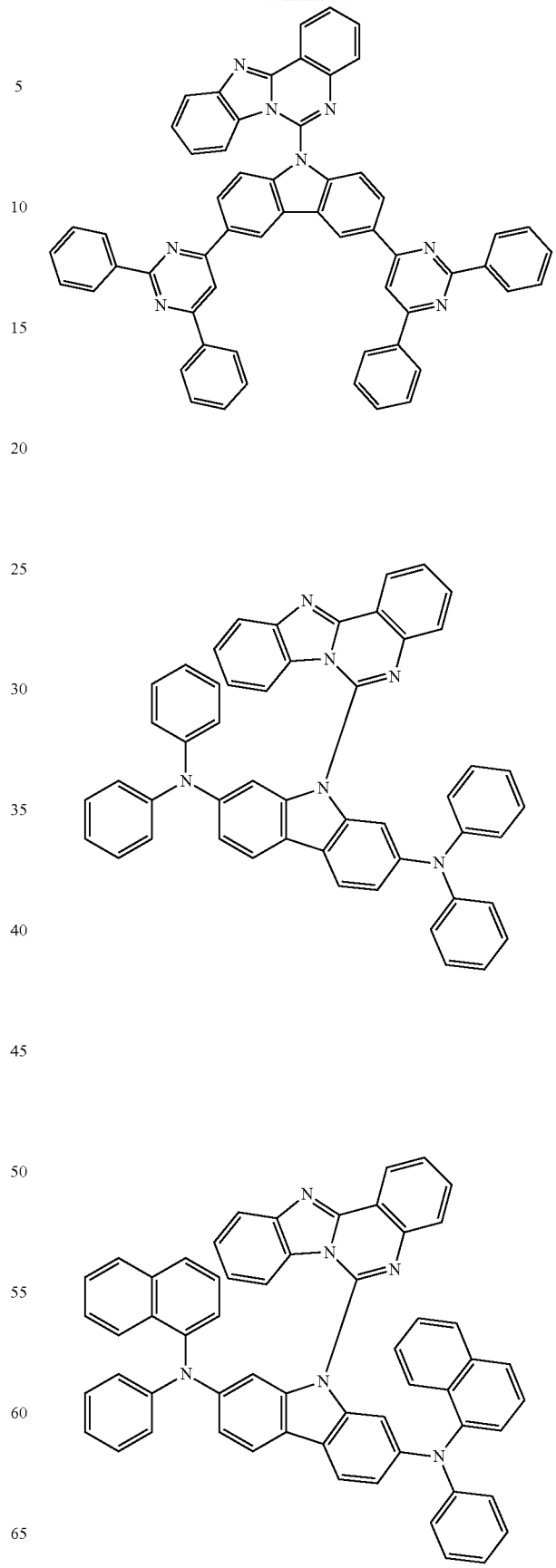

199
-continued
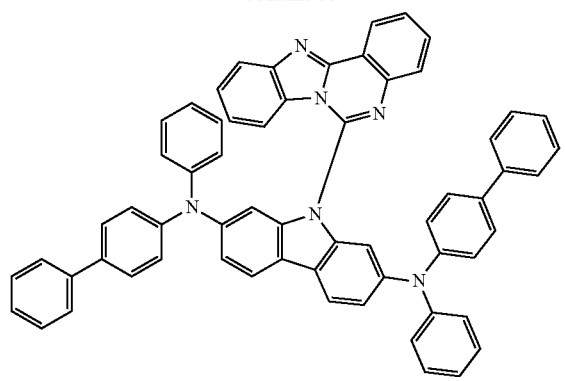
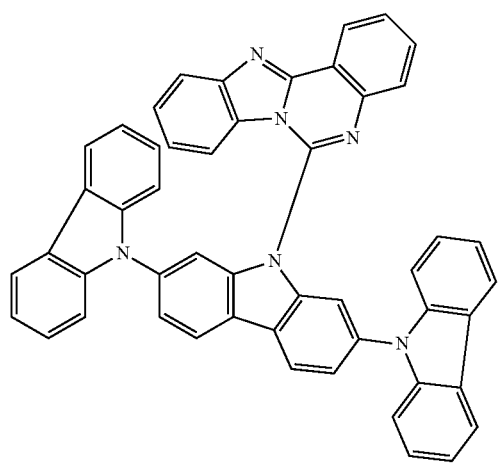
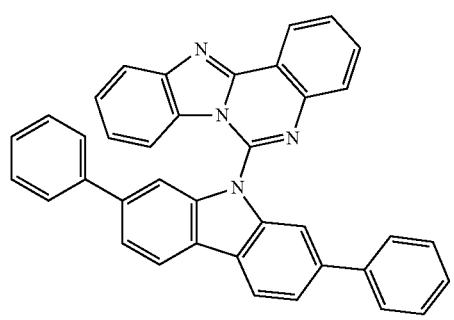
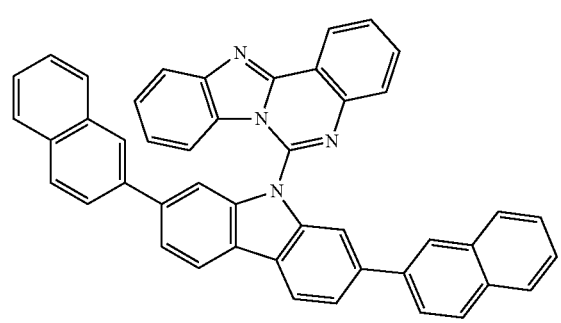
200
-continued
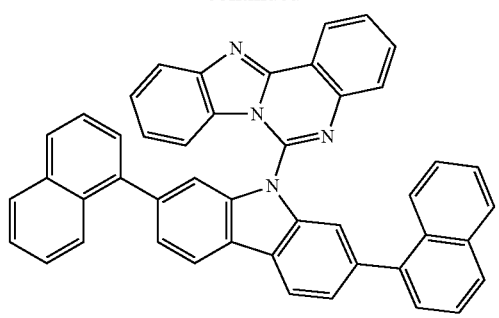
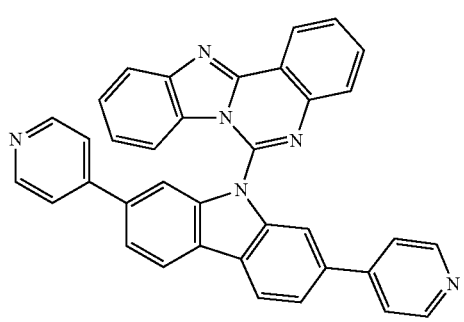
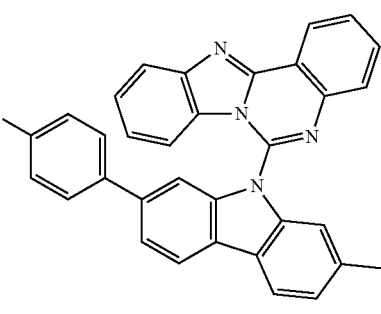
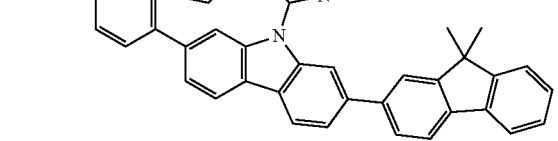
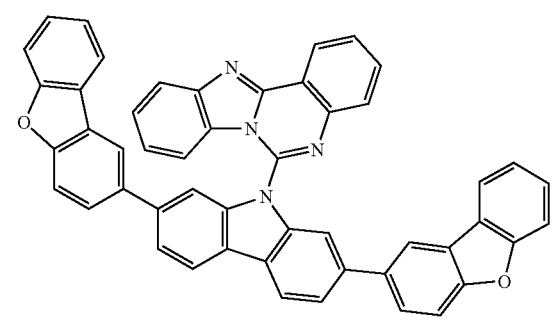

201
-continued
202
-continued
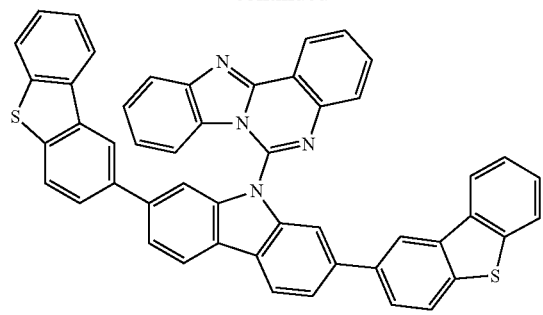
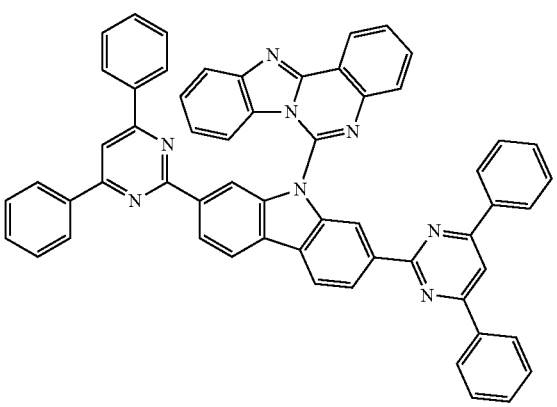
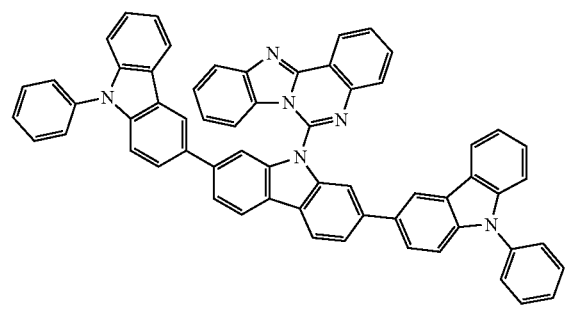
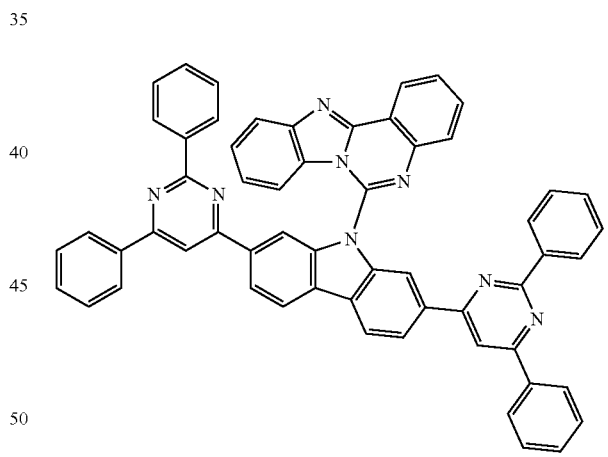
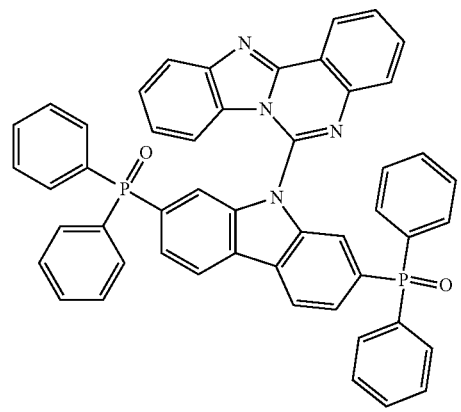
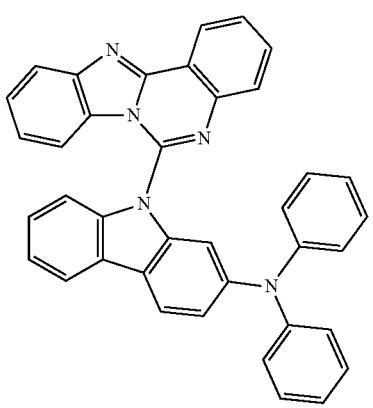
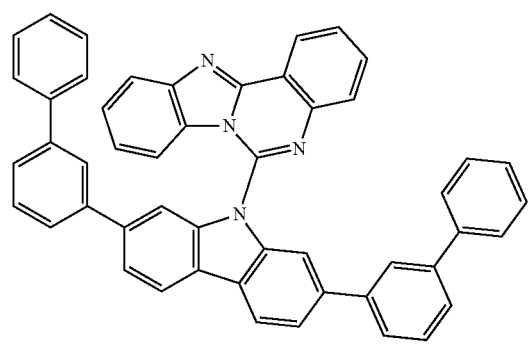

203
-continued
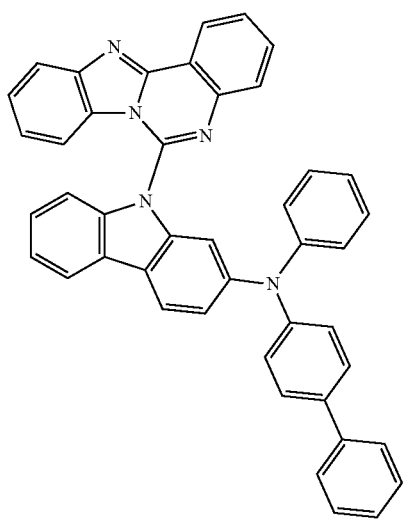
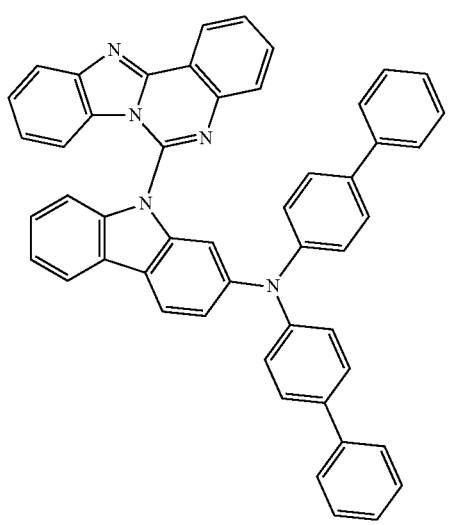
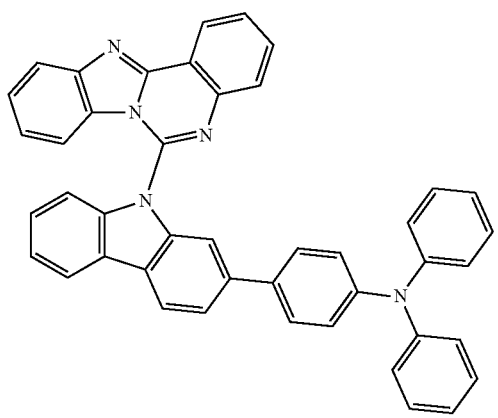
204
-continued
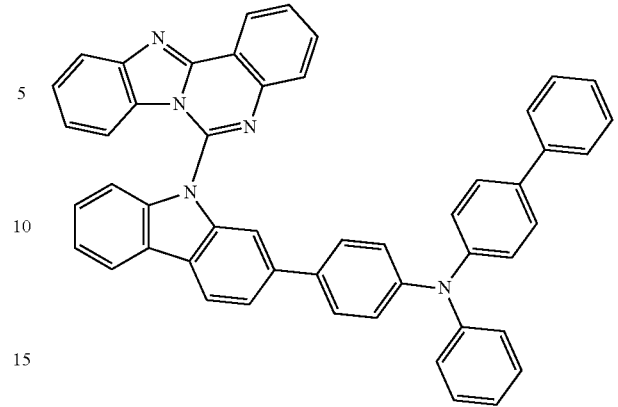
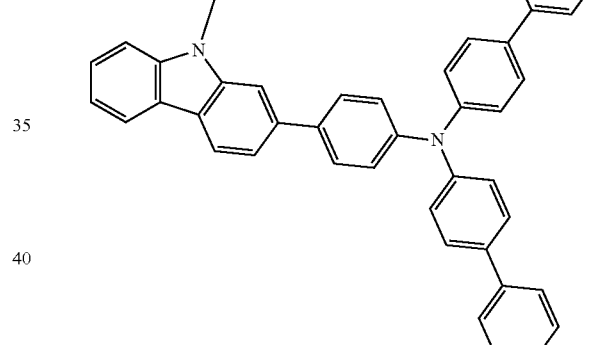
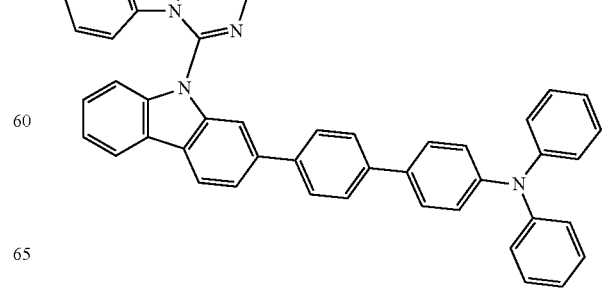

205
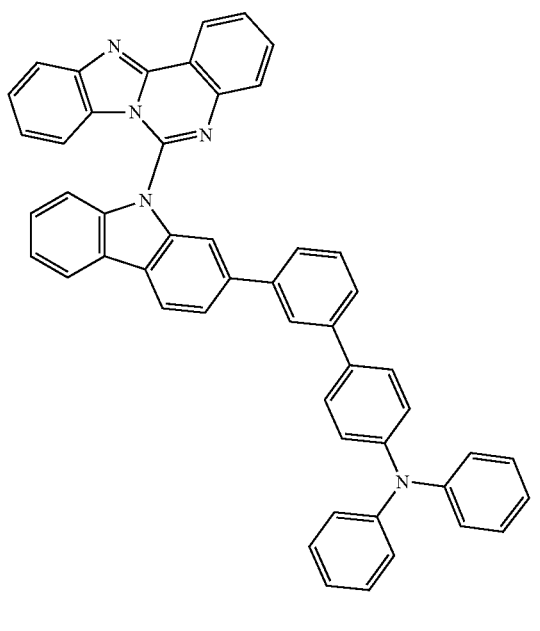
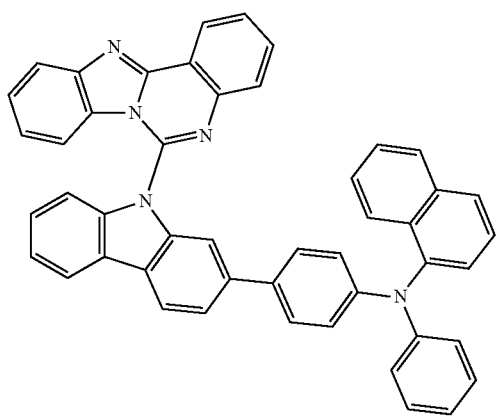
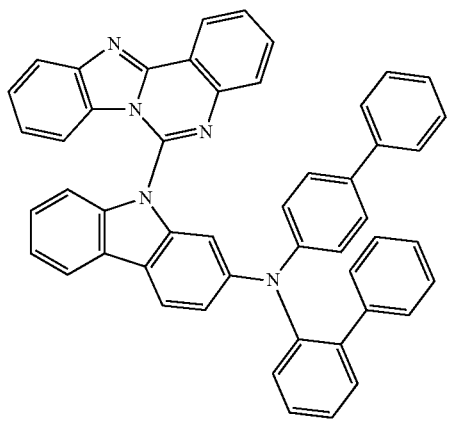
206
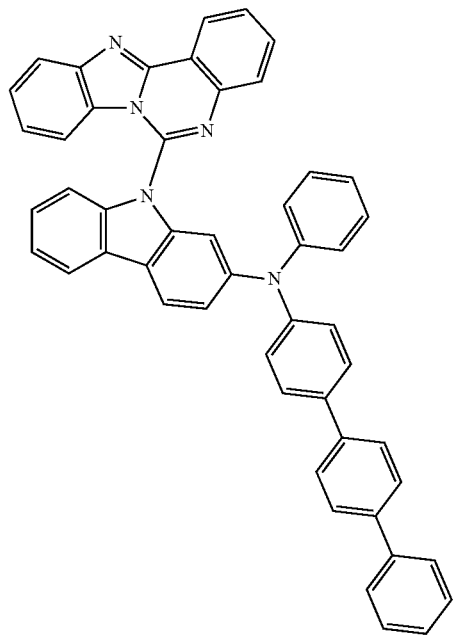
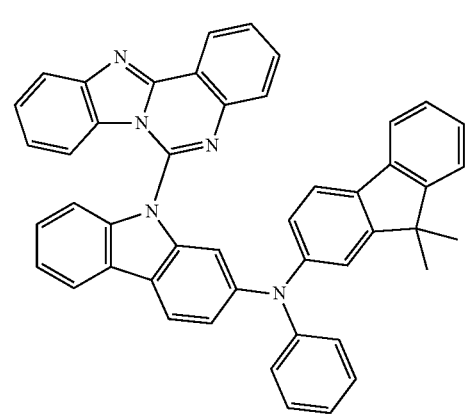
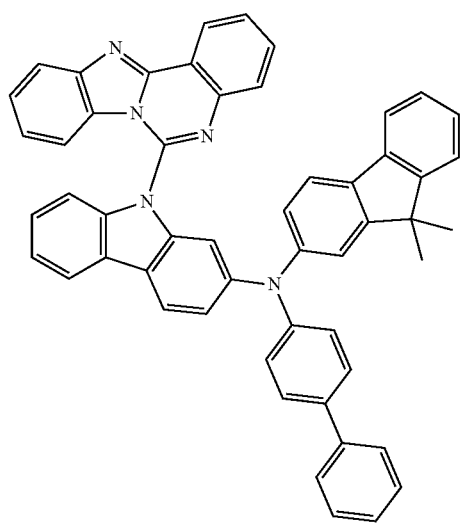

207
-continued
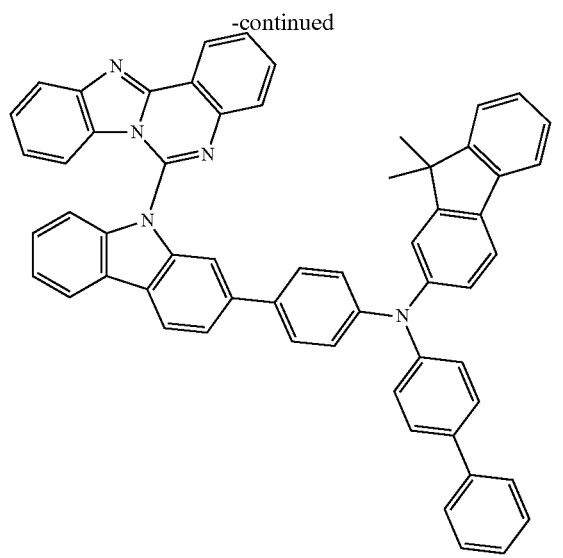
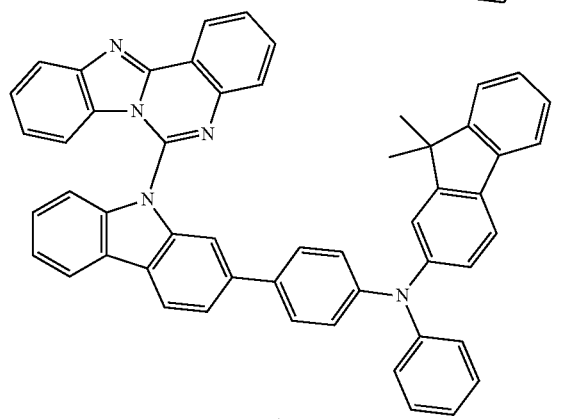
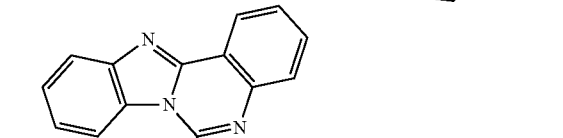
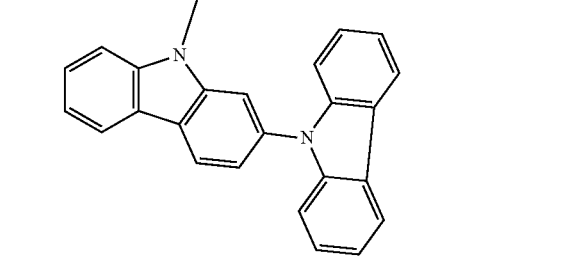
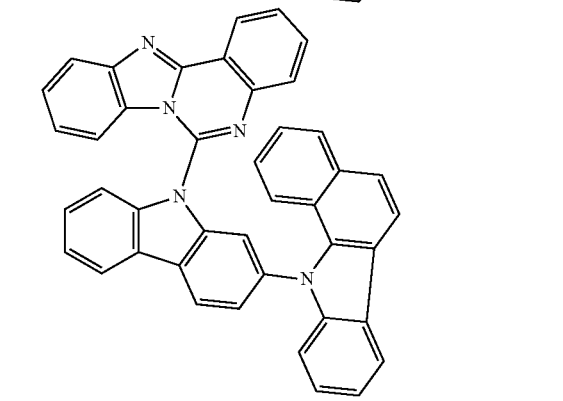
208
-continued
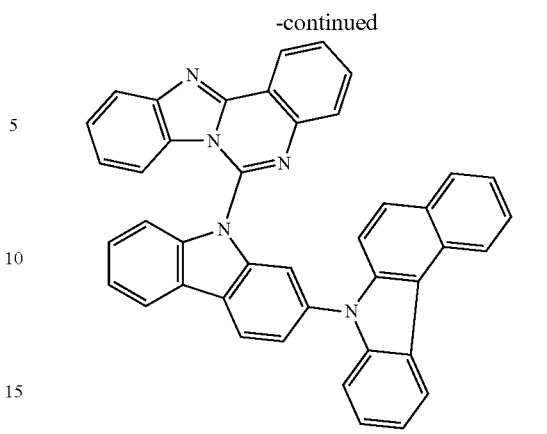
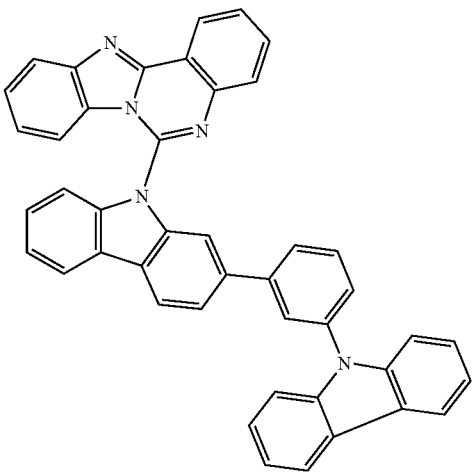
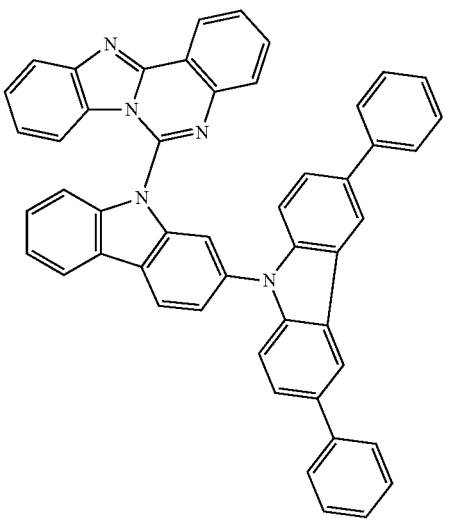

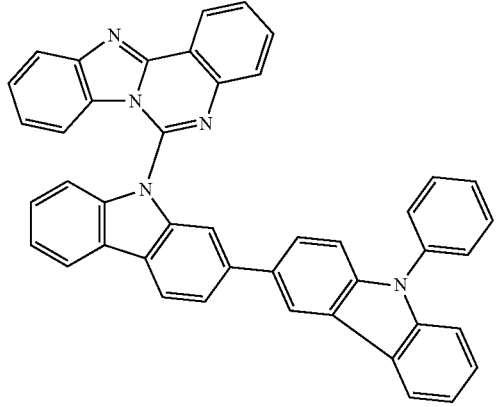
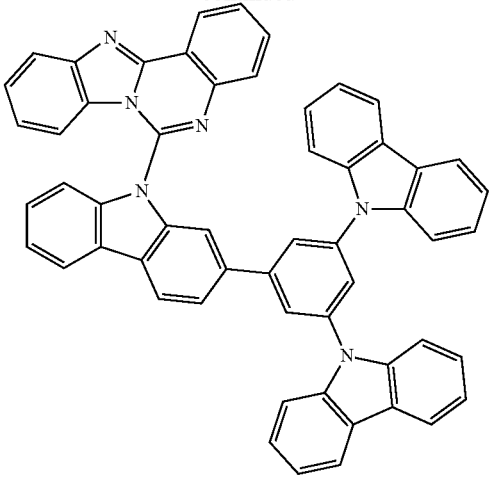
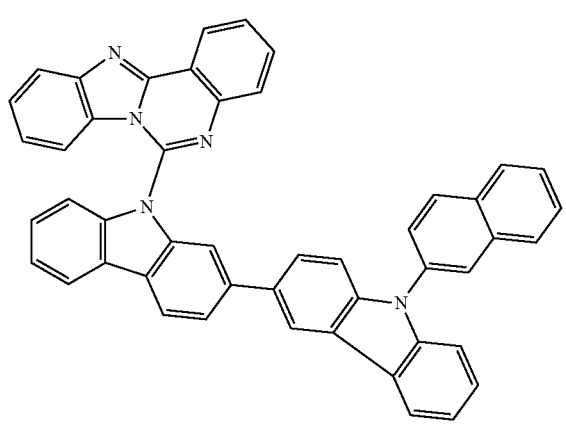
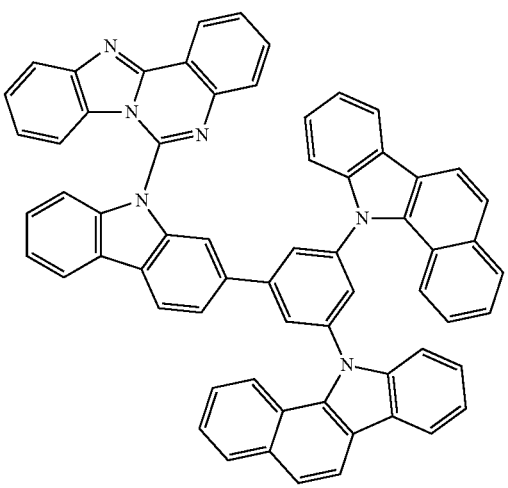
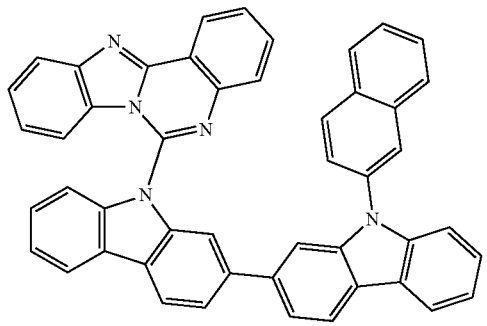
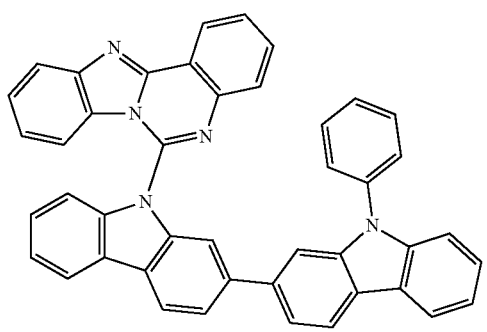
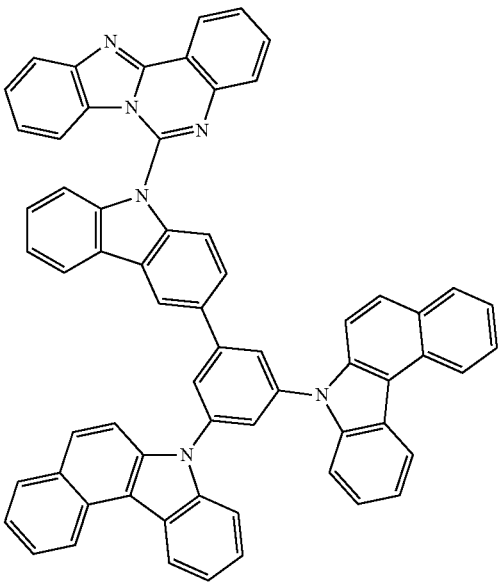

211
-continued
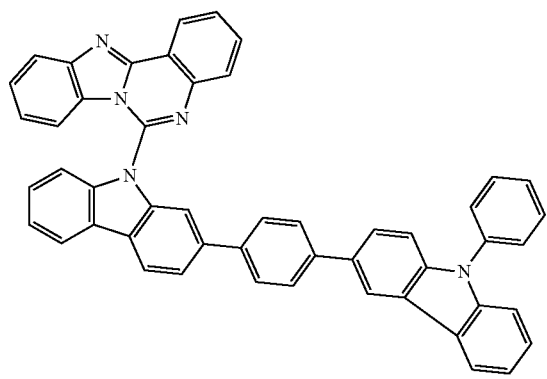
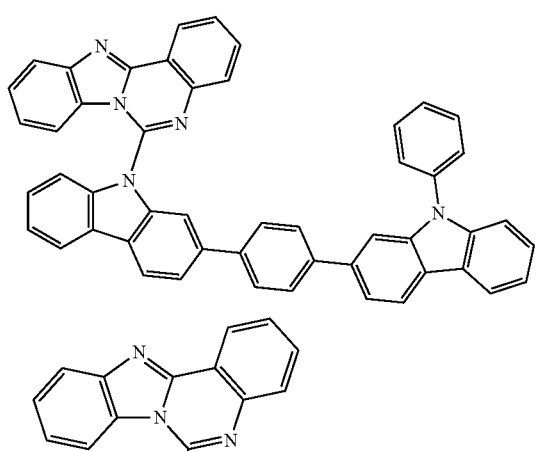
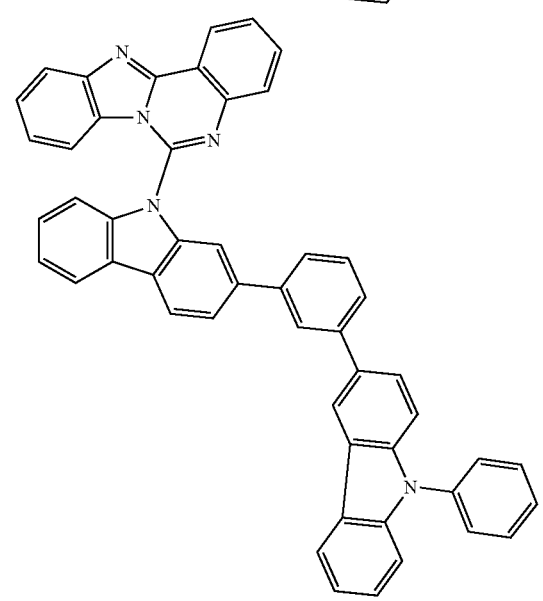
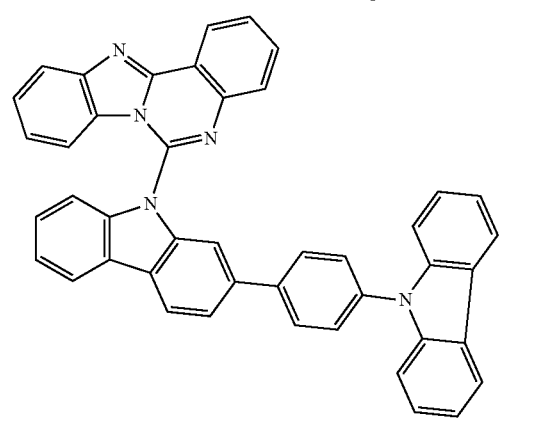
212
-continued
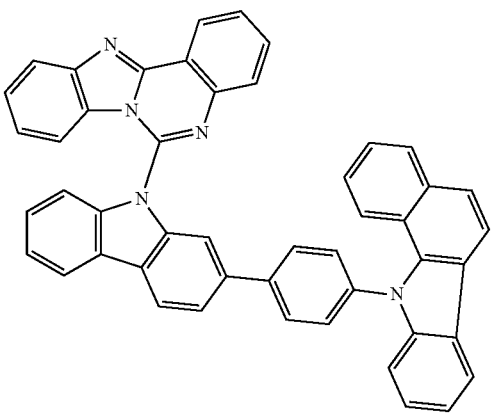
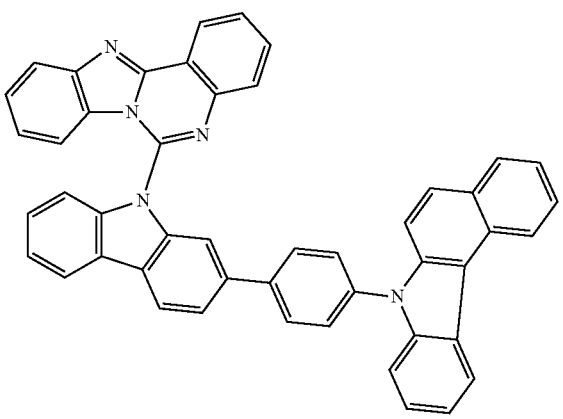
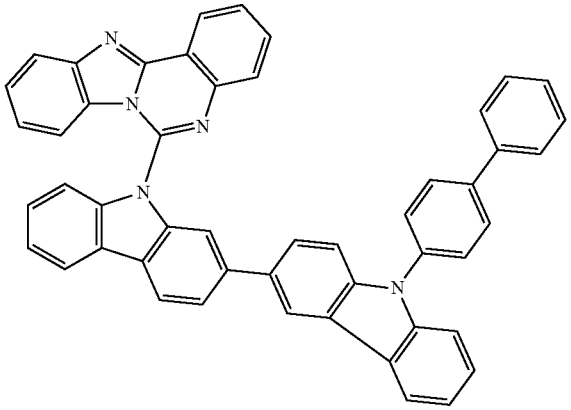
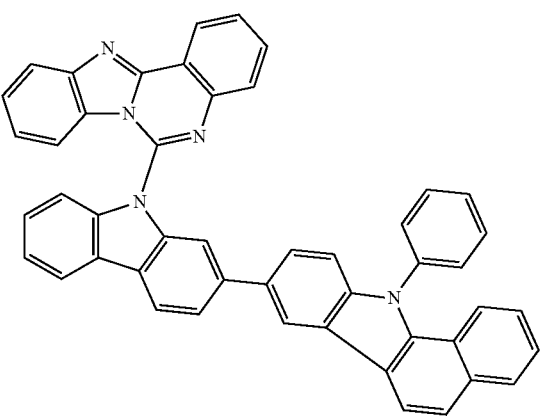

213
-continued
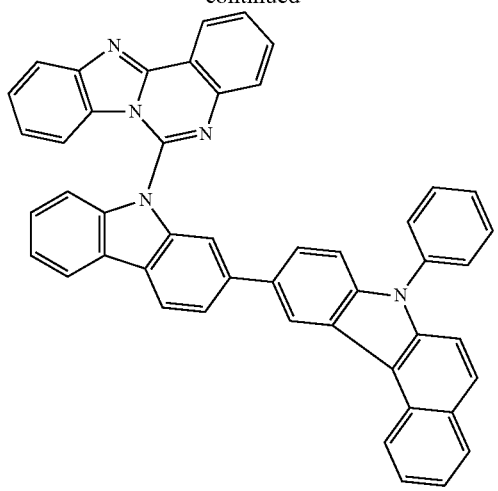
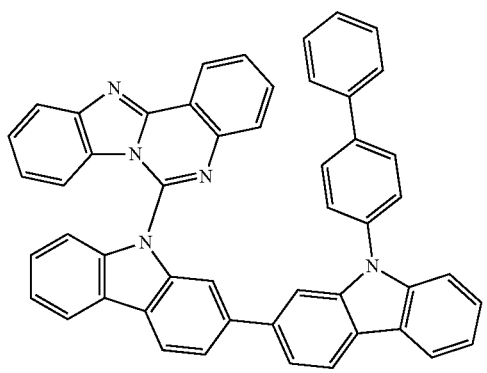
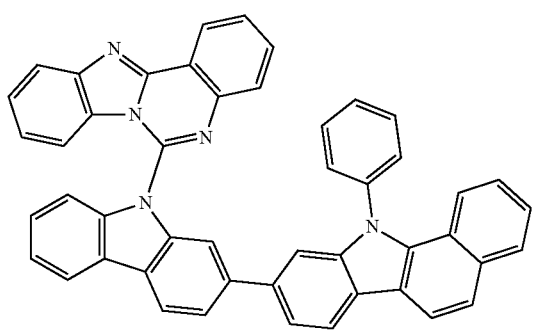
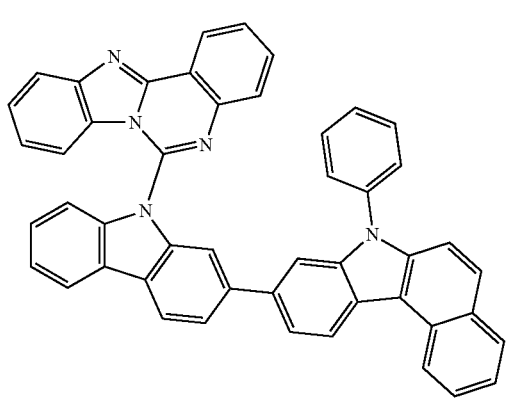
214
-continued
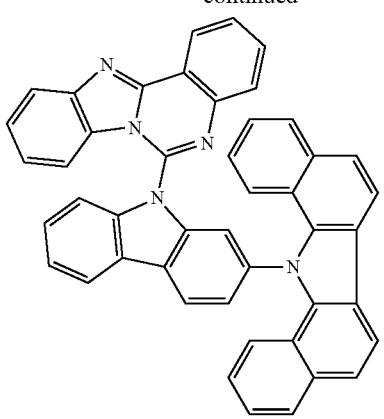
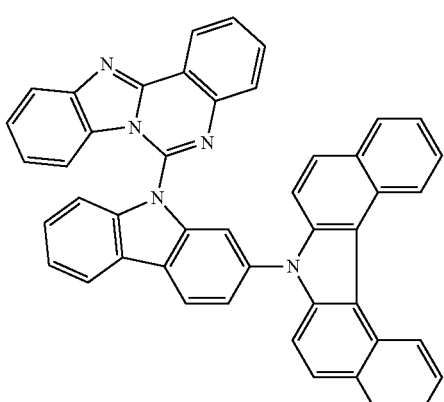
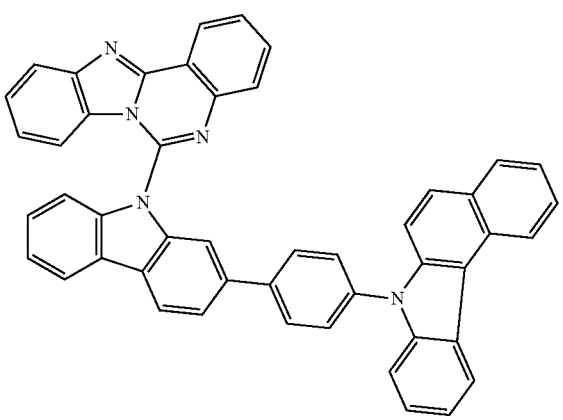

215
-continued
216
-continued
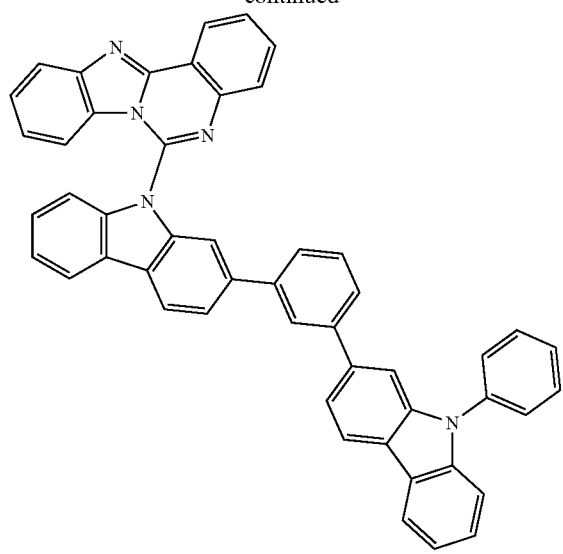
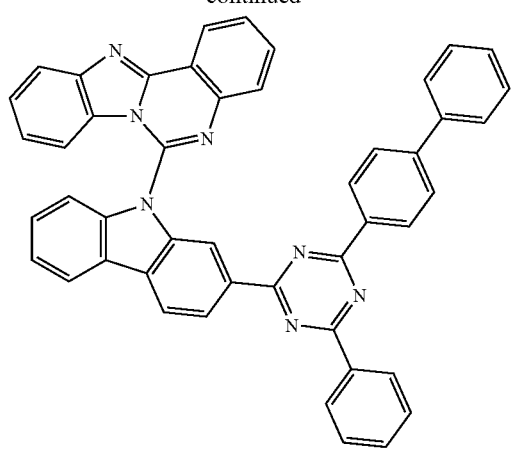
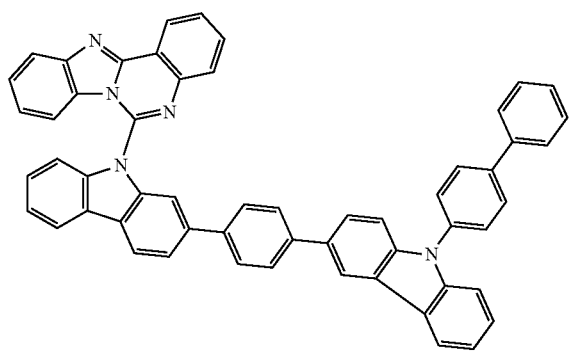
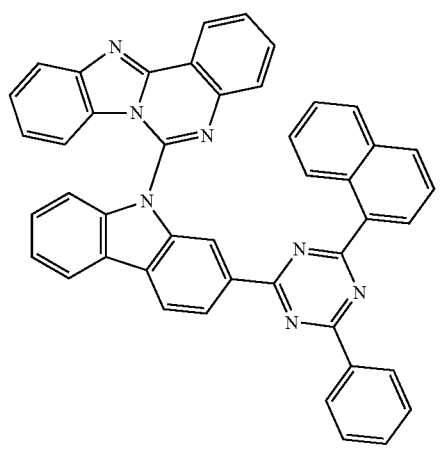
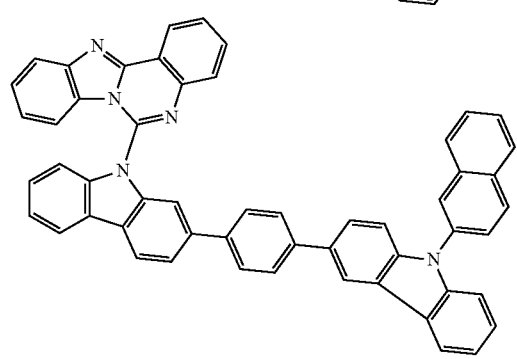
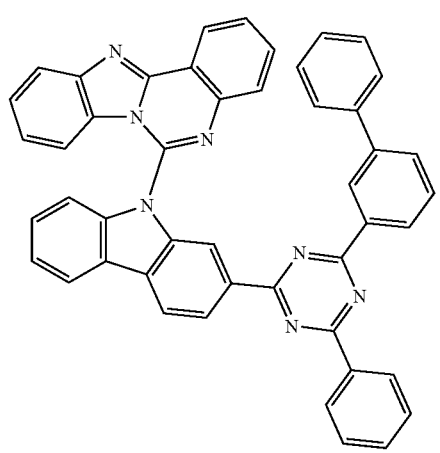

217
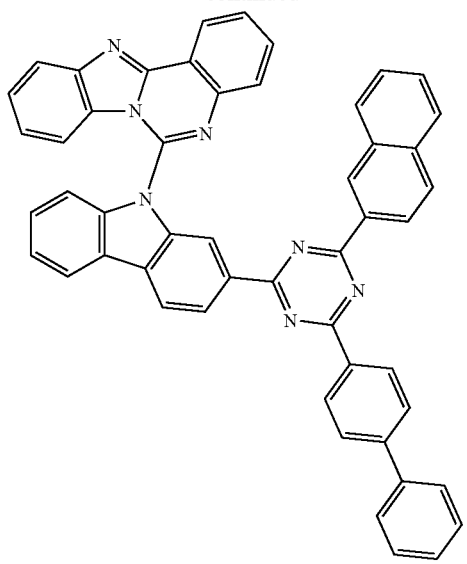
218
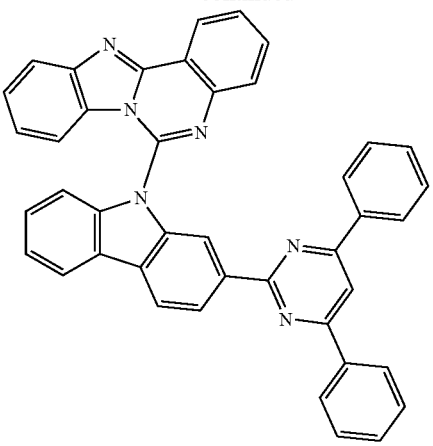
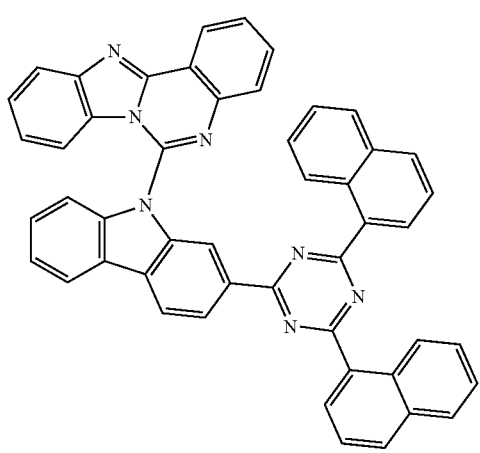
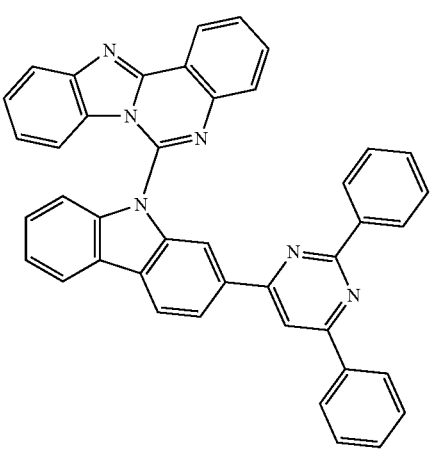
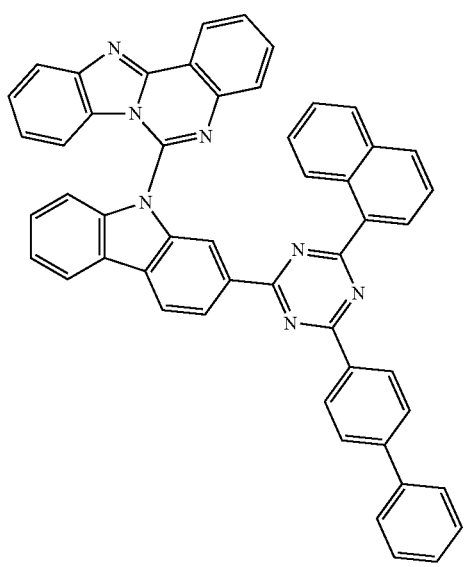
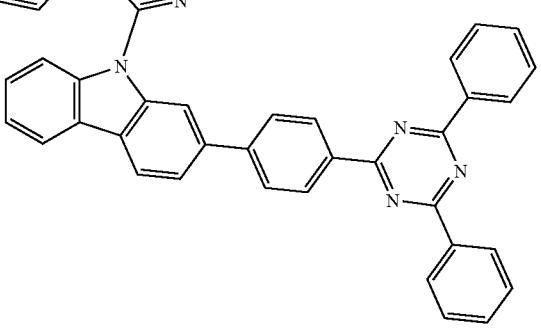

219
-continued
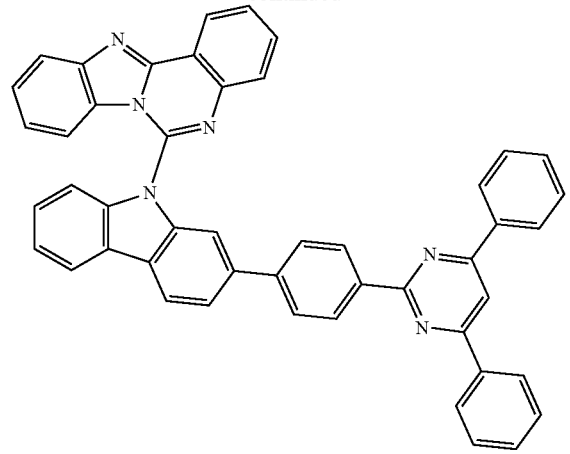
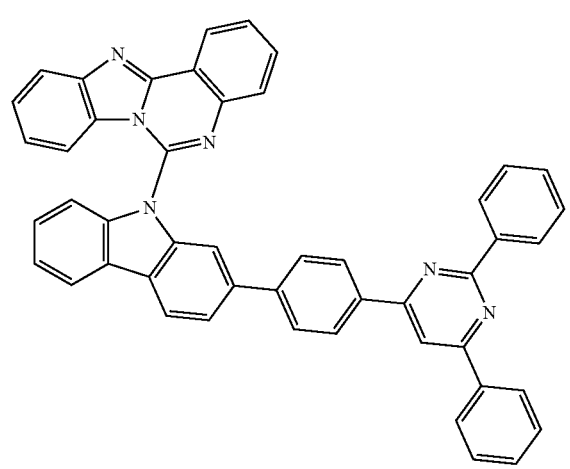
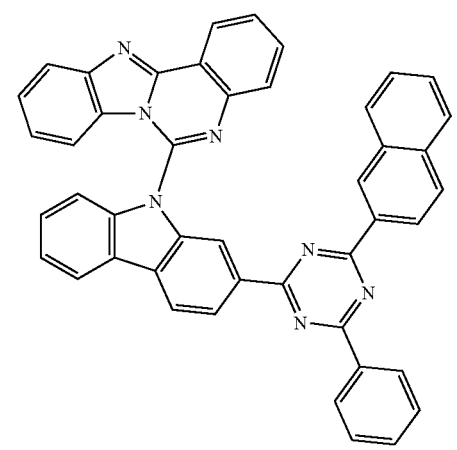
220
-continued
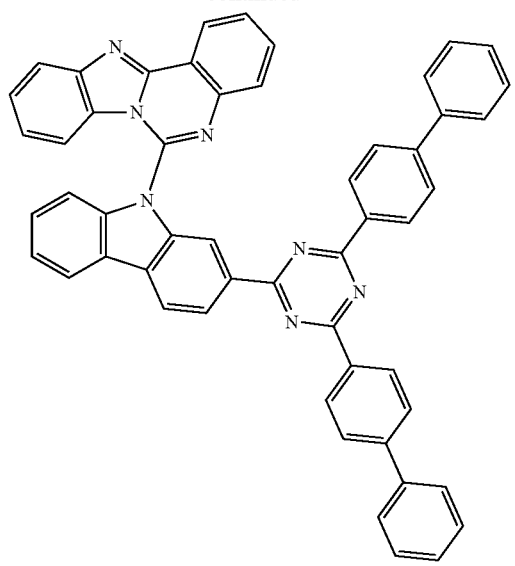
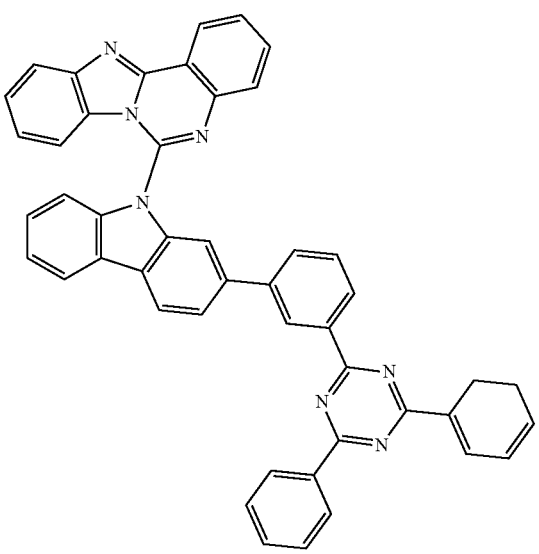
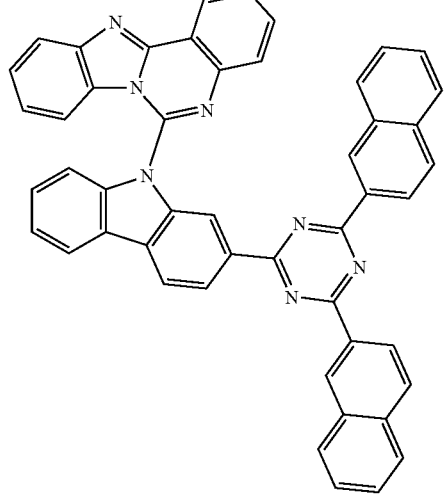

221
-continued
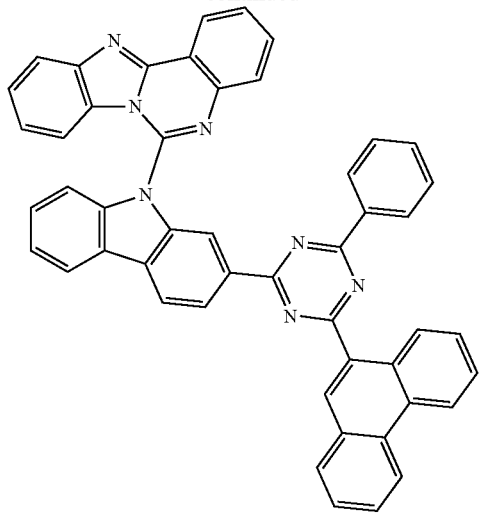
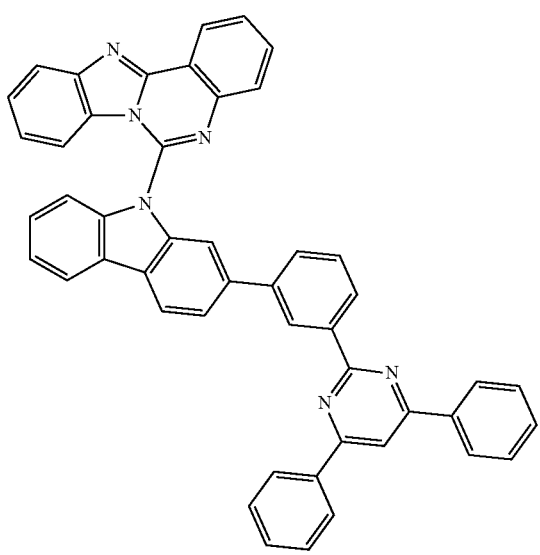
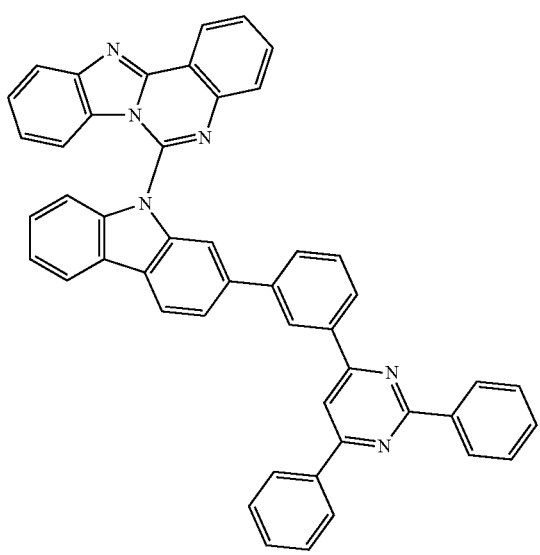
222
-continued
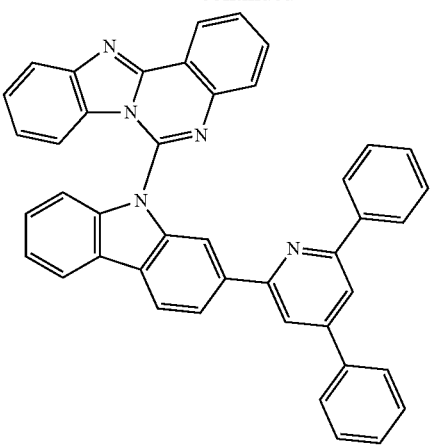
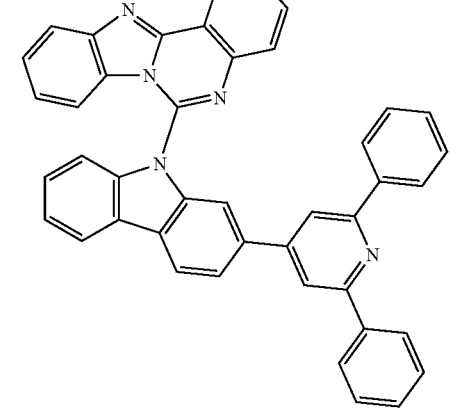
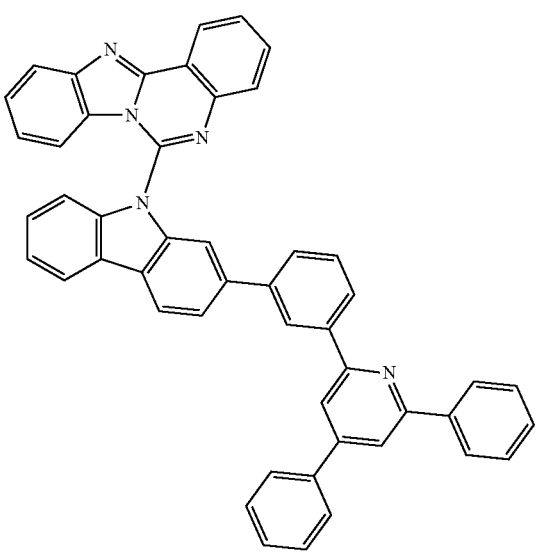

223
-continued
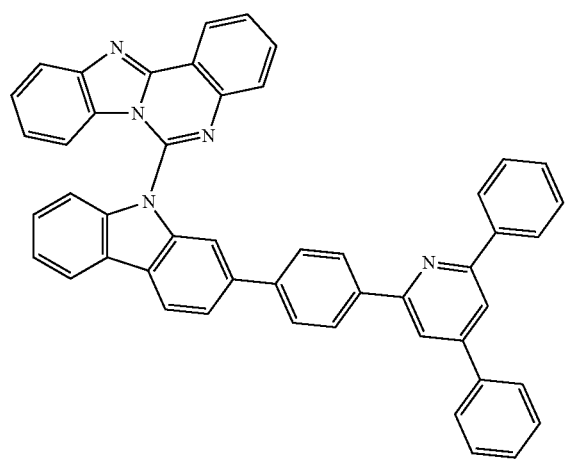
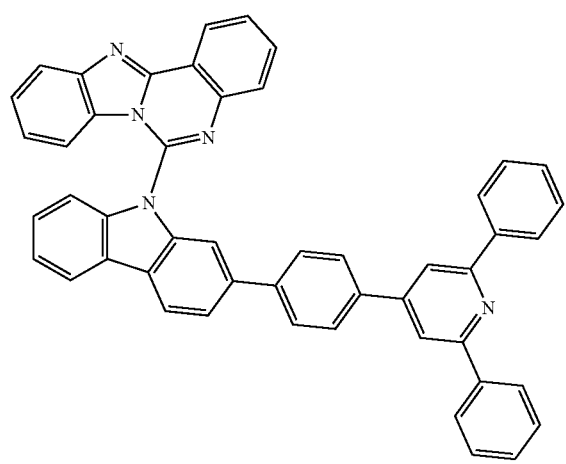
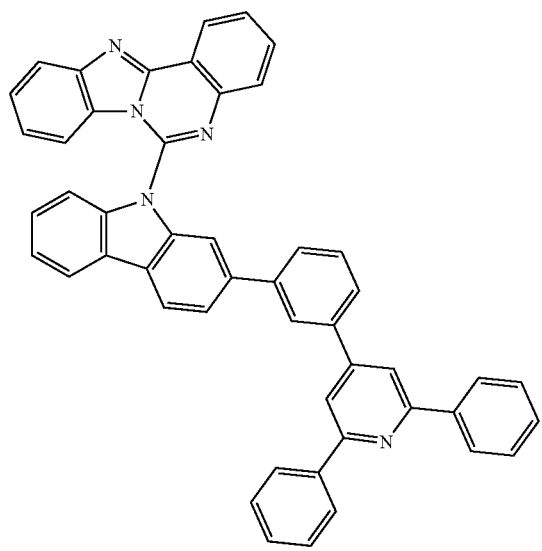
224
-continued
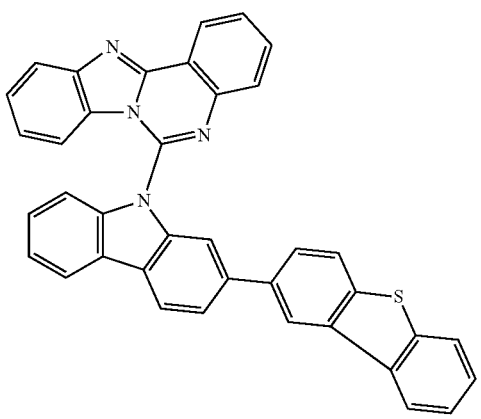
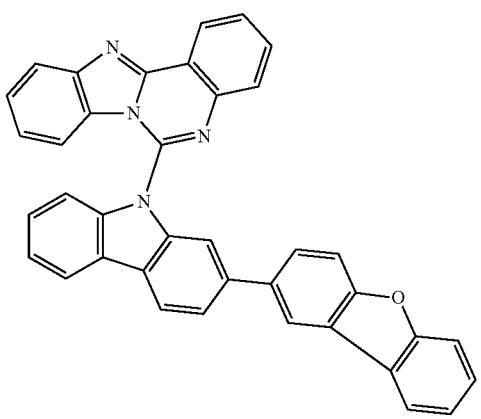
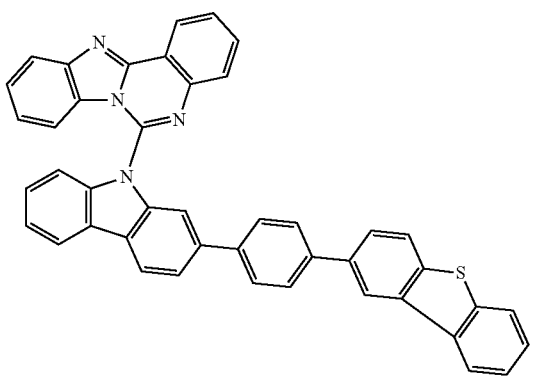
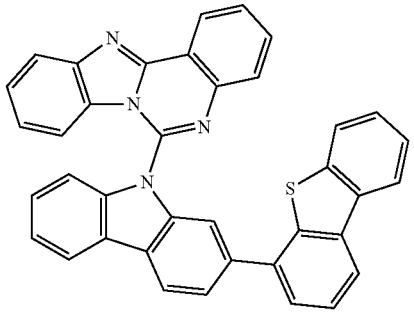

225
-continued
226
-continued
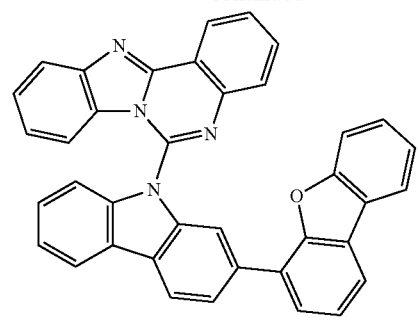
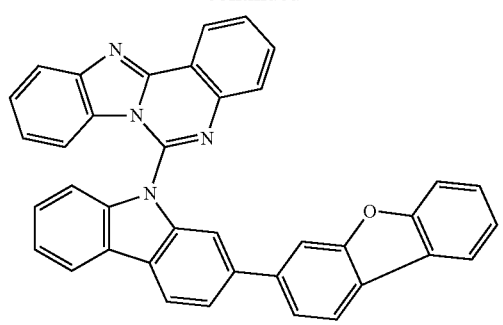
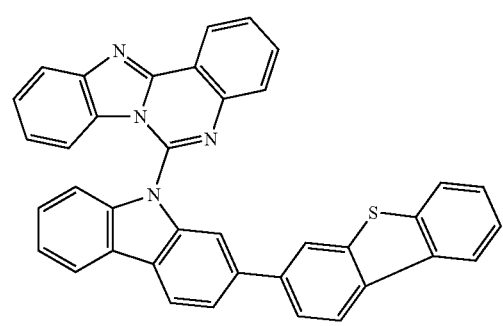
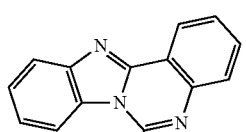
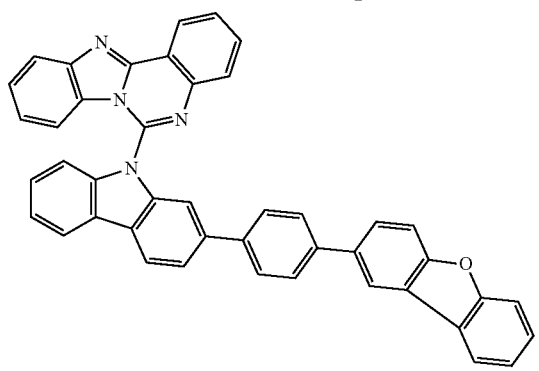
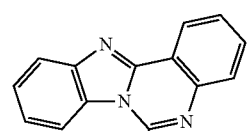
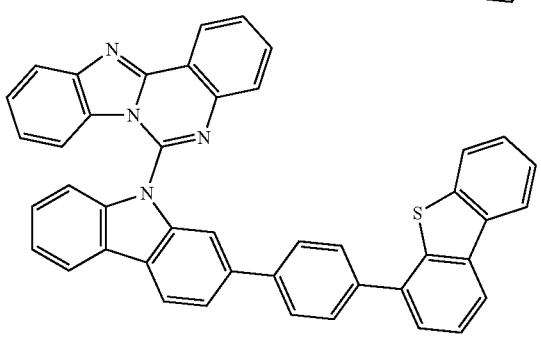
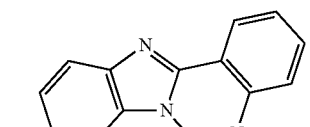
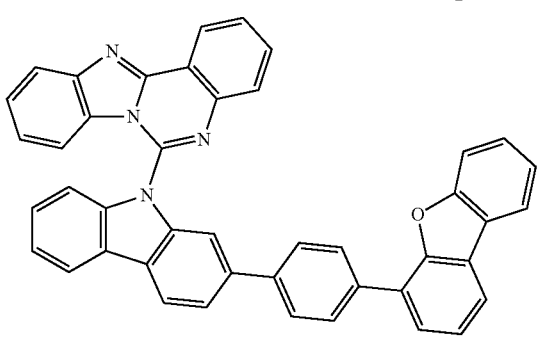
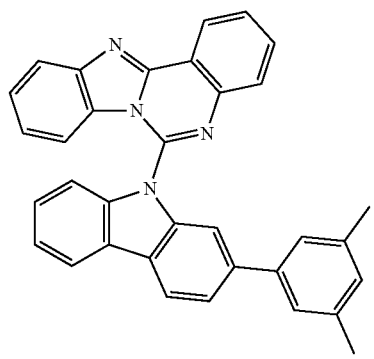

227
-continued
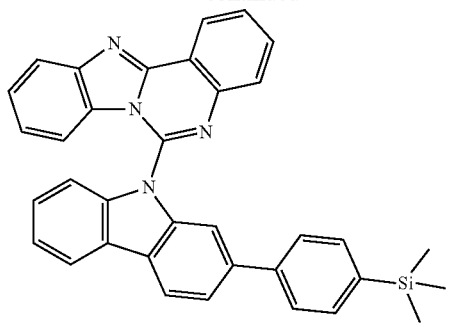
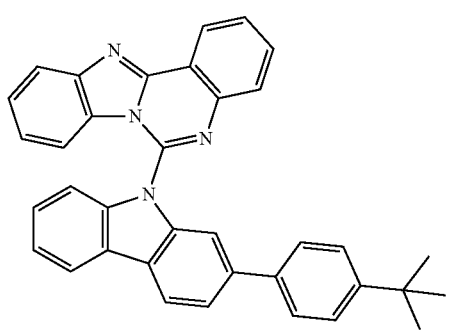
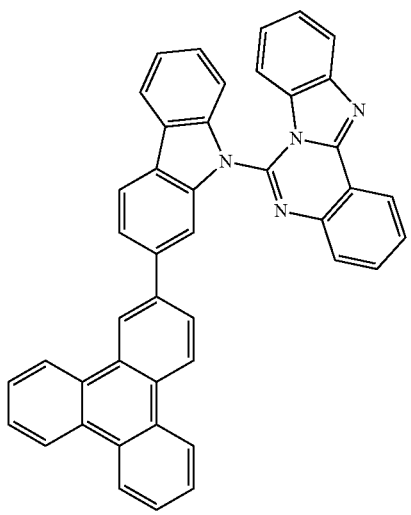
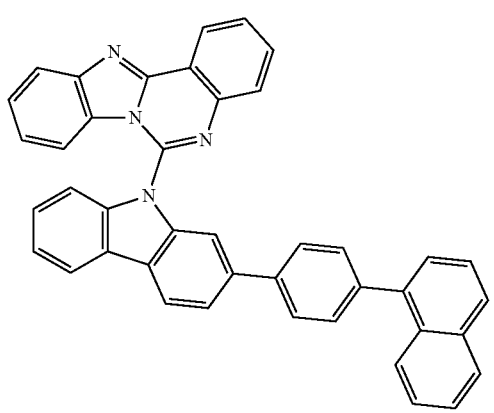
228
-continued
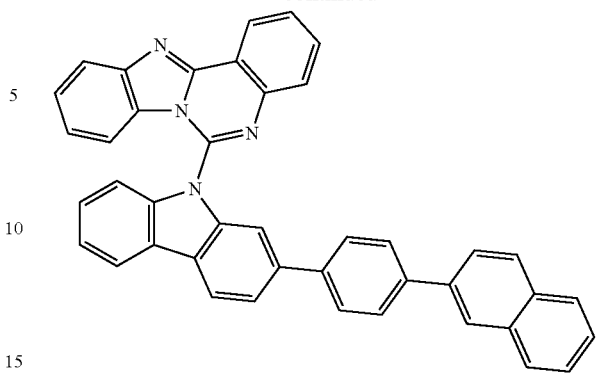
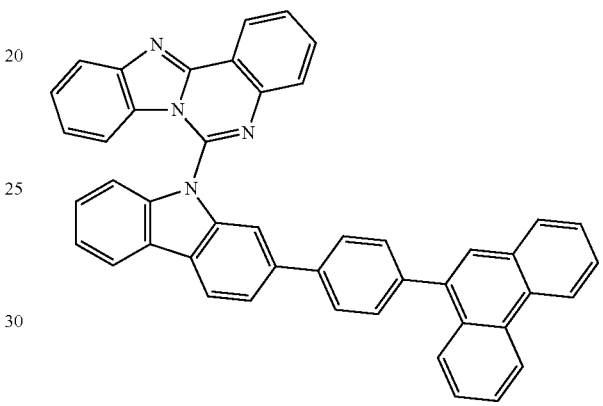
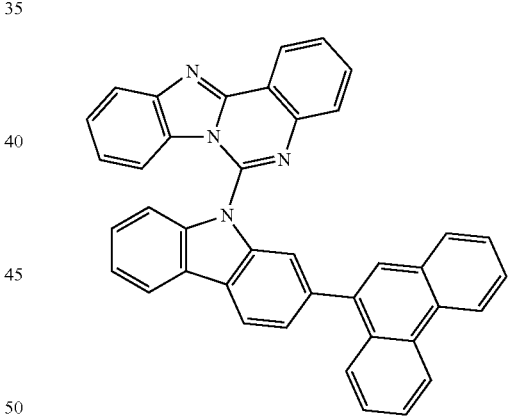
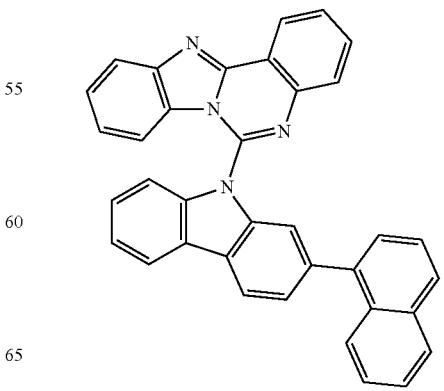

-continued
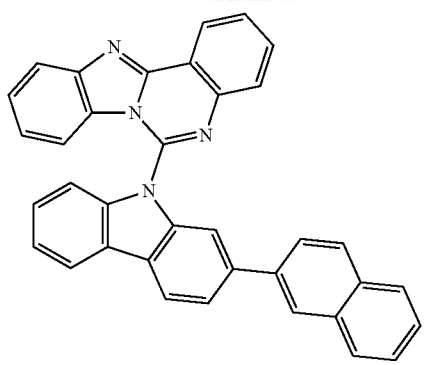
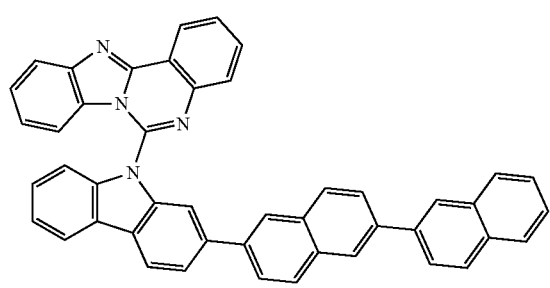
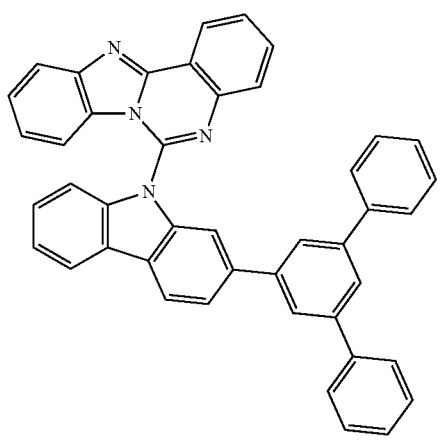
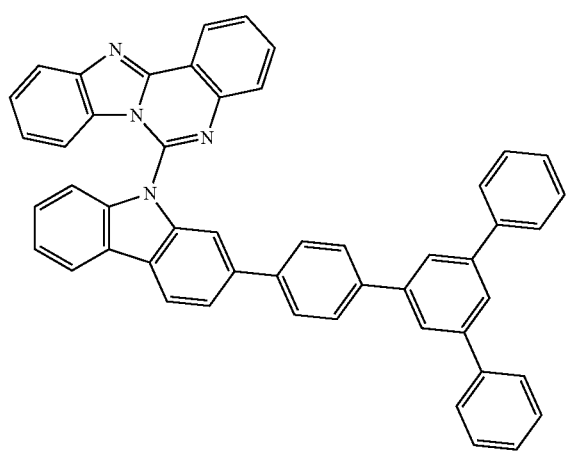
-continued
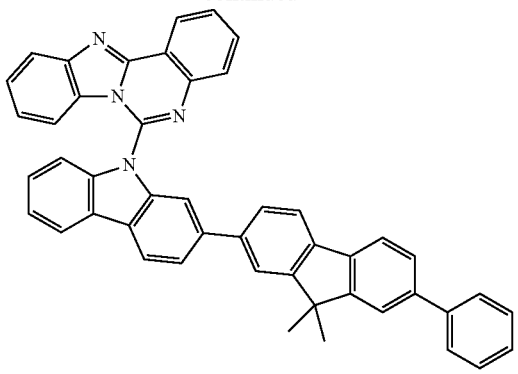
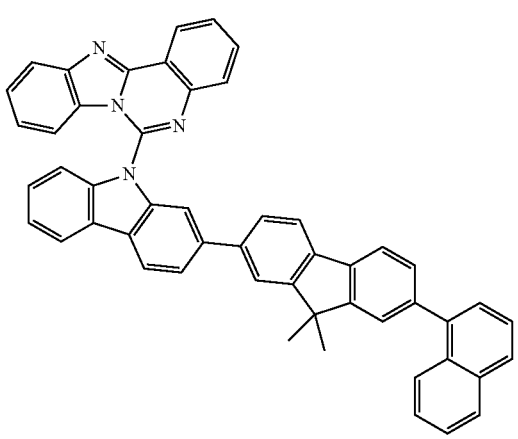
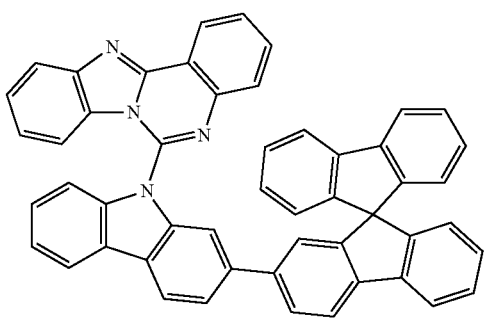
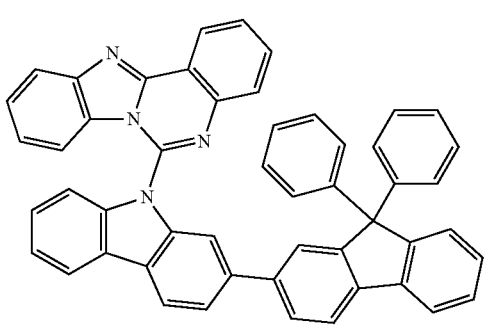

231
-continued
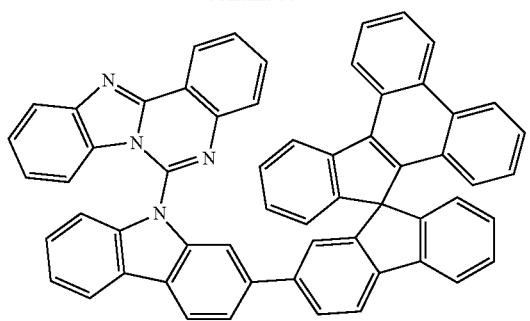
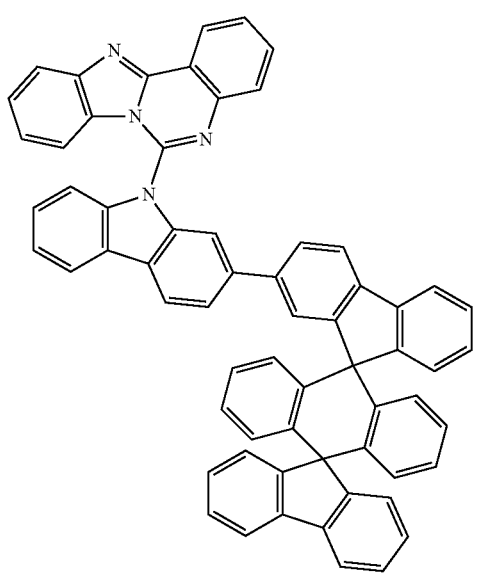
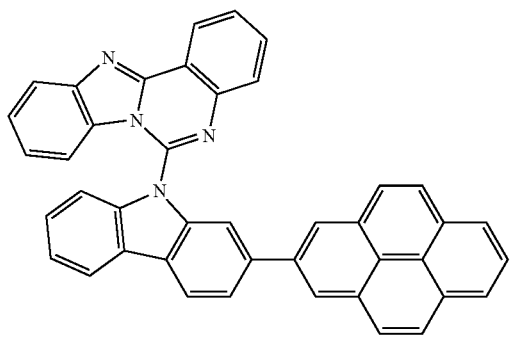
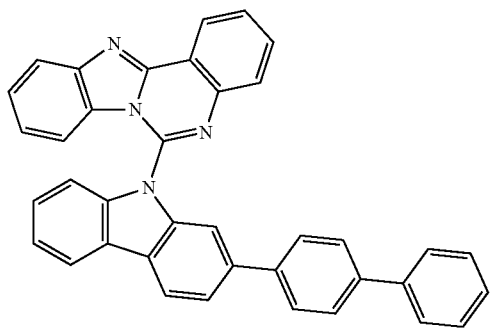
232
-continued
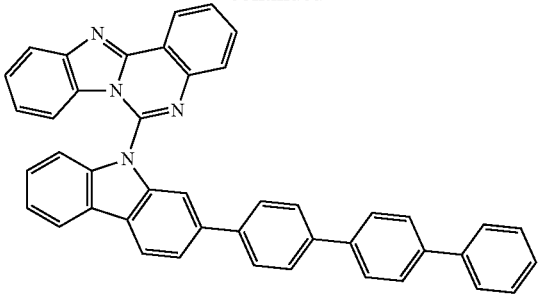
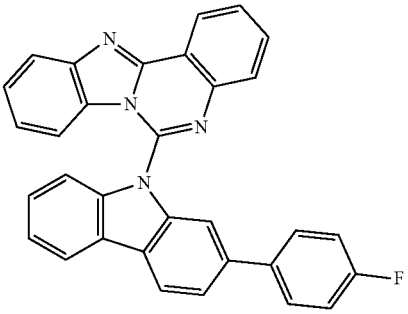
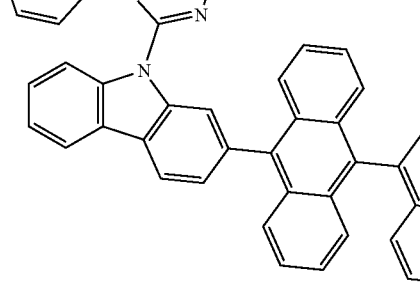
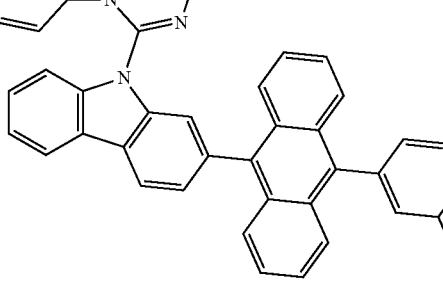
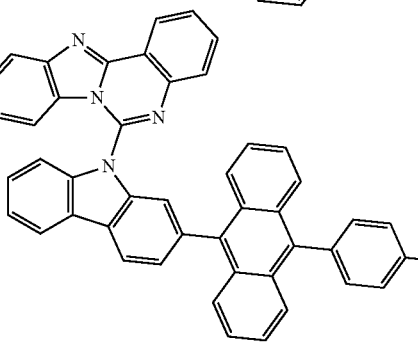

233
-continued
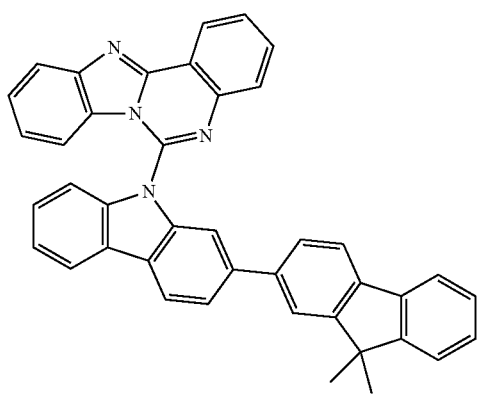
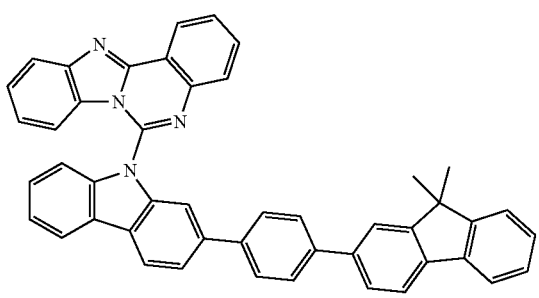
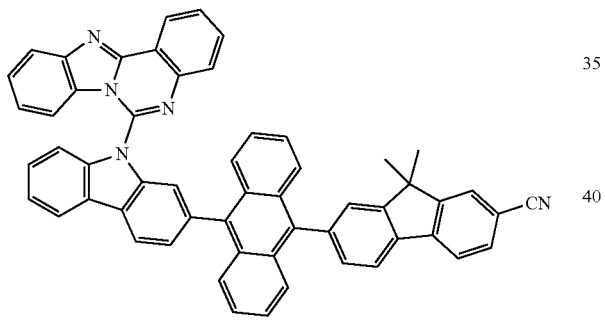
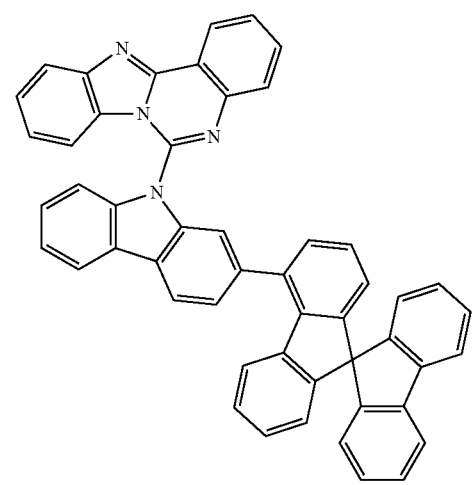
234
-continued
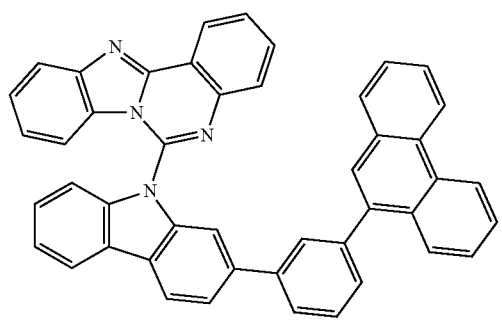
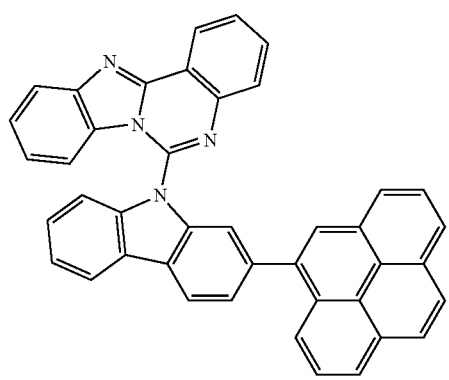
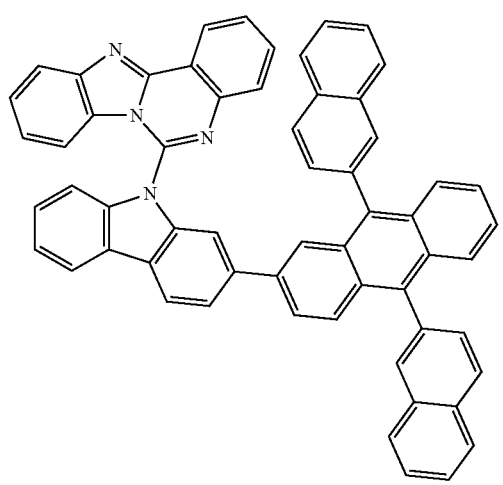
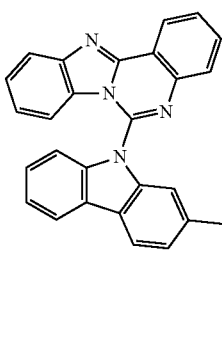

235
-continued
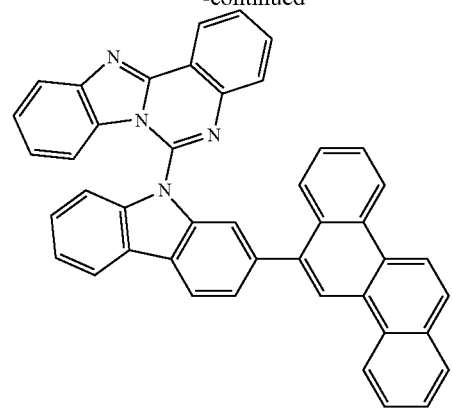
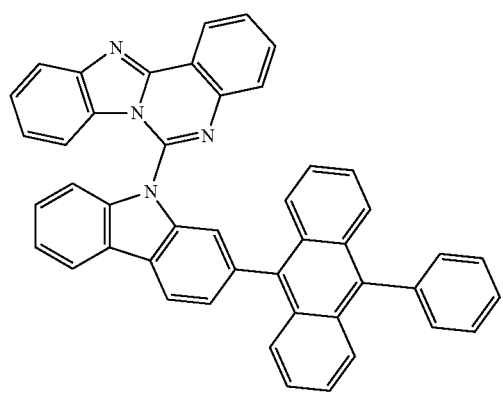
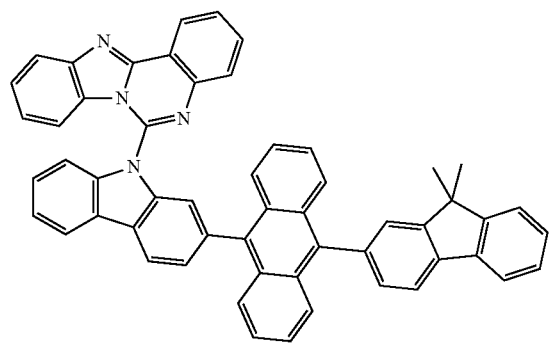
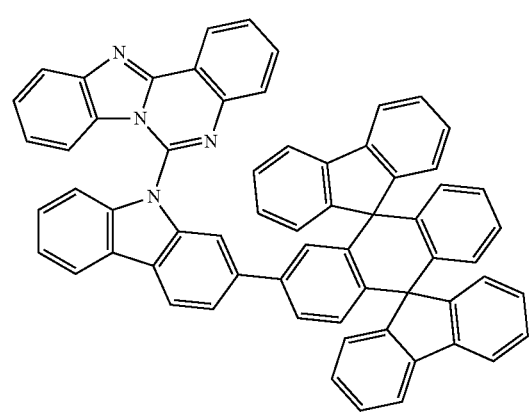
236
-continued
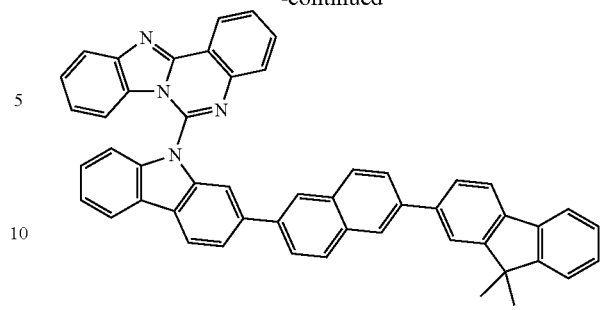
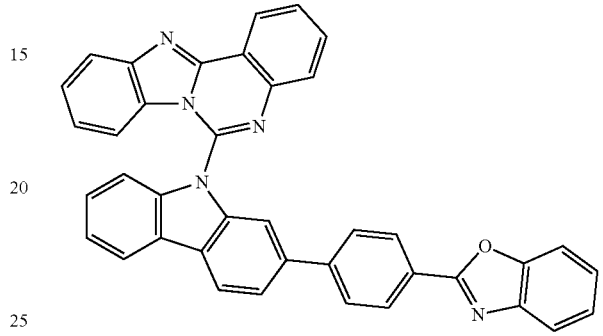
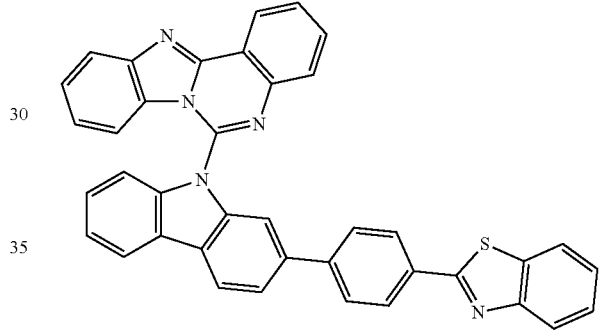
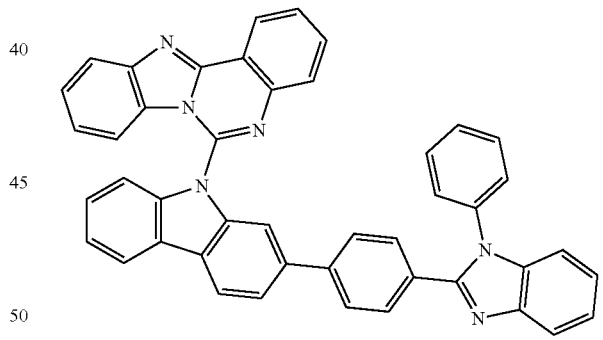
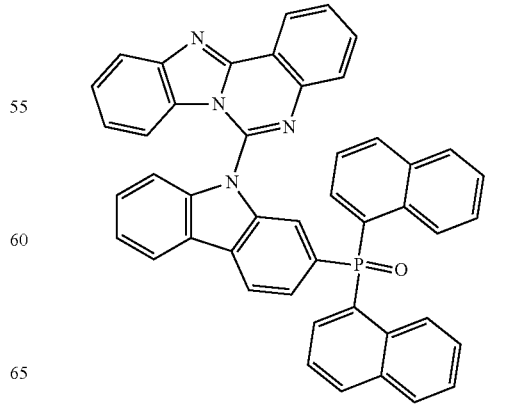

237
-continued
238
-continued
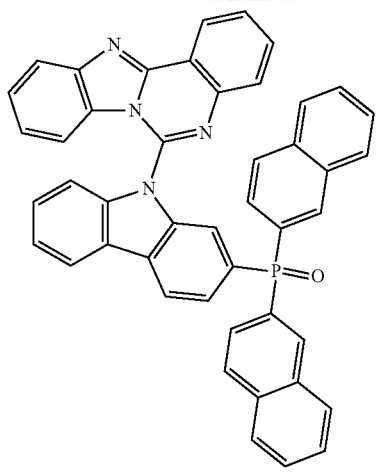
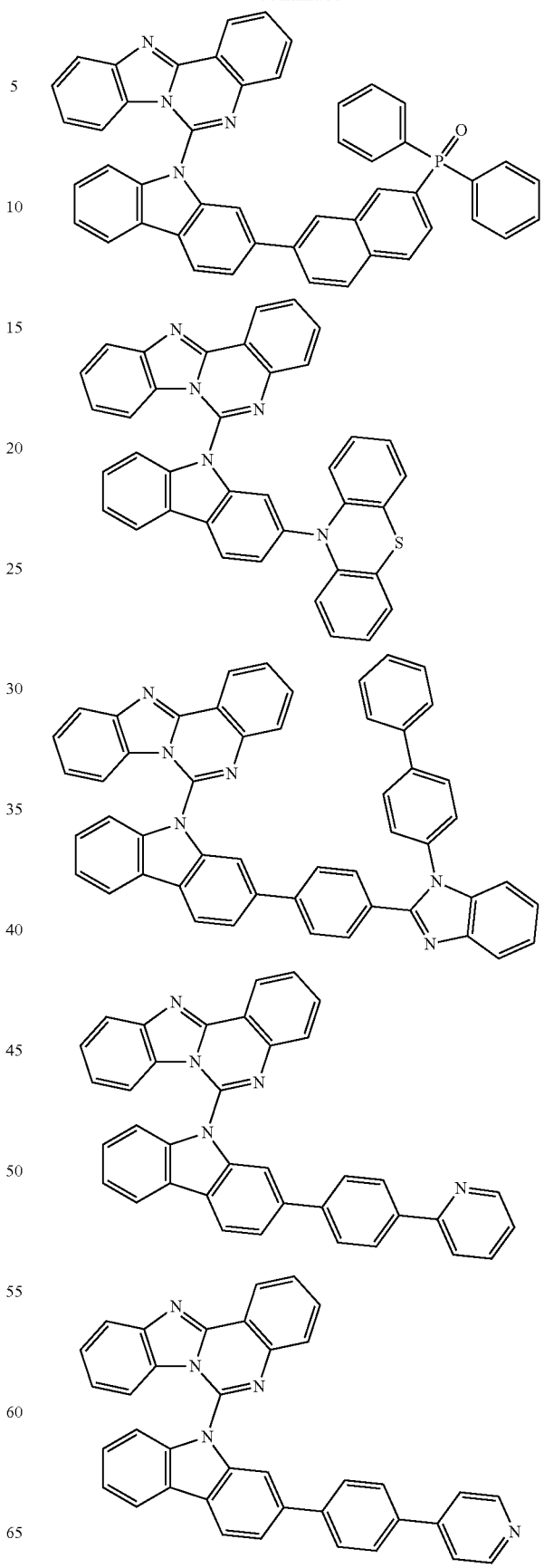

239
-continued
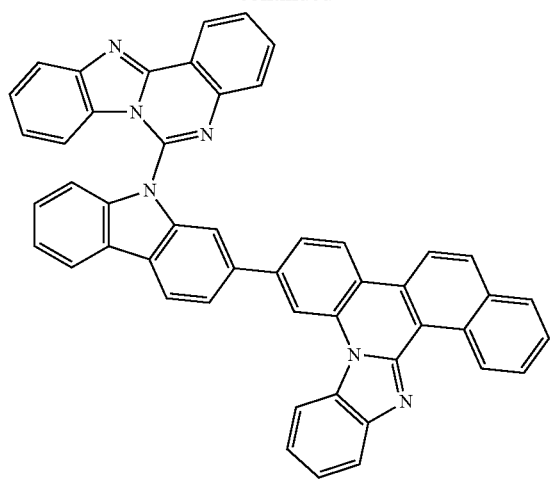
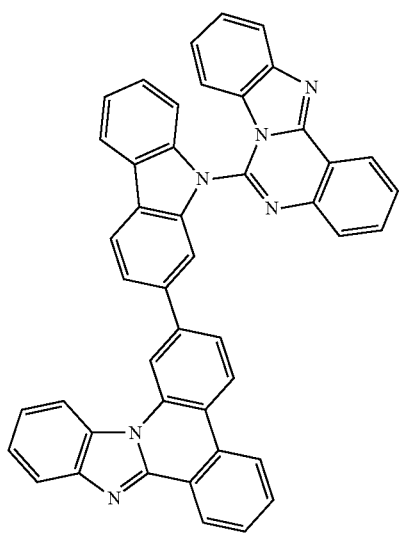
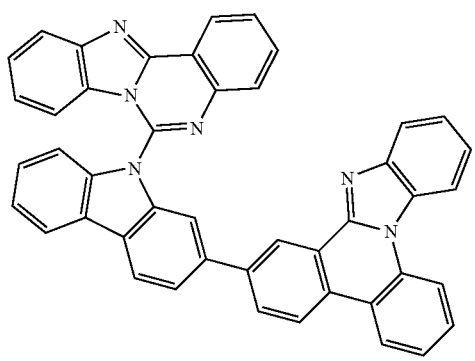
240
-continued
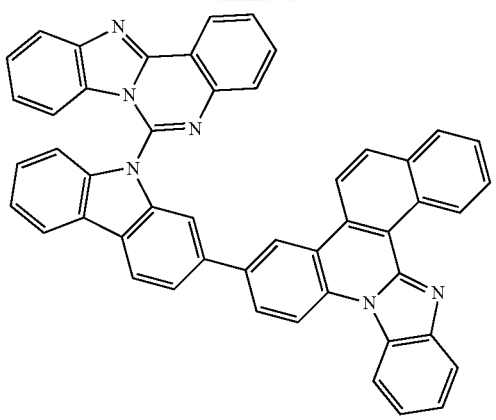
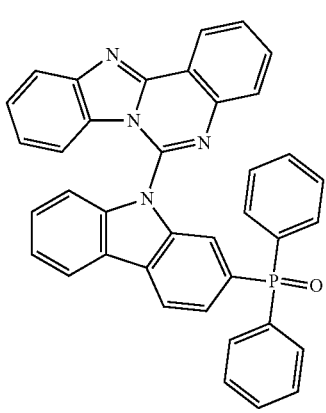
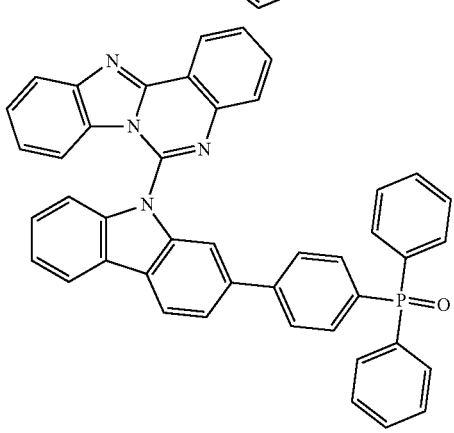
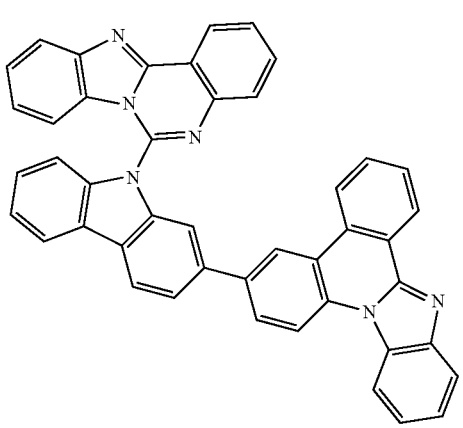

241
-continued
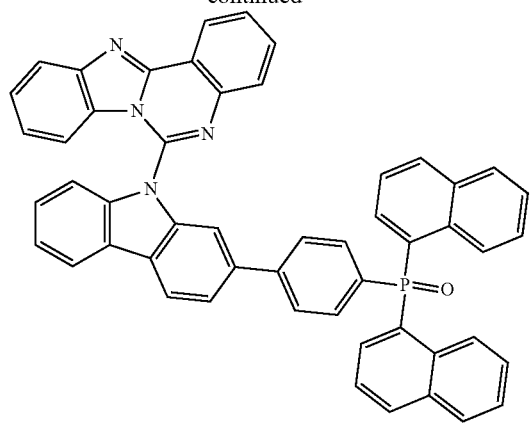
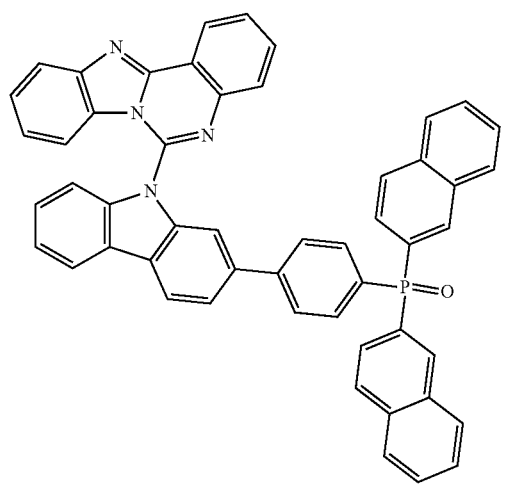
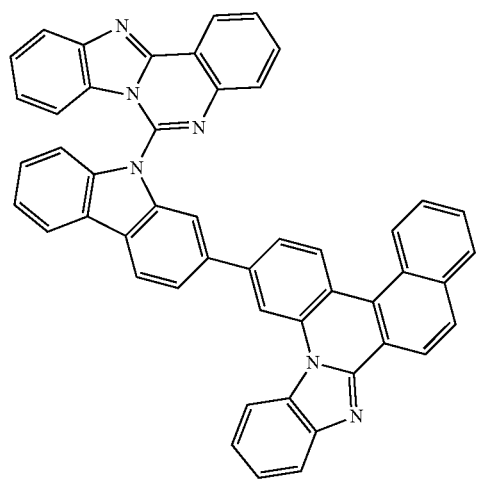
242
-continued
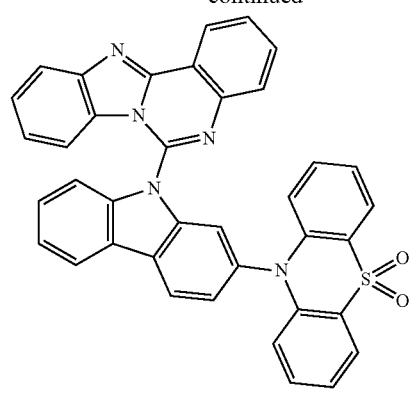
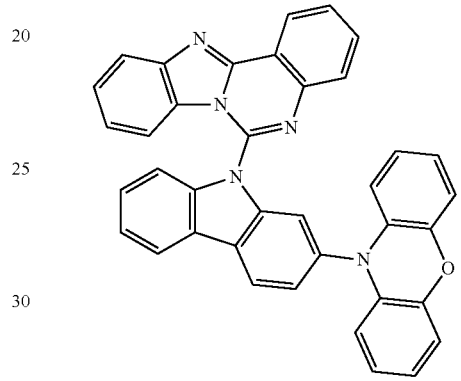
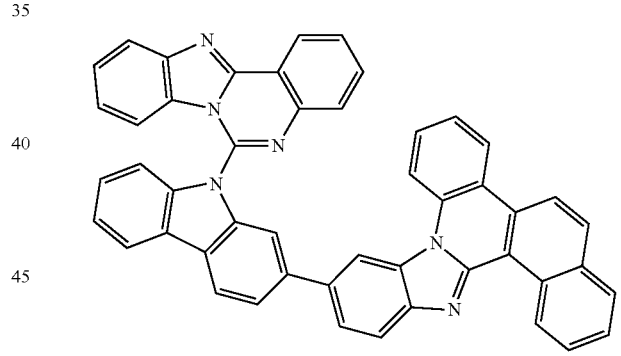
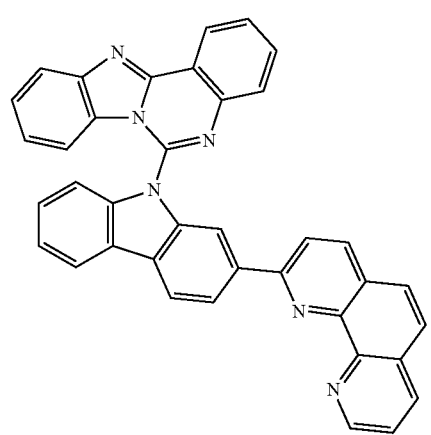

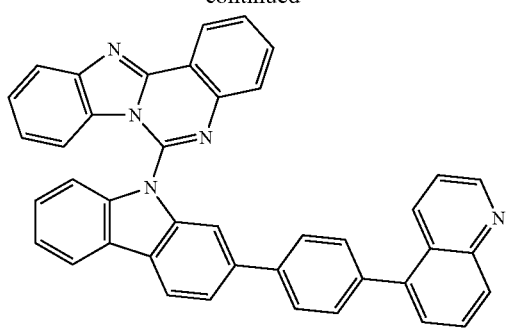
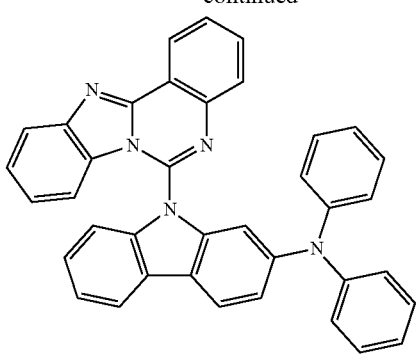
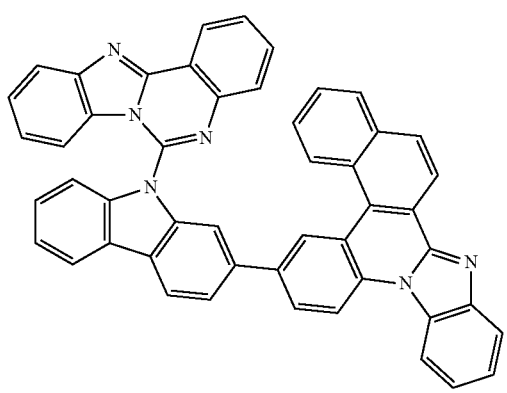
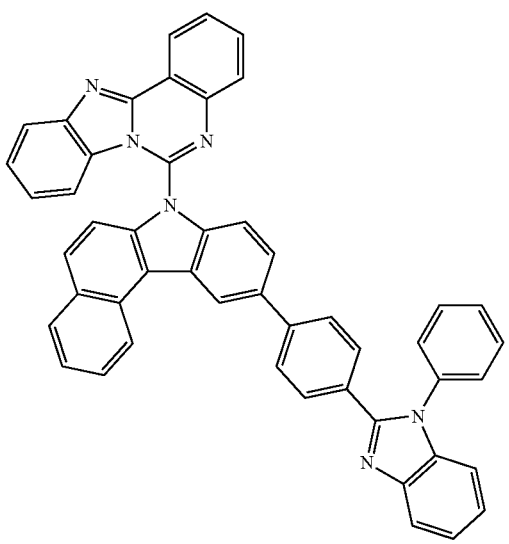
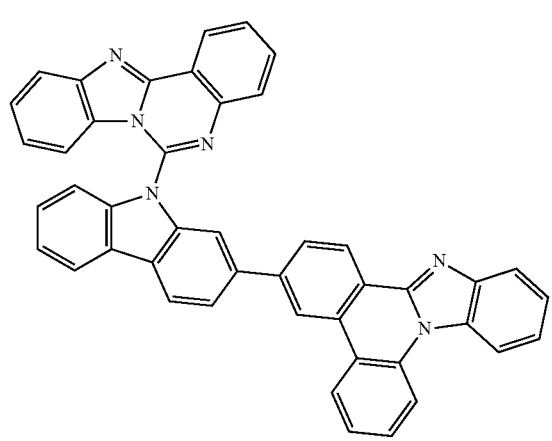
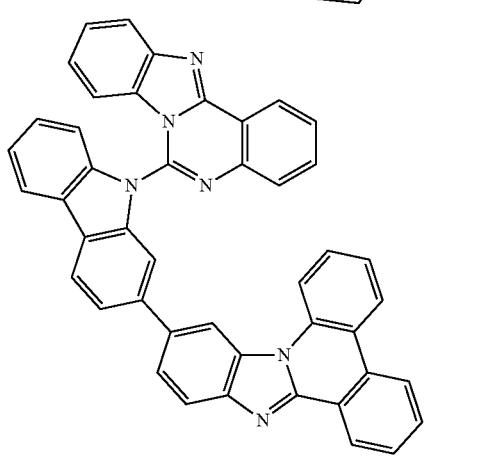
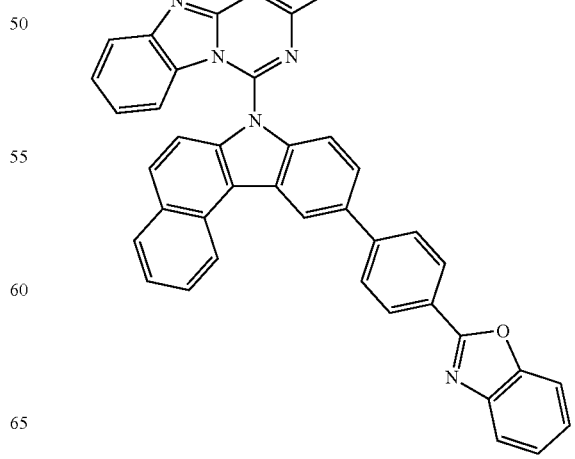

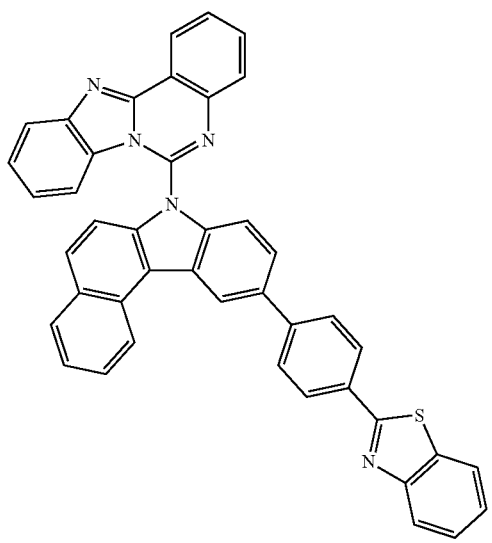

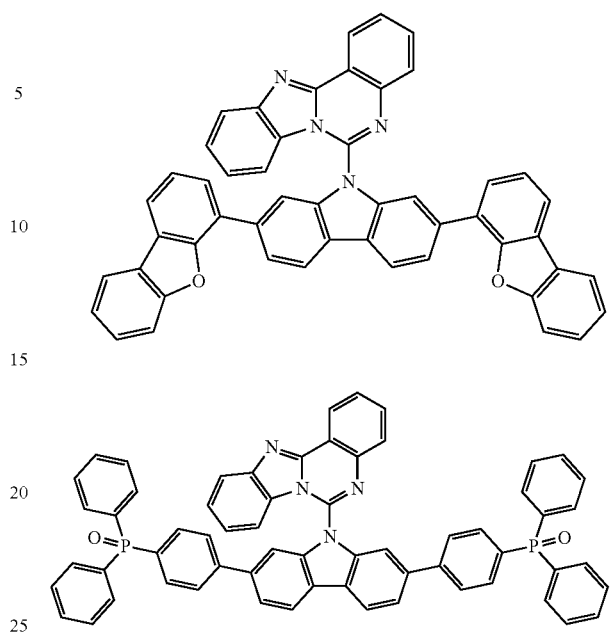

The compound according to one embodiment of the present application may be prepared using preparation methods described below.

For example, the core structure of the compound of Chemical Formula 1 may be prepared as in the following General Formulae 1 to 6. Substituents may bond thereto using methods known in the art, and the types, the positions or the number of the substituents may change depending on technologies known in the art.

[General Formula 1]

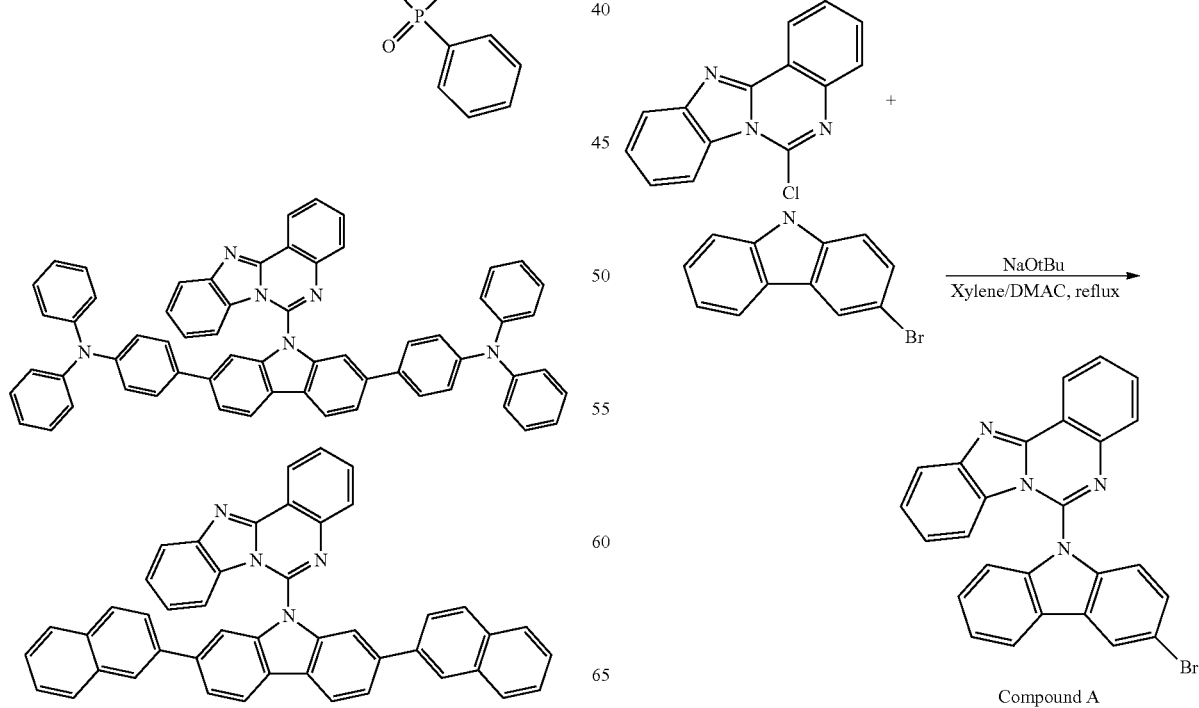

Compound A

247
-continued
[General Formula 2]
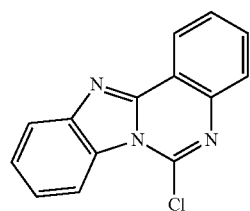
+
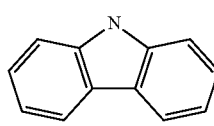 → NaOtBu / Xylene/DMAC, reflux →
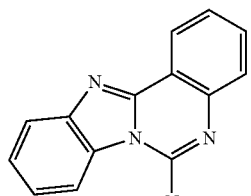
Compound B
[General Formula 3]
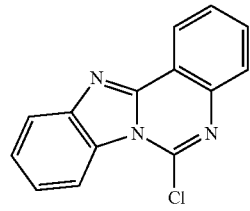
+
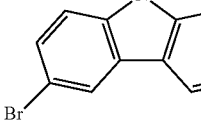 → NaOtBu / Xylene/DMAC, reflux →
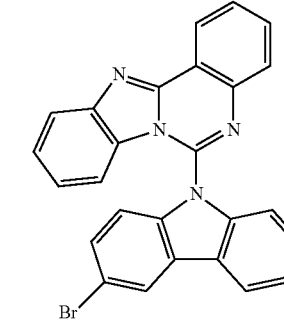
Compound C
[General Formula 4]
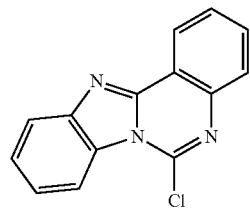
+
248
-continued
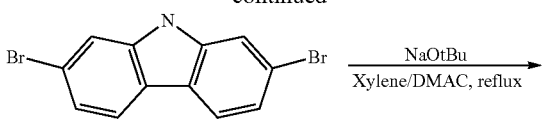 → NaOtBu / Xylene/DMAC, reflux →
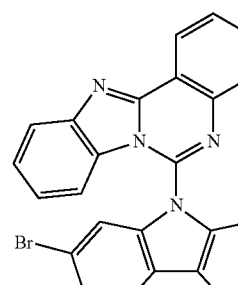
Compound D
[General Formula 5]
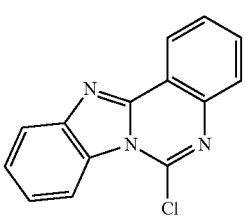
+
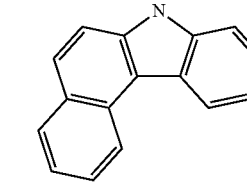 → NaOtBu / Xylene/DMAC, reflux →
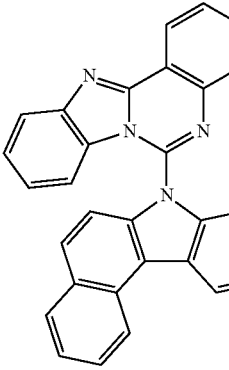
Compound E
[General Formula 6]
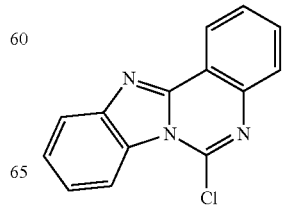
+

249

-continued

250

-continued

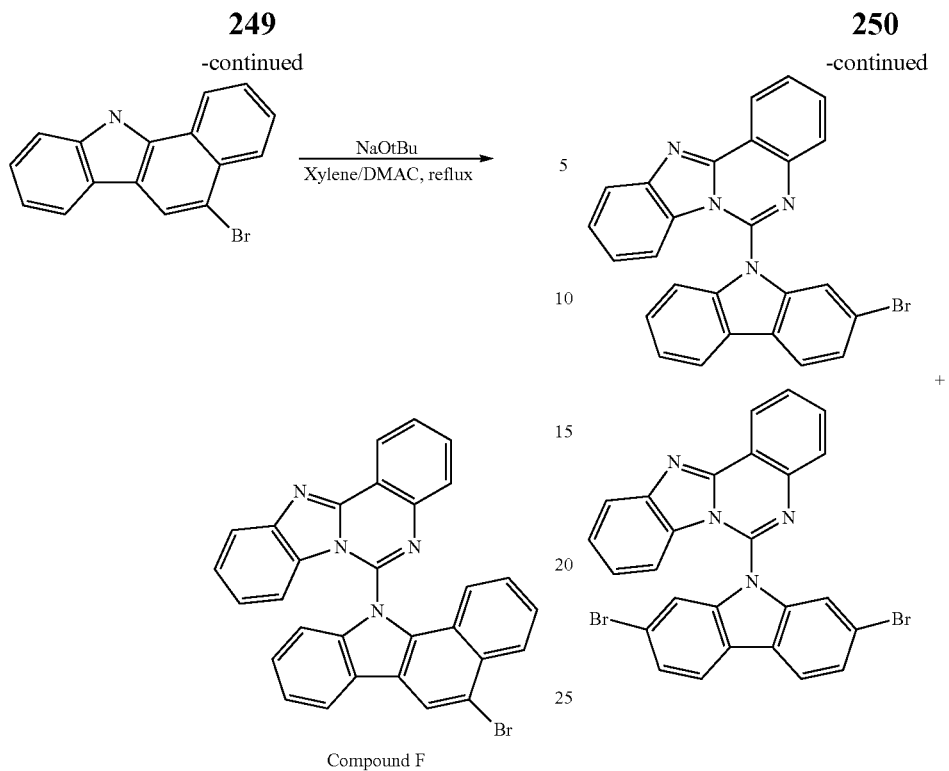

Compound F

The position of Br in the core prepared in General Formulae 1 to 6 may be a position substituted with the $-(L)_m$-Ar.

As described above, substituents may bond to the core using methods known in the art, and the types, the positions or the number of the substituents may change depending on technologies known in the art. For example, substituents such as an amine group, an aryl group and a heterocyclic group may be linked by the following General Formulae 7 to 9.

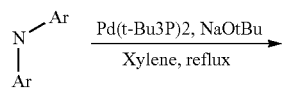

[General Formula 7]

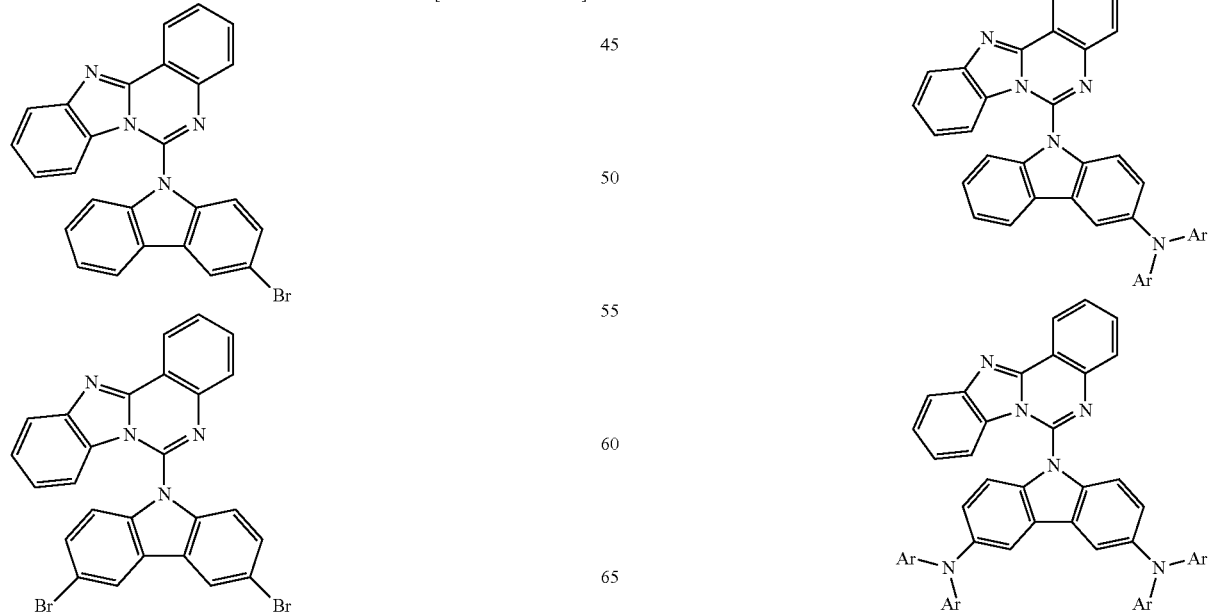

251
-continued
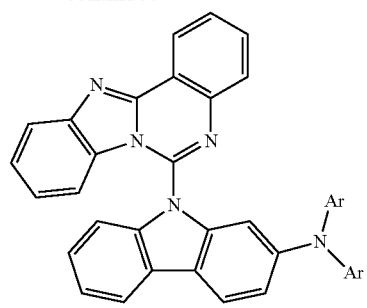
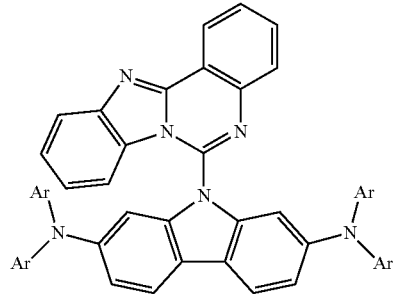
252
-continued
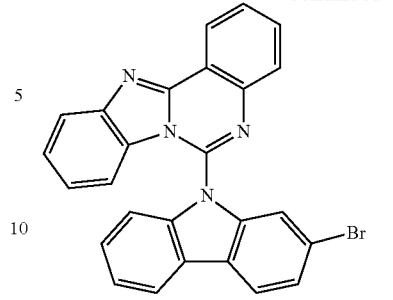
+
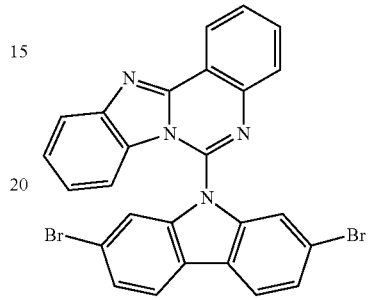
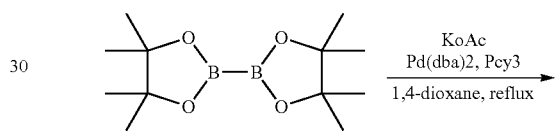
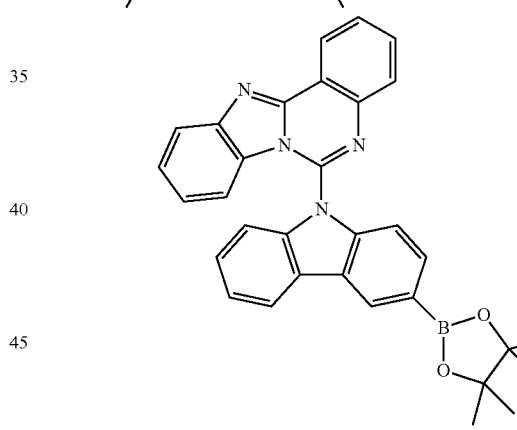
G
[General Formula 8]
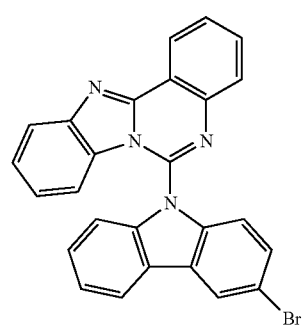
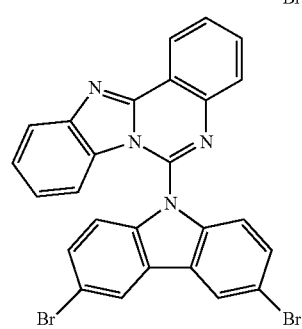
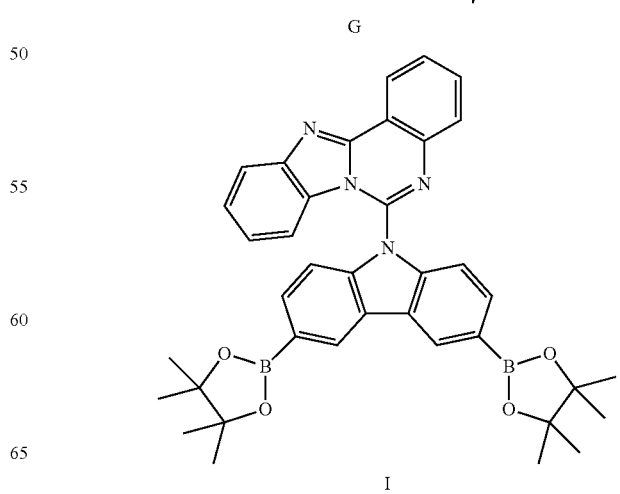
I -continued
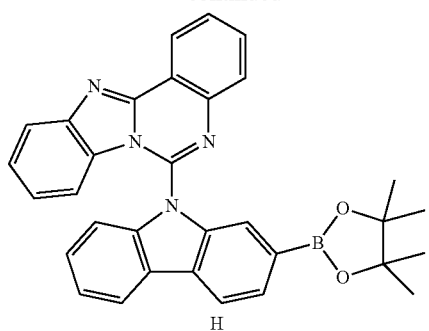
H
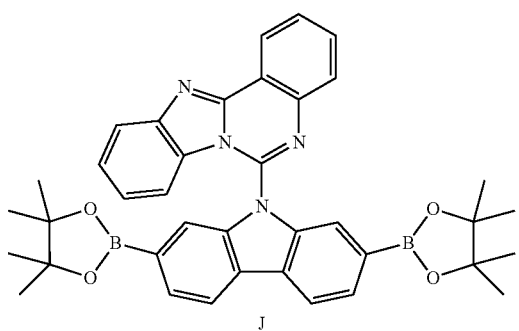
J
[General Formula 9]
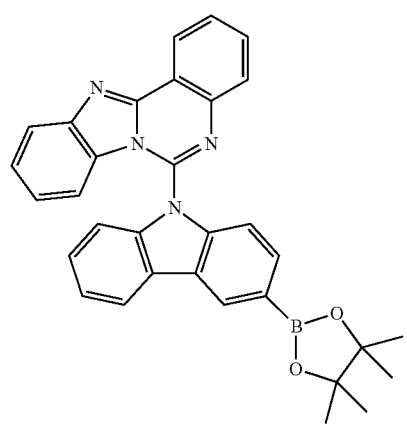
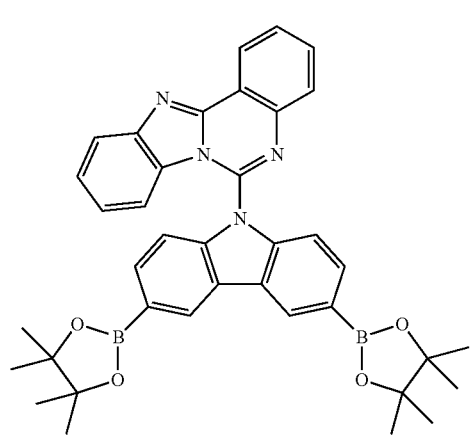
-continued
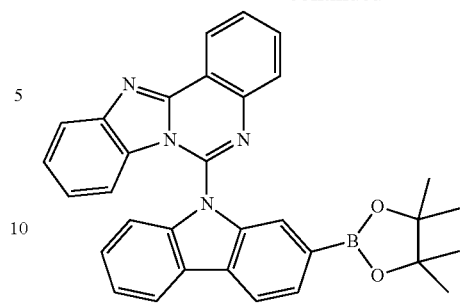
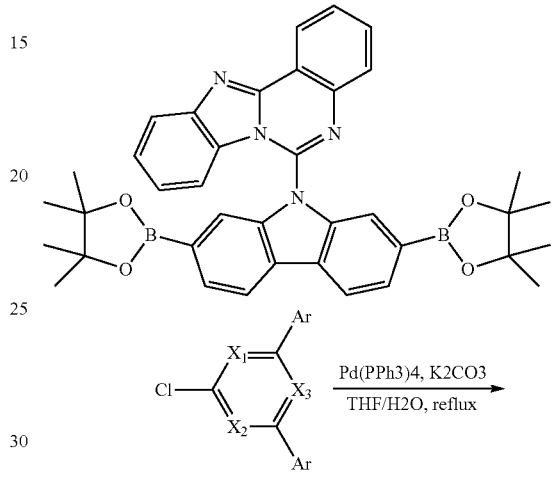
$$\text{(X1 = N or CH)} \xrightarrow{\text{Pd(PPh3)4, K2CO3}}_{\text{THF/H2O, reflux}}$$
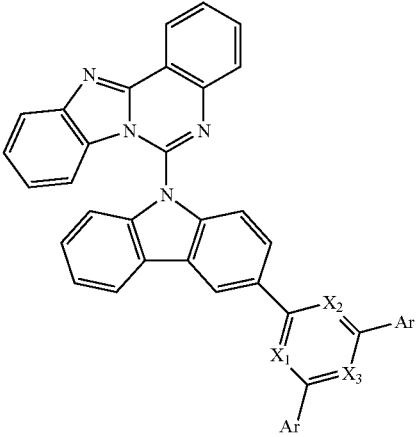
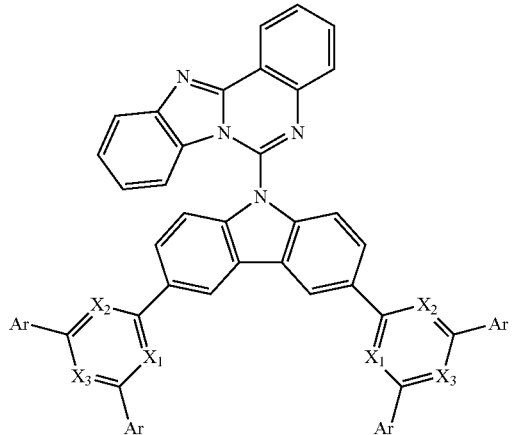

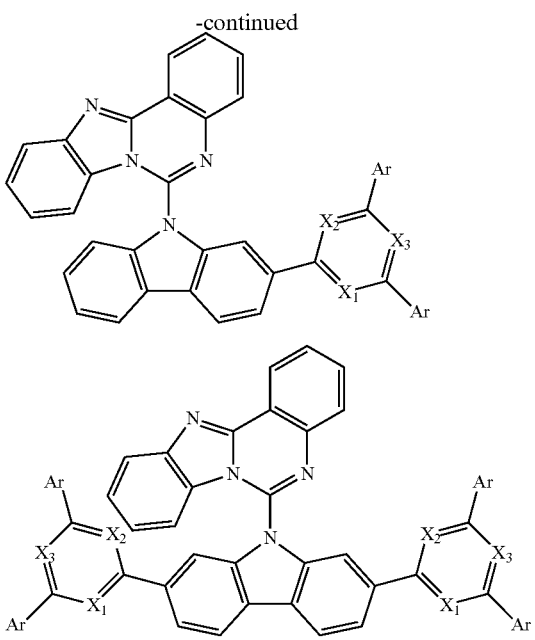

General Formula 7 represents a reaction formula linking a substituent such as amine and arylamine using a Buchwald amination. Herein, Ar means hydrogen or an additional substituent.

General Formulae 8 and 9 represents a reaction formula linking a substituent such as an aryl group and a heterocyclic group using a Borylation method and a Suzuki coupling. Particularly, General Formula 9 represents a reaction formula linking a substituent of a monocyclic aryl group or a monocyclic N-containing heterocyclic group. X1 to X3 are carbon or nitrogen, and Ar means hydrogen or an additional substituent.

General Formulae 1 to 9 are just examples of preparing the core structure of the compound according to one embodiment of the present application, and methods of linking substituents thereto, and the reaction is not limited thereto.

Another embodiment of the present specification provides an organic electronic device including the above-described compound.

In one embodiment of the present application, an organic electronic device including a first electrode; a second electrode provided opposite to the first electrode; and one or more organic material layers provided between the first electrode and the second electrode, wherein one or more layers of the organic material layers include the above-mentioned compound is provided.

One embodiment of the present specification relates to an organic electronic device comprising the compound represented by Chemical Formula 1 in one or more layers of the organic material layers, and comprises a compound of the following Chemical Formula 4 in a light emitting layer.

[Chemical Formula 4]

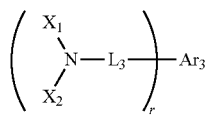

In Chemical Formula 4, $Ar_3$ is a benzofluorene skeleton, a fluoranthene skeleton, a pyrene skeleton or a chrysene skeleton, $L_3$ is a single bond, a $C_6$ to $C_{30}$ arylene group or a $C_5$ to $C_{30}$ divalent heterocyclic group, $X_1$ and $X_2$ are the same as or different from each other and each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group and a substituted or unsubstituted $C_7$ to $C_{30}$ aralkyl group, and $X_1$ and $X_2$ may bond to each other to form a saturated or unsaturated ring, r is an integer of 1 or greater, and when r is 2 or greater, $X_1$s are the same as or different from each other and $X_2$s are the same as or different from each other.

In one embodiment of the present specification, $L_3$ is a single bond or a $C_6$ to $C_{30}$ arylene group.

In another embodiment, $L_3$ is a single bond.

In one embodiment of the present specification, $Ar_3$ is a benzofluorene skeleton, a fluoranthene skeleton or a pyrene skeleton.

In another embodiment, $Ar_3$ is a pyrene skeleton.

In one embodiment of the present specification, $X_1$ and $X_2$ are the same as or different from each other, and each independently a substituted or unsubstituted $C_6$ to $C_{30}$ aryl group, a substituted or unsubstituted $C_5$ and $C_{30}$ heterocyclic group, or a substituted or unsubstituted $C_1$ to $C_{30}$ alkyl group.

In another embodiment, $X_1$ and $X_2$ are the same as or different from each other, and each independently a substituted or unsubstituted $C_6$ to $C_{30}$ aryl group.

In another embodiment, $X_1$ and $X_2$ are the same as or different from each other, and each independently a phenyl group unsubstituted or substituted with a germanium group.

In another embodiment, $X_1$ and $X_2$ are the same as or different from each other, and each independently a phenyl group unsubstituted or substituted with a trimethylgermanium group.

In one embodiment of the present specification, $Ar_3$ is a pyrene skeleton, $L_3$ is a single bond, $X_1$ and $X_2$ are the same as or different from each other, and each independently an aryl group unsubstituted or substituted with a germanium group, and r is 2 in the organic electronic device.

In another embodiment, $Ar_3$ is a pyrene skeleton, $L_3$ is a single bond, $X_1$ is a phenyl group, $X_2$ is a phenyl group substituted with a trimethylgermanium group, and r is 2 in the organic electronic device.

In one embodiment of the present specification, the compound of Chemical Formula 4 may be included as a dopant of the light emitting layer.

One embodiment of the present specification relates to an organic electronic device including the compound represented by Chemical Formula 1 in one or more layers of the organic material layers, and includes a compound of the following Chemical Formula 5 in a light emitting layer of the organic material layers.

[Chemical Formula 5]

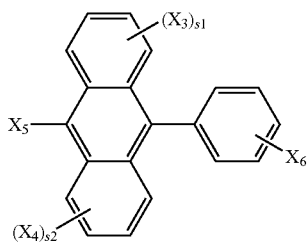

In Chemical Formula 5, $X_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

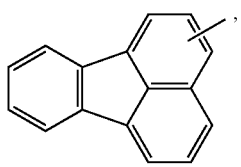

$X_6$ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group and a 3-fluoranthenyl group, $X_3$ and $X_4$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer of 0 to 4.

In one embodiment of the present specification, $X_5$ is a substituted or unsubstituted 1-naphthyl group or a substituted or unsubstituted 2-naphthyl group.

In another embodiment, $X_5$ is a substituted or unsubstituted 1-naphthyl group.

In another embodiment, $X_5$ is a 1-naphthyl group.

In one embodiment of the present specification, $X_6$ is a phenyl group, a 1-naphthyl group or a 2-naphthyl group.

In another embodiment, $X_6$ is a 2-naphthyl group.

In one embodiment of the present specification, $X_3$ and $X_4$ are the same as or different from each other, and each independently a substituted or unsubstituted $C_6$ to $C_{50}$ aryl group or a substituted or unsubstituted $C_5$ to $C_{50}$ heteroaryl group.

In one embodiment of the present specification, s1 and s2 are each an integer of 0 to 2.

In another embodiment, s1 and s2 are 0.

In one embodiment of the present specification, $X_5$ and $X_6$ are the same as or different from each other, and each independently a 1-naphthyl group or a 2-naphthyl group, and s1 and s2 are 0 in the organic electronic device.

In one embodiment of the present specification, the compound of Chemical Formula 5 may be included as a host of the light emitting layer.

One embodiment of the present specification relates to an organic electronic device including the compound represented by Chemical Formula 1 in one or more layers of the organic material layers, and includes the compound of Chemical Formula 4 and the compound of Chemical Formula 5 in a light emitting layer of the organic material layers.

In another embodiment, the compound represented by Chemical Formula 1 is included in one or more layers of the organic material layers, and, in Chemical Formula 4, $Ar_3$ is a pyrene skeleton, $L_3$ is a single bond, $X_1$ and $X_2$ are an aryl group unsubstituted or substituted with a germanium group, and r is 2, and, in Chemical Formula 5, $X_5$ and $X_6$ are the same as or different from each other and each independently a 1-naphthyl group or a 2-naphthyl group, and s1 and s2 are 0 in the organic electronic device.

In the present specification, a description of a certain member being placed "on" another member includes not only a case of the certain member adjoining the another member but a case of still another member being present between the two members.

In the present specification, a description of a certain part "including" certain constituents means capable of further including other constituents, and does not exclude other constituents unless particularly stated on the contrary.

The organic material layer of the organic electronic device of the present application may be formed in a single layer structure, but may be formed in a multilayer structure in which two or more organic material layers are laminated. For example, an organic light emitting device as a typical example of the organic electronic device of the present application may have a structure including a hole injection layer, a hole transfer layer, a light emitting layer, an electron transfer layer, an electron injection layer and the like as the organic material layer. However, the structure of the organic electronic device is not limited thereto, and may include less numbers of organic material layers.

According to one embodiment of the present application, the organic electronic device may be selected from the group consisting of an organic light emitting device, an organic phosphorescent device, an organic solar cell, an organic photo conductor (OPC) and an organic transistor.

Hereinafter, an organic light emitting device will be illustrated.

In one embodiment of the present application, the organic material layer includes a hole injection layer or a hole transfer layer, and the hole injection layer or the hole transfer layer includes the compound.

In one embodiment of the present application, the organic material layer includes a light emitting layer, and the light emitting layer includes the compound.

In another embodiment, the organic material layer includes a light emitting layer, and the light emitting layer includes the compound.

In one embodiment of the present application, the organic material layer includes an electron transfer layer or an electron injection layer, and the electron transfer layer or the electron injection layer includes the compound.

In one embodiment of the present application, the organic light emitting device includes two or more layers selected from the group consisting of a hole injection layer, a hole transfer layer, a light emitting layer, an electron transfer layer, an electron injection layer, an electron blocking layer and a hole blocking layer.

In one embodiment of the present application, the organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the compound. In one embodiment of the present application, two or more may be selected from the group consisting of an electron transfer layer, an electron injection layer, a layer carrying out electron transfer and electron injection at the same time, and a hole blocking layer as the two or more organic material layers.

In one embodiment of the present application, the organic material layer includes two or more electron transfer layers, and at least one of the two or more electron transfer layers includes the compound. Specifically, in one embodiment of the present specification, the compound may be included in one of the two or more electron transfer layers, or may be included in each of the two or more electron transfer layers.

In addition, when the compound is included in each of the two or more electron transfer layers in one embodiment of the present application, materials other than the compound may be the same as or different from each other.

In one embodiment of the present application, the organic material layer further includes, in addition to the organic material layer including the compound, a hole injection layer or a hole transfer layer including a compound including an arylamino group, a carbazole group or a benzocarbazole group.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a reverse direction structure in which a cathode, one or more organic material layers and an anode are consecutively laminated on a substrate (inverted type).

For example, structures of the organic light emitting device according to one embodiment of the present application are illustrated in FIGS. 1 and 2.

FIG. 1 illustrates a structure of an organic electronic device in which a substrate (1), an anode (2), a light emitting layer (3) and a cathode (4) are consecutively laminated. In such a structure, the compound may be included in the light emitting layer (3).

FIG. 2 illustrates a structure of an organic electronic device in which a substrate (1), an anode (2), a hole injection layer (5), a hole transfer layer (6), a light emitting layer (3), an electron transfer layer (7) and a cathode (4) are consecutively laminated. In such a structure, the compound may be included in one or more layers of the hole injection layer (5), the hole transfer layer (6), the light emitting layer (3) and the electron transfer layer (7).

In such a structure, the compound may be included in one or more layers of the hole injection layer, the hole transfer layer, the light emitting layer and the electron transfer layer.

The organic light emitting device of the present application may be prepared using materials and methods known in the art except that one or more layers of the organic material layers include the compound of the present application, that is, the compound.

When the organic light emitting device includes a plurality of organic material layers, the organic material layers may be formed with materials the same as or different from each other.

The organic light emitting device of the present application may be prepared using materials and methods known in the art except that one or more layers of the organic material layers include the compound, that is, the compound represented by Chemical Formula 1.

For example, the organic light emitting device of the present application may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed into an organic material layer through a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may be also manufactured by consecutively depositing a cathode material, an organic material layer and an anode material on a substrate (International Patent Application Laid-Open Publication No. 2003/012890). However, the manufacturing method is not limited thereto.

In one embodiment of the present application, the first electrode is an anode and the second electrode is a cathode.

In another embodiment, the first electrode is a cathode and the second electrode is an anode.

As the anode material, materials having large work function are normally preferred so that hole injection to an organic material layer is smooth. Specific examples of the anode material capable of being used in the present application include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is preferably a compound that has an ability to transfer holes, therefore, has a hole injection effect from an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes compounds, dibenzofuran derivatives, ladder-type furan compounds, pyrimidine derivatives and the like, but the material is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato) (0-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

In one embodiment of the present application, the heterocyclic compound may be included in an organic solar cell or an organic transistor in addition to the organic light emitting device.

The compound according to the present disclosure may also be used in an organic electronic device including an organic solar cell, an organic photo conductor, an organic transistor and the like under a similar principle used in the organic light emitting device.

<Preparation Example 1> Synthesis of Compound 1

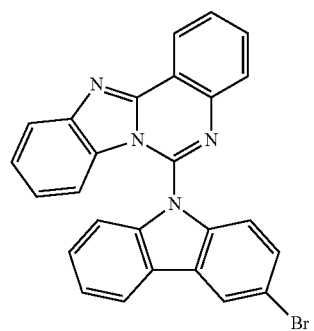

+

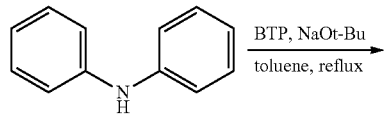

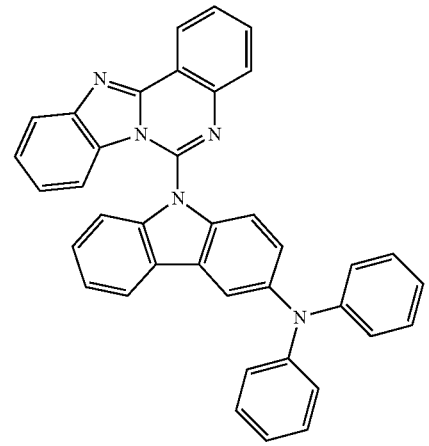

Compound 1

After introducing Compound A (10 g, 21.6 mmol), diphenylamine (4.03 g, 23.81 mmol) and NaOt-Bu (2.51 g, 25.9 mmol) in 200 ml of toluene, the temperature was raised while stirring the mixture. When the result started to reflux after raising the temperature, bis(tri-tert-butylphosphine) palladium (0.06 g, 0.11 mmol) was slowly added thereto through dropwise addition. After 3 hours, the reaction was terminated, the temperature was lowered to room temperature, and the result was concentrated under vacuum and column purified to prepare 9.64 g (81%) of Compound 1.

MS[M+H]⁺=552

<Preparation Example 2> Synthesis of Compound 2

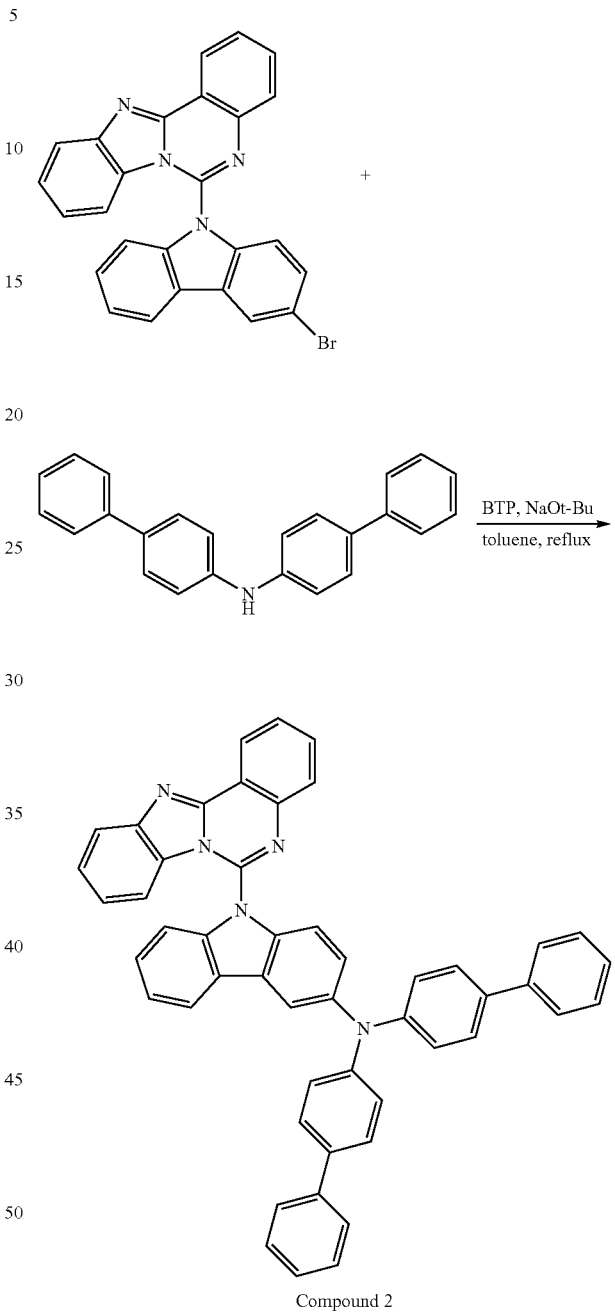

Compound 2

After introducing Compound A (10 g, 21.6 mmol), bis-biphenylamine (8.08 g, 23.81 mmol) and NaOt-Bu (2.51 g, 25.9 mmol) in 200 ml toluene, the temperature was raised while stirring the mixture. When the result started to reflux after raising the temperature, bis(tri-tert-butylphosphine) palladium (0.06 g, 0.11 mmol) was slowly added thereto through dropwise addition. After 3 hours, the reaction was terminated, the temperature was lowered to room temperature, and the result was concentrated under vacuum and column purified to prepare 13.85 g (91%) of Compound 2.

MS[M+H]⁺=704

<Preparation Example 3> Synthesis of Compound 3

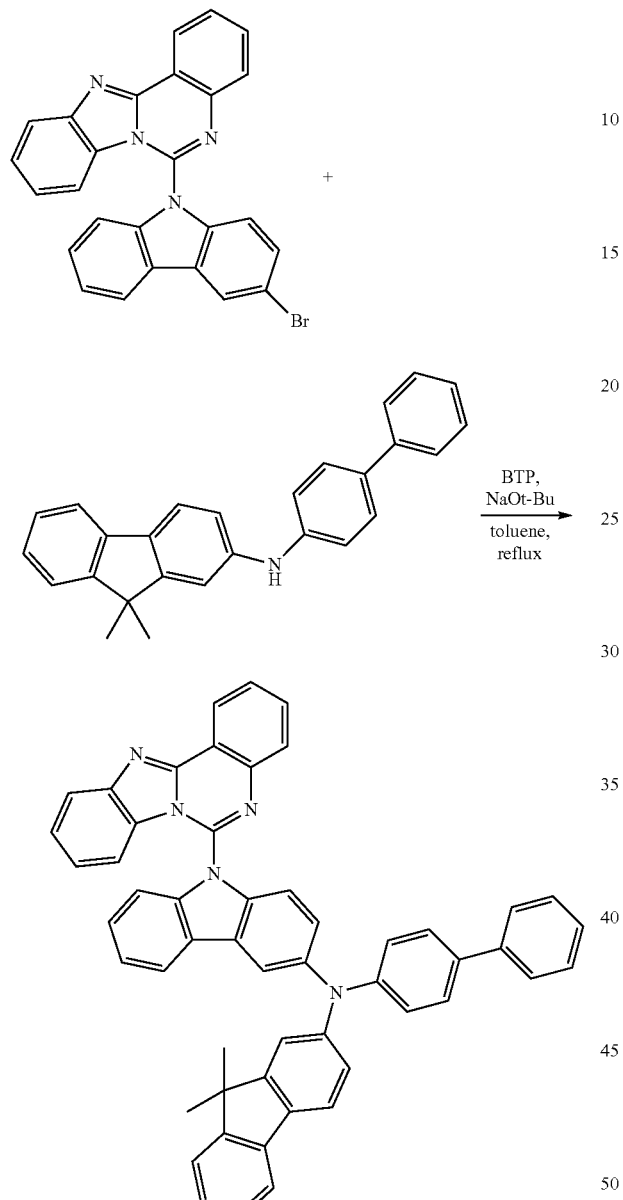

Compound 3

<Preparation Example 4> Synthesis of Compound 4

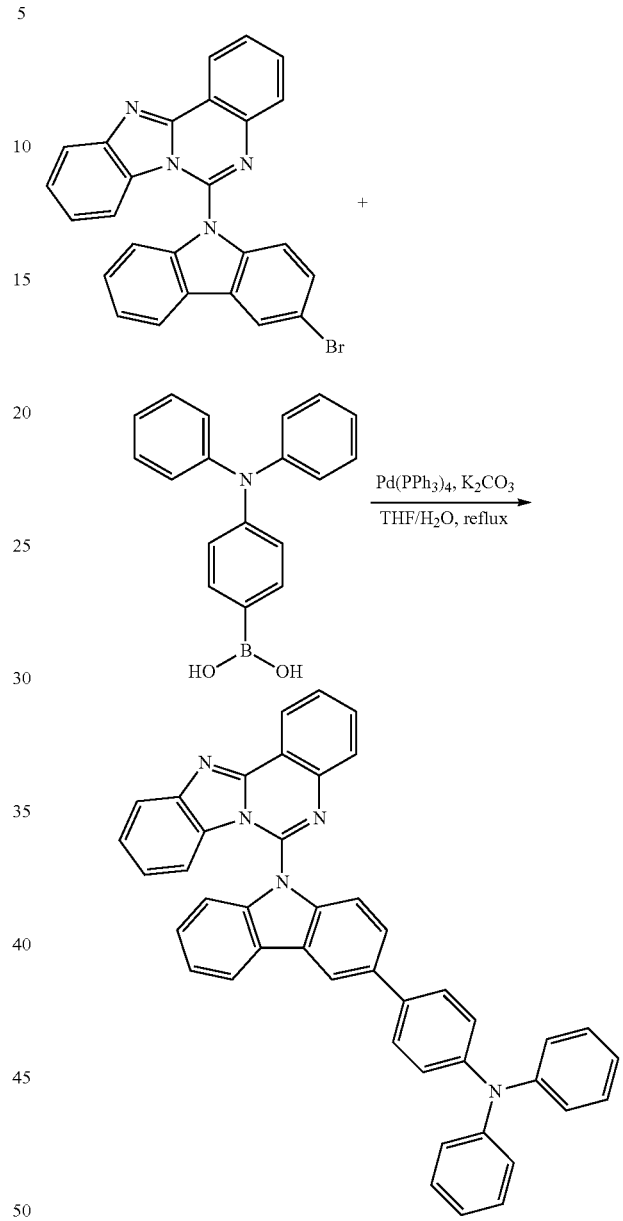

Compound 4

After introducing Compound A (10 g, 21.6 mmol), 9,9-dimethylfluorenebiphenylamine (9.05 g, 23.81 mmol) and NaOt-Bu (2.51 g, 25.9 mmol) in 200 ml of toluene, the temperature was raised while stirring the mixture. When the result started to reflux after raising the temperature, bis(tri-tert-butylphosphine)palladium (0.06 g, 0.11 mmol) was slowly added thereto through dropwise addition. After 3 hours, the reaction was terminated, the temperature was lowered to room temperature, and the result was concentrated under vacuum and column purified to prepare 14.77 g (92%) of Compound 3.

MS[M+H]$^+$=744

After completely dissolving Compound A (10 g, 21.6 mmol) and (4-(diphenylamino)phenyl)boronic acid (6.88 g, 23.81 mmol) in 200 ml of tetrahydrofuran in a 500 ml round bottom flask under nitrogen atmosphere, a 2 M aqueous potassium carbonate solution (100 ml) and then tetrakis-(triphenylphosphine)palladium (0.75 g, 0.65 mmol) were added thereto, and the result was heated and stirred for 3 hours. After lowering the temperature to room temperature, the water layer was removed, and the result was dried using anhydrous magnesium sulfate, then vacuum concentrated and recrystallized with 300 ml of ethanol to prepare Compound 4 (11.31 g, 83%).

MS[M+H]$^+$=628

<Preparation Example 5> Synthesis of Compound 5

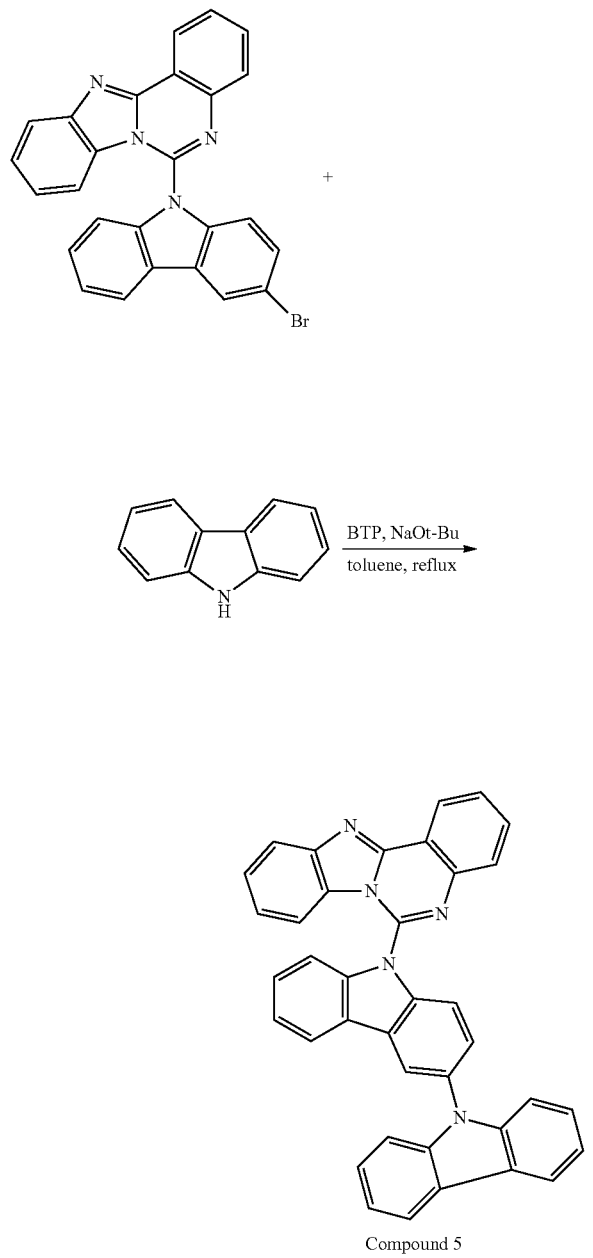

Compound 5

<Preparation Example 6> Synthesis of Compound 6

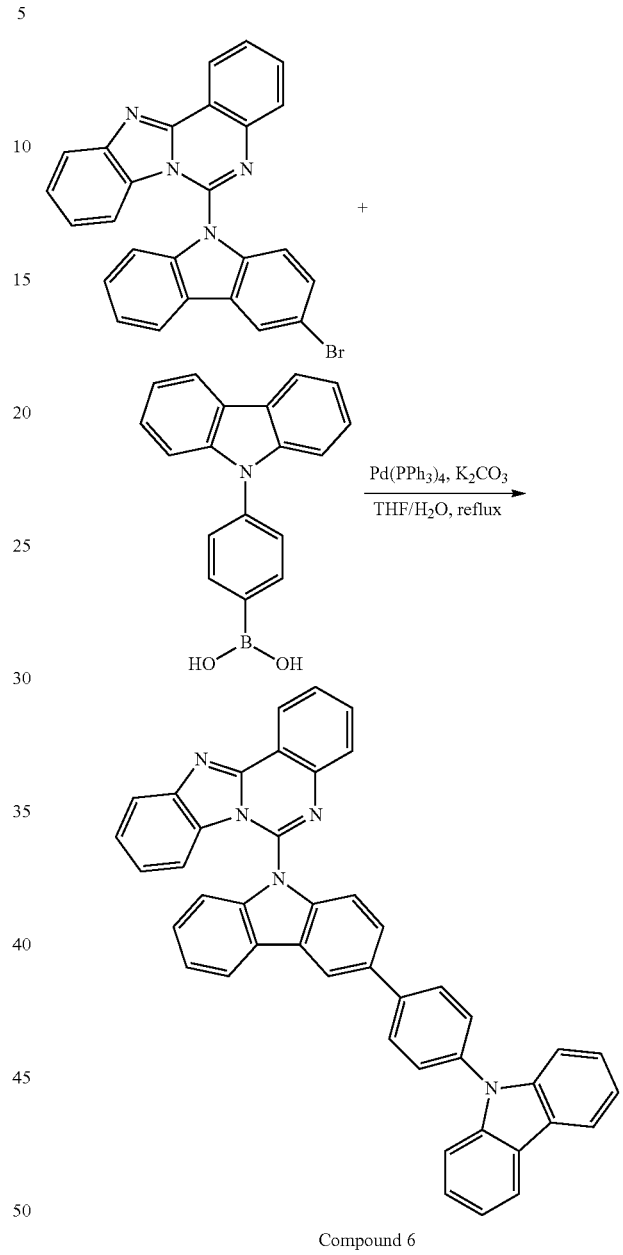

Compound 6

After introducing Compound A (10 g, 21.6 mmol), carbazole (4.01 g, 23.81 mmol) and NaOt-Bu (2.51 g, 25.9 mmol) in 200 ml of toluene, the temperature was raised while stirring the mixture. When the result started to reflux after raising the temperature, bis(tri-tert-butylphosphine) palladium (0.06 g, 0.11 mmol) was slowly added thereto through dropwise addition. After 5 hours, the reaction was terminated, the temperature was lowered to room temperature, and the result was concentrated under vacuum and column purified to prepare 10.72 g (90%) of Compound 5.

MS[M+H]$^+$=550

After completely dissolving Compound A (10 g, 21.6 mmol) and (4-(9H-carbazol-9-yl)phenyl)boronic acid (6.88 g, 23.81 mmol) in 280 ml of tetrahydrofuran in a 500 ml round bottom flask under nitrogen atmosphere, a 2 M aqueous potassium carbonate solution (140 ml) and then tetrakis-(triphenylphosphine)palladium (0.75 g, 0.65 mmol) were added thereto, and the result was heated and stirred for 6 hours. After lowering the temperature to room temperature, the water layer was removed, and the result was dried using anhydrous magnesium sulfate, then vacuum concentrated and recrystallized with 200 ml of ethyl acetate to prepare Compound 6 (10.31 g, 78%).

MS[M+H]$^+$=626

<Preparation Example 7> Synthesis of Compound 7

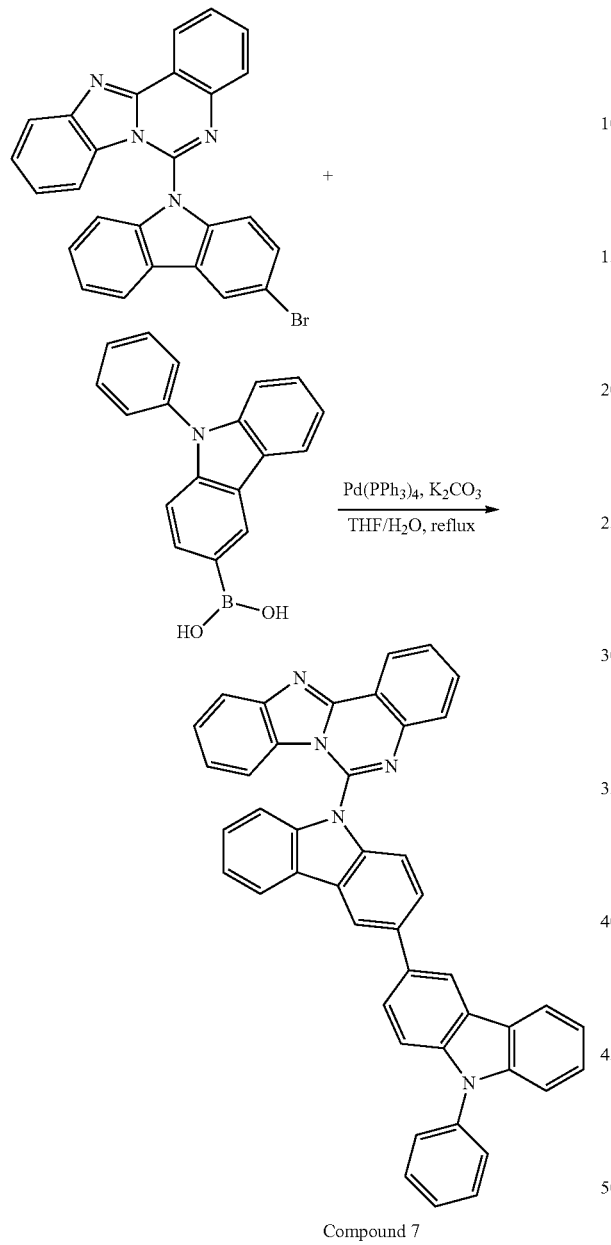

Compound 7

<Preparation Example 8> Synthesis of Compound 8

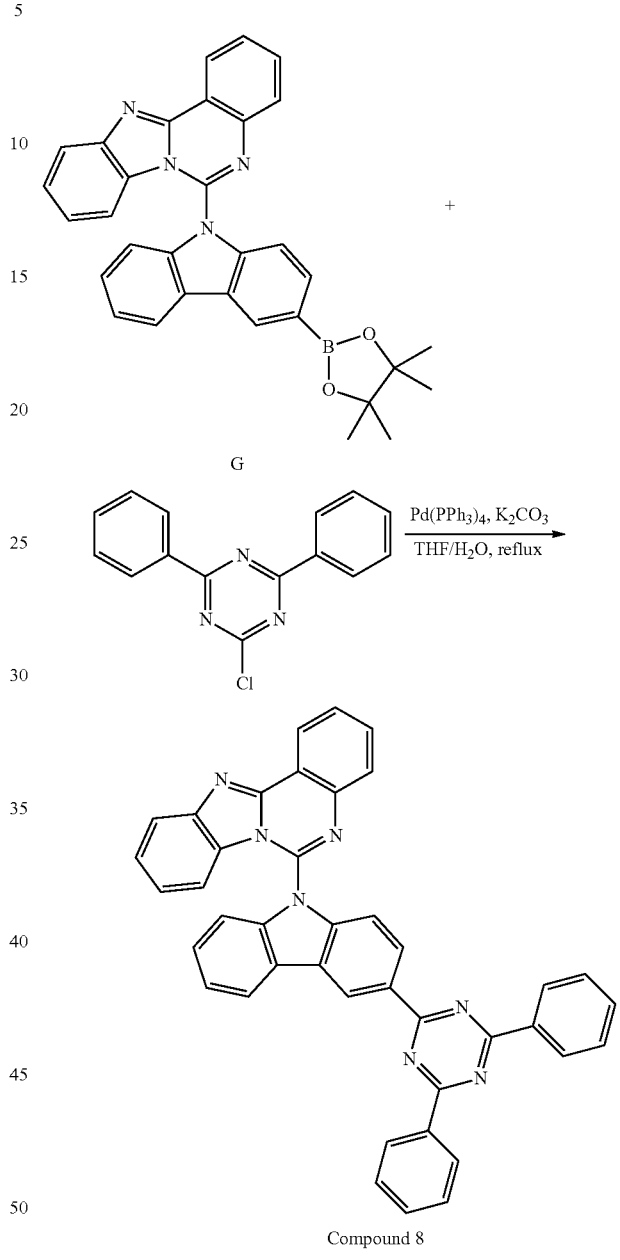

Compound 8

After completely dissolving Compound A (10 g, 21.6 mmol) and (9-phenyl-9H-carbazol-3-yl)boronic acid (6.88 g, 23.81 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.75 g, 0.65 mmol) were added thereto, and the result was heated and stirred for 2 hours. After lowering the temperature to room temperature, the water layer was removed, and the result was dried using anhydrous magnesium sulfate, then vacuum concentrated and recrystallized with 200 ml of ethyl acetate to prepare Compound 7 (12.09 g, 91%).

MS[M+H]$^+$=626

After completely dissolving Compound G (10 g, 19.61 mmol) and 2-chloro-4,6-diphenyl-1,3,5-triazine (4.76 g, 17.83 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.53 mmol) were added thereto, and the result was heated and stirred for 8 hours. After lowering the temperature to room temperature, the water layer was removed, and the result was dried using anhydrous magnesium sulfate, then vacuum concentrated and recrystallized with 300 ml of ethyl acetate to prepare Compound 8 (12.41 g, 93%).

MS[M+H]$^+$=616

<Preparation Example 9> Synthesis of Compound 9

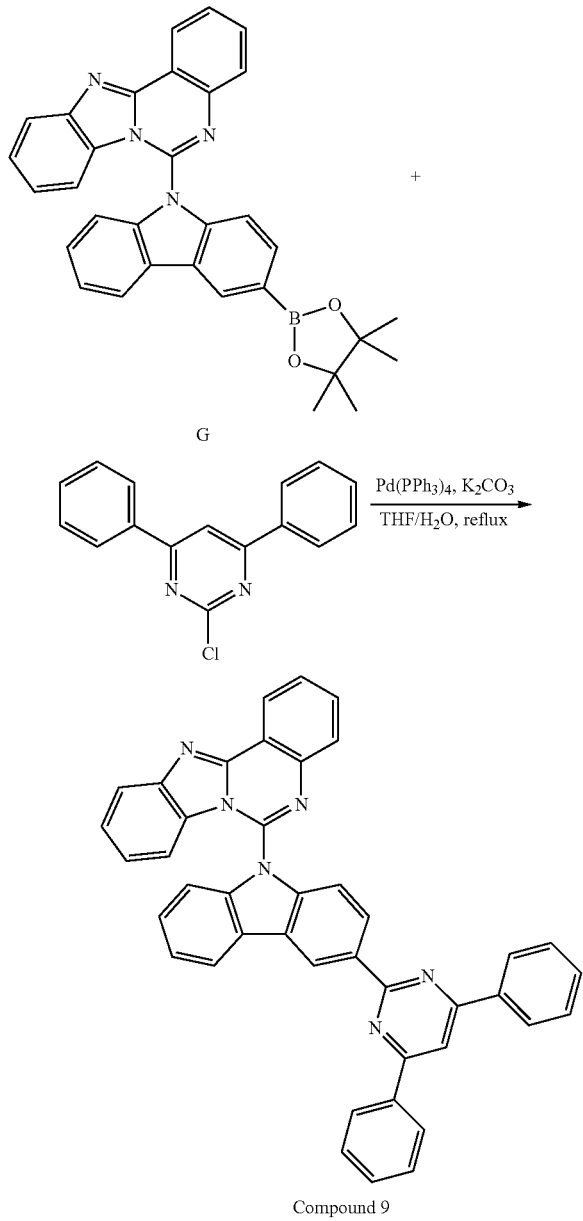

Compound 9

<Preparation Example 10> Synthesis of Compound 10

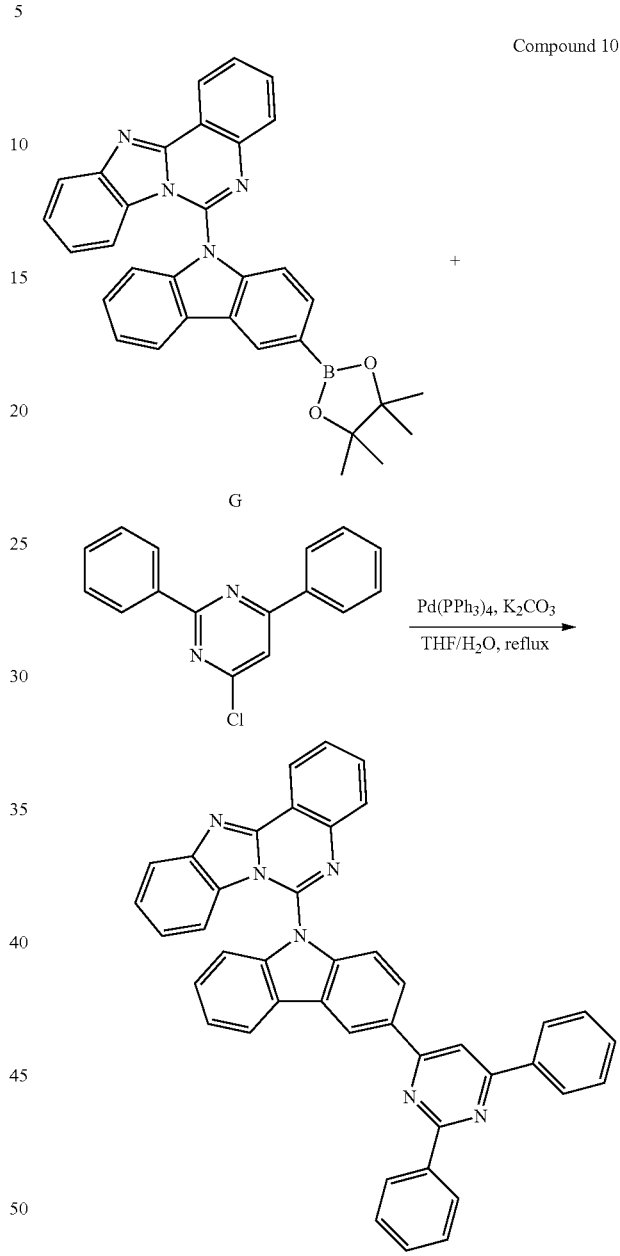

Compound 10

After completely dissolving Compound G (10 g, 19.61 mmol) and 2-chloro-4,6-diphenylpyrimidine (4.74 g, 17.83 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.53 mmol) were added thereto, and the result was heated and stirred for 5 hours. After lowering the temperature to room temperature, the water layer was removed, and the result was dried using anhydrous magnesium sulfate, then vacuum concentrated and recrystallized with 250 ml of ethyl acetate to prepare Compound 9 (10.15 g, 78%).

MS[M+H]$^+$=615

After completely dissolving Compound G (10 g, 19.61 mmol) and 4-chloro-2,6-diphenylpyrimidine (4.74 g, 17.83 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.53 mmol) were added thereto, and the result was heated and stirred for 4 hours. After lowering the temperature to room temperature, the water layer was removed, and the result was dried using anhydrous magnesium sulfate, then vacuum concentrated and recrystallized with 250 ml of ethyl acetate to prepare Compound 10 (11.32 g, 86%).

MS[M+H]$^+$=615

<Preparation Example 11> Synthesis of Compound 11

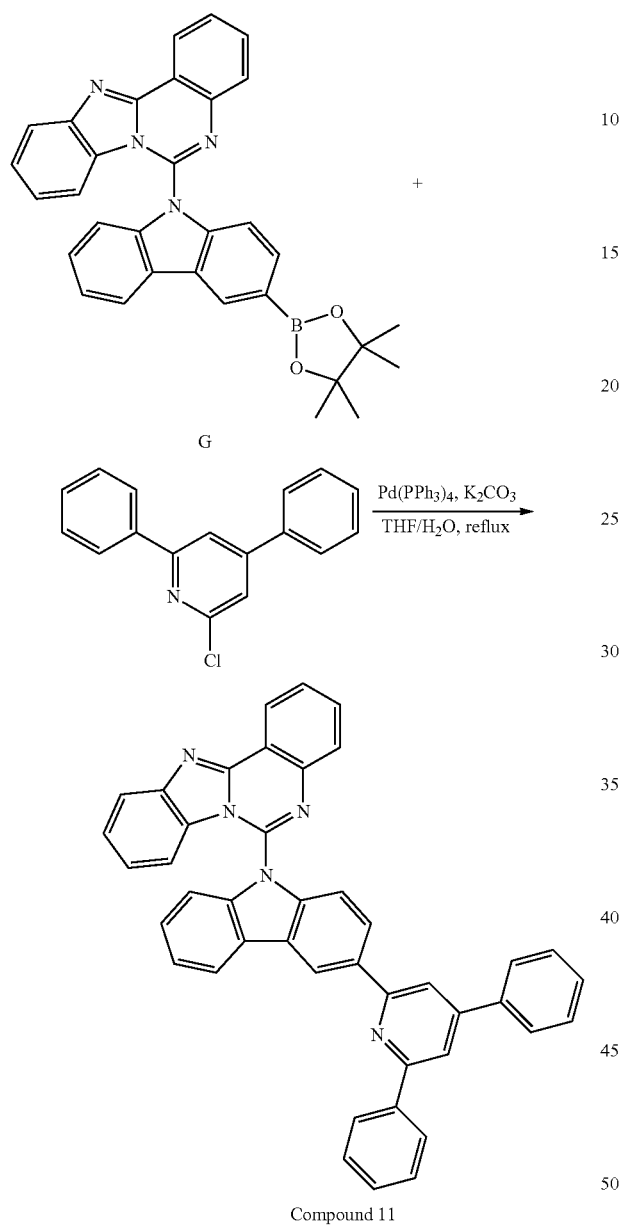

Compound 11

After completely dissolving Compound G (10 g, 19.61 mmol) and 2-chloro-4,6-diphenylpyrimidine (4.71 g, 17.83 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.62 g, 0.53 mmol) were added thereto, and the result was heated and stirred for 2 hours. After lowering the temperature to room temperature, the water layer was removed, and the result was dried using anhydrous magnesium sulfate, then vacuum concentrated and recrystallized with 280 ml of ethyl acetate to prepare Compound 11 (11.32 g, 86%).

MS[M+H]$^+$=614

<Preparation Example 12> Synthesis of Compound 12

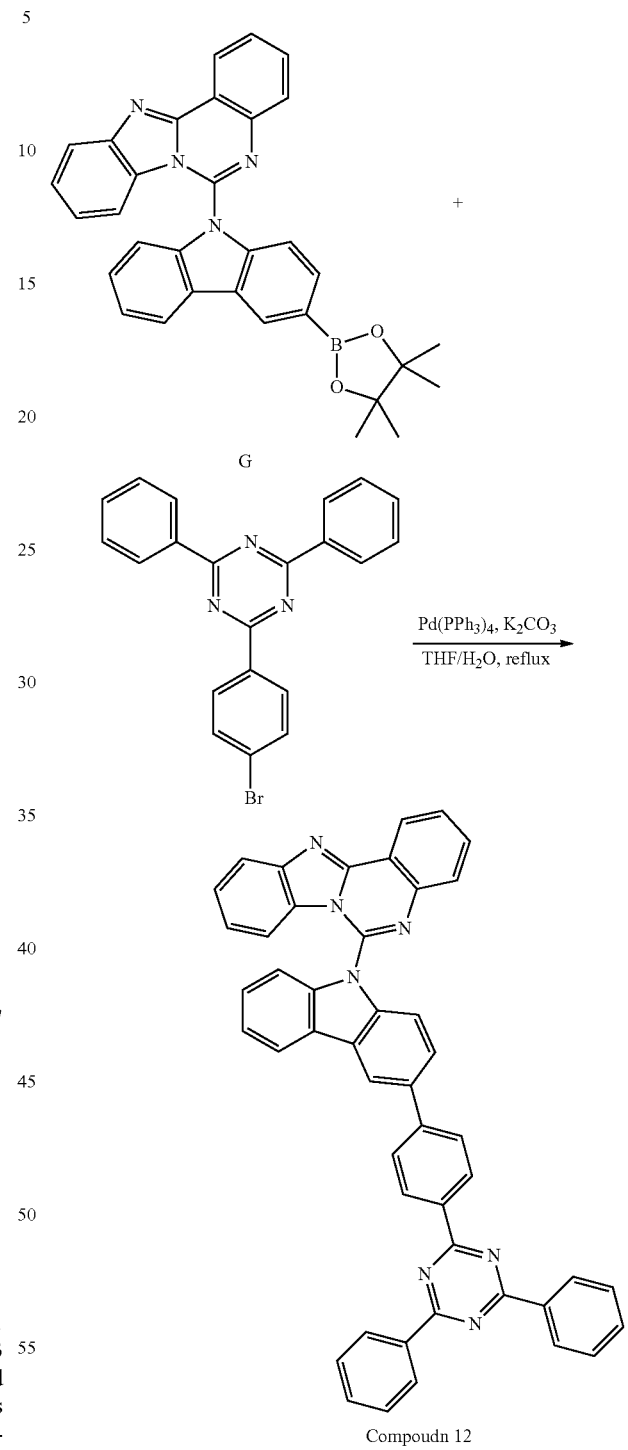

Compoudn 12

After completely dissolving Compound G (10 g, 19.61 mmol) and 2-(4-bromophenyl)-4,6-diphenyl-1,3,5-triazine (6.91 g, 17.83 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (1.24 g, 1.06 mmol) were added thereto, and the result was heated and stirred for 12 hours. After lowering the temperature to room temperature, the water layer was removed, and the result was dried using anhydrous magnesium sulfate, then vacuum concentrated and recrystallized with 500 ml of ethyl acetate to prepare Compound 12 (12.41 g, 93%).

MS[M+H]$^+$=692

<Preparation Example 13> Synthesis of Compound 13

(6.91 g, 17.83 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (1.24 g, 1.06 mmol) were added thereto, and the result was heated and stirred for 7 hours. After lowering the temperature to room temperature, the water layer was removed, and the result was dried using anhydrous magnesium sulfate, then vacuum concentrated and recrystallized with 400 ml of ethyl acetate to prepare Compound 13 (9.55 g, 64%).

MS[M+H]$^+$=693

<Preparation Example 14> Synthesis of Compound 14

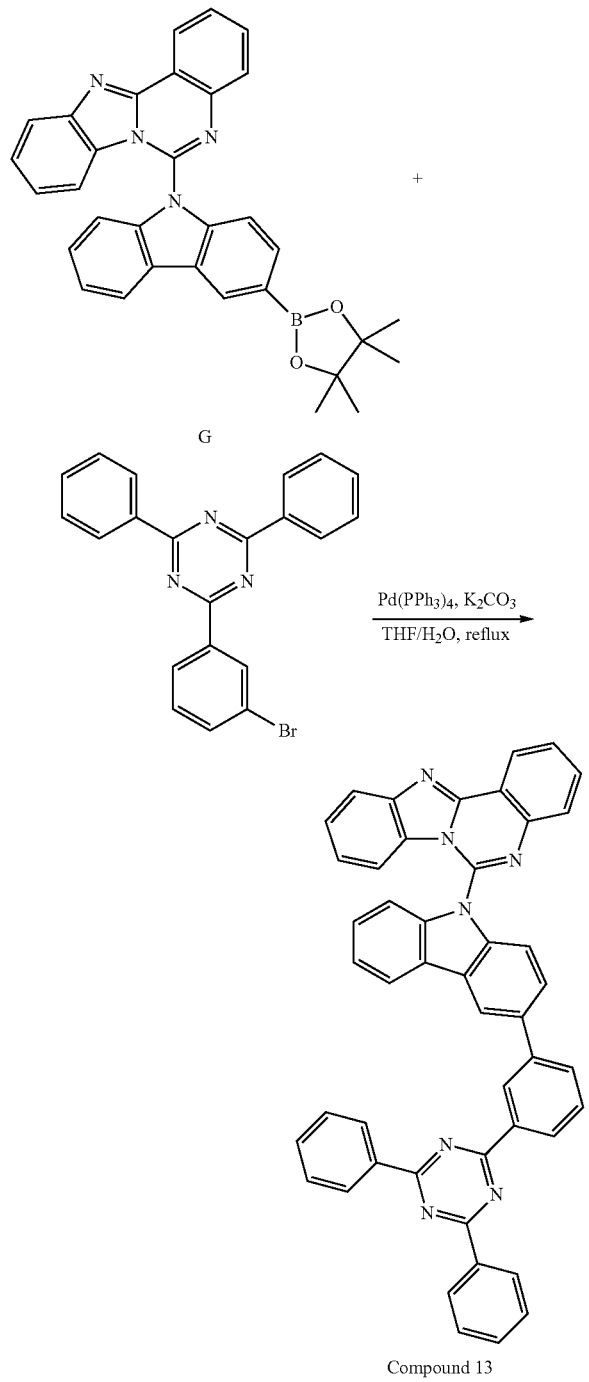

Compound 13

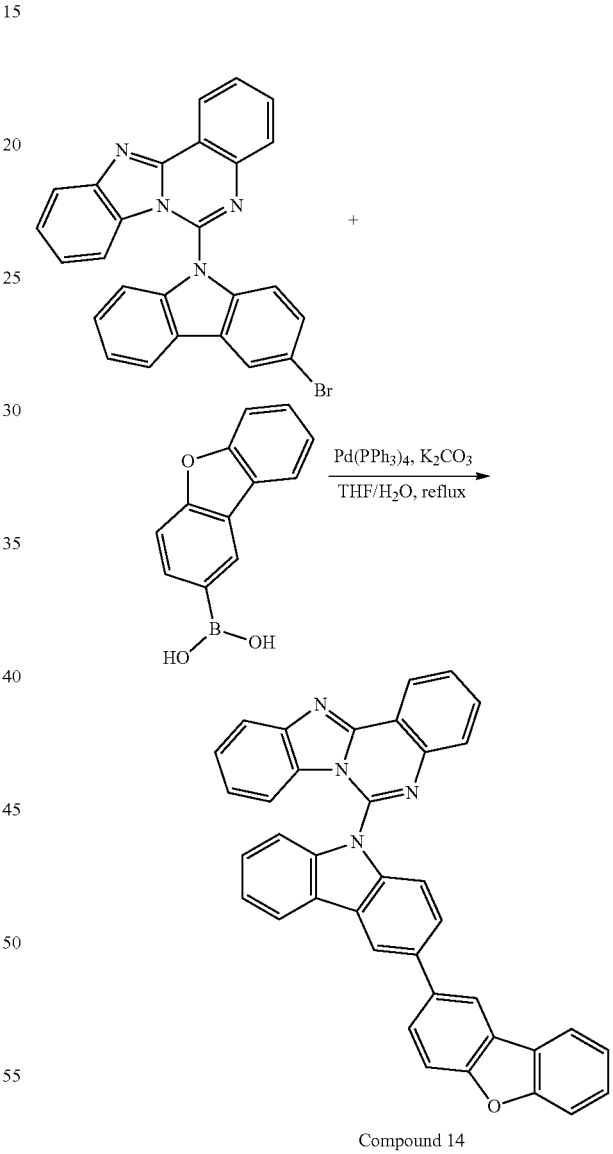

Compound 14

After completely dissolving Compound G (10 g, 19.61 mmol) and 2-(3-bromophenyl)-4,6-diphenyl-1,3,5-triazine After completely dissolving Compound A (10 g, 21.6 mmol) and dibenzo[b,d]furan-2-ylboronic acid (5.26 g, 23.81 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.75 g, 0.65 mmol) were added thereto, and the result was heated and stirred for 6 hours. After lowering the temperature to room temperature, the water layer was removed, and the result was dried using anhydrous magnesium sulfate, then vacuum concentrated and recrystallized with 300 ml of ethyl acetate to prepare Compound 14 (10.82 g, 91%).

MS[M+H]$^+$=551

<Preparation Example 15> Synthesis of Compound 15

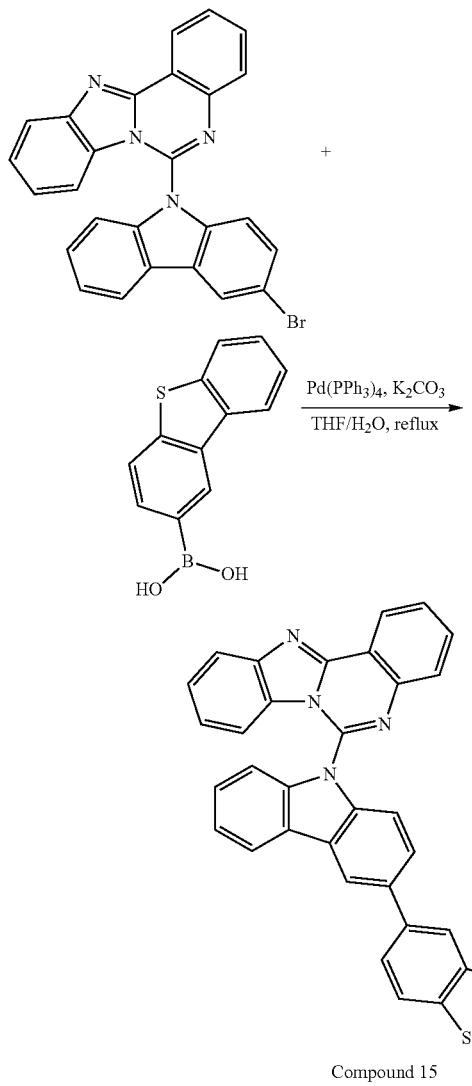

Compound 15

After completely dissolving Compound A (10 g, 21.6 mmol) and dibenzo[b,d]thiophen-2-ylboronic acid (5.32 g, 23.81 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.75 g, 0.65 mmol) were added thereto, and the result was heated and stirred for 5 hours. After lowering the temperature to room temperature, the water layer was removed, and the result was dried using anhydrous magnesium sulfate, then vacuum concentrated and recrystallized with 200 ml of ethyl acetate to prepare Compound 15 (9.44 g, 80%).

MS[M+H]$^+$=567

<Preparation Example 16> Synthesis of Compound 16

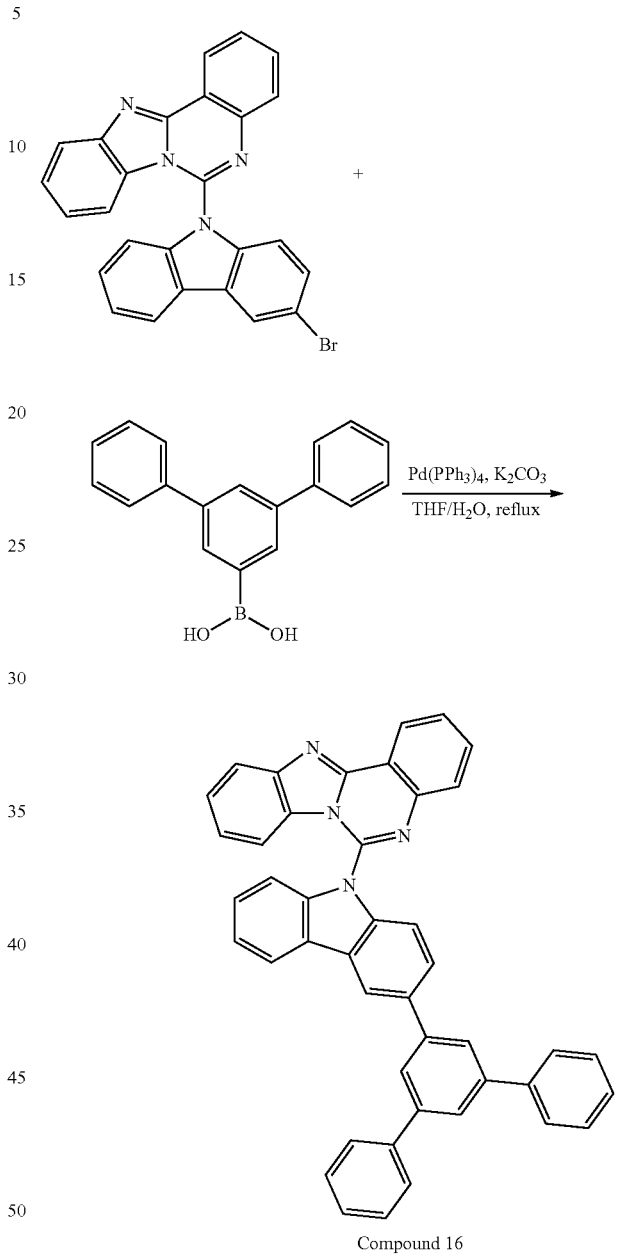

Compound 16

After completely dissolving Compound A (10 g, 21.6 mmol) and [1,1':3',1''-terphenyl]-5'-ylboronic acid (6.52 g, 23.81 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.75 g, 0.65 mmol) were added thereto, and the result was heated and stirred for 6 hours. After lowering the temperature to room temperature, the water layer was removed, and the result was dried using anhydrous magnesium sulfate, then vacuum concentrated and recrystallized with 200 ml of ethyl acetate to prepare Compound 16 (10.42 g, 78%).

MS[M+H]$^+$=613

<Preparation Example 17> Synthesis of Compound 17

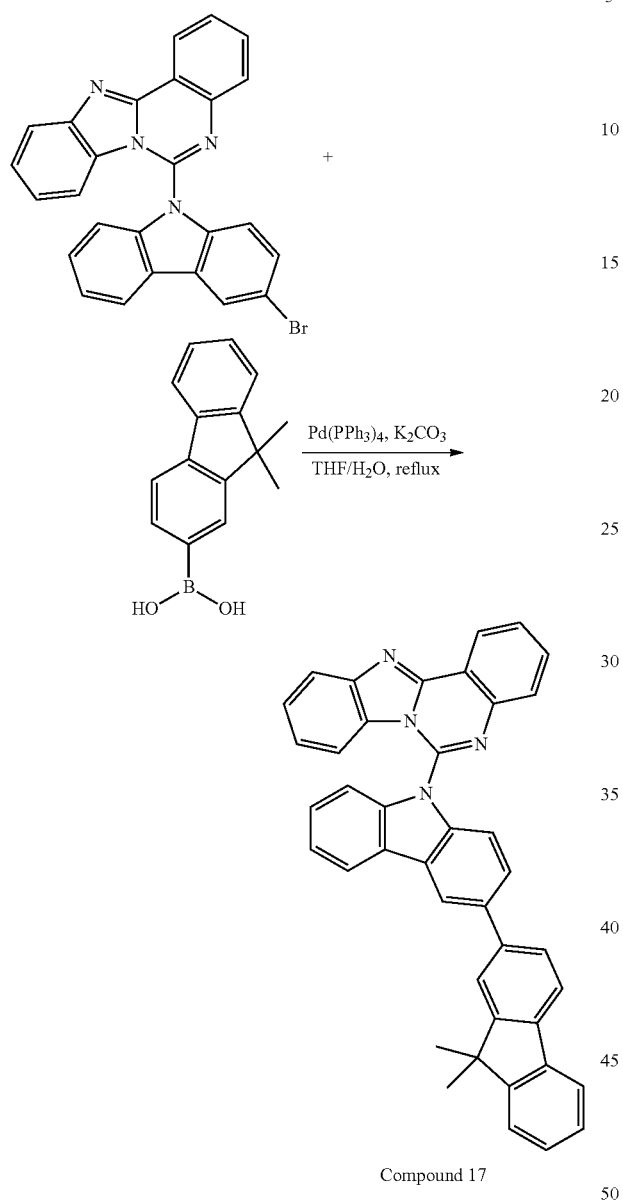

Compound 17

After completely dissolving Compound A (10 g, 21.6 mmol) and (9,9-dimethyl-9H-fluoren-2-yl)boronic acid (5.66 g, 23.81 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.75 g, 0.65 mmol) were added thereto, and the result was heated and stirred for 3 hours. After lowering the temperature to room temperature, the water layer was removed, and the result was dried using anhydrous magnesium sulfate, then vacuum concentrated and recrystallized with 200 ml of ethyl acetate to prepare Compound 17 (9.56 g, 76%).

MS[M+H]$^+$=577

<Preparation Example 18> Synthesis of Compound 18

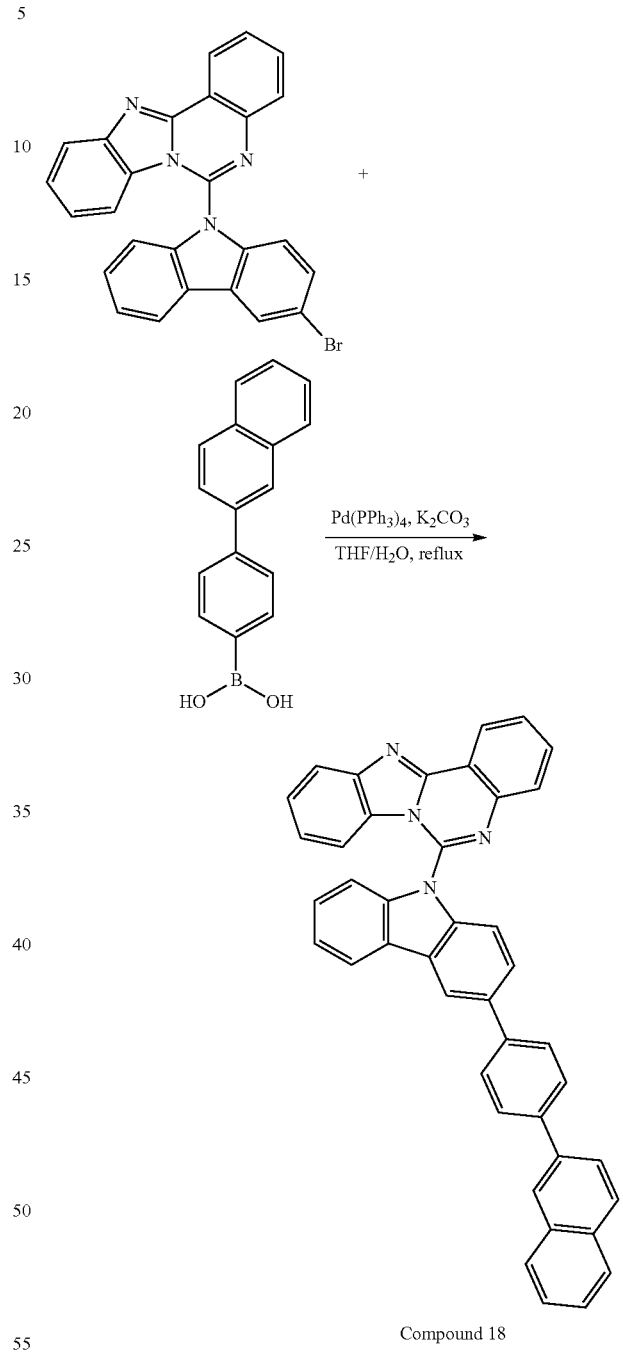

Compound 18

After completely dissolving Compound A (10 g, 21.6 mmol) and (4-(naphthalen-2-yl)phenyl)boronic acid (6.51 g, 23.81 mmol) in 320 ml of tetrahydrofuran in a 500 ml round bottom flask under nitrogen atmosphere, a 2 M aqueous potassium carbonate solution (160 ml) and then tetrakis-(triphenylphosphine)palladium (0.75 g, 0.65 mmol) were added thereto, and the result was heated and stirred for 5 hours. After lowering the temperature to room temperature, the water layer was removed, and the result was dried using anhydrous magnesium sulfate, then vacuum concentrated and recrystallized with 300 ml of ethyl acetate to prepare Compound 18 (10.22 g, 84%).

MS[M+H]$^+$=587

<Preparation Example 19> Synthesis of Compound 19

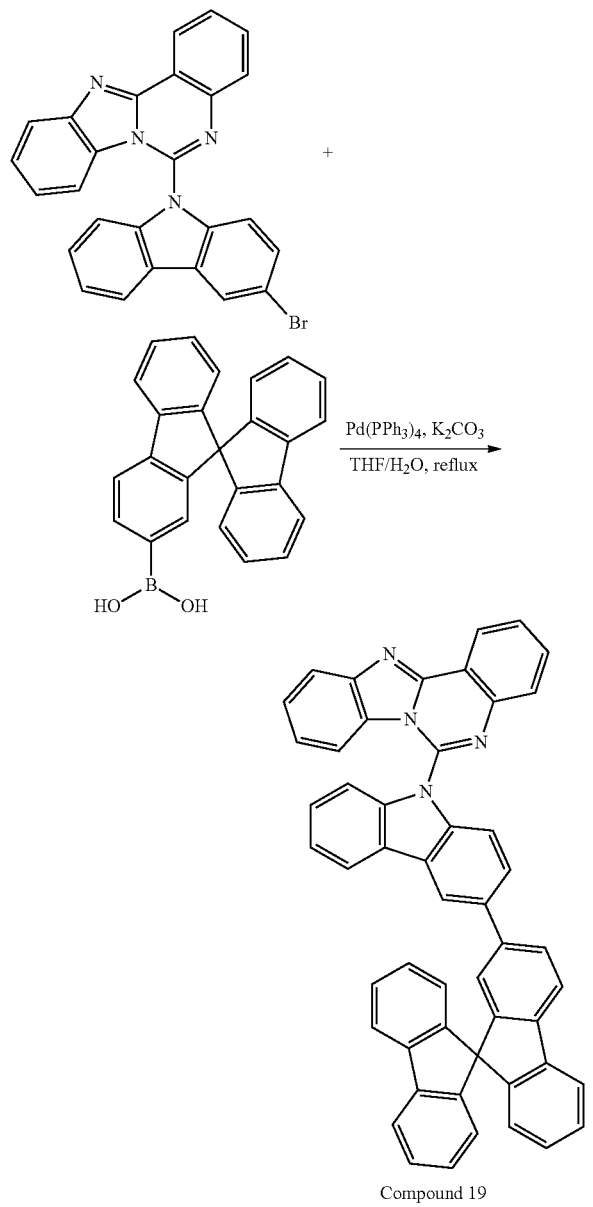

Compound 19

After completely dissolving Compound A (10 g, 21.6 mmol) and 9,9'-spirobi[fluoren]-2-ylboronic acid (8.57 g, 23.81 mmol) in 400 ml of tetrahydrofuran in a 500 ml round bottom flask under nitrogen atmosphere, a 2 M aqueous potassium carbonate solution (200 ml) and then tetrakis-(triphenylphosphine)palladium (0.75 g, 0.65 mmol) were added thereto, and the result was heated and stirred for 5 hours. After lowering the temperature to room temperature, the water layer was removed, and the result was dried using anhydrous magnesium sulfate, then vacuum concentrated and recrystallized with 300 ml of ethyl acetate to prepare Compound 19 (13.74 g, 91%).

MS[M+H]$^+$=699

<Preparation Example 20> Synthesis of Compound 20

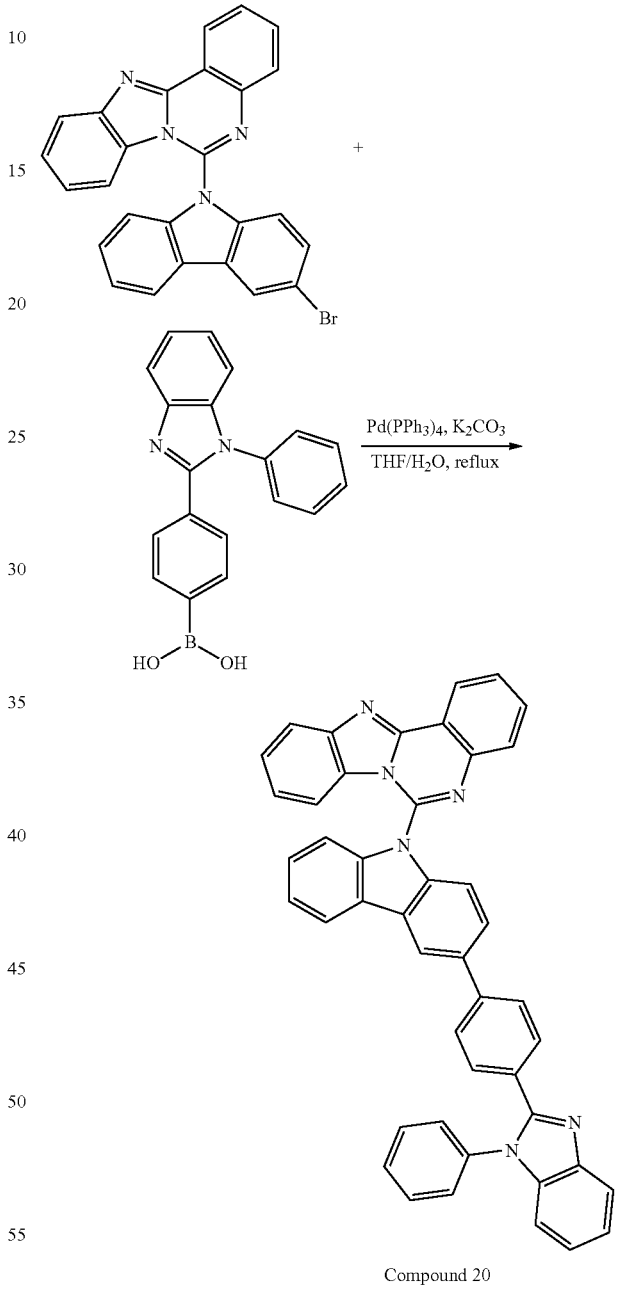

Compound 20

After completely dissolving Compound A (10 g, 21.6 mmol) and (4-(1-phenyl-1H-benzo[d]imidazol-2-yl)phenyl) boronic acid (7.48 g, 23.81 mmol) in 300 ml of tetrahydrofuran in a 500 ml round bottom flask under nitrogen atmosphere, a 2 M aqueous potassium carbonate solution (140 ml) and then tetrakis-(triphenylphosphine)palladium (0.75 g, 0.65 mmol) were added thereto, and the result was heated and stirred for 8 hours. After lowering the temperature to room temperature, the water layer was removed, and the result was dried using anhydrous magnesium sulfate, then vacuum concentrated and recrystallized with 200 ml of ethyl acetate to prepare Compound 20 (12.42 g, 87%).
MS[M+H]$^+$=653

<Preparation Example 21> Synthesis of Compound 21

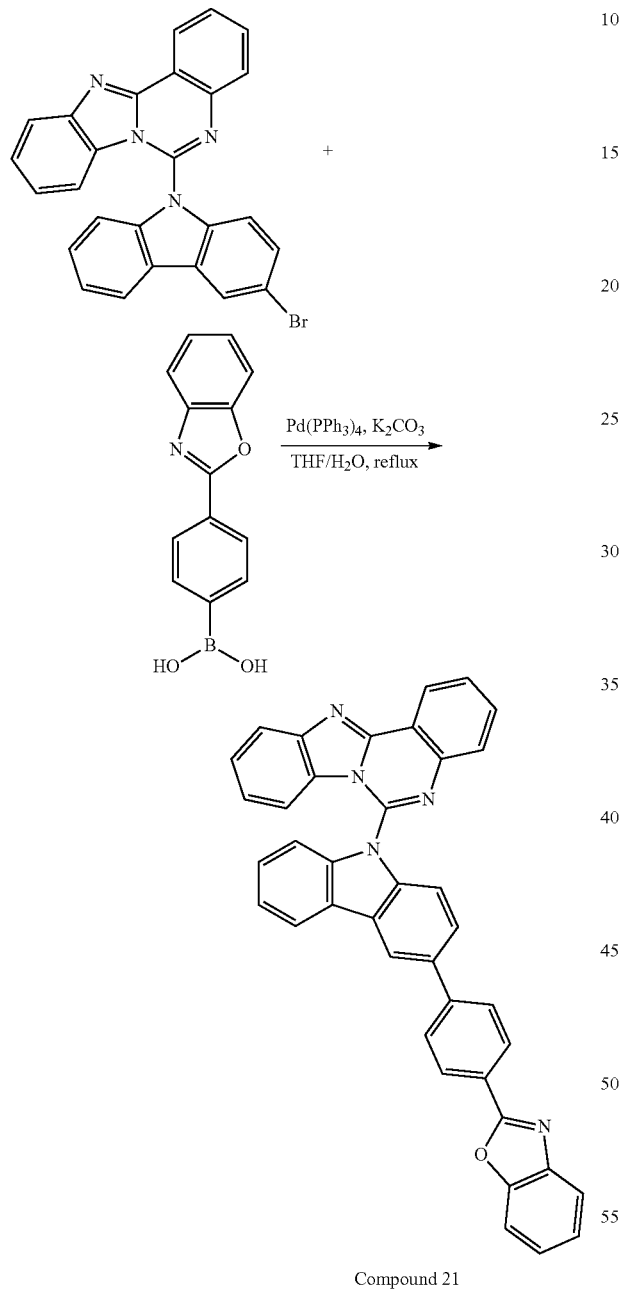

Compound 21

After completely dissolving Compound A (10 g, 21.6 mmol) and (4-(benzo[d]oxazol-2-yl)phenyl)boronic acid (5.69 g, 23.81 mmol) in 300 ml of tetrahydrofuran in a 500 ml round bottom flask under nitrogen atmosphere, a 2 M aqueous potassium carbonate solution (140 ml) and then tetrakis-(triphenylphosphine)palladium (0.75 g, 0.65 mmol) were added thereto, and the result was heated and stirred for 3 hours. After lowering the temperature to room tempera-ture, the water layer was removed, and the result was dried using anhydrous magnesium sulfate, then vacuum concentrated and recrystallized with 200 ml of ethyl acetate to prepare Compound 21 (10.11 g, 81%).
MS[M+H]$^+$=578

<Preparation Example 22> Synthesis of Compound 22

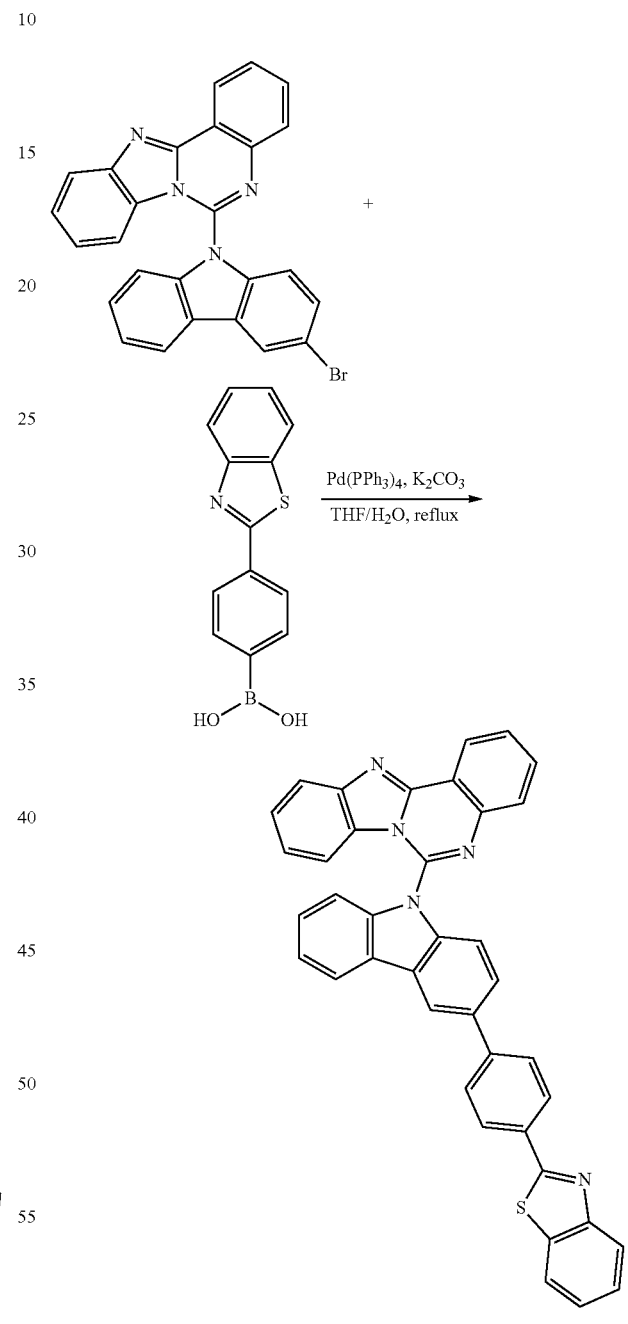

Compound 22

After completely dissolving Compound A (10 g, 21.6 mmol) and (4-(benzo[d]thiazol-2-yl)phenyl)boronic acid (5.69 g, 23.81 mmol) in 300 ml of tetrahydrofuran in a 500 ml round bottom flask under nitrogen atmosphere, a 2 M aqueous potassium carbonate solution (140 ml) and then tetrakis-(triphenylphosphine)palladium (0.75 g, 0.65 mmol)

were added thereto, and the result was heated and stirred for 3 hours. After lowering the temperature to room temperature, the water layer was removed, and the result was dried using anhydrous magnesium sulfate, then vacuum concentrated and recrystallized with 200 ml of ethyl acetate to prepare Compound 22 (9.53 g, 74%).

MS[M+H]$^+$=594

<Preparation Example 23> Synthesis of Compound 23

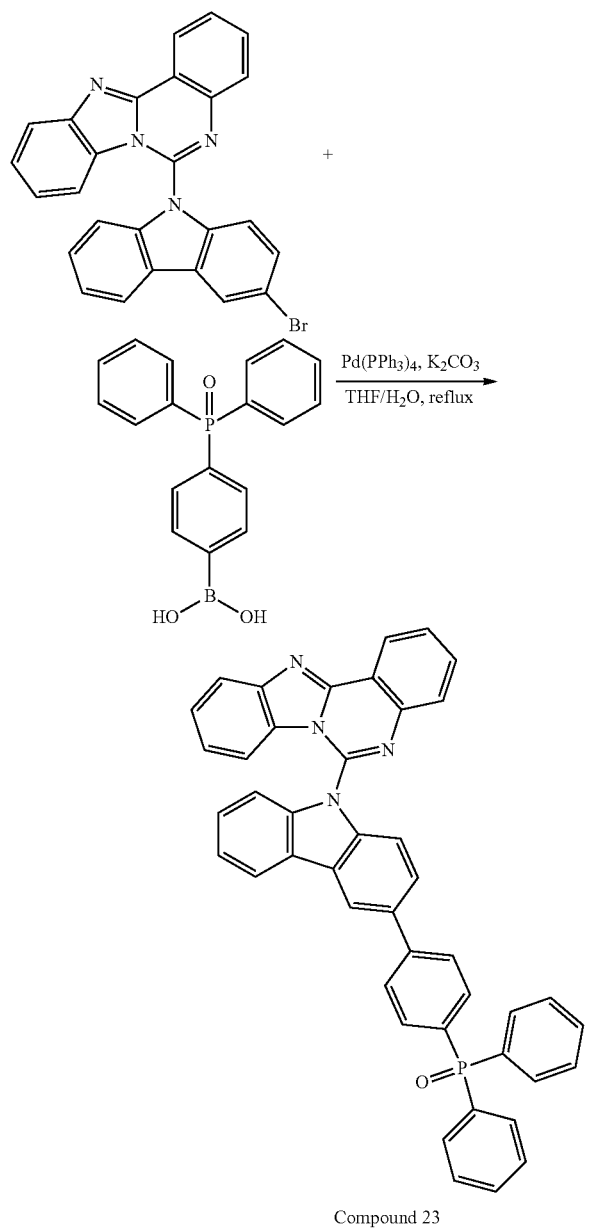

Compound 23

After completely dissolving Compound A (10 g, 21.6 mmol) and (4-(benzo[d]thiazol-2-yl)phenyl)boronic acid (6.84 g, 23.81 mmol) in 300 ml of tetrahydrofuran in a 500 ml round bottom flask under nitrogen atmosphere, a 2 M aqueous potassium carbonate solution (140 ml) and then tetrakis-(triphenylphosphine)palladium (0.75 g, 0.65 mmol) were added thereto, and the result was heated and stirred for 2 hours. After lowering the temperature to room temperature, the water layer was removed, and the result was dried using anhydrous magnesium sulfate, then vacuum concentrated and recrystallized with 200 ml of ethyl acetate to prepare Compound 23 (9.53 g, 74%).

MS[M+H]$^+$=662

<Preparation Example 24> Synthesis of Compounds 24 to 46

The following Compounds 24 to 46 were prepared in the same manner as in Preparation Examples 1 to 23, the methods preparing Compounds 1 to 23, except that, as the starting materials, Compound B was used instead of Compound A and Compound H was used instead of Compound G.

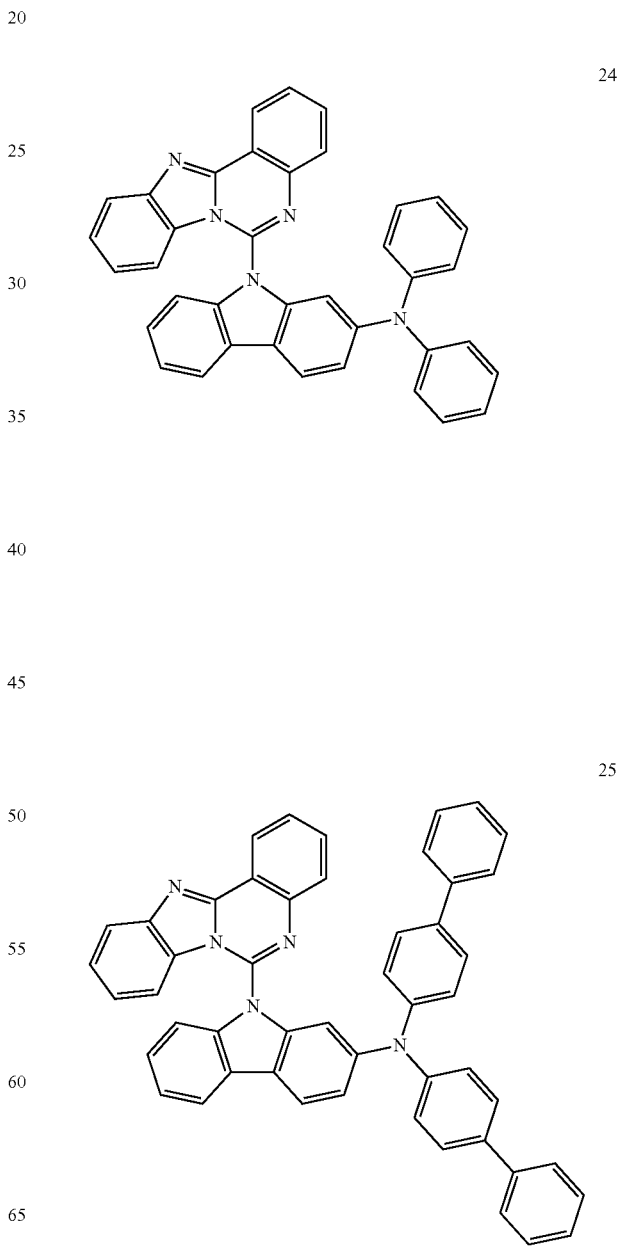

26
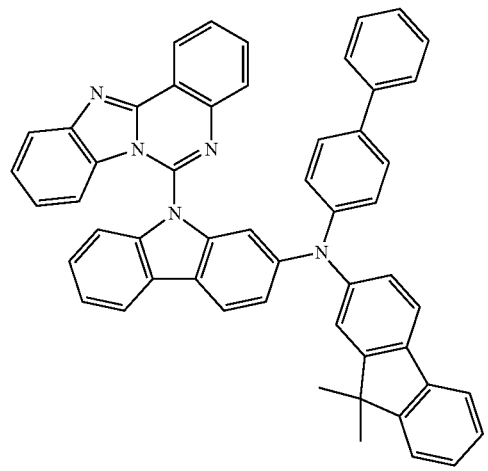
27
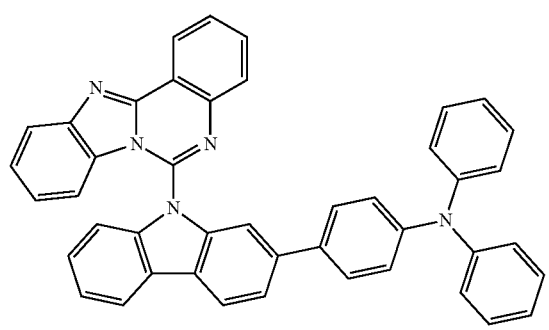
28
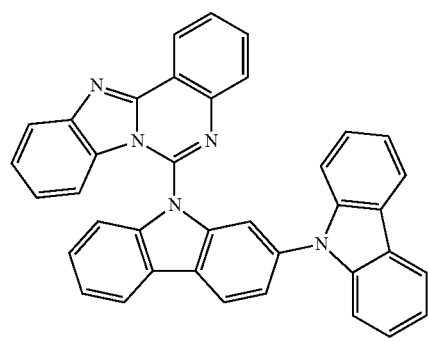
29
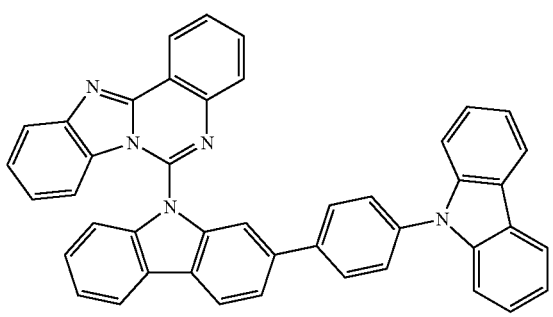
30
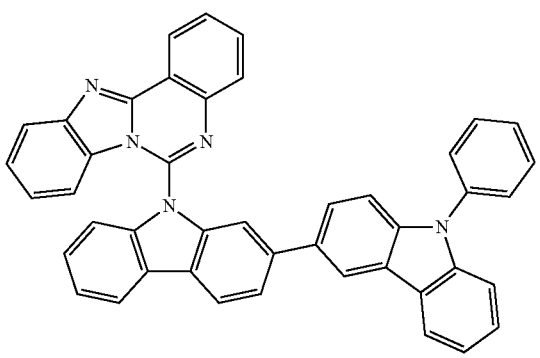
31
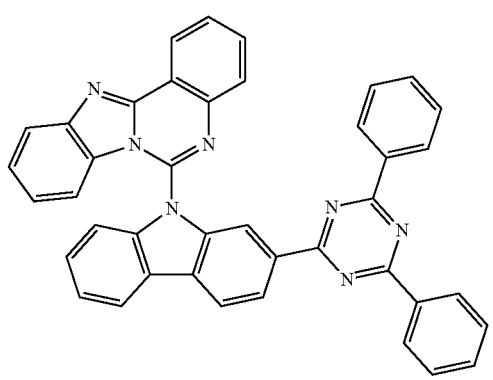
32
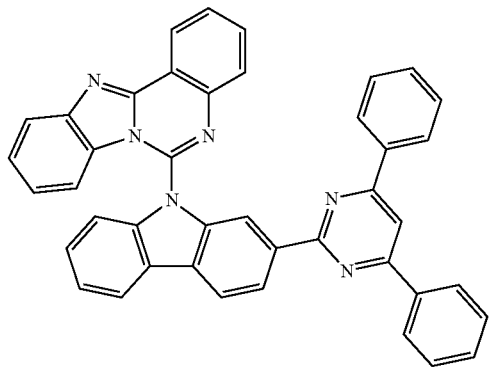
33
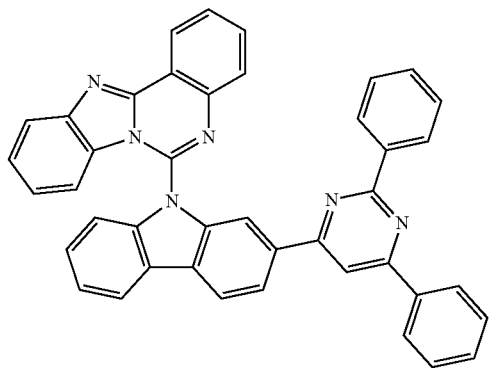

34
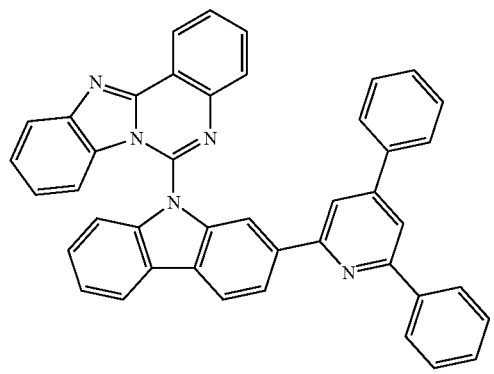
35
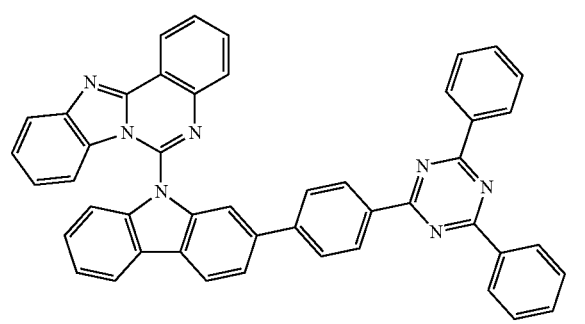
36
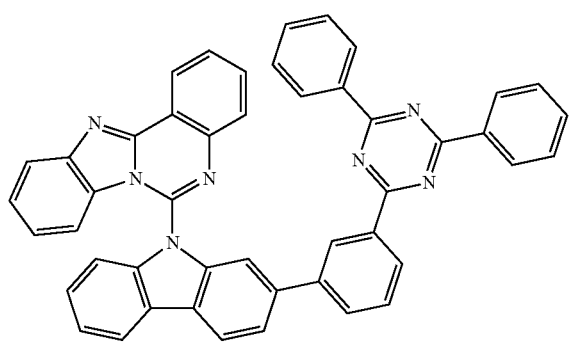
37
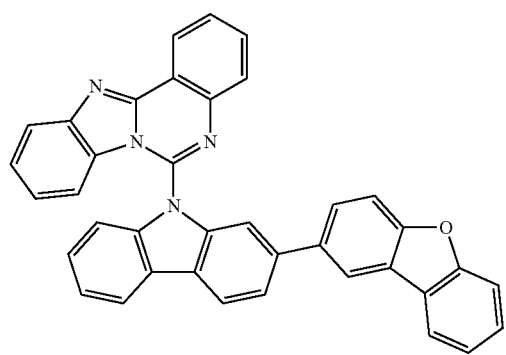
38
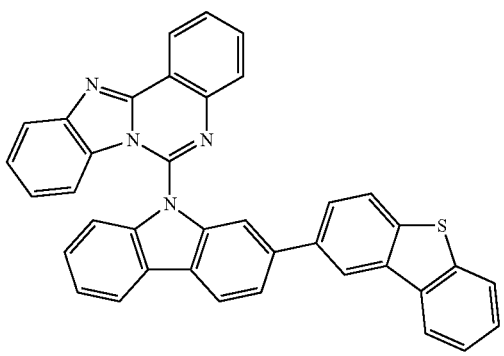
39
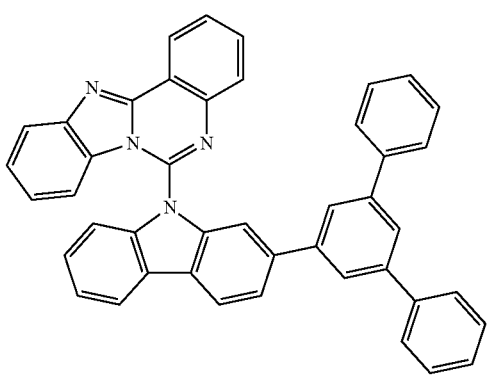
40
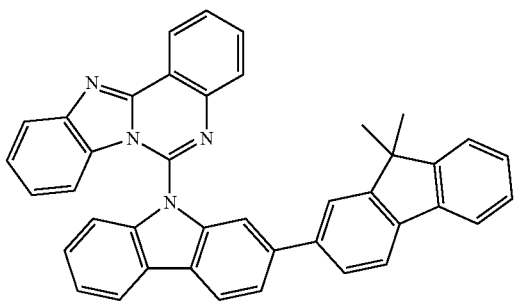
41
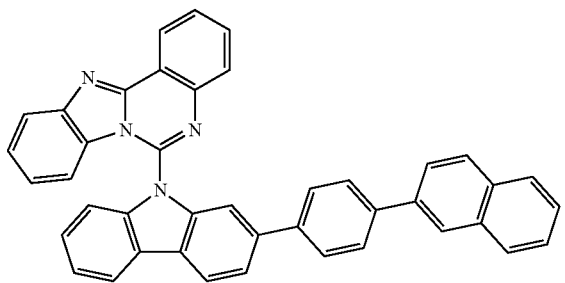

42
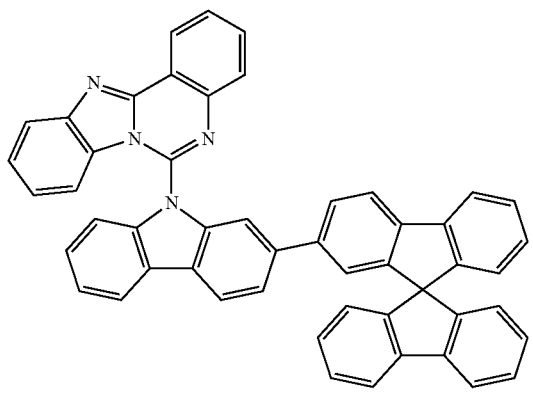
43
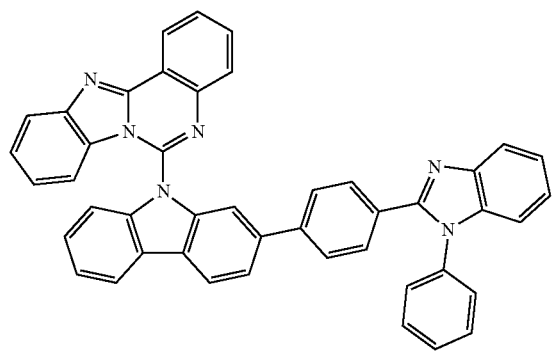
44
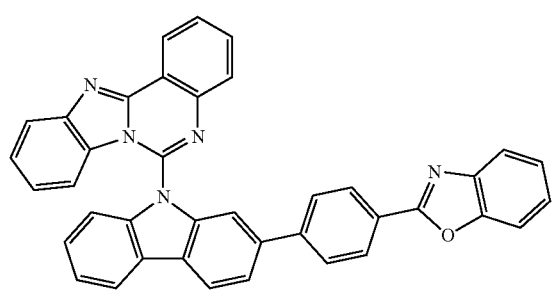
45
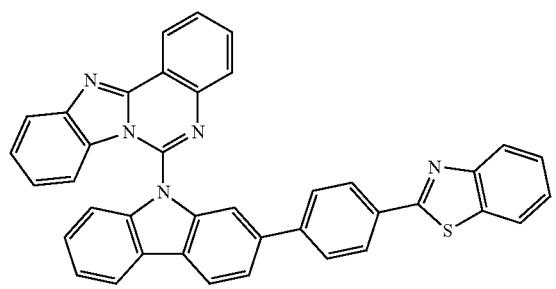
46
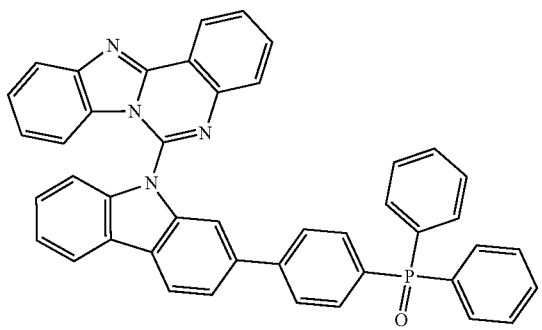
<Preparation Example 25> Synthesis of Compounds 47 to 69
The following Compounds 47 to 69 were prepared in the same manner as in Preparation Examples 1 to 23, the methods preparing Compounds 1 to 23, except that, as the starting material, Compound E was used instead of Compound A.
47
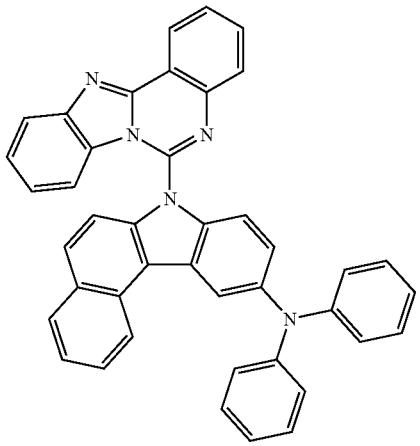
48
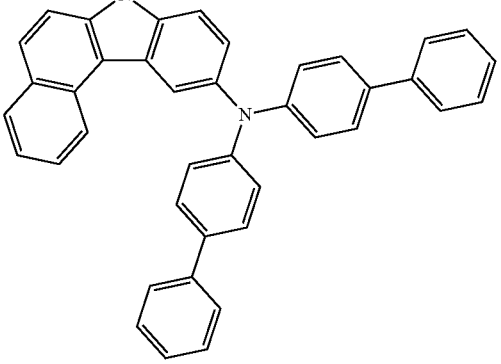

49
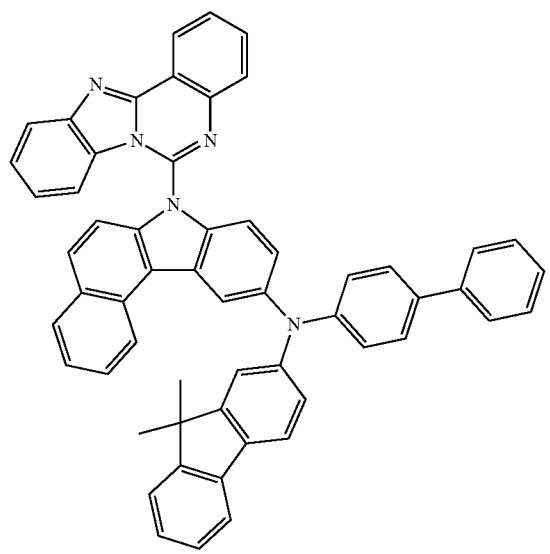
50
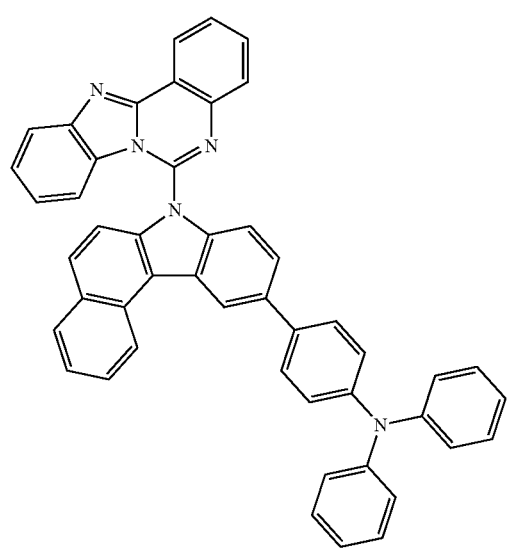
51
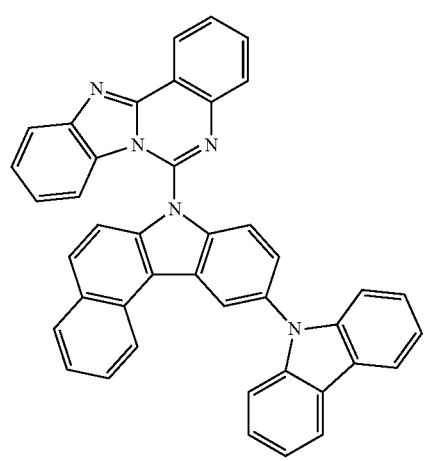
52
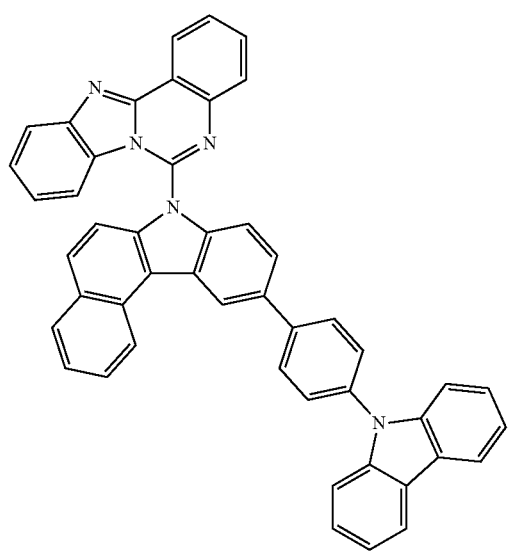
53
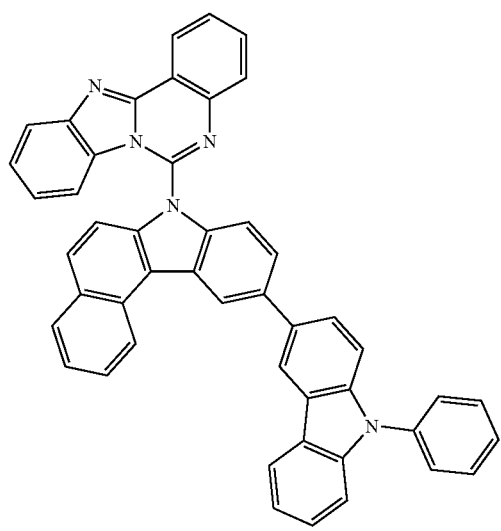
54
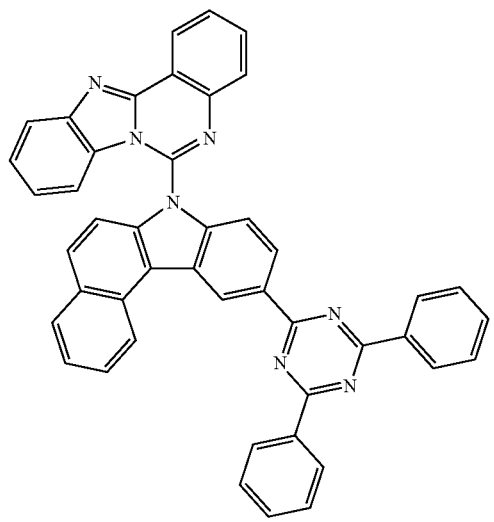

55
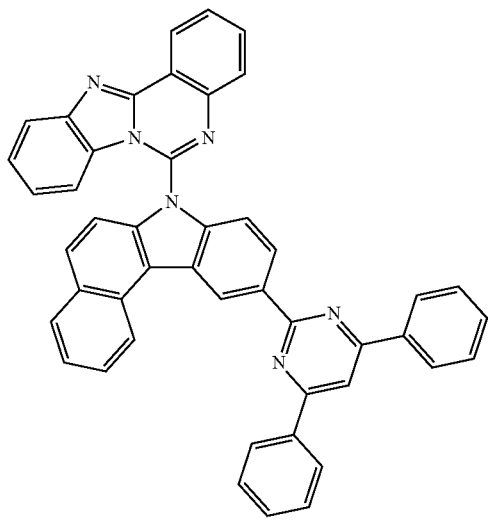
56
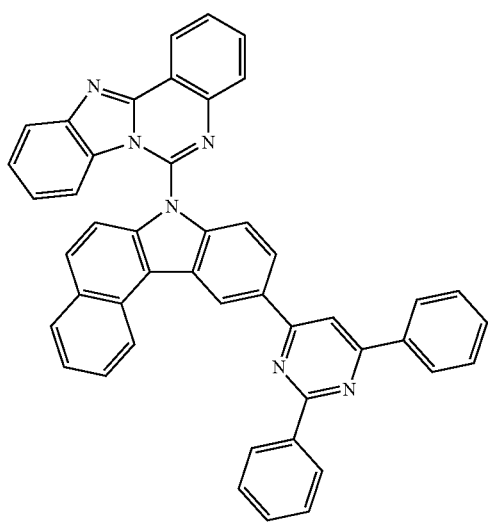
57
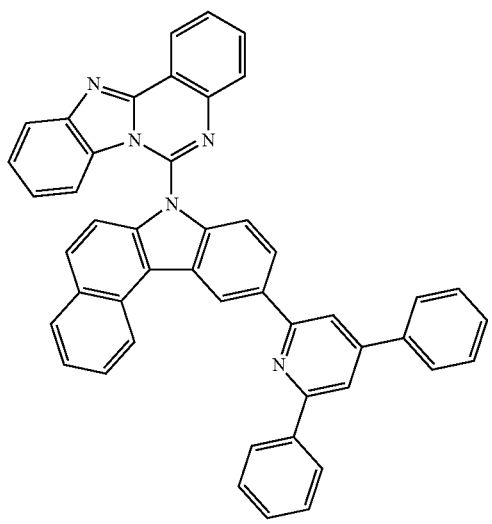
58
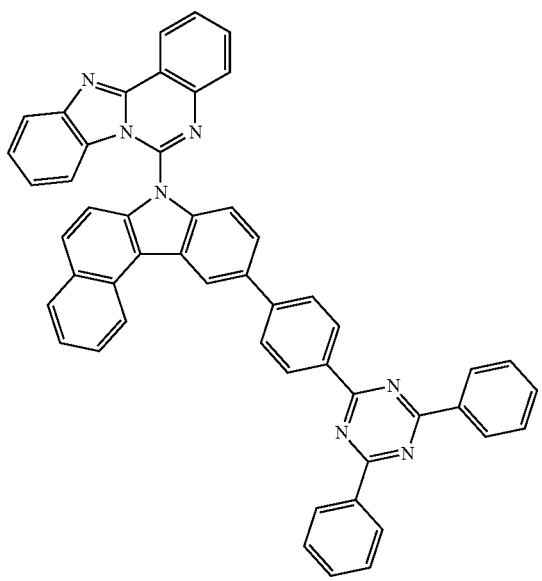
59
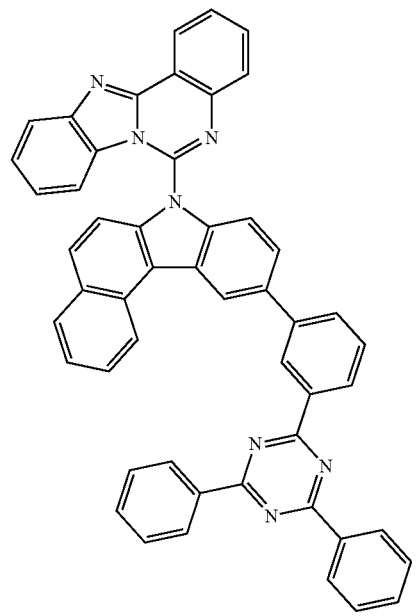

60
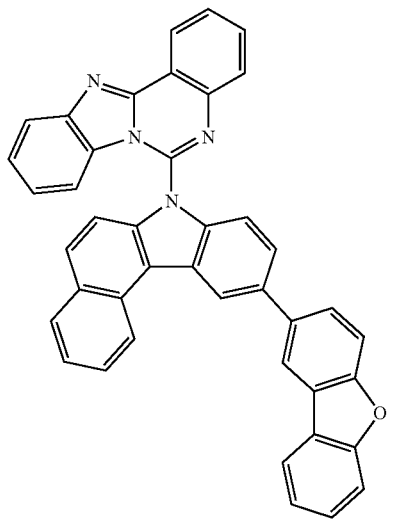
61
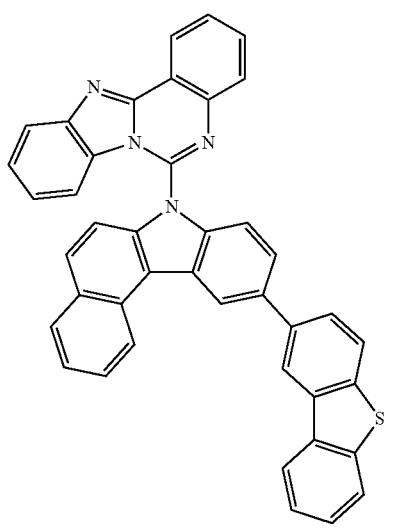
62
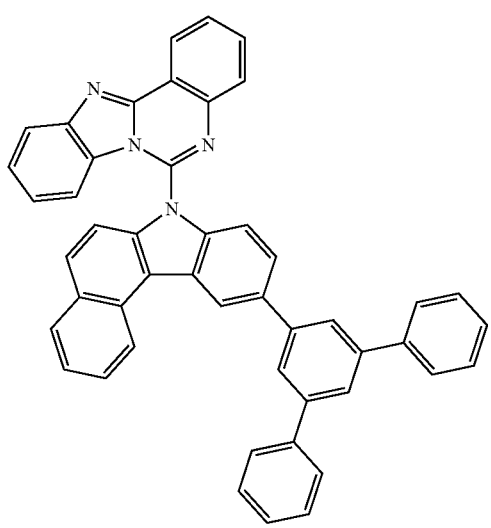
63
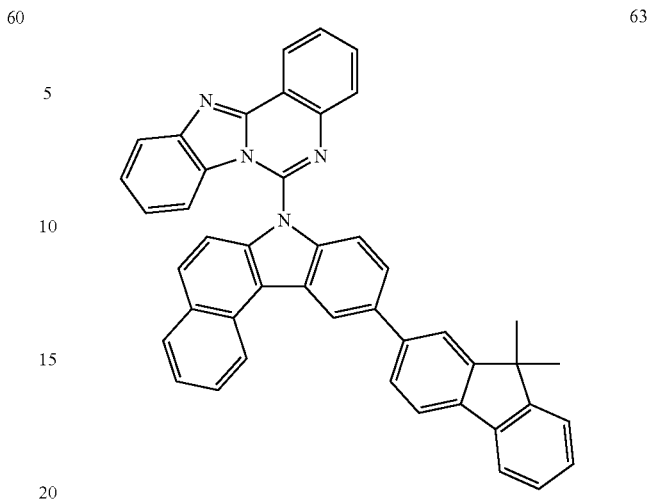
64
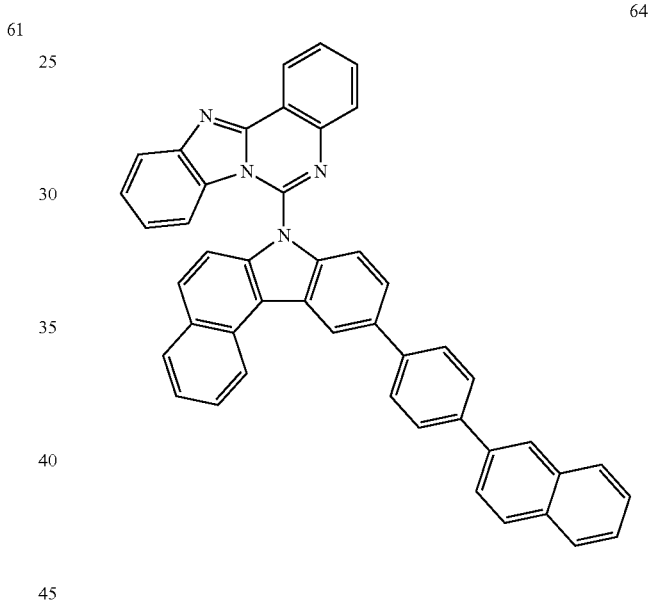
65
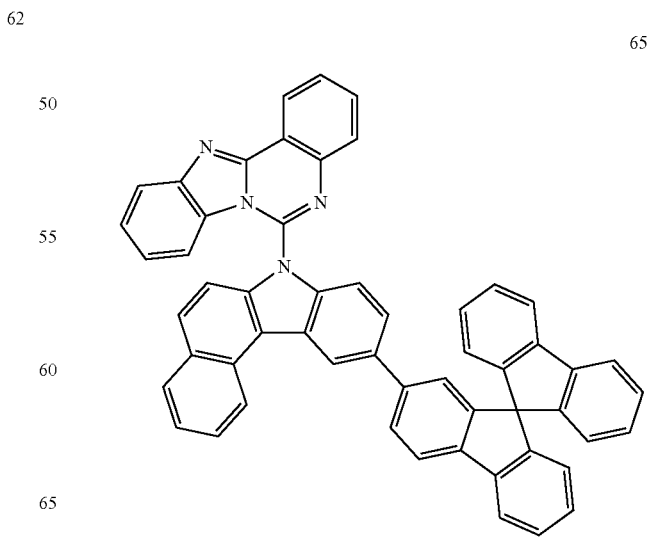

66
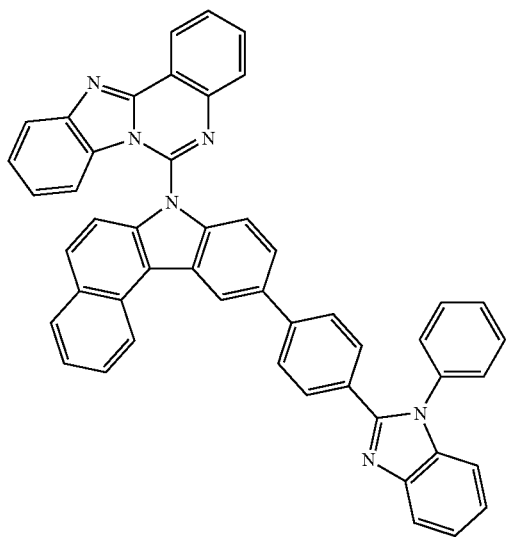
67
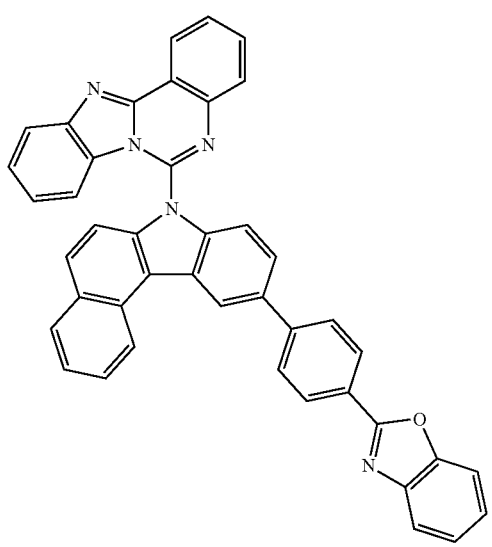
68
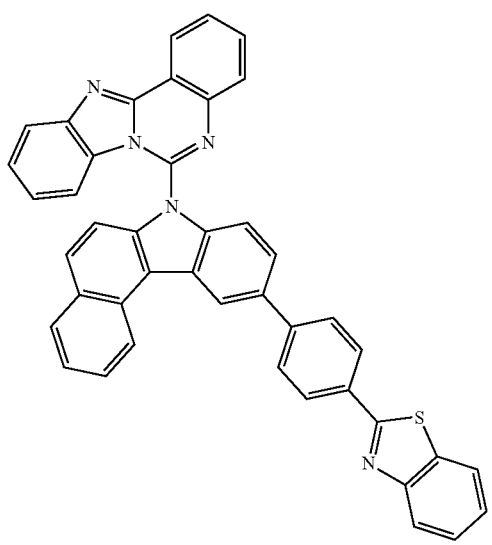
69
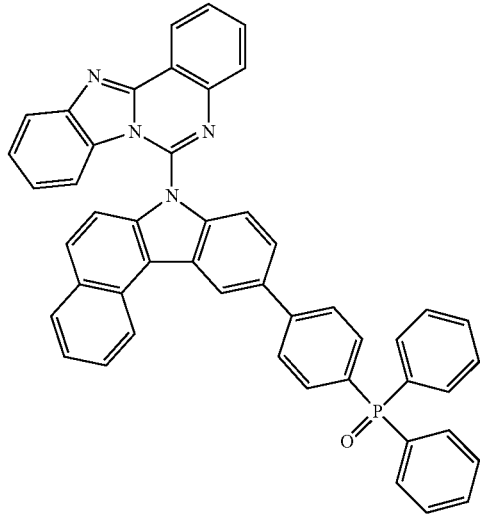
<Preparation Example 26> Synthesis of Compounds 70 to 92
The following Compounds 70 to 92 were prepared in the same manner as in Preparation Examples 1 to 23, the methods preparing Compounds 1 to 23, except that, as the starting material, Compound F was used instead of Compound A.
70
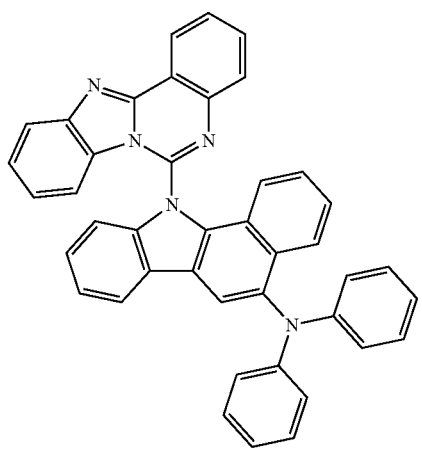

301
-continued
71
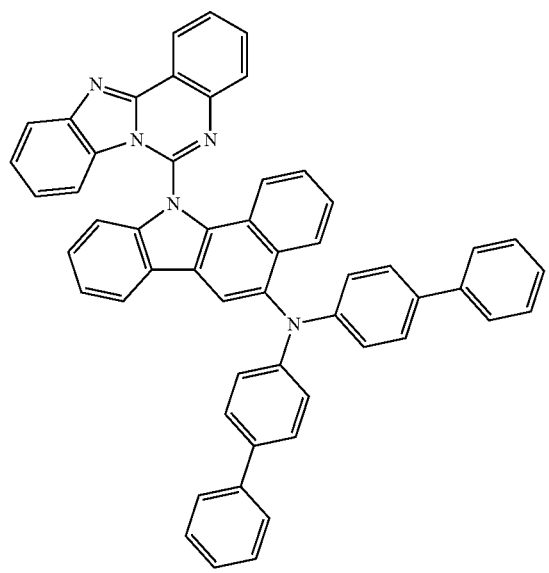
72
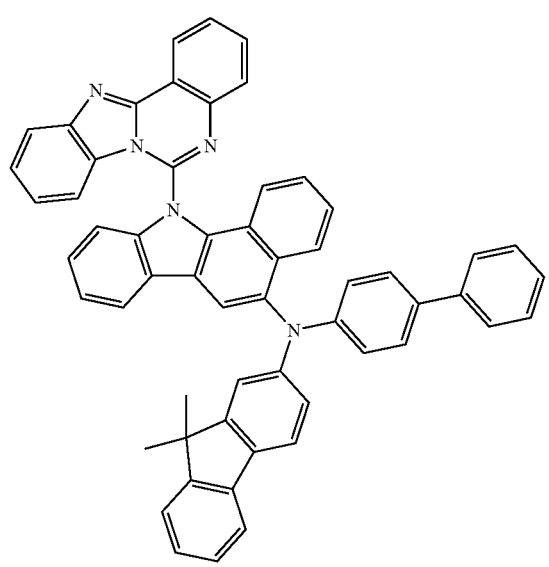
302
-continued
73
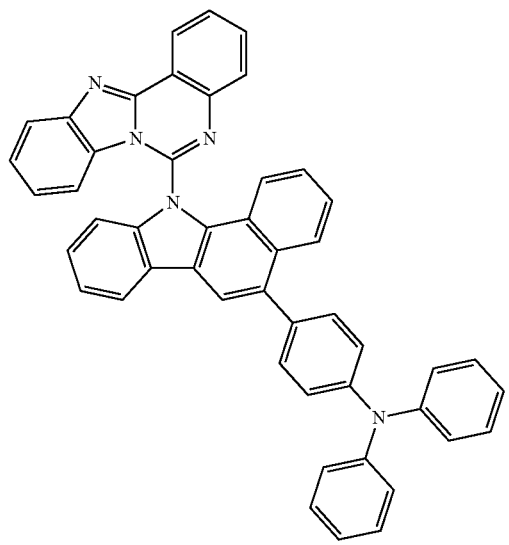
74
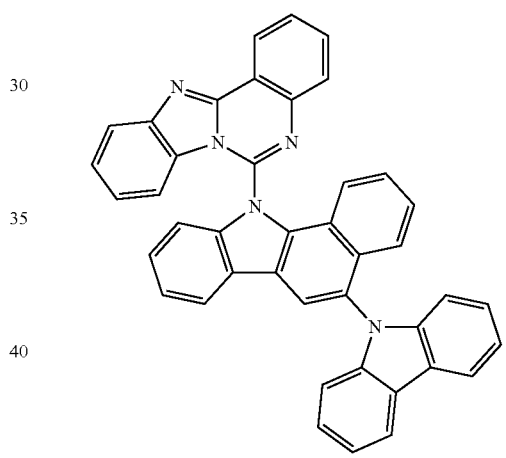
75
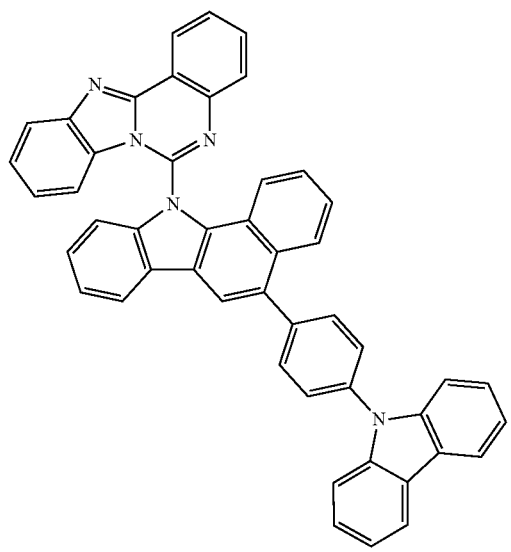

76
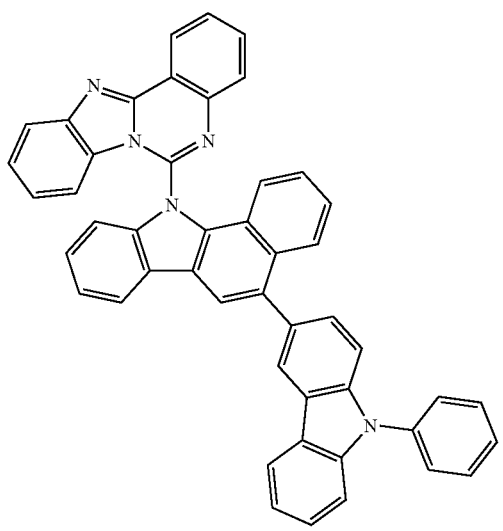
77
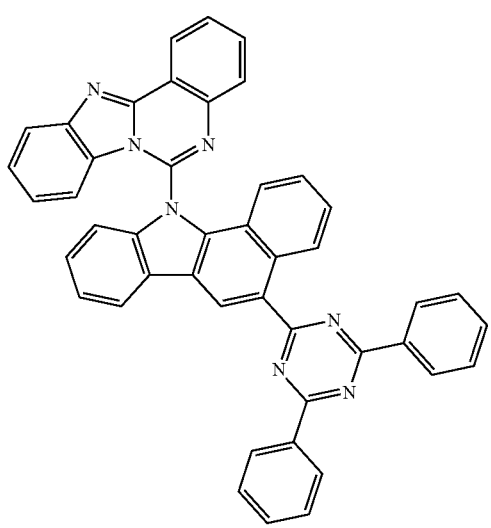
78
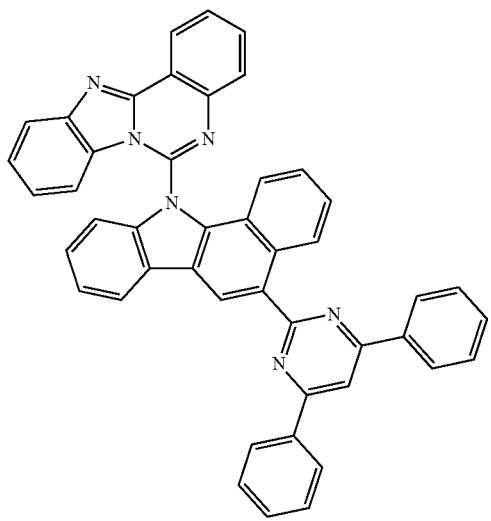
79
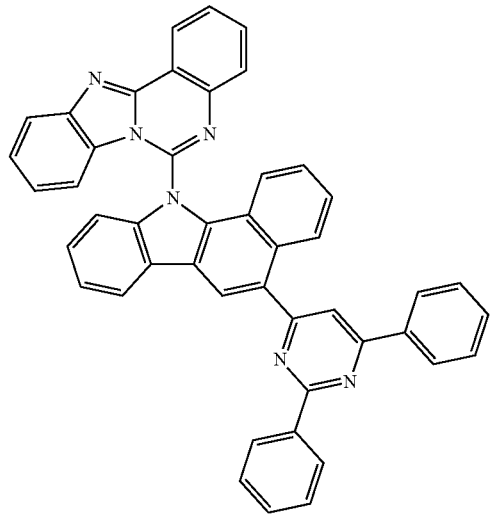
80
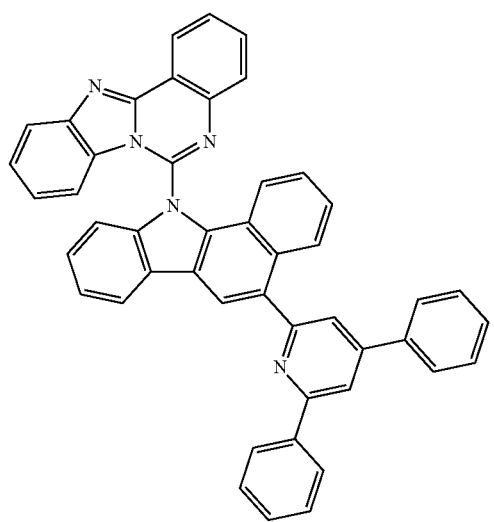
81
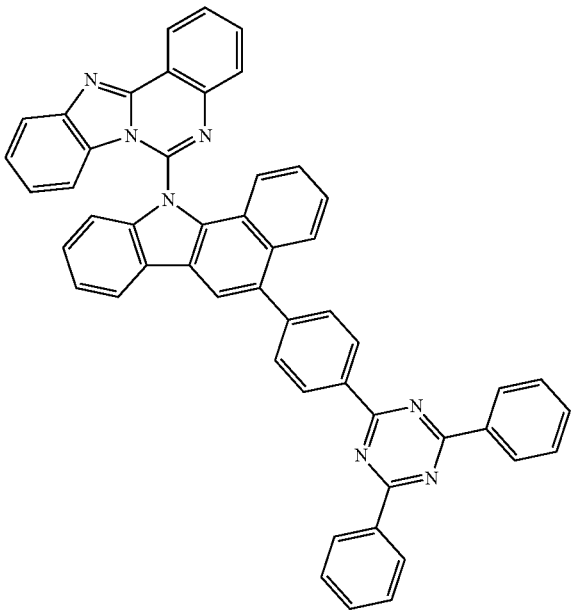

82
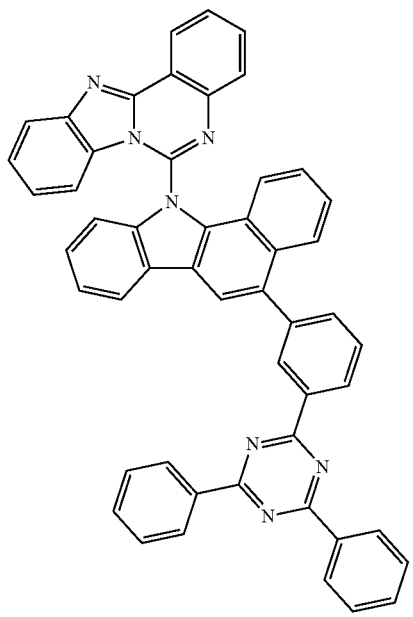
83
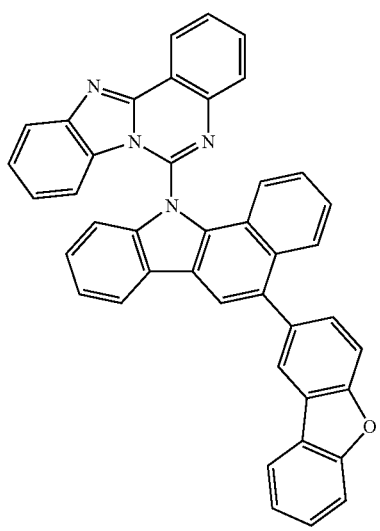
84
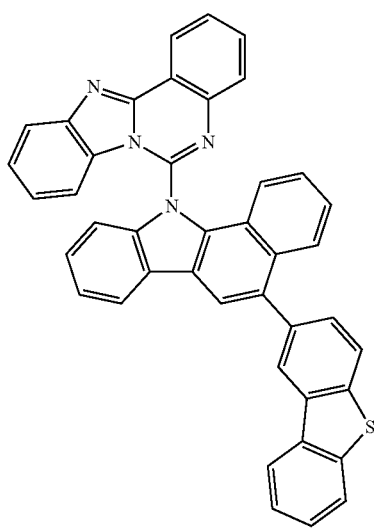
85
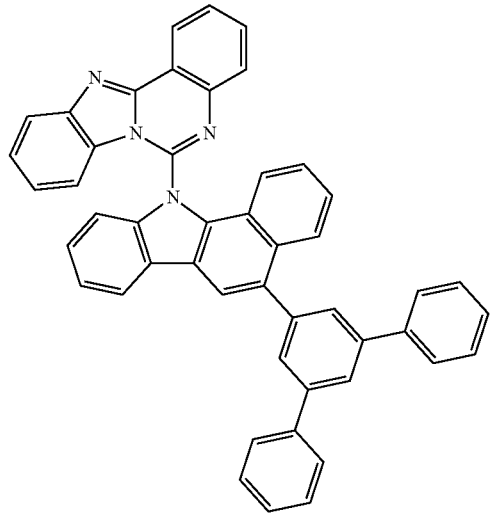
86
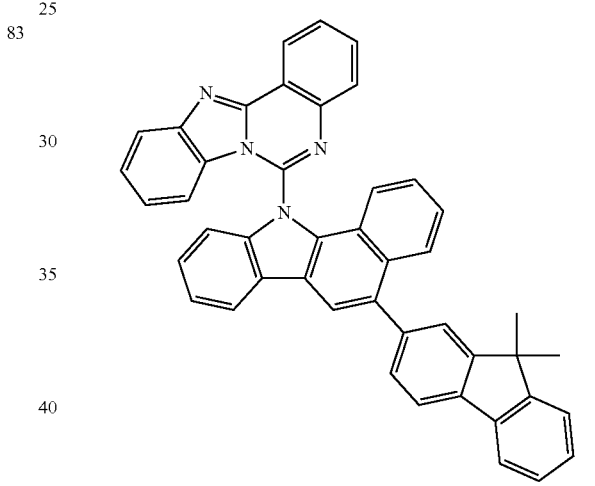
87
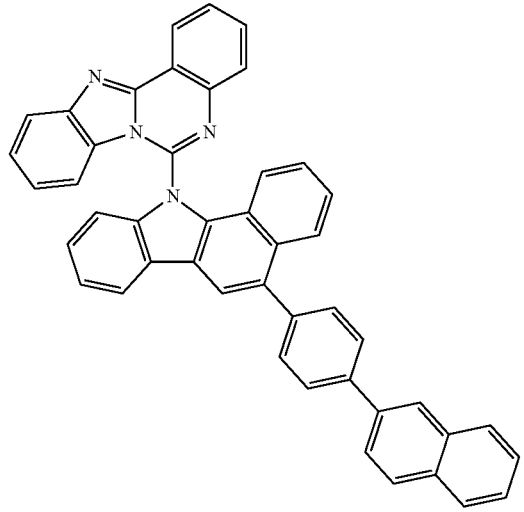

88
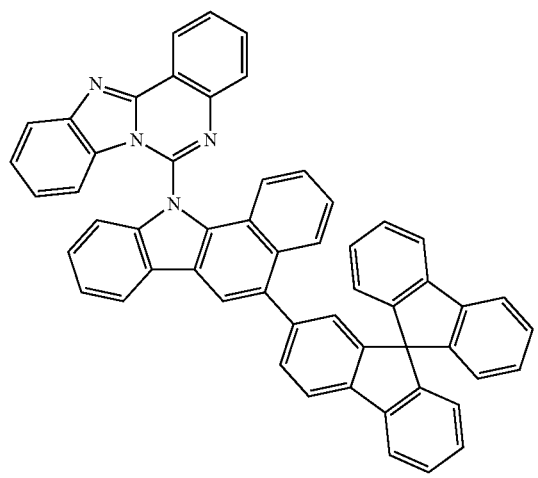
89
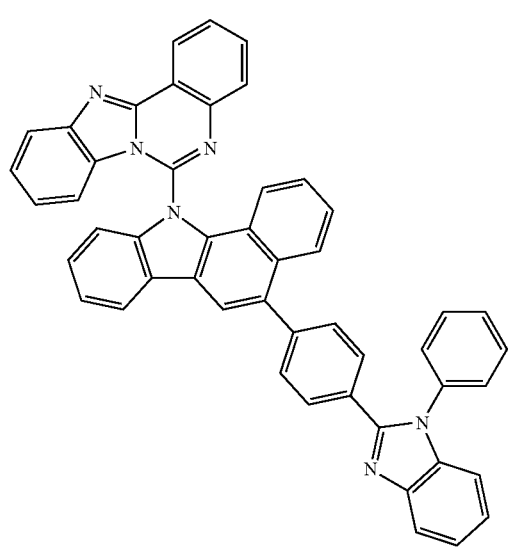
90
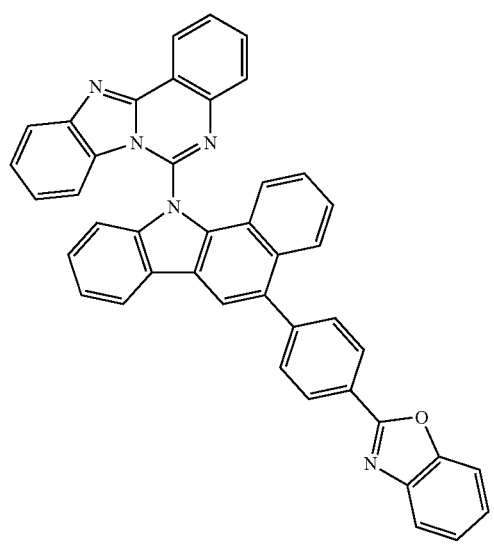
91
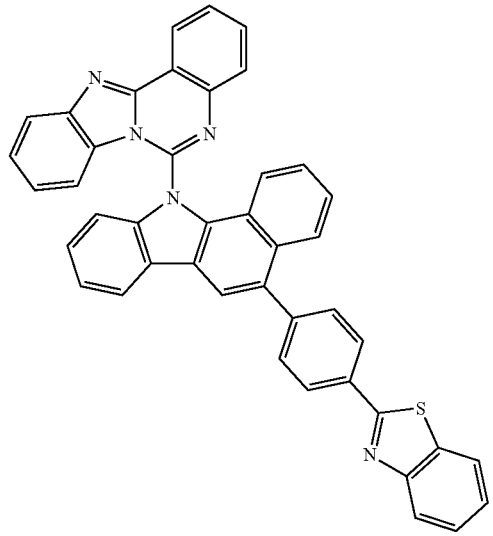
92
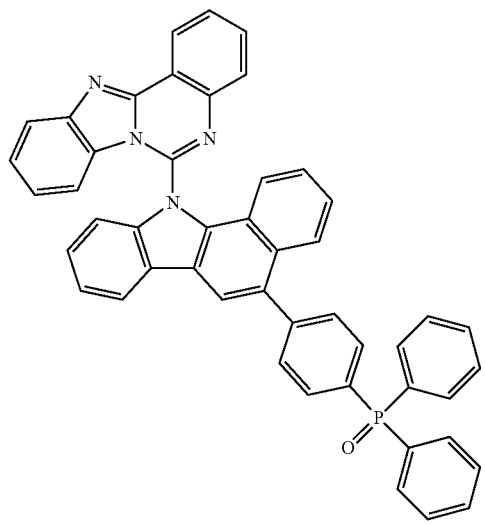
<Preparation Example 27> Synthesis of Compound 93
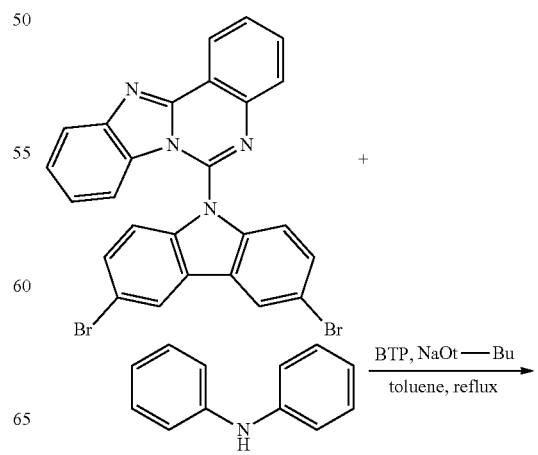

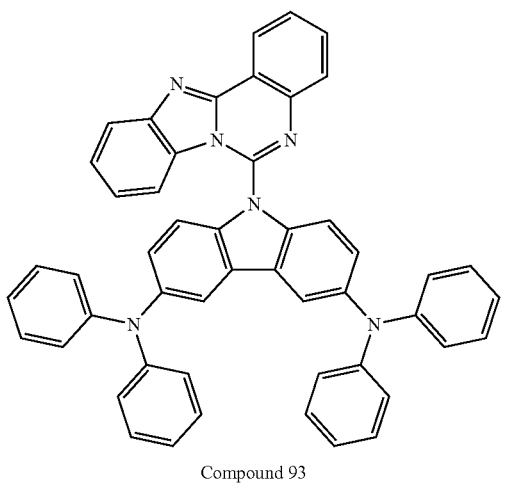

Compound 93

After introducing Compound C (10 g, 18.52 mmol), diphenylamine (6.88 g, 40.74 mmol) and NaOt-Bu (4.62 g, 48.2 mmol) in 200 ml of toluene, the temperature was raised while stirring the mixture. When the result started to reflux after raising the temperature, bis(tri-tert-butylphosphine) palladium (0.09 g, 0.18 mmol) was slowly added thereto through dropwise addition. After 5 hours, the reaction was terminated, the temperature was lowered to room temperature, and the result was concentrated under vacuum and column purified to prepare 10.42 g (80%) of Compound 93.

MS[M+H]$^+$=719

<Preparation Example 28> Synthesis of Compound 94

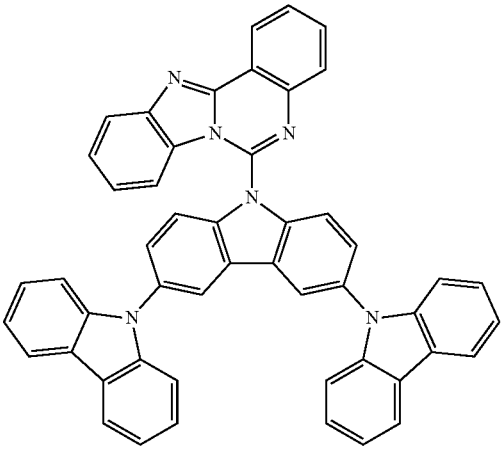

After introducing Compound C (10 g, 18.52 mmol), carbazole (6.85 g, 40.74 mmol) and NaOt-Bu (4.62 g, 48.2 mmol) in 200 ml of toluene, the temperature was raised while stirring the mixture. When the result started to reflux after raising the temperature, bis(tri-tert-butylphosphine) palladium (0.09 g, 0.18 mmol) was slowly added thereto through dropwise addition. After 5 hours, the reaction was terminated, the temperature was lowered to room temperature, and the result was concentrated under vacuum and column purified to prepare 8.42 g (71%) of Compound 94.

MS[M+H]$^+$=715

<Preparation Example 29> Synthesis of Compound 95

Compound 94

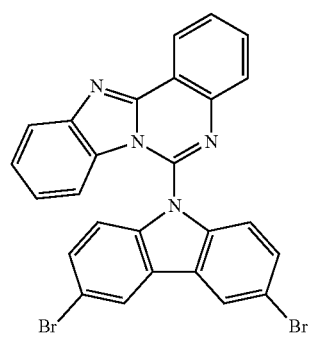

+

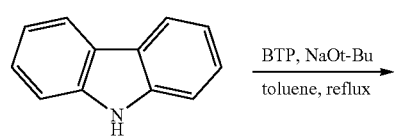

BTP, NaOt-Bu
toluene, reflux

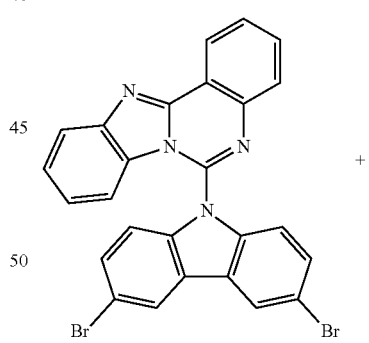

+

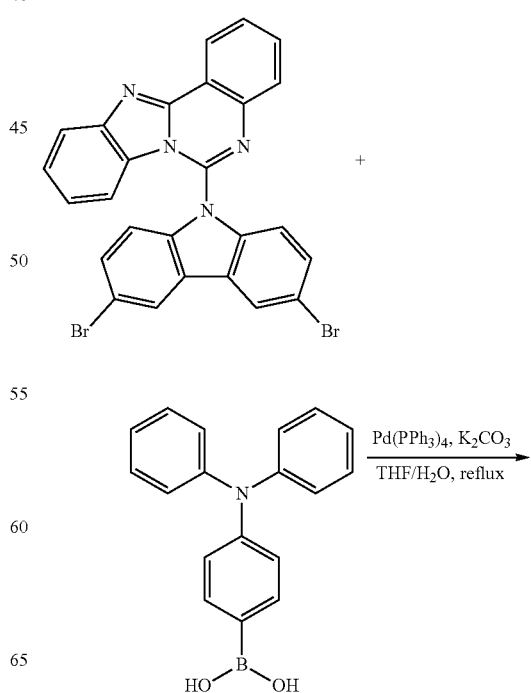

Pd(PPh$_3$)$_4$, K$_2$CO$_3$
THF/H$_2$O, reflux

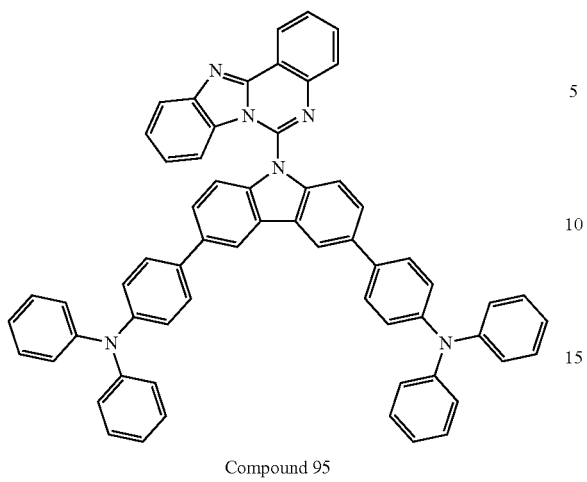

Compound 95

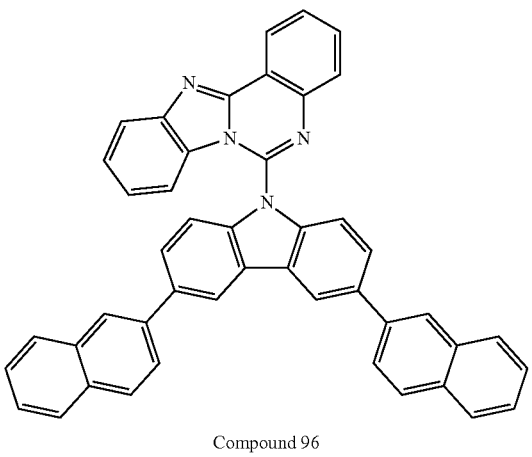

Compound 96

After completely dissolving Compound C (10 g, 18.52 mmol) and (4-(diphenylamino)phenyl)boronic acid (11.40 g, 40.74 mmol) in 320 ml of tetrahydrofuran in a 500 ml round bottom flask under nitrogen atmosphere, a 2 M aqueous potassium carbonate solution (110 ml) and then tetrakis-(triphenylphosphine)palladium (0.65 g, 0.56 mmol) were added thereto, and the result was heated and stirred for 3 hours. After lowering the temperature to room temperature, the water layer was removed, and the result was dried using anhydrous magnesium sulfate, then vacuum concentrated and recrystallized with 200 ml of ethyl acetate to prepare Compound 95 (13.54 g, 84%).

MS[M+H]$^+$=871

<Preparation Example 30> Synthesis of Compound 96

After completely dissolving Compound C (10 g, 18.52 mmol) and naphthalen-ylboronic acid (7.01 g, 40.74 mmol) in 280 ml of tetrahydrofuran in a 500 ml round bottom flask under nitrogen atmosphere, a 2 M aqueous potassium carbonate solution (120 ml) and then tetrakis-(triphenylphosphine)palladium (0.65 g, 0.56 mmol) were added thereto, and the result was heated and stirred for 1 hour. After lowering the temperature to room temperature, the water layer was removed, and the result was dried using anhydrous magnesium sulfate, then vacuum concentrated and recrystallized with 300 ml of ethyl acetate to prepare Compound 96 (9.45 g, 80%).

MS[M+H]$^+$=637

<Preparation Example 31> Synthesis of Compound 97

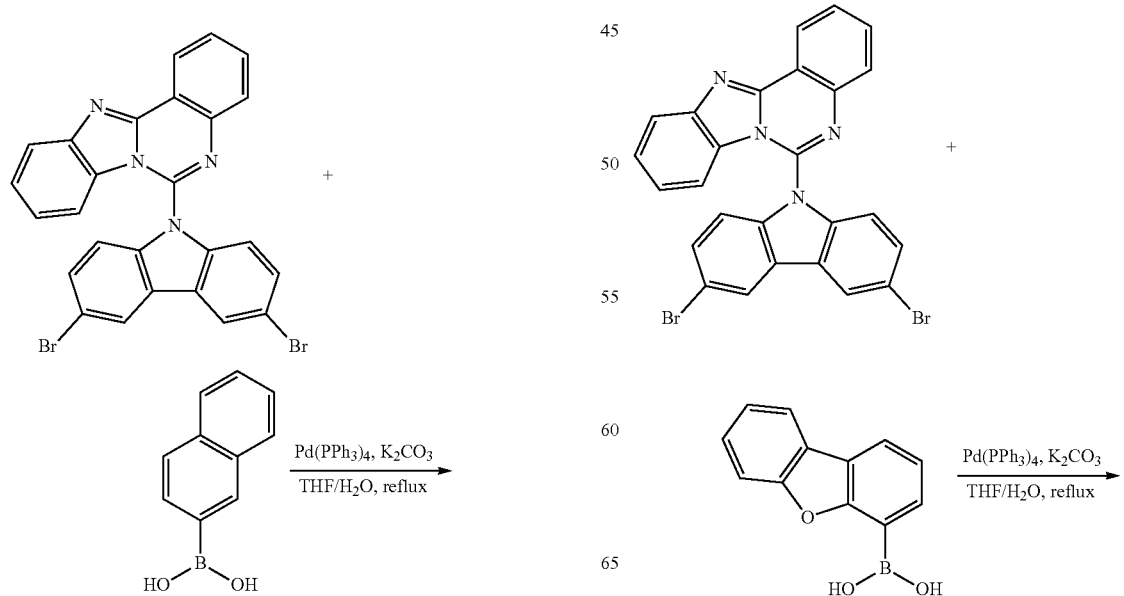

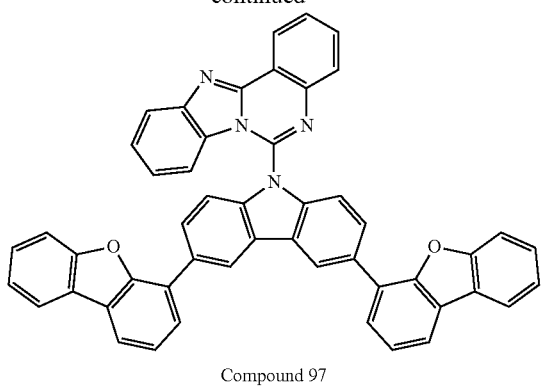

Compound 97

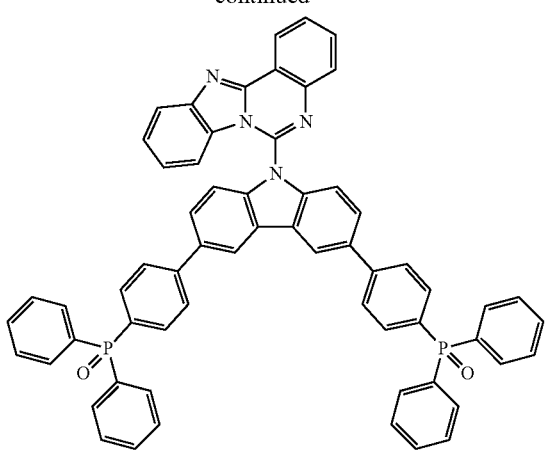

Compound 98

After completely dissolving Compound C (10 g, 18.52 mmol) and dibenzo[b,d]furan-4-ylboronic acid (8.64 g, 40.74 mmol) in 300 ml of tetrahydrofuran in a 500 ml round bottom flask under nitrogen atmosphere, a 2 M aqueous potassium carbonate solution (150 ml) and then tetrakis-(triphenylphosphine)palladium (0.65 g, 0.56 mmol) were added thereto, and the result was heated and stirred for 3 hours. After lowering the temperature to room temperature, the water layer was removed, and the result was dried using anhydrous magnesium sulfate, then vacuum concentrated and recrystallized with 300 ml of ethyl acetate to prepare Compound 97 (11.24 g, 84%).

MS[M+H]$^+$=717

<Preparation Example 32> Synthesis of Compound 98

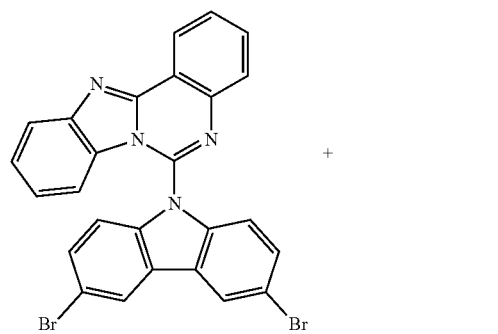

+

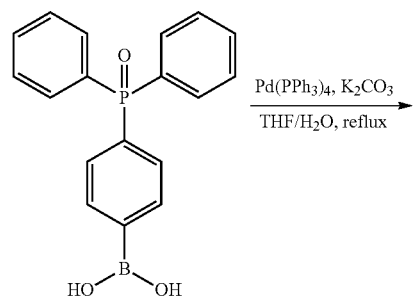

$\xrightarrow{\text{Pd(PPh}_3)_4, \text{K}_2\text{CO}_3}{\text{THF/H}_2\text{O, reflux}}$ After completely dissolving Compound C (10 g, 18.52 mmol) and dibenzo[b,d]furan-4-ylboronic acid (13.12 g, 40.74 mmol) in 360 ml of tetrahydrofuran in a 500 ml round bottom flask under nitrogen atmosphere, a 2 M aqueous potassium carbonate solution (180 ml) and then tetrakis-(triphenylphosphine)palladium (0.65 g, 0.56 mmol) were added thereto, and the result was heated and stirred for 15 hours. After lowering the temperature to room temperature, the water layer was removed, and the result was dried using anhydrous magnesium sulfate, then vacuum concentrated and recrystallized with 300 ml of ethyl acetate to prepare Compound 98 (14.15 g, 81%).

MS[M+H]$^+$=937

<Preparation Example 33> Synthesis of Compounds 99 to 104

The following Compounds 99 to 104 were prepared in the same manner as in Preparation Examples 27 to 32, the methods preparing Compounds 93 to 98, except that, as the starting material, Compound D was used instead of Compound C.

99

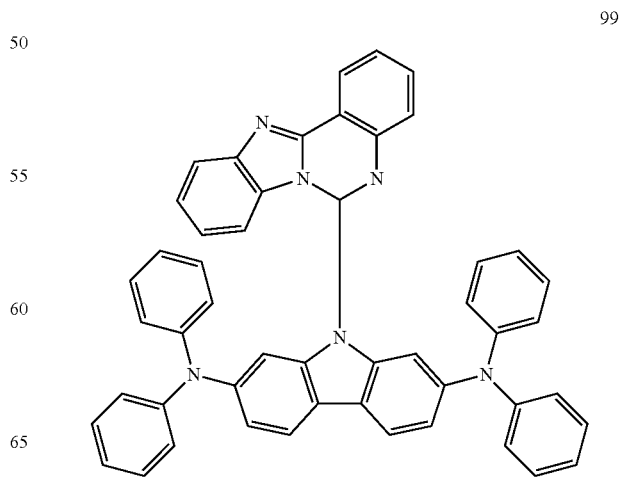

-continued

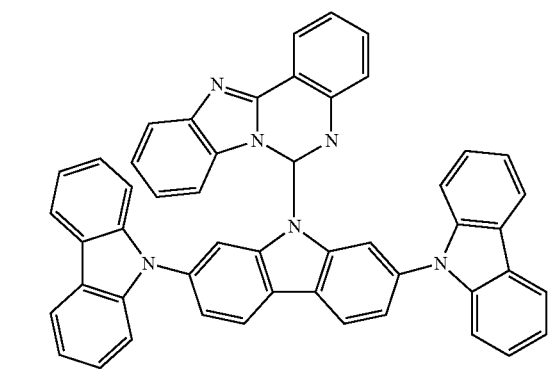

100

101

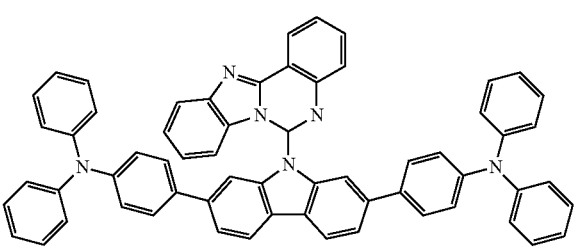

102

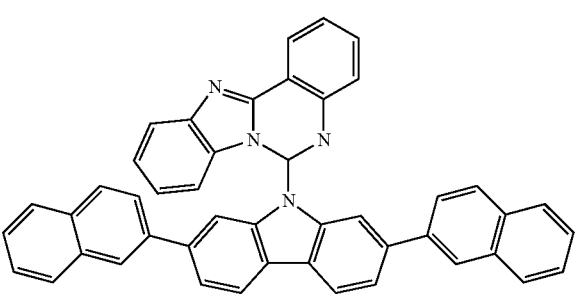

103

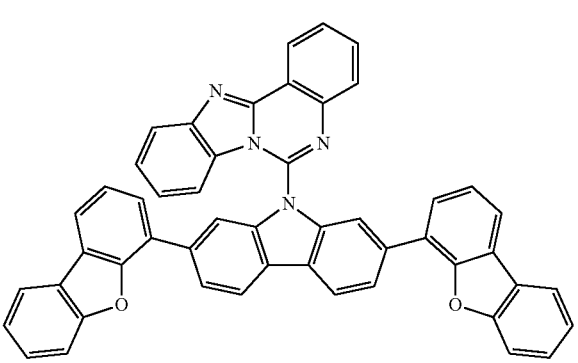

104

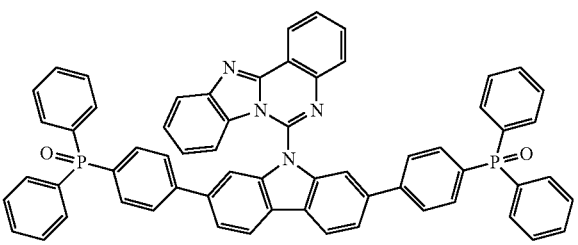

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

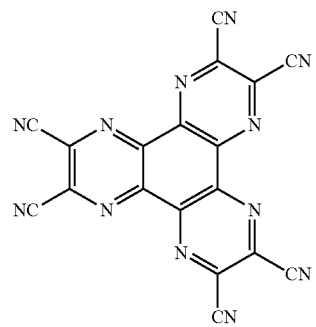

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

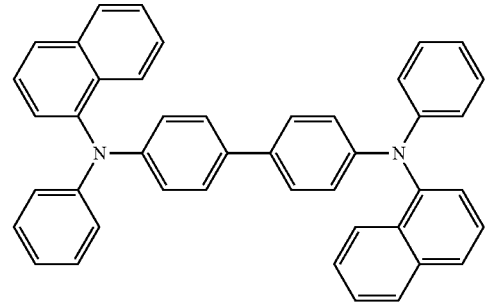

[NPB]

Subsequently, an electron blocking layer was formed on the hole transfer layer by vacuum depositing the following Compound 1 to a film thickness of 100 Å.

[Compound 1]

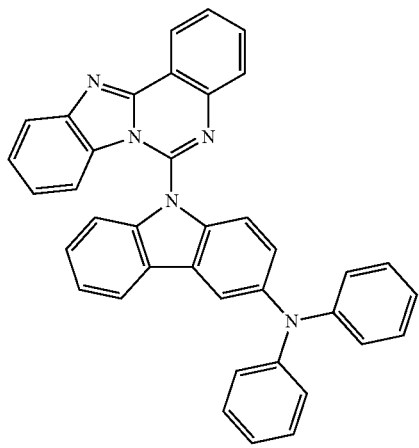

Subsequently, a light emitting layer was formed on the electron blocking layer to a film thickness of 300 Å by vacuum depositing BH and BD as follows in a weight ratio of 25:1.

[BH]

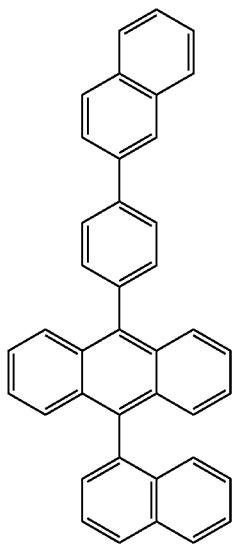

[BD]

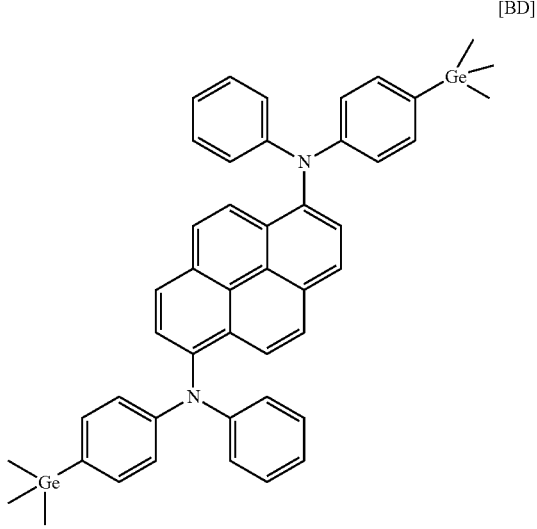

[ET1]

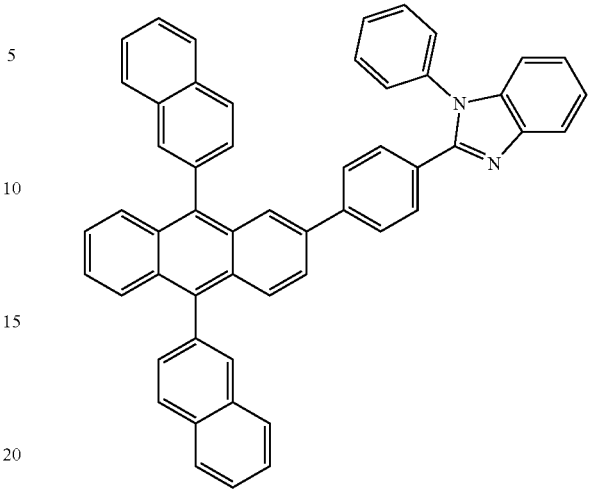

[LiQ]

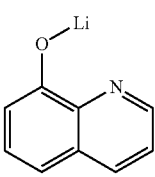

On the light emitting layer, an electron injection and transfer layer was formed to a thickness of 300 Å by vacuum depositing Compound ET1 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-6}$ torr.

Example 1-2

An organic light emitting device was manufactured in the same manner as in Example 1-1 except that Compound 2 was used instead of Compound 1.

Example 1-3

An organic light emitting device was manufactured in the same manner as in Example 1-1 except that Compound 3 was used instead of Compound 1.

Example 1-4

An organic light emitting device was manufactured in the same manner as in Example 1-1 except that Compound 4 was used instead of Compound 1.

Example 1-5

An organic light emitting device was manufactured in the same manner as in Example 1-1 except that Compound 5 was used instead of Compound 1.

Example 1-6

An organic light emitting device was manufactured in the same manner as in Example 1-1 except that Compound 6 was used instead of Compound 1.

Example 1-7

An organic light emitting device was manufactured in the same manner as in Example 1-1 except that Compound 7 was used instead of Compound 1.

Example 1-8

An organic light emitting device was manufactured in the same manner as in Example 1-1 except that Compound 24 was used instead of Compound 1.

Example 1-9

An organic light emitting device was manufactured in the same manner as in Example 1-1 except that Compound 25 was used instead of Compound 1.

Example 1-10

An organic light emitting device was manufactured in the same manner as in Example 1-1 except that Compound 26 was used instead of Compound 1.

Example 1-11

An organic light emitting device was manufactured in the same manner as in Example 1-1 except that Compound 27 was used instead of Compound 1.

Example 1-12

An organic light emitting device was manufactured in the same manner as in Example 1-1 except that Compound 28 was used instead of Compound 1.

Example 1-13

An organic light emitting device was manufactured in the same manner as in Example 1-1 except that Compound 29 was used instead of Compound 1.

Example 1-14

An organic light emitting device was manufactured in the same manner as in Example 1-1 except that Compound 30 was used instead of Compound 1.

Example 1-15

An organic light emitting device was manufactured in the same manner as in Example 1-1 except that Compound 47 was used instead of Compound 1.

Example 1-16

An organic light emitting device was manufactured in the same manner as in Example 1-1 except that Compound 48 was used instead of Compound 1.

Example 1-17

An organic light emitting device was manufactured in the same manner as in Example 1-1 except that Compound 49 was used instead of Compound 1.

Example 1-18

An organic light emitting device was manufactured in the same manner as in Example 1-1 except that Compound 50 was used instead of Compound 1.

Example 1-19

An organic light emitting device was manufactured in the same manner as in Example 1-1 except that Compound 51 was used instead of Compound 1.

Example 1-20

An organic light emitting device was manufactured in the same manner as in Example 1-1 except that Compound 52 was used instead of Compound 1.

Example 1-21

An organic light emitting device was manufactured in the same manner as in Example 1-1 except that Compound 53 was used instead of Compound 1.

Example 1-22

An organic light emitting device was manufactured in the same manner as in Example 1-1 except that Compound 70 was used instead of Compound 1.

Example 1-23

An organic light emitting device was manufactured in the same manner as in Example 1-1 except that Compound 71 was used instead of Compound 1.

Example 1-24

An organic light emitting device was manufactured in the same manner as in Example 1-1 except that Compound 72 was used instead of Compound 1.

Example 1-25

An organic light emitting device was manufactured in the same manner as in Example 1-1 except that Compound 73 was used instead of Compound 1.

Example 1-26

An organic light emitting device was manufactured in the same manner as in Example 1-1 except that Compound 74 was used instead of Compound 1.

Example 1-27

An organic light emitting device was manufactured in the same manner as in Example 1-1 except that Compound 75 was used instead of Compound 1.

Example 1-28

An organic light emitting device was manufactured in the same manner as in Example 1-1 except that Compound 76 was used instead of Compound 1.

Example 1-29

An organic light emitting device was manufactured in the same manner as in Example 1-1 except that Compound 93 was used instead of Compound 1.

Example 1-30

An organic light emitting device was manufactured in the same manner as in Example 1-1 except that Compound 94 was used instead of Compound 1.

Example 1-31

An organic light emitting device was manufactured in the same manner as in Example 1-1 except that Compound 95 was used instead of Compound 1.

Example 1-32

An organic light emitting device was manufactured in the same manner as in Example 1-1 except that Compound 99 was used instead of Compound 1.

Example 1-33

An organic light emitting device was manufactured in the same manner as in Example 1-1 except that Compound 100 was used instead of Compound 1.

Example 1-34

An organic light emitting device was manufactured in the same manner as in Example 1-1 except that Compound 101 was used instead of Compound 1.

Comparative Example 1-1

An organic light emitting device was manufactured in the same manner as in Example 1-1 except that the following Compound EB 1 (TCTA) was used instead of Compound 1.

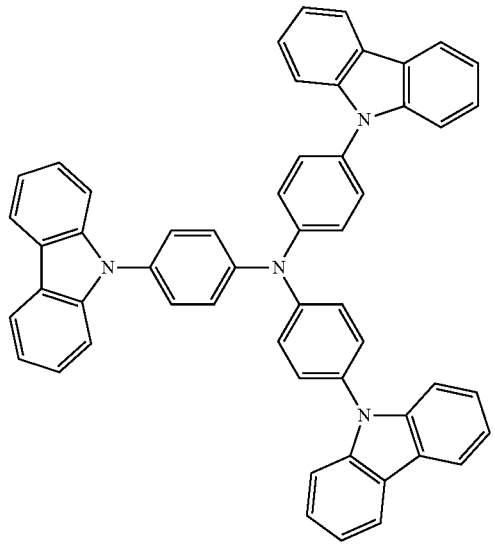

TCTA

Comparative Example 1-2

An organic light emitting device was manufactured in the same manner as in Example 1-1 except that the following Compound EB 2 was used instead of Compound 1.

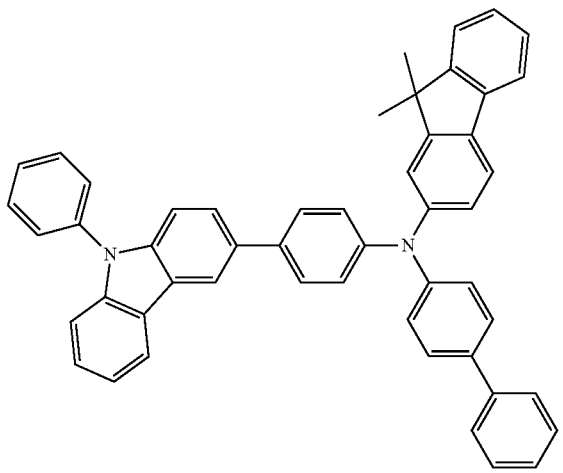

Comparative Example 1-3

An organic light emitting device was manufactured in the same manner as in Example 1-1 except that the following Compound EB 3 was used instead of Compound 1.

[EB 3]

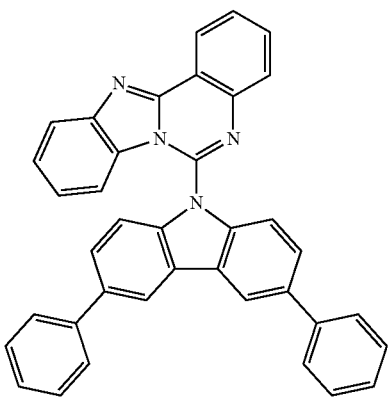

Comparative Example 1-4

An organic light emitting device was manufactured in the same manner as in Example 1-1 except that the following Compound EB 4 was used instead of Compound 1.

[EB 4]

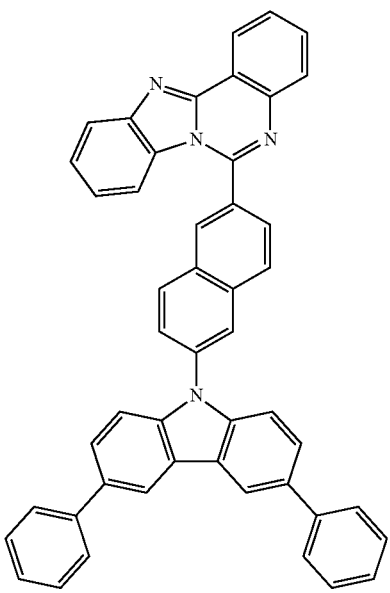

When a current was applied to the organic light emitting devices manufactured in Examples 1-1 to 1-34 and Comparative Examples 1-1 to 1-4, performance evaluation results were obtained as in the following Table 1.

TABLE 1

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 1 | 3.75 | 5.85 | (0.139, 0.122) |
| Example 1-2 | Compound 2 | 3.72 | 5.88 | (0.138, 0.126) |
| Example 1-3 | Compound 3 | 3.77 | 5.81 | (0.138, 0.127) |

TABLE 1-continued

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-4 | Compound 4 | 3.78 | 5.82 | (0.137, 0.125) |
| Example 1-5 | Compound 5 | 3.79 | 5.83 | (0.136, 0.125) |
| Example 1-6 | Compound 6 | 3.74 | 5.87 | (0.136, 0.127) |
| Example 1-7 | Compound 7 | 3.73 | 5.88 | (0.136, 0.125) |
| Example 1-8 | Compound 24 | 3.74 | 5.71 | (0.137, 0.125) |
| Example 1-9 | Compound 25 | 3.73 | 5.78 | (0.138, 0.125) |
| Example 1-10 | Compound 26 | 3.74 | 5.62 | (0.136, 0.125) |
| Example 1-11 | Compound 27 | 3.73 | 5.77 | (0.137, 0.125) |
| Example 1-12 | Compound 28 | 3.85 | 5.75 | (0.136, 0.125) |
| Example 1-13 | Compound 29 | 3.82 | 5.68 | (0.138, 0.126) |
| Example 1-14 | Compound 30 | 3.87 | 5.71 | (0.137, 0.125) |
| Example 1-15 | Compound 47 | 3.88 | 5.72 | (0.136, 0.127) |
| Example 1-16 | Compound 48 | 3.89 | 5.73 | (0.135, 0.127) |
| Example 1-17 | Compound 49 | 3.84 | 5.77 | (0.138, 0.127) |
| Example 1-18 | Compound 50 | 3.83 | 5.78 | (0.137, 0.125) |
| Example 1-19 | Compound 51 | 3.84 | 5.71 | (0.137, 0.125) |
| Example 1-20 | Compound 52 | 3.83 | 5.78 | (0.136, 0.127) |
| Example 1-21 | Compound 53 | 3.84 | 5.72 | (0.135, 0.127) |
| Example 1-22 | Compound 70 | 3.83 | 5.77 | (0.138, 0.127) |
| Example 1-23 | Compound 71 | 3.89 | 5.75 | (0.137, 0.125) |
| Example 1-24 | Compound 72 | 3.88 | 5.78 | (0.137, 0.125) |
| Example 1-25 | Compound 73 | 3.87 | 5.71 | (0.136, 0.125) |
| Example 1-26 | Compound 74 | 3.61 | 5.65 | (0.139, 0.122) |
| Example 1-27 | Compound 75 | 3.63 | 5.68 | (0.138, 0.126) |
| Example 1-28 | Compound 76 | 3.62 | 5.61 | (0.138, 0.127) |
| Example 1-29 | Compound 93 | 3.74 | 5.62 | (0.137, 0.125) |
| Example 1-30 | Compound 94 | 3.70 | 5.63 | (0.136, 0.125) |
| Example 1-31 | Compound 95 | 3.75 | 5.67 | (0.136, 0.127) |
| Example 1-32 | Compound 99 | 3.80 | 5.58 | (0.136, 0.125) |
| Example 1-33 | Compound 100 | 3.84 | 5.51 | (0.137, 0.125) |
| Example 1-34 | Compound 101 | 3.82 | 5.54 | (0.138, 0.125) |
| Comparative Example 1-1 | EB1 | 4.37 | 4.68 | (0.138, 0.125) |
| Comparative Example 1-2 | EB2 | 4.15 | 4.85 | (0.138, 0.125) |
| Comparative Example 1-3 | EB3 | 4.63 | 4.32 | (0.138, 0.126) |
| Comparative Example 1-4 | EB4 | 4.52 | 4.41 | (0.138, 0.125) |

As shown in Table 1, it was seen that the organic light emitting devices formed with the compounds of Examples 1-1 to 1-34 exhibited low voltage and high efficiency properties compared to TCTA often used as an electron blocking layer (Comparative Example 1-1), Comparative Example 1-2, Comparative Example 1-3 in which -L-Ar is a phenyl group, and Comparative Example 1-4 in which naphthalene is linked between imidazoquinazoline and carbazole as a linker. Particularly, it was seen that the organic light emitting devices using Compounds 1 to 7 prepared from Compound A had most superior low voltage and high efficiency properties.

Accordingly, it was identified that compound derivatives of the chemical formulae according to the present application had an excellent electron blocking ability exhibiting low voltage and high efficiency properties, and was capable of being used in an organic light emitting device.

Example 2

Example 2-1 to Example 2-34

Experiments were carried out in the same manner as in Example 1 except that TCTA was used as the electron blocking layer, and compounds of Examples 1-1 to 1-34 were used as the hole transfer layer instead of NPB.

Comparative Example 2-1

An experiment was carried out in the same manner as in Example 1 except that TCTA was used as the electron blocking layer, and HT 1 (NPB) was used as the hole transfer layer.

Comparative Example 2-2

An experiment was carried out in the same manner as in Example 1 except that TCTA was used as the electron blocking layer, and HT 2 was used as the hole transfer layer.

[HT 2]

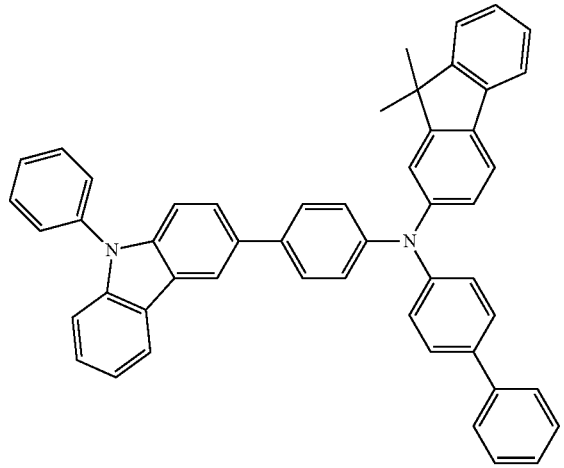

Comparative Example 2-3

An experiment was carried out in the same manner as in Example 1 except that TCTA was used as the electron blocking layer, and HT 3 was used as the hole transfer layer.

[HT 3]

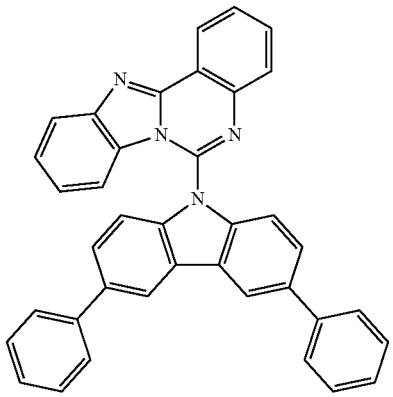

Comparative Example 2-4

An experiment was carried out in the same manner as in Example 1 except that TCTA was used as the electron blocking layer, and HT 4 was used as the hole transfer layer.

[HT 4]

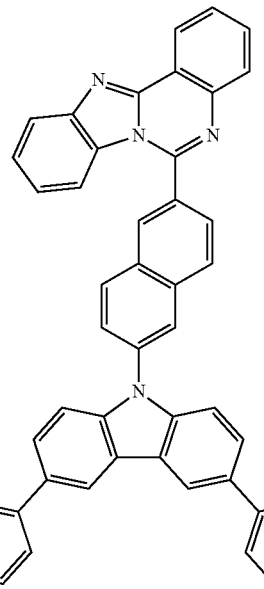

When a current was applied to the organic light emitting devices manufactured in Examples 2-1 to 2-25 and Comparative Examples 2-1 to 2-4, performance evaluation results were obtained as in the following Table 2.

TABLE 2

| | Compound (Hole Transfer Layer) | Voltage (V@10 mA/ $cm^2$) | Efficiency (cd/A@10 mA/$cm^2$) | Color Coordinate (x, y) |
|---|---|---|---|---|
| Example 2-1 | Compound 1 | 4.35 | 5.95 | (0.139, 0.122) |
| Example 2-2 | Compound 2 | 4.32 | 5.98 | (0.138, 0.126) |
| Example 2-3 | Compound 3 | 4.37 | 5.91 | (0.138, 0.127) |

TABLE 2-continued

| | Compound (Hole Transfer Layer) | Voltage (V@10 mA/cm²) | Efficiency (cd/A@10 mA/cm²) | Color Coordinate (x, y) |
|---|---|---|---|---|
| Example 2-4 | Compound 4 | 4.38 | 5.92 | (0.137, 0.125) |
| Example 2-5 | Compound 5 | 4.39 | 5.93 | (0.136, 0.125) |
| Example 2-6 | Compound 6 | 4.34 | 5.97 | (0.136, 0.127) |
| Example 2-7 | Compound 7 | 4.33 | 5.98 | (0.136, 0.125) |
| Example 2-8 | Compound 24 | 4.34 | 5.91 | (0.137, 0.125) |
| Example 2-9 | Compound 25 | 4.33 | 5.98 | (0.138, 0.125) |
| Example 2-10 | Compound 26 | 4.34 | 5.92 | (0.136, 0.125) |
| Example 2-11 | Compound 27 | 4.33 | 5.97 | (0.137, 0.125) |
| Example 2-12 | Compound 28 | 4.45 | 5.85 | (0.136, 0.125) |
| Example 2-13 | Compound 29 | 4.42 | 5.88 | (0.138, 0.126) |
| Example 2-14 | Compound 30 | 4.47 | 5.81 | (0.137, 0.125) |
| Example 2-15 | Compound 47 | 4.48 | 5.82 | (0.136, 0.127) |
| Example 2-16 | Compound 48 | 4.49 | 5.83 | (0.135, 0.127) |
| Example 2-17 | Compound 49 | 4.44 | 5.87 | (0.138, 0.127) |
| Example 2-18 | Compound 50 | 4.43 | 5.88 | (0.137, 0.125) |
| Example 2-19 | Compound 51 | 4.44 | 5.81 | (0.137, 0.125) |
| Example 2-20 | Compound 52 | 4.43 | 5.88 | (0.136, 0.127) |
| Example 2-21 | Compound 53 | 4.44 | 5.82 | (0.135, 0.127) |
| Example 2-22 | Compound 70 | 4.43 | 5.87 | (0.138, 0.127) |
| Example 2-23 | Compound 71 | 4.59 | 5.75 | (0.137, 0.125) |
| Example 2-24 | Compound 72 | 4.48 | 5.88 | (0.137, 0.125) |
| Example 2-25 | Compound 73 | 4.37 | 5.94 | (0.136, 0.125) |
| Example 2-26 | Compound 74 | 4.35 | 5.95 | (0.139, 0.122) |
| Example 2-27 | Compound 75 | 4.32 | 5.98 | (0.138, 0.126) |
| Example 2-28 | Compound 76 | 4.37 | 5.91 | (0.138, 0.127) |
| Example 2-29 | Compound 93 | 4.58 | 5.82 | (0.137, 0.125) |
| Example 2-30 | Compound 94 | 4.59 | 5.83 | (0.136, 0.125) |
| Example 2-31 | Compound 95 | 4.54 | 5.87 | (0.136, 0.127) |
| Example 2-32 | Compound 99 | 4.53 | 5.88 | (0.136, 0.125) |
| Example 2-33 | Compound 100 | 4.54 | 5.81 | (0.137, 0.125) |
| Example 2-34 | Compound 101 | 4.53 | 5.88 | (0.138, 0.125) |
| Comparative Example 2-1 | HT1 | 5.85 | 4.12 | (0.136, 0.125) |
| Comparative Example 2-2 | HT2 | 5.63 | 4.37 | (0.137, 0.125) |
| Comparative Example 2-3 | HT3 | 5.72 | 4.25 | (0.136, 0.126) |
| Comparative Example 2-4 | HT4 | 5.56 | 4.43 | (0.137, 0.126) |

As shown in Table 2, it was seen that the organic light emitting devices formed with the compounds of Examples 2-1 to 2-34 exhibited low voltage and high efficiency properties compared to NPB often used as a hole transfer layer (Comparative Example 2-1), Comparative Example 2-2, Comparative Example 2-3 in which -L-Ar is a phenyl group, and Comparative Example 2-4 in which naphthalene is linked between imidazoquinazoline and carbazole as a linker. Particularly, it was seen that the organic light emitting devices using Compounds 1 to 7 prepared from Compound A had most superior low voltage and high efficiency properties.

Accordingly, it was identified that compound derivatives of the chemical formulae according to the present application had an excellent hole transfer ability as well as an excellent electron blocking ability exhibiting low voltage and high efficiency properties, and was capable of being used in an organic light emitting device.

Example 3-1

The compounds synthesized in the synthesis examples were high-purity sublimation purified using commonly known methods, and then a green organic light emitting device was manufactured using a method as follows.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic EL device was manufactured by forming a light emitting device in the order of m-MTDATA (60 nm)/TCTA (80 nm)/Compound 5+10% Ir(ppy)₃ (300 nm)/BCP (10 nm)/Alq₃ (30 nm)/LiF (1 nm)/Al (200 nm) on the transparent ITO electrode prepared as above using Compound 5 as a host.

Structures of the m-MTDATA, the TCTA, the Ir(ppy)₃ and the BCP are each as follows.

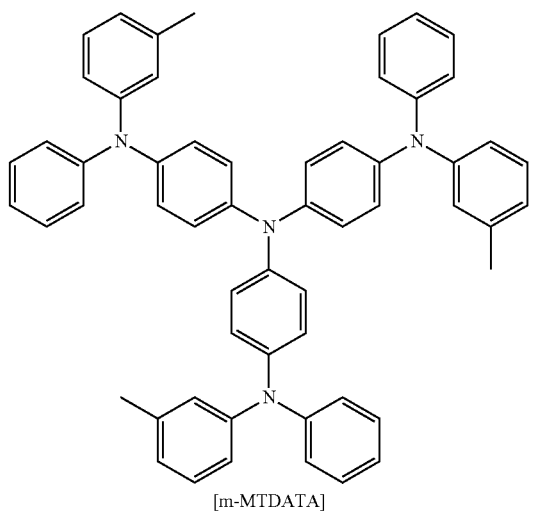

[m-MTDATA]

-continued

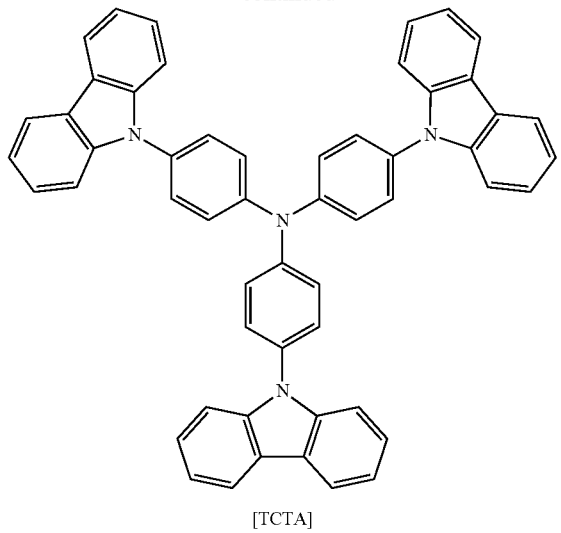

[TCTA]

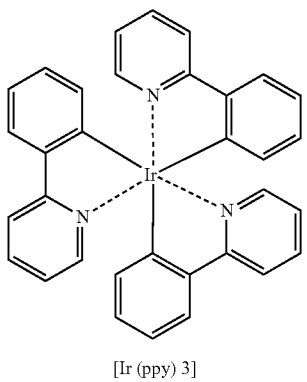

[Ir(ppy)3]

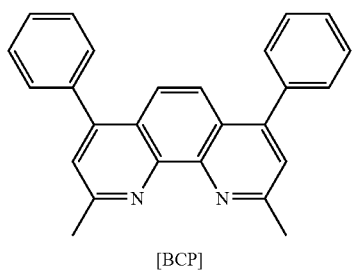

[BCP]

[Compound 5]

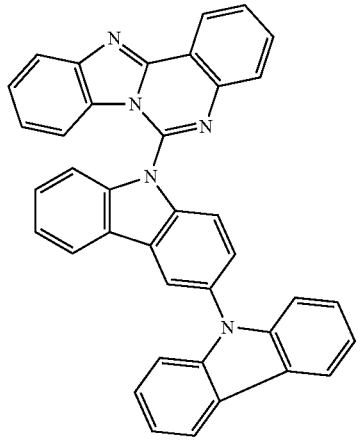

Example 3-2

An organic light emitting device was manufactured in the same manner as in Example 3-1 except that Compound 6 was used instead of Compound 5.

Example 3-3

An organic light emitting device was manufactured in the same manner as in Example 3-1 except that Compound 7 was used instead of Compound 5.

Example 3-4

An organic light emitting device was manufactured in the same manner as in Example 3-1 except that Compound 8 was used instead of Compound 5.

Example 3-5

An organic light emitting device was manufactured in the same manner as in Example 3-1 except that Compound 9 was used instead of Compound 5.

Example 3-6

An organic light emitting device was manufactured in the same manner as in Example 3-1 except that Compound 10 was used instead of Compound 5.

Example 3-7

An organic light emitting device was manufactured in the same manner as in Example 3-1 except that Compound 11 was used instead of Compound 5.

Example 3-8

An organic light emitting device was manufactured in the same manner as in Example 3-1 except that Compound 12 was used instead of Compound 5.

Example 3-9

An organic light emitting device was manufactured in the same manner as in Example 3-1 except that Compound 13 was used instead of Compound 5.

Example 3-10

An organic light emitting device was manufactured in the same manner as in Example 3-1 except that Compound 14 was used instead of Compound 5.

Example 3-11

An organic light emitting device was manufactured in the same manner as in Example 3-1 except that Compound 15 was used instead of Compound 5.

Example 3-12

An organic light emitting device was manufactured in the same manner as in Example 3-1 except that Compound 28 was used instead of Compound 5.

Example 3-13

An organic light emitting device was manufactured in the same manner as in Example 3-1 except that Compound 29 was used instead of Compound 5.

Example 3-14

An organic light emitting device was manufactured in the same manner as in Example 3-1 except that Compound 30 was used instead of Compound 5.

Example 3-15

An organic light emitting device was manufactured in the same manner as in Example 3-1 except that Compound 31 was used instead of Compound 5.

Example 3-16

An organic light emitting device was manufactured in the same manner as in Example 3-1 except that Compound 32 was used instead of Compound 5.

Example 3-17

An organic light emitting device was manufactured in the same manner as in Example 3-1 except that Compound 33 was used instead of Compound 5.

Example 3-18

An organic light emitting device was manufactured in the same manner as in Example 3-1 except that Compound 34 was used instead of Compound 5.

Example 3-19

An organic light emitting device was manufactured in the same manner as in Example 3-1 except that Compound 35 was used instead of Compound 5.

Example 3-20

An organic light emitting device was manufactured in the same manner as in Example 3-1 except that Compound 36 was used instead of Compound 5.

Example 3-21

An organic light emitting device was manufactured in the same manner as in Example 3-1 except that Compound 37 was used instead of Compound 5.

Example 3-22

An organic light emitting device was manufactured in the same manner as in Example 3-1 except that Compound 38 was used instead of Compound 5.

Example 3-23

An organic light emitting device was manufactured in the same manner as in Example 3-1 except that Compound 51 was used instead of Compound 5.

Example 3-24

An organic light emitting device was manufactured in the same manner as in Example 3-1 except that Compound 52 was used instead of Compound 5.

Example 3-25

An organic light emitting device was manufactured in the same manner as in Example 3-1 except that Compound 53 was used instead of Compound 5.

Example 3-26

An organic light emitting device was manufactured in the same manner as in Example 3-1 except that Compound 54 was used instead of Compound 5.

Example 3-27

An organic light emitting device was manufactured in the same manner as in Example 3-1 except that Compound 55 was used instead of Compound 5.

Example 3-28

An organic light emitting device was manufactured in the same manner as in Example 3-1 except that Compound 56 was used instead of Compound 5.

Example 3-29

An organic light emitting device was manufactured in the same manner as in Example 3-1 except that Compound 57 was used instead of Compound 5.

Example 3-30

An organic light emitting device was manufactured in the same manner as in Example 3-1 except that Compound 58 was used instead of Compound 5.

Example 3-31

An organic light emitting device was manufactured in the same manner as in Example 3-1 except that Compound 59 was used instead of Compound 5.

Example 3-32

An organic light emitting device was manufactured in the same manner as in Example 3-1 except that Compound 60 was used instead of Compound 5.

Example 3-33

An organic light emitting device was manufactured in the same manner as in Example 3-1 except that Compound 61 was used instead of Compound 5.

Example 3-34

An organic light emitting device was manufactured in the same manner as in Example 3-1 except that Compound 74 was used instead of Compound 5.

Example 3-35

An organic light emitting device was manufactured in the same manner as in Example 3-1 except that Compound 75 was used instead of Compound 5.

Example 3-36

An organic light emitting device was manufactured in the same manner as in Example 3-1 except that Compound 76 was used instead of Compound 5.

Example 3-37

An organic light emitting device was manufactured in the same manner as in Example 3-1 except that Compound 77 was used instead of Compound 5.

Example 3-38

An organic light emitting device was manufactured in the same manner as in Example 3-1 except that Compound 78 was used instead of Compound 5.

Example 3-39

An organic light emitting device was manufactured in the same manner as in Example 3-1 except that Compound 79 was used instead of Compound 5.

Example 3-40

An organic light emitting device was manufactured in the same manner as in Example 3-1 except that Compound 80 was used instead of Compound 5.

Example 3-41

An organic light emitting device was manufactured in the same manner as in Example 3-1 except that Compound 81 was used instead of Compound 5.

Example 3-42

An organic light emitting device was manufactured in the same manner as in Example 3-1 except that Compound 82 was used instead of Compound 5.

Example 3-43

An organic light emitting device was manufactured in the same manner as in Example 3-1 except that Compound 83 was used instead of Compound 5.

Example 3-44

An organic light emitting device was manufactured in the same manner as in Example 3-1 except that Compound 84 was used instead of Compound 5.

Comparative Example 3-1

An organic light emitting device was manufactured in the same manner as in Example 3-1 except that GH 1 (CBP) was used instead of Compound 5.

[GH 1]

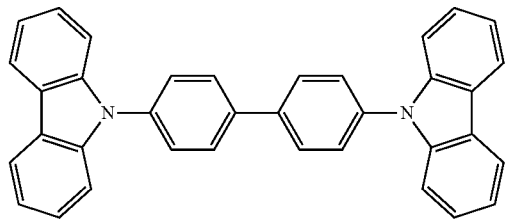

When a current was applied to the organic light emitting devices manufactured in Examples 3-1 to 3-44 and Comparative Example 3-1 (CBP), performance evaluation results were obtained as in the following Table 3.

TABLE 3

| | Compound (Host) | Voltage (V@10 mA/ cm$^2$) | Efficiency (cd/A@10 mA/cm$^2$) | EL Peak (nm) |
|---|---|---|---|---|
| Example 3-1 | Compound 5 | 6.88 | 41.93 | 517 |
| Example 3-2 | Compound 6 | 6.96 | 42.24 | 516 |
| Example 3-3 | Compound 7 | 6.85 | 41.79 | 518 |
| Example 3-4 | Compound 8 | 6.19 | 46.15 | 517 |
| Example 3-5 | Compound 9 | 6.28 | 44.31 | 515 |
| Example 3-6 | Compound 10 | 6.23 | 45.63 | 516 |
| Example 3-7 | Compound 11 | 6.29 | 45.62 | 516 |
| Example 3-8 | Compound 12 | 6.17 | 46.64 | 517 |
| Example 3-9 | Compound 13 | 6.14 | 46.68 | 518 |
| Example 3-10 | Compound 14 | 6.48 | 44.83 | 517 |
| Example 3-11 | Compound 15 | 6.46 | 45.24 | 516 |
| Example 3-12 | Compound 28 | 6.84 | 41.94 | 518 |
| Example 3-13 | Compound 29 | 6.95 | 42.22 | 517 |
| Example 3-14 | Compound 30 | 6.83 | 41.75 | 515 |
| Example 3-15 | Compound 31 | 6.15 | 46.16 | 516 |
| Example 3-16 | Compound 32 | 6.24 | 44.34 | 516 |
| Example 3-17 | Compound 33 | 6.25 | 45.62 | 517 |
| Example 3-18 | Compound 34 | 6.27 | 45.64 | 518 |
| Example 3-19 | Compound 35 | 6.15 | 46.66 | 517 |
| Example 3-20 | Compound 36 | 6.13 | 46.67 | 516 |
| Example 3-21 | Compound 37 | 6.42 | 44.41 | 518 |
| Example 3-22 | Compound 38 | 6.47 | 45.55 | 517 |
| Example 3-23 | Compound 51 | 6.82 | 41.74 | 515 |
| Example 3-24 | Compound 52 | 6.94 | 42.62 | 516 |
| Example 3-25 | Compound 53 | 6.81 | 41.55 | 516 |
| Example 3-26 | Compound 54 | 6.18 | 46.16 | 517 |
| Example 3-27 | Compound 55 | 6.27 | 44.94 | 518 |
| Example 3-28 | Compound 56 | 6.23 | 45.32 | 517 |
| Example 3-29 | Compound 57 | 6.24 | 45.14 | 516 |
| Example 3-30 | Compound 58 | 6.11 | 46.46 | 518 |
| Example 3-31 | Compound 59 | 6.16 | 46.37 | 517 |
| Example 3-32 | Compound 60 | 6.45 | 44.71 | 515 |
| Example 3-33 | Compound 61 | 6.44 | 45.65 | 516 |
| Example 3-34 | Compound 74 | 6.85 | 41.44 | 516 |
| Example 3-35 | Compound 75 | 6.9 | 42.82 | 517 |
| Example 3-36 | Compound 76 | 6.81 | 41.65 | 518 |
| Example 3-37 | Compound 77 | 6.16 | 46.46 | 518 |
| Example 3-38 | Compound 78 | 6.24 | 44.54 | 517 |
| Example 3-39 | Compound 79 | 6.28 | 45.32 | 515 |
| Example 3-40 | Compound 80 | 6.24 | 45.44 | 516 |
| Example 3-41 | Compound 81 | 6.16 | 46.16 | 516 |
| Example 3-42 | Compound 82 | 6.15 | 46.67 | 517 |
| Example 3-43 | Compound 83 | 6.41 | 44.71 | 518 |
| Example 3-44 | Compound 84 | 6.43 | 45.55 | 518 |
| Comparative Example 3-1 | GH 1 (CBP) | 7.27 | 32.52 | 517 |

As shown in Table 3, it was identified that the organic light emitting devices of Examples 3-1 to 3-44 using the compounds according to one embodiment of the present application as a green host material of a light emitting layer exhibited superior performance in terms of current efficiency and driving voltage compared to the organic light emitting device of Comparative Example 3-1 using existing CBP.

Example 4-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

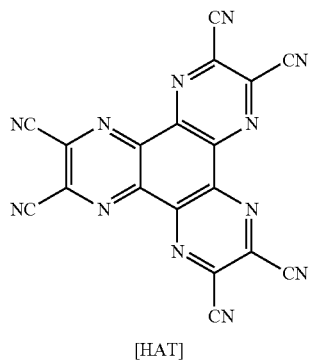

[HAT]

A hole transfer layer was formed on the hole injection layer by vacuum depositing the following compound 4-4'-bis[N-(1-naphthyl)-N-phenylamino]biphenyl (NPB) (400 Å), a material transferring holes.

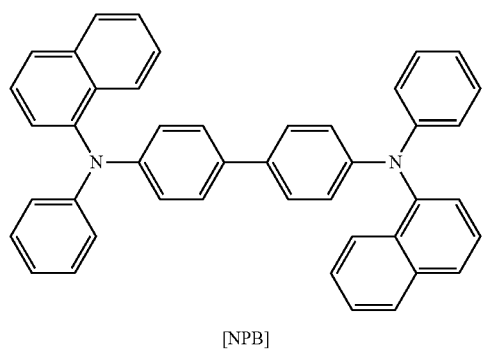

[NPB]

Subsequently, a light emitting layer was formed on the hole transfer layer to a film thickness of 300 Å by vacuum depositing BH and BD as follows in a weight ratio of 25:1.

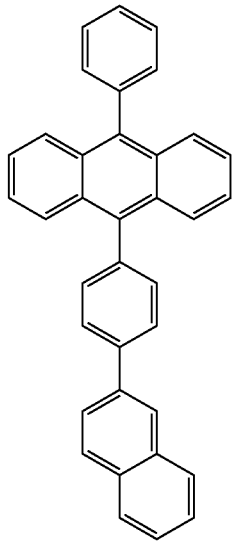

[BH]

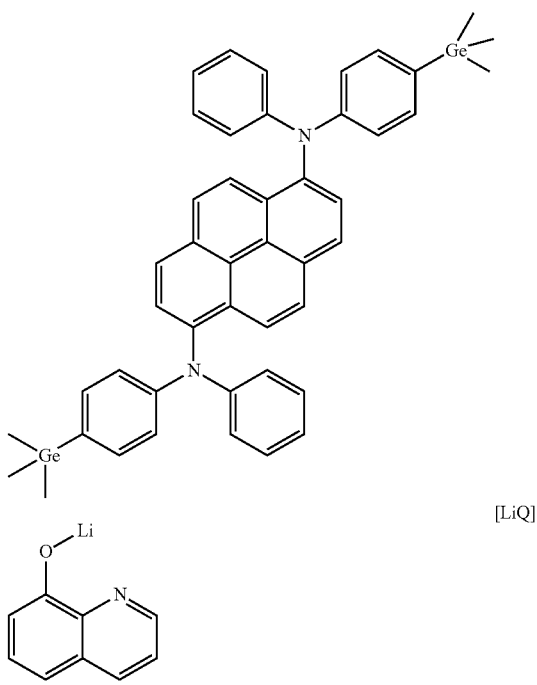

[BD]

[LiQ]

On the light emitting layer, an electron injection and transfer layer was formed to a thickness of 300 Å by vacuum depositing Compound 8 prepared in Preparation Example 8 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 4-2

An experiment was carried out in the same manner as in Example 4-1 except that Compound 9 was used instead of Compound 8 as the electron transfer layer.

Example 4-3

An experiment was carried out in the same manner as in Example 4 except that Compound 10 was used instead of Compound 8 as the electron transfer layer.

Example 4-4

An experiment was carried out in the same manner as in Example 4 except that Compound 11 was used instead of Compound 8 as the electron transfer layer.

Example 4-5

An experiment was carried out in the same manner as in Example 4 except that Compound 12 was used instead of Compound 8 as the electron transfer layer.

Example 4-6

An experiment was carried out in the same manner as in Example 4 except that Compound 13 was used instead of Compound 8 as the electron transfer layer.

Example 4-7

An experiment was carried out in the same manner as in Example 4 except that Compound 14 was used instead of Compound 8 as the electron transfer layer.

Example 4-8

An experiment was carried out in the same manner as in Example 4 except that Compound 15 was used instead of Compound 8 as the electron transfer layer.

Example 4-9

An experiment was carried out in the same manner as in Example 4 except that Compound 16 was used instead of Compound 8 as the electron transfer layer.

Example 4-10

An experiment was carried out in the same manner as in Example 4 except that Compound 17 was used instead of Compound 8 as the electron transfer layer.

Example 4-11

An experiment was carried out in the same manner as in Example 4 except that Compound 19 was used instead of Compound 8 as the electron transfer layer.

Example 4-12

An experiment was carried out in the same manner as in Example 4 except that Compound 20 was used instead of Compound 8 as the electron transfer layer.

Example 4-13

An experiment was carried out in the same manner as in Example 4 except that Compound 21 was used instead of Compound 8 as the electron transfer layer.

Example 4-14

An experiment was carried out in the same manner as in Example 4 except that Compound 22 was used instead of Compound 8 as the electron transfer layer.

Example 4-15

An experiment was carried out in the same manner as in Example 4 except that Compound 23 was used instead of Compound 8 as the electron transfer layer.

Example 4-16

An experiment was carried out in the same manner as in Example 4 except that Compound 31 was used instead of Compound 8 as the electron transfer layer.

Example 4-17

An experiment was carried out in the same manner as in Example 4 except that Compound 35 was used instead of Compound 8 as the electron transfer layer.

Example 4-18

An experiment was carried out in the same manner as in Example 4 except that Compound 40 was used instead of Compound 8 as the electron transfer layer.

Example 4-19

An experiment was carried out in the same manner as in Example 4 except that Compound 42 was used instead of Compound 8 as the electron transfer layer.

Example 4-20

An experiment was carried out in the same manner as in Example 4 except that Compound 43 was used instead of Compound 8 as the electron transfer layer.

Example 4-21

An experiment was carried out in the same manner as in Example 4 except that Compound 44 was used instead of Compound 8 as the electron transfer layer.

Example 4-22

An experiment was carried out in the same manner as in Example 4 except that Compound 45 was used instead of Compound 8 as the electron transfer layer.

Example 4-23

An experiment was carried out in the same manner as in Example 4 except that Compound 46 was used instead of Compound 8 as the electron transfer layer.

Example 4-24

An experiment was carried out in the same manner as in Example 4 except that Compound 54 was used instead of Compound 8 as the electron transfer layer.

Example 4-25

An experiment was carried out in the same manner as in Example 4 except that Compound 58 was used instead of Compound 8 as the electron transfer layer.

Example 4-26

An experiment was carried out in the same manner as in Example 4 except that Compound 63 was used instead of Compound 8 as the electron transfer layer.

Example 4-27

An experiment was carried out in the same manner as in Example 4 except that Compound 65 was used instead of Compound 8 as the electron transfer layer.

Example 4-28

An experiment was carried out in the same manner as in Example 4 except that Compound 66 was used instead of Compound 8 as the electron transfer layer.

Example 4-29

An experiment was carried out in the same manner as in Example 4 except that Compound 67 was used instead of Compound 8 as the electron transfer layer.

Example 4-30

An experiment was carried out in the same manner as in Example 4 except that Compound 68 was used instead of Compound 8 as the electron transfer layer.

Example 4-31

An experiment was carried out in the same manner as in Example 4 except that Compound 69 was used instead of Compound 8 as the electron transfer layer.

Example 4-32

An experiment was carried out in the same manner as in Example 4 except that Compound 77 was used instead of Compound 8 as the electron transfer layer.

Example 4-33

An experiment was carried out in the same manner as in Example 4 except that Compound 81 was used instead of Compound 8 as the electron transfer layer.

Example 4-34

An experiment was carried out in the same manner as in Example 4 except that Compound 84 was used instead of Compound 8 as the electron transfer layer.

Example 4-35

An experiment was carried out in the same manner as in Example 4 except that Compound 85 was used instead of Compound 8 as the electron transfer layer.

Example 4-36

An experiment was carried out in the same manner as in Example 4 except that Compound 86 was used instead of Compound 8 as the electron transfer layer.

Example 4-37

An experiment was carried out in the same manner as in Example 4 except that Compound 88 was used instead of Compound 8 as the electron transfer layer.

Example 4-38

An experiment was carried out in the same manner as in Example 4 except that Compound 89 was used instead of Compound 8 as the electron transfer layer.

Example 4-39

An experiment was carried out in the same manner as in Example 4 except that Compound 90 was used instead of Compound 8 as the electron transfer layer.

Example 4-40

An experiment was carried out in the same manner as in Example 4 except that Compound 91 was used instead of Compound 8 as the electron transfer layer.

Example 4-41

An experiment was carried out in the same manner as in Example 4 except that Compound 92 was used instead of Compound 8 as the electron transfer layer.

Example 4-42

An experiment was carried out in the same manner as in Example 4 except that Compound 94 was used instead of Compound 8 as the electron transfer layer.

Example 4-43

An experiment was carried out in the same manner as in Example 4 except that Compound 98 was used instead of Compound 8 as the electron transfer layer.

Example 4-44

An experiment was carried out in the same manner as in Example 4 except that Compound 100 was used instead of Compound 8 as the electron transfer layer.

Example 4-45

An experiment was carried out in the same manner as in Example 4 except that Compound 104 was used instead of Compound 8 as the electron transfer layer.

Comparative Example 4-1

An experiment was carried out in the same manner as in Example 1 except that the following Compound ET 1 was used instead of Compound 8 as the electron transfer layer.

[ET 1]

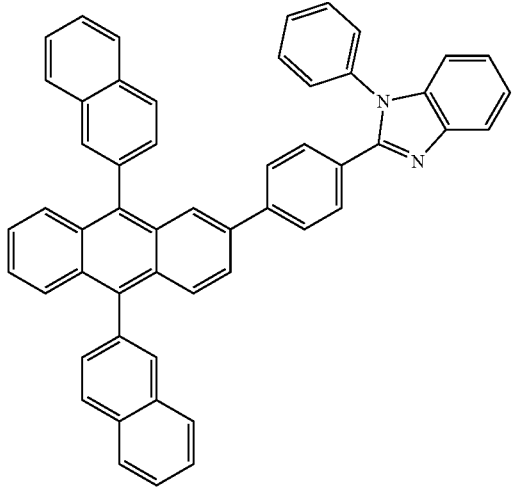

Comparative Example 4-2

An experiment was carried out in the same manner as in Example 1 except that the following Compound ET 2 was used instead of Compound 8 as the electron transfer layer.

[ET 2]

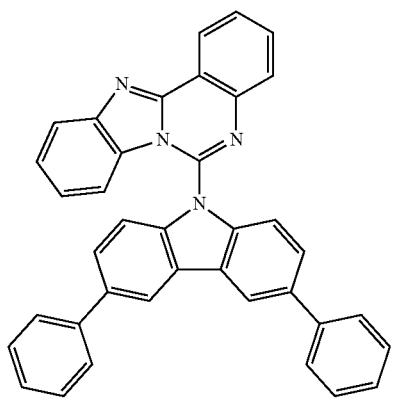

When a current was applied to the organic light emitting devices manufactured in Examples 4-1 to 4-44 and Comparative Examples 4-1 and 4-2, results of Table 4 were obtained.

TABLE 4

| | Compound (Electron Transfer Layer) | Voltage (V@10 mA/ $cm^2$) | Efficiency (cd/A@10 mA/$cm^2$) | EL Peak (nm) |
|---|---|---|---|---|
| Example 4-1 | Compound 8 | 6.88 | 41.93 | 517 |
| Example 4-2 | Compound 9 | 6.96 | 42.24 | 516 |
| Example 4-3 | Compound 10 | 6.85 | 41.79 | 518 |
| Example 4-4 | Compound 11 | 6.19 | 46.15 | 517 |
| Example 4-5 | Compound 12 | 6.28 | 44.31 | 515 |
| Example 4-6 | Compound 13 | 6.23 | 45.63 | 516 |
| Example 4-7 | Compound 14 | 6.29 | 45.62 | 516 |
| Example 4-8 | Compound 15 | 6.17 | 46.64 | 517 |
| Example 4-9 | Compound 17 | 6.14 | 46.68 | 518 |
| Example 4-10 | Compound 19 | 6.48 | 44.83 | 517 |
| Example 4-11 | Compound 20 | 6.46 | 45.24 | 516 |

TABLE 4-continued

| | Compound (Electron Transfer Layer) | Voltage (V@10 mA/ $cm^2$) | Efficiency (cd/A@10 mA/$cm^2$) | EL Peak (nm) |
|---|---|---|---|---|
| Example 4-12 | Compound 21 | 6.84 | 41.94 | 518 |
| Example 4-13 | Compound 22 | 6.95 | 42.22 | 517 |
| Example 4-14 | Compound 23 | 6.83 | 41.75 | 515 |
| Example 4-15 | Compound 31 | 6.15 | 46.16 | 516 |
| Example 4-16 | Compound 35 | 6.24 | 44.34 | 516 |
| Example 4-17 | Compound 40 | 6.25 | 45.62 | 517 |
| Example 4-18 | Compound 42 | 6.27 | 45.64 | 518 |
| Example 4-19 | Compound 43 | 6.15 | 46.66 | 517 |
| Example 4-20 | Compound 44 | 6.13 | 46.67 | 516 |
| Example 4-21 | Compound 45 | 6.42 | 44.41 | 518 |
| Example 4-22 | Compound 46 | 6.47 | 45.55 | 517 |
| Example 4-23 | Compound 54 | 6.82 | 41.74 | 515 |
| Example 4-24 | Compound 58 | 6.94 | 42.62 | 516 |
| Example 4-25 | Compound 63 | 6.81 | 41.55 | 516 |
| Example 4-26 | Compound 65 | 6.18 | 46.16 | 517 |
| Example 4-27 | Compound 66 | 6.27 | 44.94 | 518 |
| Example 4-28 | Compound 67 | 6.23 | 45.32 | 517 |
| Example 4-29 | Compound 68 | 6.24 | 45.14 | 516 |
| Example 4-30 | Compound 69 | 6.11 | 46.46 | 518 |
| Example 4-31 | Compound 77 | 6.16 | 46.37 | 517 |
| Example 4-32 | Compound 81 | 6.45 | 44.71 | 515 |
| Example 4-33 | Compound 84 | 6.44 | 45.65 | 516 |
| Example 4-34 | Compound 85 | 6.85 | 41.44 | 516 |
| Example 4-35 | Compound 86 | 6.9 | 42.82 | 517 |
| Example 4-36 | Compound 88 | 6.81 | 41.65 | 518 |
| Example 4-37 | Compound 89 | 6.16 | 46.46 | 518 |
| Example 4-38 | Compound 90 | 6.24 | 44.54 | 517 |
| Example 4-39 | Compound 91 | 6.28 | 45.32 | 515 |
| Example 4-40 | Compound 92 | 6.24 | 45.44 | 516 |
| Example 4-41 | Compound 94 | 6.16 | 46.16 | 516 |
| Example 4-42 | Compound 98 | 6.15 | 46.67 | 517 |
| Example 4-43 | Compound 100 | 6.41 | 44.71 | 518 |
| Example 4-44 | Compound 104 | 6.43 | 45.55 | 518 |
| Comparative Example 4-1 | ET 1 | 7.27 | 32.52 | 517 |
| Comparative Example 4-2 | ET 2 | 7.45 | 30.16 | 517 |

As shown in Table 4, it was identified that the compounds according to one embodiment of the present application had excellent electron transfer and injection abilities and was able to be used in an organic light emitting device.

Hereinbefore, preferred embodiments of the present application (electron blocking layer, hole transfer layer, green light emitting layer, red light emitting layer and electron injection layer) have been described, however, the present application is not limited thereto, and various modifications may be made within the scope of the claims and the detailed descriptions of the disclosure, and the modifications are also included in the scope of the present application.

The invention claimed is:

1. A compound represented by the following Chemical Formula 1, 2, or 3:

[Chemical Formula 1]

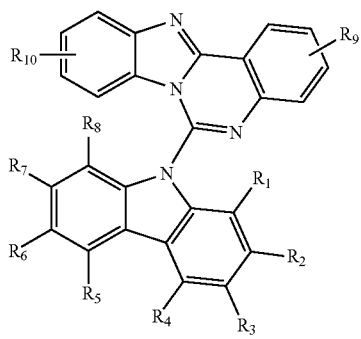

[Chemical Formula 2]

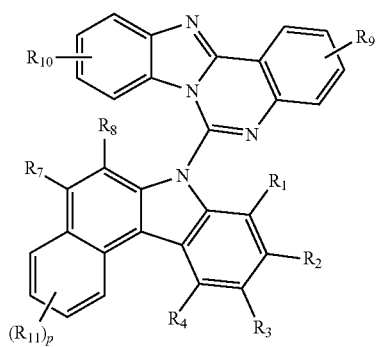

[Chemical Formula 3]

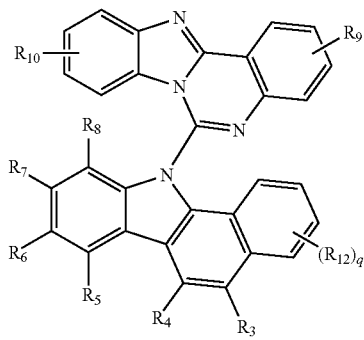

wherein, in Chemical Formula 1, 2, or 3,
one or two of $R_1$ to $R_8$ is $-(L)_m-(Ar)_n$, and the rest are hydrogen,
L is a direct bond or a phenylene group,
m is an integer of 1 to 3,
when m is an integer of 2 or greater, a plurality of Ls are the same as or different from each other,
Ar is a phenyl group substituted with at least one selected from the group consisting of a C1 to C20 alkyl group and a C6 to C20 aryl group; a substituted or unsubstituted multicyclic aryl group selected from naphthalene or fluorene; a substituted or unsubstituted heterocyclic group selected from carbazole, triazine, pyrimidine, pyridine, dibenzofuran, dibenzothiophene, benzimidazole, benzothiazole, or benzoxazole; a substituted or unsubstituted aryl amine group; or a substituted or unsubstituted phosphoryl group,
n is 1 or 2, and when n is 2, a plurality of Ars are the same as or different from each other,
$R_9$ and $R_{10}$ are hydrogen,
$R_{11}$ and $R_{12}$ are the same as or different from each other, and each independently hydrogen; deuterium; a halogen group; a nitro group; a cyano group; an ester group; a carbonyl group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; or a substituted or unsubstituted heterocyclic group, and
p and q are each an integer of 0 to 4.

2. The compound of claim 1, wherein $R_3$ is $-(L)_m-(Ar)_n$.

3. The compound of claim 1, wherein $R_2$ is $-(L)_m-(Ar)_n$.

4. The compound of claim 1, wherein $R_3$ and $R_6$ are $-(L)_m-(Ar)_n$, and $R_3$ and $R_6$ are the same as or different from each other.

5. The compound of claim 1, wherein $R_2$ and $R_7$ are $-(L)_m-(Ar)_n$, and R2 and R7 are the same as or different from each other.

6. The compound of claim 1, wherein the compound represented by Chemical Formula 1 is any one selected from among the following structural formulae:

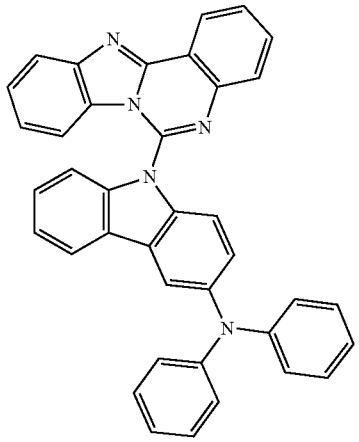

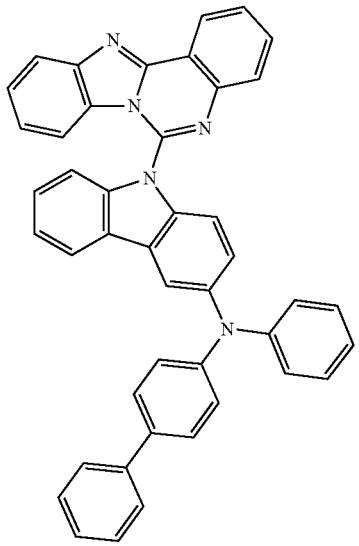

345
-continued
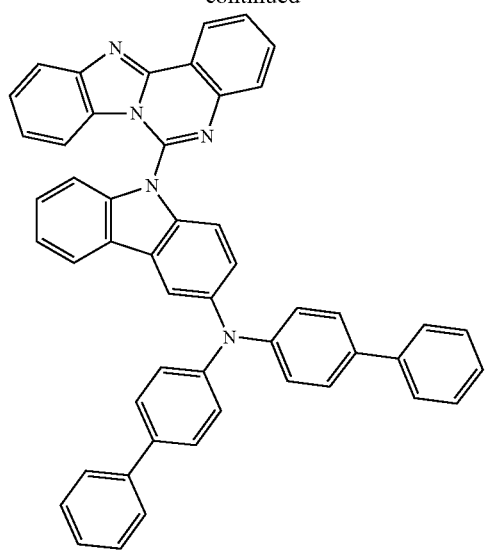
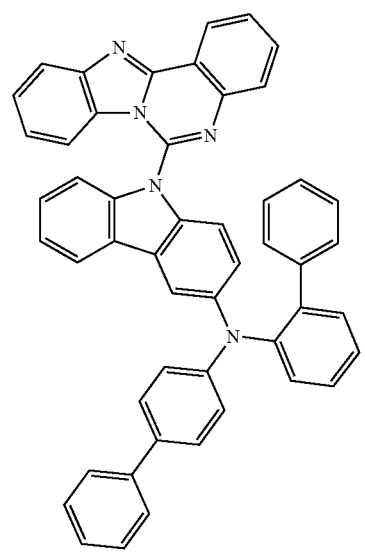
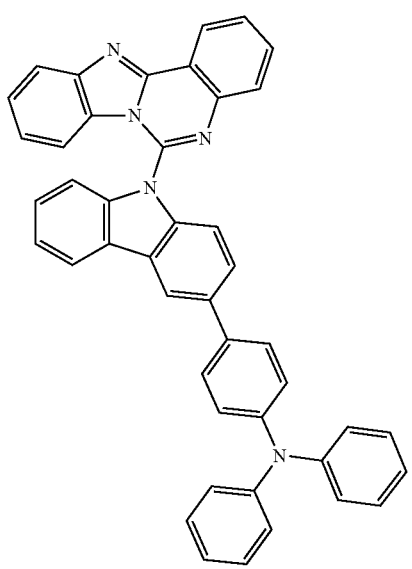
346
-continued
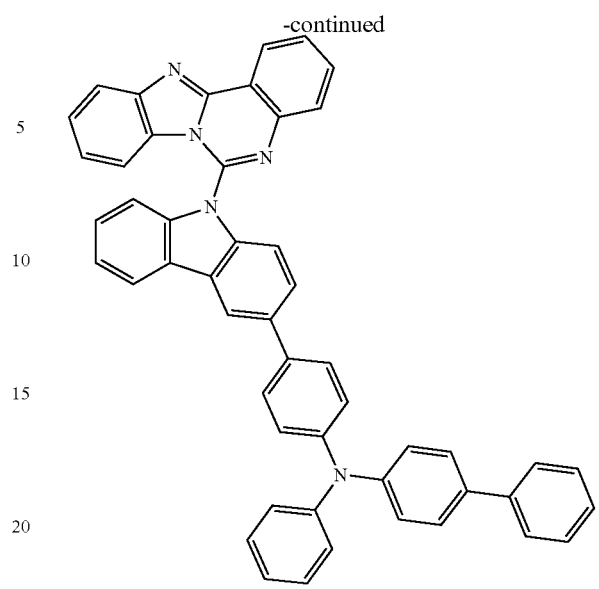
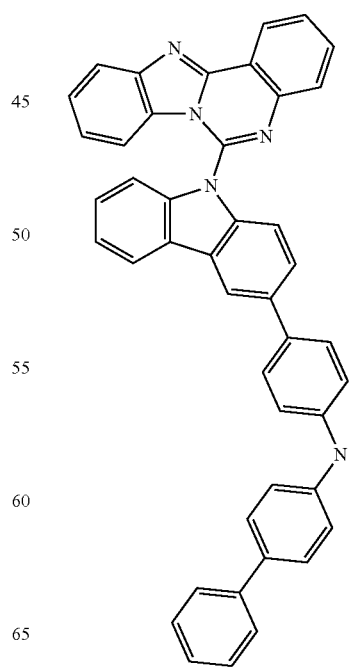

347
-continued
348
-continued
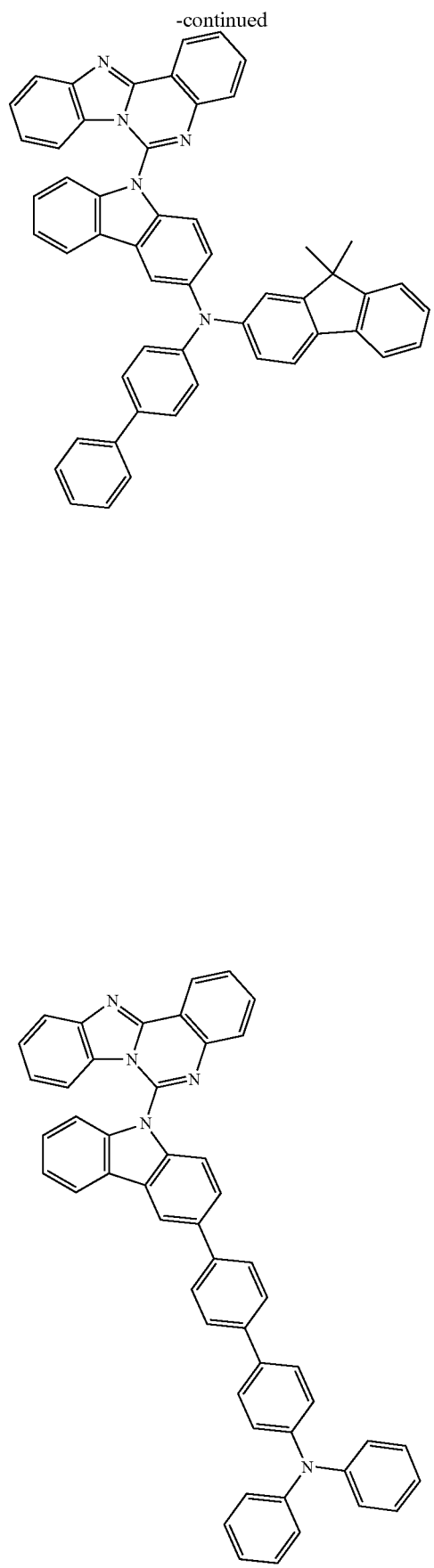
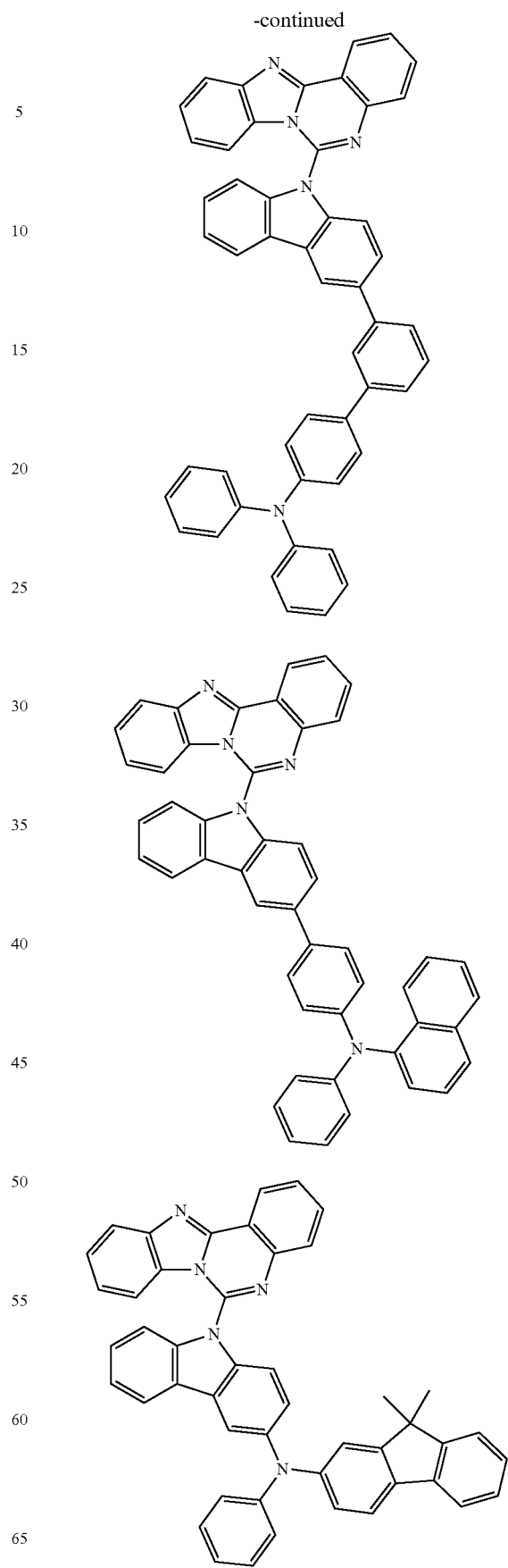

349
-continued
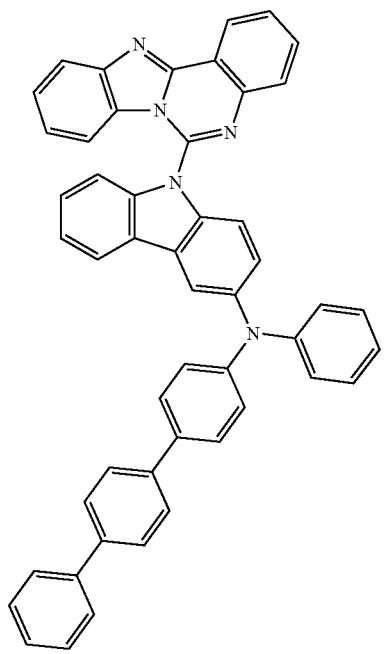
350
-continued
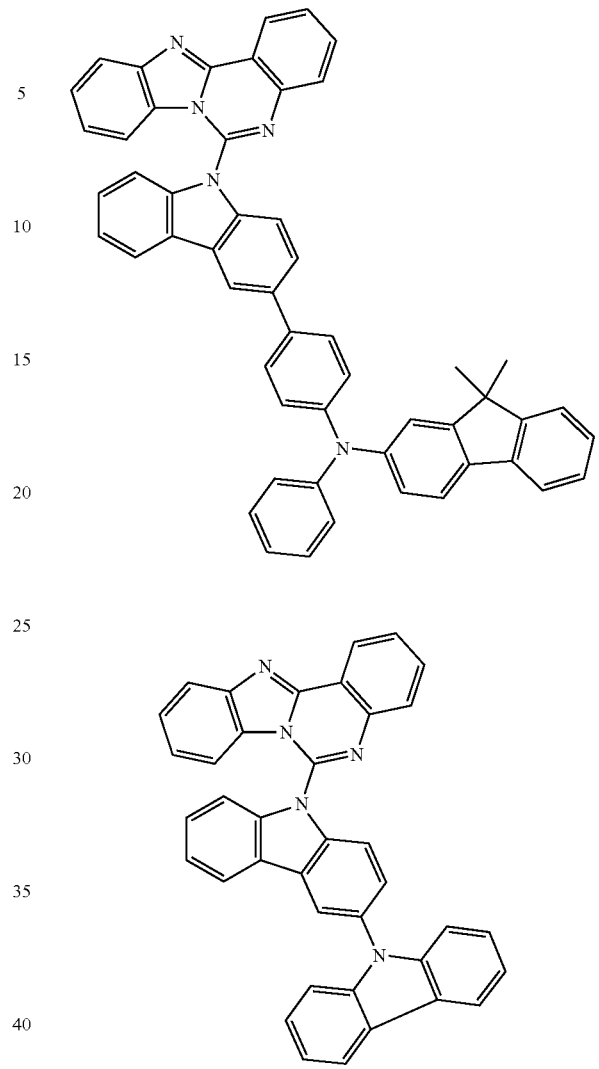
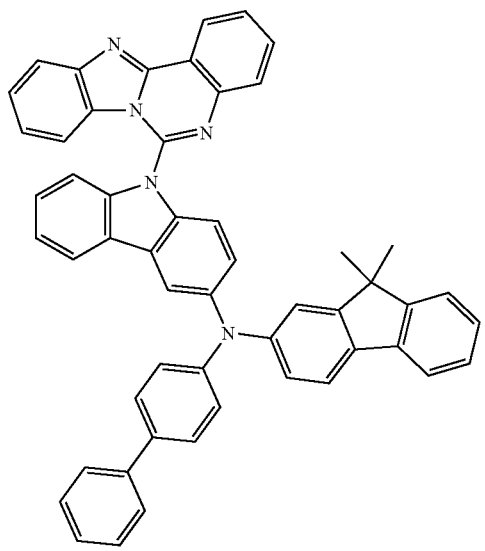
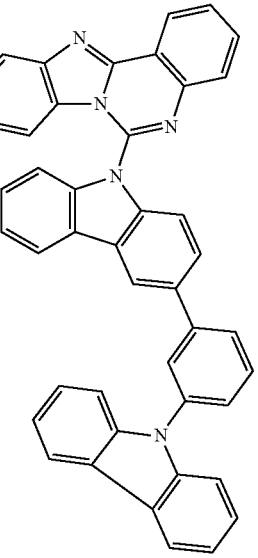

| 351 | 352 |
|---|---|
| -continued | -continued |
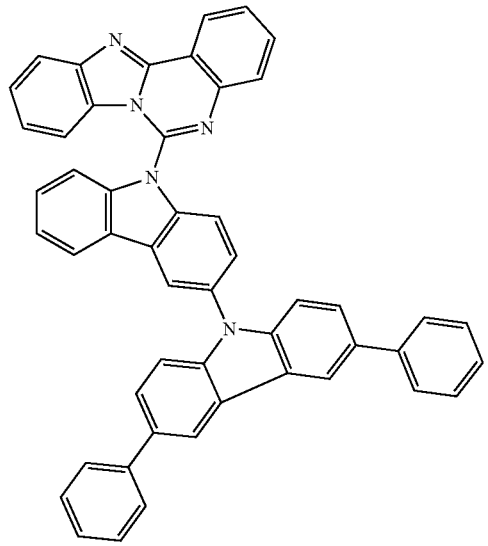
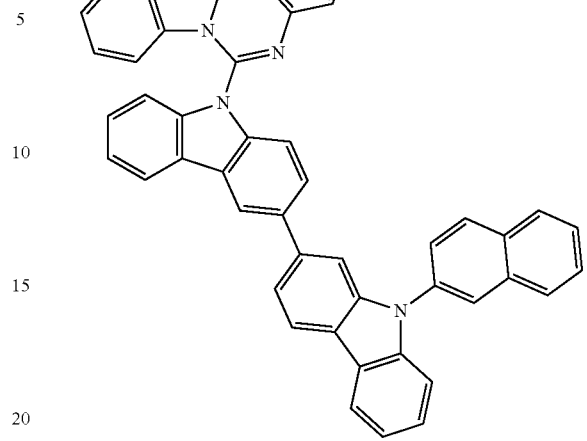
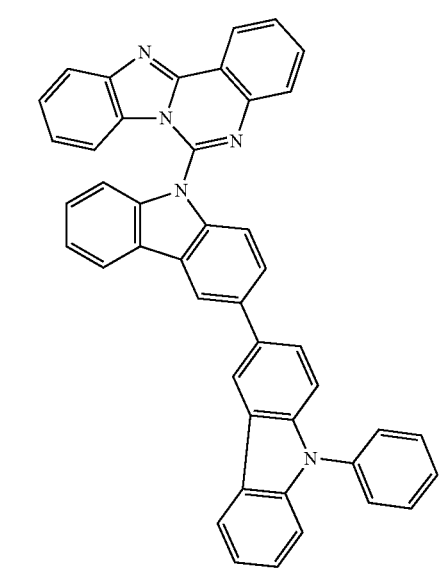
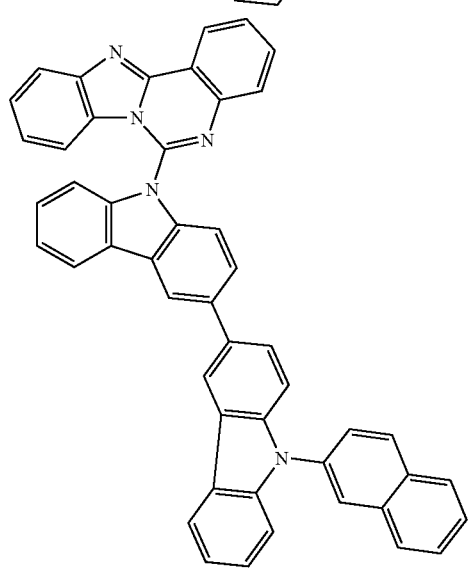
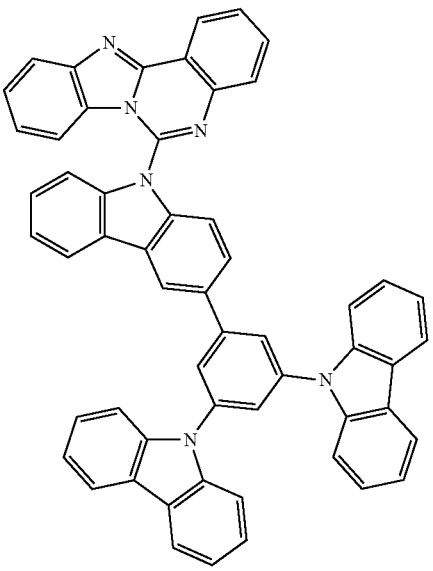

353
-continued
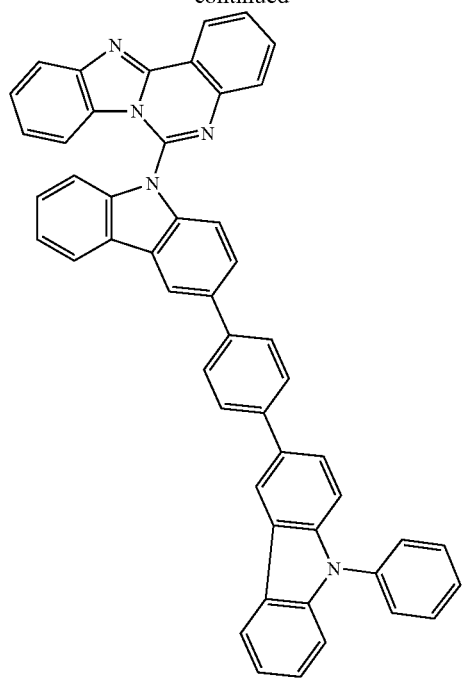
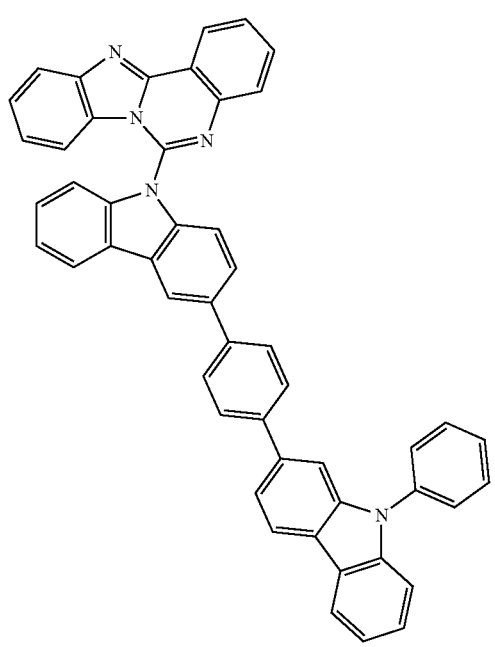
354
-continued
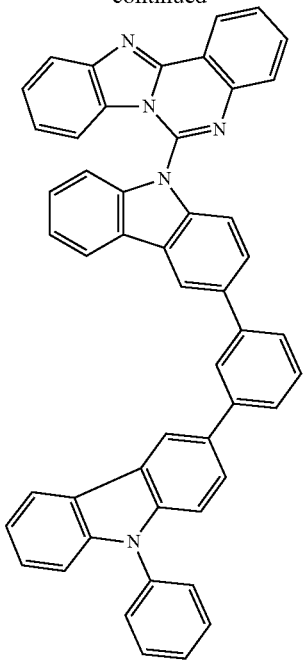
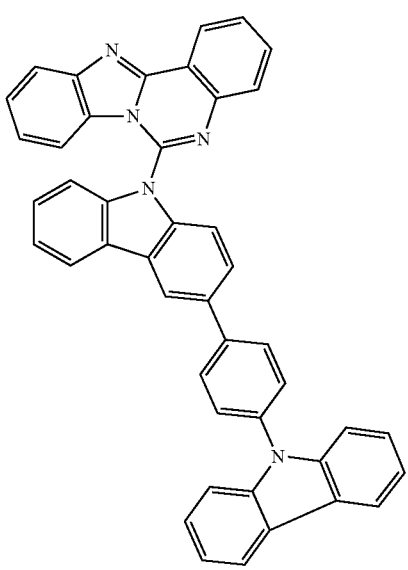

355
-continued
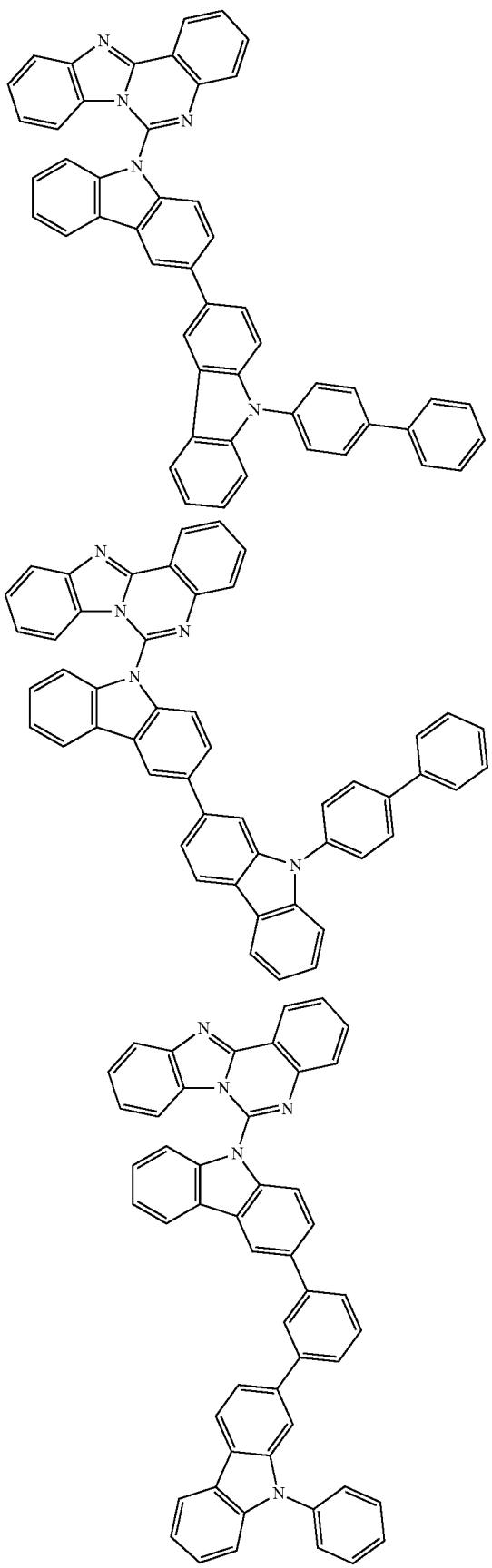
356
-continued
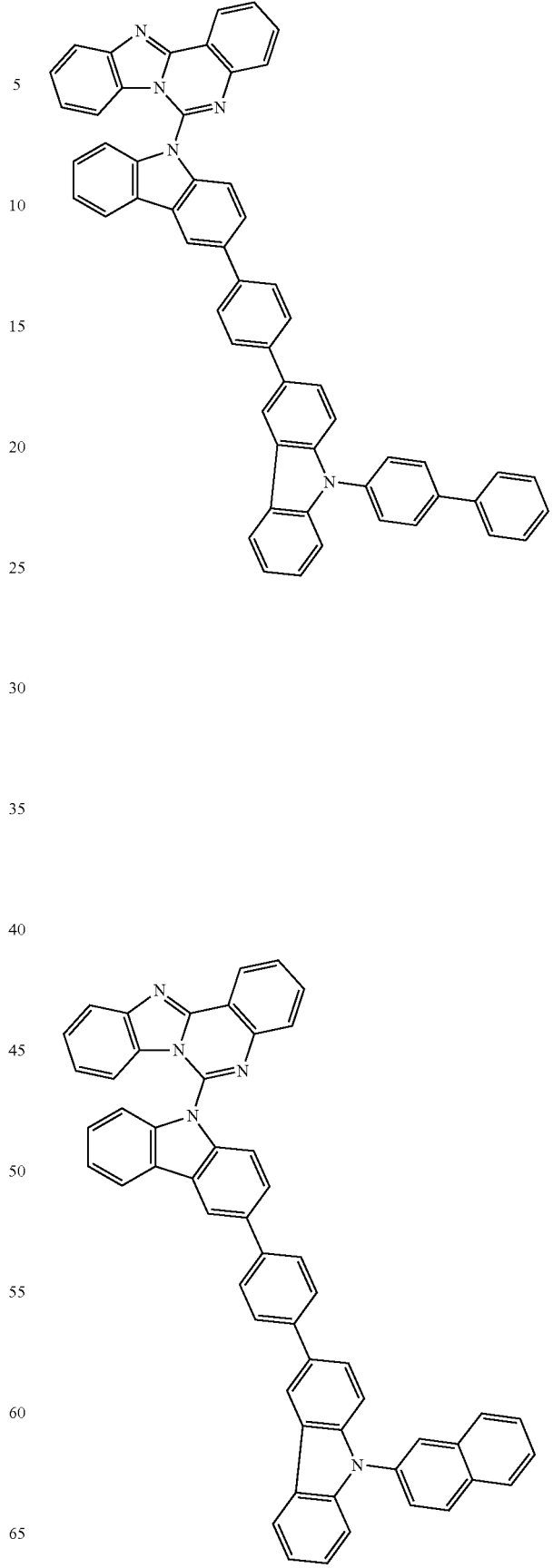

357
-continued
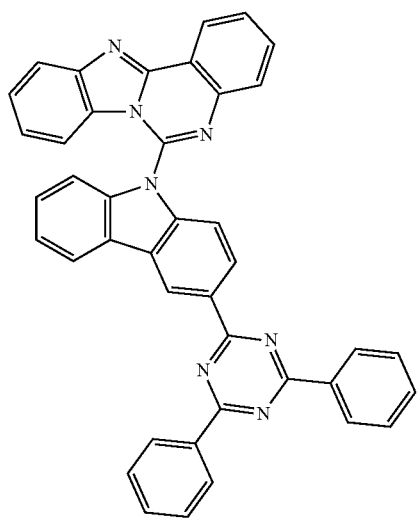
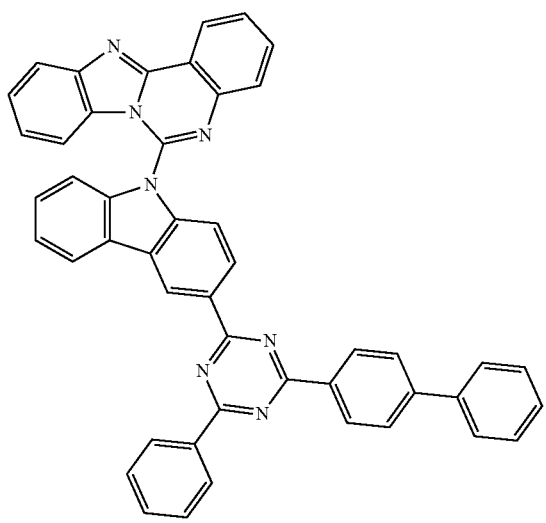
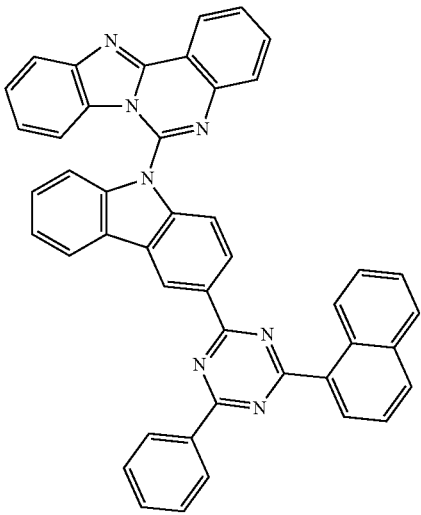
358
-continued
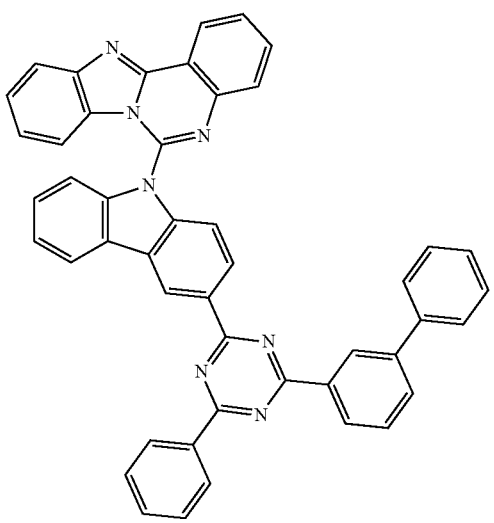
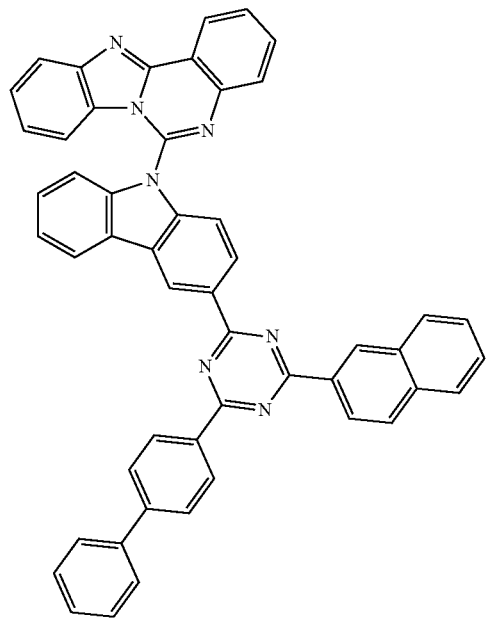
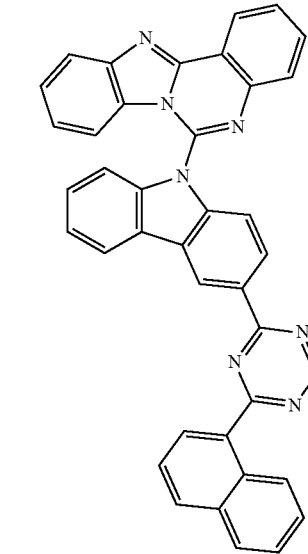

359
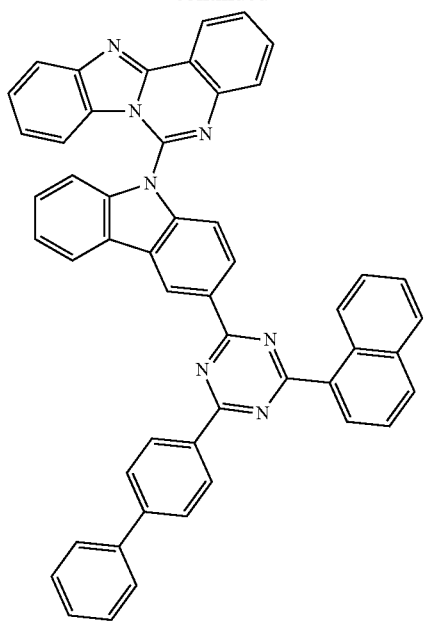
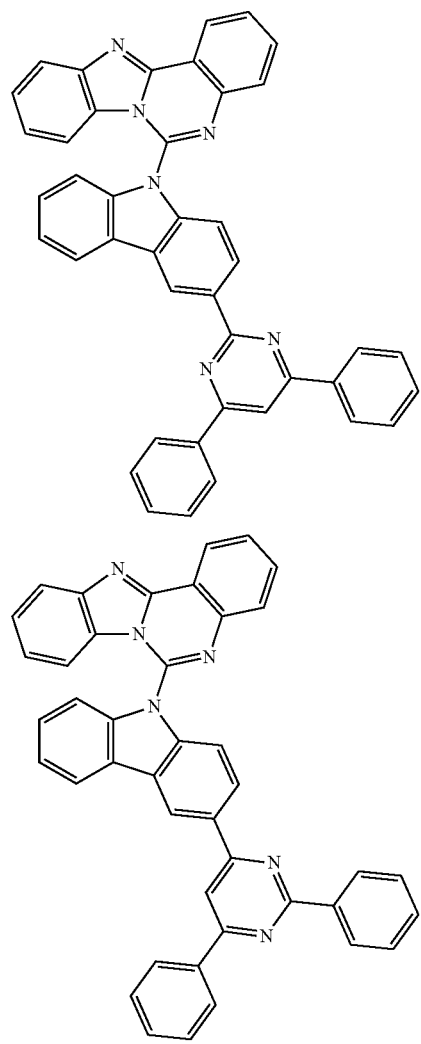
360
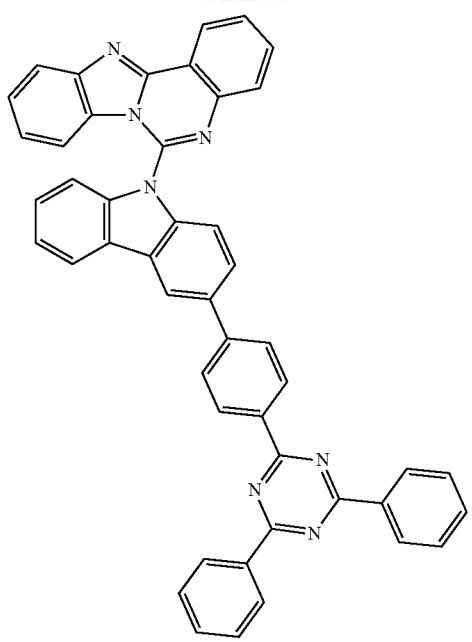
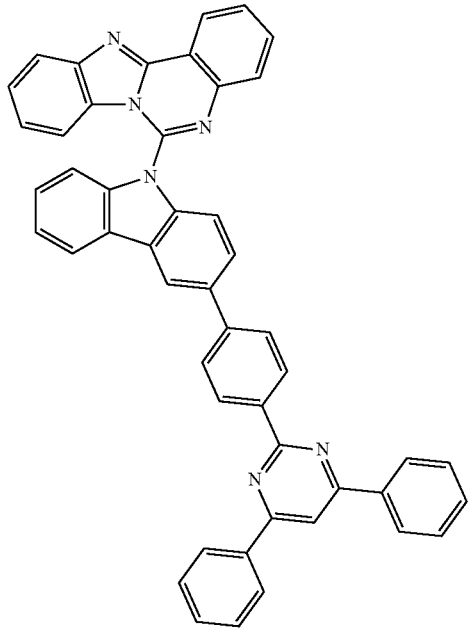

361
-continued
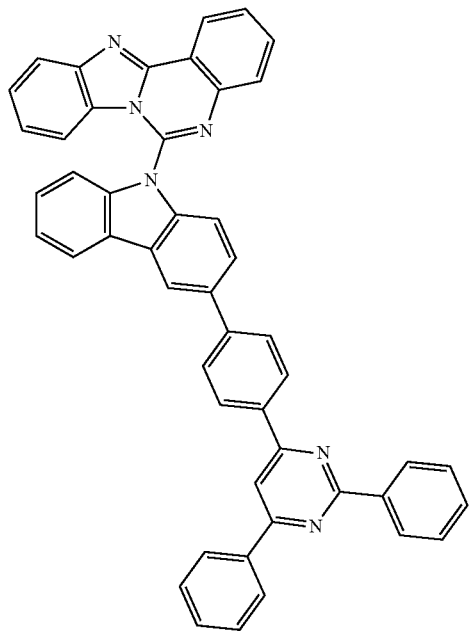
362
-continued
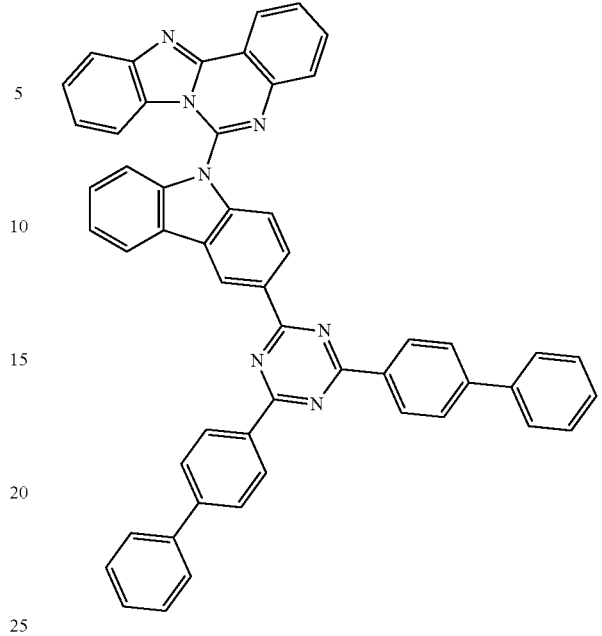
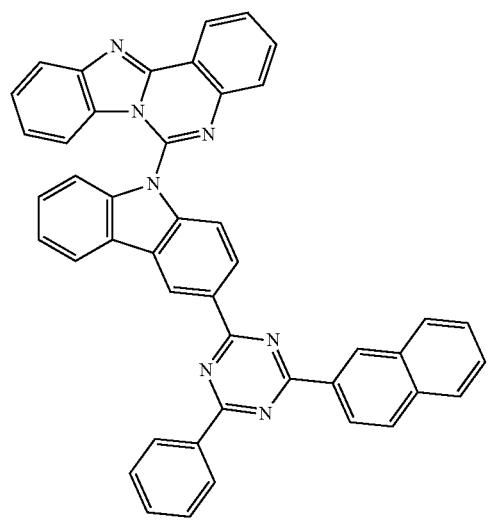
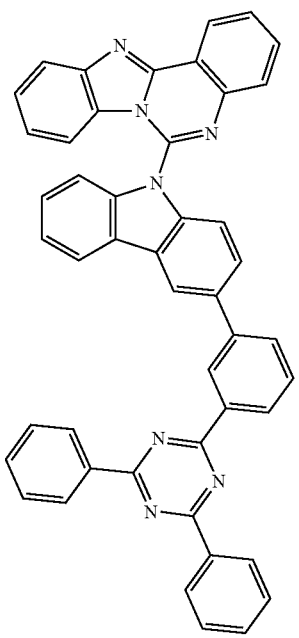

363
-continued
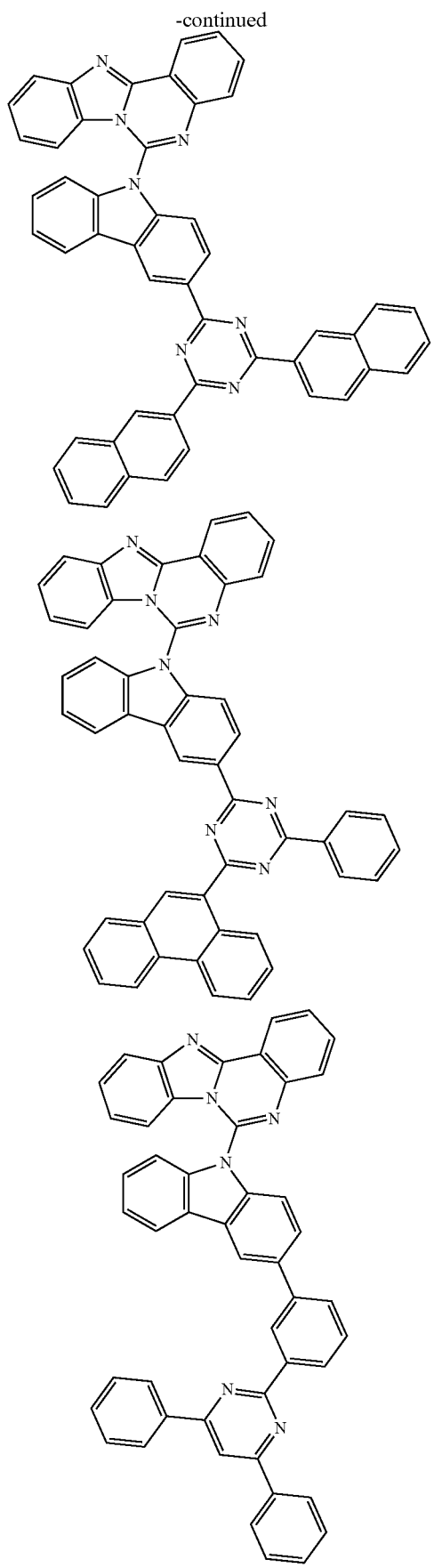
364
-continued
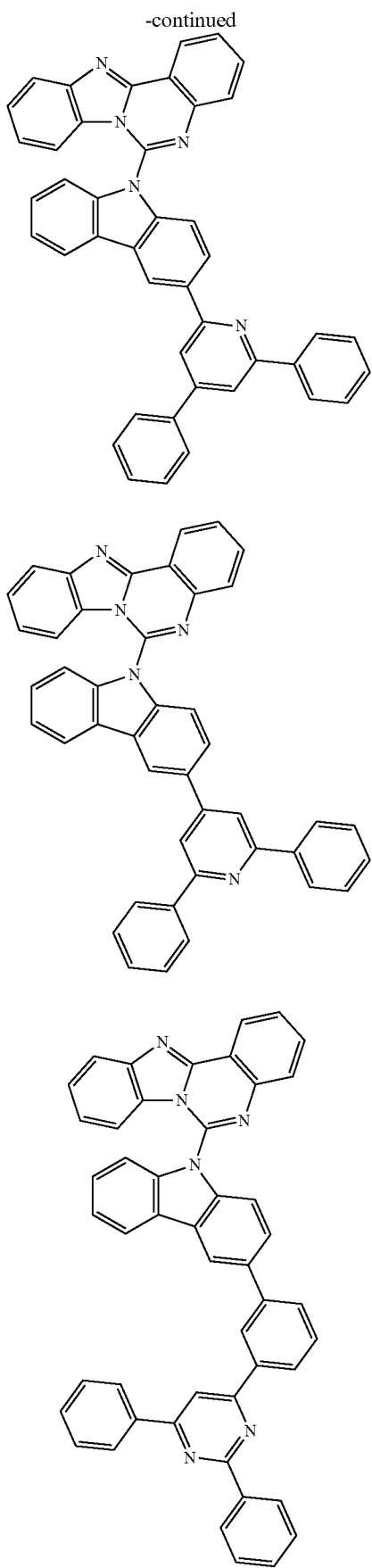

365
-continued
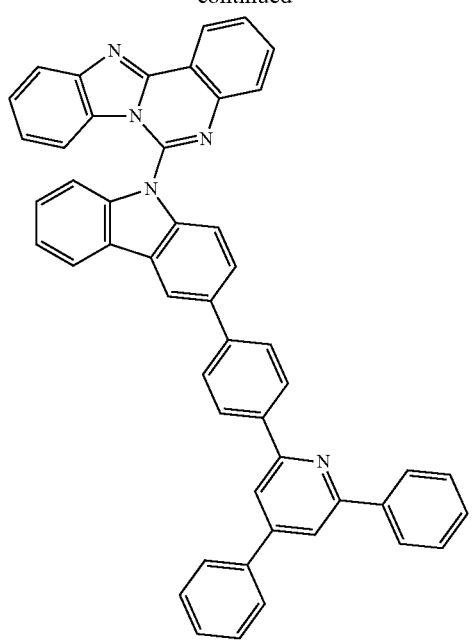
366
-continued
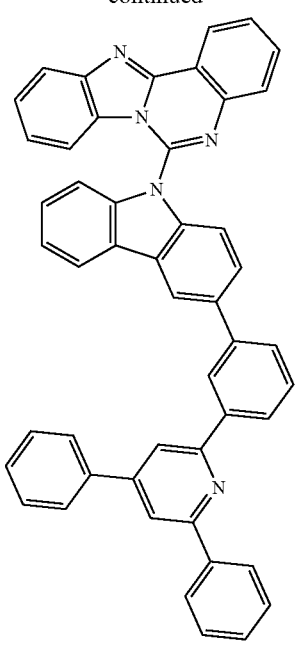
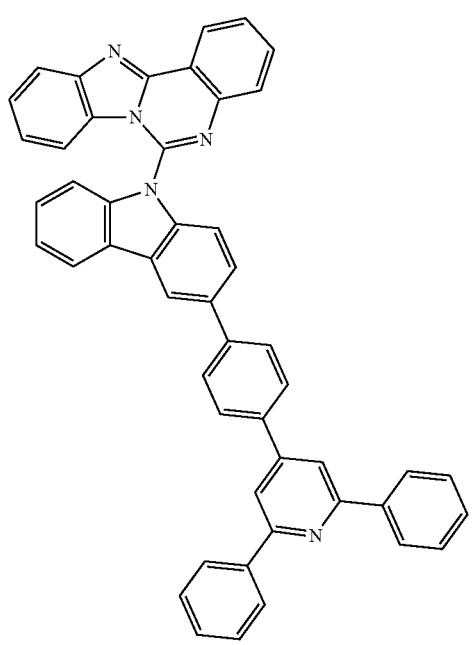
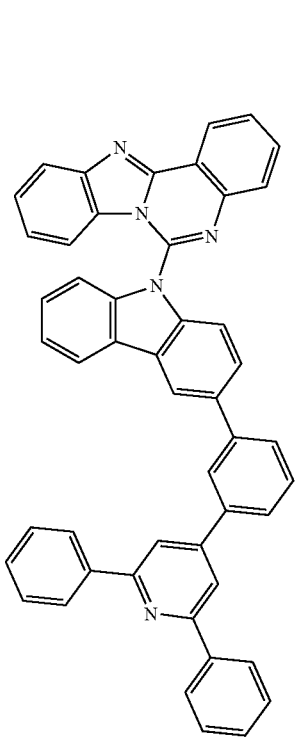

367
-continued
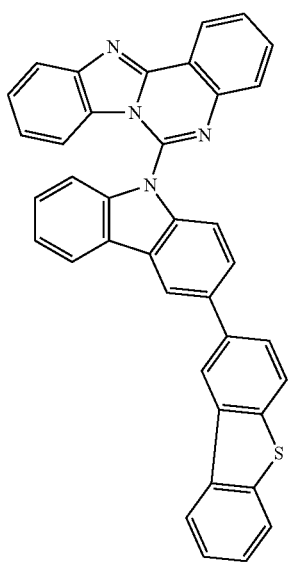
368
-continued
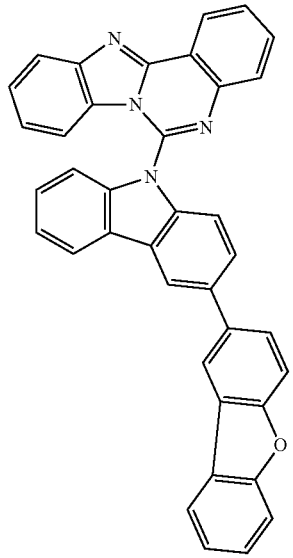
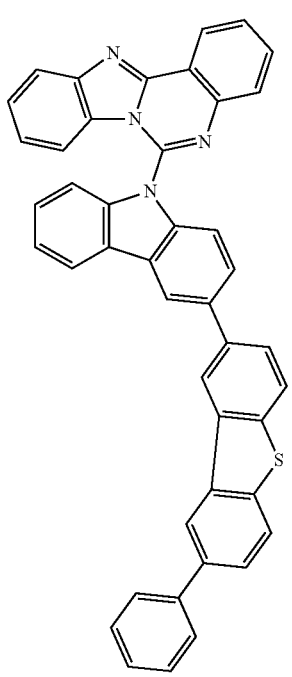
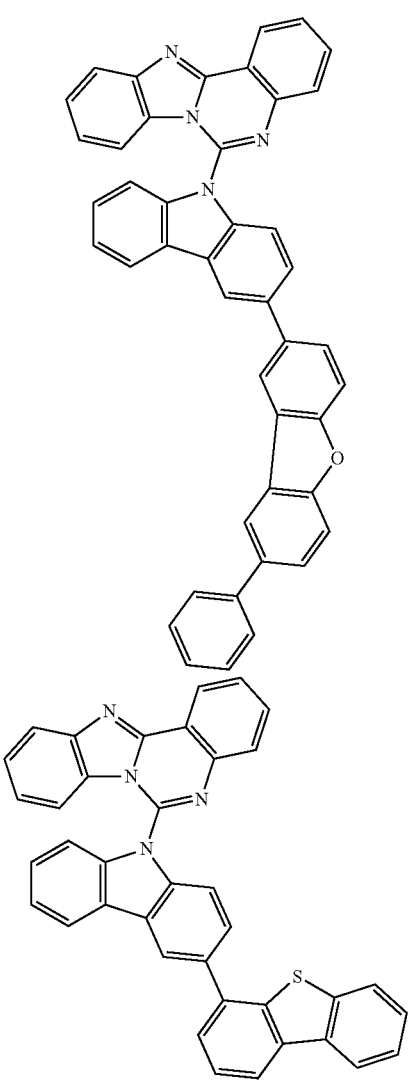

369
-continued
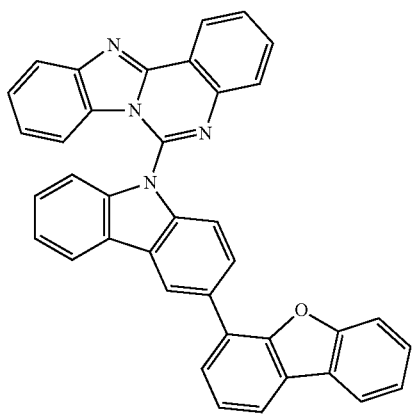
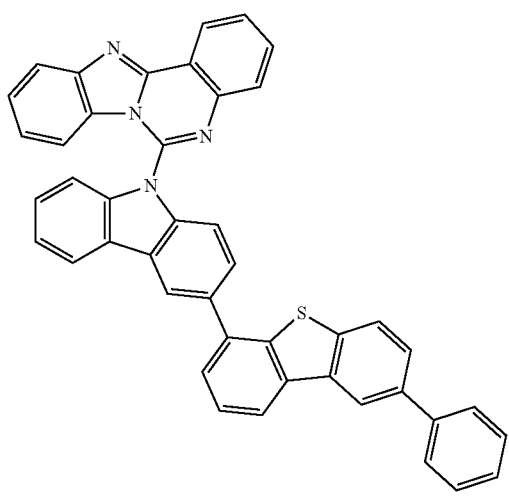
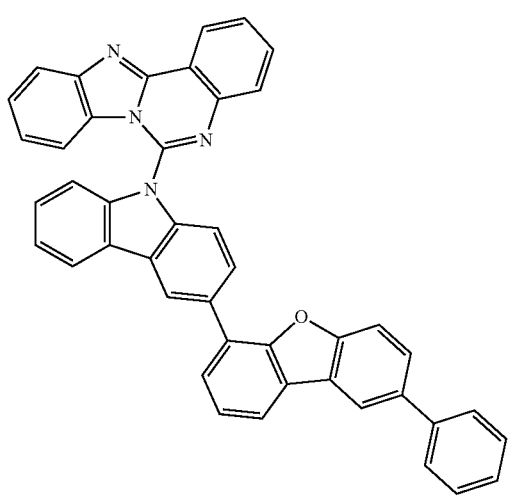
370
-continued
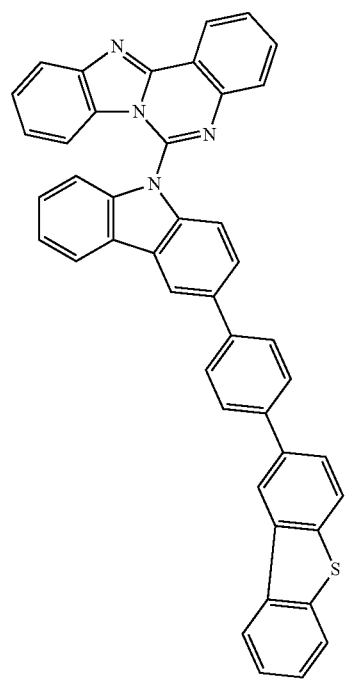
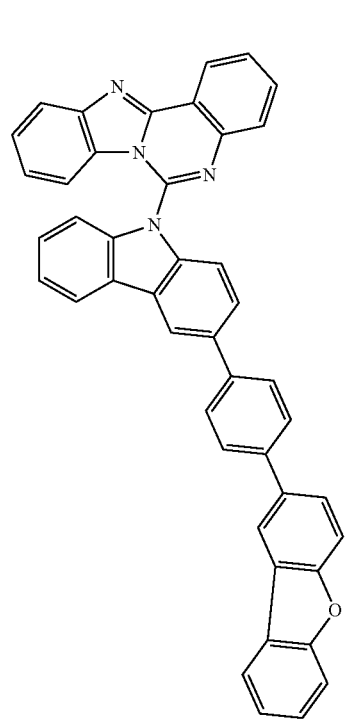

371
-continued
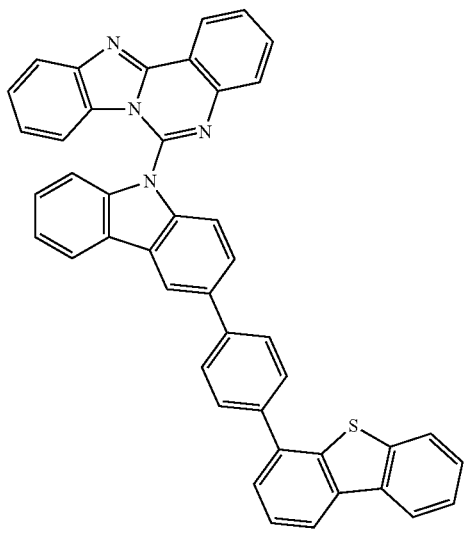
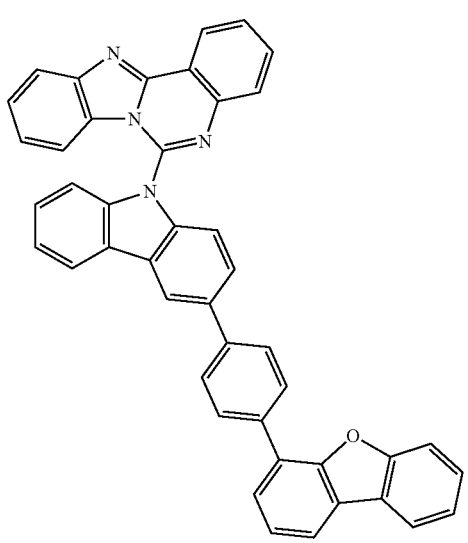
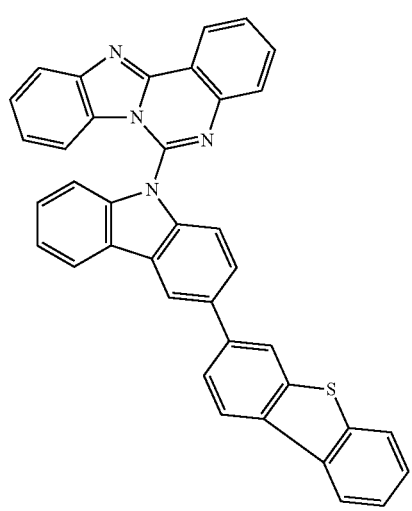
372
-continued
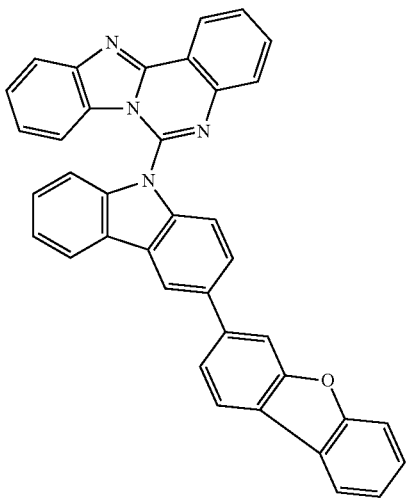
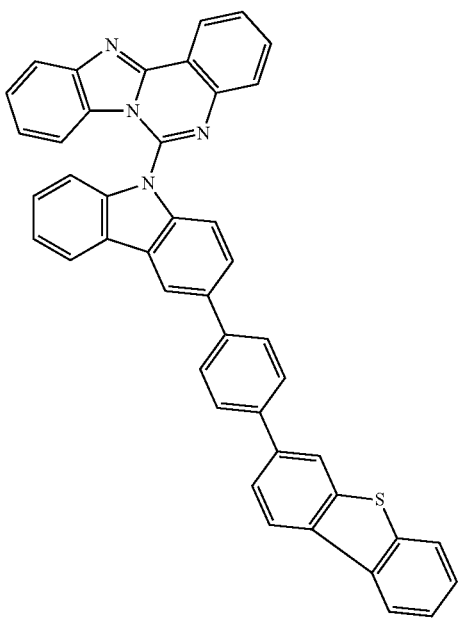

373
-continued
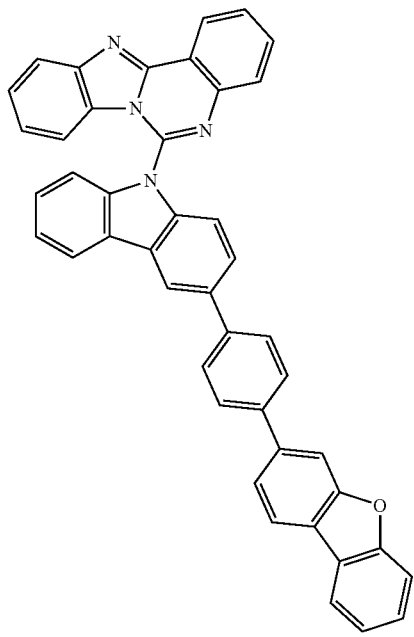
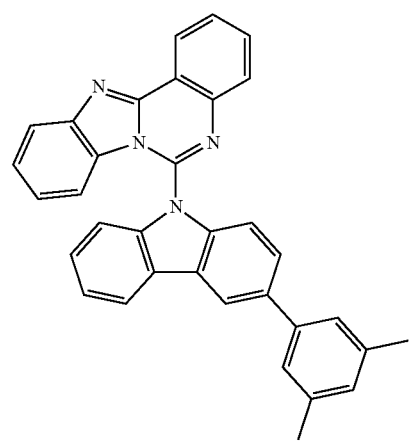
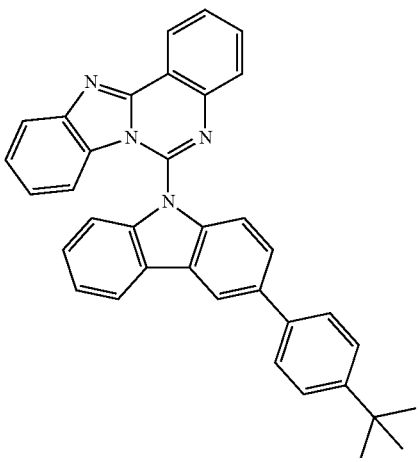
374
-continued
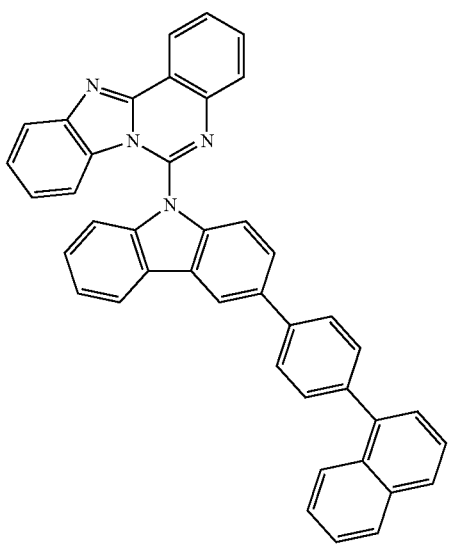
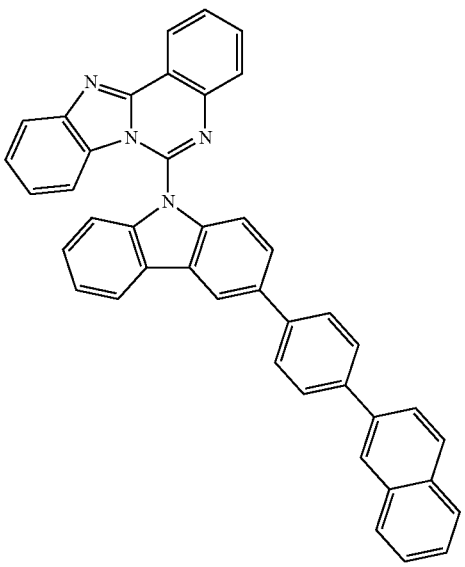
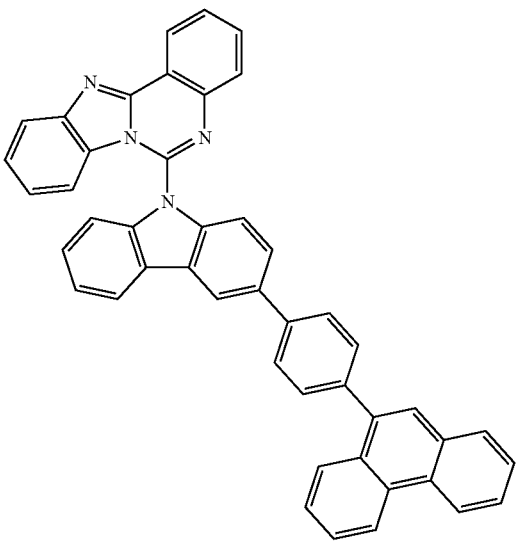

375
-continued
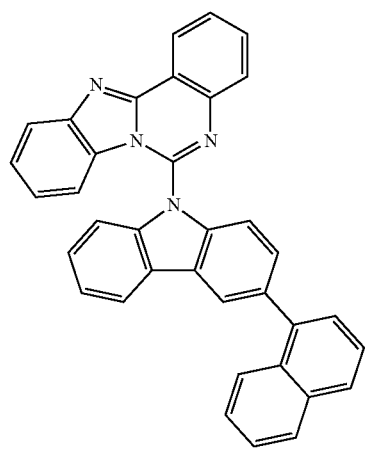
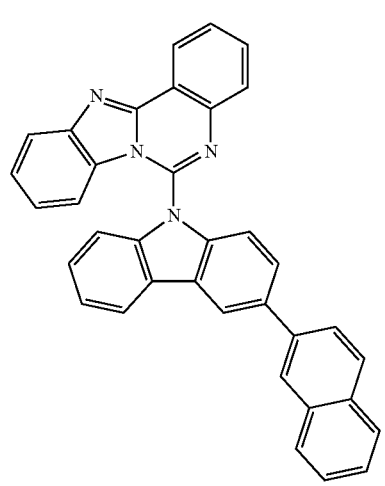
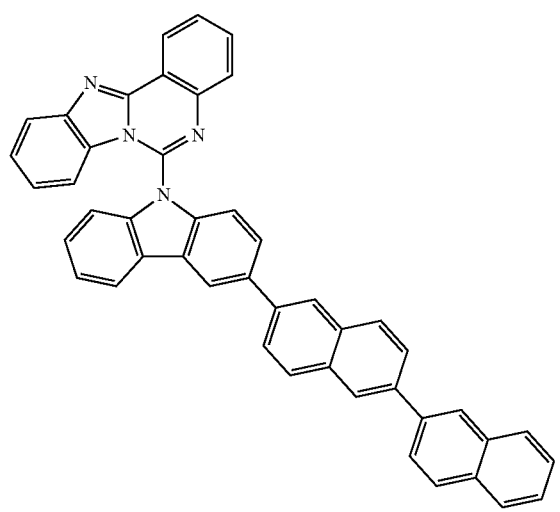
376
-continued
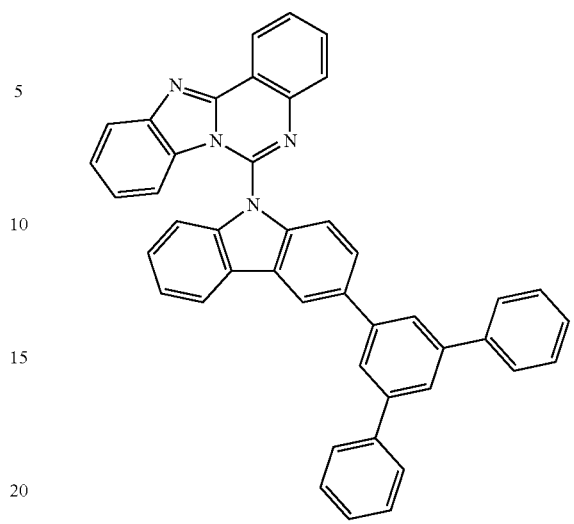
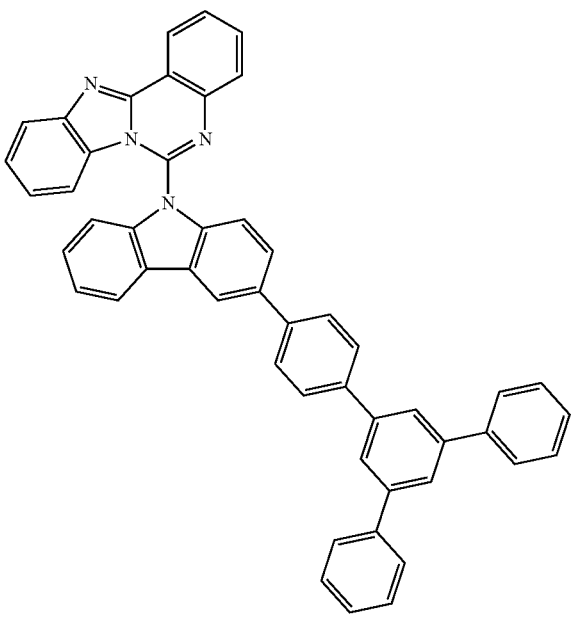

377
-continued
378
-continued
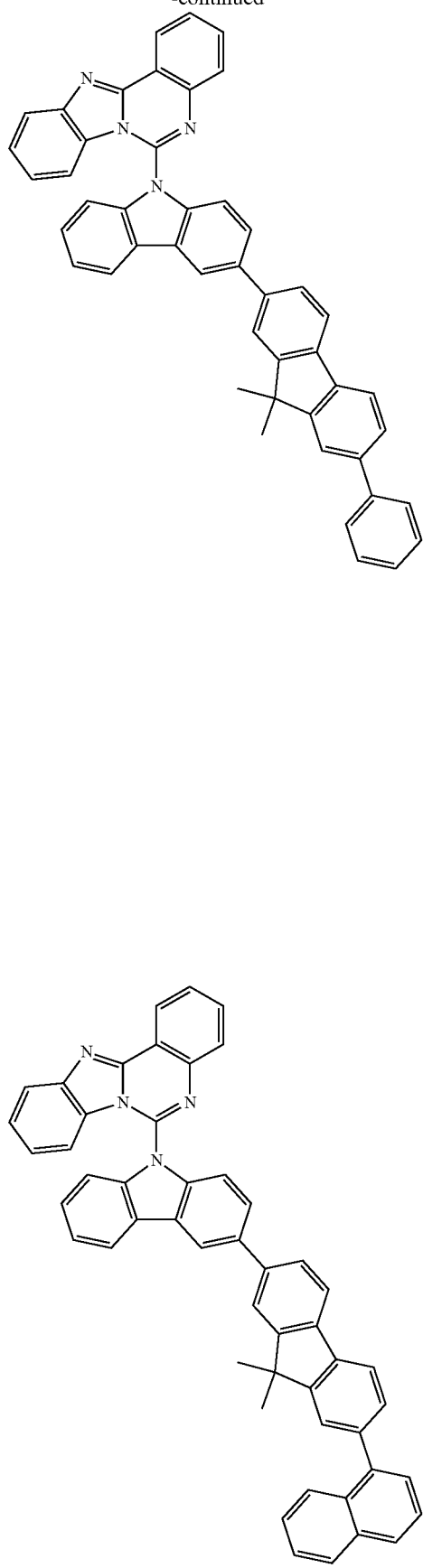
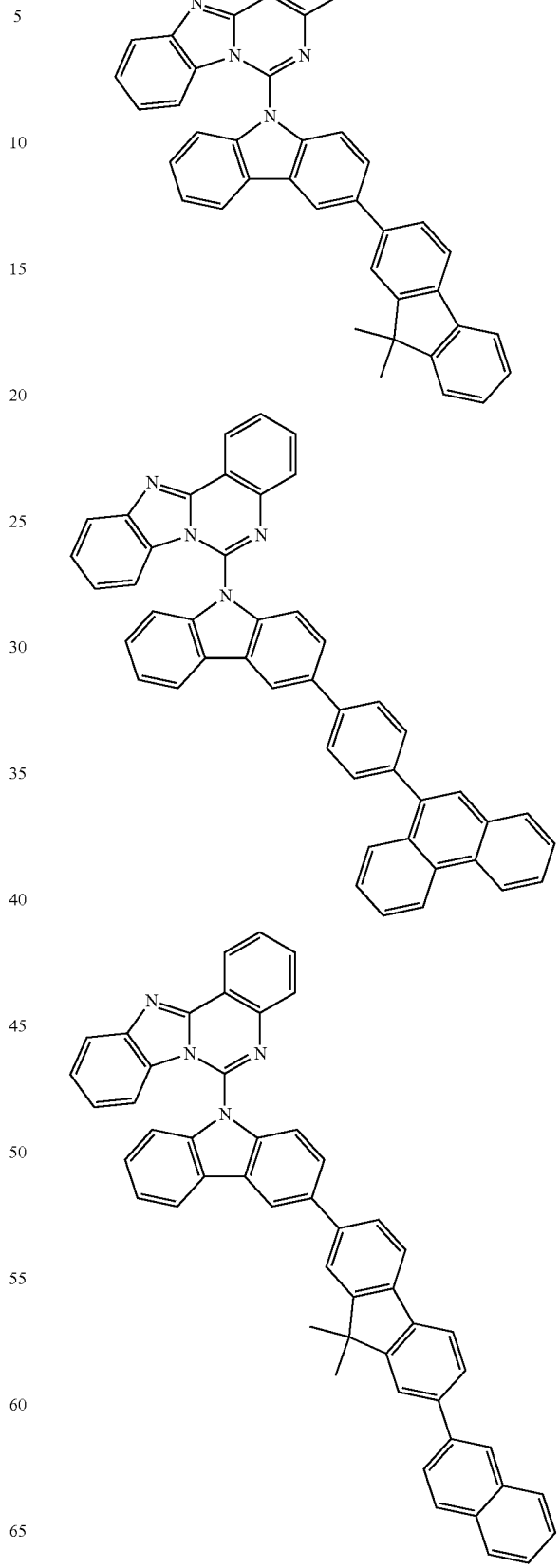

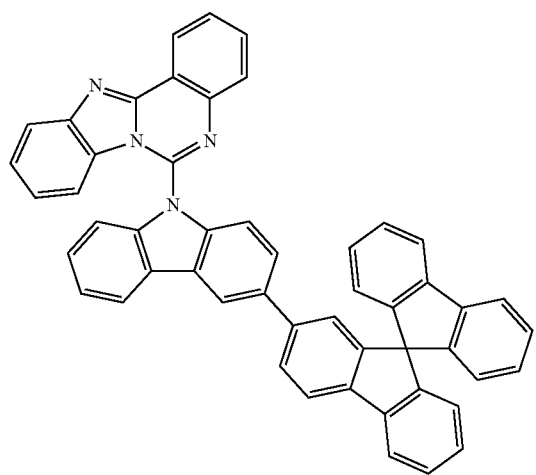
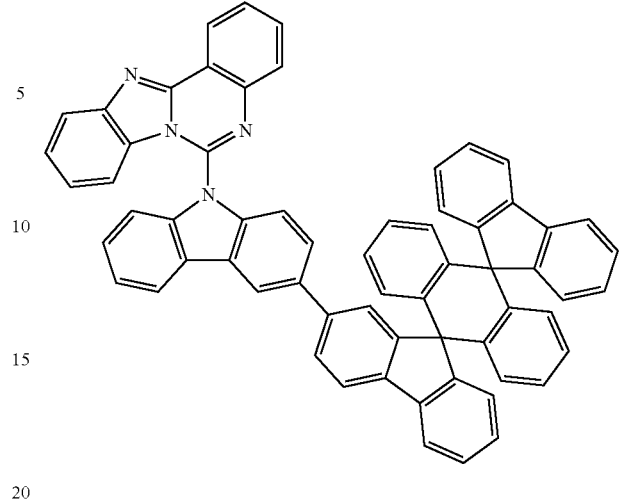
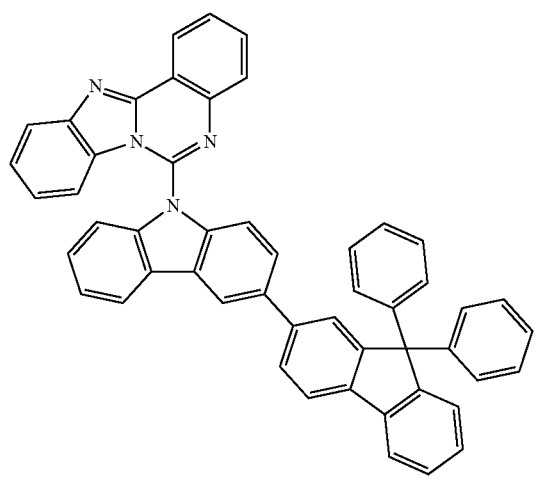
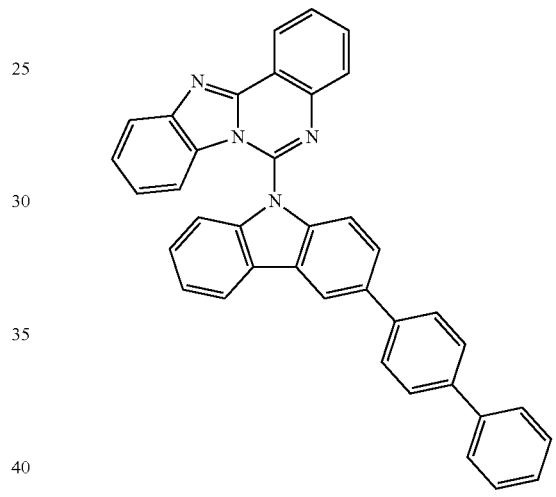
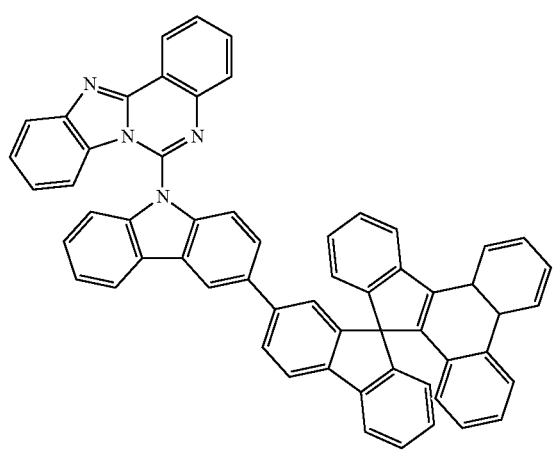
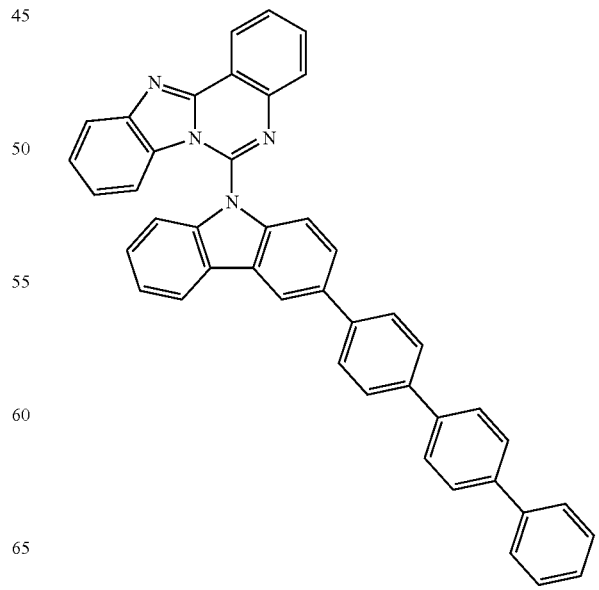

381
-continued
382
-continued
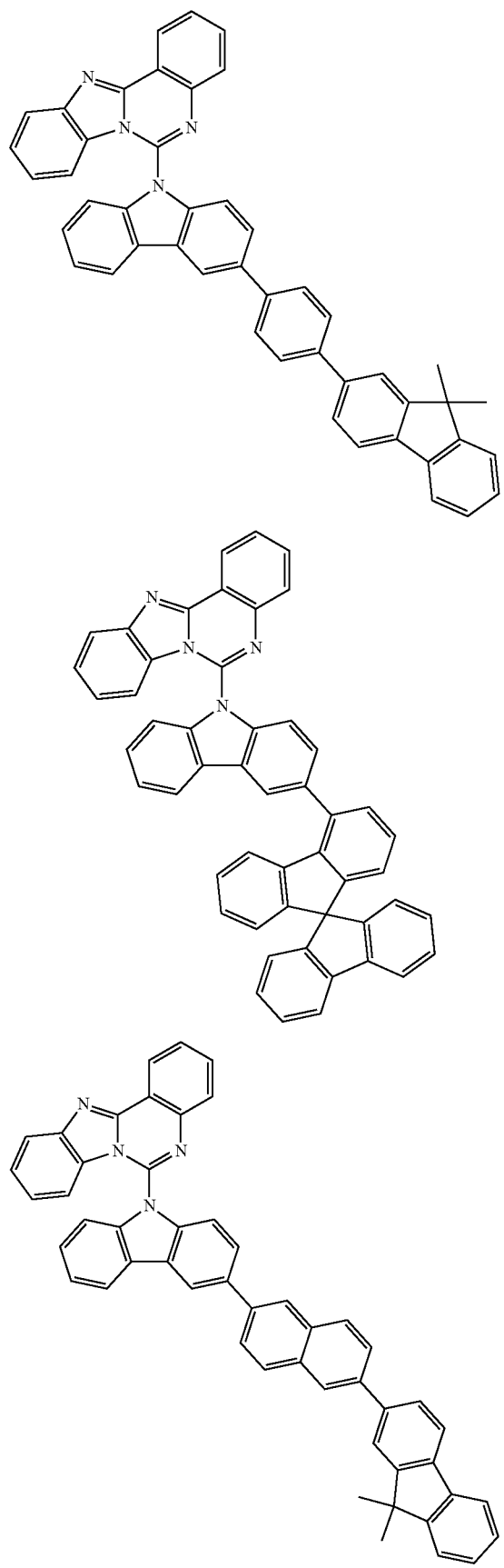

383
-continued
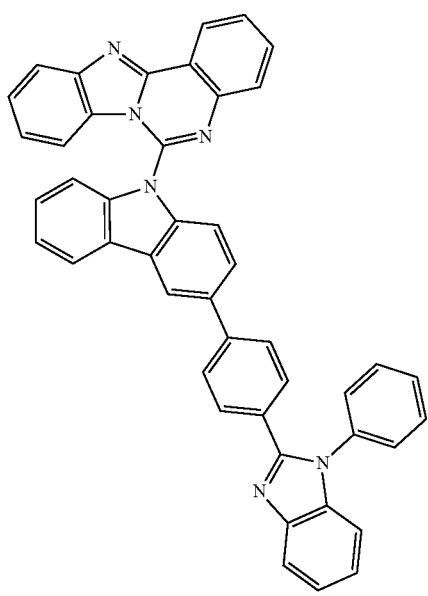
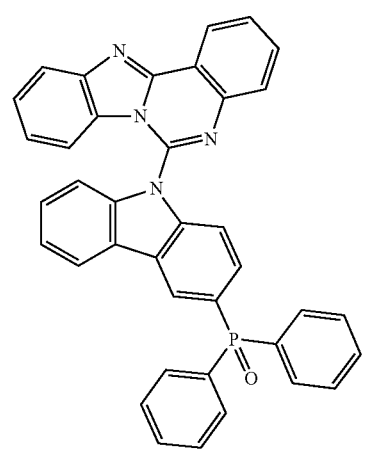
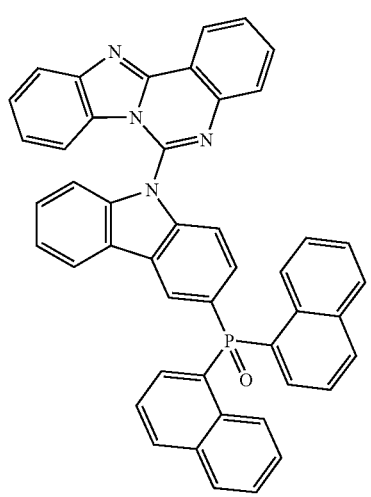
384
-continued
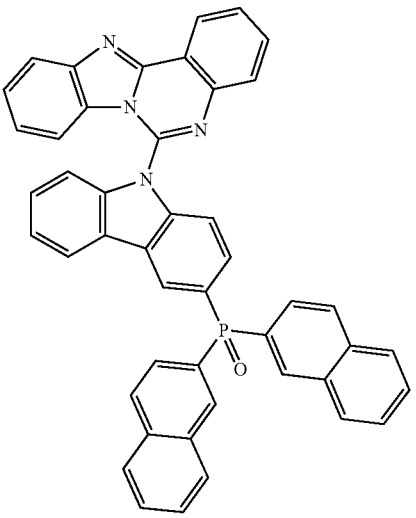
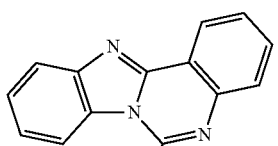
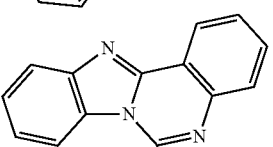
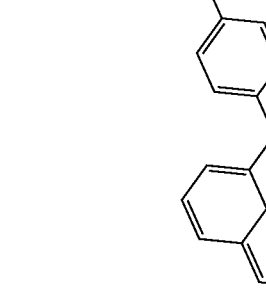

385
-continued
386
-continued
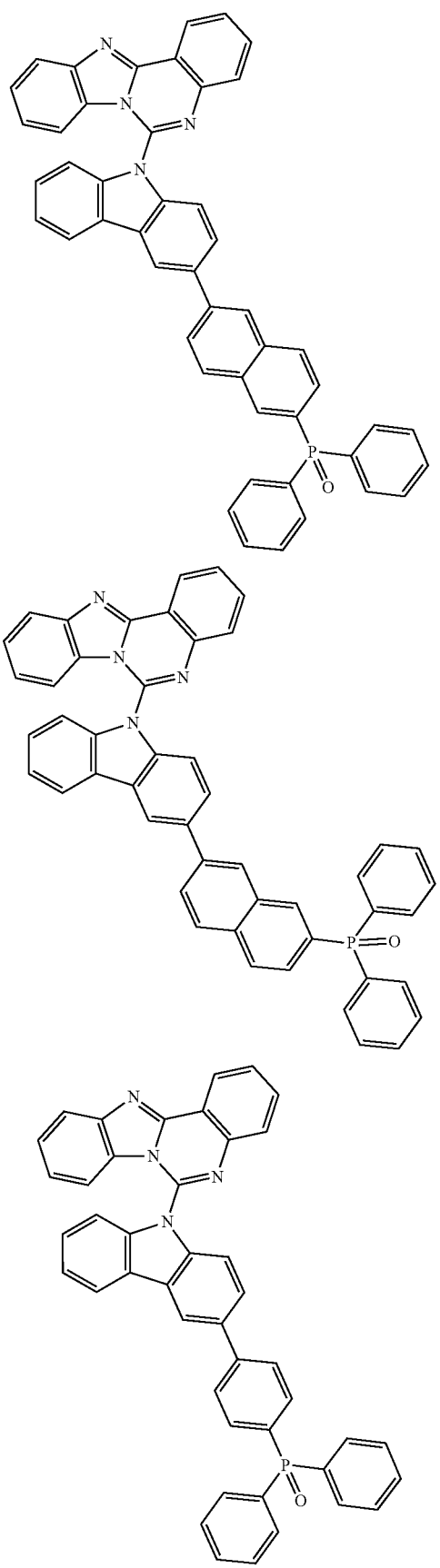
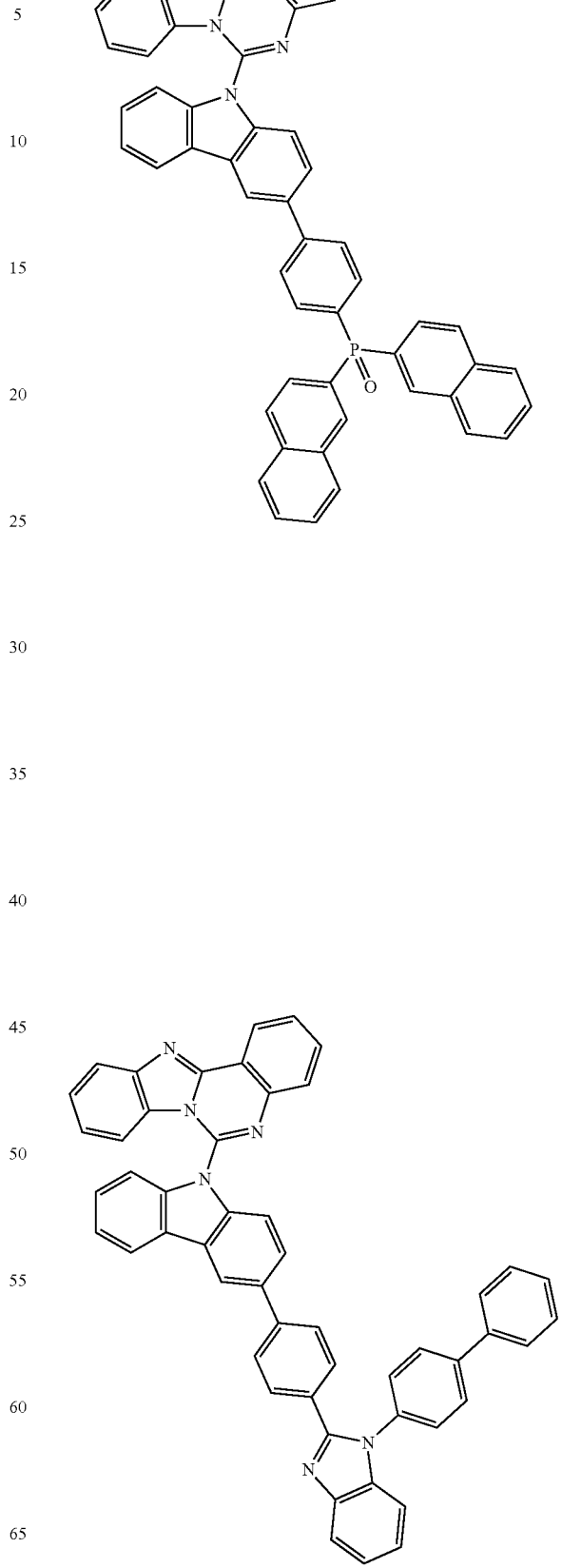

387
-continued
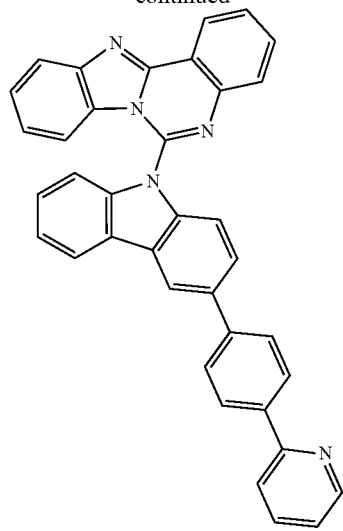
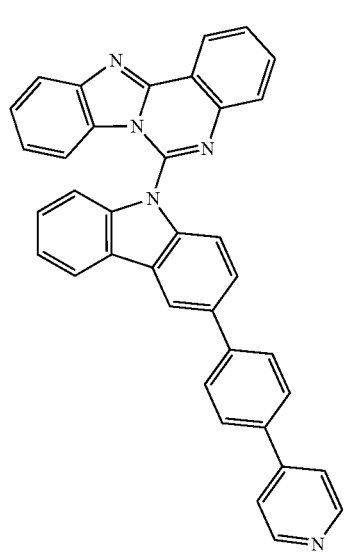
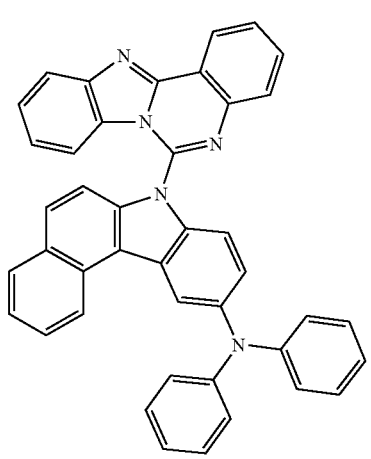
388
-continued
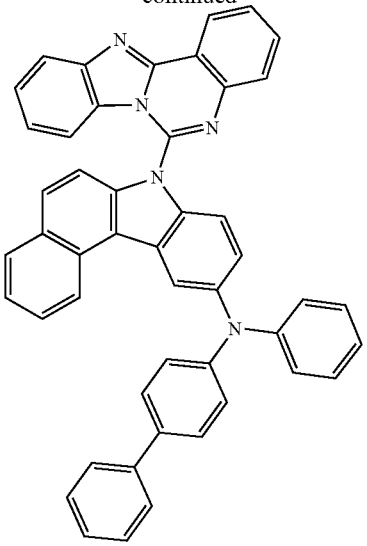

389
-continued
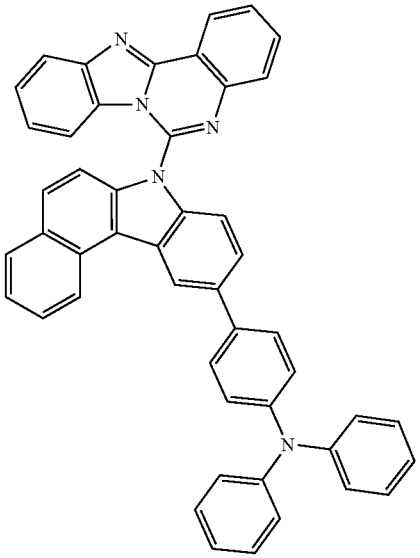
390
-continued
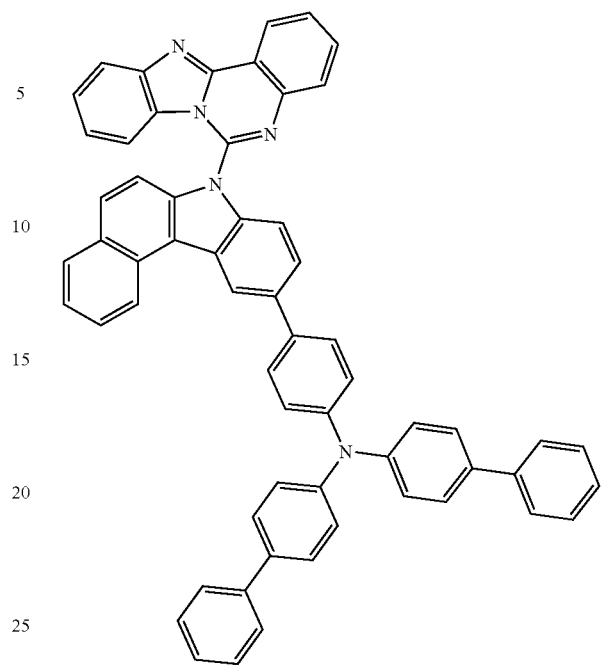
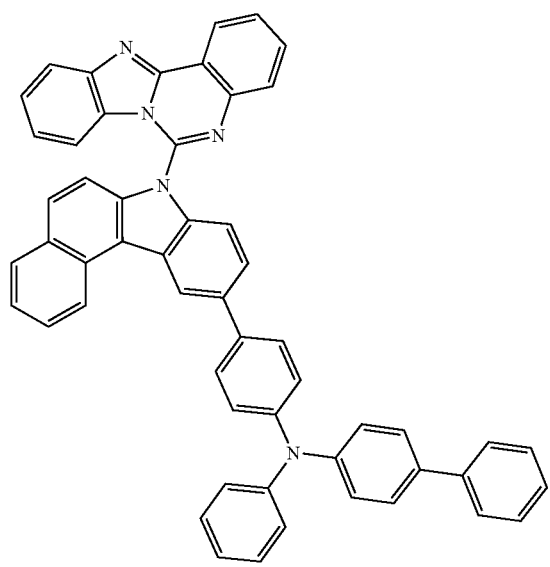
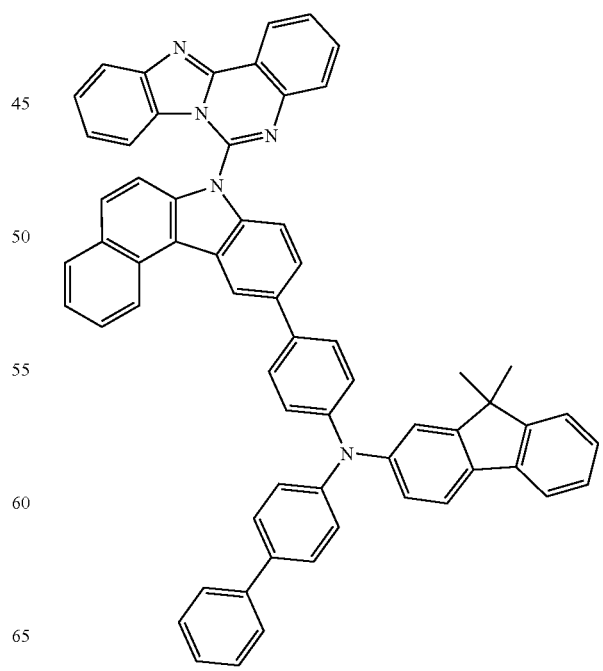

391
-continued
392
-continued
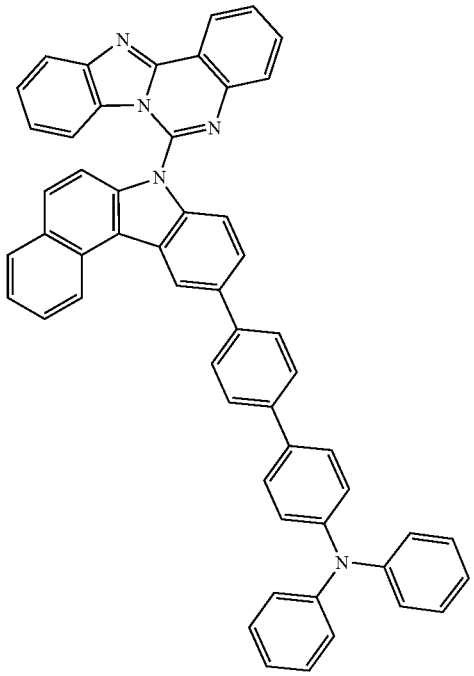
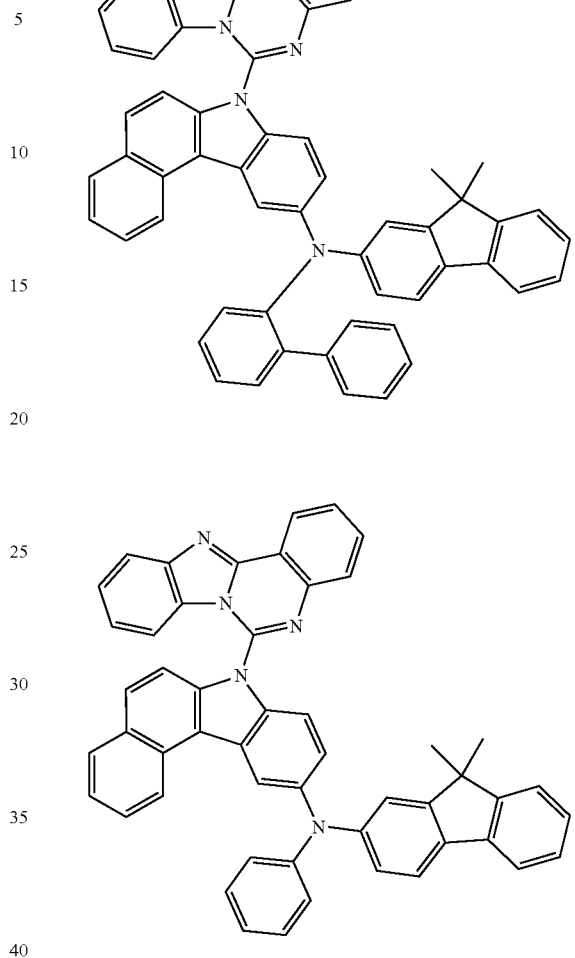
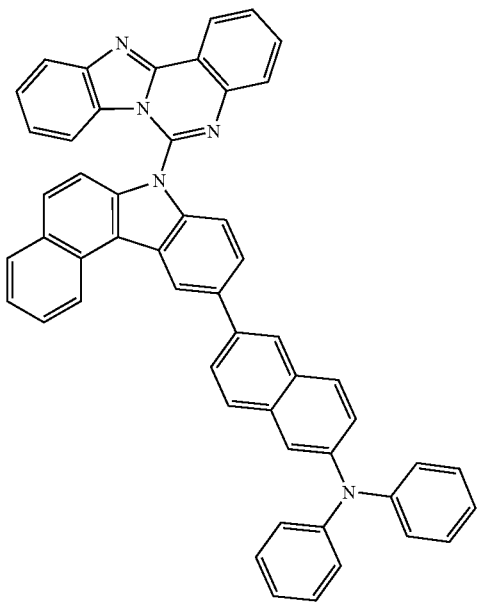
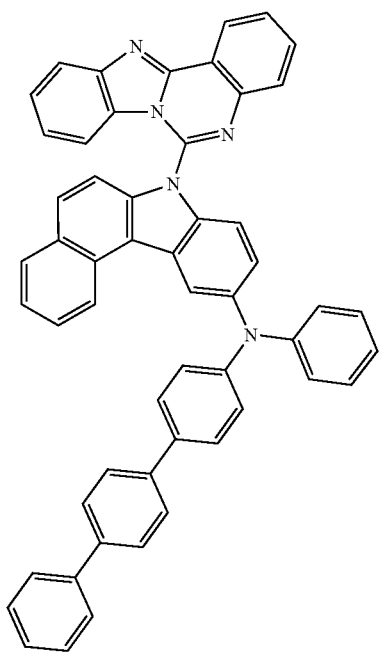

393
-continued
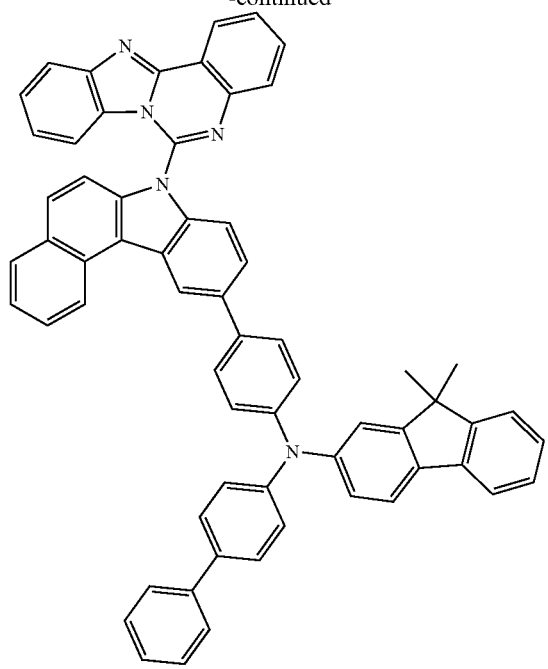
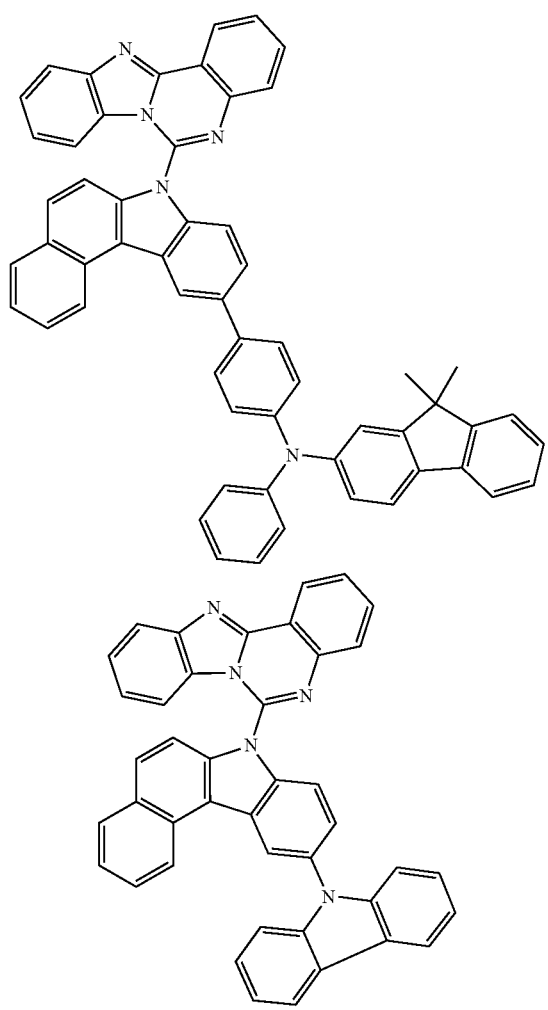
394
-continued
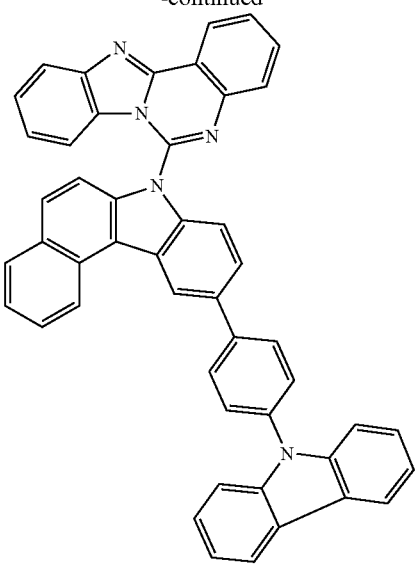
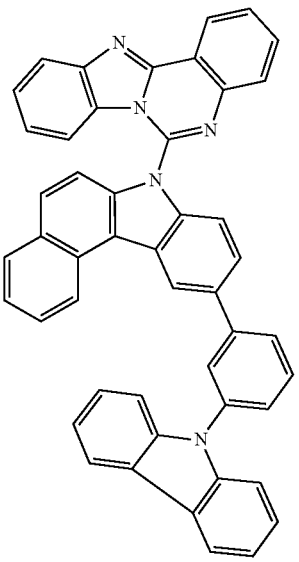

395
-continued
396
-continued
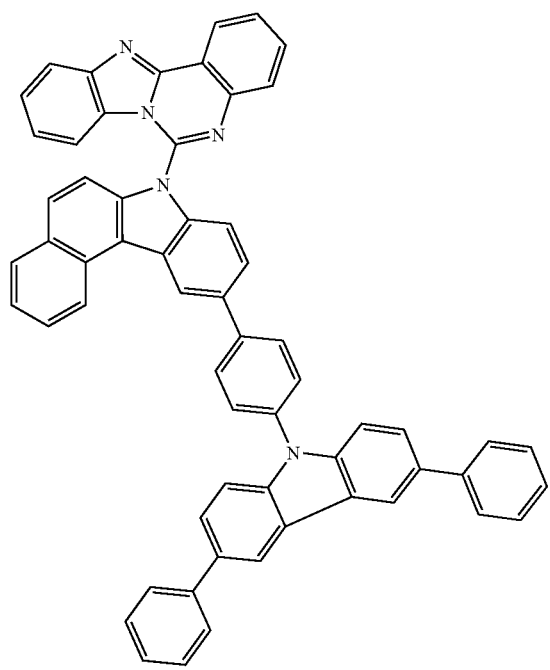
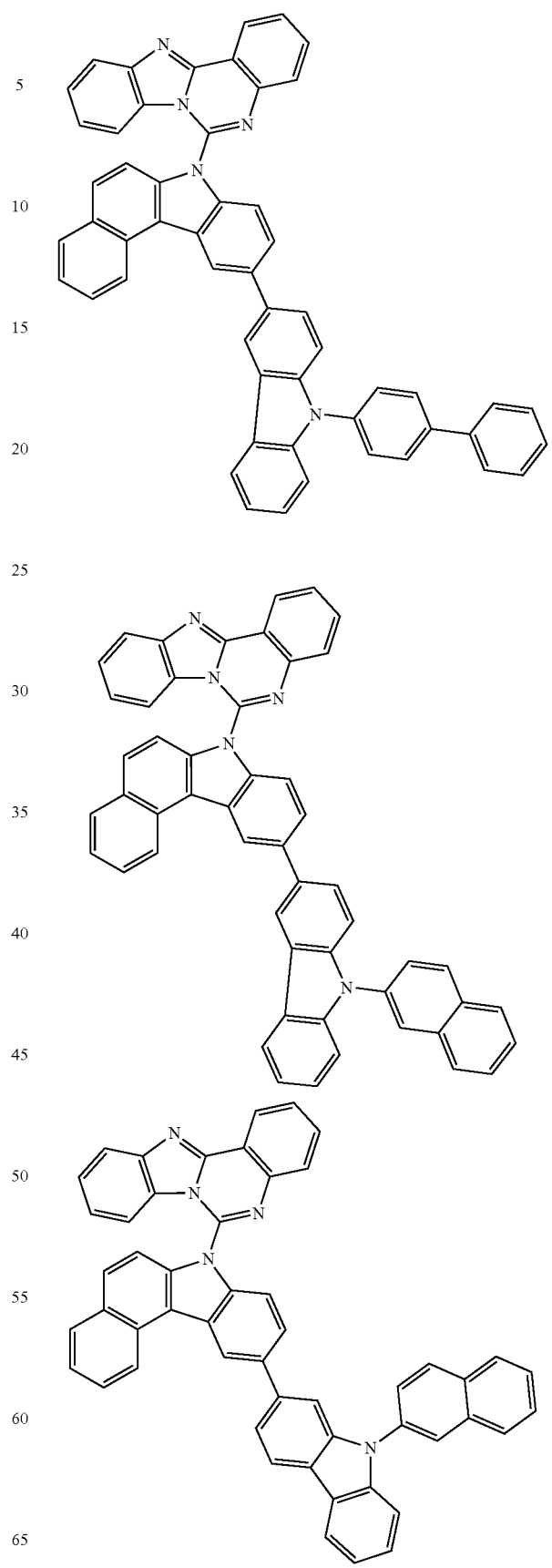

397
-continued
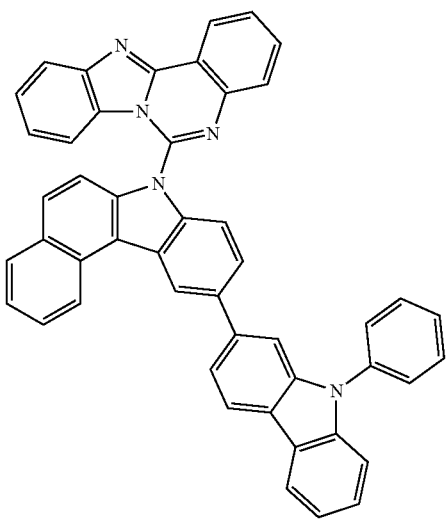
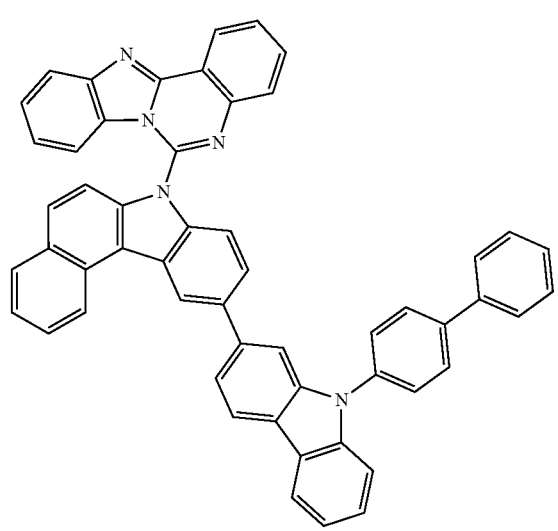
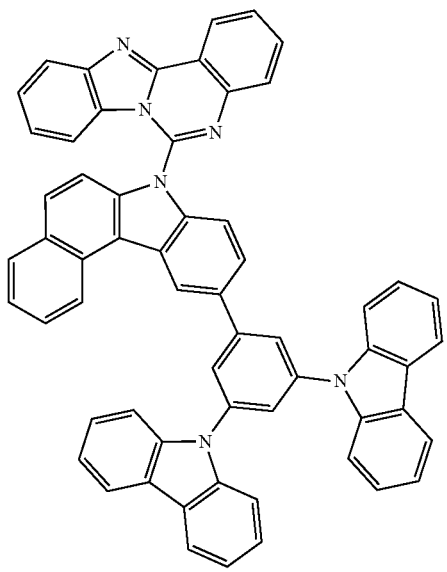
398
-continued
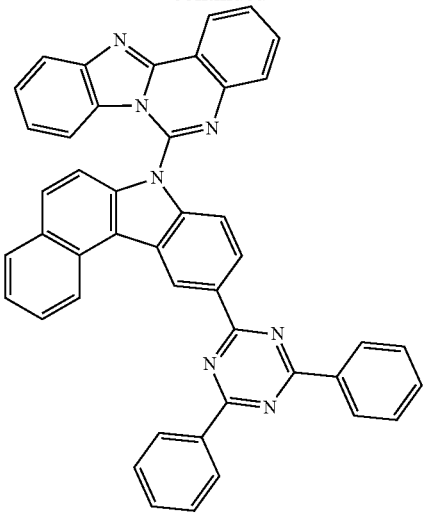
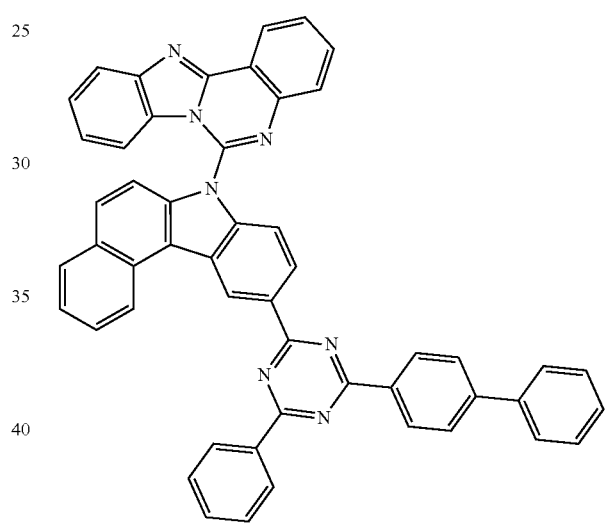
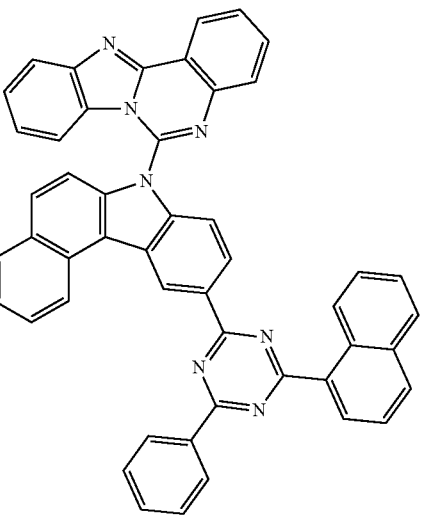

399
-continued
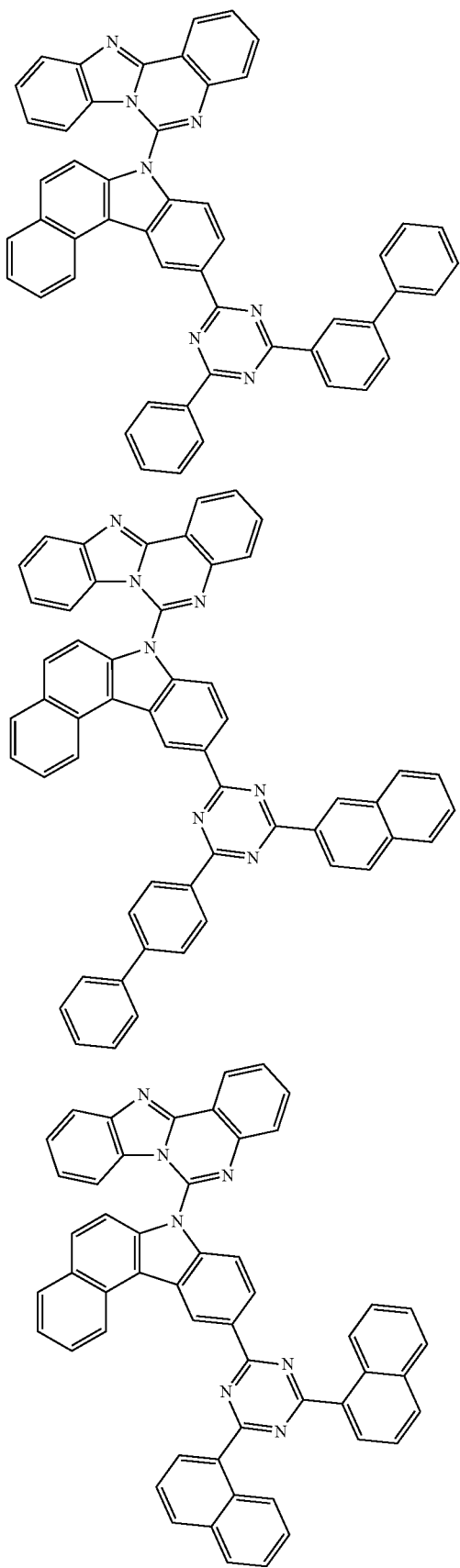
400
-continued
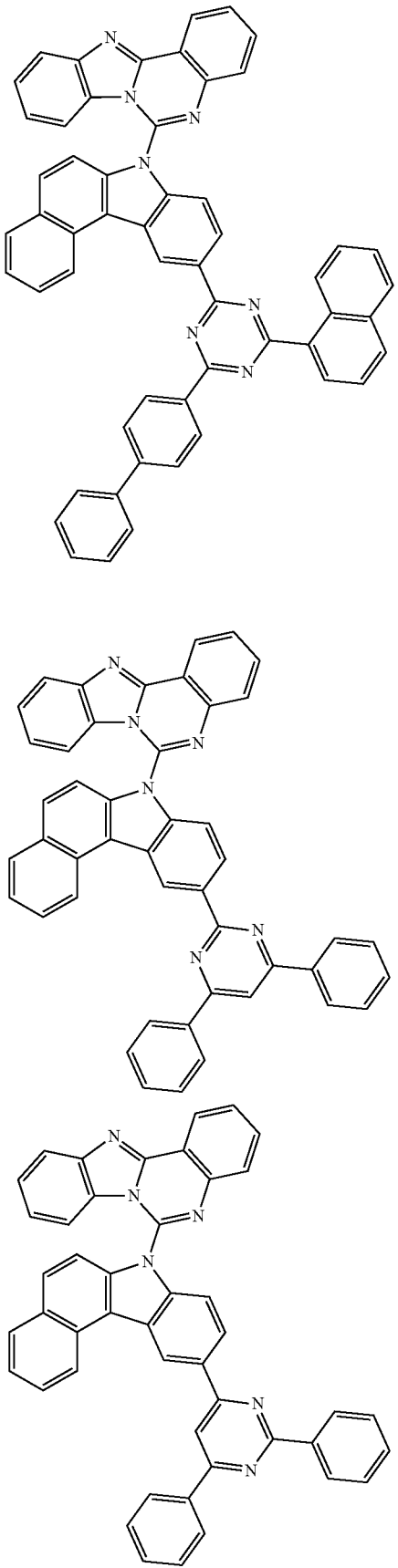

401
-continued
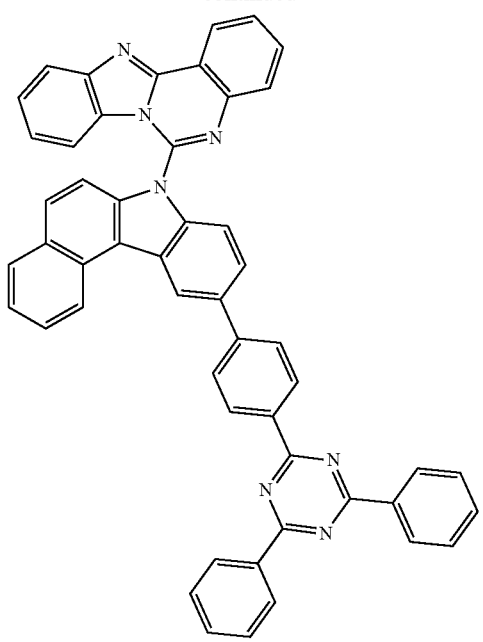
402
-continued
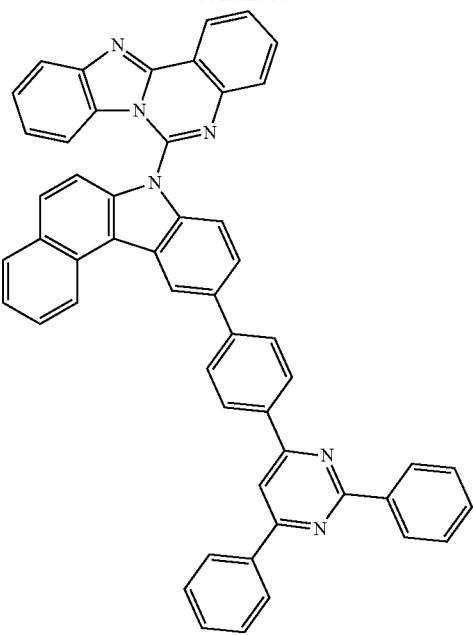
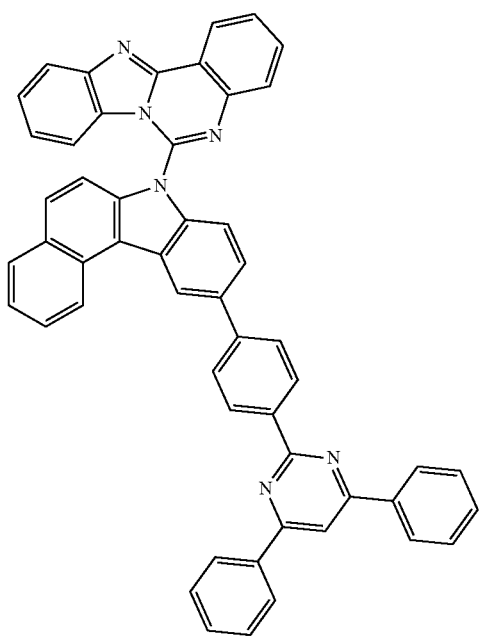
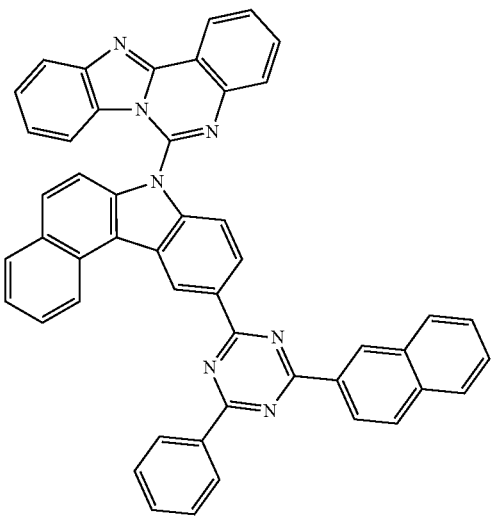

403
-continued
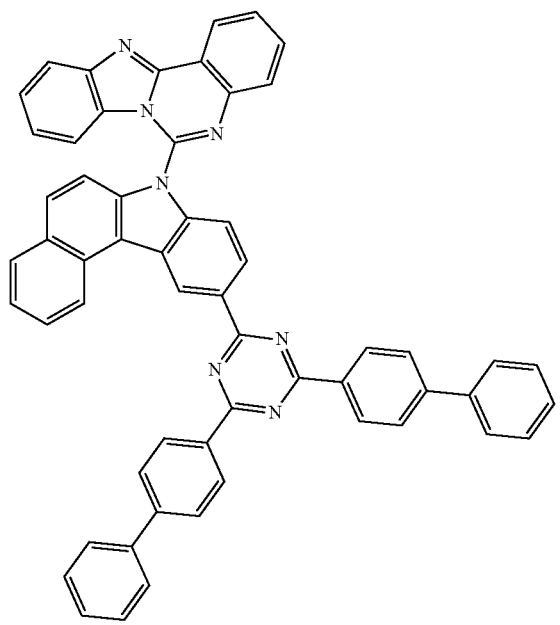
404
-continued
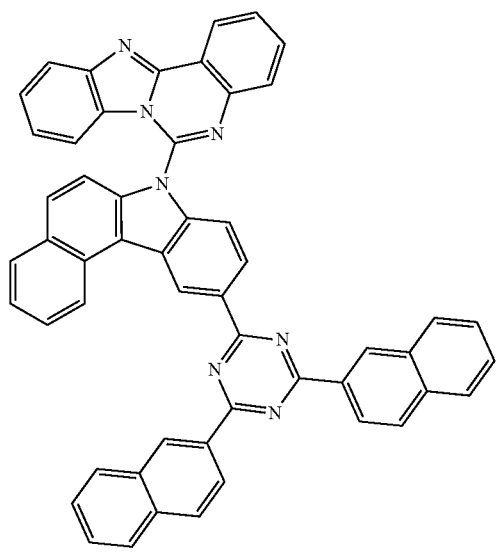
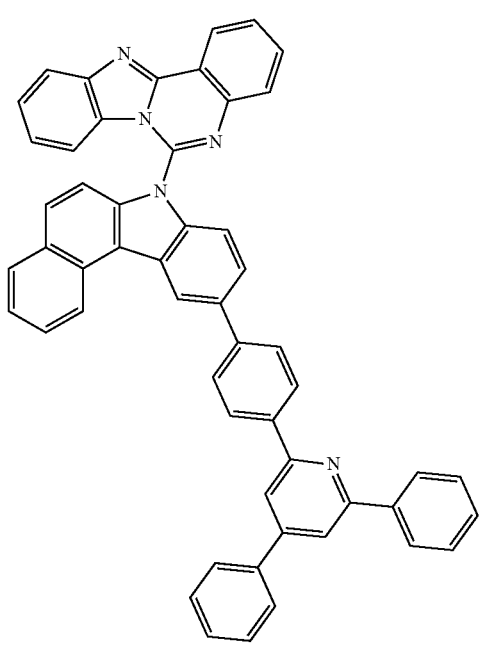
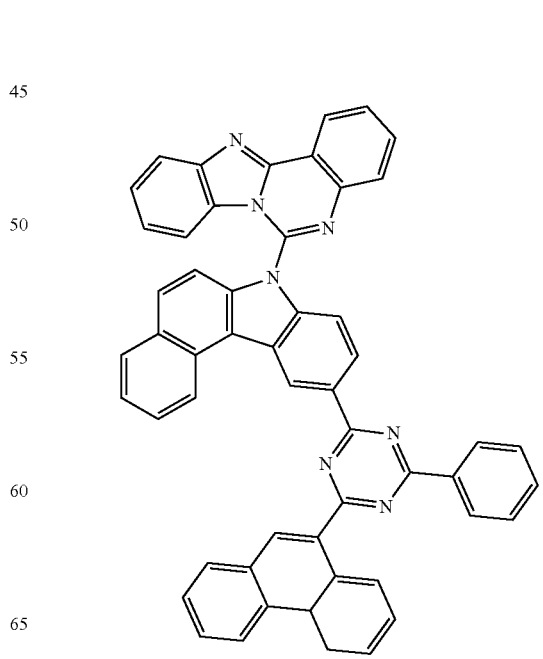

405
-continued
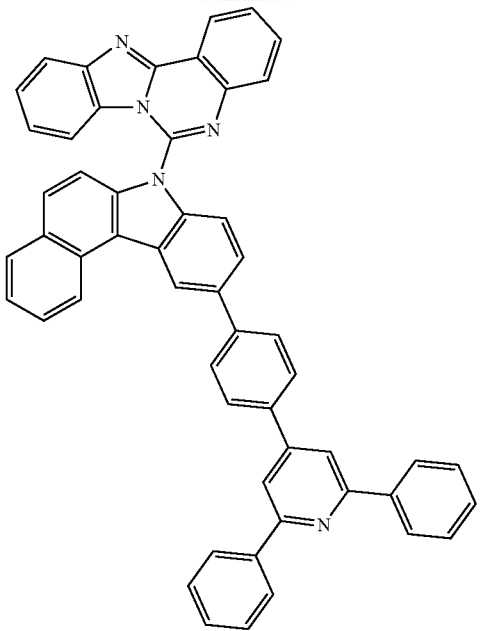
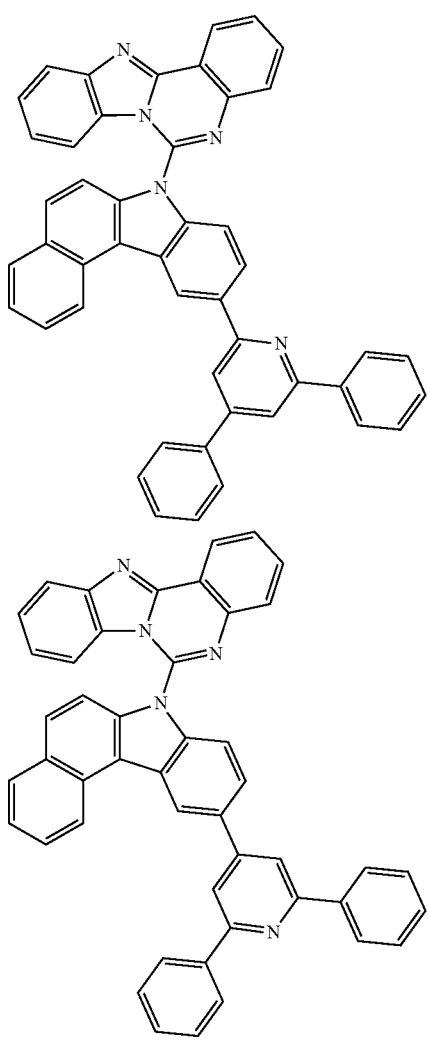
406
-continued
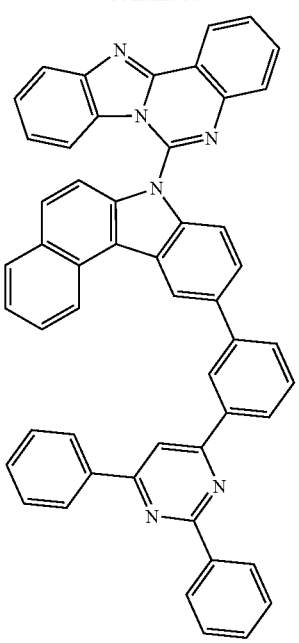
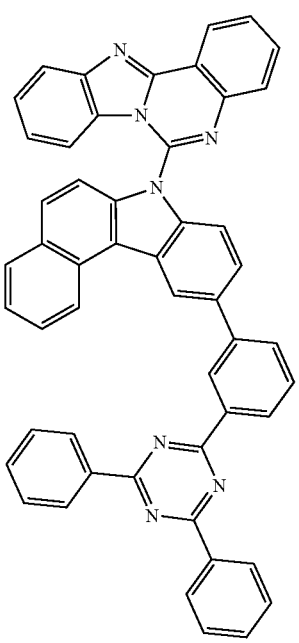

407
-continued
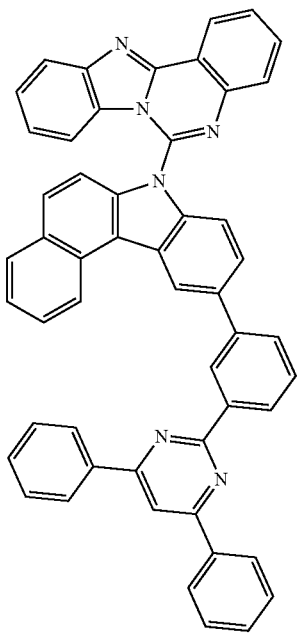
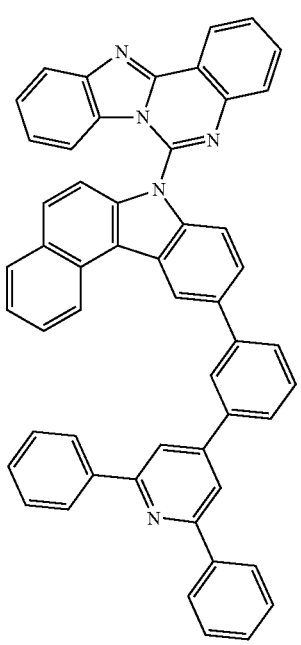
408
-continued
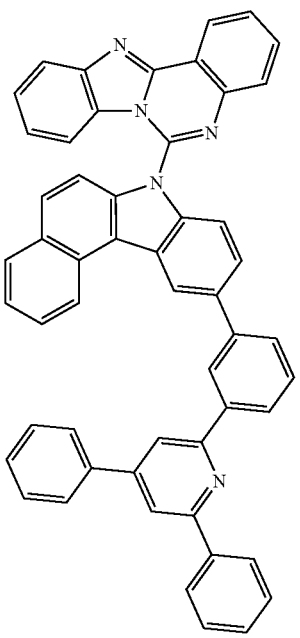

409
-continued
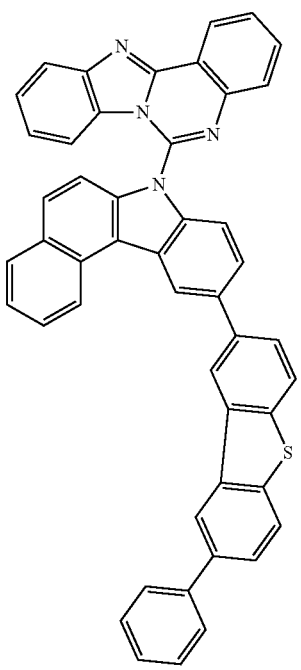
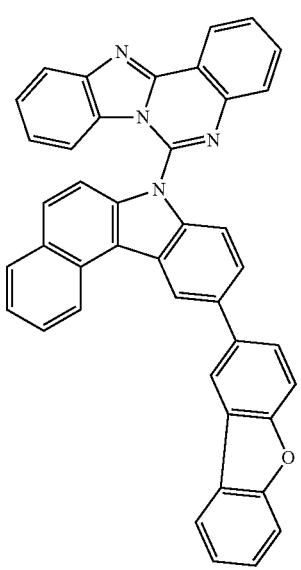
410
-continued
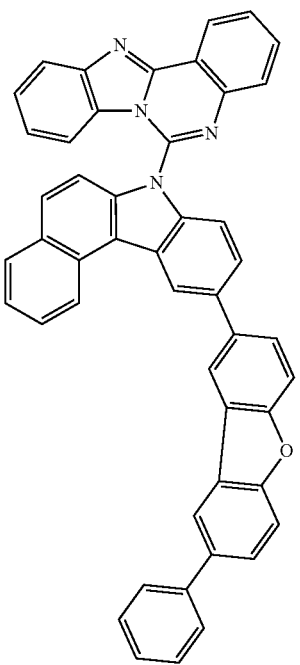
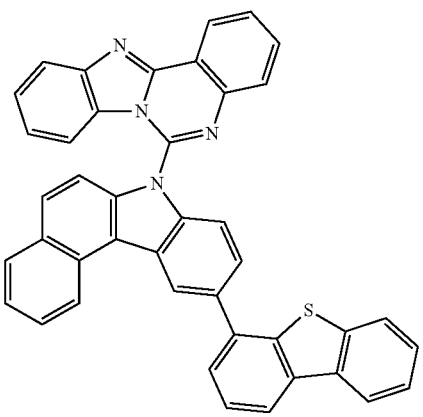
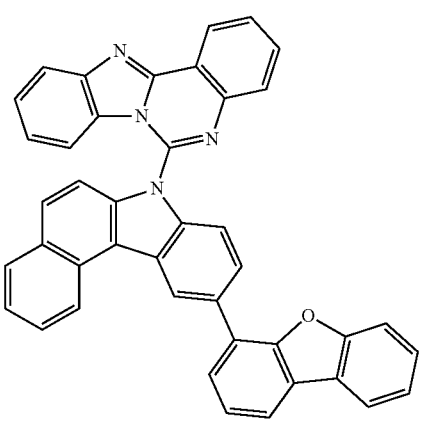

411
-continued
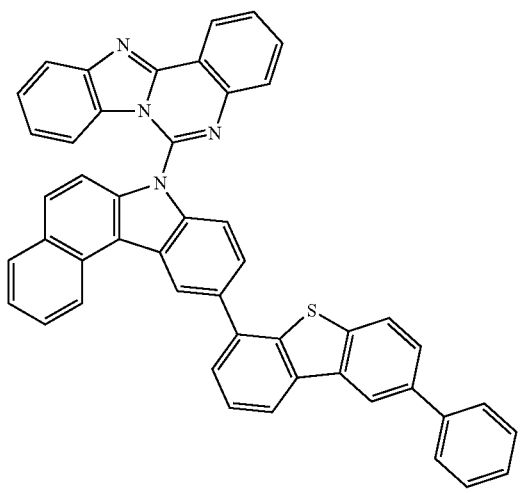
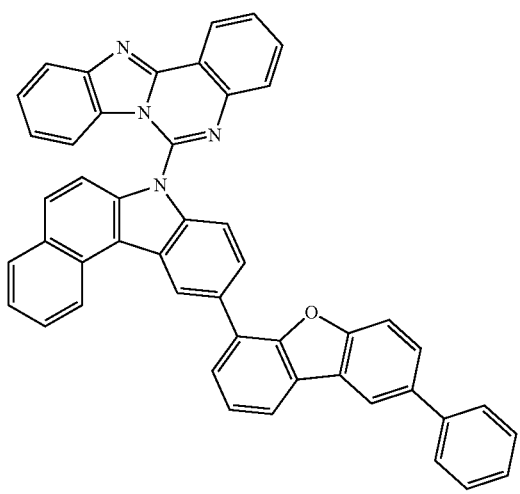
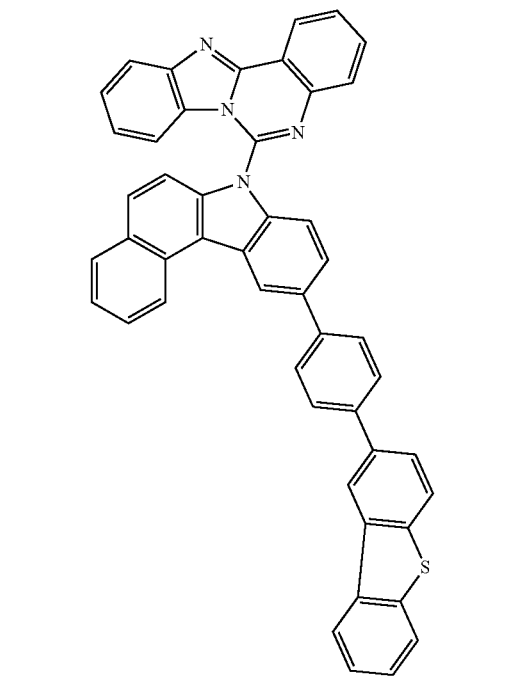
412
-continued
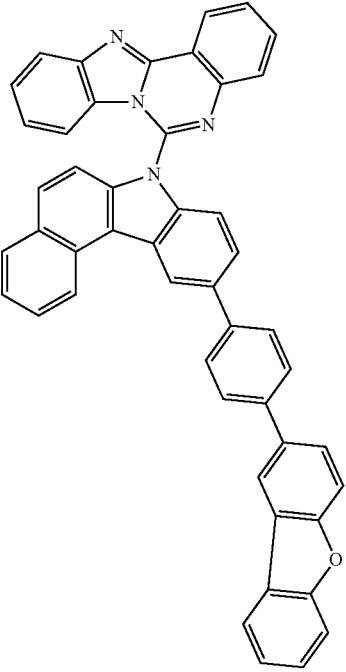
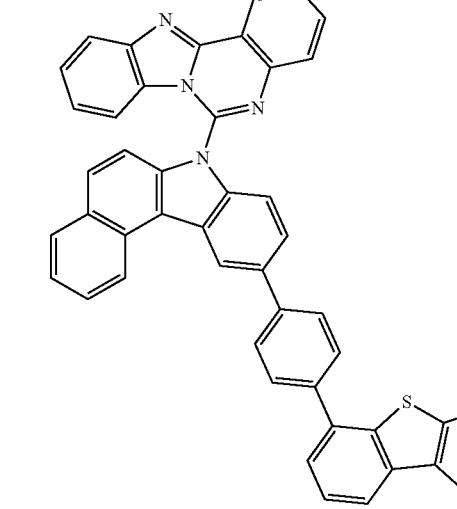
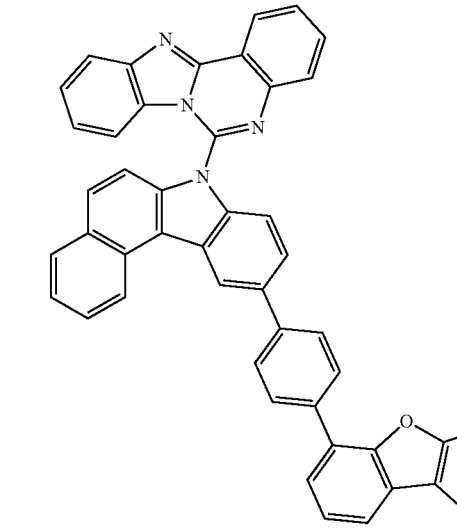

413
-continued
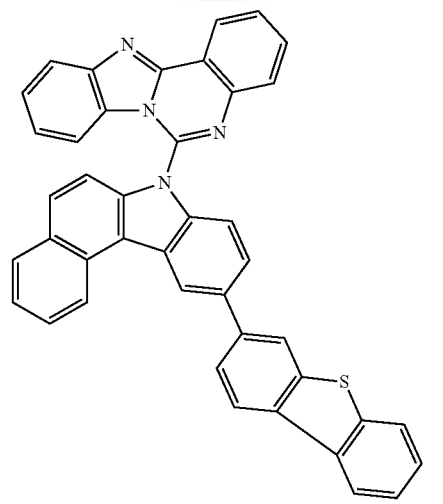
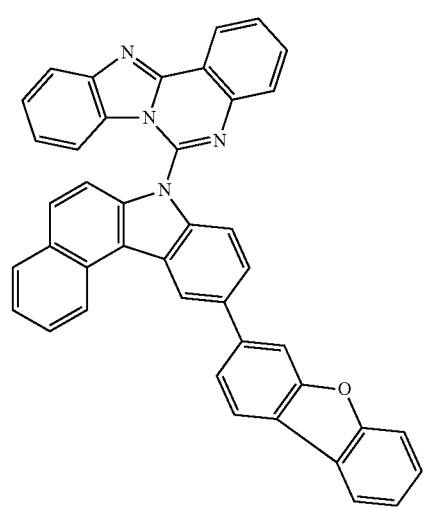
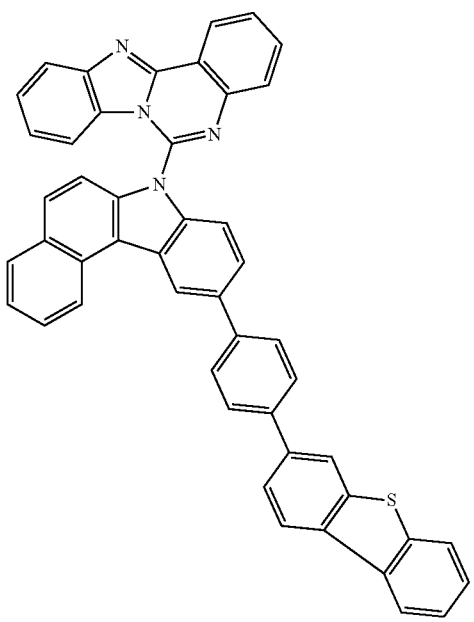
414
-continued
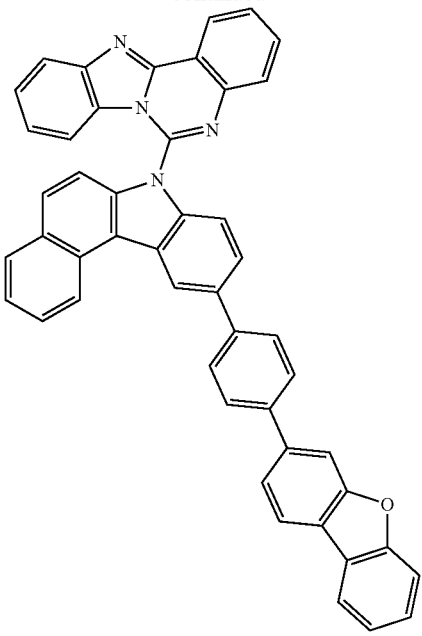
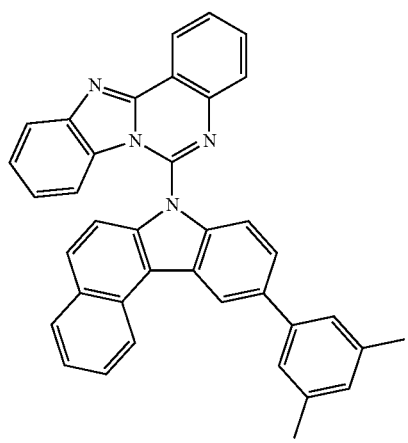
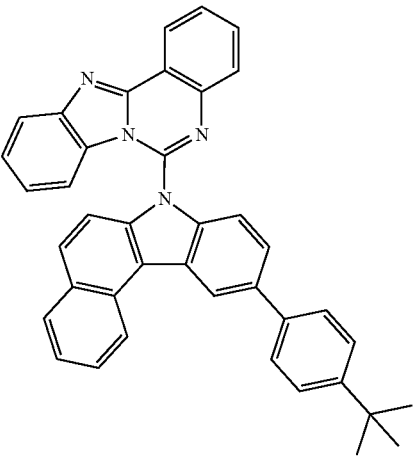

415
-continued
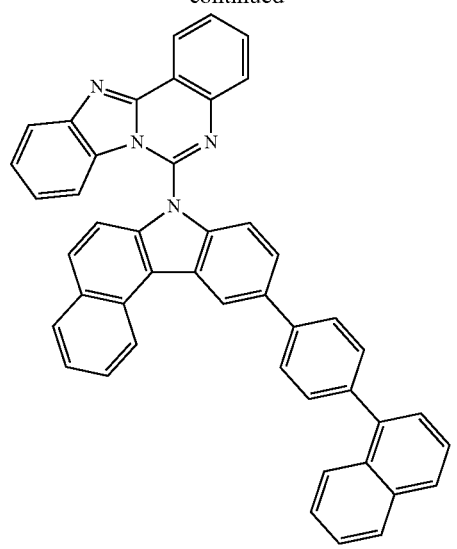
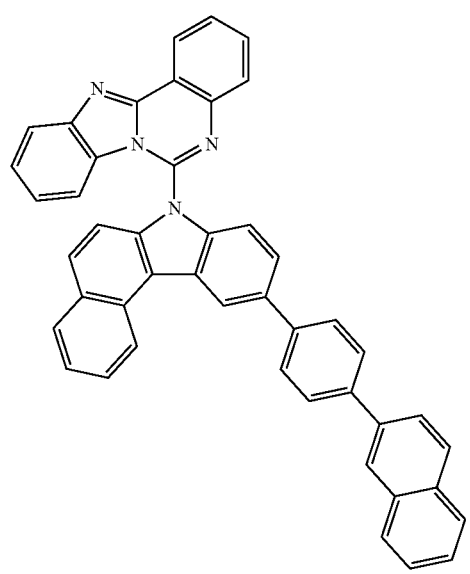
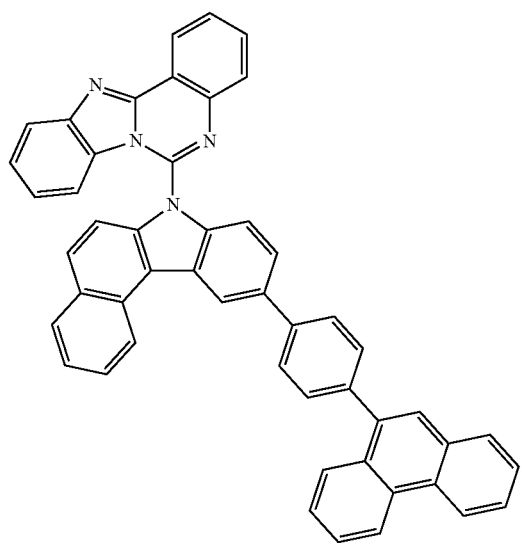
416
-continued
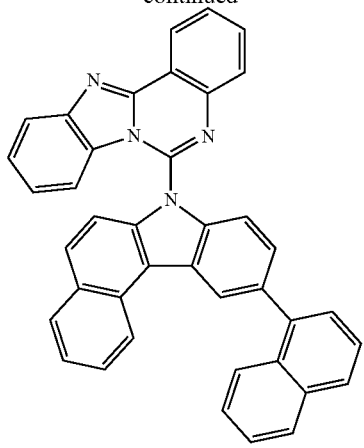
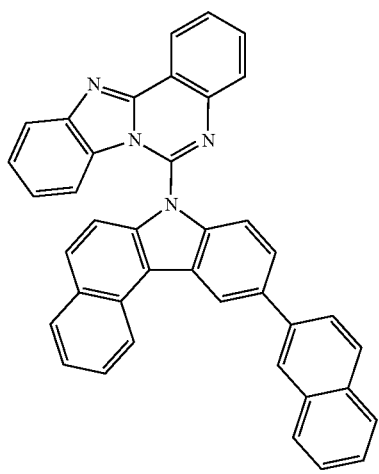
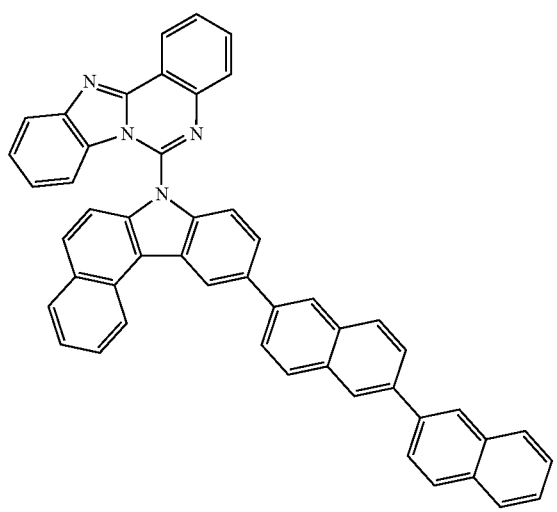

417
-continued
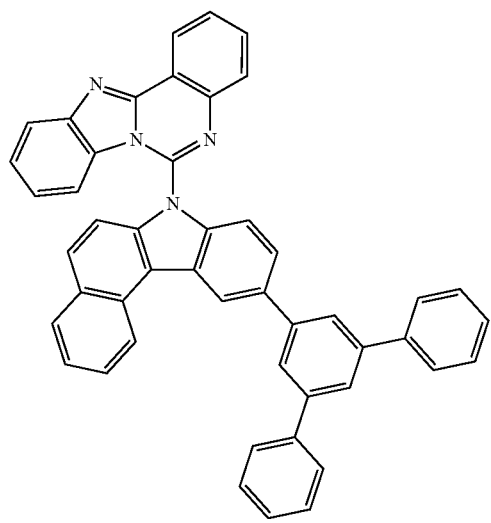
418
-continued
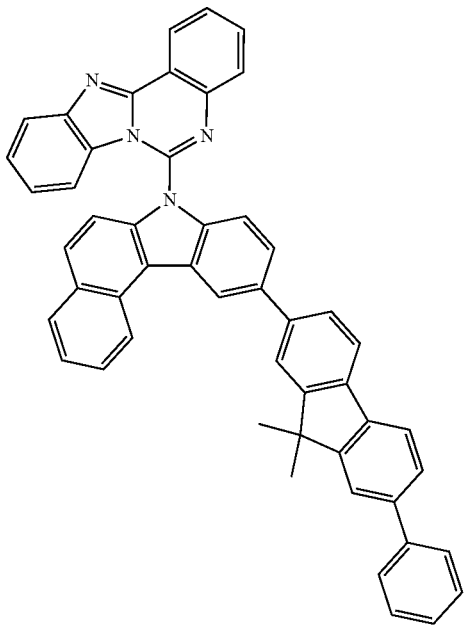
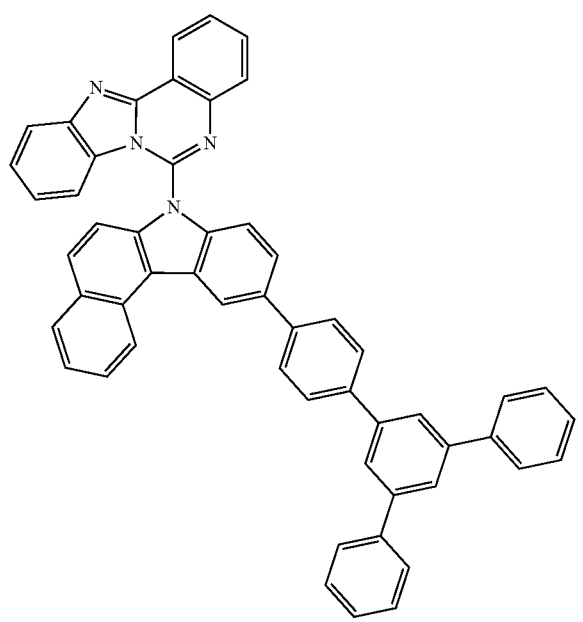
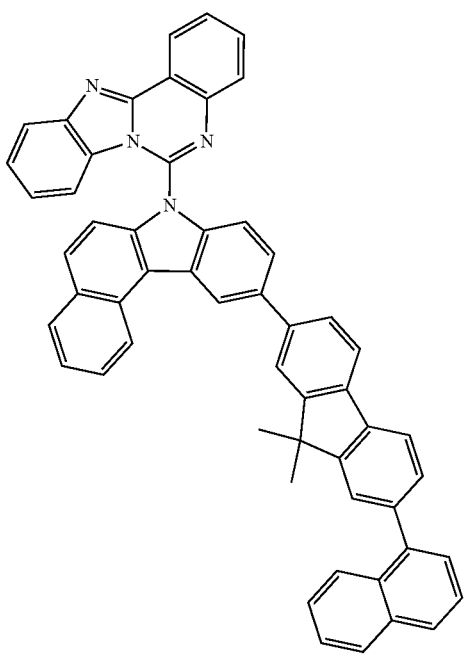

419
-continued
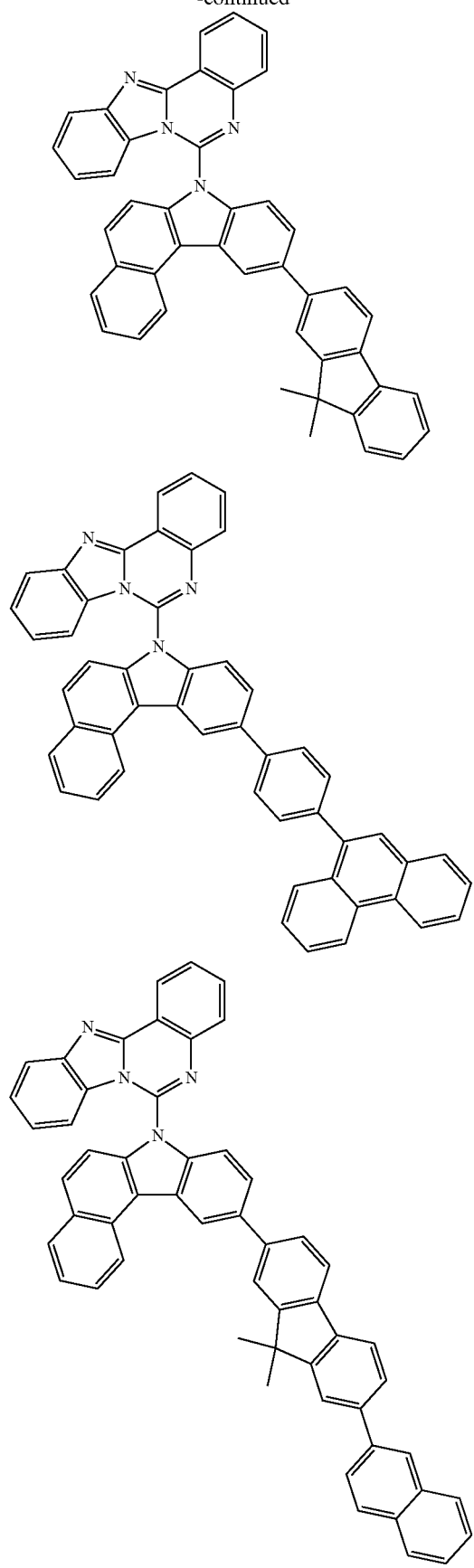
420
-continued
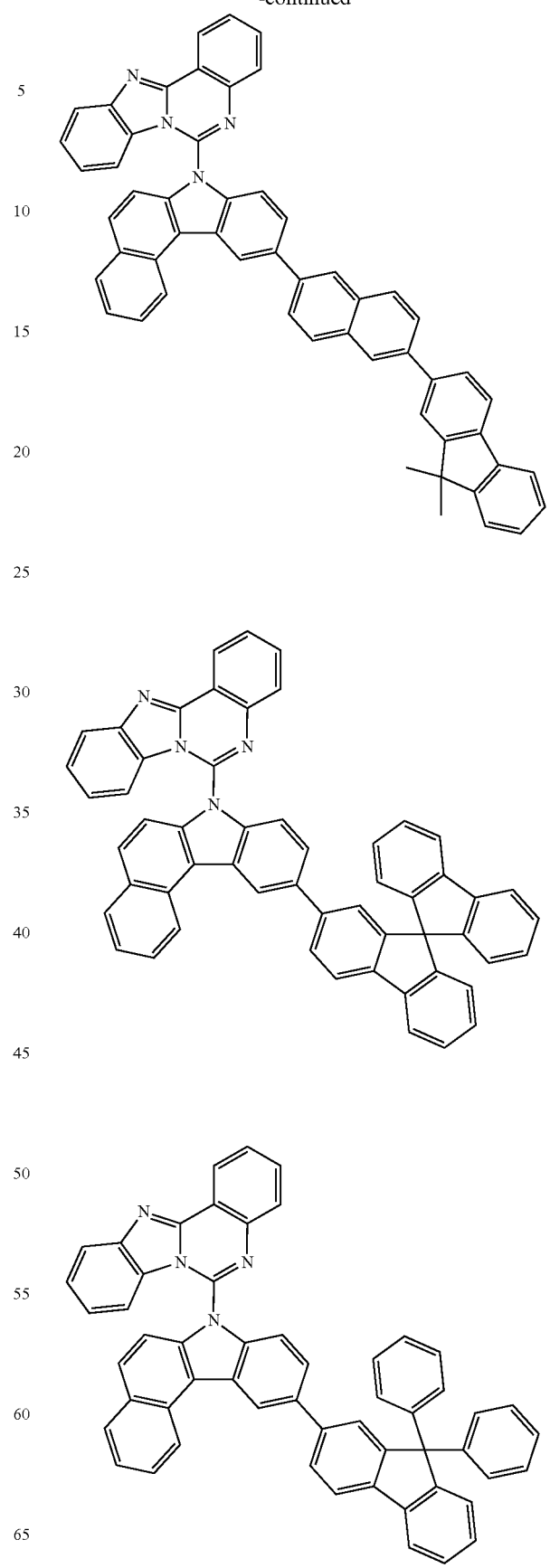

421
-continued
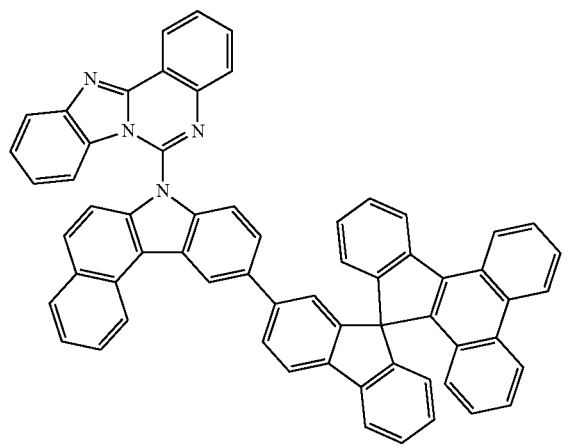
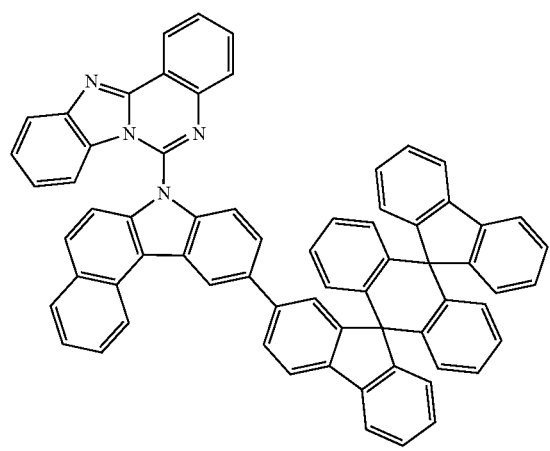
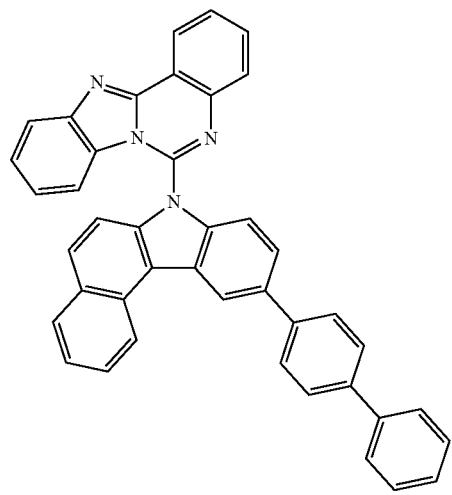
422
-continued
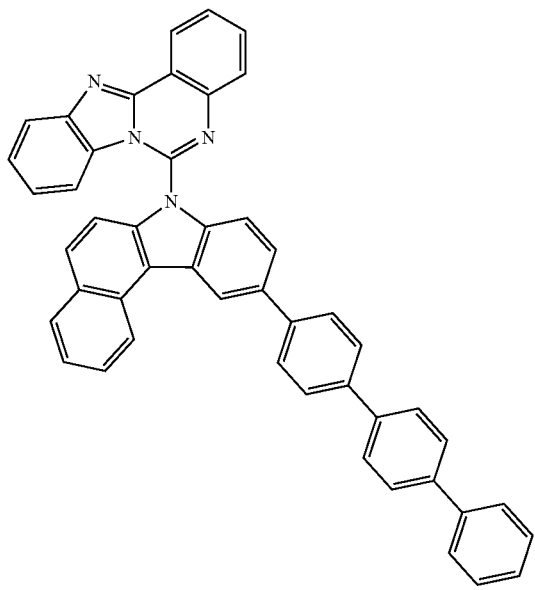
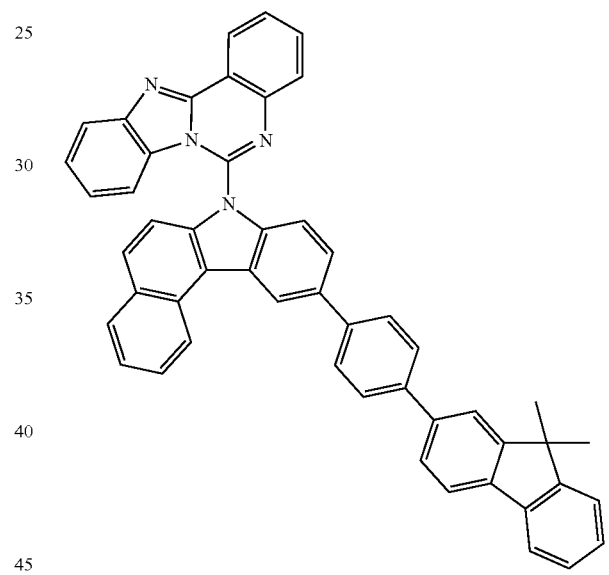
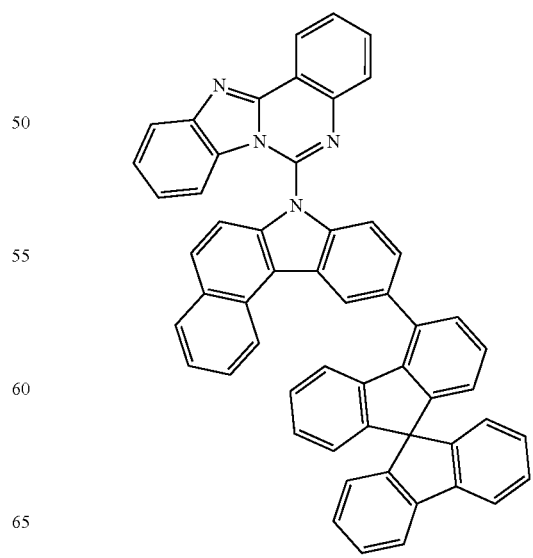

423
-continued
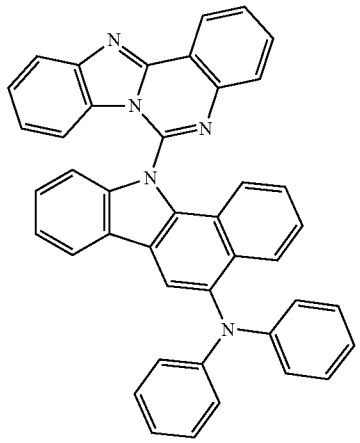
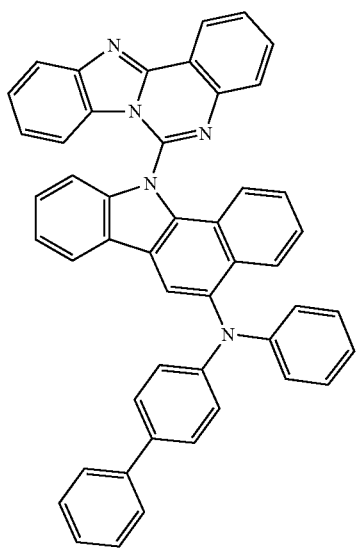
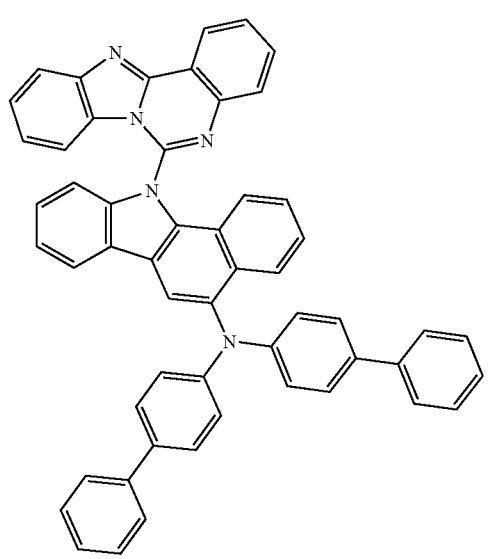
424
-continued
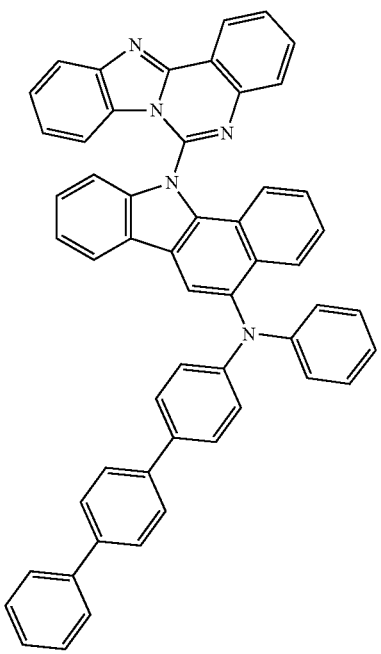
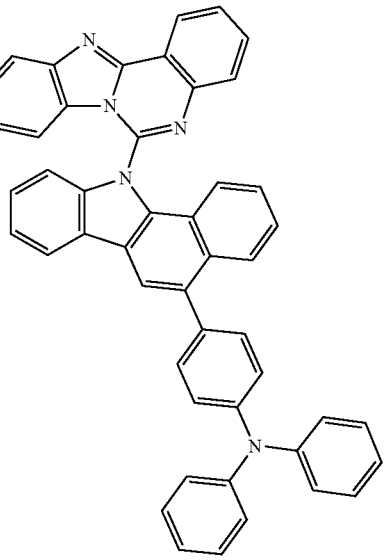

425
-continued
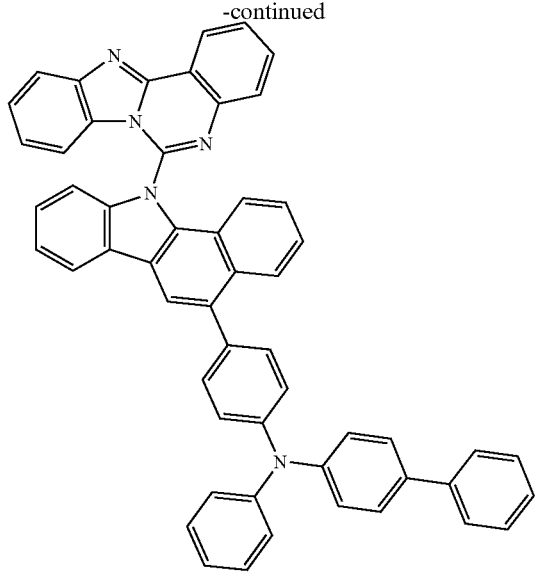
426
-continued
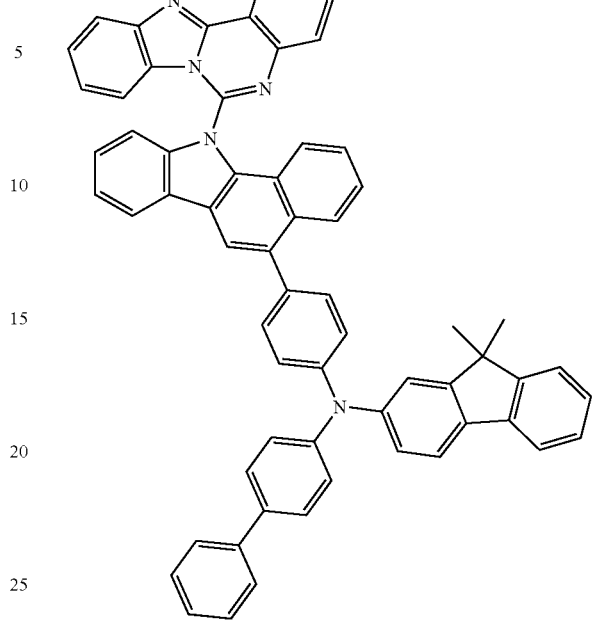
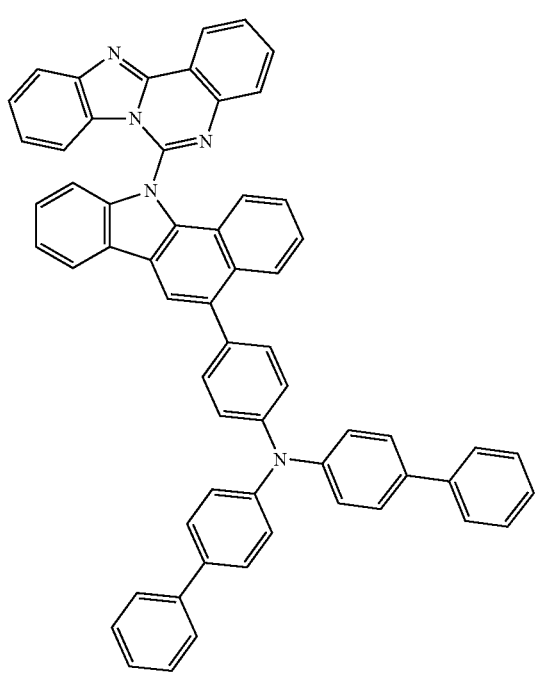
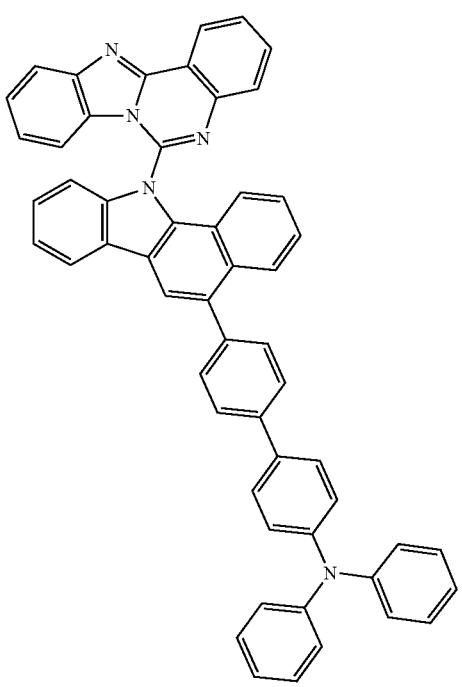

427
-continued
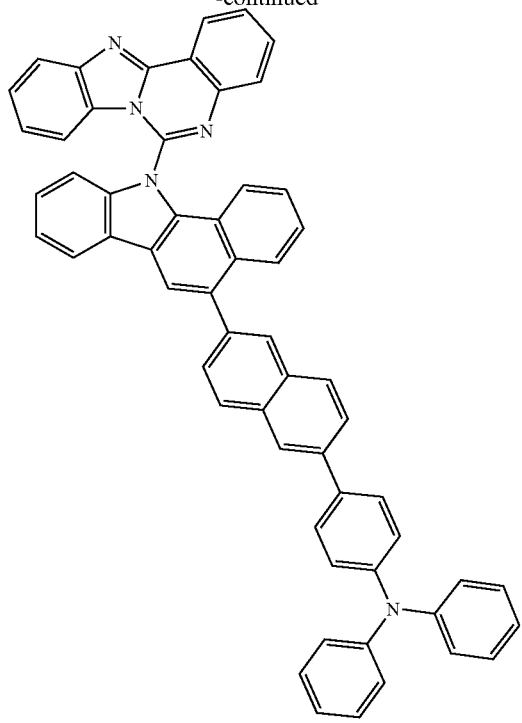
428
-continued
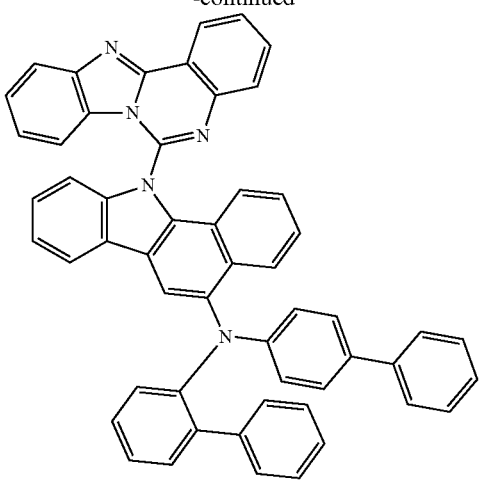
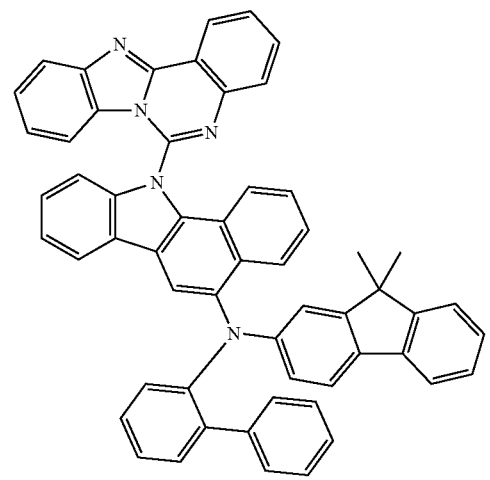
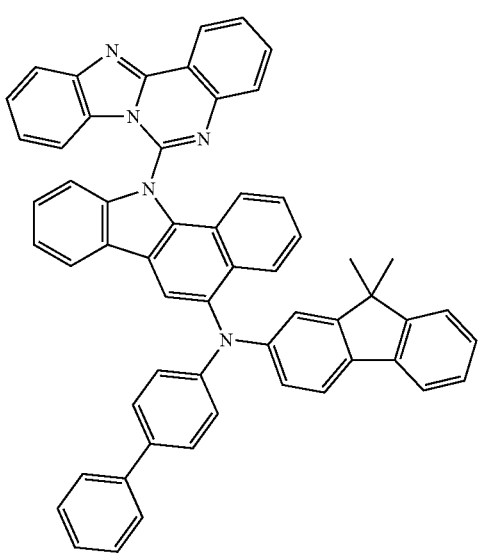
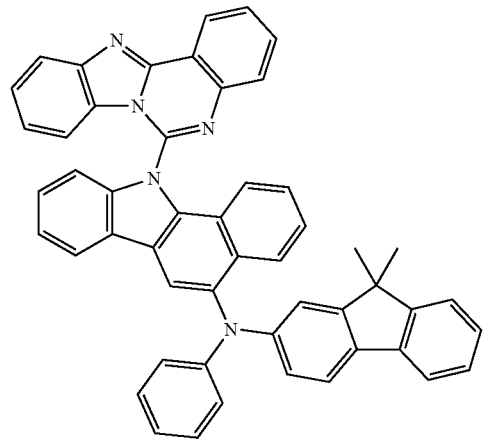
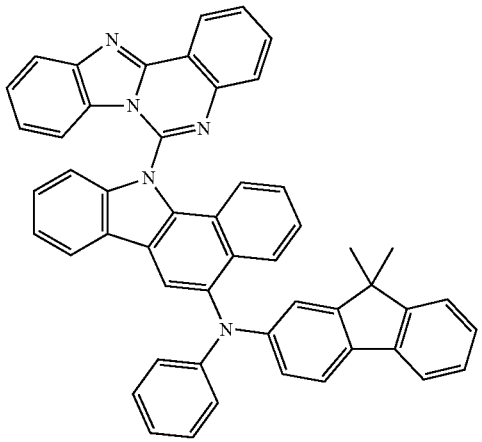

429
-continued
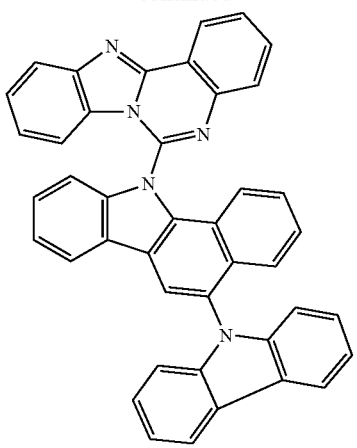
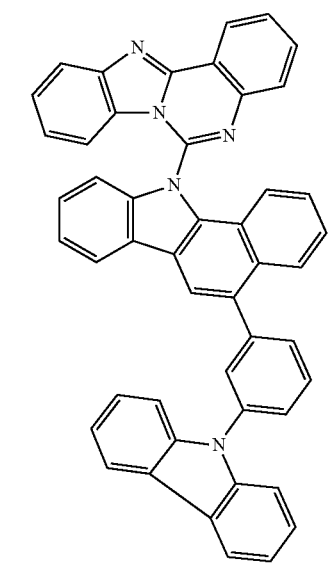
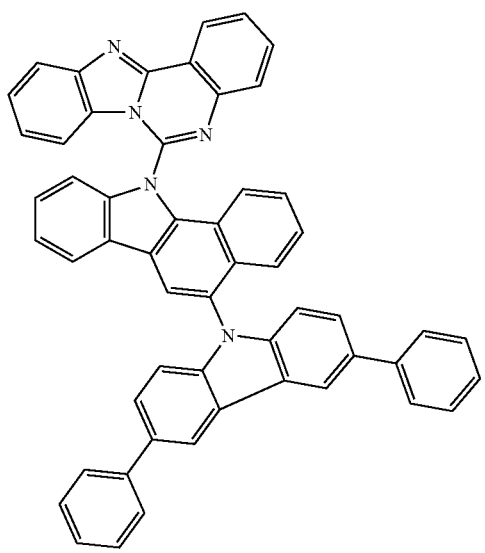
430
-continued
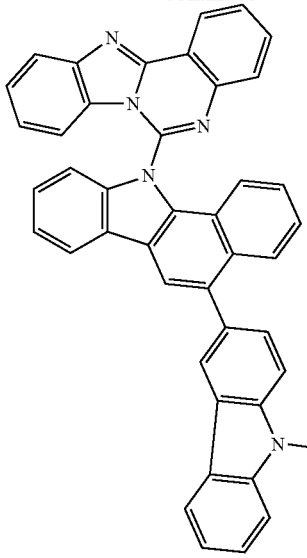
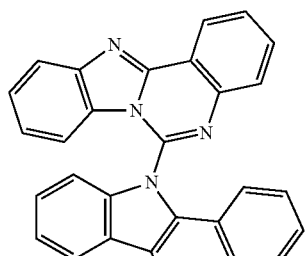
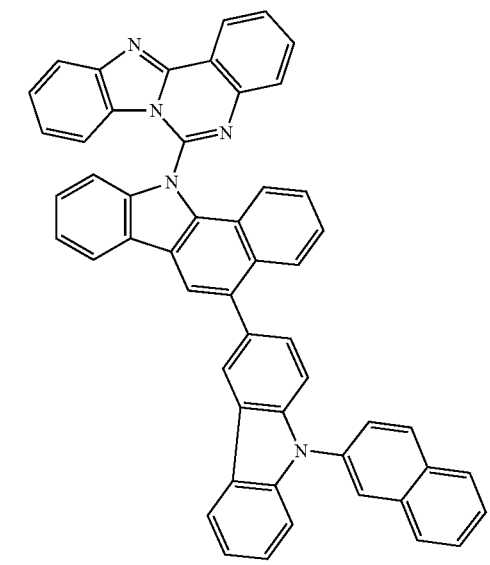
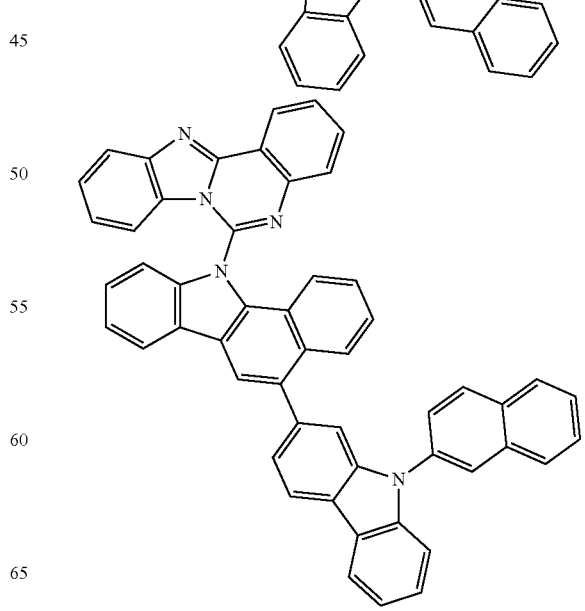

431
-continued
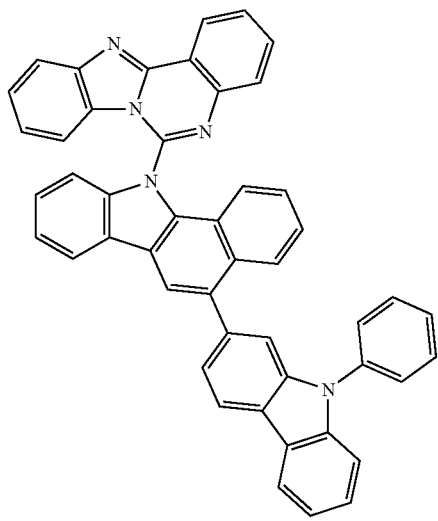
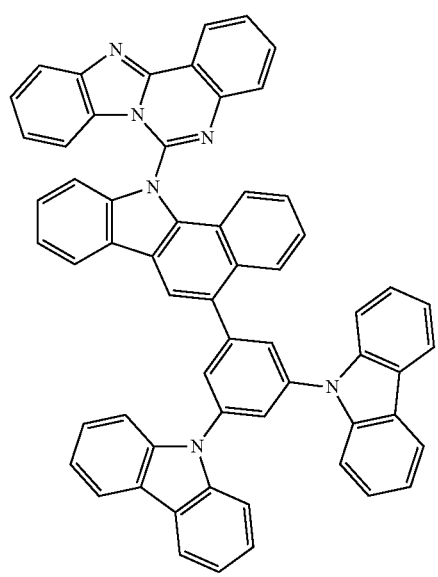
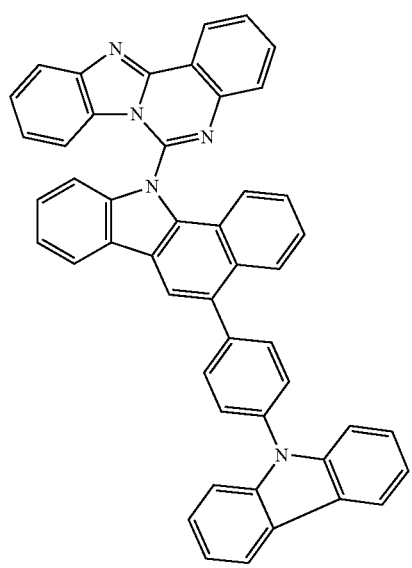
432
-continued
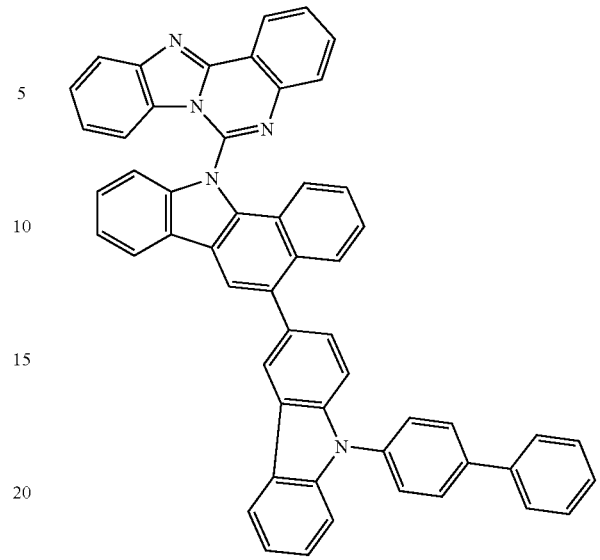
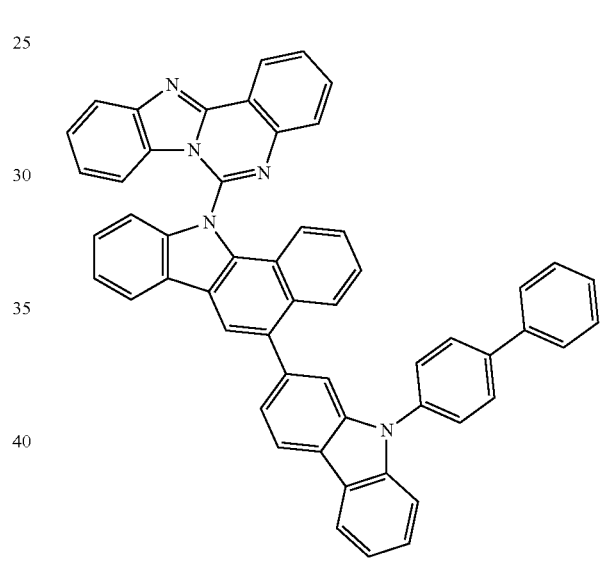
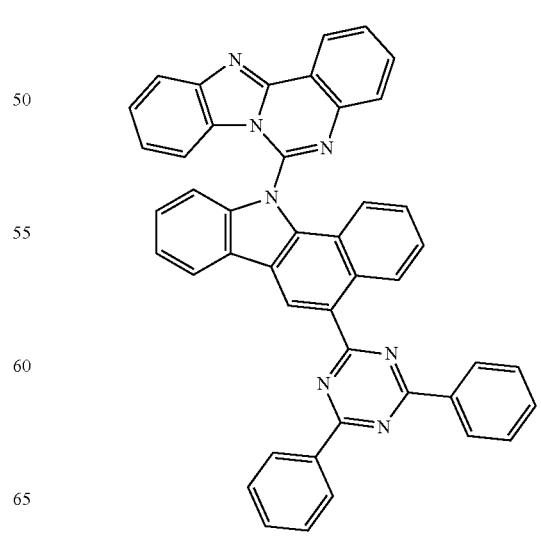

433
-continued
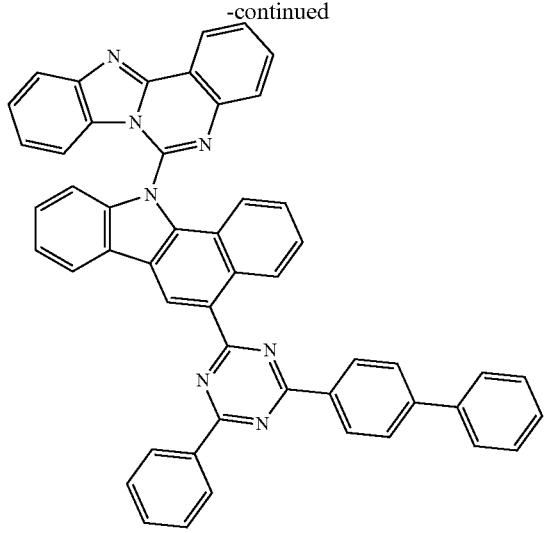
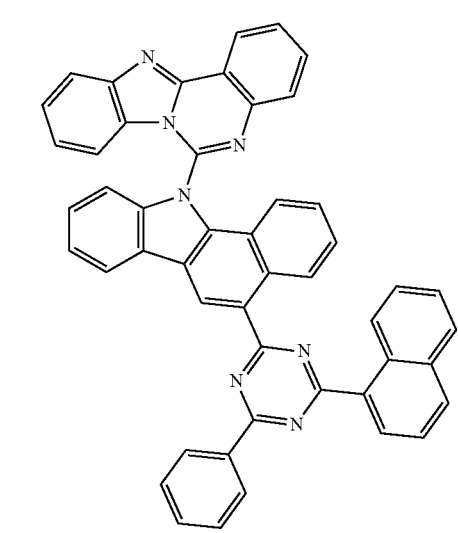
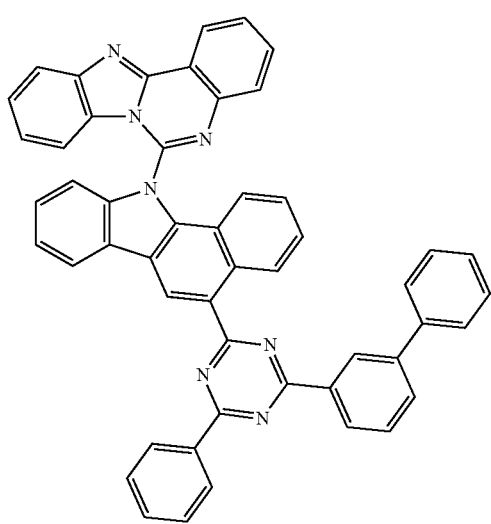
434
-continued
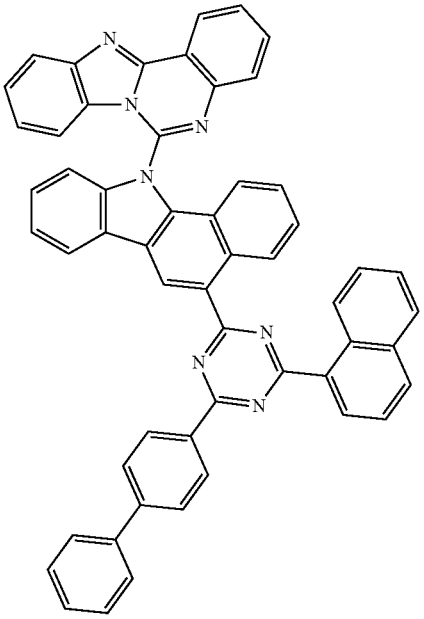
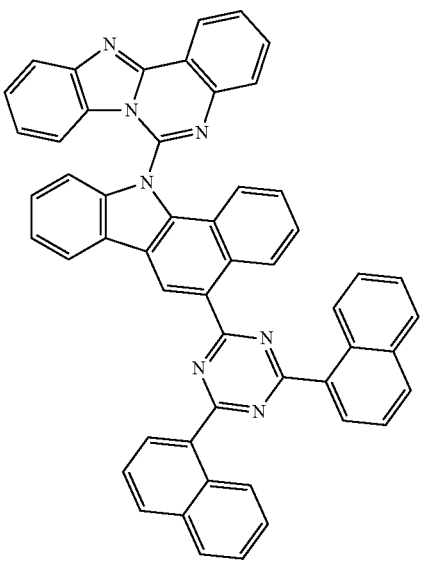

435
-continued
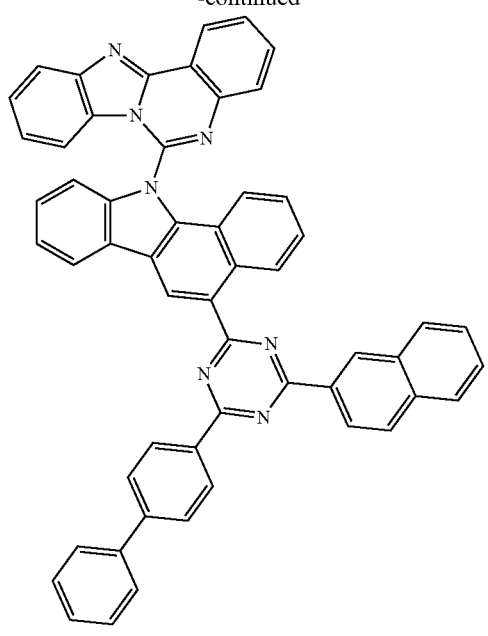
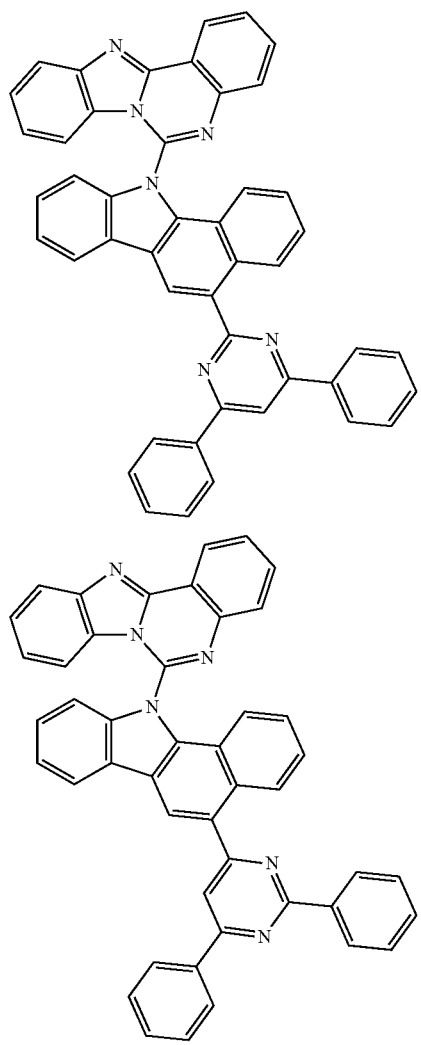
436
-continued
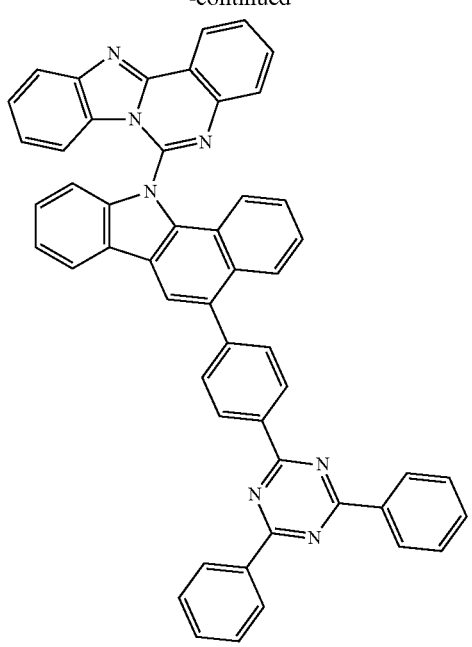
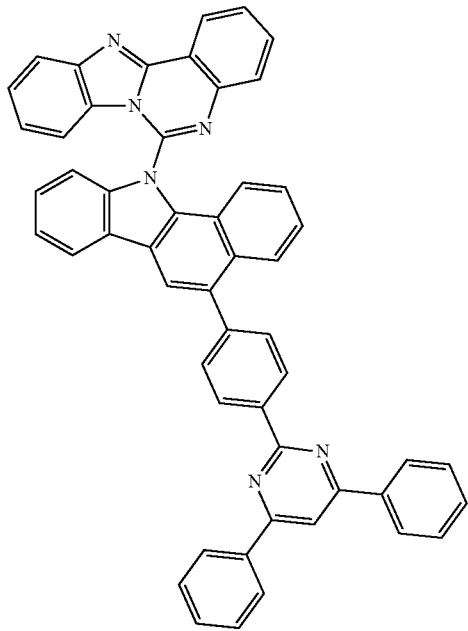

437
-continued
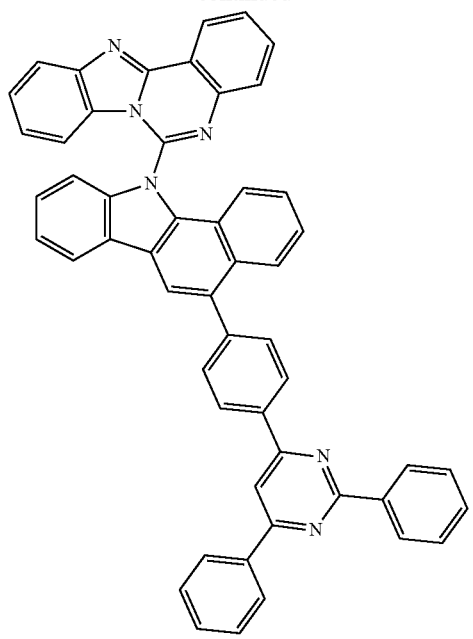
438
-continued
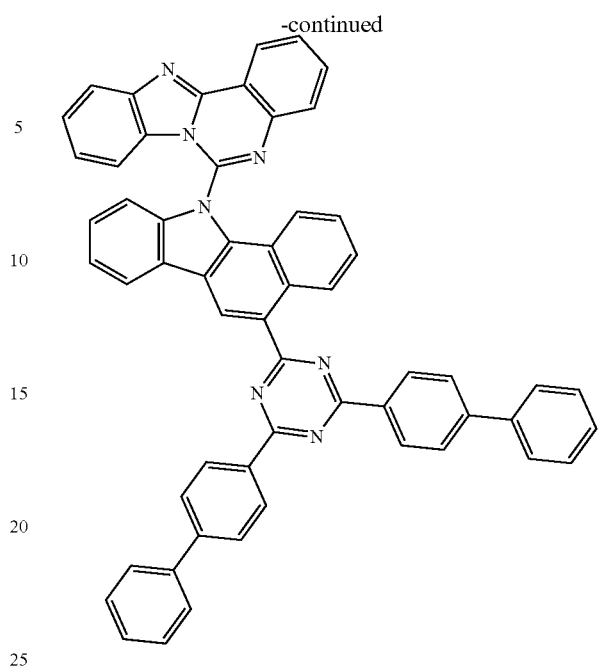
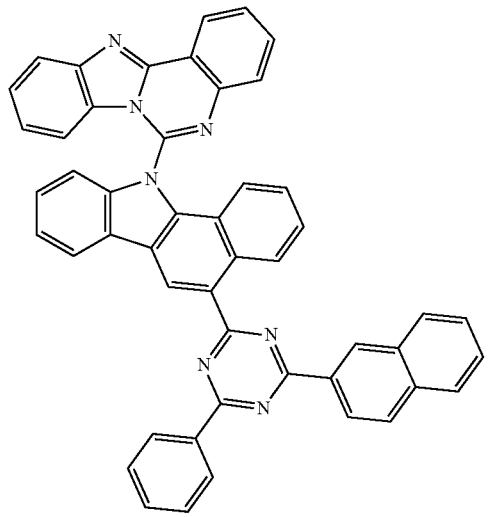
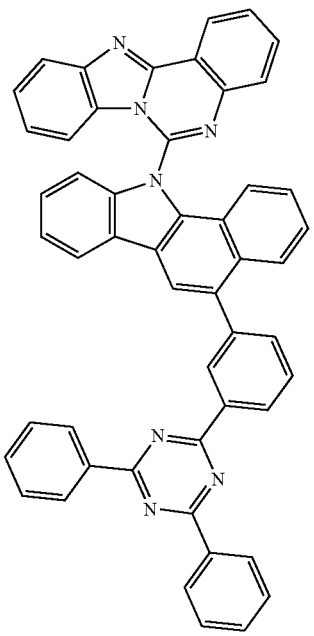

439
-continued
440
-continued
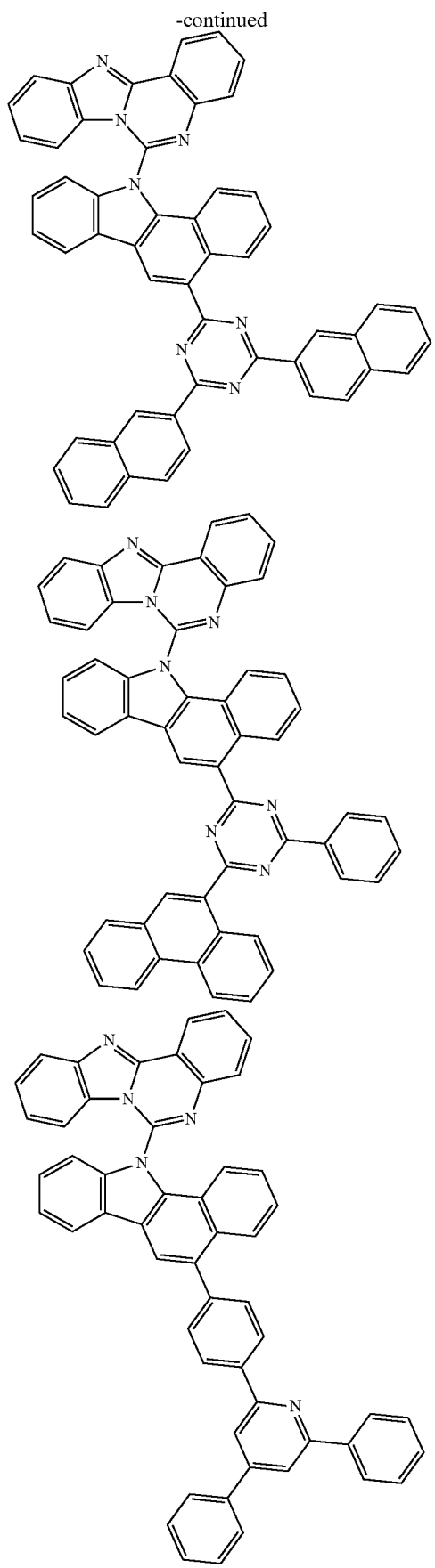
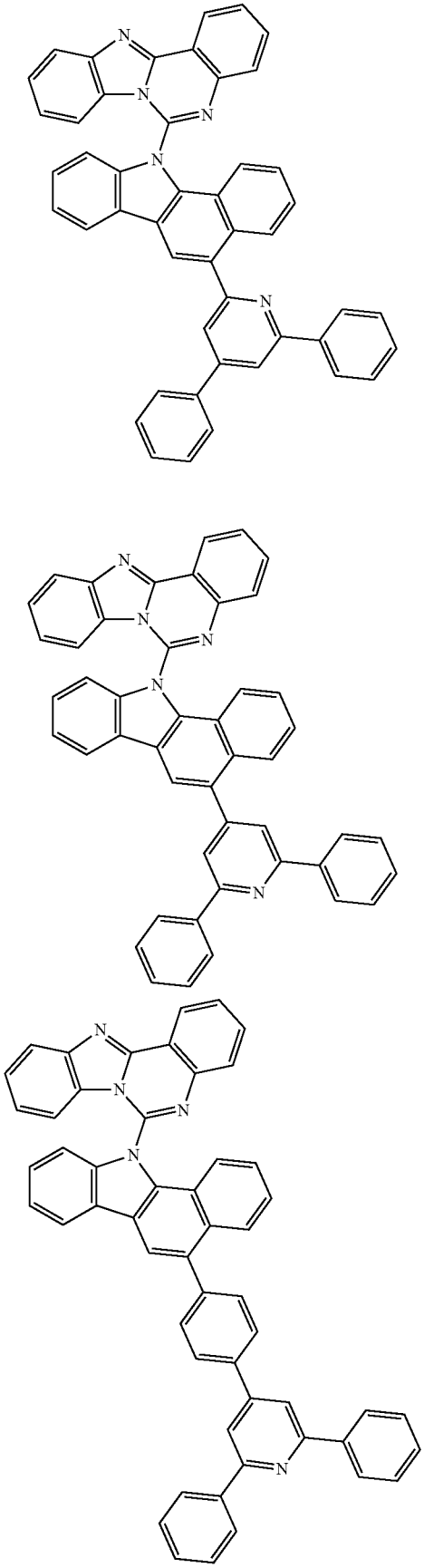

441
-continued
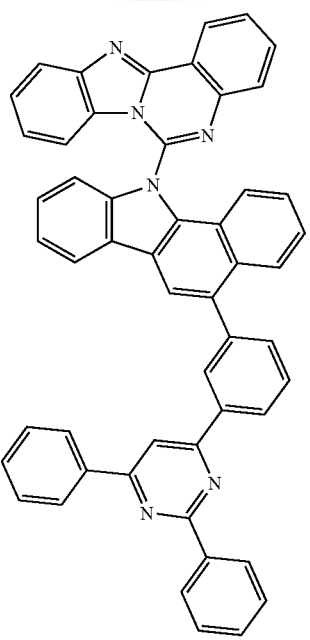
442
-continued
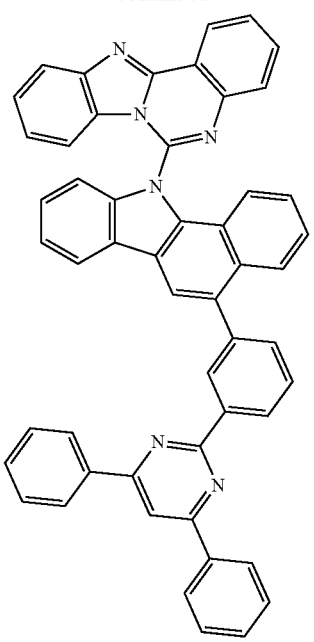
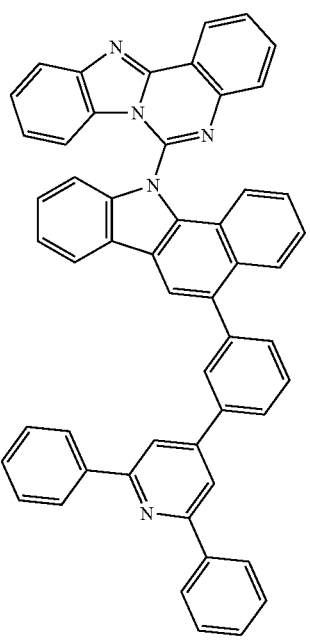
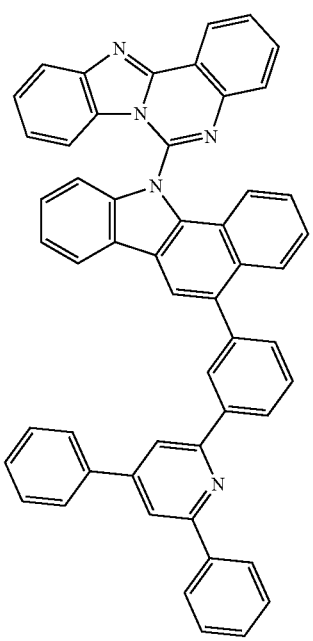

443
-continued
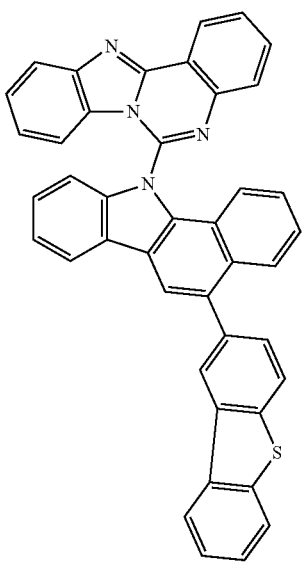
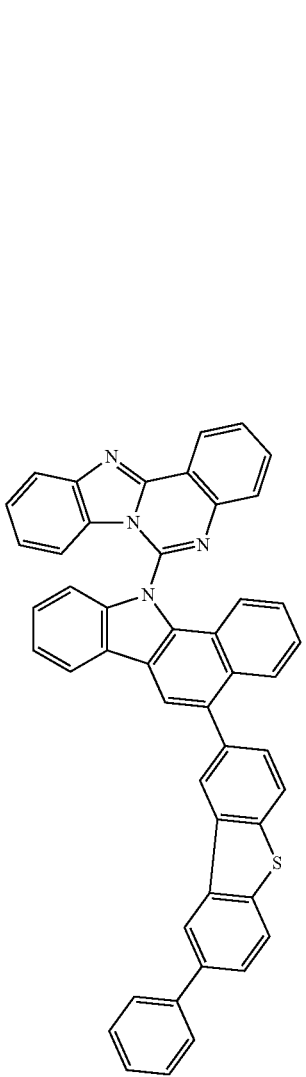
444
-continued
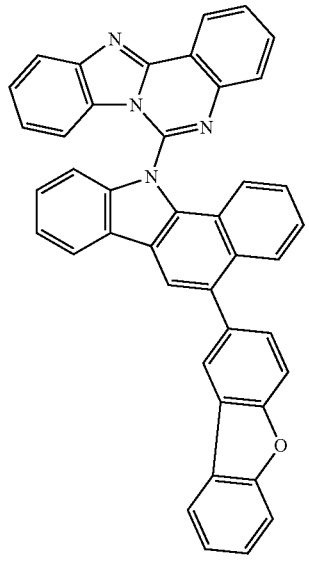

445
-continued
446
-continued
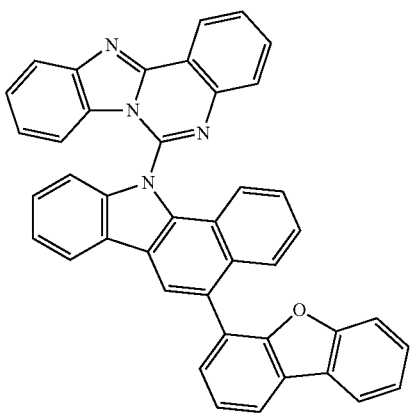
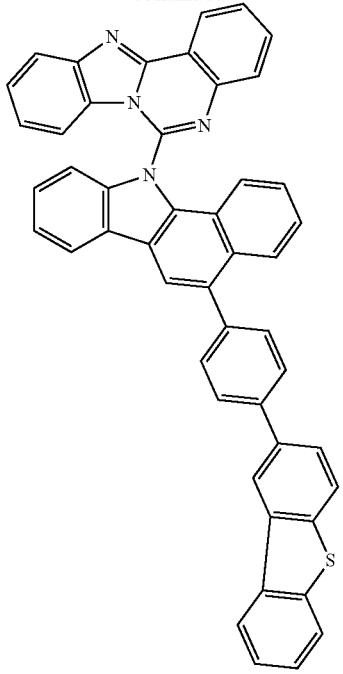
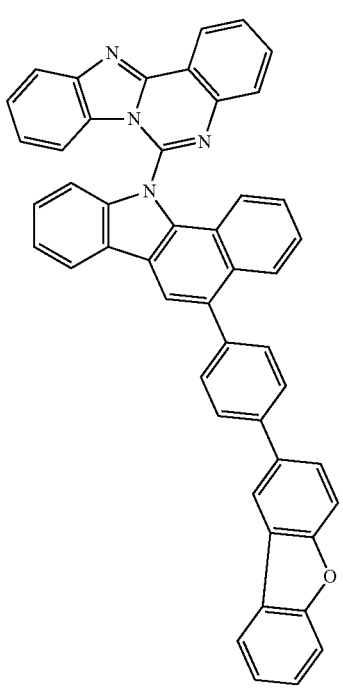

447
-continued
448
-continued
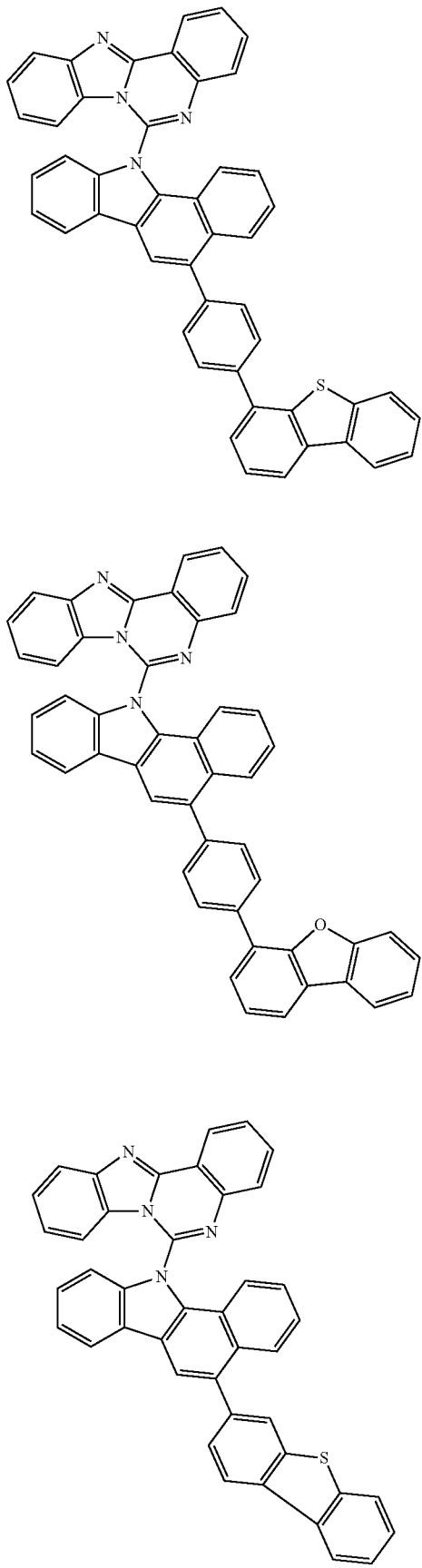
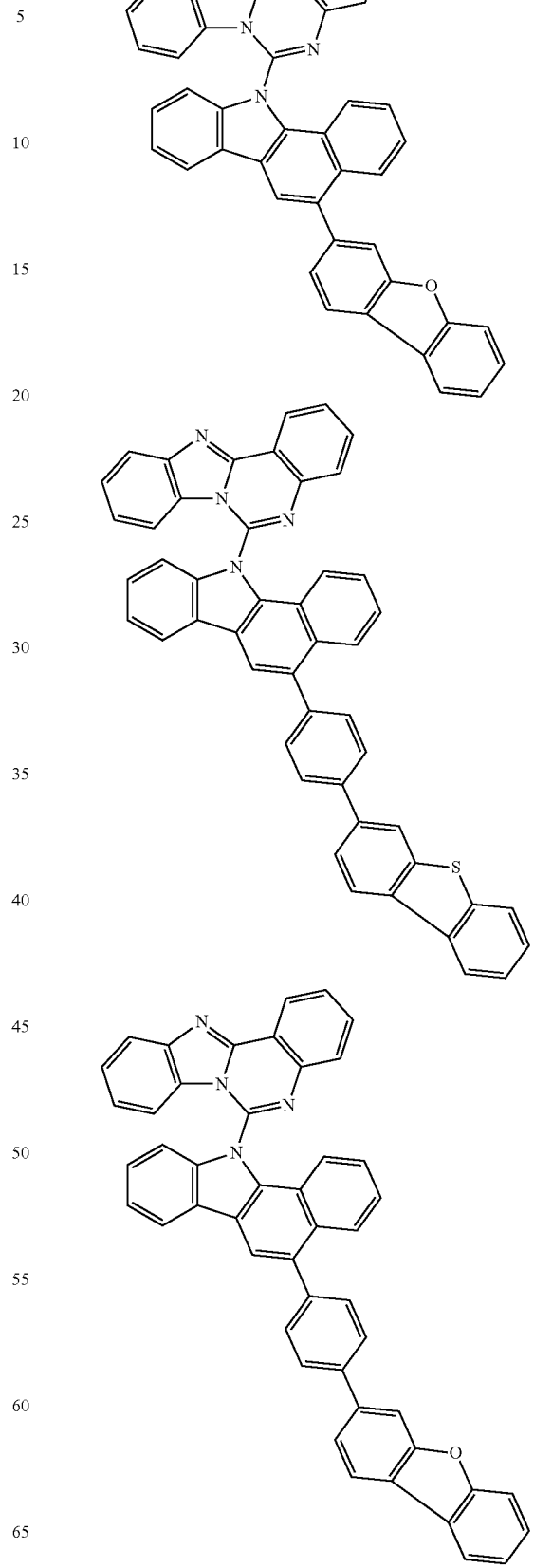

449
-continued
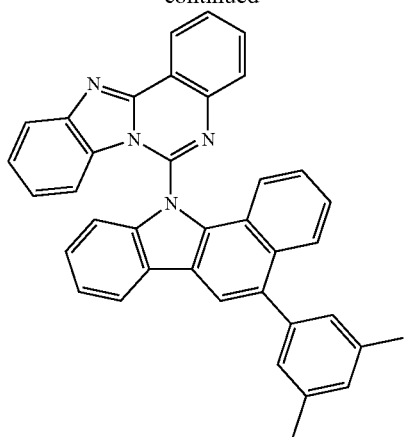
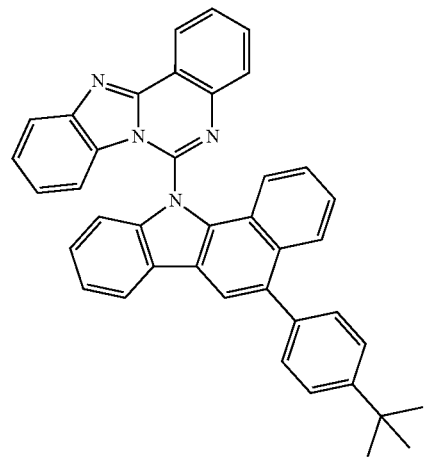
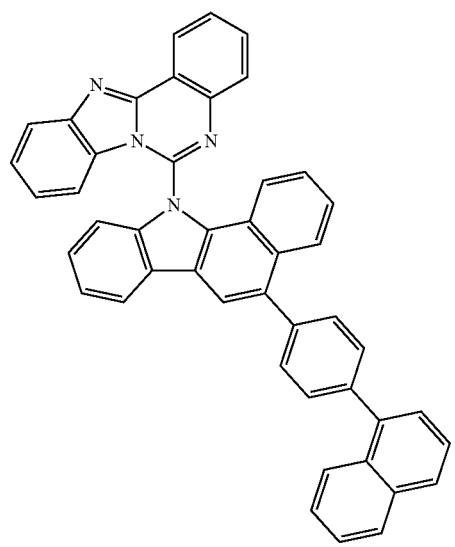
450
-continued
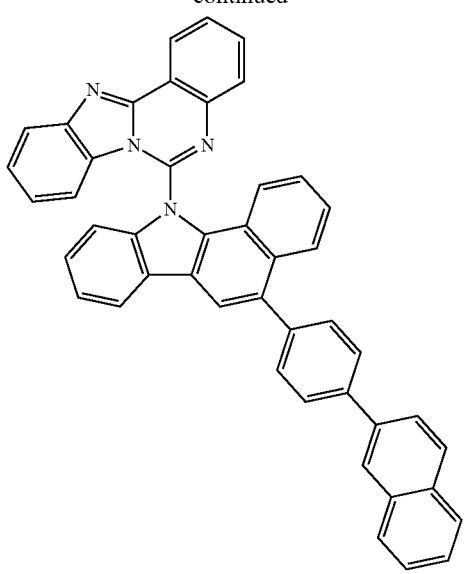
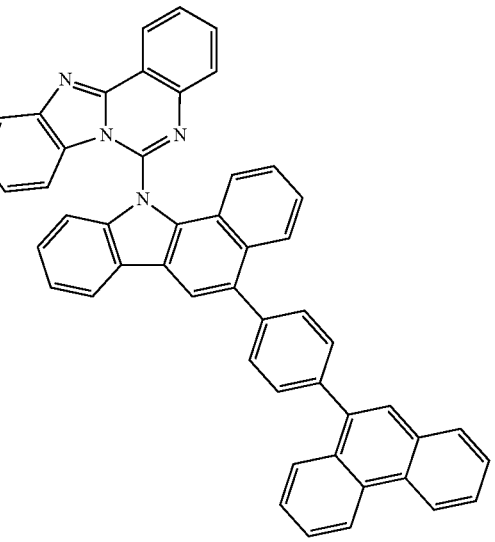
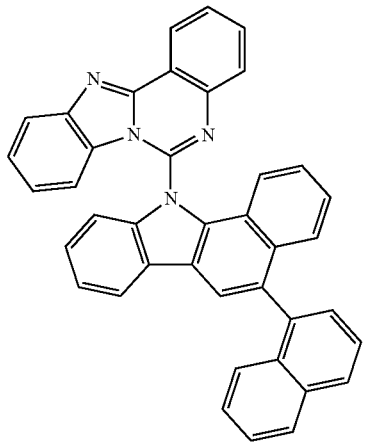

451
-continued
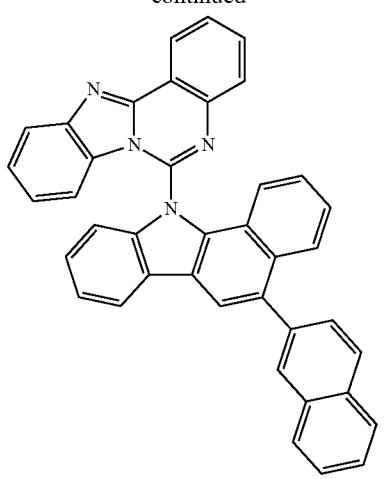
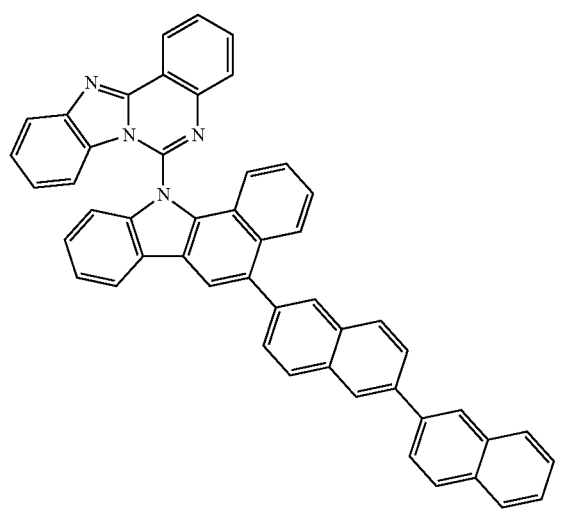
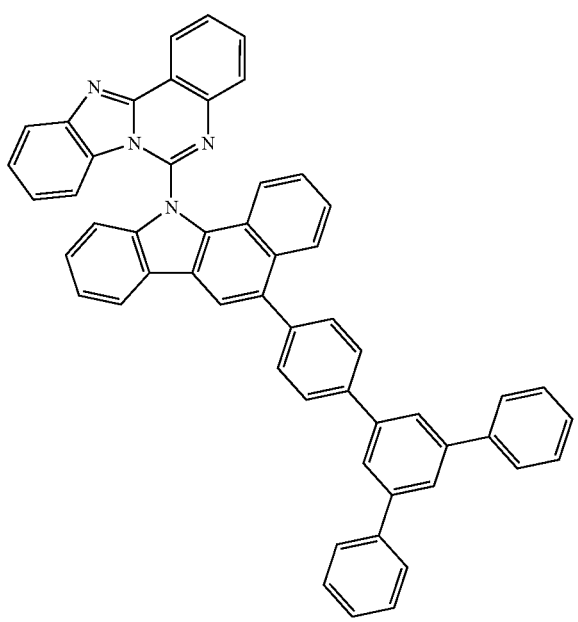
452
-continued
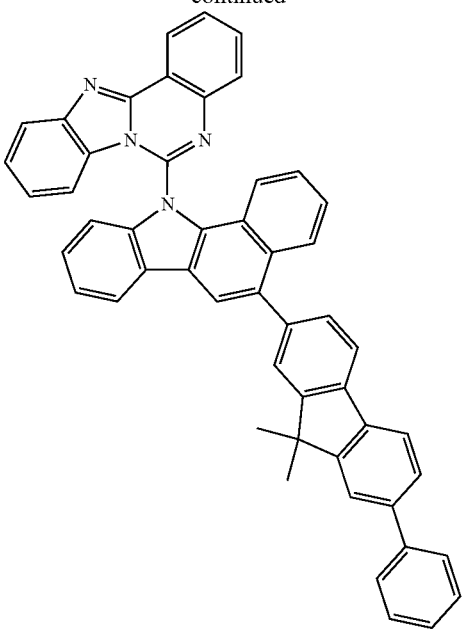
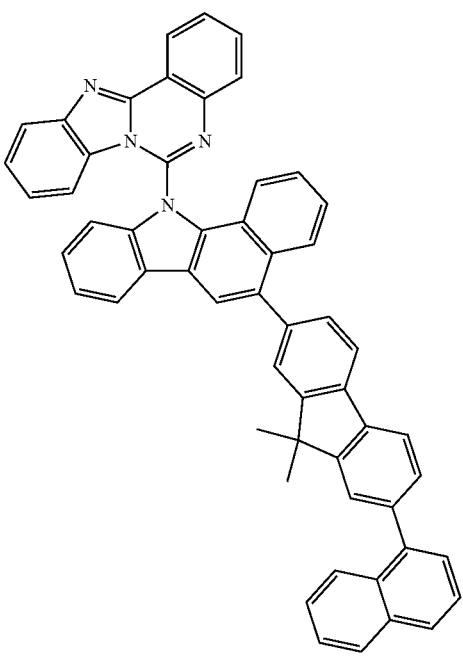

453
-continued
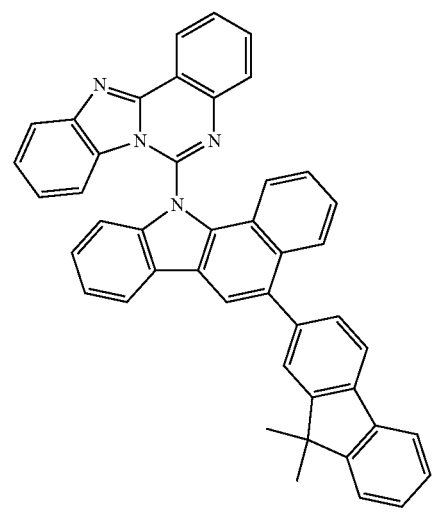
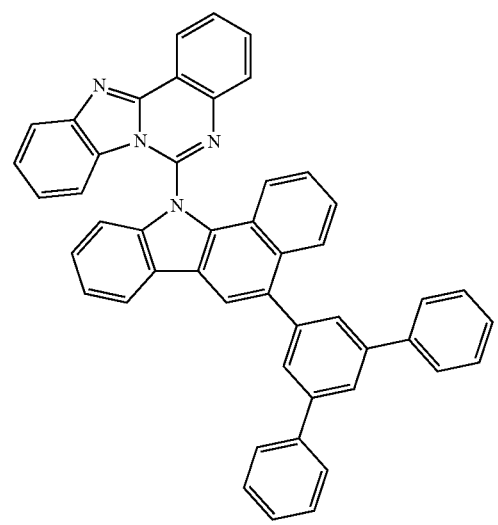
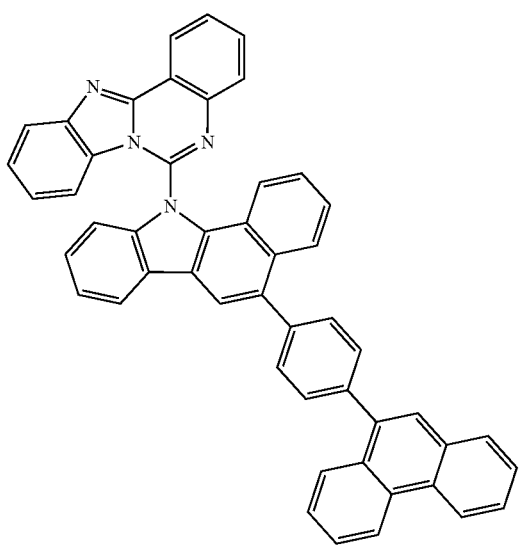
454
-continued
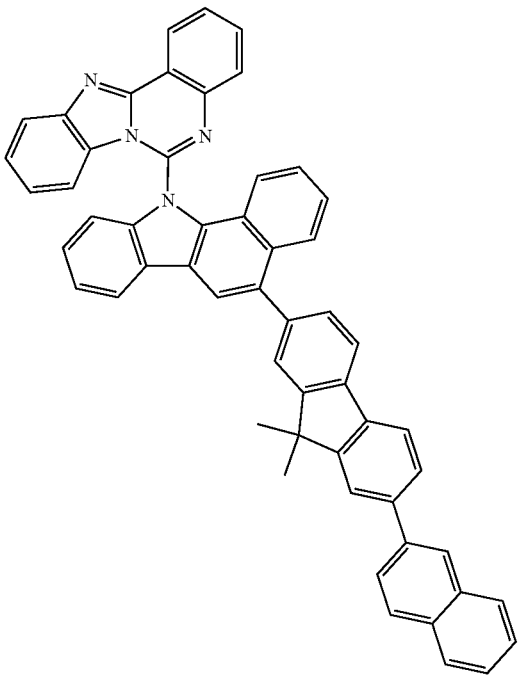
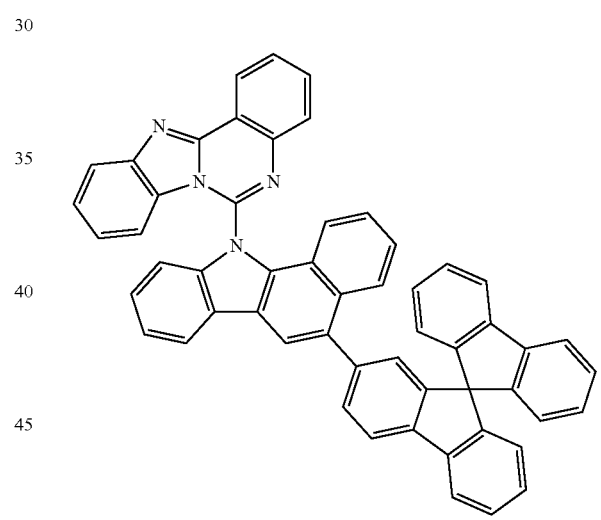
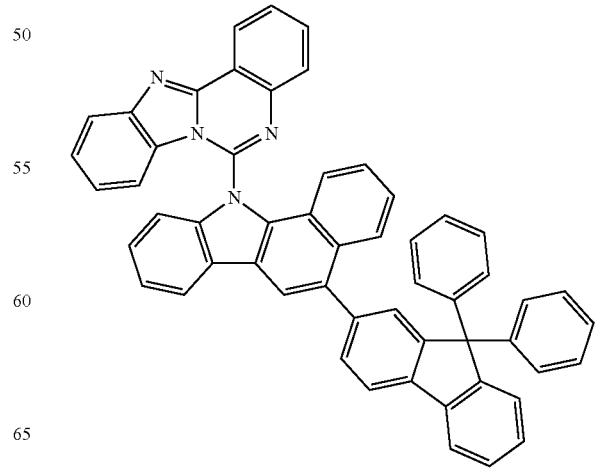

455
-continued
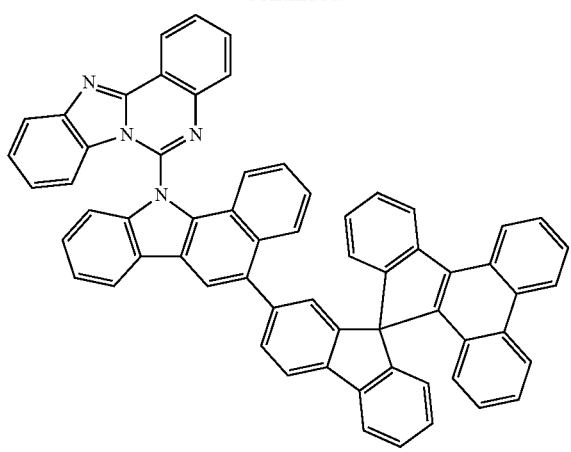
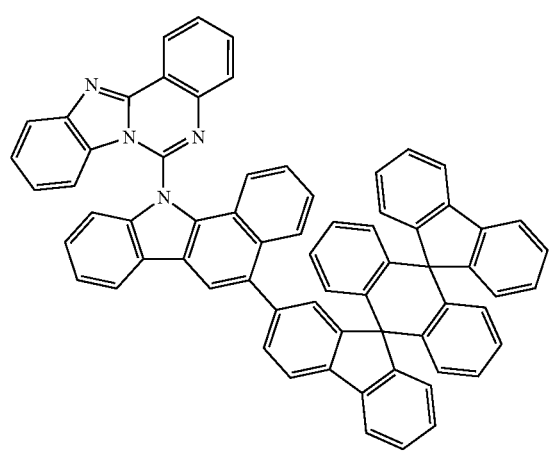
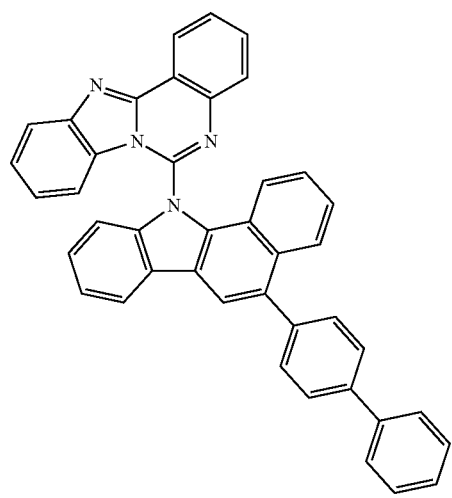
456
-continued
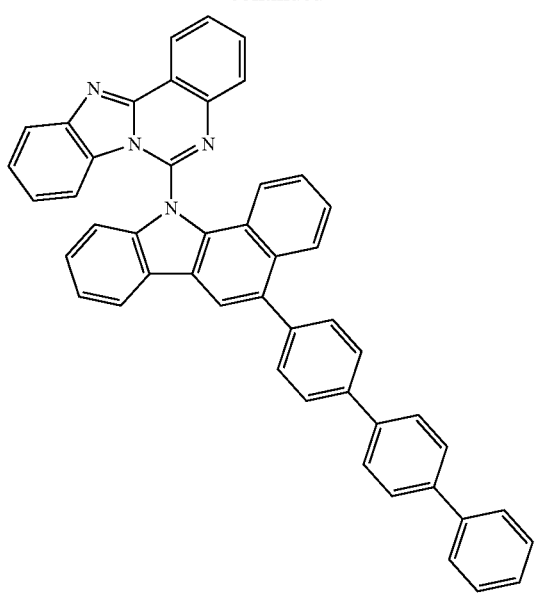
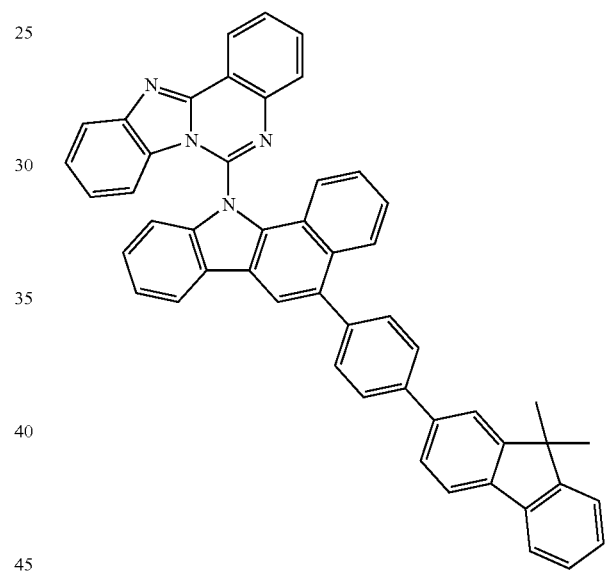
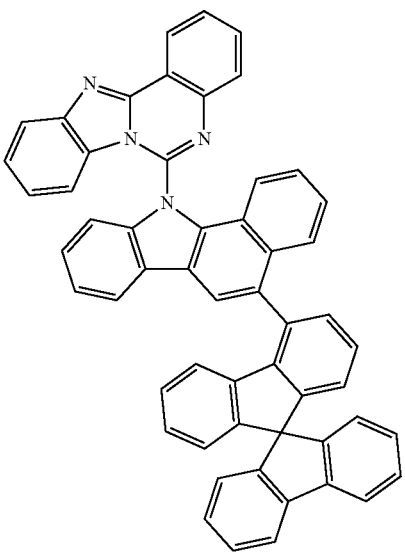

457
-continued
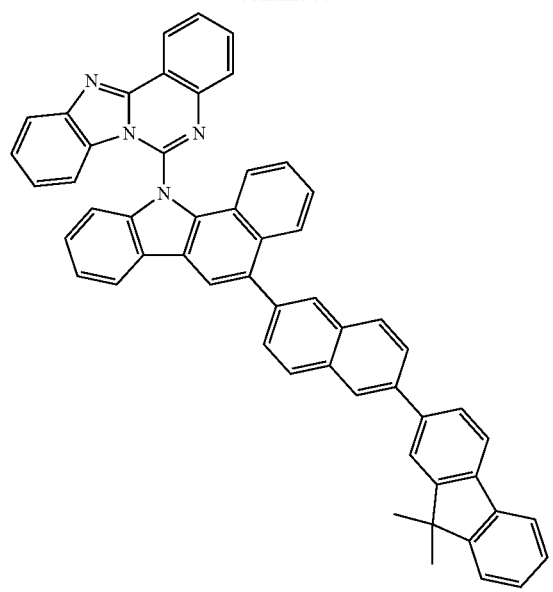
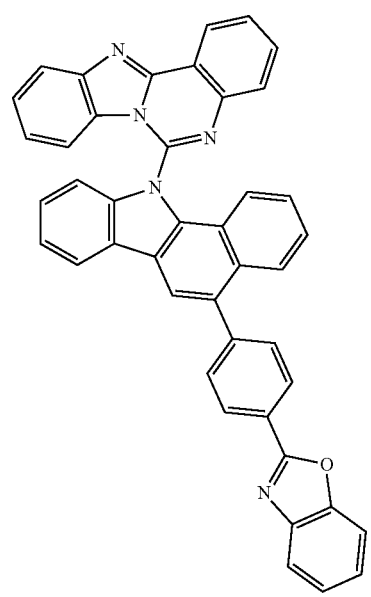
458
-continued
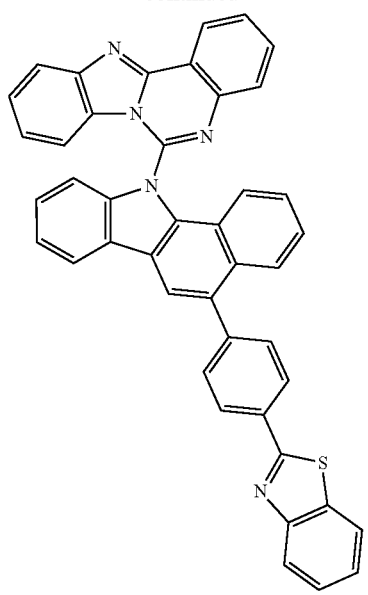
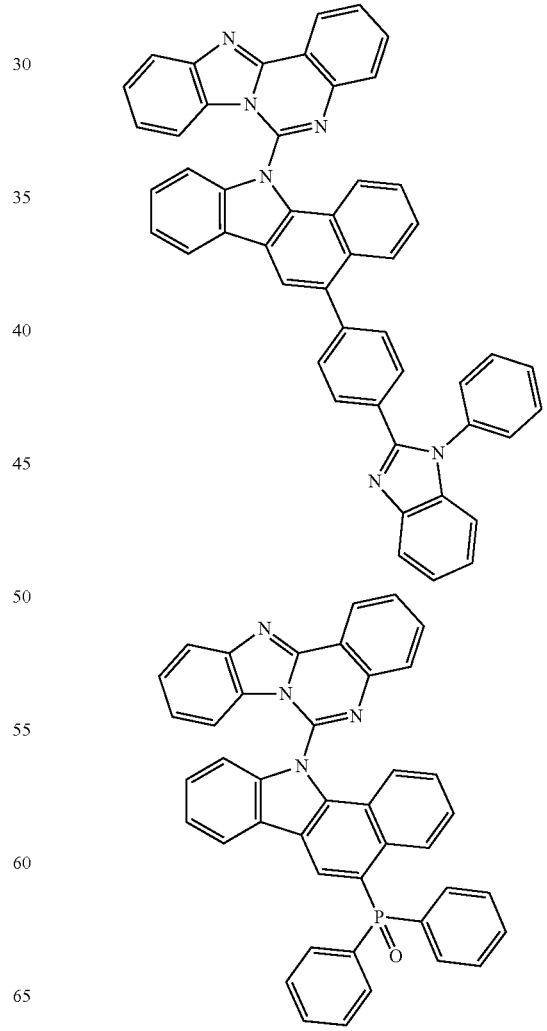

459
-continued
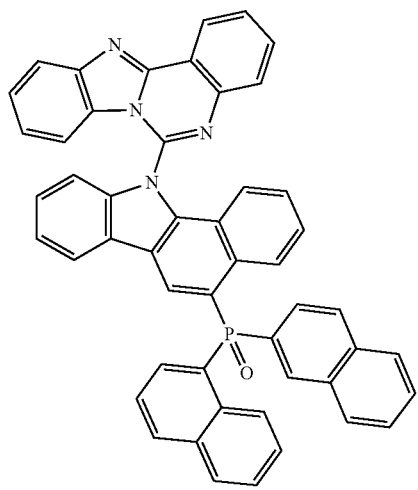
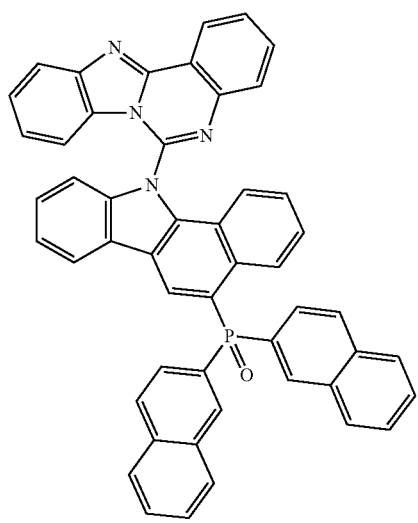
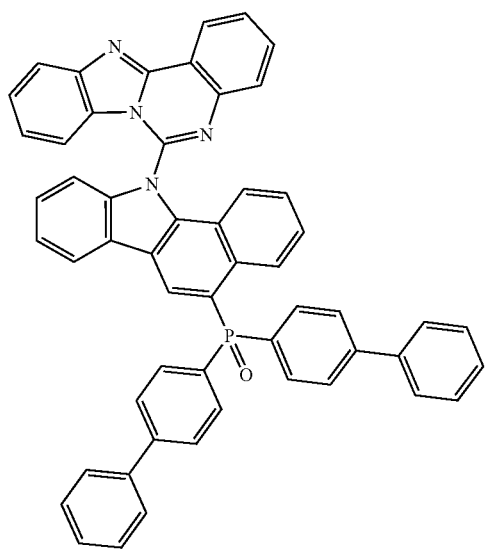
460
-continued
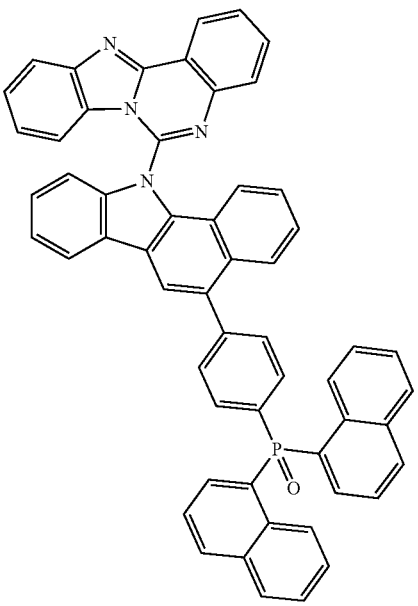
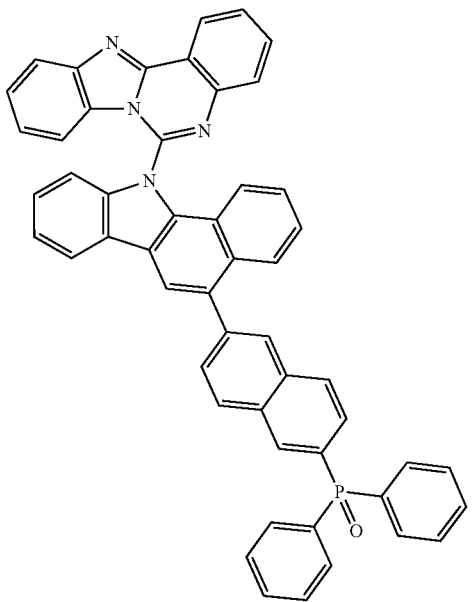

461
-continued
462
-continued
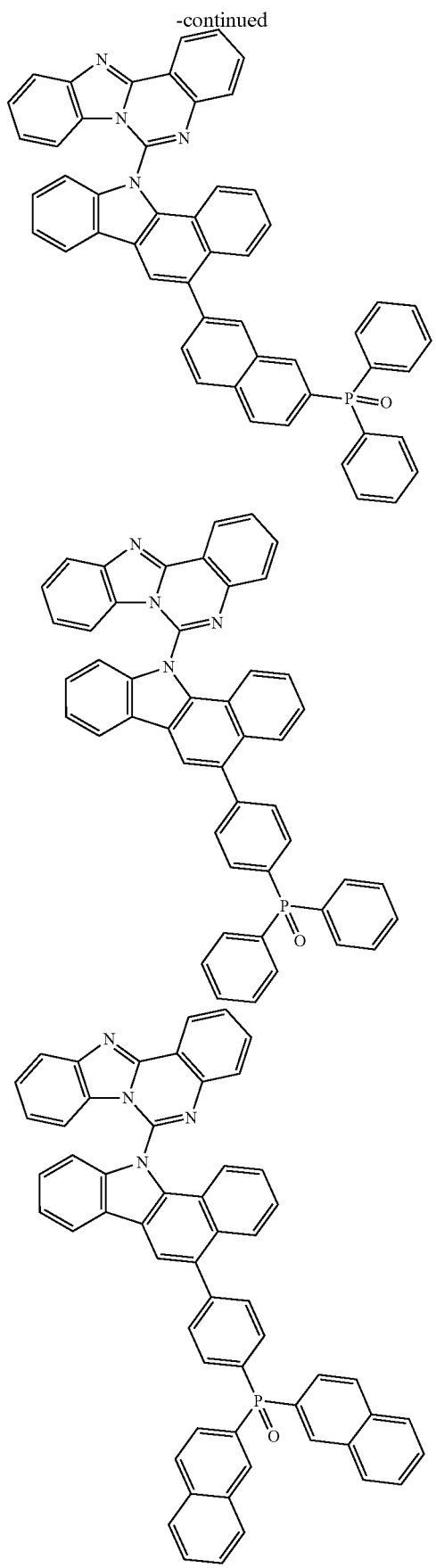
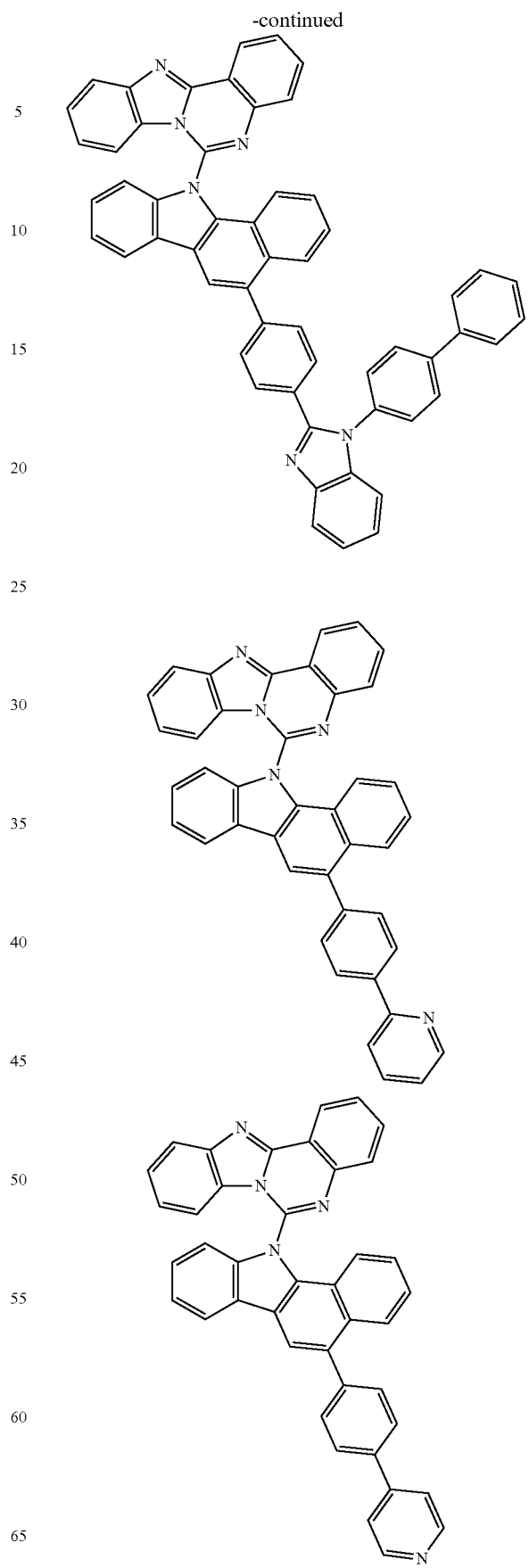

463
-continued
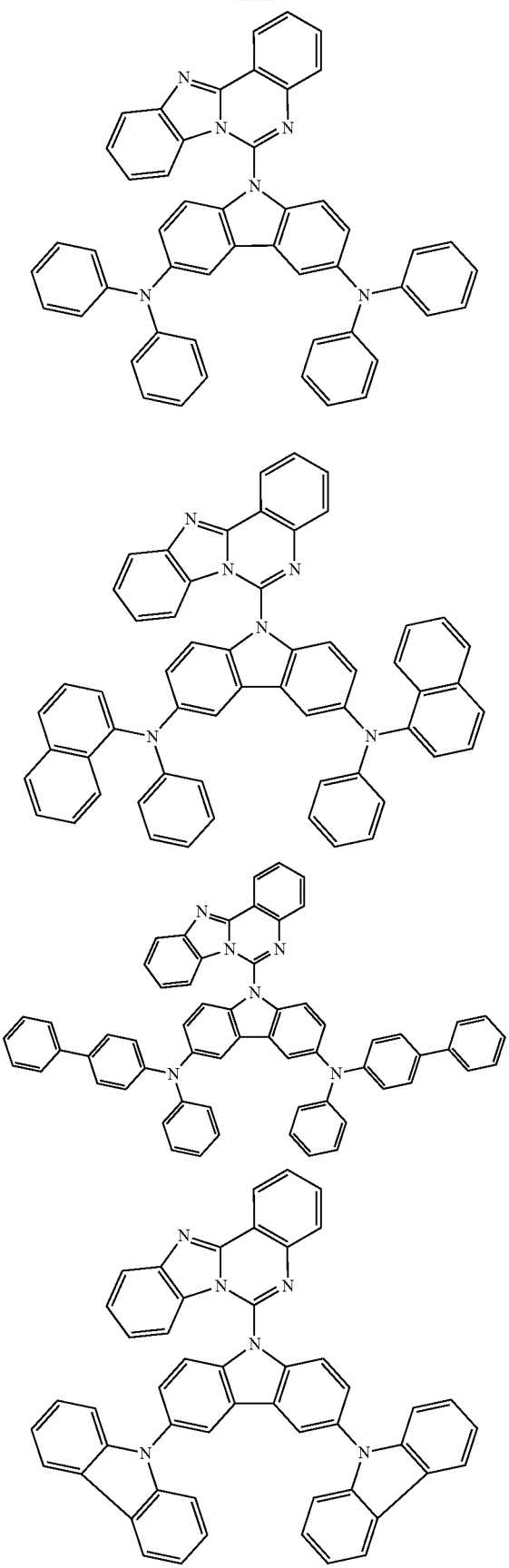
464
-continued
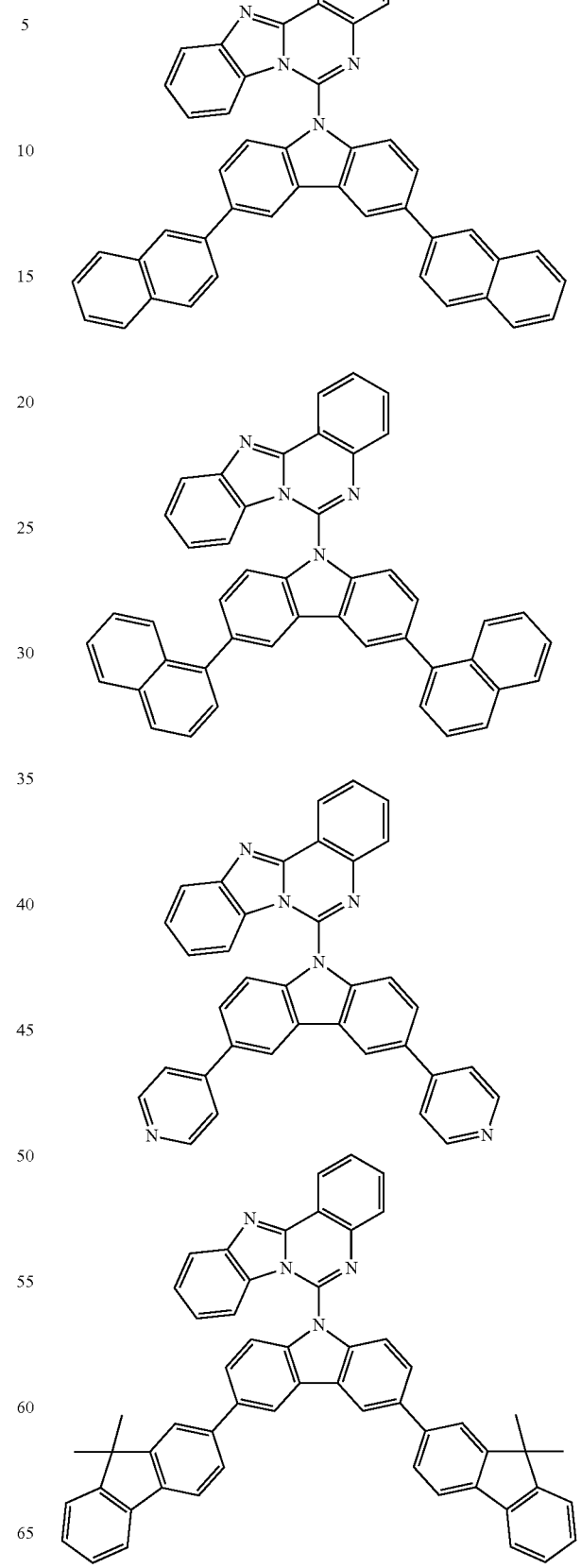

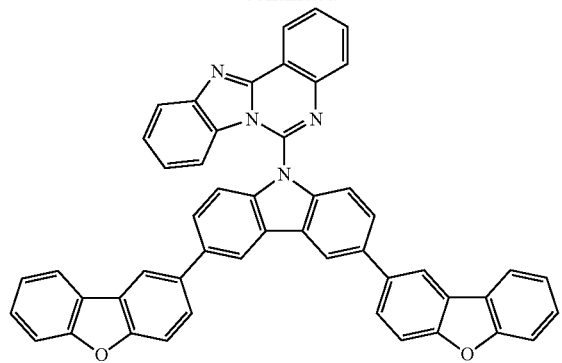
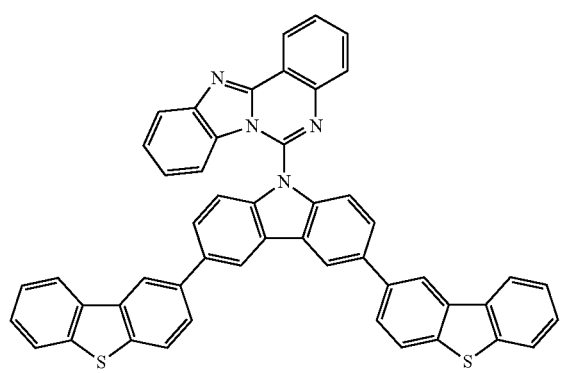
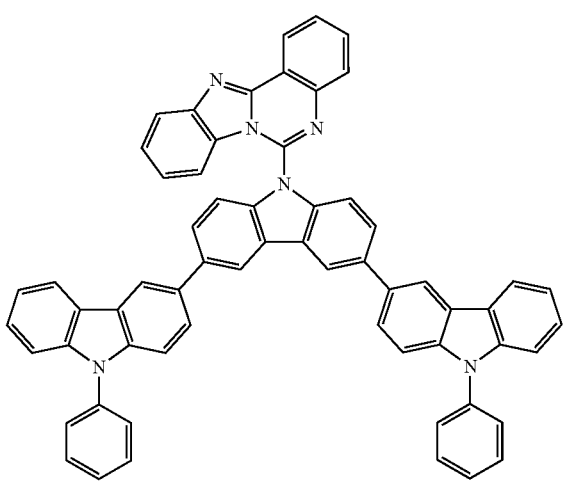
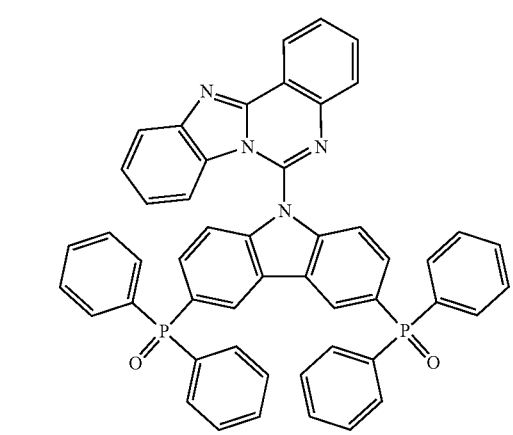
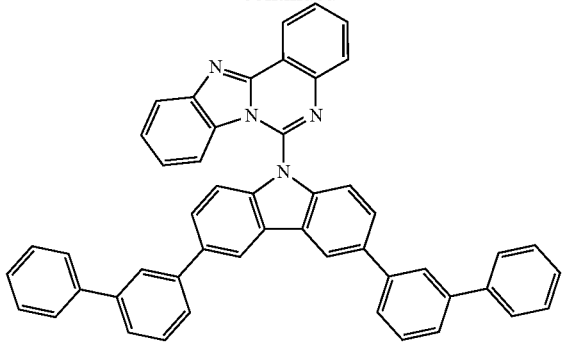

467
-continued
468
-continued
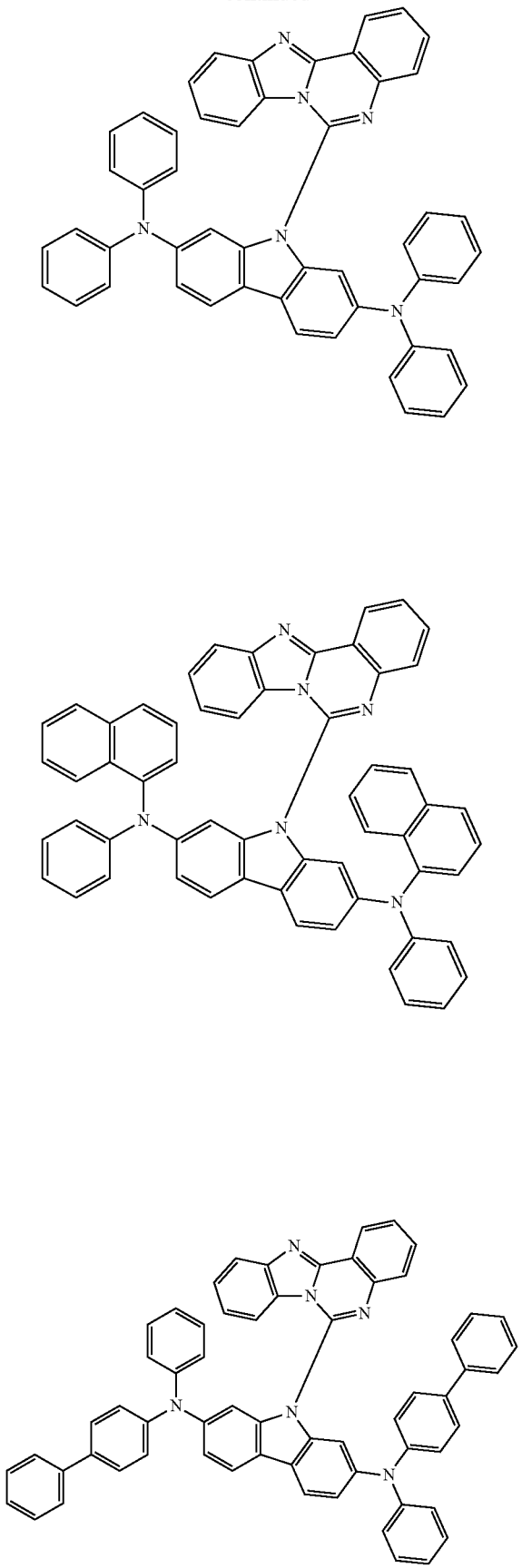
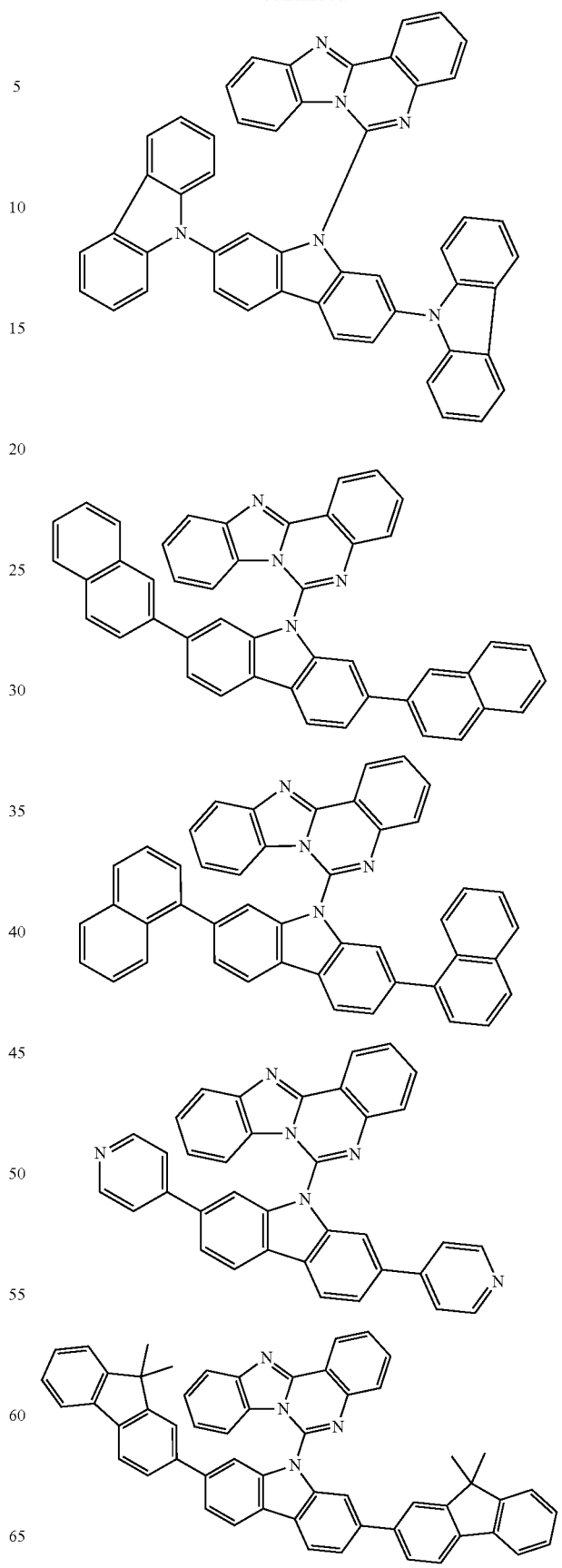

469
-continued
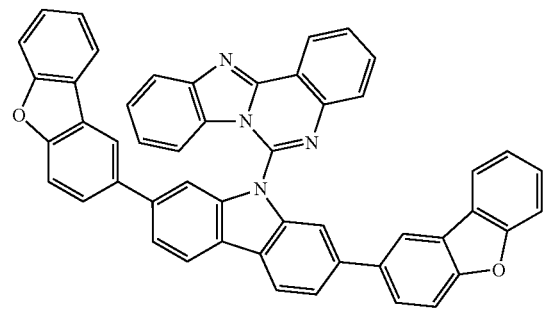
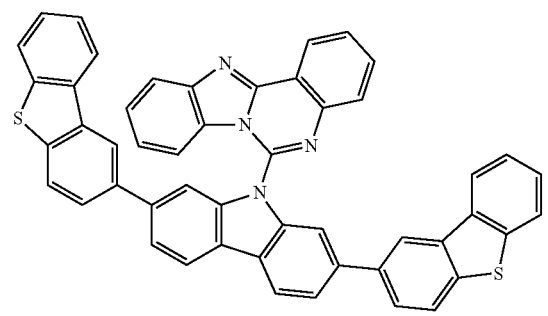
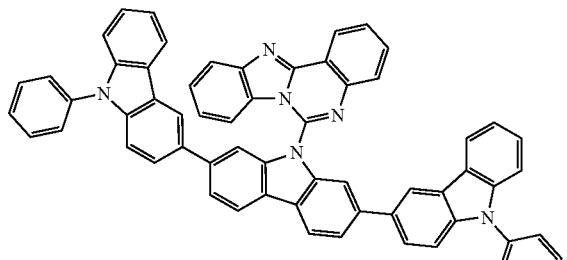
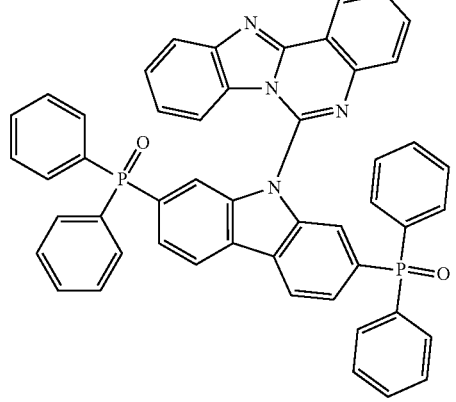
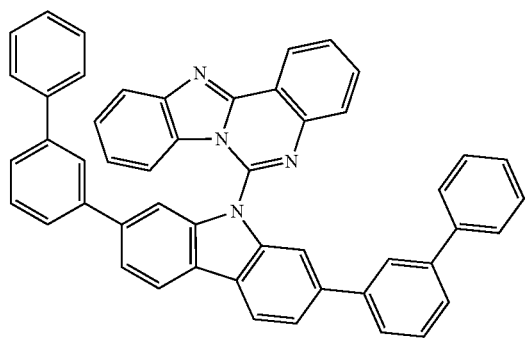
470
-continued
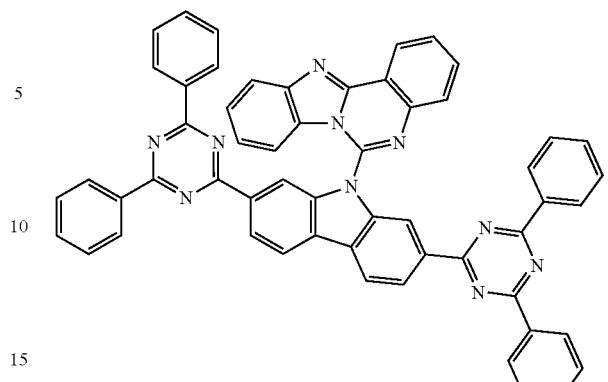
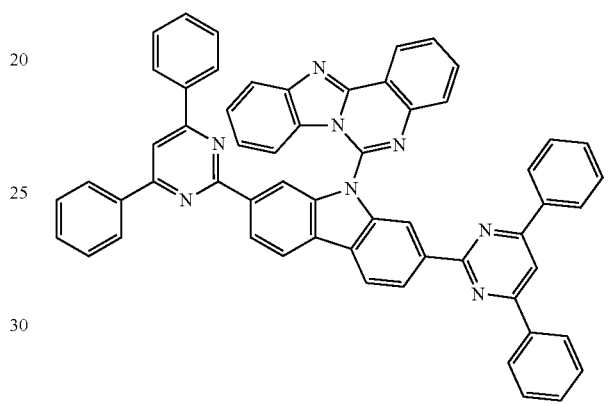
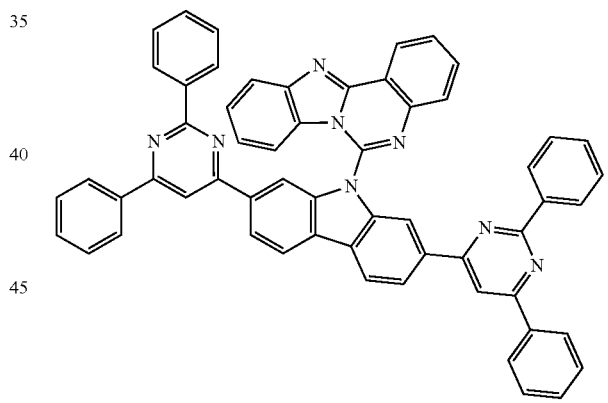
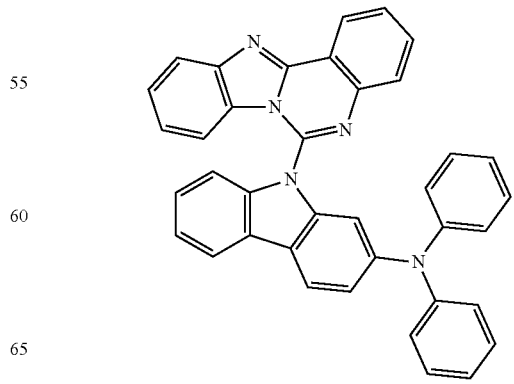

471
-continued
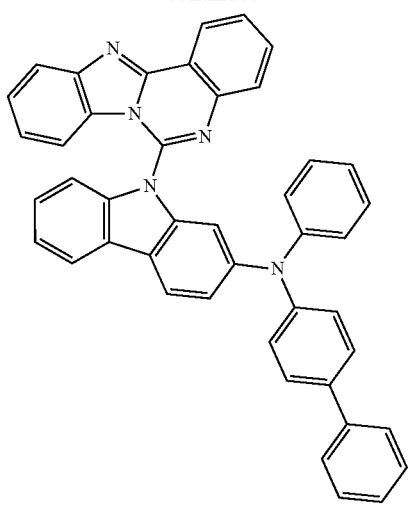
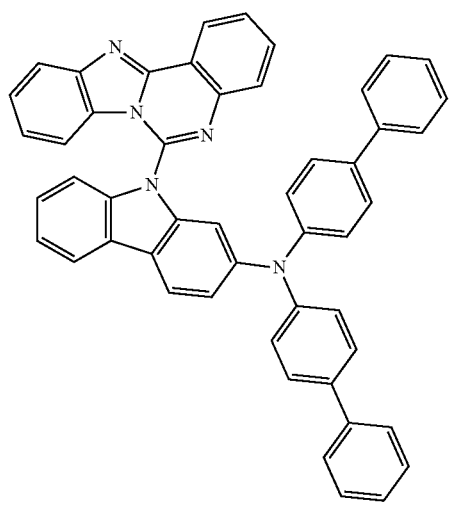
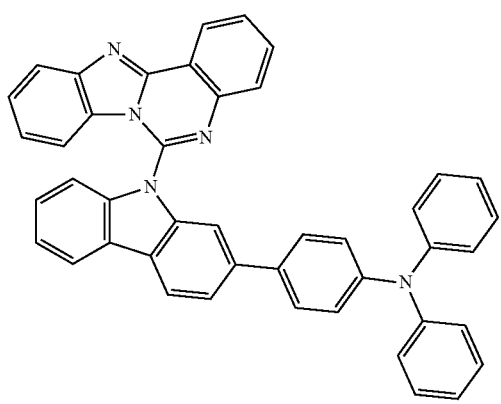
472
-continued
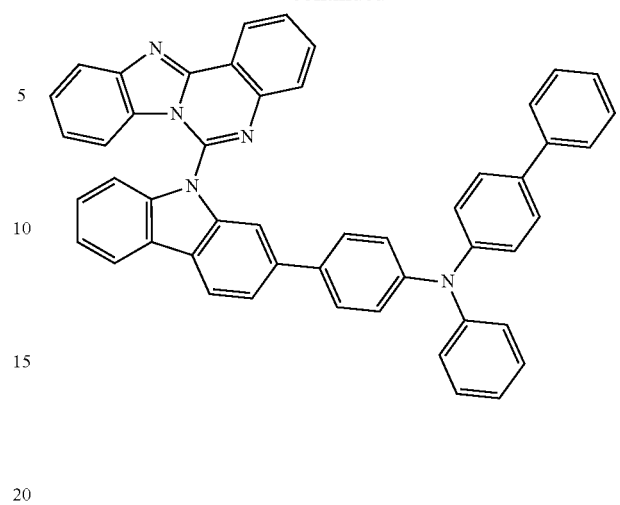
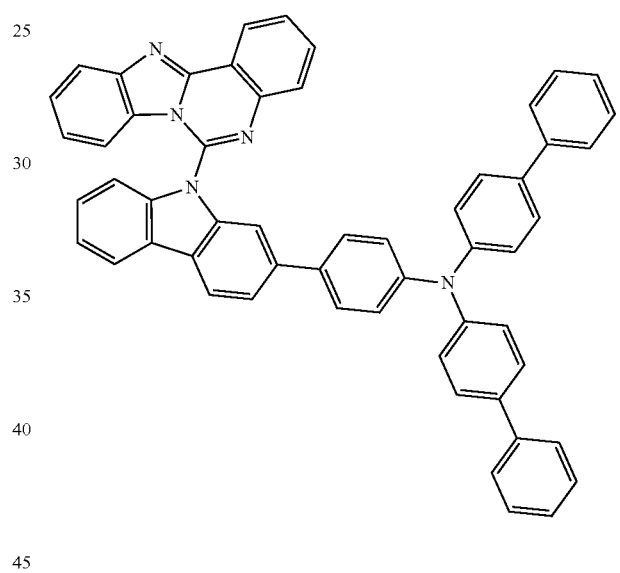
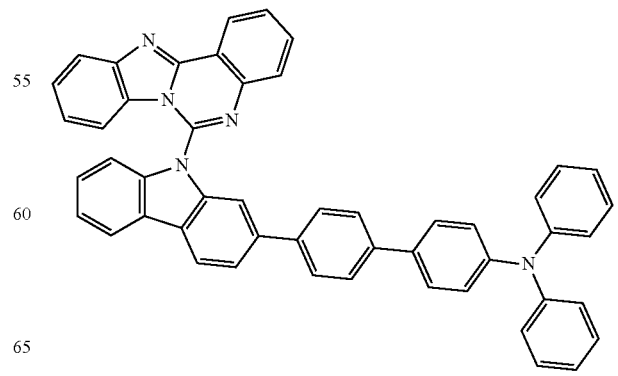

473
-continued
474
-continued
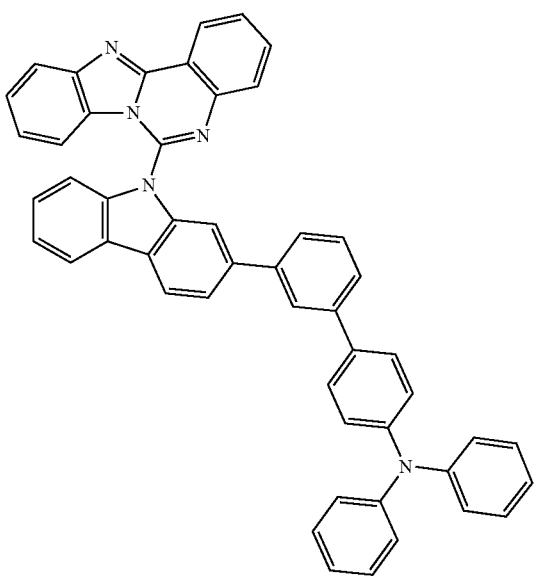
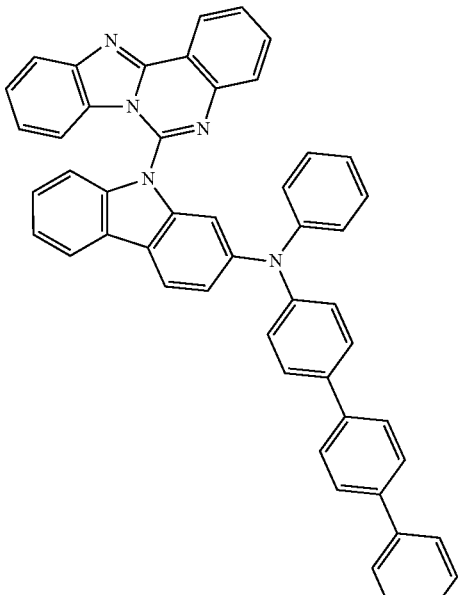

475
-continued
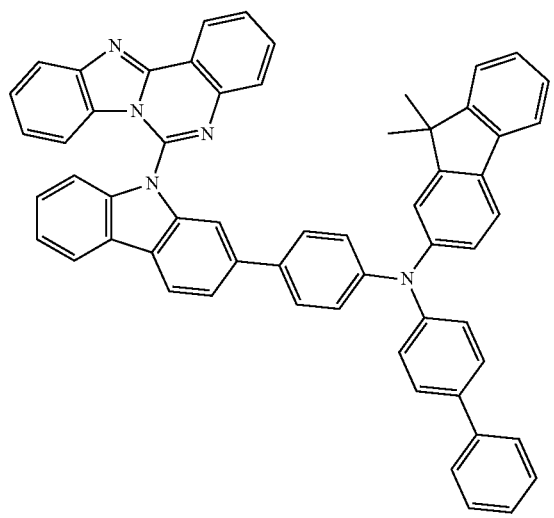
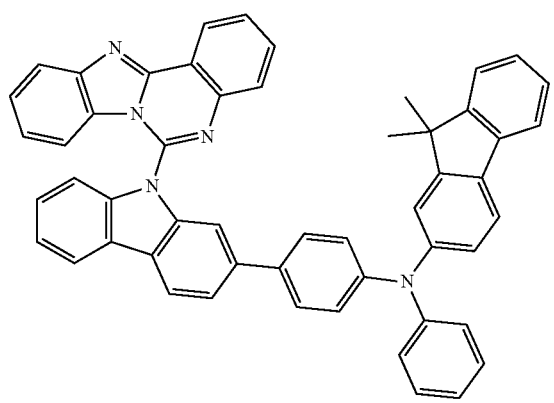
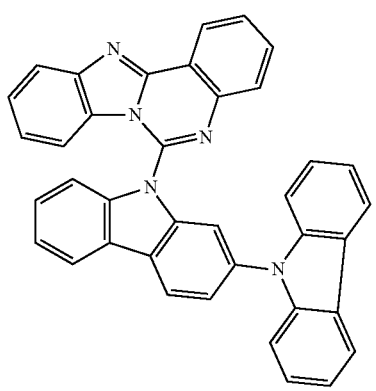
476
-continued
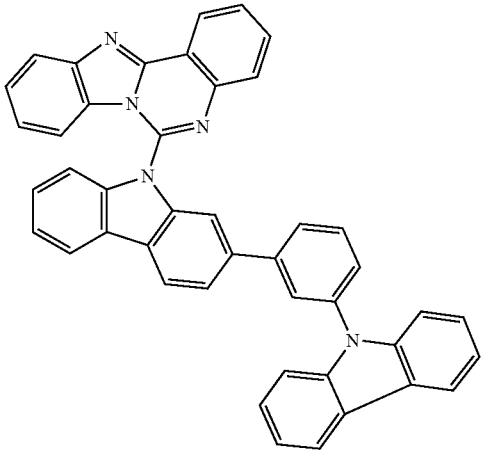
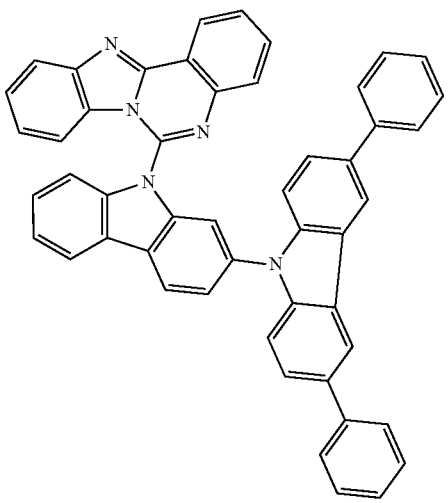
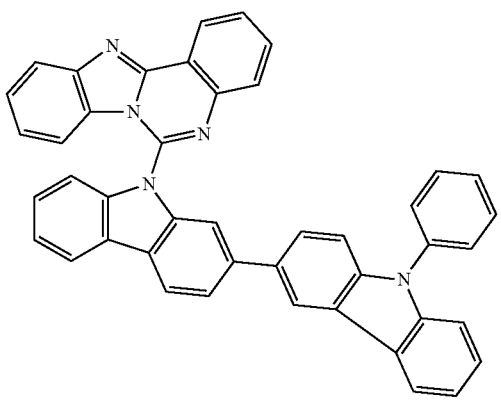

477
-continued
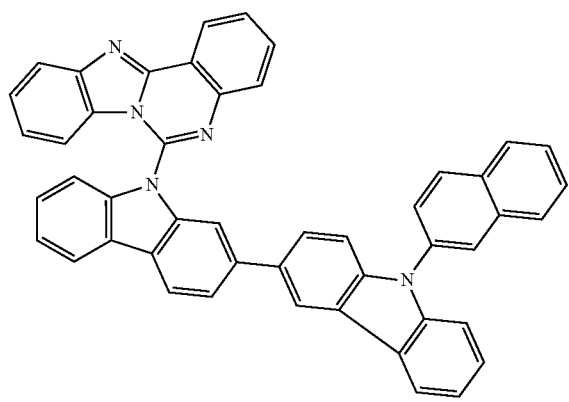
478
-continued
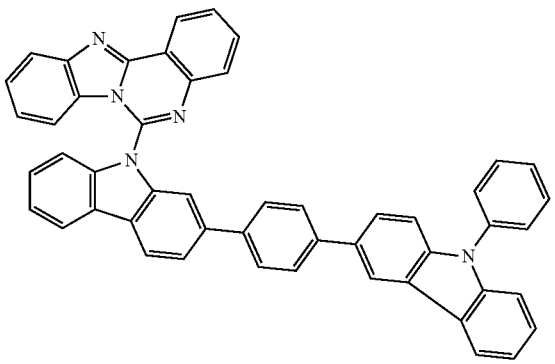
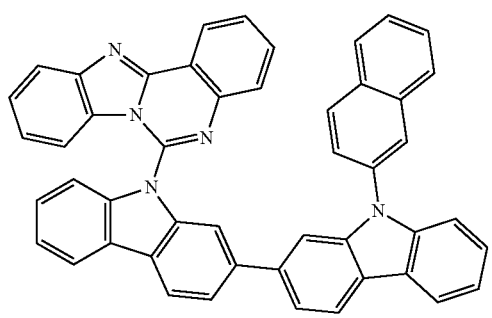
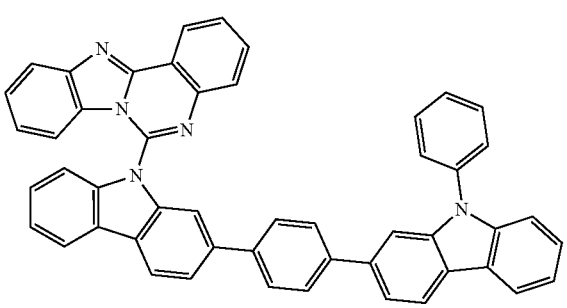
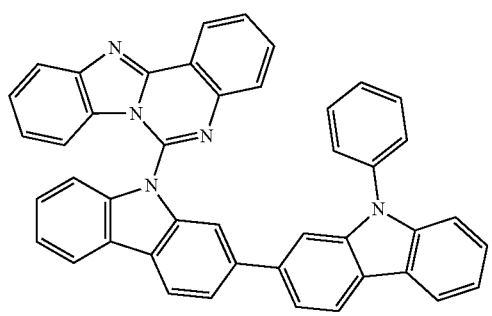
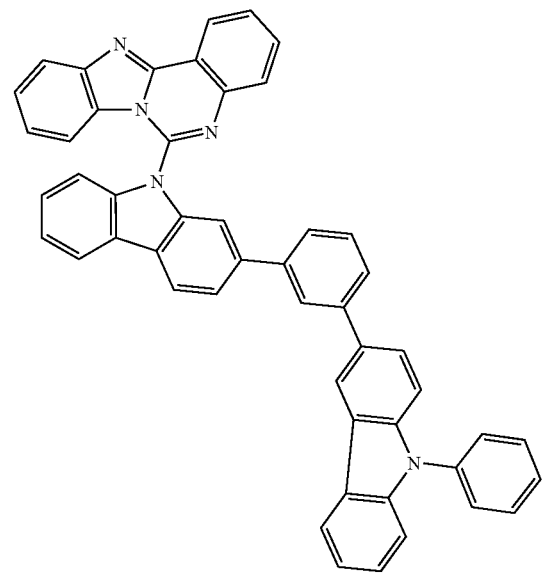
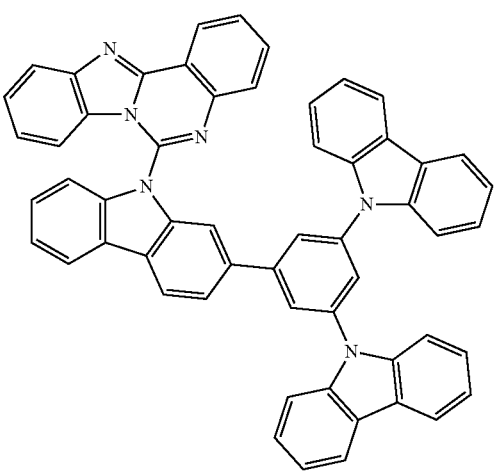
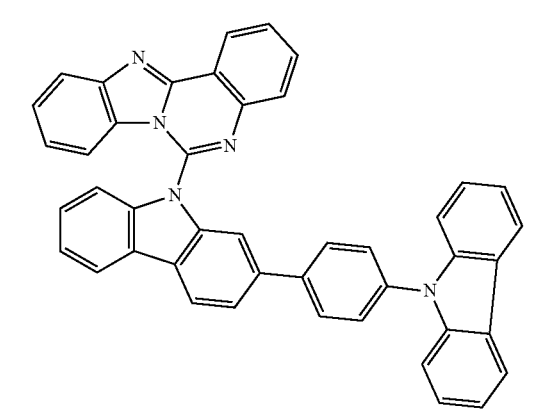

479
-continued
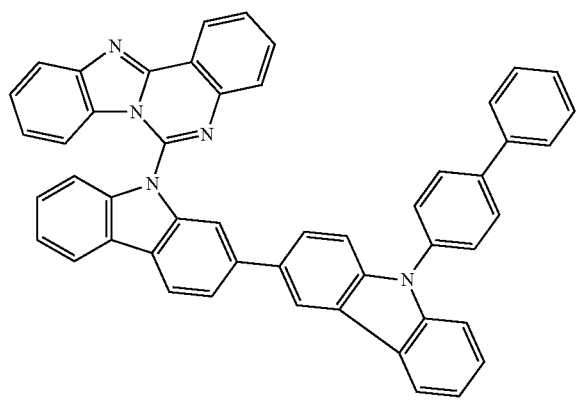
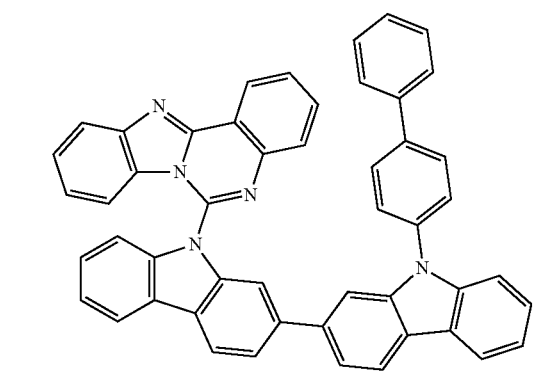
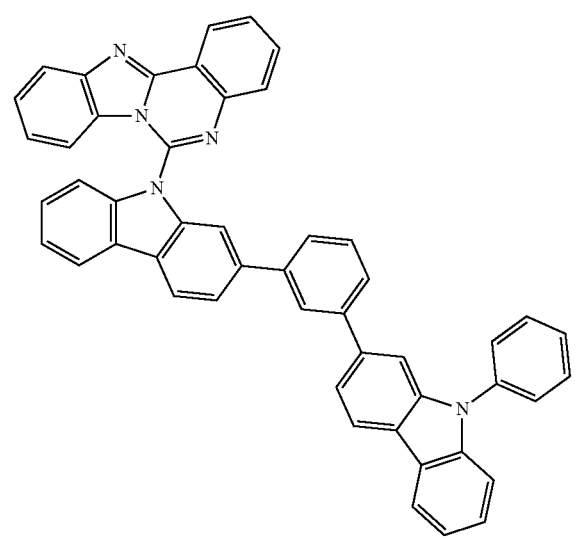
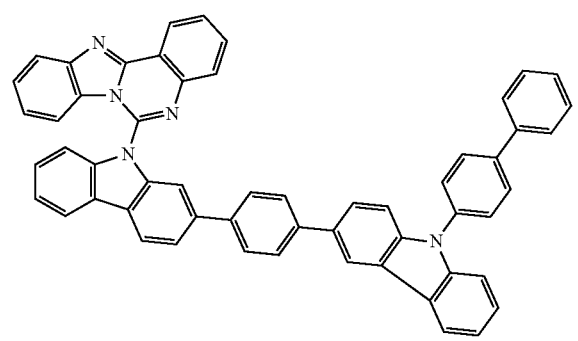
480
-continued
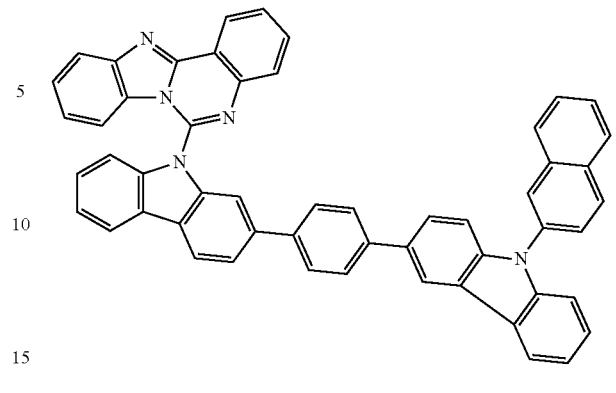
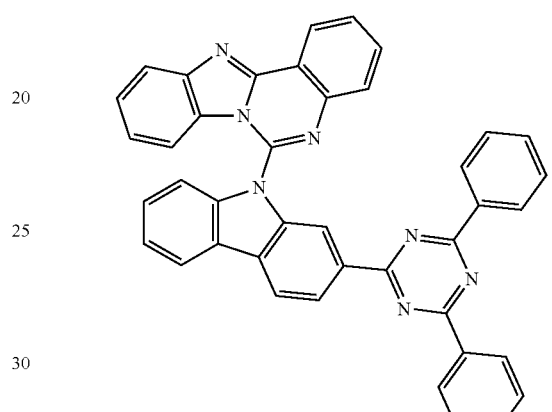
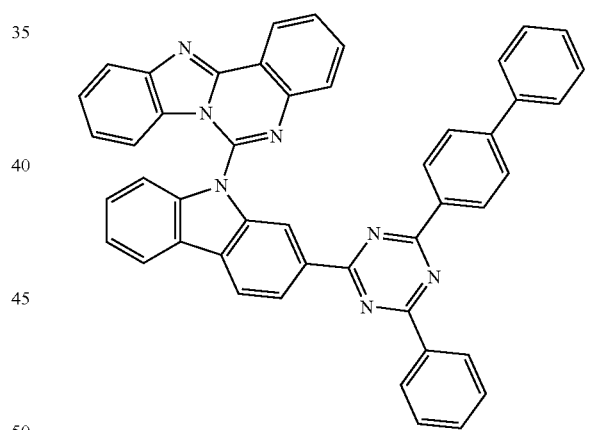
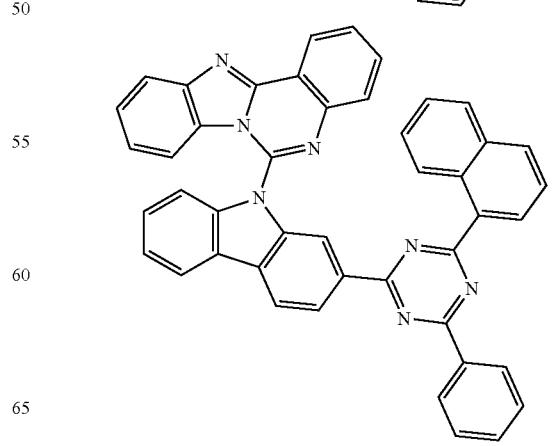

481
-continued
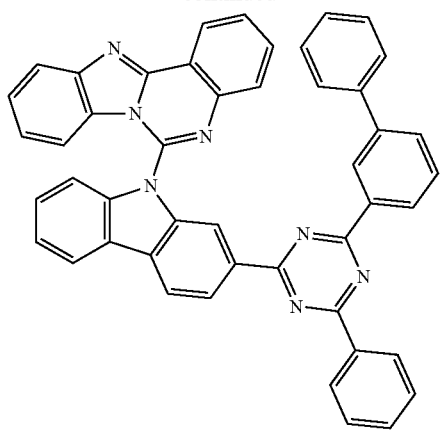
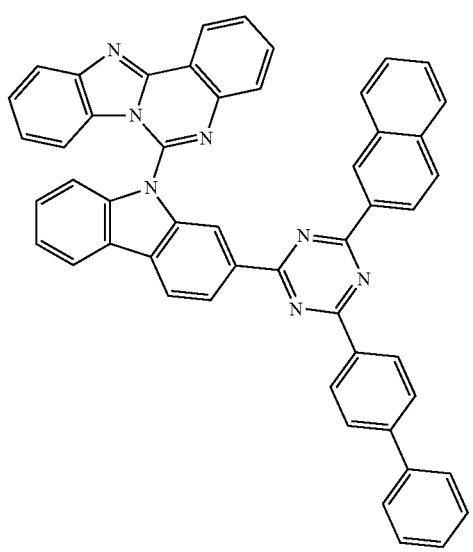
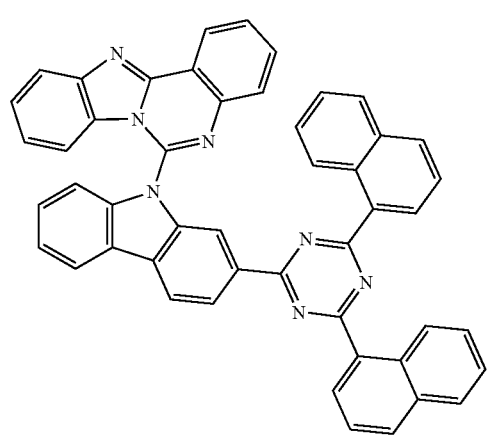
482
-continued
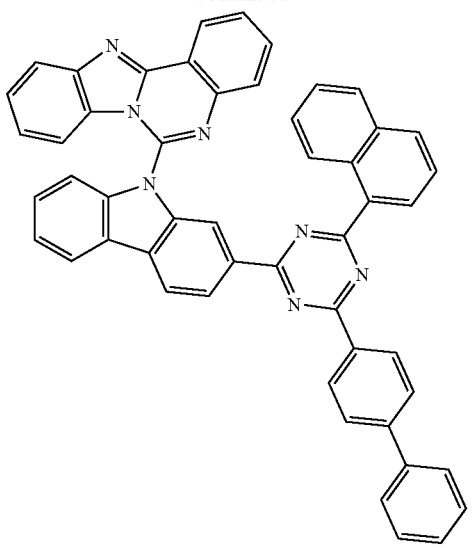
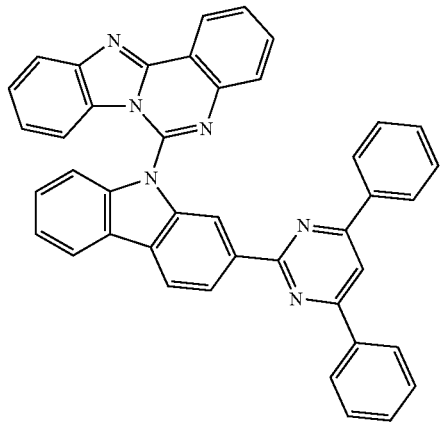
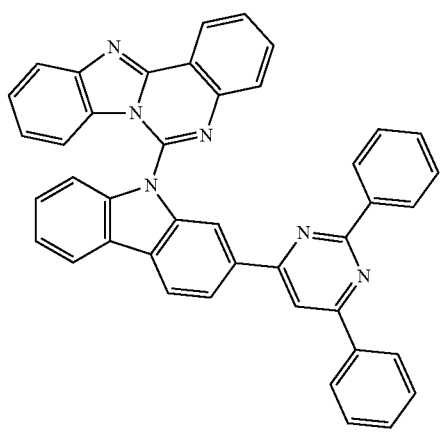

483
-continued
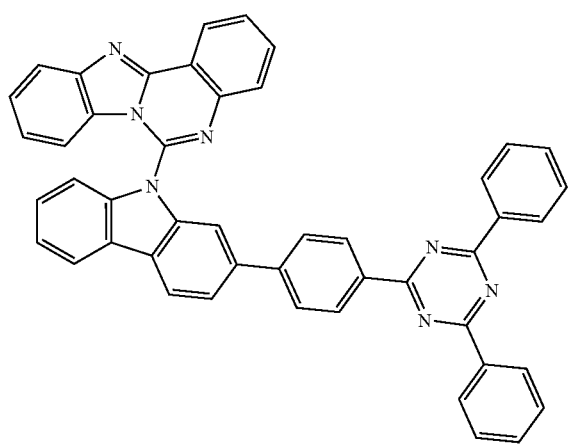
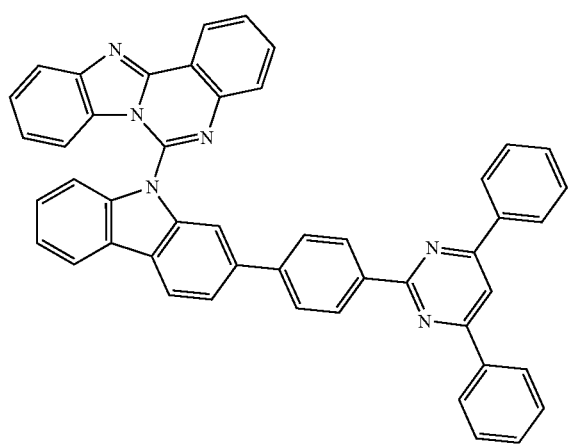
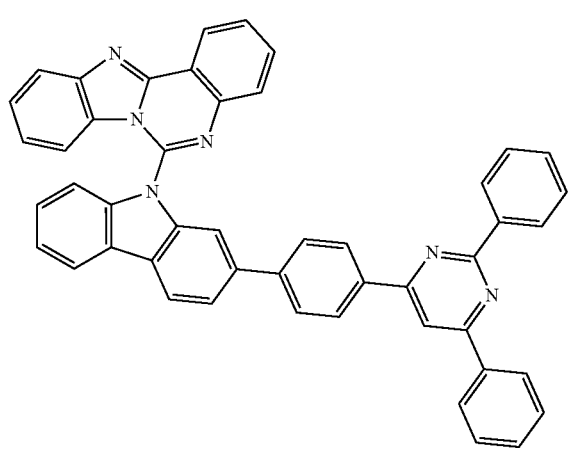
484
-continued
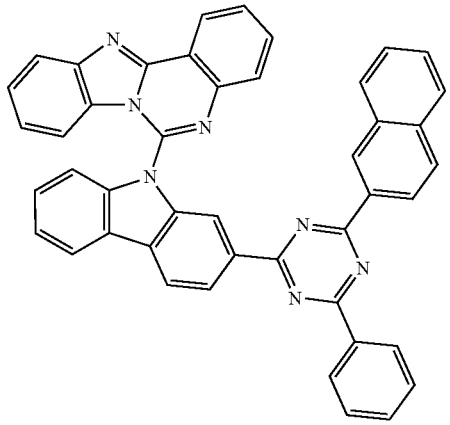
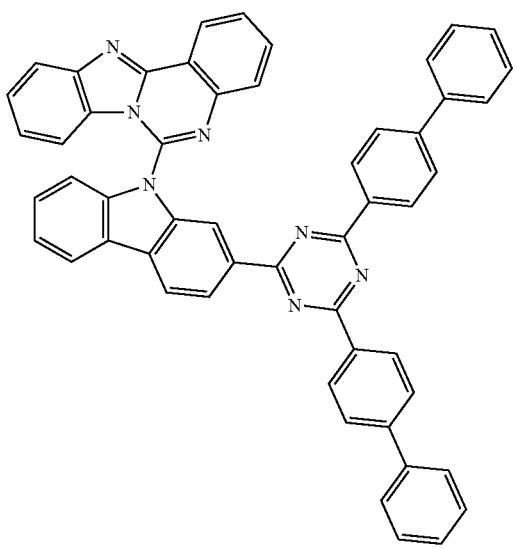
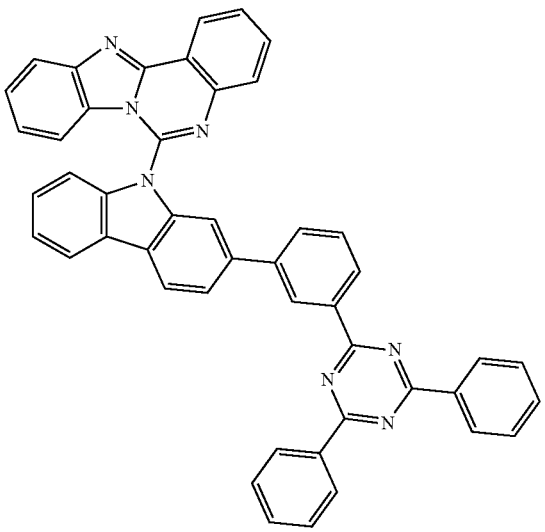

485
-continued
486
-continued
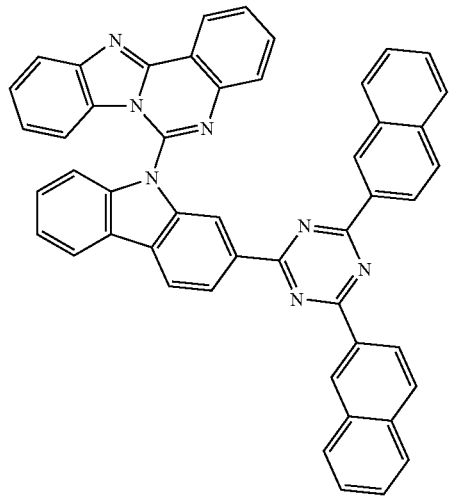
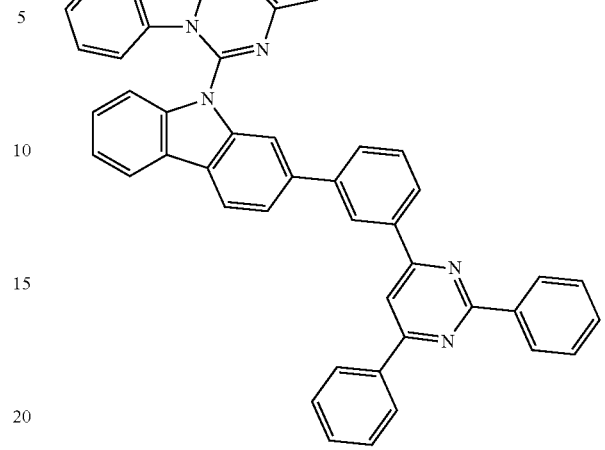
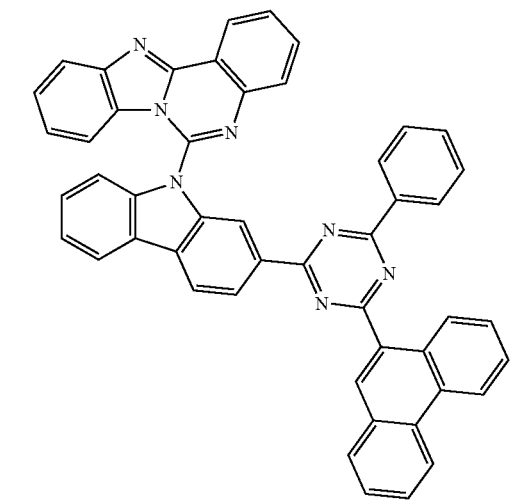
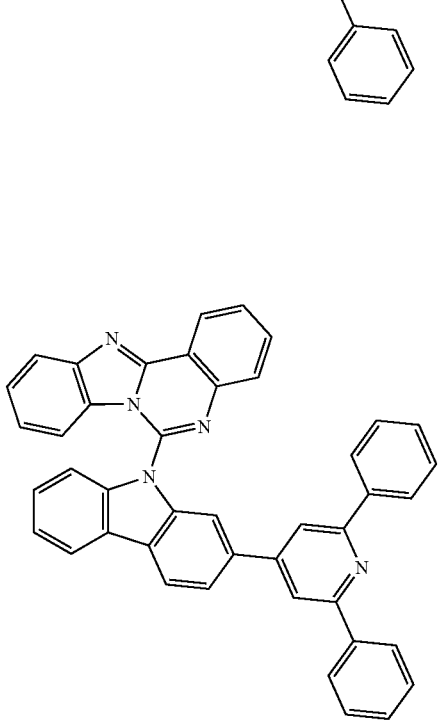
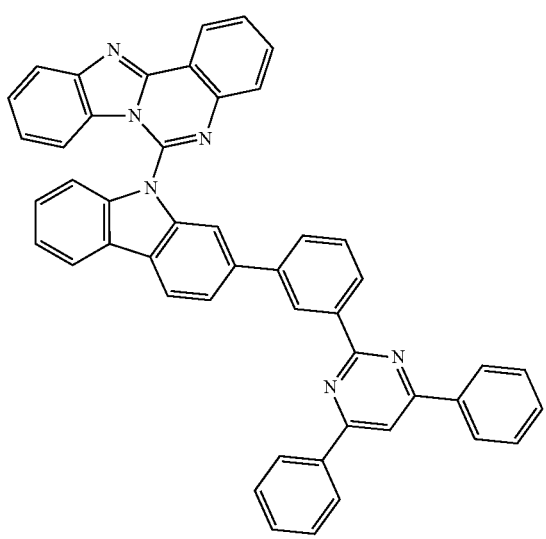

487
-continued
488
-continued
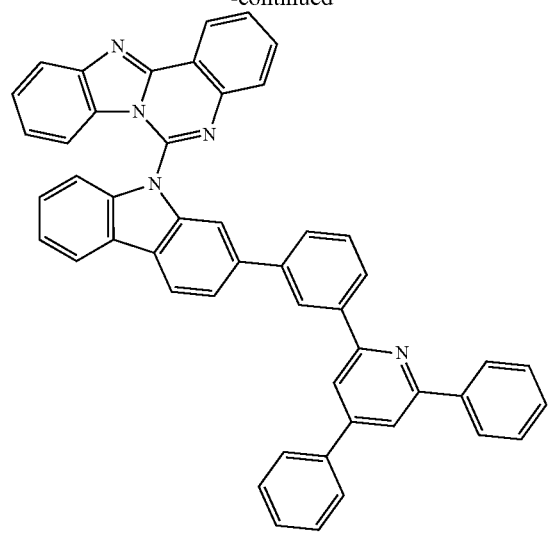
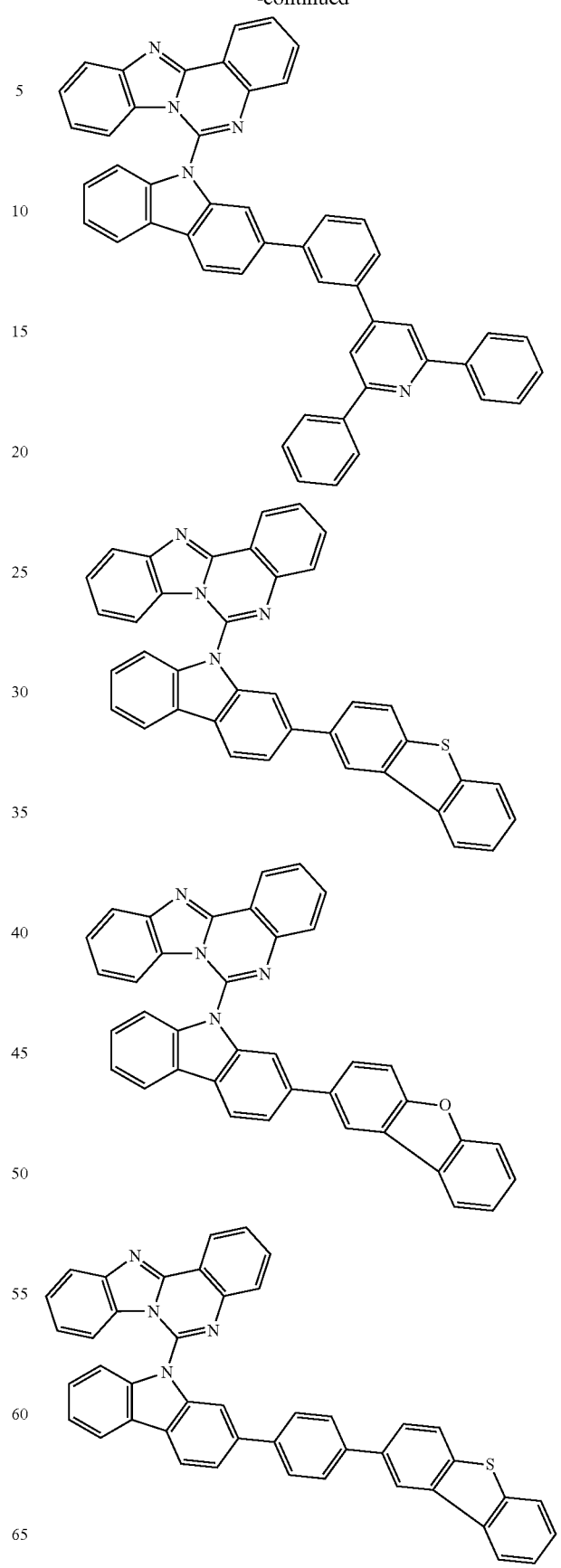

489
-continued
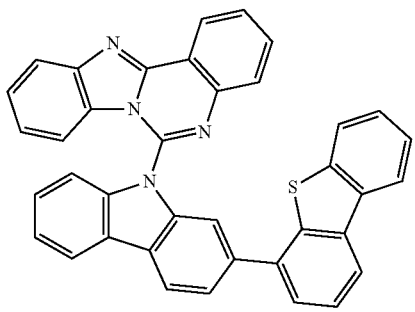
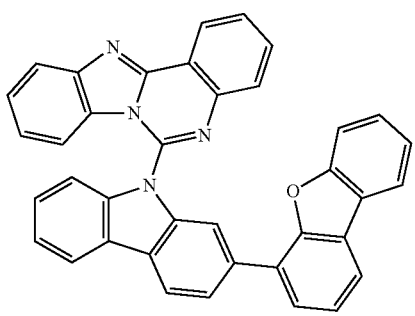
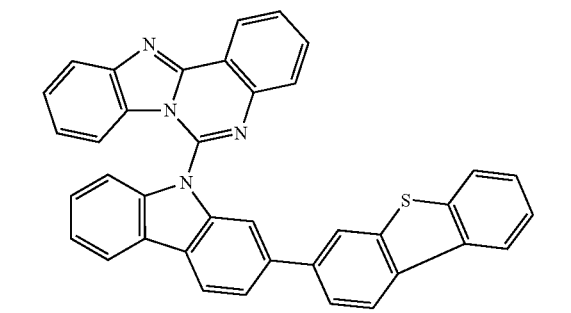
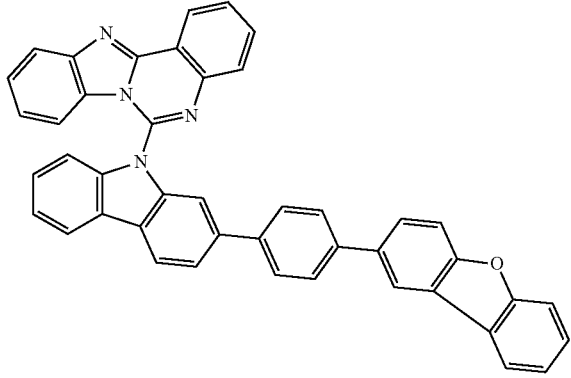
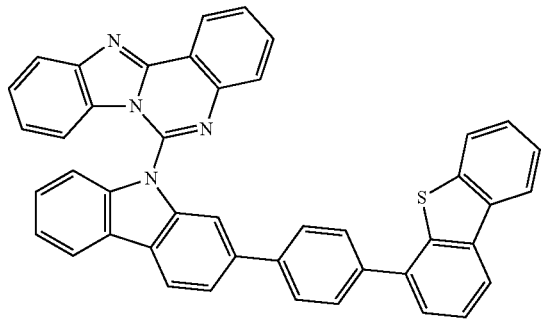
490
-continued
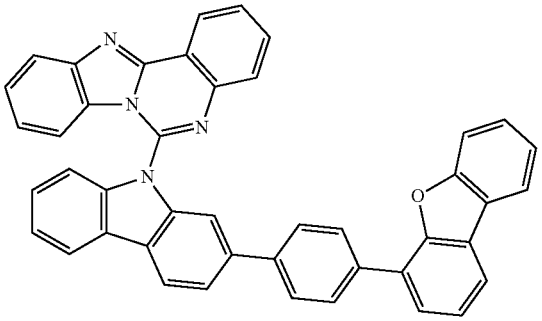
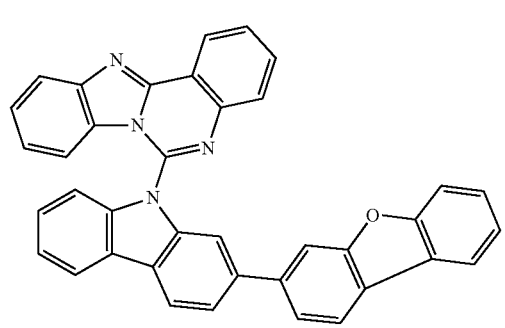
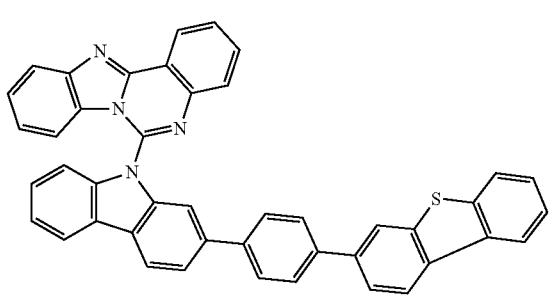
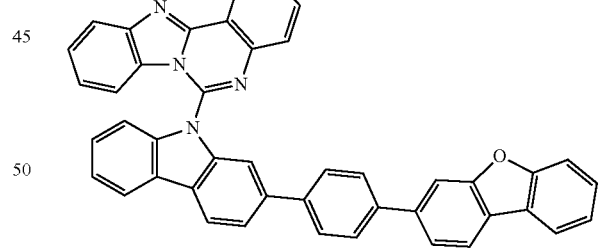
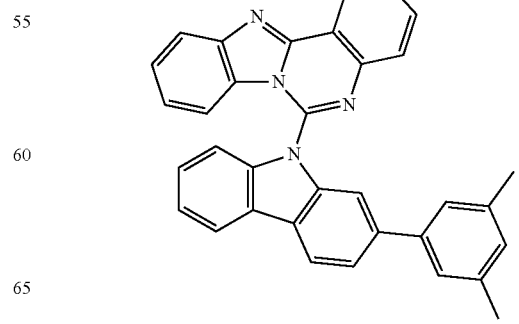

491
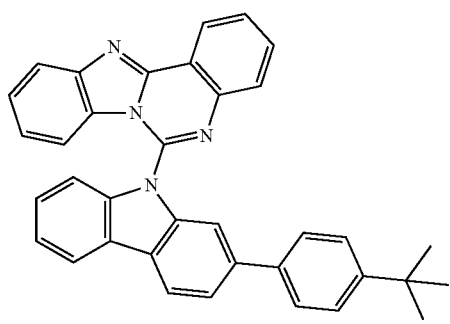
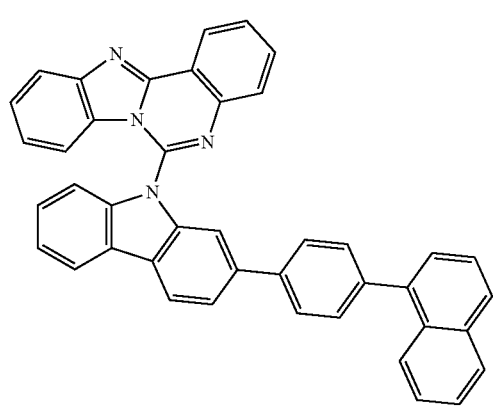
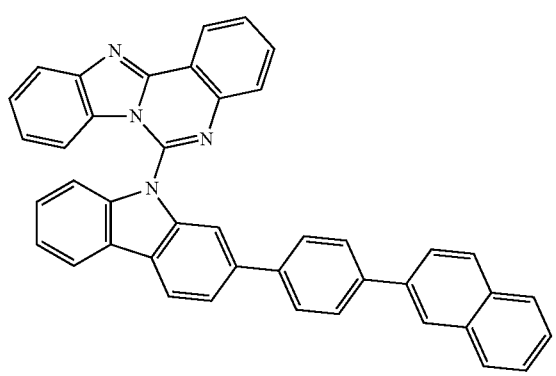
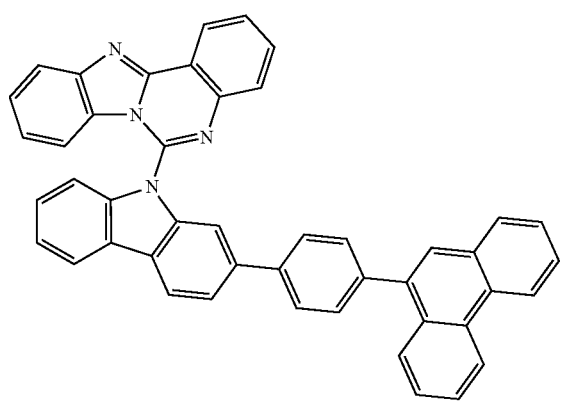
492
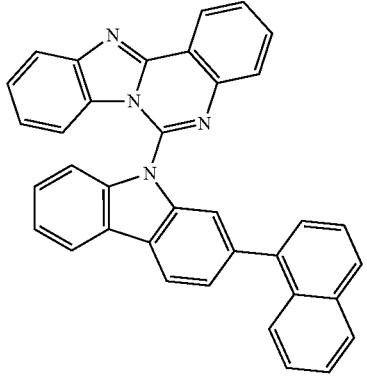
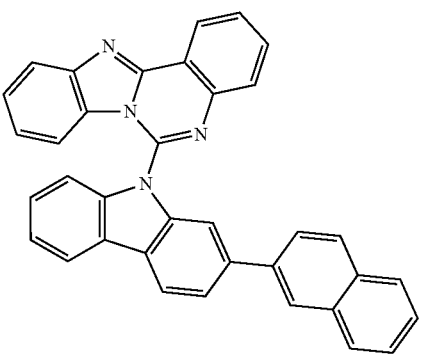
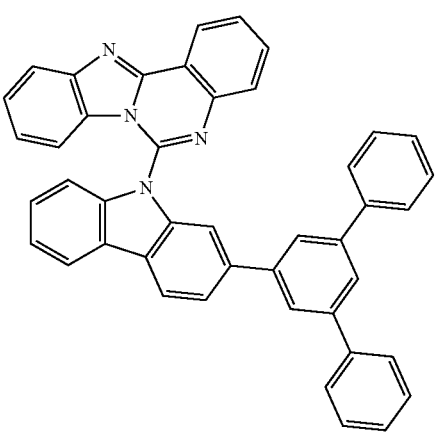

493
-continued
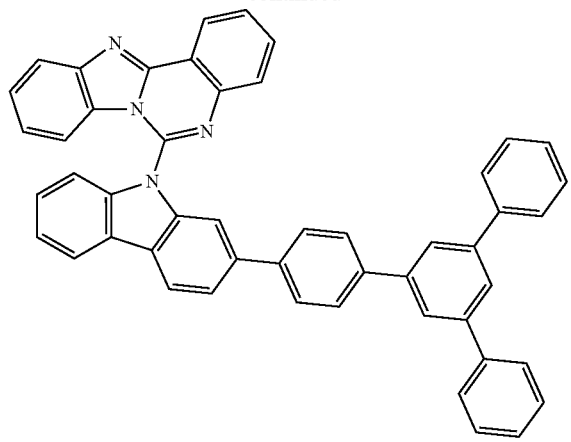
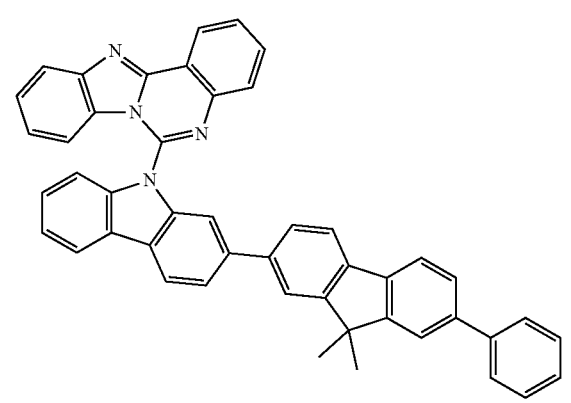
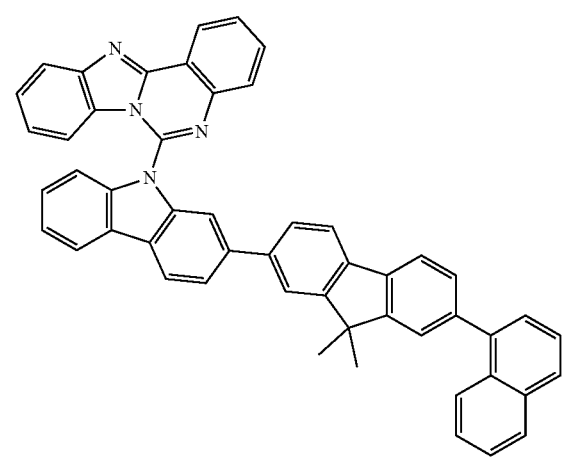
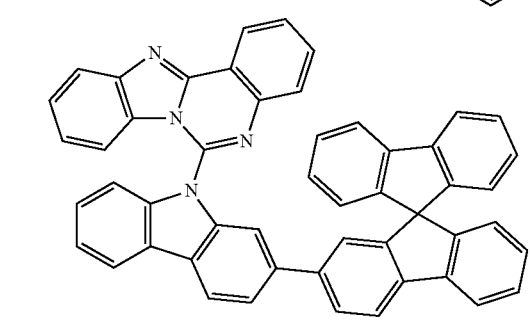
494
-continued
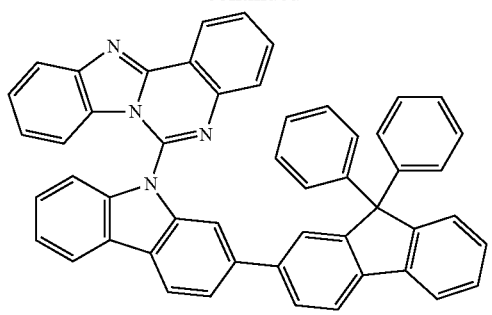
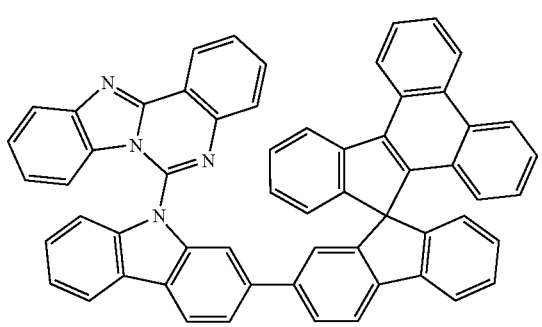
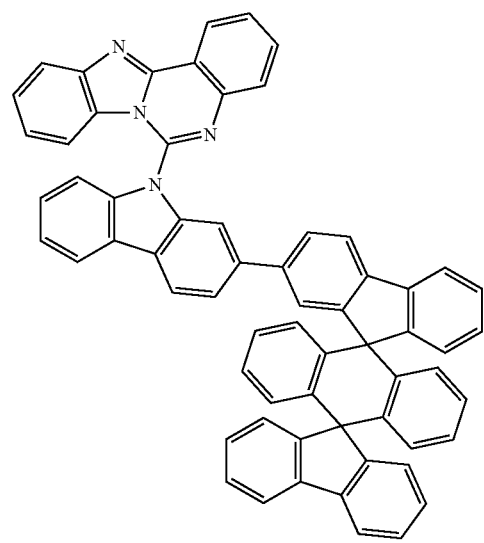
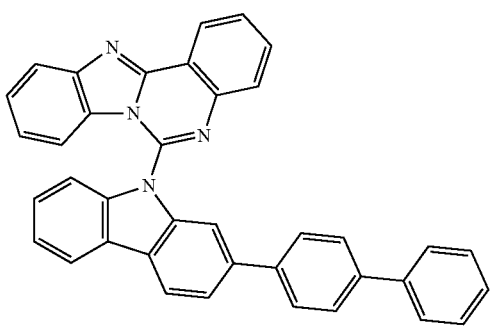

495
-continued
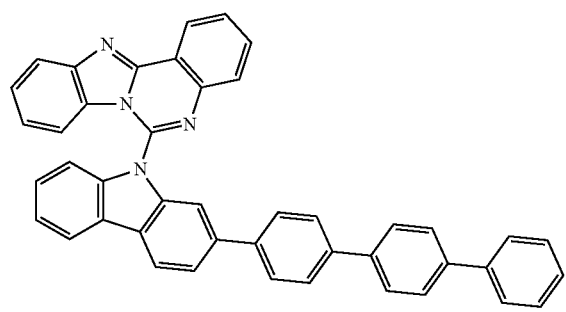
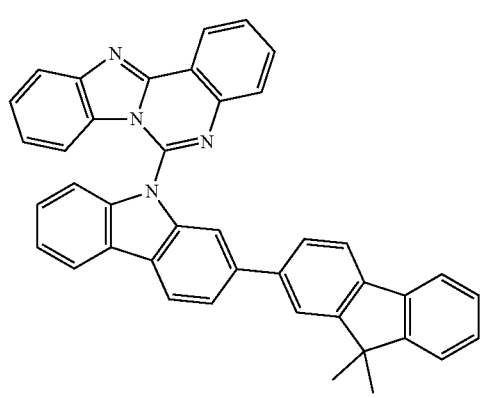
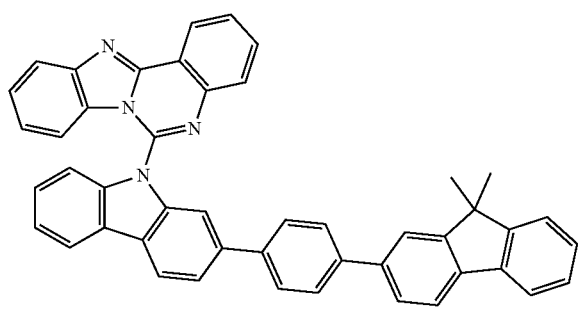
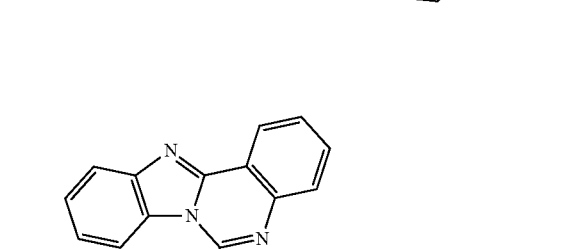
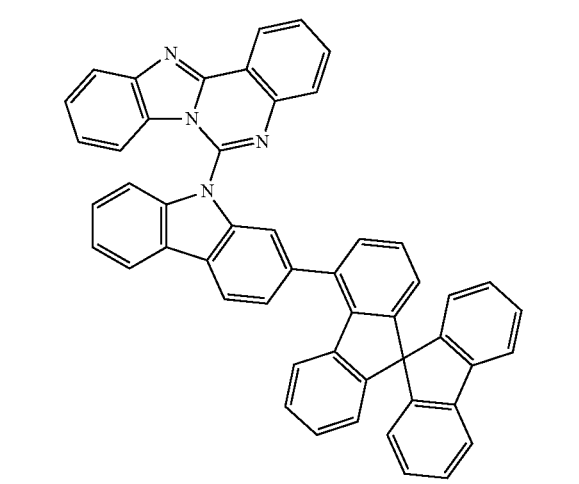
496
-continued
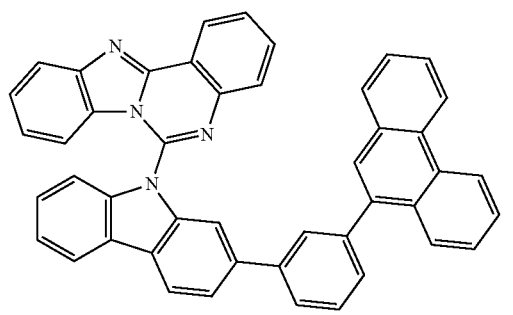
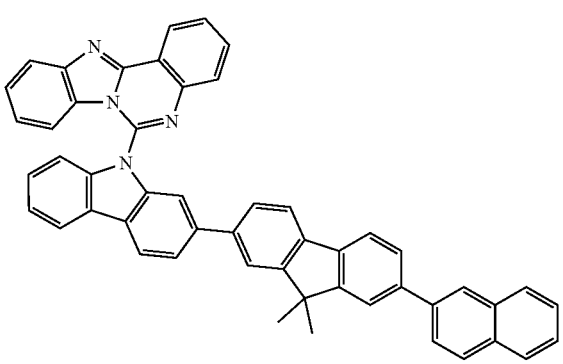
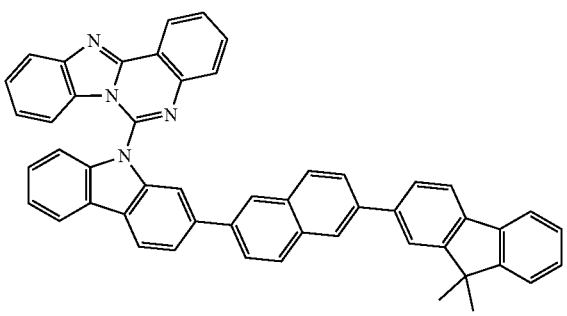
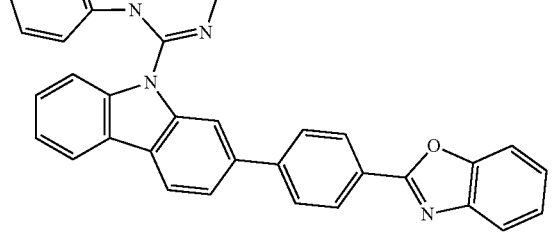
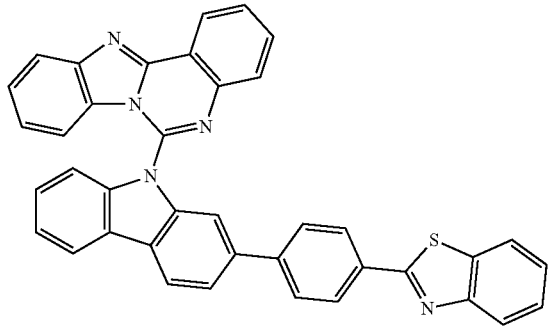

497
-continued
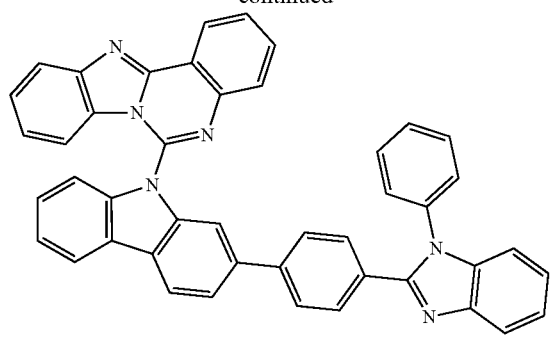
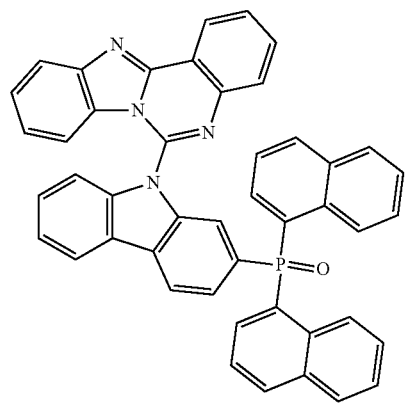
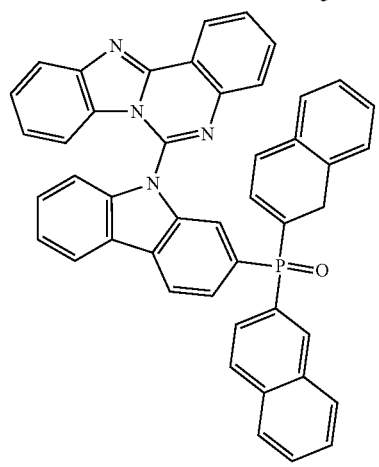
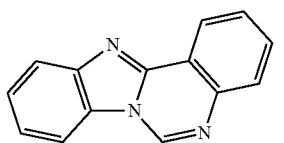
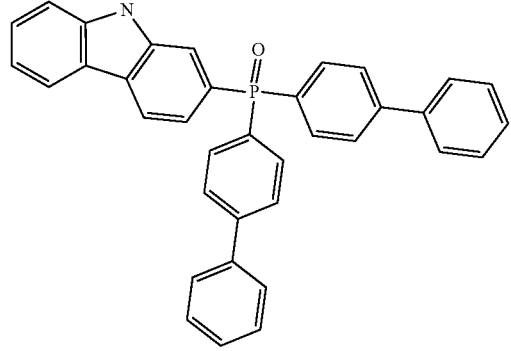
498
-continued
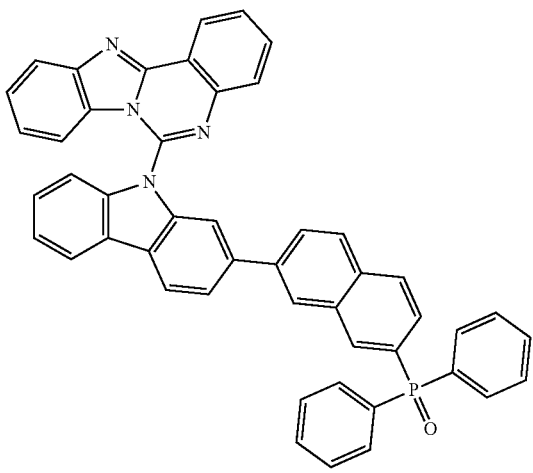
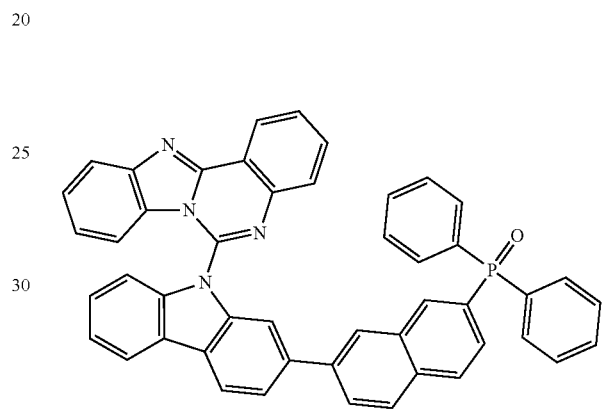
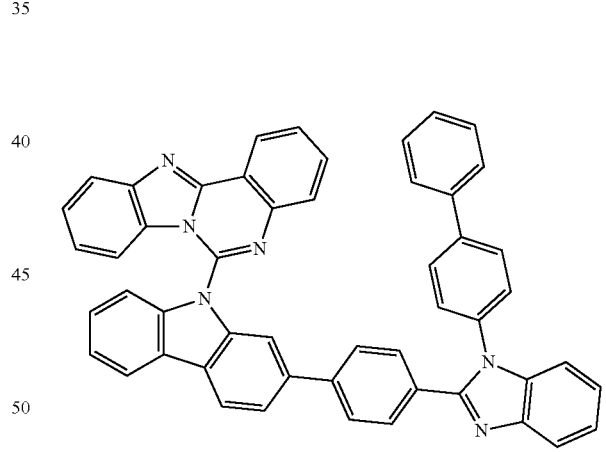
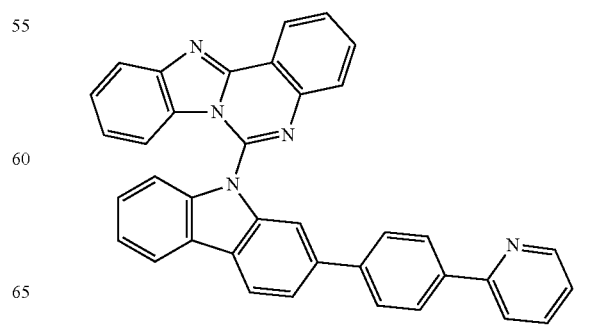

499
-continued
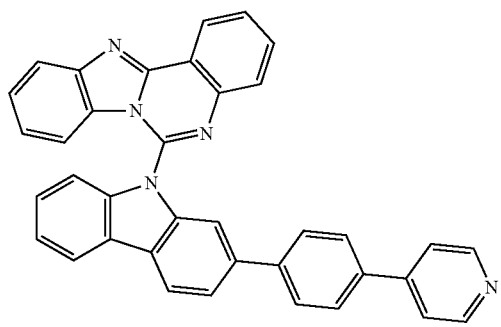
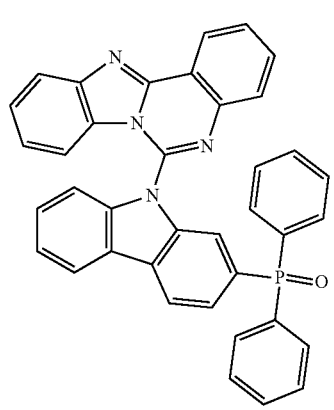
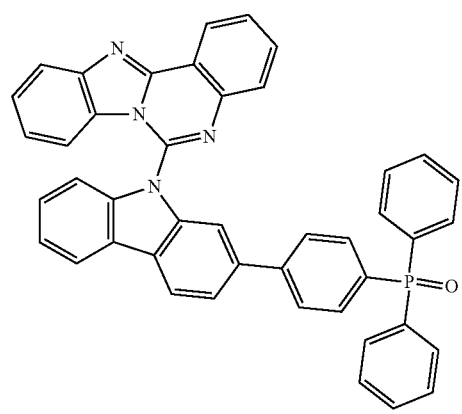
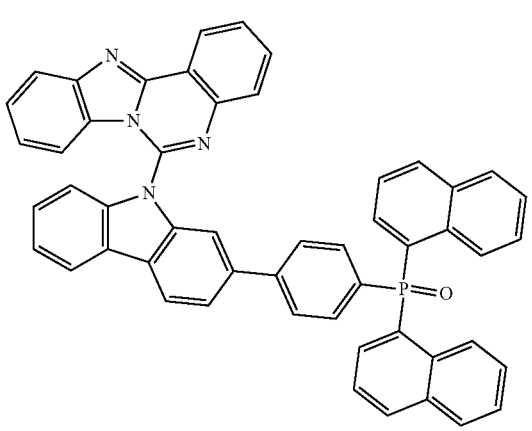
500
-continued
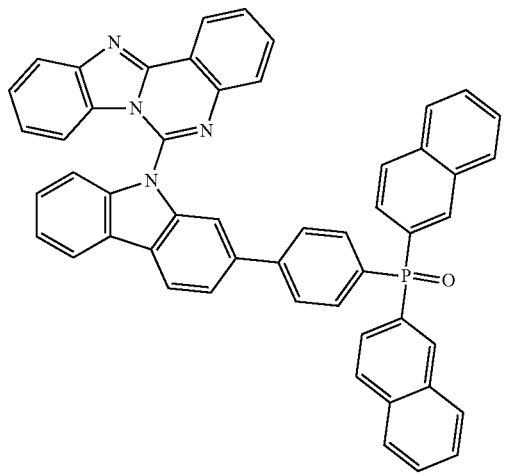
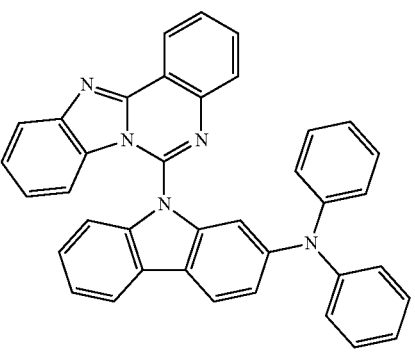
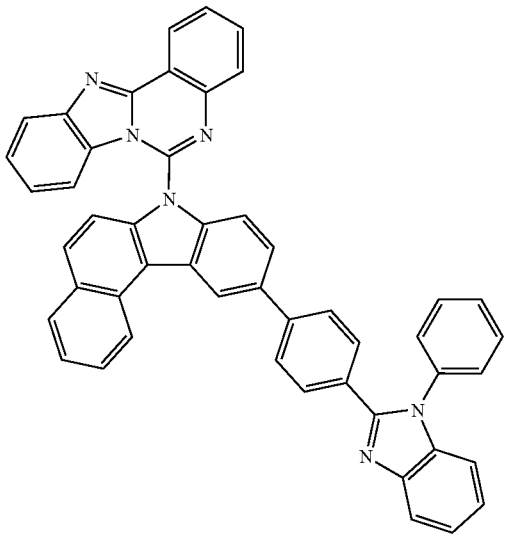

501
-continued

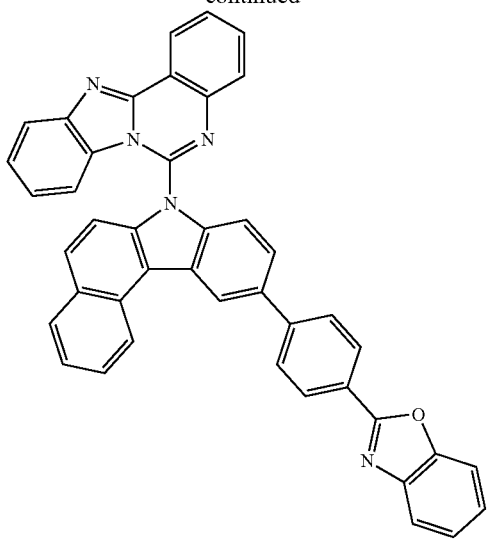

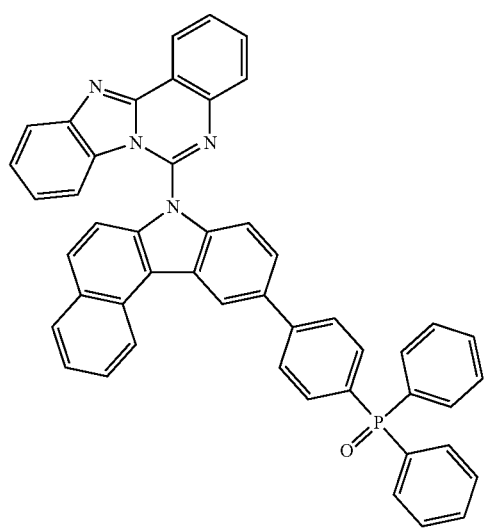

502
-continued

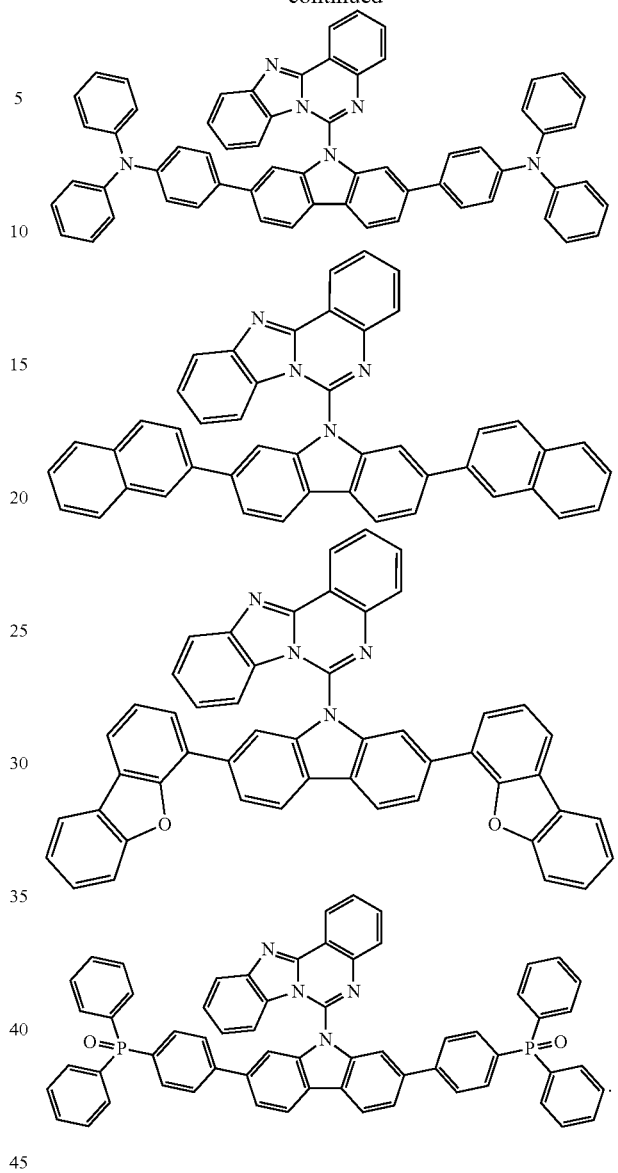

7. An organic electronic device as an organic light emitting device comprising:
a first electrode;
a second electrode provided opposite to the first electrode; and
one or more organic material layers provided between the first electrode and the second electrode,
wherein one or more layers of the organic material layers comprise the compound of claim 1.

8. The organic electronic device of claim 7, wherein the organic material layer comprises a hole injection layer or a hole transfer layer, and the hole injection layer or the hole transfer layer comprises the compound.

9. The organic electronic device of claim 7, wherein the organic material layer comprises a light emitting layer, and the light emitting layer comprises the compound.

10. The organic electronic device of claim 7, wherein the organic material layer comprises an electron transfer layer or an electron injection layer, and the electron transfer layer or the electron injection layer comprises the compound.

11. The organic electronic device of claim 7 comprising two or more layers selected from the group consisting of a hole injection layer, a hole transfer layer, a light emitting layer, an electron transfer layer, an electron injection layer, an electron blocking layer and a hole blocking layer.

12. The organic electronic device of claim 7, which is selected from the group consisting of an organic light emitting device, an organic phosphorescent device, an organic solar cell, an organic photo conductor (OPC) and an organic transistor.

13. The organic electronic device of claim 7, wherein the organic material layer comprises a light emitting layer comprising a compound of the following Chemical Formula 4:

[Chemical Formula 4]

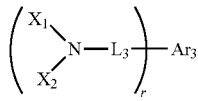

wherein, in Chemical Formula 4,
$Ar_3$ is a benzofluorene skeleton, a fluoranthene skeleton, a pyrene skeleton or a chrysene skeleton,
$L_3$ is a single bond, a $C_6$ to $C_{30}$ arylene group or a $C_5$ to $C_{30}$ divalent heterocyclic group,
$X_1$ and $X_2$ are the same as or different from each other and each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group and a substituted or unsubstituted $C_7$ to $C_{30}$ aralkyl group, and $X_1$ and $X_2$ bond to each other to form a saturated or unsaturated ring,
r is an integer of 1 or greater, and
when r is 2 or greater, $X_1$s are the same as or different from each other and $X_2$s are the same as or different from each other.

14. The organic electronic device of claim 13, wherein $Ar_3$ is a pyrene skeleton, $L_3$ is a single bond, $X_1$ and $X_2$ are the same as or different from each other and each independently an aryl group unsubstituted or substituted with a germanium group, and r is 2.

15. The organic electronic device of claim 7, wherein the organic material layer comprises a light emitting layer comprising a compound of the following Chemical Formula 5:

[Chemical Formula 5]

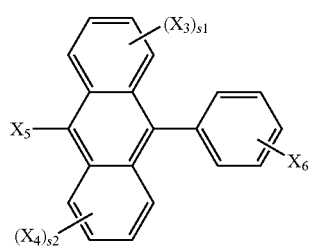

wherein, in Chemical Formula 5,
$X_5$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

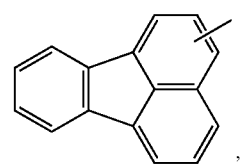

, $X_6$ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl- 1-naphthyl group, a 4-methyl-1-anthryl group, a 4"-methylbiphenylyl group, a 4"-t-butyl-p-terphenyl-4-yl group and a 3-fluoranthenyl group, $X_3$ and $X_4$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer of 0 to 4.

16. The organic electronic device of claim 15, wherein $X_5$ and $X_6$ are the same as or different from each other and each independently a 1-naphthyl group or a 2-naphthyl group, and s1 and s2 are 0.

* * * * *